(12) United States Patent
Sato et al.

(10) Patent No.: US 8,273,766 B2
(45) Date of Patent: Sep. 25, 2012

(54) TETRAHYDROISOQUINOLINE COMPOUND

(75) Inventors: Seiichi Sato, Tokyo (JP); Junya Tagashira, Tokyo (JP); Shunji Takemura, Tokyo (JP); Yoshiharu Miyake, Tokyo (JP); Tetsuya Ishikawa, Tokyo (JP); Toshiharu Arai, Tokyo (JP); Takahiro Ito, Tokyo (JP); Takuya Hara, Tokyo (JP)

(73) Assignee: Kowa Company, Ltd., Aichi (JP)

( * ) Notice: Subject to any disclaimer, the term of this patent is extended or adjusted under 35 U.S.C. 154(b) by 431 days.

(21) Appl. No.: 12/531,318

(22) PCT Filed: Apr. 3, 2008

(86) PCT No.: PCT/JP2008/056677
§ 371 (c)(1),
(2), (4) Date: Sep. 15, 2009

(87) PCT Pub. No.: WO2008/123582
PCT Pub. Date: Oct. 16, 2008

(65) Prior Publication Data
US 2010/0120844 A1    May 13, 2010

Related U.S. Application Data

(60) Provisional application No. 60/909,997, filed on Apr. 4, 2007, provisional application No. 60/939,415, filed on May 22, 2007.

(51) Int. Cl.
*C07D 217/18* (2006.01)
*A61K 31/47* (2006.01)

(52) U.S. Cl. ............... 514/307; 546/148; 546/149

(58) Field of Classification Search .............. None
See application file for complete search history.

(56) References Cited

U.S. PATENT DOCUMENTS

| 5,294,621 | A | 3/1994 | Russell |
| 6,768,024 | B1 | 7/2004 | Watson-Straughan et al. |
| 2004/0110744 | A1 | 6/2004 | Velker et al. |
| 2005/0250814 | A1 | 11/2005 | Zhou et al. |

FOREIGN PATENT DOCUMENTS

| JP | 2004-529132 | 9/2004 |
| JP | 2006-514618 | 5/2006 |
| WO | 00/51607 | 9/2000 |
| WO | 00/53600 | 9/2000 |
| WO | 00/66551 | 11/2000 |
| WO | 02/12166 | 2/2002 |
| WO | 02/26708 | 4/2002 |
| WO | 02/26723 | 4/2002 |
| WO | 02/46164 | 6/2002 |
| WO | 02/059081 | 8/2002 |
| WO | 02/076979 | 10/2002 |
| WO | 03/041641 | 5/2003 |
| WO | 03/068759 | 8/2003 |
| WO | 03/099287 | 12/2003 |
| WO | 2004/042351 | 5/2004 |
| WO | 2004/058762 | 7/2004 |
| WO | 2005/009775 | 2/2005 |
| WO | 2005/026113 | 3/2005 |
| WO | 2006/013073 | 2/2006 |
| WO | 2006/015851 | 2/2006 |
| WO | 2006/028284 | 3/2006 |

OTHER PUBLICATIONS

West, Anthony R., Solid State Chemistry and its Applications, Wiley, New York, 1988, pp. 358 & 365.*
Combadiere et al., J. Biol Chem 270, p. 16491-16494, 1995.
Heath et al., J. Clin. Invest. 99, p. 178-184, 1997.
Kitayama et al., J. Clin. Invest. 101, p. 2017-2024, 1998.
Kampen et al., Blood. 95, p. 1911-1917, 2000.
Ying et al., J Immunol 163, p. 6321-6329, 1999.
Humbles et al., Proc Natl Acad Sci USA 99, p. 1479-1484, 2002.
Justice et al., Am J Physiol Lung Cell Mol Physiol 284, p. L169-L178, 2003.
Bertrand et al., Expert Opin Investig Drugs 9, p. 43-52, 2000.
Elsner et al., Allergy 59, p. 1243-1258, 2004.
Amerio et al., Curr Drug Targets Inflamm Allergy 2, p. 81-94, 2003.
Naya et al., Bioorganic & Medicinal Chemistry Letters 11, p. 1219-1223, 2001.
Suzuki et al., Biochem Biophys Res Commun 339, p. 1217-1223, 2006.
Kauffman et al., J. Org. Chem. 71, p. 8975-8977, 2006.
Dhanak et al., Bioorganic & Medicinal Chemistry Letters 11, p. 1445-1450, 2001.
Naya et al., Chem. Pham. Bull. 51, p. 697-701, 2003.
Bryan et al., Am J Respir Crit Care Med 165, p. 1602-1609, 2002.
Wacker et al., Bioorganic & Medicinal Chemistry Letters 12, p. 1785-1789, 2002.
Varnes et al., Bioorganic & Medicinal Chemistry Letters 14, p. 1645-1649, 2004.
De Lucca et al., J. Med. Chem. 45, p. 3794-3804, 2002.
Batt et al., Bioorganic & Medicinal Chemistry Letters 15, p. 787-791, 2005.
Watson et al., Bioorganic & Medicinal Chemistry Letters 16, p. 5695-5699, 2006.
Gong et al., Bioorganic & Medicinal Chemistry Letters 13, p. 3597-3600, 2003. International Search Report issued with respect to PCT/JP2008/056677, mailed May 20, 2008.
Extended European Search Report issued with respect to European App. No. 08 73 9784.0, dated Aug. 4, 2011.

* cited by examiner

*Primary Examiner* — Zinna Northington Davis
(74) *Attorney, Agent, or Firm* — Greenblum & Bernstein, P.L.C.

(57) ABSTRACT

The present invention relates a specific tetrahydroisoquinoline compound which is useful as a chemokine receptor type 3 (CCR3) antagonist, and a pharmaceutical composition comprising the same as an active ingredient. The tetrahydroisoquinoline compound of the present invention is useful for the treatment or prevention of a disease in which CCR3 participates.

13 Claims, 2 Drawing Sheets

TETRAHYDROISOQUINOLINE COMPOUND

This application is the National Stage of PCT/JP2008/056677, filed Apr. 3, 2008, which claims priority to U.S. Provisional Application No. 60/909,997, filed Apr. 4, 2007, and U.S. Provisional Application No. 60/939,415, filed May 22, 2007.

TECHNICAL FIELD

The present invention relates to a specific tetrahydroisoquinoline compound which is useful as a chemokine receptor type 3 (CCR3) antagonist, and a pharmaceutical composition comprising the same as an active ingredient. The tetrahydroisoquinoline compound of the present invention is useful for the treatment or prevention of a CCR3-participated disease.

BACKGROUND ART

A chemokine receptor type 3 (which is hereinafter referred to as CCR3) as a member of a chemokine receptor family is a seven-pass transmembrane G protein-coupled receptor which is expressed in a part of eosinophils, basophils, or helper T cells (Non-Patent Document 1).

Eotaxin, which is a CCR3 ligand, is one type of chemokine, named as a chemotactic cytokine, which binds specifically to a CCR3, thus leading to an increased intracellular calcium concentration and a induction of cell shape change, which consequently, results in an increased cell motility function (Non-Patent Document 2). Further, it is suggested that when a CCR3 is activated in eosinophils, the expression of adhesion molecules onto the surface of the eosinophils is increased, thereby promoting infiltration of the eosinophils into a tissue (Non-Patent Document 3), and the secretion of cytotoxic basic proteins, called an MBP (Major Basic Protein) or an ECP (Eosinophil Cationic Protein), which is present in the granules in the cell, from the granules, are caused, which consequently acts to the tissue damage (Non-Patent Document 4).

It has been reported from the studies which compare the levels of a CCR3 expression with ones in healthy people, that the mRNA levels and the protein levels are significantly increased in the airway biopsies of the patients with asthma, and that from the studies using a knockout mouse in which a CCR3 is deleted by genetic engineering technique, the studies which administer a neutralizing antibody for a CCR3 protein, or in a pathologic model, and the like due to the antigen sensitization and challenge, result in a decrease in the number of the eosinophils in a bronchoalveolar lavage fluid and an improvement of enhanced airway hyperresponsiveness (Non-Patent Documents 5 to 7).

From the findings described above, the CCR3 is deeply involved in the incidence and progression of diseases such as asthma, allergic rhinitis, allergic conjunctivitis, atopic dermatitis, and the like, which are characterized by eosinophilic infiltration into a local lesion, and the CCR3 antagonist is expected to be effective in the prevention or treatment of these diseases in patients (Non-Patent Documents 8 to 14).

Hitherto, as the CCR3 antagonist, there have been reported a linear alkylamine derivative (Patent Document 1), a piperidine derivative (Patent Documents 2 to 4, Non-Patent Documents 11, 15 to 21), a morpholine derivative (Patent Documents 5 to 7), a pyrrolidine derivative (Patent Documents 8 and 9), a piperazine derivative (Patent Documents 10 and 11), a bicyclopiperidine derivative (Non-Patent Document 22), an azetidine derivative (Patent Document 12), and the like.

Furthermore, there has been reported a CCR3 antagonist having a tetrahydroisoquinoline skeleton (Patent Documents 13 and 14), but the compound of the present invention is different from the compounds as disclosed in these documents in the structure and the intensity of the activity.

In addition, as other tetrahydroisoquinoline compounds, there have been known a compound represented by the general formula (i) (Patent Document 15), a compound represented by the general formula (ii) (Patent Document 16), and the like, but these documents neither disclose nor suggest the CCR3 antagonistic activity, and do not disclose a specific tetrahydroisoquinoline compound represented by the formula (1) of the present invention.

[Chem. 1]

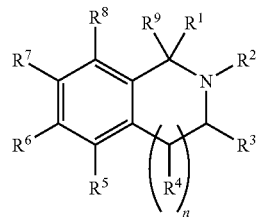

(i)

(for the definition of each symbol, refer to this publication)

[Chem. 2]

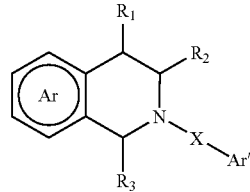

(ii)

(for the definition of each symbol, refer to this publication)

Patent Document 1: Pamphlet of International Publication No. WO2002/59081
Patent Document 2: Pamphlet of International Publication No. WO2000/53600
Patent Document 3: Pamphlet of International Publication No. WO2005/09775
Patent Document 4: Pamphlet of International Publication No. WO2006/13073
Patent Document 5: Pamphlet of International Publication No. WO2002/26723
Patent Document 6: Pamphlet of International Publication No. WO2003/99287
Patent Document 7: Pamphlet of International Publication No. WO2006/28284
Patent Document 8: Pamphlet of International Publication No. WO2000/51607
Patent Document 9: Pamphlet of International Publication No. WO2004/58762
Patent Document 10: Pamphlet of International Publication No. WO2003/68759
Patent Document 11: Pamphlet of International Publication No. WO2006/015851
Patent Document 12: Pamphlet of International Publication No. WO2005/26113

Patent Document 13: Pamphlet of International Publication No. WO2002/26708
Patent Document 14: Pamphlet of International Publication No. WO2003/41641
Patent Document 15: Pamphlet of International Publication No. WO2002/46164
Patent Document 16: U.S. Pat. No. 5,294,621
Non-Patent Document 1: J. Biol Chem 270 (1995) 16491-16494
Non-Patent Document 2: J. Clin. Invest. 99 (1997) 178-187
Non-Patent Document 3: J. Clin. Invest. 101 (1998) 2017-2024
Non-Patent Document 4: Blood. 95 (2000) 1911-1917
Non-Patent Document 5: J. Immunol. 163 (1999) 6321-6329
Non-Patent Document 6: Proc Natl Acad Sci USA. 99 (2002) 1479-1484
Non-Patent Document 7: Am J Physiol Lung Cell Mol. Physiol. 284 (2003) L169-L178
Non-Patent Document 8: Expert Opin Investig Drugs. 9 (2000) 43-52
Non-Patent Document 9: Allergy 59 (2004) 1243-1258
Non-Patent Document 10: Curr Drug Targets Inflamm Allergy 2 (2003) 81-94
Non-Patent Document 11: Bioorganic & Medicinal Chemistry Letters 11 (2001) 1219-1223
Non-Patent Document 12: Biochem Biophys Res Commun. 339 (2006) 1217-1223
Non-Patent Document 13: J. Org. Chem. 71 (2006) 8975-8977
Non-Patent Document 14: Bioorganic & Medicinal Chemistry Letters 11 (2001) 1445-1450
Non-Patent Document 15: Chem. Pham. Bull. 51 (6) 697-701 (2003)
Non-Patent Document 16: Am J Respir Crit. Care Med Vol 165. pp 1602-1609, 2002
Non-Patent Document 17: Bioorganic & Medicinal Chemistry Letters 12 (2002) 1785-1789
Non-Patent Document 18: Bioorganic & Medicinal Chemistry Letters 14 (2004) 1645-1649
Non-Patent Document 19: J. Med. Chem. 2002, 45, 3794-3804
Non-Patent Document 20: Bioorganic & Medicinal Chemistry Letters 15 (2005) 787-791
Non-Patent Document 21: Bioorganic & Medicinal Chemistry Letters 16 (2006) 5695-5699
Non-Patent Document 22: Bioorganic & Medicinal Chemistry Letters 13 (2003) 3597-3600

DISCLOSURE OF THE INVENTION

Problem that the Invention is to Solve

It is an object of the present invention to provide a novel compound having a CCR3 antagonistic activity.

Means for Solving the Problem

Under these circumstances, the present inventors have made extensive studies, and as a result, they have found that a tetrahydroisoquinoline compound represented by the following formula (1) has an antagonistic activity for CCR3, thereby completing completion of the present invention. The tetrahydroisoquinoline compound of the present invention is a novel compound, and is completely different from the structure of known CCR3 antagonists since it has a tetrahydroisoquinoline skeleton.

Thus, the present invention includes a tetrahydroisoquinoline compound represented by the formula (1) or a pharmaceutically acceptable salt thereof. Further, the present invention includes the following embodiments.

1. A tetrahydroisoquinoline compound represented by the following formula (1):

[Chem. 3]

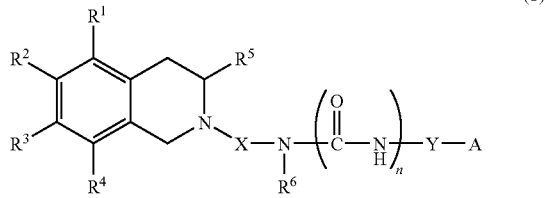

(1)

(wherein
$R^1$, $R^2$, $R^3$, and $R^4$, which are the same or different, each represent —H, -halogen, $C_{1-6}$ alkyl which may be substituted, —OH, —O—$C_{1-6}$ alkyl, —SH, —S—$C_{1-6}$ alkyl, —COOH, —CO—$C_{1-6}$ alkyl, —CO—O—$C_{1-6}$ alkyl, —CO—NH—$C_{1-6}$ alkyl, —$NO_2$, —$NH_2$, —NH—$C_{1-6}$ alkyl, —N($C_{1-6}$ alkyl)$_2$, or —NH—CO—$C_{1-6}$ alkyl, $R^5$ represents $C_{1-6}$ alkyl which may be substituted, $C_{3-10}$ cycloalkyl which may be substituted, $C_{6-14}$ aryl which may be substituted, —$C_{1-6}$ alkylene-$C_{3-10}$ cycloalkyl which may be substituted, or —$C_{1-6}$ alkylene-$C_{6-14}$ aryl which may be substituted, $R^6$ represents —H, —$C_{1-6}$ alkyl which may be substituted, or —Y'-A', X represents $C_{1-6}$ alkylene, Y and Y', which are the same or different, each represent a single bond or $C_{1-6}$ alkylene, A and A', which are the same or different, each represent $C_{6-14}$ aryl which may be substituted or 3- to 15-membered heterocyclic group which may be substituted, and n represents 0 or 1), a pharmaceutically acceptable salt thereof, or a solvate thereof.

2. The tetrahydroisoquinoline compound, a pharmaceutically acceptable salt thereof, or a solvate thereof according to 1. above, wherein n is 0 and A is a group represented by the following formula:

[Chem. 4]

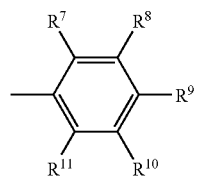

(wherein $R^7$, $R^8$, $R^9$, $R^{10}$, and $R^{11}$, which are the same or different, each represent —H, -halogen, —OH, $C_{1-6}$ alkyl which may be substituted, —O—$C_{1-6}$ alkyl, —S—$C_{1-6}$ alkyl, —$SO_2$—$C_{1-6}$ alkyl, —$SO_2$-halogeno-$C_{1-6}$ alkyl, —COOH, —CO—$C_{1-6}$ alkyl, —CO—O—$C_{1-6}$ alkyl, —CO—$NH_2$, —CO—NH($C_{1-6}$ alkyl), —CO—N($C_{1-6}$ alkyl)$_2$, —$SO_2$NH($C_{1-6}$ alkyl), —$SO_2$N($C_{1-6}$ alkyl)$_2$, —$NO_2$, —CN, $C_{6-14}$ aryl, a 3- to 15-membered heterocyclic group, or —N($R^{12}$)($R^{13}$) (wherein $R^{12}$ and $R^{13}$, which are the same or different, each represent —H, $C_{3-10}$ cycloalkyl, $C_{6-14}$ aryl, 3- to 15-membered heterocyclic group, —$C_{1-6}$ alkylene-$C_{3-10}$ cycloalkyl, —$C_{1-6}$ alkylene-$C_{6-14}$ aryl, —$C_{1-6}$ alkylene-3- to 15-membered hetero ring, $C_{1-6}$ alkyl which may be substituted, —CO—$C_{1-6}$ alkyl, —$SO_2$—$C_{1-6}$ alkyl, or —$SO_2$-halogeno-$C_{1-6}$ alkyl)).

3. The tetrahydroisoquinoline compound, a pharmaceutically acceptable salt thereof, or a solvate thereof according to 2. above, wherein X is ethylene, Y is methylene, and $R^6$ is —H.

4. The tetrahydroisoquinoline compound, a pharmaceutically acceptable salt thereof, or a solvate thereof according to 3. above, wherein $R^1$ and $R^4$ are —H, and $R^2$ and $R^3$, which are the same or different, each represent —H or -halogen.

5. The tetrahydroisoquinoline compound, a pharmaceutically acceptable salt thereof, or a solvate thereof according to 4. above, wherein $R^5$ is benzyl which may be substituted.

6. The tetrahydroisoquinoline compound, a pharmaceutically acceptable salt thereof, or a solvate thereof according to 5. above, wherein $R^5$ is halogenobenzyl.

7. The tetrahydroisoquinoline compound, a pharmaceutically acceptable salt thereof, or a solvate thereof according to 1. above, wherein n is 0, $R^5$ is —$C_{1-6}$ alkylene-$C_{6-14}$ aryl which may be substituted, and A and A', which are the same or different, each represent a 3- to 15-membered heterocyclic group which may be substituted, or naphthyl.

8. The tetrahydroisoquinoline compound, a pharmaceutically acceptable salt thereof, or a solvate thereof according to 7. above, wherein A and A', which are the same or different, each represent a heterocyclic group which may be substituted, said heterocyclic group being selected from pyridyl, pyridyl N-oxide, pyrimidinyl, imidazolyl, pyrrolyl, thienyl, furyl, thiazolyl, quinolyl, indolyl, and benzoimidazolyl, or naphthyl.

9. The tetrahydroisoquinoline compound, a pharmaceutically acceptable salt thereof, or a solvate thereof according to 8. above, wherein $R^1$, $R^2$, $R^3$, and $R^4$, which are the same or different, each represent —H or -halogen, X is ethylene, Y is methylene, and $R^6$ is —H.

10. A tetrahydroisoquinoline compound, a pharmaceutically acceptable salt thereof, or a solvate thereof selected from:

N-(4-tert-butylbenzyl)-2-[3-(4-fluorobenzyl)-3,4-dihydroisoquinolin-2(1H)-yl]ethanamine,
N-(3-acetylbenzyl)-2-[3-(4-fluorobenzyl)-3,4-dihydroisoquinolin-2(1H)-yl]ethanamine,
3-[[2-[3-(4-fluorobenzyl)-3,4-dihydroisoquinolin-2(1H)-yl]ethylamino]methyl]-N,N-diethylbenzamide,
N-(4-tert-butylbenzyl)-2-[6-fluoro-3-(4-fluorobenzyl)-3,4-dihydroisoquinolin-2(1H)-yl]ethanamine,
N-(3-acetylbenzyl)-2-[6-fluoro-3-(4-fluorobenzyl)-3,4-dihydroisoquinolin-2(1H)-yl]ethanamine,
N-[3-(methanesulfonylamino)benzyl]-2-[6-fluoro-3-(4-fluorobenzyl)-3,4-dihydroisoquinolin-2(1H)-yl]ethanamine,
N-(3,5-dimethanesulfonylaminobenzyl)-2-[6-fluoro-3-(4-fluorobenzyl)-3,4-dihydroisoquinolin-2(1H)-yl]ethanamine,
4-[[2-[6-fluoro-3-(4-fluorobenzyl)-3,4-dihydroisoquinolin-2(1H)-yl]ethylamino]methyl]-N-isopropylaniline,
4-[[2-[6-fluoro-3-(4-fluorobenzyl)-3,4-dihydroisoquinolin-2(1H)-yl]ethylamino]methyl]-N-ethylaniline,
N-[4-(4-morpholino)benzyl]-2-[6-fluoro-3-(4-fluorobenzyl)-3,4-dihydroisoquinolin-2(1H)-yl]ethanamine,
4-[[2-[6-fluoro-3-(4-fluorobenzyl)-3,4-dihydroisoquinolin-2(1H)-yl]ethylamino]methyl]-N-(2-methoxyethyl)aniline,
3-[[2-[6-fluoro-3-(4-fluorobenzyl)-3,4-dihydroisoquinolin-2(1H)-yl]ethylamino]methyl]-N,N-diethylbenzamide,
N-[4-(1-hydroxy-1-methylethyl)benzyl]-2-[6-fluoro-3-(4-fluorobenzyl)-3,4-dihydroisoquinolin-2(1H)-yl]ethanamine,
3-[[2-[6-fluoro-3-(4-fluorobenzyl)-3,4-dihydroisoquinolin-2(1H)-yl]ethylamino]methyl]benzamide,
N-(4-tert-butylbenzyl)-2-[3-(4-chlorobenzyl)-6-fluoro-3,4-dihydroisoquinolin-2(1H)-yl]ethanamine,
N-(3-methanesulfonylaminobenzyl)-2-[3-(4-chlorobenzyl)-6-fluoro-3,4-dihydroisoquinolin-2(1H)-yl]ethanamine,
4-[[2-[7-fluoro-3-(4-fluorobenzyl)-3,4-dihydroisoquinolin-2(1H)-yl]ethylamino]methyl]-N-isopropylaniline,
N-(pyridin-4-yl)methyl-2-[3-(4-fluorobenzyl)-3,4-dihydroisoquinolin-2(1H)-yl]ethanamine, and
N-(pyridin-4-yl)methyl-2-[6-fluoro-3-(4-fluorobenzyl)-3,4-dihydroisoquinolin-2(1H)-yl]ethanamine.

11. A pharmaceutical composition comprising the tetrahydroisoquinoline compound, a pharmaceutically acceptable salt thereof, or a solvate thereof as described in any one of 1. to 10. above, and a pharmaceutically acceptable carrier.

12. A chemokine receptor type 3 (CCR3) antagonist comprising the tetrahydroisoquinoline compound, a pharmaceutically acceptable salt thereof, or a solvate thereof as described in any one of 1. to 10. above as an active ingredient.

13. An agent for preventing or treating asthma, allergic rhinitis, sinusitis, allergic conjunctivitis, atopic dermatitis, ulcerative colitis, Crohn's disease, rheumatoid arthritis, an autoimmune disease, HIV infection or a disease caused from HIV infection, comprising the tetrahydroisoquinoline compound, a pharmaceutically acceptable salt thereof, or a solvate thereof as described in any one of 1. to 10. above as an active ingredient.

Effect of the Invention

The tetrahydroisoquinoline compound of the present invention exhibits an excellent CCR3 antagonistic action, and is useful as an agent for preventing or treating CCR3-participated diseases (particularly, allergic or autoimmune diseases such as asthma, allergic rhinitis, sinusitis, allergic conjunctivitis, atopic dermatitis, ulcerative colitis, Crohn's disease, rheumatoid arthritis, and the like, HIV infections and encephalitis and dementia caused thereby, and the like).

BEST MODE FOR CARRYING OUT THE INVENTION

Figure 1:
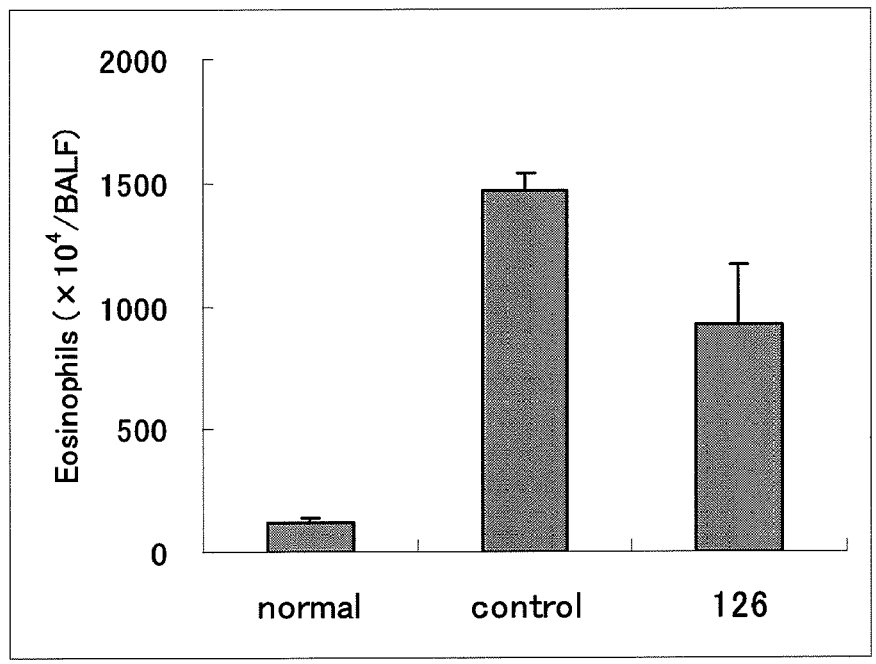
FIG. 1 is a graph showing an inhibitory action on pulmonary eosinophilic infiltration in an ovalbumin-induced guinea pig eosinophil infiltration model by the compound according to the present invention.

Hereinafter, the present invention will be described in more detail.

In the present specification, the expression "which may be substituted" means that "which is not substituted", or "which has one to a maximum substitution number of the substituents which are the same as or different from one another".

The "alkyl" may be in the linear or branched form. Accordingly, the "$C_{1-6}$ alkyl" is specifically methyl, ethyl, propyl, isopropyl, butyl, isobutyl, sec-butyl, tert-butyl, pentyl, isopentyl, neopentyl, hexyl, isohexyl, or the like, or a structural isomer thereof, and preferably methyl, ethyl, propyl, isopropyl, butyl, isobutyl, tert-butyl, isopentyl, or isohexyl.

The "alkylene" means a divalent group formed by removal of one hydrogen at any position of the alkyl. Accordingly, the "$C_{1-6}$ alkylene" is specifically methylene, ethylene, methylmethylene, dimethylmethylene, propylene, butylene, pentylene, hexylene, or the like. It is preferably $C_{1-3}$ alkylene, and more preferably methylene, ethylene, or propylene.

The "cycloalkyl" means a $C_{3-10}$ non-aromatic hydrocarbon ring, and it may form a bridged ring or a spiro ring. Further, it may have a partially unsaturated bond or may be condensed with a benzene ring. Here, if the benzene ring is condensed, the binding arm is on the non-aromatic ring. Accordingly, the "$C_{3-10}$ cycloalkyl" is specifically cyclopropyl, cyclobutyl, cyclopentyl, cyclohexyl, cyclooctyl, cyclohexenyl, cyclooctanedienyl, adamantyl, norbornyl, indanyl having a binding arm at a 1- to 3-position, or the like, and preferably cyclopropyl, cyclobutyl, cyclopentyl, or cyclohexyl.

Furthermore, the "—$C_{1-6}$ alkylene-$C_{3-10}$ cycloalkyl" refers to a group in which one binding arm of the $C_{1-6}$ alkylene is bonded to the $C_{3-10}$ cycloalkyl as described above. Specifically, examples thereof include cyclopropylmethyl, cyclopropylethyl, cyclopropylpropyl, cyclopentylmethyl, cyclopentylethyl, cyclopentylpropyl, cyclohexylmethyl, cyclohexylethyl, cyclohexylpropyl, and the like.

The "halogen" means a halogen group, and specifically, examples thereof include fluoro (—F), chloro (—Cl), bromo (—Br), iodo (—I), and the like, preferably fluoro and chloro, and most preferably fluoro.

The "aryl" means a monocyclic to tricyclic $C_{6-14}$ aromatic hydrocarbon ring. Accordingly, examples of the "$C_{6-14}$ aryl" specifically include phenyl, naphthyl, azulenyl, indenyl, anthryl, phenanthryl, fluorenyl, and the like, and preferably phenyl.

Furthermore, the "—$C_{1-6}$ alkylene-$C_{6-14}$ aryl" refers to a group in which one binding arm of the $C_{1-6}$ alkylene is bonded to the $C_{6-14}$ aryl as described above. Specifically, examples thereof include benzyl, phenethyl, phenylpropyl, phenylbutyl, phenylpentyl, phenylhexyl, naphthylmethyl, naphthylethyl, naphthylpropyl, naphthylbutyl, naphthylpentyl, naphthylhexyl, indenylmethyl, indenylethyl, indenylpropyl, azulenylmethyl, azulenylethyl, azulenylpropyl, anthrylmethyl, anthrylethyl, anthryipropyl, phenanthrylmethyl, phenanthrylethyl, phenanthryipropyl, fluorenylmethyl, fluorenylethyl, fluorenylpropyl, and the like.

The "heterocyclic group" means a 3- to 15-membered (preferably, 5- to 10-membered) monocyclic to tricyclic heterocyclic group containing 1 to 4 hetero atoms each selected from oxygen, sulfur, and nitrogen atoms, and examples thereof include a saturated ring, an aromatic ring, and a partially hydrogenated ring group thereof. Accordingly, examples of the "3- to 15-membered heterocyclic group" specifically include pyridyl, pyrazinyl, pyrimidyl, pyridazinyl, imidazolyl, pyrrolidyl, pyrrolyl, thienyl, furyl, pyranyl, thiazolyl, pyrazolyl, oxazolyl, isooxazolyl, quinolyl, isoquinolyl, tetrahydroquinolyl, tetrahydroisoquinolyl, piperidyl, piperazinyl, tetrahydrofuranyl, tetrahydropyranyl, morpholinyl, indolyl, isoindolyl, indolinyl, benzimidazolyl, tetrahydrobenzoimidazolyl, tetrahydropyranyl, chromanyl, and the like.

Furthermore, the "—$C_{1-6}$ alkylene-3- to 15-membered heterocyclic group" refers to a group in which one binding arm of the $C_{1-6}$ alkylene is bonded to the 3- to 15-membered heterocyclic group as described above. Specifically, examples thereof include pyridylmethyl, pyridylethyl, pyridylpropyl, tetrahydropyranylmethyl, tetrahydropyranylethyl, tetrahydropyranylpropyl, morpholinylmethyl, morpholinylethyl, morpholinylpropyl, and the like.

The "halogeno-$C_{1-6}$ alkyl" means a group in which any one or more hydrogen atoms of the "$C_{1-6}$ alkyl" are substituted with the same or different "halogen" as described above. Specifically, examples thereof include trifluoromethyl, pentafluoroethyl, and the like, and preferably trifluoromethyl.

Furthermore, the "halogenobenzyl" means a benzyl group in which any one or more hydrogen atoms on the benzene ring are substituted with the same or different "halogen" as described above. Specifically, examples thereof include 2-fluorobenzyl, 3-fluorobenzyl, 4-fluorobenzyl, 2-bromobenzyl, 3-bromobenzyl, 4-bromobenzyl, 2-chlorobenzyl, 3-chlorobenzyl, 4-chlorobenzyl, 3,4-difluorobenzyl, 3,5-difluorobenzyl, 3,4-dibromobenzyl, 3,5-dibromobenzyl, 3,4-dichlorobenzyl, 3,5-dichlorobenzyl, and the like, and preferably 2-fluorobenzyl, 4-fluorobenzyl, 2-chlorobenzyl, and 4-chlorobenzyl.

The substituent for the "$C_{1-6}$ alkyl which may be substituted", the "$C_{3-10}$ cycloalkyl which may be substituted", the "$C_{6-14}$ aryl which may be substituted", the "3- to 15-membered heterocyclic group which may be substituted", the "—$C_{1-6}$ alkylene-$C_{3-10}$ cycloalkyl which may be substituted", and the "—$C_{1-6}$ alkylene-aryl which may be substituted" is not particularly limited as long as it may be used as a substituent for these groups. Preferably it is a group such as -halogen, —$NH_2$, —$NH(C_{1-4}$ alkyl), —$N(C_{1-4}$ alkyl)$_2$, —CO—$NH_2$, —CO—$NH(C_{1-4}$ alkyl), —CO—$N(C_{1-4}$ alkyl)$_2$, —NH—CO—($C_{1-4}$ alkyl), —NH—CO—$O(C_{1-4}$ alkyl), —CN, —$NO_2$, a $C_{1-4}$ alkyl group, —$O(C_{1-4}$ alkyl), —OH, —$S(C_{1-4}$ alkyl), —SH, —$CF_3$, —$OCF_3$, —$SO_2NH_2$, —$SO_2NH(C_{1-4}$ alkyl), —$SO_2N(C_{1-4}$ alkyl)$_2$, —$NHSO_1(C_{1-4}$ alkyl), —$N(SO_2C_{1-4}$ alkyl)$_2$, —COOH, —CO—$O(C_{1-4}$ alkyl), and the like, and more preferably -halogen, —$NH_2$, —$NH(C_{1-3}$ alkyl), —$N(C_{1-3}$ alkyl)$_2$, —CO—$NH_2$, —CO—$NH(C_{1-3}$ alkyl), —CO—$N(C_{1-3}$ alkyl)$_2$, —NH—CO—($C_{1-3}$ alkyl), —NH—CO—$O(C_{1-3}$ alkyl), —CN, —$NO_2$, a $C_{1-3}$ alkyl group, —$O(C_{1-3}$ alkyl), —OH, —$S(C_{1-3}$ alkyl), —SH, —$CF_3$, —$OCF_3$, —$SO_2NH_2$, —$SO_2NH(C_{1-3}$ alkyl), —$SO_2N$ ($C_{1-3}$ alkyl)$_2$, —$NHSO_2(C_{1-3}$ alkyl), —$N(SO_2C_{1-3}$ alkyl)$_2$, —COOH, —CO—$O(C_{1-3}$ alkyl), and the like.

The "$C_{1-6}$ alkyl which may be substituted", the "$C_{3-10}$ cycloalkyl which may be substituted", the "$C_{6-14}$ aryl which may be substituted", the "3- to 15-membered heterocyclic group which may be substituted", the "—$C_{1-6}$ alkylene-$C_{3-10}$ cycloalkyl which may be substituted", and the "—$C_{1-6}$ alkylene-aryl which may be substituted" is preferably unsubstituted or has one to three (most preferably one) substituents as described above.

Preferred embodiments of the present invention will be described below.

(A) A tetrahydroisoquinoline compound represented by the general formula (1) in which n is 0 and A is a group represented by the following formula, a pharmaceutically acceptable salt thereof, or a solvate thereof.

[Chem. 5]

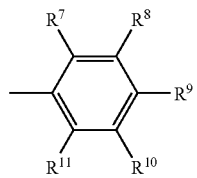

(wherein $R^7$, $R^8$, $R^9$, $R^{10}$, and $R^{11}$, which are the same or different, each represent —H, -halogen, —OH, $C_{1-6}$ alkyl which may be substituted, —O—$C_{1-6}$ alkyl, —S—$C_{1-6}$ alkyl, —$SO_2$—$C_{1-6}$ alkyl, —$SO_2$-halogeno-$C_{1-6}$ alkyl, —COOH, —CO—$C_{1-6}$ alkyl, —CO—O—$C_{1-6}$ alkyl, —CO—$NH_2$, —CO—NH($C_{1-6}$ alkyl), —CO—N($C_{1-6}$ alkyl)$_2$, —$SO_2$NH ($C_{1-6}$ alkyl), —$SO_2$N($C_{1-6}$ alkyl)$_2$, —$NO_2$, —CN, $C_{6-14}$ aryl, a 3- or 15-membered heterocyclic group, or, —N($R^{12}$)($R^{13}$) (wherein $R^{12}$ and $R^{13}$, which are the same or different, each represent —H, $C_{3-10}$ cycloalkyl, $C_{6-14}$ aryl, a 3- or 15-membered heterocyclic group, —$C_{1-6}$ alkylene-$C_{3-10}$ cycloalkyl, —$C_{1-6}$ alkylene-$C_{6-14}$ aryl, —$C_{1-6}$ alkylene-3- or 15-membered hetero ring, $C_{1-6}$ alkyl which may be substituted, —CO—$C_{1-6}$ alkyl, —$SO_2$—$C_{1-6}$ alkyl, or —$SO_2$-halogeno-$C_{1-6}$ alkyl)).

(B) The tetrahydroisoquinoline compound represented by the general formula (1) in which X is ethylene, Y is methylene, and $R^6$ is —H, a pharmaceutically acceptable salt thereof, or a solvate thereof.

(C) The tetrahydroisoquinoline compound represented by the general formula (1) in which $R^1$ and $R^4$ are —H, and $R^2$ and $R^3$, which are the same or different, each represent —H or -halogen, a pharmaceutically acceptable salt thereof, or a solvate thereof.

(D) The tetrahydroisoquinoline compound represented by the general formula (1) in which $R^5$ is benzyl which may be substituted, a pharmaceutically acceptable salt thereof, or a solvate thereof.

(E) The tetrahydroisoquinoline compound represented by the general formula (1) in which $R^5$ is halogenobenzyl, a pharmaceutically acceptable salt thereof, or a solvate thereof.

(F) The tetrahydroisoquinoline compound represented by the general formula (1) in which n is 0, $R^5$ is —$C_{1-6}$ alkylene-$C_{6-14}$ aryl which may be substituted (more preferably, benzyl which may be substituted), and A and A', which are the same or different, each represent a 3- to 15-membered heterocyclic group which may be substituted, or naphthyl, a pharmaceutically acceptable salt thereof, or a solvate thereof.

(G) The tetrahydroisoquinoline compound represented by the general formula (1) in which A and A', which are the same or different, each represent a heterocyclic group which may be substituted, said heterocyclic group being selected from pyridyl, pyridyl N-oxide, pyrimidinyl, imidazolyl, pyrrolyl, thienyl, furyl, thiazolyl, quinolyl, indolyl, and benzoimidazolyl, and naphthyl, a pharmaceutically acceptable salt thereof, or a solvate thereof.

(H) The tetrahydroisoquinoline compound represented by the general formula (1) in which $R^1$, $R^2$, $R^3$, and $R^4$, which are the same or different, each represent —H or -halogen, X is ethylene, Y is methylene, and $R^6$ is —H, a pharmaceutically acceptable salt thereof, or a solvate thereof.

Other preferred embodiments of the present invention include the preferred embodiments as described above or any combination of the ranges of the preferable substituents.

As the compound of the present invention, the following compound, a pharmaceutically acceptable salt thereof, or a solvate thereof is particularly preferred.

N-(4-tert-butylbenzyl)-2-[3-(4-fluorobenzyl)-3,4-dihydroisoquinolin-2(1H)-yl]ethanamine (Example 96), N-(3-acetylbenzyl)-2-[3-(4-fluorobenzyl)-3,4-dihydroisoquinolin-2(1H)-yl]ethanamine (Example 106), 3-[[2-[3-(4-fluorobenzyl)-3,4-dihydroisoquinolin-2(1H)-yl]ethylamino]methyl]-N,N-diethylbenzamide (Example 115), N-(4-tert-butylbenzyl)-2-[6-fluoro-3-(4-fluorobenzyl)-3,4-dihydroisoquinolin-2(1H)-yl]ethanamine (Example 121), N-(3-acetylbenzyl)-2-[6-fluoro-3-(4-fluorobenzyl)-3,4-dihydroisoquinolin-2(1H)-yl]ethanamine (Example 122), N-[3-(methanesulfonylamino)benzyl]-2-[6-fluoro-3-(4-fluorobenzyl)-3,4-dihydroisoquinolin-2(1H)-yl]ethanamine (Example 126), N-(3,5-dimethanesulfonylaminobenzyl)-2-[6-fluoro-3-(4-fluorobenzyl)-3,4-dihydroisoquinolin-2(1H)-yl]ethanamine (Example 133), 4-[[2-[6-fluoro-3-(4-fluorobenzyl)-3,4-dihydroisoquinolin-2(1H)-yl]ethylamino]methyl]-N-isopropylaniline (Example 138), 4-[[2-[6-fluoro-3-(4-fluorobenzyl)-3,4-dihydroisoquinolin-2(1H)-yl]ethylamino]methyl]-N-ethylaniline (Example 139), N-[4-(4-morpholino)benzyl]-2-[6-fluoro-3-(4-fluorobenzyl)-3,4-dihydroisoquinolin-2(1H)-yl]ethanamine (Example 140), 4-[[2-[6-fluoro-3-(4-fluorobenzyl)-3,4-dihydroisoquinolin-2(1H)-yl]ethylamino]methyl]-N-(2-methoxyethyl)aniline (Example 150), 3-[[2-[6-fluoro-3-(4-fluorobenzyl)-3,4-dihydroisoquinolin-2(1H)-yl]ethylamino]methyl]-N,N-diethylbenzamide (Example 151), N-[4-(1-hydroxy-1-methylethyl)benzyl]-2-[6-fluoro-3-(4-fluorobenzyl)-3,4-dihydroisoquinolin-2(1H)-yl]ethanamine (Example 154), 3-[[2-[6-fluoro-3-(4-fluorobenzyl)-3,4-dihydroisoquinolin-2(1H)-yl]ethylamino]methyl]benzamide (Example 155), N-(4-tert-butylbenzyl)-2-[3-(4-chlorobenzyl)-6-fluoro-3,4-dihydroisoquinolin-2(1H)-yl]ethanamine (Example 156), N-(3-methanesulfonylaminobenzyl)-2-[3-(4-chlorobenzyl)-6-fluoro-3,4-dihydroisoquinolin-2(1H)-yl]ethanamine (Example 157), 4-[[2-[7-fluoro-3-(4-fluorobenzyl)-3,4-dihydroisoquinolin-2(1H)-yl]ethylamino]methyl]-N-isopropylaniline (Example 161), N-(pyridin-4-yl)methyl-2-[3-(4-fluorobenzyl)-3,4-dihydroisoquinolin-2(1H)-yl]ethanamine (Example 171), and N-(pyridin-4-yl)methyl-2-[6-fluoro-3-(4-fluorobenzyl)-3,4-dihydroisoquinolin-2(1H)-yl]ethanamine (Example 180).

Further, the compound of the present invention includes any compound which is metabolized in vivo to be converted into the compound of the present invention, that is, a prodrug. Examples of the group for forming the prodrug of the compound of the present invention include the groups as described in "Progress in Medicine", Lifescience Medica, Vol. 5, p. 2157-2161 (1985), and the groups as described in "Iyakuhin no Kaihatsu (Development of Medicines)", Hirokawa Shoten, Vol. 7, Bunshi Sekkei (Molecular Design)", pp. 163-198 (1990).

"Production Methods"

Representative production methods for the compound of the present invention are described below.

The compound (1) of the present invention can be prepared from a 1,2,3,4-tetrahydroisoquinoline derivative represented by the general formula (2).

The 1,2,3,4-tetrahydroisoquinoline derivative represented by the general formula (2) can be prepared, for example, by the following production method.

[Production Method 1]

[Chem. 6]

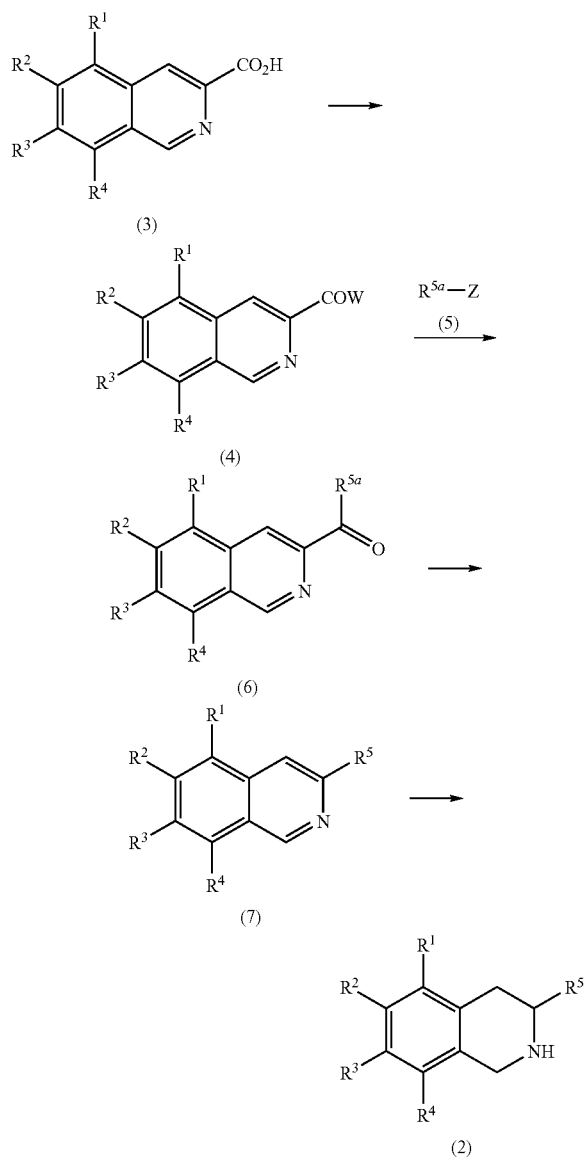

(wherein $R^1$ to $R^5$ represent the same as defined above, W represents chlorine, bromine, iodine, hydroxyl, methoxy, ethoxy, propyloxy, acetoxy, N,O-dimethylhydroxylamine, or the like, and Z represents magnesium chloride, magnesium bromide, lithium, or the like. Further, $R^{5a}$ represents one having a shorter chain by one carbon than the $R^5$, and $R^{5a}$—$CH_2$— represents $R^5$.)

An isoquinoline derivative (4) is obtained from an isoquinoline derivative represented by the general formula (3) by a generally used method (Comprehensive Organic Transformations Second Edition, John Wiley & Sons, Inc.). A desired product (W=chlorine) is obtained, for example, by allowing an equivalent amount or excessive amount of oxalyl chloride or thionyl chloride to undergo a reaction in a solvent in the presence or absence of a base.

Alternatively, a desired product (W=N,O-dimethylhydroxylamine, methoxy, ethoxy, or acetoxy) is obtained, for example, by allowing an equivalent amount or excessive amount of N,O-dimethylhydroxylamine, methanol, ethanol, or acetic anhydride to undergo a reaction in a solvent in the presence or absence of a base.

At this time, as the reaction reagent, DCC, WSC, oxalyl chloride, thionyl chloride, or the like may be used.

As the solvent, for example, dichloromethane, chloroform, tetrahydrofuran, toluene, dioxane, methanol, ethanol, ethyl acetate, acetonitrile, propionitrile, water, or the like may be used singly or in combination thereof.

Examples of the base include pyridine, triethylamine, diisopropylethylamine, potassium carbonate, sodium carbonate, potassium hydroxide, sodium hydroxide, lithium hydroxide, and the like.

The reaction condition is a temperature from −80 to 180° C., and preferably from −30 to 130° C., and a time from 1 minute to 5 days, and preferably from 15 minutes to 3 days.

A ketone product (6) is obtained by reacting the isoquinoline derivative (4) obtained in the above-described reaction with an equivalent amount or excessive amount of a reaction reagent $R^{5a}$—Z (5) in a solvent.

As the solvent, for example, tetrahydrofuran, toluene, dioxane, diethyl ether, chloroform, or the like may be used singly or in combination thereof without limitation to these.

The reaction condition is a temperature from −80 to 180° C., and preferably from −30 to 130° C., and a time from 1 minute to 5 days, and preferably from 15 minutes to 3 days.

An isoquinoline product (7) is obtained by reacting the ketone product (6) obtained in the above-described reaction with hydrazine, and the like in the presence or absence of a base in a solvent, by reducing the ketone product (6) with palladium chloride, palladium black, platinum oxide, rhodium-alumina, or the like under a hydrogen atmosphere, or by reducing the ketone product (6) with an equivalent amount or excessive amount of a reducing agent such as sodium borohydride, lithium borohydride, zinc borohydride, lithium aluminum hydride, lithium aluminum hydride, or the like.

As the solvent, for example, methanol, ethanol, propanol, ethylene glycol, propanediol, tetrahydrofuran, toluene, dioxane, diethyl ether, chloroform, water, or the like may be used singly or in combination thereof.

Examples of the base include pyridine, triethylamine, diisopropylethylamine, potassium carbonate, sodium carbonate, potassium hydroxide, sodium hydroxide, lithium hydroxide, and the like.

The hydrogen pressure in the catalytic reduction reaction is usually from normal pressure to 50 atm, and preferably from normal pressure to 10 atm.

The reaction condition is a temperature from 80 to 380° C., and preferably from 100 to 200° C., and a time from 1 minute to 5 days, and preferably from 1 hour to 3 days.

The 1,2,3,4-tetrahydroisoquinoline derivative (2) is obtained by reducing the isoquinoline product (7) obtained in the above-described reaction with an equivalent amount or excessive amount of a reducing agent such as sodium borohydride, lithium borohydride, zinc borohydride, lithium aluminum hydride, lithium aluminum hydride, or the like, by adding an equivalent amount or excessive amount of nickel chloride to the reducing agent, or by reducing the isoquinoline product (7) with palladium chloride, palladium black, platinum oxide, rhodium-alumina, or the like under a hydrogen atmosphere.

As the solvent, for example, methanol, ethanol, propanol, ethyl acetate, water, or the like may be used singly or in combination thereof.

The hydrogen pressure in the catalytic reduction reaction is usually from normal pressure to 50 atm, and preferably from normal pressure to 10 atm.

The reaction condition is a temperature from −80 to 180° C., and preferably from −30 to 130° C., and a time from 1 minute to 5 days, and preferably from 1 hour to 3 days.

Furthermore, the 1,2,3,4-tetrahydroisoquinoline derivative represented by the general formula (2) can be prepared using the following method.

[Production Method 2]

[Chem. 7]

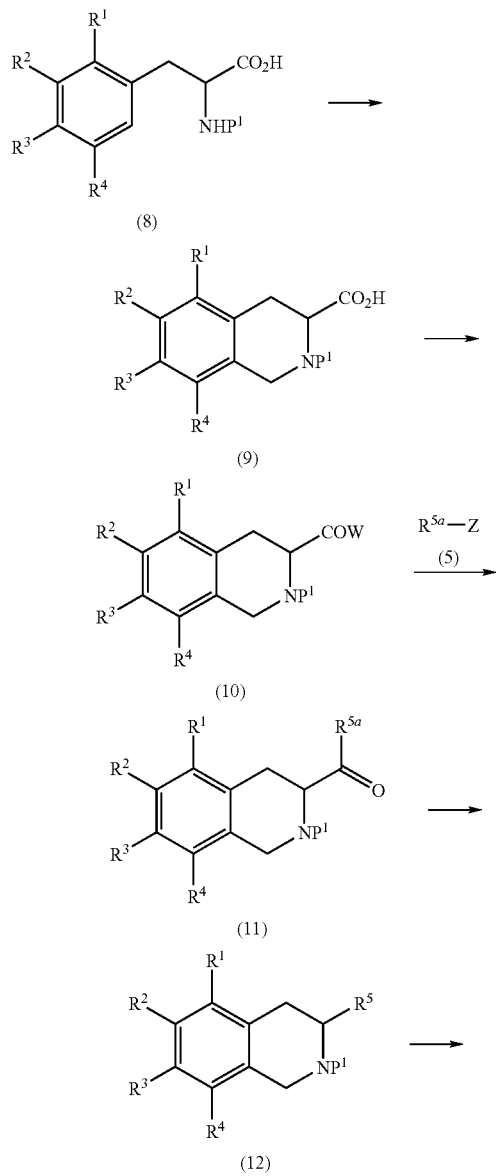

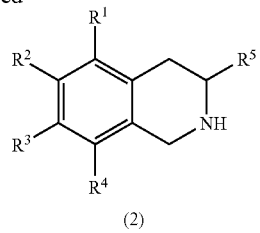

(wherein $R^1$ to $R^5$ and $R^{5a}$ and W, and Z represent the same meaning as defined above, and $P^1$ represents a protecting group)

A 1,2,3,4-tetrahydroisoquinoline isoquinoline derivative (9) is obtained by reacting the phenylalanine derivative represented by the general formula (8) with an equivalent amount or excessive amount of an aqueous formaldehyde solution, paraformaldehyde, and the like in the presence or absence of an acid or a base. The protecting group, $P^1$, is not particularly limited, but it is one which can be introduced by a generally used method (Protective Groups in Organic Synthesis Third Edition, John Wiley & Sons, Inc.), and the like, and examples thereof include methyl carbamate, ethyl carbamate, 9-fluorenylmethyl carbamate, 9-(2-sulfo)fluorenylmethyl carbamate, 9-(2,7-dibromo)fluorenylmethyl carbamate, 2,7-di-tert-butyl-[9-(10,10-dioxo-10,10,10,10-tetrahydrothioxanthyl)]methyl carbamate, 4-methoxyphenacyl carbamate, 2,2,2-trichloroethyl carbamate, 2-trimethylsilylethyl carbamate, 2-phenethylethyl carbamate, 1-(1-adamantyl)-1-methylethyl carbamate, 1,1-dimethyl-2-haloethyl carbamate, 1,1-dimethyl-2,2-dibromoethyl carbamate, 1-methyl-1-(4-biphenyl)ethyl carbamate, 1-(3,5-di-tert-butylphenyl)-1-methylethyl carbamate, 2-(N,N-dicyclohexylcarboxyamide)ethyl carbamate, tert-butyl carbamate, 1-adamantyl carbamate, vinyl carbamate, methanesulfonyl, benzenesulfonyl, 2-methoxycarbonylethylsulfonyl, and the like.

As the solvent, for example, tetrahydrofuran, toluene, dioxane, diethyl ether, chloroform, or the like may be used singly or in combination thereof.

As the acid, for example, hydrochloric acid, sulfuric acid, bromic acid, acetic acid, trifluoroacetic acid, or the like may be used singly or in combination thereof.

Examples of the base include pyridine, triethylamine, diisopropylethylamine, potassium carbonate, sodium carbonate, and the like.

The reaction condition is a temperature from −80 to 180° C., and preferably from −30 to 130° C., and a time from 1 minute to 5 days, and preferably from 1 hour to 3 days.

A 1,2,3,4-tetrahydroisoquinoline derivative (10) is obtained from the 1,2,3,4-tetrahydroisoquinoline derivative represented by the general formula (9) in the same manner as in the method for synthesizing the isoquinoline derivative (4) of Production Example 1.

A ketone product (11) is obtained from the 1,2,3,4-tetrahydroisoquinoline derivative (10) obtained in the above-described reaction in the same manner as in the method for synthesizing the ketone product (6) of Production Example 1.

A tetrahydroisoquinoline derivative (12) is obtained by reducing the ketone product (11) obtained in the above-described reaction with an equivalent amount or excessive amount of a reducing agent such as sodium borohydride, lithium borohydride, zinc borohydride, lithium aluminum hydride, lithium aluminum hydride, or the like, by adding an equivalent amount or excessive amount of nickel chloride to the reducing agent, or by reducing the ketone product (11) with palladium chloride, palladium black, platinum oxide, rhodium-alumina, or the like under a hydrogen atmosphere.

As the solvent, for example, methanol, ethanol, propanol, ethyl acetate, water, or the like may be used singly or in combination thereof.

The hydrogen pressure in the catalytic reduction reaction is usually from normal pressure to 50 atm, and preferably from normal pressure to 10 atm.

The reaction condition is a temperature from −80 to 180° C., and preferably from −30 to 130° C., and a time from 1 minute to 5 days, and preferably from 1 hour to 3 days.

The 1,2,3,4-tetrahydroisoquinoline derivative (2) is obtained by deprotecting the 1,2,3,4-tetrahydroisoquinoline derivative (12) obtained in the above-described reaction with reference to a generally used method (Protective Groups in Organic Synthesis Third Edition, John Wiley & Sons, Inc.), and the like for the protection/deprotection condition for the protecting group. For example, a desired product is obtained by performing deprotection through heating under an acidic condition.

As the solvent, for example, tetrahydrofuran, toluene, dioxane, diethyl ether, chloroform, or the like may be used singly or in combination thereof.

As the acid, hydrochloric acid, sulfuric acid, bromic acid, acetic acid, trifluoroacetic acid, or the like may be used singly or in combination thereof.

The reaction condition is a temperature from 0 to 250° C., and preferably from 30 to 200° C., and a time from 1 minute to 5 days, and preferably from 1 hour to 3 days.

Furthermore, the 1,2,3,4-tetrahydroisoquinoline derivative represented by the general formula (12) can be prepared using the following method.

[Production Method 3]

(wherein $R^1$ to $R^5$, $P^1$ and Z represent the same as defined above)

A ketone product (17) is obtained from the phenyl acetic acid derivative represented by the general formula (13) in the same manner as in the method for synthesizing the ketone product (6) of Production Example 1. Further, the ketone product (17) is also obtained from the carboxylic acid product (15) in the same manner.

An amine product (18) is obtained by reacting the ketone product (17) obtained in the above-described reaction with an equivalent amount or excessive amount of an amine such as ammonium acetate, ammonium formate, ammonium carbonate, ammonium hydroxide, ammonium chloride, or the like, and sodium borohydride, sodium triacetoxyborohydride, sodium cyanoborohydride, or the like.

As the solvent, for example, methanol, ethanol, propanol, tetrahydrofuran, toluene, dioxane, diethyl ether, or the like may be used singly or in combination thereof.

The reaction condition is a temperature from −80 to 180° C., and preferably from −30 to 130° C., and a time from 1 minute to 5 days, and preferably from 1 hour to 3 days.

An amine-protected product (19) is obtained by introducing the same protecting group as for the phenylalanine derivative (8) of Production Example 2 to the amine product (18) obtained in the above-described reaction with a generally used method (Protective Groups in Organic Synthesis Third Edition, John Wiley & Sons, Inc.).

A 1,2,3,4-tetrahydroisoquinoline derivative (12) is obtained from the amine-protected product (19) obtained in the above-described reaction in the same manner as in the

[Chem. 8]

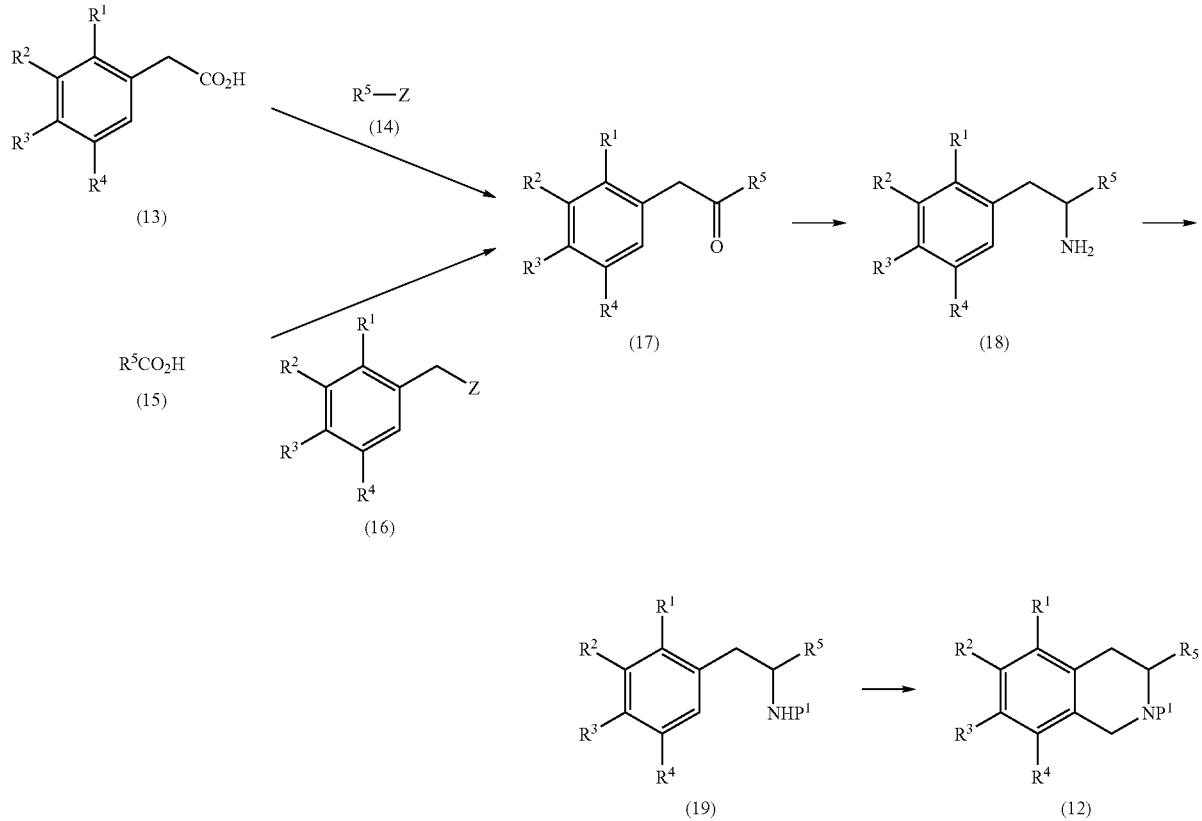

method for synthesizing the 1,2,3,4-tetrahydroisoquinolineisoquinoline derivative (9) of Production Example 2.

Furthermore, a 1,3-bis-2-propanone product, which is symmetric among the ketone products represented by the general formula (17), can be prepared using the following method.

[Production Method 4]

[Chem. 9]

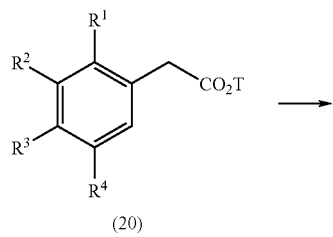
(20)

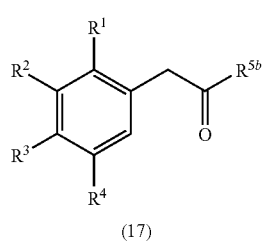
(17)

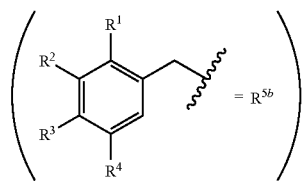

(wherein $R^1$ to $R^4$ represent the same meaning as defined above, and T represents methoxy, ethoxy, or the like)

The ketone product (17) is obtained by reacting an ester product represented by the general formula (20) with an equivalent amount or excessive amount of isopropylmagnesium bromide, tert-butyl magnesium bromide, tert-butoxypotassium, or the like. As the solvent, for example, diethyl ether, tetrahydrofuran, toluene, dioxane, methanol, ethanol, propanol, or the like may be used singly or in combination thereof. The reaction condition is a temperature from −100 to 100° C., and preferably from −80 to 60° C., and a time from 1 minute to 5 days, and preferably from 1 hour to 3 days.

Furthermore, the 1,2,3,4-tetrahydroisoquinoline derivative represented by the general formula (2) can be prepared using the following method.

[Production Method 5]

[Chem. 10]

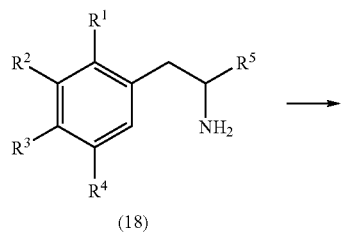
(18)

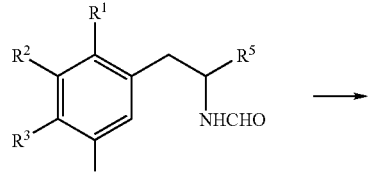
(21)

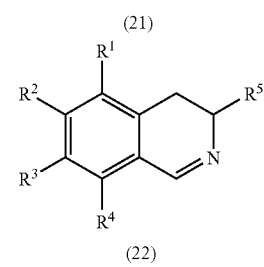
(22)

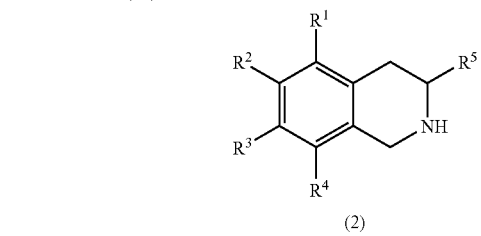
(2)

(wherein $R^1$ to $R^5$ represent the same as defined above)

A formyl product (21) is obtained by reacting the amine product represented by the general formula (18) with an equivalent amount or excessive amount of formic acid in the presence or absence of an acid or a base in a solvent.

At this time, as the reaction reagent, acetic anhydride, DCC, WSC, oxalyl chloride, or the like may be used.

As the solvent, for example, tetrahydrofuran, toluene, dioxane, methanol, ethanol, ethyl acetate, acetonitrile, propionitrile, water, or the like may be used singly or in combination thereof.

As the acid, for example, hydrochloric acid, sulfuric acid, bromic acid, acetic acid, trifluoroacetic acid, or the like may be used singly or in combination thereof.

Examples of the base include pyridine, triethylamine, diisopropylethylamine, potassium carbonate, sodium carbonate, potassium hydroxide, sodium hydroxide, lithium hydroxide, and the like.

The reaction condition is a temperature from −80 to 180° C., and preferably from −30 to 130° C., and a time from 1 minute to 5 days, and preferably from 15 minutes to 3 days.

A 3,4-dihydroisoquinoline product (22) is obtained by reacting the formyl product (21) obtained in the above-described reaction with an equivalent amount or excessive amount of PPA and phosphorous pentoxide in a solvent.

As the solvent, for example, tetrahydrofuran, toluene, dioxane, diethyl ether, chloroform, or the like may be used singly or in combination thereof.

The reaction condition is a temperature from 0 to 300° C., and preferably from 50 to 250° C., and a time from 1 minute to 5 days, and preferably from 1 hour to 3 days.

The 1,2,3,4-tetrahydroisoquinoline derivative (2) is obtained by reducing the 3,4-dihydroisoquinoline product (22) obtained in the above-described reaction with palladium chloride, palladium black, platinum oxide, rhodium alumina, or the like under a hydrogen atmosphere, in the presence or absence of an acid, or by reducing the 3,4-dihydroisoquinoline product (22) with an equivalent amount or excessive amount of sodium borohydride, lithium borohydride, zinc borohydride, lithium aluminum hydride, lithium aluminum hydride, or the like.

As the solvent, for example, methanol, ethanol, propanol, ethylene glycol, propanediol, tetrahydrofuran, toluene, dioxane, diethyl ether, chloroform, water, or the like may be used singly or in combination thereof.

As the acid, for example, hydrochloric acid, sulfuric acid, bromic acid, acetic acid, trifluoroacetic acid, or the like may be used singly or in combination thereof.

The hydrogen pressure in the catalytic reduction reaction is usually from normal pressure to 50 atm, and preferably from normal pressure to 10 atm.

The reaction condition is a temperature from −100 to 200° C., and preferably from −50 to 150° C., and a time from 1 minute to 5 days, and preferably from 1 hour to 3 days.

Furthermore, the amine product represented by the general formula (18) can be prepared using a known method (J. Am. Chem. Soc. 1997, 119, 9913-9914. J. Org. Chem. 1999, 64, 1278-1284., and the like).

[Production Method 6]

The reaction condition is a temperature from −80 to 180° C., and preferably from −30 to 130° C., and a time from 1 minute to 5 days, and preferably from 15 minutes to 3 days.

A sulfinamide product (27) is obtained by reacting the N-sulfinylimine product (24) obtained in the above-described reaction with an equivalent amount or excessive amount of a Grignard reagent or a lithium reagent which is represented by the general formula (14) in a solvent, or by reacting the compound (26) with an equivalent amount or excessive amount of a Grignard reagent or a lithium reagent which is represented by the general formula (16) in a solvent.

As the solvent, for example, tetrahydrofuran, toluene, dioxane, diethyl ether, chloroform, dichloromethane or the like may be used singly or in combination thereof.

The reaction condition is a temperature from −100 to 180° C., and preferably from −80 to 130° C., and a time from 1 minute to 5 days, and preferably from 15 minutes to 3 days.

The amine product (18) is obtained by removing sulfine from the sulfinamide product (27) obtained in the above-described reaction in the presence or absence of an acid in a solvent.

[Chem. 11]

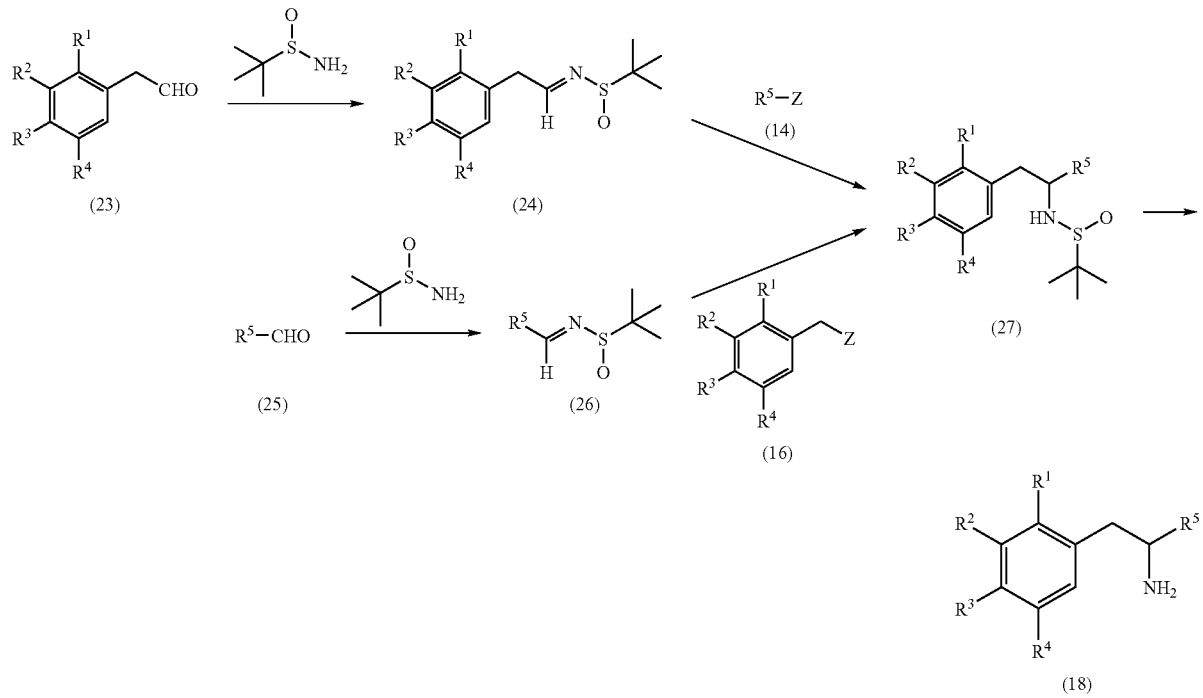

(wherein $R^1$ to $R^5$ and Z represent the same as defined above)

An N-sulfinylimine product (24) is obtained by reacting a phenylacetaldehyde derivative represented by the general formula (23) with an equivalent amount or excessive amount of tert-butanesulfinamide in a solvent. Further, an N-sulfinylimine product (26) is also obtained from an aldehyde product (25) in the same manner.

At this time, as the reaction reagent, magnesium sulfate, copper sulfate, PPTS, titanium (IV) methoxide, titanium(IV) ethoxide, or the like may be used.

As the solvent, for example, tetrahydrofuran, toluene, dioxane, diethyl ether, chloroform, dichloromethane or the like may be used singly or in combination thereof.

As the acid, for example, hydrochloric acid, sulfuric acid, bromic acid, acetic acid, trifluoroacetic acid, or the like may be used singly or in combination thereof. As the solvent, for example, methanol, ethanol, propanol, ethylene glycol, propanediol, tetrahydrofuran, toluene, dioxane, diethyl ether, chloroform, water, or the like may be used singly or in combination thereof. The reaction condition is a temperature from −80 to 180° C., and preferably from −30 to 130° C., and a time from 1 minute to 5 days, and preferably from 15 minutes to 3 days.

Furthermore, the 1,2,3,4-tetrahydroisoquinoline derivative represented by the general formula (2) can be prepared using a known method (Can. J. Chem. 1994, 72, 23). This reaction route may be represented by the chemical reaction scheme as follows.

21

[Production Method 7]

[Chem. 12]

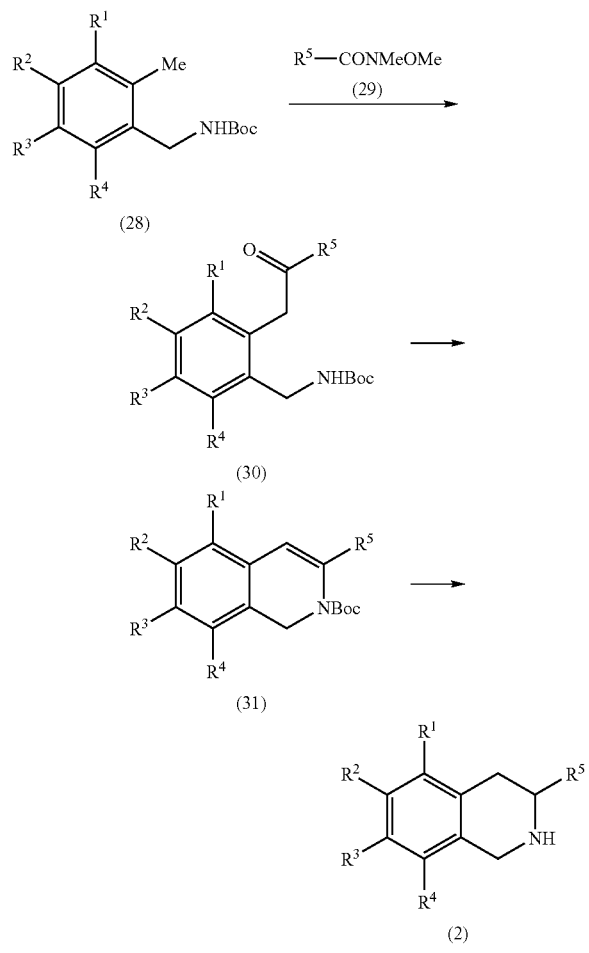

(wherein $R^1$ to $R^5$ represent the same as defined above)

A ketone product (30) is obtained by reacting an N-Boc-2-methyl-benzylamine product represented by the general formula (28) with an equivalent amount or excessive amount of N-methoxy-N-methylamide product (29) in the presence of an equivalent amount or excessive amount of a reagent in a solvent.

At this time, as the reaction reagent, n-butyllithium, tert-butyllithium, sec-butyllithium, methyllithium, ethyllithium, or the like may be used singly or in combination thereof.

As the solvent, for example, tetrahydrofuran, diethyl ether, toluene, dioxane, ethyl acetate, or the like may be used singly or in combination thereof.

The reaction condition is a temperature from −100 to 50° C., and preferably from −80 to 30° C., and a time from 1 minute to 5 days, and preferably from 15 minutes to 3 days.

A 1,2-dihydroisoquinoline product (31) is obtained by subjecting the ketone product (30) obtained in the above-described reaction to the deprotection reaction and the ring-closing reaction at once in the presence or absence of an acid in a solvent.

As the acid, hydrochloric acid, sulfuric acid, bromic acid, acetic acid, trifluoroacetic acid, or the like may be used singly or in combination thereof. As the solvent, for example, tetrahydrofuran, diethyl ether, toluene, dioxane, ethyl acetate,

22 chloroform, dichloromethane, water, or the like may be used singly or in combination thereof. A desired product is obtained by the reaction under a reaction condition of a temperature from −80 to 180° C., and preferably from −50 to 150° C., and a time from 1 minute to 5 days, preferably from 1 hour to 3 days.

The 1,2,3,4-tetrahydroisoquinoline derivative (2) is obtained by reducing the 1,2-dihydroisoquinoline product (31) obtained in the above-described reaction with an equivalent amount or excessive amount of a reducing agent such as sodium borohydride, lithium borohydride, lithium aluminum hydride, or the like, by adding an equivalent amount or excessive amount of nickel chloride, or the like to the reducing agent, or by reducing the 1,2-dihydroisoquinoline product (31) with palladium chloride, palladium black, platinum oxide, rhodium alumina, or the like under a hydrogen atmosphere.

As the solvent, for example, methanol, ethanol, propanol, ethyl acetate, water, or the like may be used singly or in combination thereof.

The hydrogen pressure in the catalytic reduction reaction is usually from normal pressure to 50 atm, and preferably from normal pressure to 10 atm.

The reaction condition is a temperature from −80 to 180° C., and preferably from −30 to 130° C., and a time from 1 minute to 5 days, and preferably from 1 hour to 3 days.

Furthermore, the 1,2,3,4-tetrahydroisoquinoline derivative represented by the general formula (2) can be prepared using the following method.

[Production Method 8]

[Chem. 13]

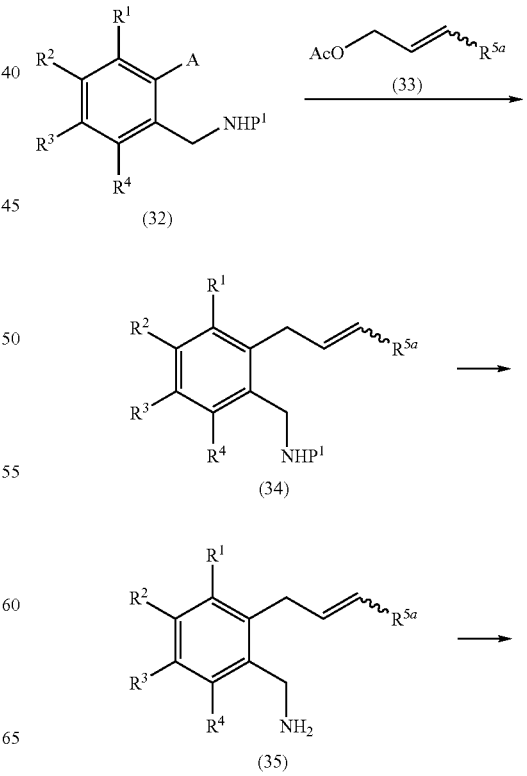

-continued

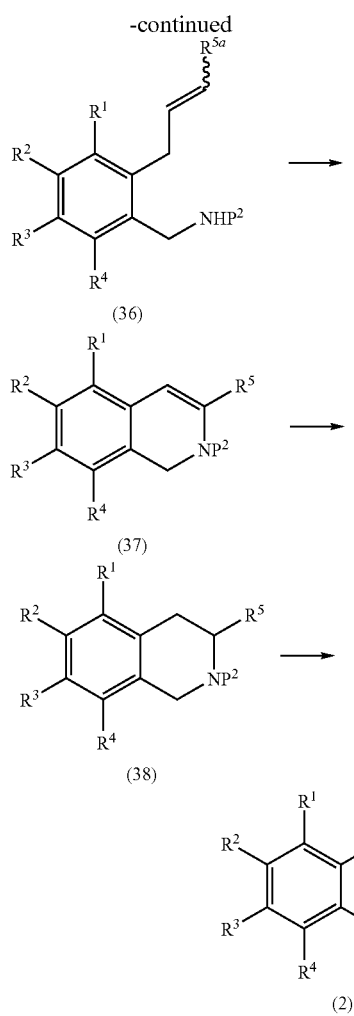

(wherein $R^1$ to $R^{5a}$, and $P^1$ represent the same meaning as defined above, $P^2$ represents a protecting group, and A represents a halogen or the like)

A benzylamine-protected product (34) is obtained by reacting a benzylamine-protected product represented by the general formula (32) with an equivalent amount or excessive amount of an olefin product (33) in the presence of an equivalent amount or excessive amount of a reagent in a solvent. As the reaction reagent, bistributyltin, $PdCl_2(dppf)_2$, or the like may be used singly or in combination thereof. As the solvent, for example, dimethylformamide, tetrahydrofuran, diethyl ether, toluene, dioxane, ethyl acetate, or the like may be used singly or in combination thereof. The reaction condition is a temperature from −30 to 230° C., and preferably from 0 to 200° C., and a time from 1 minute to 5 days, and preferably from 15 minutes to 3 days.

A benzylamine product (35) is obtained by deprotecting the benzylamine-protected product represented by the general formula (34) in the same manner as in the method for synthesizing the 1,2,3,4-tetrahydroisoquinoline derivative (2) of Production Method 2 with reference to a generally used method (Protective Groups in Organic Synthesis Third Edition, John Wiley & Sons, Inc.) for the protection/deprotection conditions for the protecting group.

A benzylamine product-protected product (36) is obtained by deprotecting the benzylamine product represented by the general formula (35) with reference to a generally used method (Protective Groups in Organic Synthesis Third Edition, John Wiley & Sons, Inc.) for the protection/deprotection conditions for the protecting group.

A 3,4-dihydroisoquinoline product (37) is obtained by allowing the benzylamine-protected product represented by the general formula (36) to undergo a reaction in the presence of an equivalent amount or excessive amount of a reagent in a solvent in the presence or absence of a base. At this time, as the reaction reagent, $PdCl_2(CH_3CN)_2$, $PdCl_2(dppf)_2$, benzoquinone, lithium chloride, or the like may be used singly or in combination thereof. As the solvent, for example, dimethyl formamide, tetrahydrofuran, diethyl ether, toluene, dioxane, ethyl acetate, or the like may be used singly or in combination thereof. Examples of the base include pyridine, triethylamine, diisopropylethylamine, potassium carbonate, sodium carbonate, potassium hydroxide, sodium hydroxide, lithium hydroxide, or the like. The reaction condition is a temperature from −30 to 230° C., and preferably from 0 to 200° C., and a time from 1 minute to 5 days, and preferably from 15 minutes to 3 days.

A 1,2,3,4-tetrahydroisoquinoline derivative (38) is obtained by reducing the 3,4-dihydroisoquinoline product represented by the general formula (37) in the same manner as in the method for synthesizing the 1,2,3,4-tetrahydroisoquinoline derivative (2) of Production Method 6.

The 1,2,3,4-tetrahydroisoquinoline derivative (2) is obtained by deprotecting the 1,2,3,4-tetrahydroisoquinoline derivative represented by the general formula (38) in the same manner as in the method for synthesizing the 1,2,3,4-tetrahydroisoquinoline derivative (2) of Production Method 2 with reference to a generally used method (Protective Groups in Organic Synthesis Third Edition, John Wiley & Sons, Inc.) for the protection/deprotection conditions for the protecting group.

The compound (1) of the present invention can be prepared from the 1,2,3,4-tetrahydroisoquinoline derivative represented by the general formula (2). The compound (1) of the present invention can be prepared by various methods. The Production Method is not particularly limited, and for example, the Production can be carried out according to the following reaction process.

1. Method for preparing a 1,2,3,4-tetrahydroisoquinoline derivative with n=0.

[Production Method 9]

[Chem. 14]

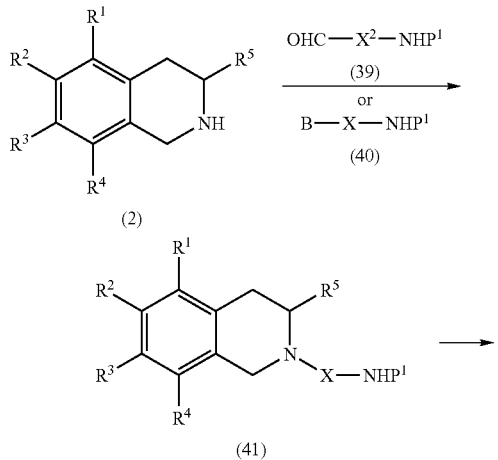

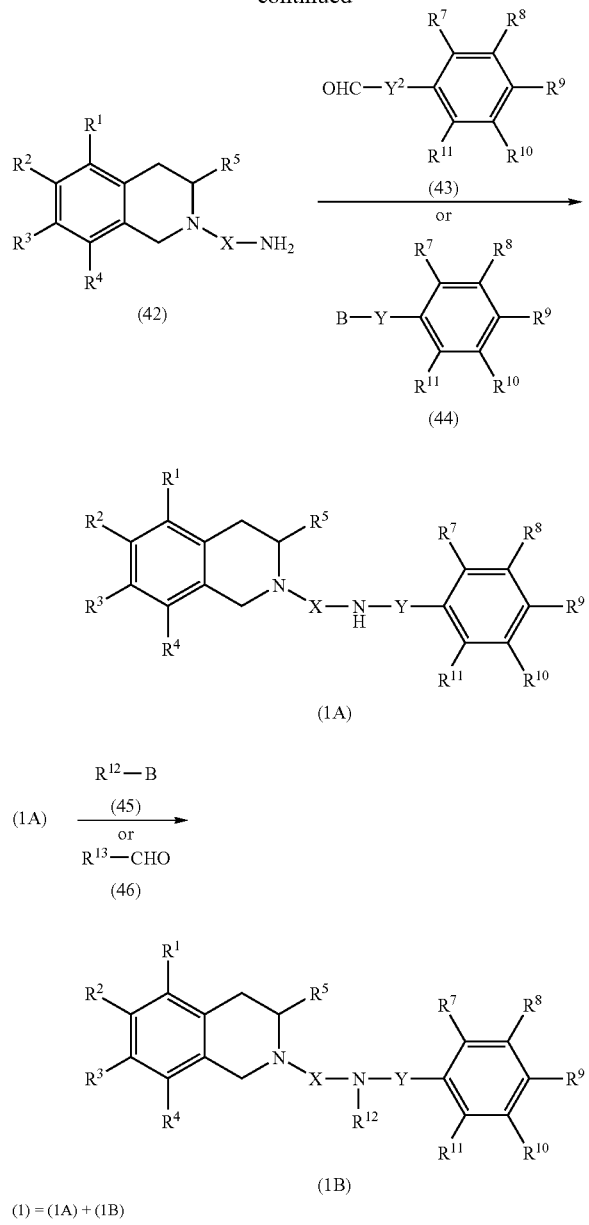

(wherein $R^1$ to $R^{11}$, and $P^1$ represent the same as defined above. $R^{12}$ represents the same groups as $R^6$ excepting a hydrogen atom, $R^{13}$ represents a shorter chain by one carbon than the $R^{12}$, and $R^{13}$—$CH_2$— represents $R^{12}$. Also, $X^2$ represents a shorter chain by one carbon than the X, and $Y^2$ represents a shorter chain by one carbon than the Y. That is, $X^2$—$CH_2$— represents X and $Y^2$—$CH_2$— represents Y. B represents a leaving group such as halogen, a methanesulfonyloxy group, and the like.)

A desired product (41) is obtained by reacting the 1,2,3,4-tetrahydroisoquinoline derivative represented by the general formula (2) with an equivalent amount or excessive amount of aldehyde product (39) in the presence or absence of an acid and in the presence or absence of a desiccant such as MS (Molecular Sieve) and the like in a solvent. At this time, as the reaction reagent, sodium borohydride, sodium triacetoxyborohydride, sodium cyanoborohydride, or the like may be used. As the solvent, for example, tetrahydrofuran, toluene, dioxane, methanol, ethanol, ethyl acetate, acetonitrile, propionitrile, water, or the like may be used singly or in combination thereof. Examples of the acid include acetic acid and the like. The reaction condition is a temperature from −80 to 150° C., and preferably from 0 to 100° C., and a time from 1 minute to 5 days, and preferably from 15 minutes to 3 days.

1,2,3,4-tetrahydroisoquinoline derivative (41) is obtained by reacting the 1,2,3,4-tetrahydroisoquinoline derivative (2) with an equivalent amount or excessive amount of compound (40) in the presence or absence of a base in a solvent. As the solvent, for example, chloroform, dichloromethane, tetrahydrofuran, toluene, dioxane, methanol, ethanol, ethyl acetate, acetonitrile, propionitrile, water, or the like may be used singly or in combination thereof. Examples of the base include pyridine, triethylamine, diisopropylethylamine, potassium carbonate, sodium carbonate, potassium hydroxide, sodium hydroxide, lithium hydroxide, and the like. The reaction condition is a temperature from −80 to 180° C., and preferably from −30 to 130° C., and a time from 1 minute to 5 days, and preferably from 15 minutes to 3 days.

Examples of the protecting group, $P^1$, of the 1,2,3,4-tetrahydroisoquinoline derivative (41) obtained in the above-described reaction include methyl carbamate, ethyl carbamate, 9-fluorenylmethyl carbamate, 9-(2-sulfo) fluorenylmethyl carbamate, 9-(2,7-dibromo)fluorenylmethyl carbamate, 2,7-di-tert-butyl-[9-(10,10-dioxo-10,10,10,10-tetrahydrothioxanthyl)]methyl carbamate, 4-methoxyphenacyl carbamate, 2,2,2-trichloroethyl carbamate, 2-trimethylsilylethyl carbamate, 2-phenethylethyl carbamate, 1-(1-adamantyl)-1-methylethyl carbamate, 1,1-dimethyl-2-haloethyl carbamate, 1,1-dimethyl-2,2-dibromoethyl carbamate, 1-methyl-1-(4-biphenyl)ethyl carbamate, 1-(3,5-di-tert-butylphenyl)-1-methylethyl carbamate, 2-(N,N-dicyclohexylcarboxyamide)ethyl carbamate, tert-butyl carbamate, 1-adamantyl carbamate, vinyl carbamate, phthalimide, and the like. As for the removal of the protecting group, a 1,2,3,4-tetrahydroisoquinoline derivative (42) is obtained by performing deprotection with reference to a generally used method (Protective Groups in Organic Synthesis Third Edition, John Wiley & Sons, Inc.) for the protection/deprotection conditions for the protecting group.

A 1,2,3,4-tetrahydroisoquinoline derivative (1A) is obtained by reacting the 1,2,3,4-tetrahydroisoquinoline derivative (42) obtained in the above-described reaction with an equivalent amount or excessive amount of the aldehyde product (43) in the presence or absence of an acid and in the presence or absence of a desiccant such as MS (Molecular Sieves) and the like, in a solvent reaction. Examples of the reaction reagent include sodium borohydride, sodium triacetoxyborohydride, sodium cyanoborohydride, and the like. As the solvent, for example, tetrahydrofuran, toluene, dioxane, methanol, ethanol, ethyl acetate, acetonitrile, propionitrile, water, or the like may be used singly or in combination thereof. Examples of the acid include acetic acid and the like. The reaction condition is a temperature from −80 to 150° C., and preferably from 0 to 100° C., and a time from 1 minute to 5 days, and preferably from 15 minutes to 3 days.

Further, the 1,2,3,4-tetrahydroisoquinoline derivative (1A) is obtained by reacting the 1,2,3,4-tetrahydroisoquinoline derivative (42) with an equivalent amount or excessive amount of the compound (44) in the presence or absence of a base in a solvent. As the solvent, for example, chloroform, dichloromethane, tetrahydrofuran, toluene, dioxane, methanol, ethanol, ethyl acetate, acetonitrile, propionitrile, water, or the like may be used singly or in combination thereof. Examples of the base include pyridine, triethylamine, diisopropylethylamine, potassium carbonate, sodium carbonate, potassium hydroxide, sodium hydroxide, lithium hydroxide, and the like. The reaction condition is a temperature from −80 to 180° C., and preferably from −30 to 130° C., and a time from 1 minute to 5 days, and preferably from 15 minutes to 3 days.

A compound (1B) is obtained by reacting the 1,2,3,4-tetrahydroisoquinoline derivative (1A) obtained in the above-described reaction with an equivalent amount or excessive amount of the compound (45) in the presence or absence of a base or an acid in a solvent. That is, the compound of the general formula (1) in which $R^6$ is other than a hydrogen atom is obtained. As the solvent, for example, tetrahydrofuran, toluene, dioxane, diethyl ether, or the like may be used singly or in combination thereof. Examples of the base include pyridine, triethylamine, diisopropylethylamine, potassium carbonate, sodium carbonate, sodium hydroxide, potassium hydroxide, n-butyllithium, sec-butyllithium, tert-butyllithium, methyllithium, and the like. The reaction condition is a temperature from −180 to 180° C., and preferably from −80 to 80° C. and a time from 1 minute to 7 days, and preferably from 1 hour to 5 days.

1,2,3,4-tetrahydroisoquinoline derivative (1B) is obtained by reacting the 1,2,3,4-tetrahydroisoquinoline derivative (1A) obtained by the above-described reaction with an equivalent amount or excessive amount of aldehyde product (46) in the presence or absence of an acid and in the presence or absence of a desiccant such as MS (Molecular Sieve) and the like in a solvent. At this time, as the reaction reagent, sodium borohydride, sodium triacetoxyborohydride, sodium cyanoborohydride, or the like may be used. As the solvent, for example, tetrahydrofuran, toluene, dioxane, methanol, ethanol, ethyl acetate, acetonitrile, propionitrile, water, or the like may be used singly or in combination thereof. Examples of the acid include acetic acid and the like. The reaction condition is a temperature from −80 to 150° C., and preferably from 0 to 100° C., and a time from 1 minute to 5 days, and preferably from 15 minutes to 3 days.

Furthermore, the 1,2,3,4-tetrahydroisoquinoline derivative represented by the general formula (1A) can be prepared using the following method.

[Production Method 10]

[Chem. 15]

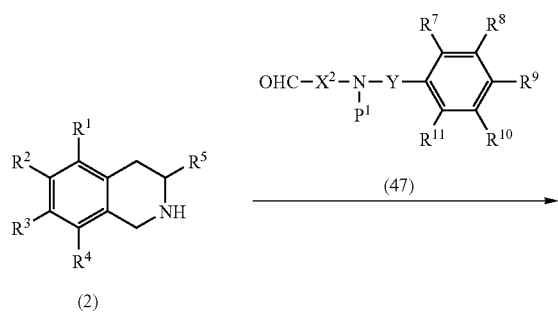

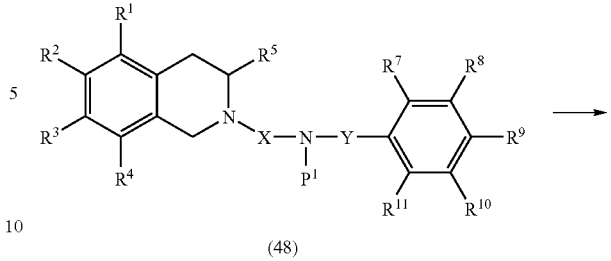

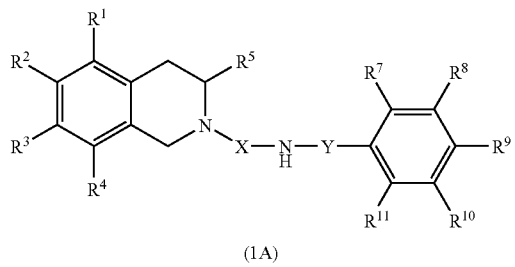

(wherein $R^1$ to $R^{11}$, $P^1$, X, $X^2$ and Y represent the same as defined above)

A desired product (48) is obtained by reacting the 1,2,3,4-tetrahydroisoquinoline derivative represented by the general formula (2) with an equivalent amount or excessive amount of aldehyde product (47) in the presence or absence of an acid in a solvent. At this time, as the reaction reagent, sodium borohydride, sodium triacetoxyborohydride, sodium cyanoborohydride, or the like may be used. As the solvent, for example, tetrahydrofuran, toluene, dioxane, methanol, ethanol, ethyl acetate, acetonitrile, propionitrile, water, or the like may be used singly or in combination thereof. Examples of the acid include acetic acid and the like. The reaction condition is a temperature from −80 to 150° C., and preferably from 0 to 100° C., and a time from 1 minute to 5 days, and preferably from 15 minutes to 3 days.

Examples of the protecting group, $P^1$, of the 1,2,3,4-tetrahydroisoquinoline derivative (48) obtained in the above-described reaction include methyl carbamate, ethyl carbamate, 9-fluorenylmethyl carbamate, 9-(2-sulfo)fluorenylmethyl carbamate, 9-(2,7-dibromo)fluorenylmethyl carbamate, 2,7-di-tert-butyl-[9-(10,10-dioxo-10,10,10,10-tetrahydrothioxanthyl)]methyl carbamate, 4-methoxyphenacyl carbamate, 2,2,2-trichloroethyl carbamate, 2-trimethylsilylethyl carbamate, 2-phenethylethyl carbamate, 1-(1-adamantyl)-1-methylethyl carbamate, 1,1-dimethyl-2-haloethyl carbamate, 1,1-dimethyl-2,2-dibromoethyl carbamate, 1-methyl-1-(4-biphenyl)ethyl carbamate, 1-(3,5-di-tert-butylphenyl)-1-methylethyl carbamate, 2-(N,N-dicyclohexylcarboxyamide)ethyl carbamate, tert-butyl carbamate, 1-adamantyl carbamate, vinyl carbamate, and the like. As for the removal of the protecting group, a 1,2,3,4-tetrahydroisoquinoline derivative (1A) is obtained by performing deprotection with reference to a generally used method (Protective Groups in Organic Synthesis Third Edition, John Wiley & Sons, Inc.) for the protection/deprotection conditions for the protecting group.

Furthermore, the 1,2,3,4-tetrahydroisoquinoline derivative represented by the general formula (1A) can be prepared using the following method.

[Production Method 11]

[Chem. 16]

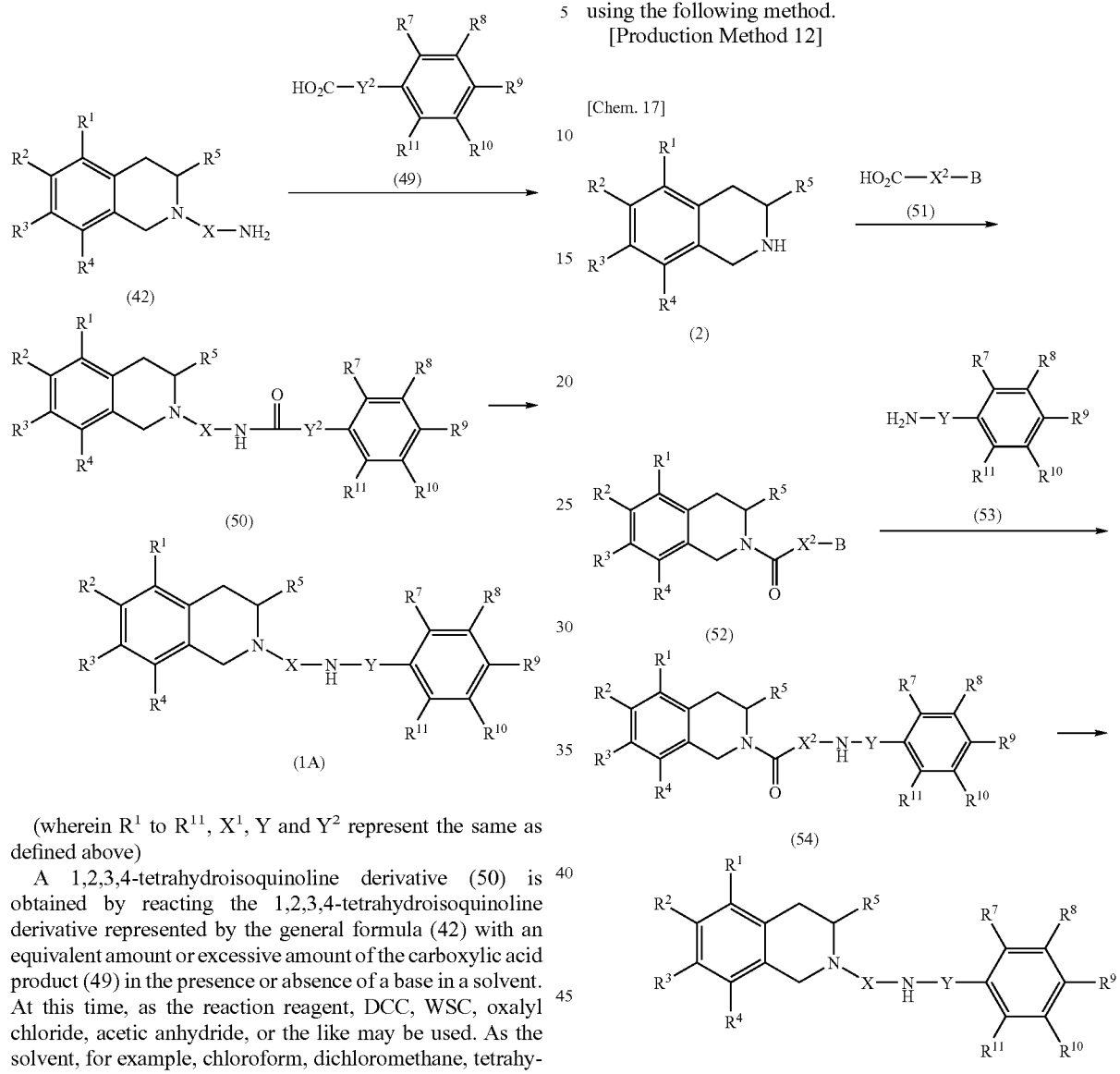

(wherein $R^1$ to $R^{11}$, $X^1$, Y and $Y^2$ represent the same as defined above)

A 1,2,3,4-tetrahydroisoquinoline derivative (50) is obtained by reacting the 1,2,3,4-tetrahydroisoquinoline derivative represented by the general formula (42) with an equivalent amount or excessive amount of the carboxylic acid product (49) in the presence or absence of a base in a solvent. At this time, as the reaction reagent, DCC, WSC, oxalyl chloride, acetic anhydride, or the like may be used. As the solvent, for example, chloroform, dichloromethane, tetrahydrofuran, toluene, dioxane, methanol, ethanol, ethyl acetate, acetonitrile, propionitrile, water, or the like may be used singly or in combination thereof. Examples of the base include pyridine, triethylamine, diisopropylethylamine, potassium carbonate, sodium carbonate, potassium hydroxide, sodium hydroxide, lithium hydroxide, and the like. The reaction condition is a temperature from −80 to 180° C., and preferably from −30 to 130° C., and a time from 1 minute to 5 days, and preferably from 15 minutes to 3 days.

The 1,2,3,4-tetrahydroisoquinoline derivative (1A) is obtained by reducing the 1,2,3,4-tetrahydroisoquinoline derivative (50) obtained in the above-described reaction with an equivalent amount or excessive amount of a reducing agent such as sodium borohydride, lithium borohydride, zinc borohydride, lithium aluminum hydride, lithium aluminum hydride, borane, and the like. As the solvent, for example, tetrahydrofuran, toluene, dioxane, diethyl ether, or the like may be used singly or in combination thereof. The reaction condition is a temperature from −80 to 180° C., and preferably from −30 to 130° C., and a time from 1 minute to 5 days, and preferably from 1 hour to 3 days.

Furthermore, the 1,2,3,4-tetrahydroisoquinoline derivative represented by the general formula (1A) can be prepared using the following method.

[Production Method 12]

[Chem. 17]

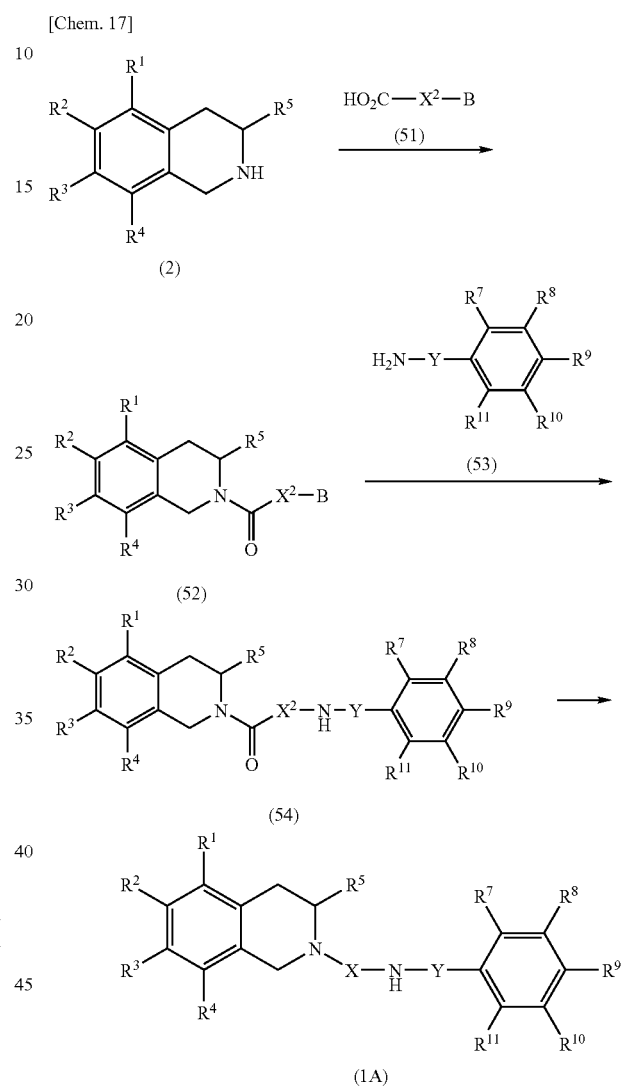

(wherein $R^1$ to $R^{11}$, B, X, $X^2$ and Y represent the same as defined above)

A 1,2,3,4-tetrahydroisoquinoline derivative (52) is obtained by reacting the 1,2,3,4-tetrahydroisoquinoline derivative represented by the general formula (2) with an equivalent amount or excessive amount of the carboxylic acid product (51) in the presence or absence of a base in a solvent. At this time, as the reaction reagent, DCC, WSC, oxalyl chloride, acetic anhydride, or the like may be used. As the solvent, for example, chloroform, dichloromethane, tetrahydrofuran, toluene, dioxane, methanol, ethanol, ethyl acetate, acetonitrile, propionitrile, water, or the like may be used singly or in combination thereof. Examples of the base include pyridine, triethylamine, diisopropylethylamine, potassium carbonate, sodium carbonate, potassium hydroxide, sodium hydroxide, lithium hydroxide, and the like. The reaction condition is a temperature from −80 to 180° C., and preferably from −30 to 130° C., and a time from 1 minute to 5 days, and preferably from 15 minutes to 3 days.

1,2,3,4-tetrahydroisoquinoline derivative (54) is obtained by reacting the 1,2,3,4-tetrahydroisoquinoline derivative represented by the general formula (52) with an equivalent amount or excessive amount of amine product (53) in the presence or absence of a base in a solvent. As the solvent, for example, chloroform, dichloromethane, tetrahydrofuran, toluene, dioxane, methanol, ethanol, ethyl acetate, acetonitrile, propionitrile, water, or the like may be used singly or in combination thereof. Examples of the base include pyridine, triethylamine, diisopropylethylamine, potassium carbonate, sodium carbonate, potassium hydroxide, sodium hydroxide, lithium hydroxide, and the like. The reaction condition is a temperature from −80 to 180° C., and preferably from −30 to 130° C., and a time from 1 minute to 5 days, and preferably from 15 minutes to 3 days.

The 1,2,3,4-tetrahydroisoquinoline derivative (1A) is obtained by reducing a 1,2,3,4-tetrahydroisoquinoline derivative represented by the general formula (54) with reference to a method for synthesizing the 1,2,3,4-tetrahydroisoquinoline derivative (1A) of Production Method 10 or to a generally used method (Comprehensive Organic Transformations Second Edition, John Wiley & Sons, Inc.).

2. Method for preparing a 1,2,3,4-tetrahydroisoquinoline derivative with n=1.

[Production Method 13]

(wherein $R^1$ to $R^{13}$, X, and Y represent the same meaning as defined above, and Q represents a urea coupling reagent such as isocyanate, phenyl carbamate, and the like)

A 1,2,3,4-tetrahydroisoquinoline derivative (1C) is obtained by reacting the 1,2,3,4-tetrahydroisoquinoline derivative (42) obtained in Production Method 11 with an equivalent amount or excessive amount of the compound (55) in the presence or absence of a base in a solvent.

As the solvent, for example, chloroform, dichloromethane, tetrahydrofuran, toluene, dioxane, ethyl acetate, acetonitrile, or the like may be used singly or in combination thereof.

Examples of the base include pyridine, triethylamine, diisopropylethylamine, potassium carbonate, sodium carbonate, potassium hydroxide, sodium hydroxide, lithium hydroxide, and the like.

The reaction condition is a temperature from −80 to 150° C., and preferably from 0 to 150° C., and a time from 1 minute to 5 days, and preferably from 15 minutes to 3 days.

Further, the 1,2,3,4-tetrahydroisoquinoline derivative (1C) is obtained by reacting the 1,2,3,4-tetrahydroisoquinoline derivative (42) with an equivalent amount or excessive amount of the amine product (56) using a reaction reagent in the presence or absence of a base in a solvent.

As the solvent, for example, chloroform, dichloromethane, tetrahydrofuran, toluene, dioxane, ethyl acetate, acetonitrile, or the like may be used singly or in combination thereof.

[Chem. 18]

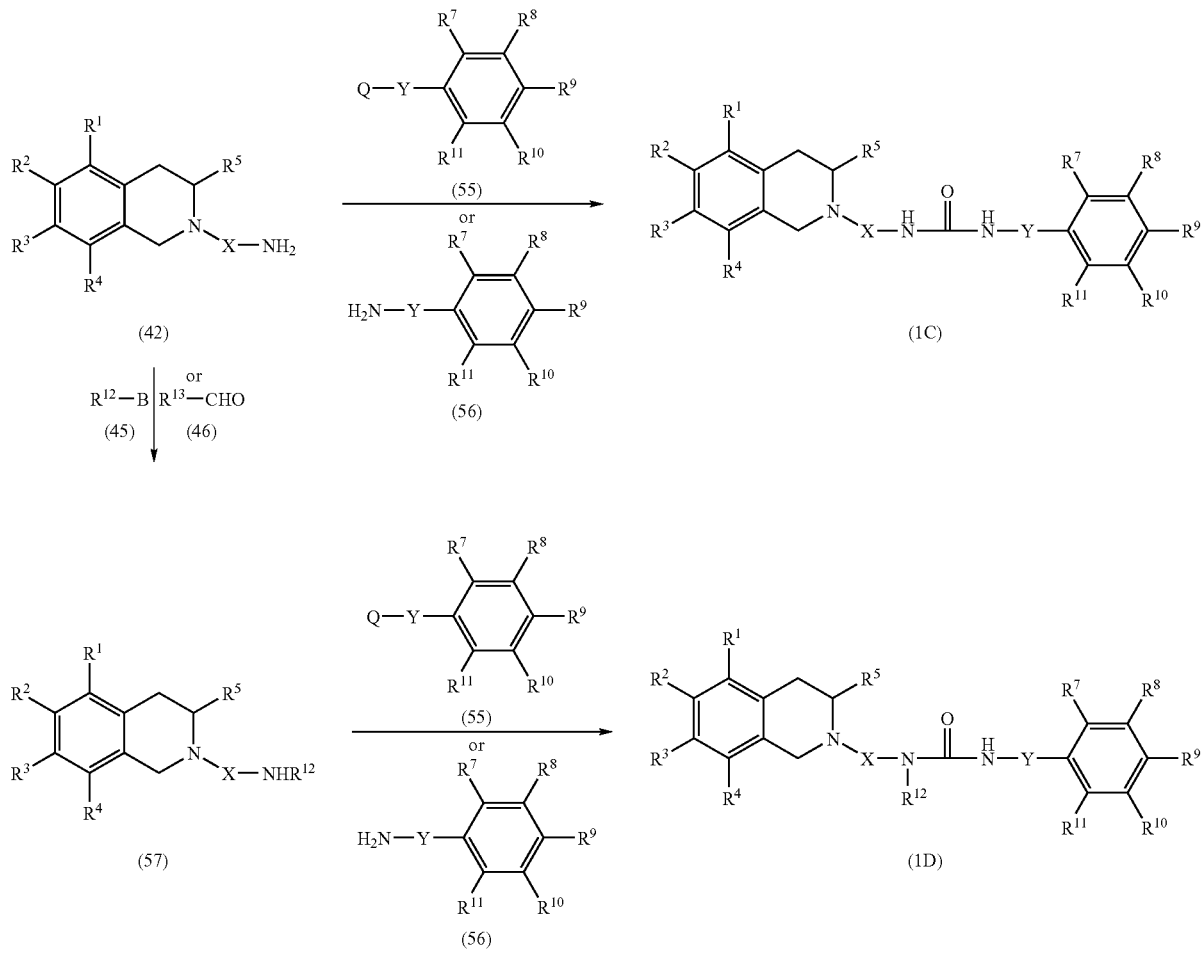

Examples of the base include pyridine, triethylamine, diisopropylethylamine, potassium carbonate, sodium carbonate, potassium hydroxide, sodium hydroxide, lithium hydroxide, and the like.

Examples of the reaction reagent include CDI, triphosgene, and the like.

The reaction condition is a temperature from −80 to 180° C., and preferably from 0 to 150° C., and a time from 1 minute to 5 days, and preferably from 15 minutes to 3 days.

Furthermore, a 1,2,3,4-tetrahydroisoquinoline derivative (1D) is obtained via the compound (57) prepared by the same method as for the alkylation reaction described in Production Method 9.

Further, a desired product is obtained by suitably modifying the substituent of $R^1$ to $R^{13}$, or the like in the general formula as above, as occasion demands, by oxidation, reduction, alkylation, amidation, esterification, hydrolysis, reductive amination, and the like, with reference to a generally used method (Comprehensive Organic Transformations Second Edition, John Wiley & Sons, Inc.).

The compound of the present invention thus prepared can be isolated/purified as its free compound, or a salt thereof by carrying out a salt formation treatment using a conventional method. The isolation/purification can be carried out by a conventional method such as extraction, concentration, removal by evaporation, crystallization, filtration, recrystallization, various types of chromatography, and the like.

Further, the present invention also includes various hydrates, solvates, and crystalline polymorphic substances of the compound of the present invention or a pharmaceutically acceptable acid addition salt thereof.

The pharmaceutically acceptable salt of the 1,2,3,4-tetrahydroisoquinoline compound represented by the formula (1) is also included in the present invention. Examples of the pharmaceutically acceptable salt of the tetrahydroisoquinoline compound represented by the formula (1) specifically include acid addition salts with inorganic acids (for example, hydrochloric acid, hydrobromic acid, hydroiodic acid, sulfuric acid, nitric acid, phosphoric acid, and the like), or organic acids (for example, formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid, and the like), and the like, addition salts with inorganic bases (for example, sodium, potassium, calcium, magnesium, and the like) and organic bases (for example, methylamine, ethylamine, ethanolamine, lysine, ornithine and the like), ammonium salt, and the like.

The solvates of the tetrahydroisoquinoline compound represented by the formula (1) or a pharmaceutically acceptable salt include various hydrates or solvates (for example, solvates with alcohols such as ethanol, and the like).

Various isomers can be isolated by making use of the difference in the physicochemical properties between isomers by a conventional method. For example, an optically pure isomer can be derived from the racemic mixture by means of common racemic resolution methods, such as a method for inducing a diastereomer salt with a common optically active acid such as tartaric acid, and the like for optical resolution, and the like. Also, a diastereomer mixture can be separated, for example, by fractional crystallization, various types of chromatography, or the like. In addition, an optically active compound can be prepared by using a suitable optically active starting material.

Furthermore, the tetrahydroisoquinoline compound represented by the general formula (1) has an asymmetric carbon at a 3-position on the tetrahydroisoquinoline skeleton. The present invention includes isomers having a steric coordination depending on the asymmetric carbon, for example, a racemic product, or any one of the optically active products.

The pharmaceutical composition of the present invention is a composition containing the tetrahydroisoquinoline compound represented by the general formula (1), a pharmaceutically acceptable salt thereof, or a solvate thereof as an active ingredient, and the compound of the present invention may be used singly, or usually in combination with a pharmaceutically acceptable carrier and/or diluent.

The administration route of the pharmaceutical composition is not particularly limited, and can be suitably selected according to the purpose of treatment. For example, the composition may be any one of oral preparations, injections, suppositories, ointments, inhalations, eye drops, nose drops, patches, and the like. The pharmaceutical composition suitable for these administration forms can be prepared by using a known method for a preparation.

In the case of the preparation of the oral solid, a tablet, a coated tablet, a granule, a powder, a capsule, or the like, can be prepared by adding a pharmaceutically acceptable excipient, and further, if necessary, a binder, a disintegrant, a lubricant, a colorant, a flavor enhancer, an aroma enhancer, or the like can be added to the compound represented by the general formula (1), and then using a conventional method. Any additive which is generally in use in the art may be used. Examples of the excipient include lactose, sucrose, sodium chloride, dextrose, starch, calcium carbonate, kaolin, microcrystalline cellulose, silicic acid, and the like. Examples of the binding agent include water, ethanol, propanol, a simple syrup, a glucose liquid, a starch liquid, a gelatin liquid, carboxymethyl cellulose, hydroxypropyl cellulose, hydroxypropylstarch, methyl cellulose, ethyl cellulose, shellac, calcium phosphate, polyvinylpyrrolidone, and the like. Examples of the disintegrant include dried starch, sodium alginate, powdered agar, sodium hydrogen carbonate, calcium carbonate, sodium lauryl sulfate, monoglyceride stearate, lactose, and the like. Examples of the lubricant include refined talc, stearate, borax, polyethylene glycol, and the like. Examples of the flavor enhancer include sucrose, orange peel, citric acid, tartaric acid, and the like.

In the case of the preparation of the oral liquid, an oral liquid, a syrup, an elixir, or the like, can be prepared by adding a flavor enhancer, a buffer, a stabilizer, an aroma enhancer, or the like to the compound represented by the general formula (1), and then using a conventional method. Examples of the flavor enhancer include those as mentioned above, examples of the buffer include sodium citrate, and the like, and examples of the stabilizing agent include tragacanth, gum arabic, gelatin, and the like.

In the case of the preparation of the injections, subcutaneous, intramuscular and intravenous injections can be prepared by adding a pH adjusting agent, a buffer, a stabilizer, a tonicity agent, a local anesthetic, and the like, to the compound represented by the general formula (1), and then using a conventional method. Examples of the pH adjusting agent and the buffer include sodium citrate, sodium acetate, sodium phosphate, and the like. Examples of the stabilizer include sodium pyrosulfite, EDTA, thioglycolic acid, thiolactic acid, and the like. Examples of the local anesthetic include procaine hydrochloride, lidocaine hydrochloride, and the like. Examples of the tonicity agent include sodium chloride, glucose, and the like.

In the case of the preparation of the suppositories, the suppositories can be prepared by adding a known carrier for a suppository, for example, polyethylene glycol, lanolin, cacao butter, fatty acid triglyceride, and the like, and further, if necessary a surfactant (for example, Tween (registered trademark)), or the like to the compound represented by the general formula (1), and then using a conventional method.

In the case of the preparation of the ointments, the ointments are mixed and prepared by blending a generally used base, a stabilizer, a wetting agent, a preservative, and the like, if necessary, into the compound represented by the general formula (1), and then using a conventional method. Examples of the base include liquid paraffin, white petrolatum, white beeswax, octyl dodecylalcohol, paraffin, and the like. Examples of the preservative agent include methyl p-hydroxybenzoate, ethyl p-hydroxybenzoate, propyl p-hydroxybenzoate, and the like.

In addition to these, an inhalation, an eye drop, and a nose drop can be prepared using a conventional method.

The dose of the compound represented by the general formula (1) varies depending on the age, weight, and symptom, the administration form, and the administration frequency, but it is usually preferable to administer 1 mg to 1000 mg per day of the compound represented by the general formula (1) in one portion or dividing it several portions in an oral or parenteral administration mode to an adult.

EXAMPLES

Hereinbelow, the present invention is described in detail with reference to Examples, but the present invention is not limited to these Examples. Furthermore, Production Examples for representative starting materials are shown as Reference Examples.

Example 1

Production of N-benzyl-2-[3-benzyl-3,4-dihydroisoquinolin-2(1H)-yl]ethanamine a) Production of
N-methoxy-N-methylisoquinoline-3-carboxyamide

[Chem. 19]

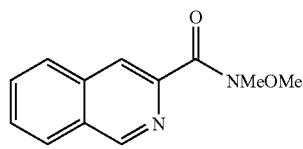

200 mg of 3-isoquinolinecarboxylic acid, 169 mg of N,O-dimethylhydroxylamine monohydrochloride, 332 mg of WSC, and 582 mg of triethylamine were dissolved in 2 mL of dichloromethane, followed by stirring at room temperature for 3 hours. Water was added to the reaction liquid, followed by extraction with chloroform. The organic layer was then washed with saturated brine, dried over anhydrous sodium sulfate, and then concentrated under reduced pressure. The residue obtained was purified using silica gel chromatography (chloroform alone) to obtain 169 mg (yield 67%) of a title compound as a pale yellow solidified product.

$^1$H-NMR (CDCl$_3$) δ: 3.47 (3H, s), 3.80 (3H, s), 7.69 (1H, ddd, J=1.2, 8.0, 8.0 Hz), 7.76 (1H, ddd, J=1.2, 8.0, 8.0 Hz), 7.92 (1H, d, J=8.0 Hz), 8.02 (1H, d, J=8.0 Hz), 8.14 (1H, s), 9.25 (1H, s).

b) Production of 3-benzoylisoquinoline

[Chem. 20]

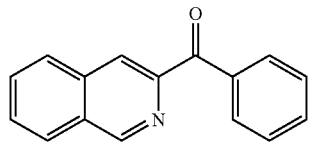

Under an argon gas stream, 168 mg of N-methoxy-N-methylisoquinoline-3-carboxyamide was dissolved in 1 mL of anhydrous THF, followed by stirring under cooling with ice. To the reaction liquid was slowly added 0.8 mL of phenyl magnesium bromide (1 mol/L THF solution), followed by continuously stirring for 30 minutes. Water was added to the reaction liquid, followed by extraction with chloroform. The organic layer was washed with diluted hydrochloric acid and saturated brine, dried over anhydrous sodium sulfate, and then concentrated under reduced pressure. The residue obtained was purified by silica gel chromatography (chloroform alone) to obtain 154 mg (yield 77%) of a title compound as a yellow oily substance.

$^1$H-NMR (CDCl$_3$) δ: 7.51 (2H, dd, J=7.5, 7.5 Hz), 7.61 (1H, dd, J=1.2, 7.5 Hz), 7.76 (1H, ddd, J=1.2, 7.8, 7.8 Hz), 7.80 (1H, ddd, J=1.2, 7.8, 7.8 Hz), 8.01 (1H, d, J=7.8 Hz), 8.05-8.12 (3H, m), 8.47 (1H, s), 9.34 (1H, s).

c) Production of 3-benzylisoquinoline

[Chem. 21]

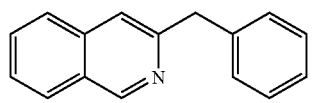

303 mg of 3-benzoyl isoquinoline and 9.75 g of hydrazine hydrate were dissolved in 10 mL of ethylene glycol at room temperature, followed by stirring at 150° C. After 10 minutes, to the reaction liquid was added 3.65 g of pulverized potassium hydroxide, followed by warming to 180° C. and continuously reacting for additional 2 hours. After completion of the reaction, the reaction liquid was left to be cooled, and water was added thereto, followed by extraction with diethyl ether. The organic layer was washed with saturated brine, dried over anhydrous sodium sulfate, and then concentrated under reduced pressure. The residue obtained was purified using silica gel chromatography (diethyl ether:n-hexane=1:1) to obtain 280 mg (yield 95%) of a title compound as a light yellow solid.

¹H-NMR (CDCl₃) δ: 4.32 (2H, s), 7.20-7.27 (5H, m), 7.43 (1H, s), 7.54 (1H, m), 7.61-7.67 (1H, m), 7.72 (1H, d, J=8.3 Hz), 7.94 (1H, d, J=8.1 Hz), 9.22 (1H, s).

d) Production of 3-benzyl-1,2,3,4-tetrahydroisoquinoline

[Chem. 22]

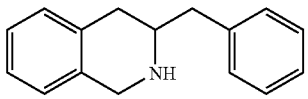

2.21 g of 3-benzylisoquinoline and 2.88 g of nickel dichloride.hexahydrate were dissolved in 50 mL of methanol at room temperature, and 4.58 g of sodium borohydride was added thereto over 30 minutes, followed by further stirring at room temperature for 4 hours. After completion of the reaction, water was added to the reaction liquid, followed by extraction with chloroform. The organic layer was washed with saturated brine, dried over anhydrous sodium sulfate, and then concentrated under reduced pressure. The residue obtained was purified using silica gel chromatography (chloroform:methanol=100:1→50:1) to obtain 1.85 g (yield 82%) of a title compound as a light yellow oily substance.

¹H-NMR (CDCl₃) δ: 2.66 (1H, dd, J=10.5, 16.1 Hz), 2.74-2.92 (3H, m), 3.13-3.23 (1H, m), 4.03 (2H, s), 6.98-7.15 (4H, m), 7.25-7.36 (5H, m).

e) Production of tert-butyl 2-[3-benzyl-3,4-dihydroisoquinolin-2(1H)-yl]ethyl carbamate

[Chem. 23]

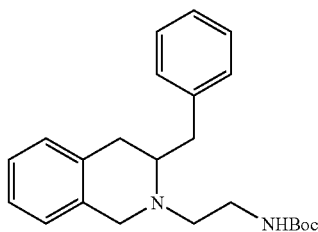

116 mg of 3-benzyl-1,2,3,4-tetrahydroisoquinoline was dissolved in 2 mL of toluene, and MS-4A (100 mg), 91 mg of N-Boc-2-aminoacetaldehyde, 95.9 mg of sodium triacetoxyborohydride, and 0.01 mL of acetic acid were added thereto at room temperature, followed by stirring overnight. After completion of the reaction, a saturated aqueous sodium hydrogen carbonate solution was added to the reaction liquid, followed by extraction with chloroform. The organic layer was washed with saturated brine, dried over anhydrous sodium sulfate, and then concentrated under reduced pressure. The residue obtained was purified using silica gel chromatography (chloroform:methanol=20:1) to obtain 145 mg of a title compound as a pale yellow oily substance.

¹H-NMR (CDCl₃) δ: 1.44 (9H, s), 2.51 (1H, dd, J=9.8, 13.2 Hz), 2.58 (1H, dd, J=2.4, 16.6 Hz), 2.68-2.95 (4H, m), 3.18-3.37 (3H, m), 3.84 (2H, s), 5.00 (1H, brs), 7.02-7.32 (9H, m).

f) Production of 2-[3-benzyl-3,4-dihydroisoquinolin-2(1H)-yl]ethanamine

[Chem. 24]

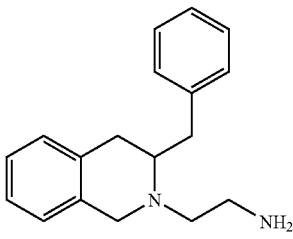

To a solution of 145 mg of tert-butyl 2-[3-benzyl-3,4-dihydroisoquinolin-2(1H)-yl]ethyl carbamate in 2 mL of ethyl acetate was added 2 mL of a 4N hydrochloric acid/ethyl acetate solution at room temperature, followed by stirring at room temperature overnight. After completion of the reaction, to the reaction liquid was added a saturated aqueous sodium hydrogen carbonate solution, followed by extraction with chloroform. The organic layer was washed with saturated brine, dried over anhydrous sodium sulfate, and then concentrated under reduced pressure. The residue obtained was purified using PLC (chloroform:methanol=20:1) to obtain 73.9 mg (yield of two steps 54%) of a title compound as a pale yellow oily substance.

¹H-NMR (CDCl₃) δ: 2.34 (2H, brs), 2.53 (1H, dd, J=9.9, 13.3 Hz), 2.59 (1H, dd, J=4.4, 16.9 Hz), 2.68-2.90 (5H, m), 2.93 (1H, dd, J=5.0, 13.3 Hz), 3.23-3.31 (1H, m), 3.85 (2H, s), 7.04-7.09 (2H, m), 7.12-7.18 (3H, m), 7.20 (1H, dd, J=7.3, 7.3 Hz), 7.25-7.36 (3H, m).

g) Production of N-benzyl-2-[3-benzyl-3,4-dihydroisoquinolin-2(1H)-yl]ethanamine

[Chem. 25]

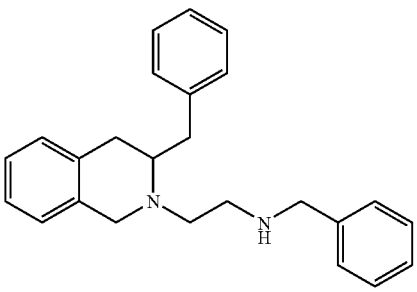

26 mg of 2-[3-benzyl-3,4-dihydroisoquinolin-2(1H)-yl]ethanamine was dissolved in 1 mL of toluene, and MS-4A (30 mg), 10.4 mg of benzaldehyde, 18 mg of sodium triacetoxyborohydride, and 0.01 mL of acetic acid were added thereto at room temperature, followed by stirring overnight. After completion of the reaction, to the reaction liquid was added a saturated aqueous sodium hydrogen carbonate solution, followed by extraction with chloroform. The organic layer was washed with saturated brine, dried over anhydrous sodium sulfate, and then concentrated under reduced pressure. The residue obtained was purified using PLC (chloroform:methanol=20:1) to obtain 24.4 mg (yield 70%) of a title compound as a pale yellow oily substance.

¹H-NMR (CDCl₃) δ: 2.49 (1H, dd, J=9.8, 13.2 Hz), 2.56 (1H, dd, J=3.8, 16.5 Hz), 2.45-2.66 (1H, br), 2.75-2.96 (6H, m), 3.20-3.28 (1H, m), 3.78 (2H, s), 3.81 (2H, s), 7.01-7.08 (2H, m), 7.09-7.21 (5H, m), 7.22-7.34 (7H, m).

Example 2

Production of N-benzyl-N-methyl-2-[3-benzyl-3,4-dihydroisoquinolin-2(1H)-yl]ethanamine

[Chem. 26]

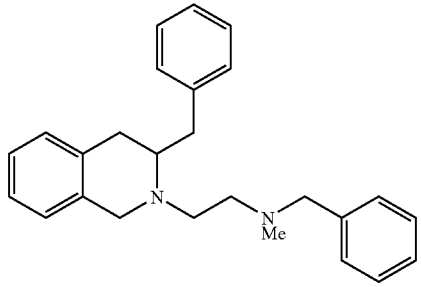

The reaction and treatment were carried out in the same manner as in Example 1-g) using N-benzyl-2-[3-benzyl-3,4-dihydroisoquinolin-2(1H)-yl]ethanamine obtained in Example 1 as a starting material and using paraformaldehyde to obtain a title compound as a pale yellow oily substance.

¹H-NMR (CDCl₃) δ: 2.29 (3H, s), 2.44 (1H, dd, J=10.5, 12.8 Hz), 2.57 (1H, dd, J=4.4, 16.6 Hz), 2.61-2.73 (2H, m), 2.75-2.87 (2H, m), 2.88-2.95 (1H, m), 2.97 (1H, dd, J=3.2, 12.8 Hz), 3.18-3.30 (1H, m), 3.57 (2H, s), 3.83 (1H, d, J=15.7 Hz), 3.90 (1H, d, J=15.7 Hz), 7.01-7.05 (2H, m), 7.06-7.10 (2H, m), 7.11-7.16 (2H, m), 7.16-7.22 (1H, m), 7.23-7.30 (3H, m), 7.31-7.36 (4H, m).

Example 3

Production of N-benzyl-3-[3-benzyl-3,4-dihydroisoquinolin-2(1H)-yl]propanamine a) Production of N-3-[[3-benzyl-3,4-dihydroisoquinolin-2(1H)-yl]propyl]phthalimide

[Chem. 27]

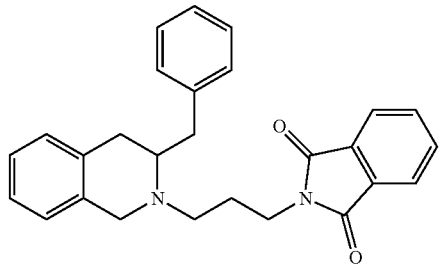

79.4 mg of 3-benzyl-1,2,3,4-tetrahydroisoquinoline obtained in Example 1-d) was dissolved in 1 mL of toluene, and 98.4 mg of potassium carbonate and 114 mg of N-(3-bromopropyl)phthalimide were added thereto at room temperature, followed by stirring at 100° C. for 4 days. After completion of the reaction, to the reaction liquid was added a saturated aqueous sodium hydrogen carbonate solution, followed by extraction with chloroform. The organic layer was washed with saturated brine, dried over anhydrous sodium sulfate, and then concentrated under reduced pressure. The residue obtained was purified using PLC (chloroform:methanol=20:1) to obtain 52.8 mg (yield 36%) of a title compound as a pale yellow solid.

¹H-NMR (CDCl₃) δ: 1.96 (2H, tt, J=6.9, 6.9 Hz), 2.40 (1H, dd, J=10.4, 12.8 Hz), 2.51 (1H, dd, J=3.4, 16.1 Hz), 2.68 2.83 (3H, m), 2.90 (1H, dd, J=2.9, 16.1 Hz), 3.18-3.27 (1H, m), 3.76 (1H, d, J=14.8 Hz), 3.80 (2H, t, J=6.8 Hz), 3.83 (1H, d, J=14.8 Hz), 6.96-7.05 (2H, m), 7.07-7.12 (4H, m), 7.17 (1H, dd, J=7.3, 7.3 Hz), 7.23-7.29 (2H, m), 7.65 (2H, dd, J=2.9, 5.4 Hz), 7.79 (2H, dd, J=2.9, 5.4 Hz).

b) Production of 3-[3-benzyl-3,4-dihydroisoquinolin-2(1H)-yl]propanamine

[Chem. 28]

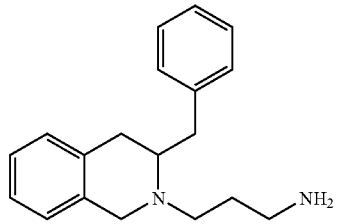

38.8 mg of N-3-[[3-benzyl-3,4-dihydroisoquinolin-2(1H)-yl]propyl]phthalimide was dissolved in 2 mL of methanol, and 100 μL of hydrazine monohydrate was added thereto at room temperature, followed by continuously reacting under reflux for 4 hours. After completion of the reaction, water was added to the reaction liquid, followed by extraction with chloroform. The organic layer was washed with saturated brine, dried over anhydrous sodium sulfate, and then concentrated under reduced pressure. The residue obtained was purified using PLC (chloroform:methanol=10:1) to obtain 23.5 mg (yield 71%) of a title compound as a pale yellow oily substance.

¹H-NMR (CDCl₃) δ: 1.74 (2H, tt, J=7.0, 7.0 Hz), 2.45 (1H, dd, J=10.2, 13.0 Hz), 2.59 (1H, dd, J=4.0, 16.5 Hz), 2.68-2.85 (5H, m), 2.97 (1H, dd, J=3.9, 13.0 Hz), 3.22-3.30 (1H, m), 3.82 (1H, d, J=15.9 Hz), 3.89 (1H, d, J=15.9 Hz), 7.03-7.08 (2H, m), 7.11-7.16 (4H, m), 7.20 (1H, dd, J=7.4, 7.4 Hz), 7.25-7.31 (2H, m).

c) Production of N-benzyl-3-[3-benzyl-3,4-dihydroisoquinolin-2(1H)-yl]propanamine

[Chem. 29]

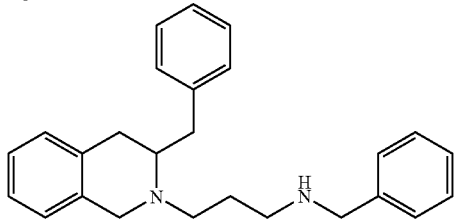

The reaction and treatment were carried out in the same manner as in Example 1-g) to obtain a title compound as a pale yellow oily substance.

$^1$H-NMR (CDCl$_3$) δ: 1.85 (2H, tt, J=7.0, 7.0 Hz), 2.46 (1H, dd, J=10.2, 13.0 Hz), 2.58 (1H, dd, J=4.0, 16.5 Hz), 2.66-2.88 (5H, m), 2.93 (1H, dd, J=3.9, 13.0 Hz), 3.22-3.33 (1H, m), 3.76 (2H, s), 3.86 (1H, s), 3.87 (1H, s), 7.00-7.34 (14H, m).

Example 4

Production of N-phenethyl 2-[3-benzyl-3,4-dihydroisoquinolin-2(1H)-yl]ethanamine

[Chem. 30]

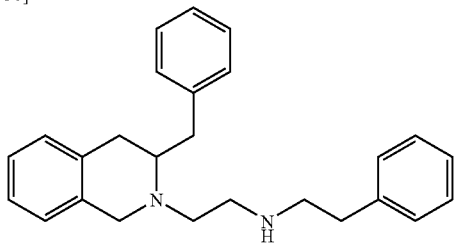

The reaction and treatment were carried out in the same manner as in Example 1-g) using phenyl acetaldehyde instead of benzaldehyde to obtain a title compound as a pale yellow oily substance.

$^1$H-NMR (CDCl$_3$) δ: 2.46 (1H, dd, J=10.5, 12.9 Hz), 2.58 (1H, dd, J=4.3, 16.5 Hz), 2.77-2.86 (8H, m), 2.95 (1H, d, J=3.2 Hz), 2.98 (1H, d, J=3.2 Hz), 3.21-3.26 (1H, m), 3.83 (1H, d, J=16.0 Hz), 3.91 (1H, d, J=16.0 Hz), 7.03-7.06 (2H, m), 7.11-7.29 (12H, m).

Example 5

Production of N-phenyl-2-[3-benzyl-3,4-dihydroisoquinolin-2(1H)-yl]ethanamine a) Production of 2-(2-anilinoacetyl)-3-benzyl-1,2,3,4-tetrahydroisoquinoline

[Chem. 31]

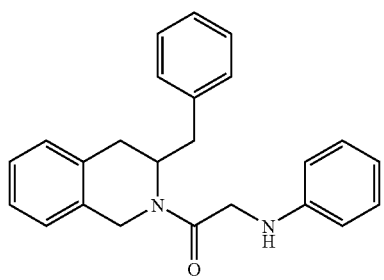

89 mg of 3-benzyl-1,2,3,4-tetrahydroisoquinoline obtained in Example 1-d) was dissolved in 2 mL of methylene chloride, and 53 mg of N,N-dimethylaniline, 73 mg of bromoacetylbromide were added thereto, followed by stirring under ice-cooling for 30 minutes. After completion of the reaction, water was added thereto, followed by extraction with chloroform. The chloroform layer was washed with brine and then dried over anhydrous sodium sulfate, and the solvent was removed by evaporation, followed by purification using PLC (hexane:ethyl acetate=1:1) to obtain 120 mg (yield 88%) of 2-(2-bromoacetyl)-3-benzyl-1,2,3,4-tetrahydroisoquinoline as a yellow oily substance. 34 mg of this product was dissolved in 10 mg of aniline, 15 mg of potassium carbonate, and 1 mL of acetonitrile, followed by stirring at 60° C. for 4 hours. After completion of the reaction, the reaction liquid was filtered with ethyl acetate, concentrated under reduced pressure, and purified using PTLC (chloroform:methanol=10:1) to obtain 28 mg (yield 72%) of a title compound as a yellow oily substance.

$^1$H-NMR (CDCl$_3$) δ: 2.54 (0.5H, dd, J=9.8, 13.2 Hz), 2.68-2.94 (3H, m), 3.09 (0.5H, dd, J=3.9, 15.9 Hz), 3.44 (0.5H, d, J=15.6 Hz), 3.85 (0.5H, d, J=15.6 Hz), 3.90 (0.5H, d, J=15.9), 3.97 (0.5H, d, J=15.9), 4.27-4.32 (0.5H, m), 4.46 (0.5H, d, J=18.0 Hz), 4.53 (0.5H, d, J=15.9 Hz), 4.64 (0.5H, d, J=15.9 Hz), 4.77 (0.5H, br), 4.94 (0.5H, br), 5.17-5.23 (0.5H, m), 5.27 (0.5H, d, J=18.0 Hz), 6.53 (1H, d, J=8.5 Hz), 6.65 (1H, d, J=8.5 Hz), 6.70 (0.5H, d, J=7.4 Hz), 6.73 (0.5H, d, J=7.4 Hz), 7.10-7.33 (11H, m).

b) Production of N-phenyl-2-[3-benzyl-3,4-dihydroisoquinolin-2(1H)-yl]ethanamine

[Chem. 32]

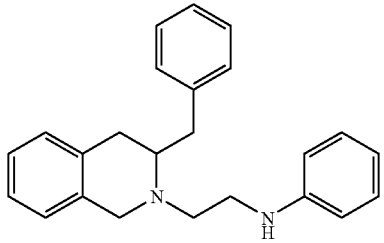

10 mg of 2-(2-anilinoacetyl)-3-benzyl-1,2,3,4-tetrahydroisoquinoline was dissolved in 1 mL of THF, and 1.1 mg of LAH was added thereto under an argon atmosphere, followed by stirring under ice-cooling 2 hours. After completion of the reaction, 2N hydrochloric acid was added thereto, and when foaming was stopped, a saturated aqueous sodium bicarbonate solution was added thereto, followed by extraction with ethyl acetate. The organic layer was washed with brine and then dried over anhydrous sodium sulfate, and the solvent was removed by evaporation, followed by purification using PLC (chloroform:methanol=10:1) to obtain 2.5 mg (yield 26%) of a title compound as a pale yellow oily substance.

$^1$H-NMR (CDCl$_3$) δ: 2.66 (1H, dd, J=10.6, 16.5 Hz), 2.79 (1H, dd, J=3.6, 16.2 Hz), 2.80-2.92 (2H, m), 3.14-3.19 (1H, m), 3.32 (2H, t, J=5.2 Hz), 3.84 (2H, t, J=5.2 Hz), 4.03 (2H, s), 6.67 (2H, d, J=7.3 Hz), 6.74 (1H, dd, J=7.3, 7.3 Hz), 7.00-7.07

Example 6

Production of N-benzyl-2-[3-(4-chlorobenzyl)-3,4-dihydroisoquinolin-2(1H)-yl]ethanamine a) Production of 3-(4-chlorobenzyl)-1,2,3,4-tetrahydroisoquinoline

[Chem. 33]

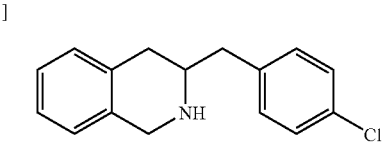

The reaction and treatment were carried out in the same manner as in Example 1-a, b, c, and d) using 4-chlorophenyl magnesium bromide instead of phenyl magnesium bromide to obtain a title compound as a pale yellow oily substance.

$^1$H-NMR (CDCl$_3$) δ: 2.51-2.61 (1H, m), 2.70-2.87 (3H, m), 3.07-3.13 (1H, m), 3.99 (2H, s), 6.98-7.03 (2H, m), 7.08-7.10 (2H, m), 7.15 (2H, d, J=7.8 Hz), 7.27 (2H, d, J=7.8 Hz).

b) Production of tert-butyl 2-[3-(4-chlorobenzyl)-3,4-dihydroisoquinolin-2(1H)-yl]ethylcarbamate

[Chem. 34]

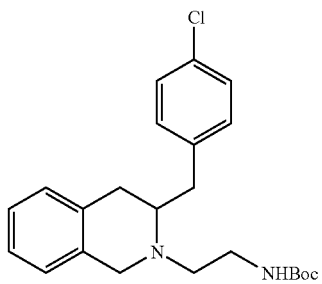

The reaction and treatment were carried out in the same manner as in Example 1-e) to obtain a title compound as a pale yellow oily substance.

$^1$H-NMR (CDCl$_3$) δ: 1.44 (9H, s), 2.47 (1H, dd, J=9.4, 13.3 Hz), 2.54 (1H, dd, J=4.0, 16.5 Hz), 2.68-2.73 (1H, m), 2.78-2.88 (3H, m), 3.20-3.34 (3H, m), 3.80 (1H, d, J=17.0 Hz), 3.84 (1H, d, J=17.0 Hz), 7.05-7.07 (4H, m), 7.15-7.18 (1H, m), 7.24-7.27 (2H, m).

c) Production of N-benzyl-2-[3-(4-chlorobenzyl)-3,4-dihydroisoquinolin-2(1H)-yl]ethanamine

[Chem. 35]

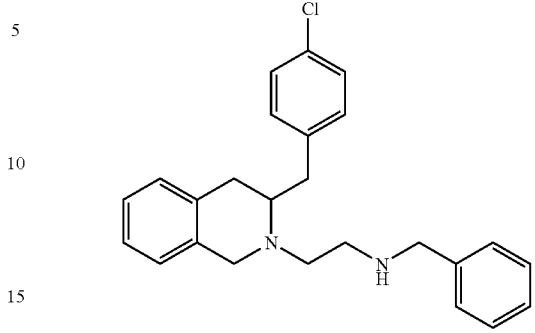

The reaction and treatment were carried out in the same manner as in Examples 1-f and g) to obtain a title compound as a pale yellow oily substance.

$^1$H-NMR (CDCl$_3$) δ: 2.45 (1H, dd, J=9.8, 13.2 Hz), 2.52 (1H, dd, J=3.6, 16.5 Hz), 2.75-2.79 (3H, m), 2.81-2.89 (3H, m), 3.16-3.22 (1H, m), 3.77 (2H, s), 3.79 (2H, s), 6.96-7.06 (3H, m), 7.10-7.19 (3H, m), 7.24-7.31 (5H, m), 7.35-7.37 (2H, m).

Example 7

Production of N-benzyl-2-[3-(3-chlorobenzyl)-3,4-dihydroisoquinolin-2(1H)-yl]ethanamine a) Production of 3-(3-chlorobenzyl)-1,2,3,4-tetrahydroisoquinoline

[Chem. 36]

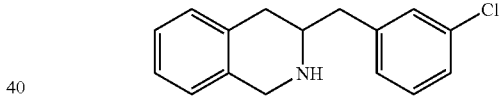

The reaction and treatment were carried out in the same manner as in Example 1-a, b, c, and d) using 3-chlorophenyl magnesium bromide instead of phenyl magnesium bromide to obtain a title compound as a pale yellow oily substance.

$^1$H-NMR (CDCl$_3$) δ: 2.53-2.65 (1H, m), 2.73-2.87 (3H, m), 3.11-3.19 (1H, m), 4.03 (2H, s), 6.99-7.02 (1H, m), 7.04-7.07 (1H, m), 7.10-7.15 (3H, m), 7.22-7.28 (3H, m).

b) Production of tert-butyl 2-[3-(3-chlorobenzyl)-3,4-dihydroisoquinolin-2(1H)-yl]ethylcarbamate

[Chem. 37]

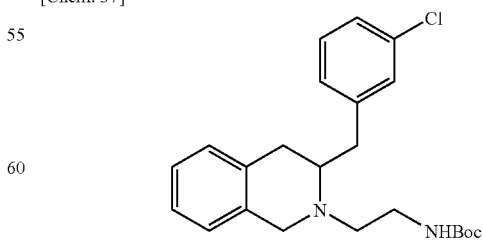

The reaction and treatment were carried out in the same manner as in Example 1-e) to obtain a title compound as a pale yellow oily substance.

¹H-NMR (CDCl₃) δ: 1.44 (9H, s), 2.48 (1H, dd, J=9.5, 13.2 Hz), 2.55 (1H, dd, J=3.8, 16.5 Hz), 2.68-2.73 (1H, m), 2.77-2.89 (3H, m), 3.19-3.34 (3H, m), 3.80 (1H, d, J=16.2 Hz), 3.85 (1H, d, J=16.2 Hz), 7.00 (1H, d, J=7.1 Hz), 7.04-7.08 (2H, m), 7.12-7.21 (5H, m).

c) Production of N-benzyl-2-[3-(3-chlorobenzyl)-3,4-dihydroisoquinolin-2(1H)-yl]ethanamine

[Chem. 38]

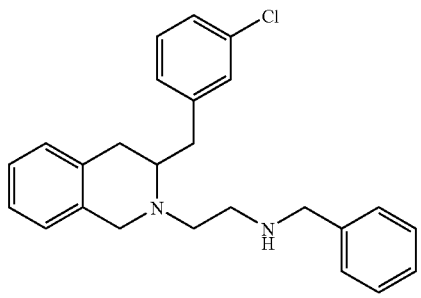

The reaction and treatment were carried out in the same manner as in Examples 1-f and g) to obtain a title compound as a pale yellow oily substance.

¹H-NMR (CDCl₃) δ: 2.46 (1H, dd, J=9.8, 13.4 Hz), 2.51 (1H, dd, J=3.6, 16.6 Hz), 2.74-2.78 (3H, m), 2.81-2.88 (3H, m), 3.16-3.22 (1H, m), 3.77 (2H, s), 3.80 (2H, s), 7.01-7.06 (2H, m), 7.11-7.19 (2H, m), 7.20 (1H, d, J=8.8 Hz), 7.22 (1H, d, J=8.8 Hz), 7.26-7.32 (5H, m), 7.36-7.38 (2H, m).

Example 8

Production of N-benzyl-2-[3-(2-chlorobenzyl)-3,4-dihydroisoquinolin-2(1H)-yl]ethanamine a) Production of 3-(2-chlorobenzoyl)isoquinoline

[Chem. 39]

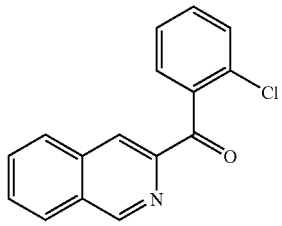

Under an argon atmosphere, to a solution of 120 mg of N-methoxy-N-methyl isoquinoline-3-carboxyamide obtained in Example 1-a), 159 mg of 2-bromochlorobenzene, and 0.14 mL of TMEDA in 3 mL of THF was added portionwise a BuLi (1.57 M) solution at −78° C. The reaction liquid was stirred at the same temperature for 10 minutes, and further stirred for 1 hour under ice-cooling. After completion of the reaction, to the reaction liquid were added ice water and ammonium chloride, followed by extraction with ethyl acetate. The organic layer was washed with brine and then dried over anhydrous sodium sulfate, and the solvent was removed by evaporation to obtain 171 mg of a crude composition. This was purified by PLC (hexane:ethyl acetate=1:1) to obtain 97 mg (yield 65%) of a title compound as a yellow oily substance.

¹H-NMR (CDCl₃) δ: 7.40-7.48 (3H, m), 7.55 (1H, m), 7.75-7.83 (2H, m), 8.01-8.07 (2H, m), 8.54 (1H, s), 9.29 (1H, m).

b) Production of 3-(2-chlorobenzyl)isoquinoline

[Chem. 40]

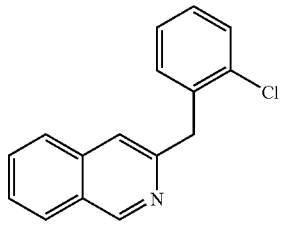

The reaction and treatment were carried out in the same manner as in Example 1-c) to obtain a title compound as a yellow oily substance.

¹H-NMR (CDCl₃) δ: 4.45 (2H, s), 7.18-7.42 (5H, m), 7.54 (1H, m), 7.64 (1H, m), 7.71 (1H, m), 7.94 (1H, m), 9.23 (1H, s).

c) Production of 3-(2-chlorobenzyl)-1,2,3,4-tetrahydroisoquinoline

[Chem. 41]

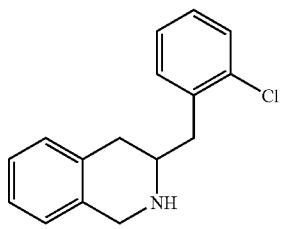

The reaction and treatment were carried out in the same manner as in Example 1-d) to obtain a title compound as a light yellow oily substance.

¹H-NMR (CDCl₃) δ: 2.64-2.81 (2H, m), 2.90-3.05 (2H, m), 3.28 (1H, m), 4.05 (2H, s), 7.00-7.40 (8H, m).

d) Production of N-benzyl-2-[3-(2-chlorobenzyl)-3,4-dihydroisoquinolin-2(1H)-yl]ethanamine

[Chem. 42]

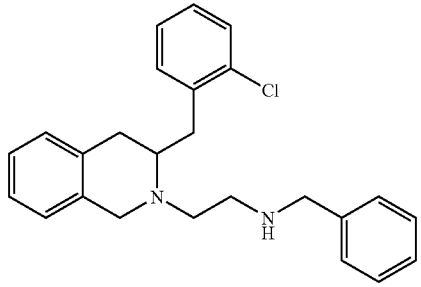

The reaction and treatment were carried out in the same manner as in Examples 1-e, f and g) to obtain a title compound as a yellow oily substance.

$^1$H-NMR (CDCl$_3$) δ: 2.50-2.61 (2H, m), 2.75-2.90 (4H, m), 2.96-3.11 (2H, m), 3.37 (1H, m), 3.79 (2H, s), 3.82 (2H, s), 7.02-7.34 (13H, m).

Example 9

Production of N-benzyl-2-[3-(3,4-dichlorobenzyl)-3,4-dihydroisoquinolin-2(1H)-yl]ethanamine a) Production of 3-(3,4-dichlorobenzoyl)isoquinoline

[Chem. 43]

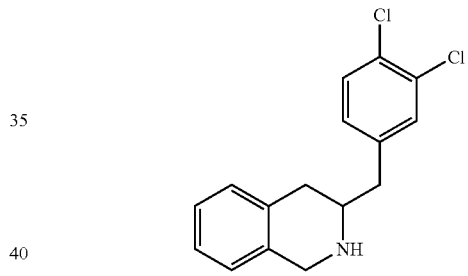

The reaction and treatment were carried out in the same manner as in Example 1-a, b) using 3,4-dichlorophenyl magnesium bromide instead of phenyl magnesium bromide to obtain a title compound as a white solid.

$^1$H-NMR (CDCl$_3$) δ: 7.59 (1H, d, J=12.7 Hz), 7.77-7.85 (2H, m), 7.97-8.13 (3H, m), 8.27 (1H, d, J=2.8 Hz), 8.55 (1H, s), 9.33 (1H, s).

b) Production of 3-(3,4-dichlorobenzyl)isoquinoline

[Chem. 44]

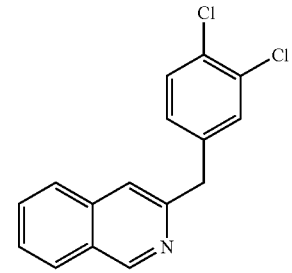

The reaction and treatment were carried out in the same manner as in Example 1-c) to obtain a title compound as a yellow solid.

$^1$H-NMR (CDCl$_3$) δ: 4.25 (2H, s), 7.16 (1H, dd, J=1.9, 8.3 Hz), 7.37 (1H, d, J=8.3 Hz), 7.40 (1H, d, J=1.9 Hz), 7.45 (1H, s), 7.57 (1H, ddd, J=1.2, 7.5, 7.5 Hz), 7.67 (1H, ddd, J=1.2, 7.5, 7.5 Hz), 7.75 (1H, brd, J=8.3 Hz), 7.95 (1H, brd, J=8.3 Hz), 9.21 (1H, s).

c) Production of 3-(3,4-dichlorobenzyl)-1,2,3,4-tetrahydroisoquinoline

[Chem. 45]

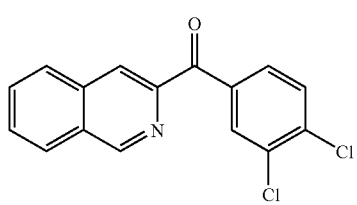

The reaction and treatment were carried out in the same manner as in Example 1-d) to obtain a title compound as a pale yellow oily substance.

$^1$H-NMR (CDCl$_3$) δ: 2.56-2.87 (4H, m), 3.09-3.19 (1H, m), 4.02 (2H, s), 7.00-7.12 (5H, m), 7.24-7.38 (2H, m).

d) Production of tert-butyl 2-[3-(3,4-dichlorobenzyl)-3,4-dihydroisoquinolin-2(1H)-yl]ethylcarbamate

[Chem. 46]

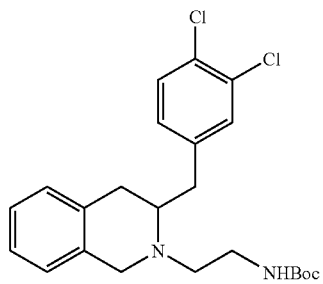

The reaction and treatment were carried out in the same manner as in Example 1-e) to obtain a title compound as a pale yellow oily substance.

$^1$H-NMR (CDCl$_3$) δ: 1.42 (9H, s), 2.46 (1H, dd, J=9.5, 13.3 Hz), 2.51 (1H, dd, J=4.1, 16.2 Hz), 2.68-2.87 (4H, m), 3.20-3.29 (3H, m), 3.77 (1H, d, J=16.1 Hz), 3.83 (1H, d, J=16.1 Hz), 7.03-7.05 (2H, m), 7.11-7.16 (2H, m), 7.21-7.27 (3H, m).

e) Production of N-benzyl-2-[3-(3,4-dichlorobenzyl)-3,4-dihydroisoquinolin-2(1H)-yl]ethanamine

[Chem. 47]

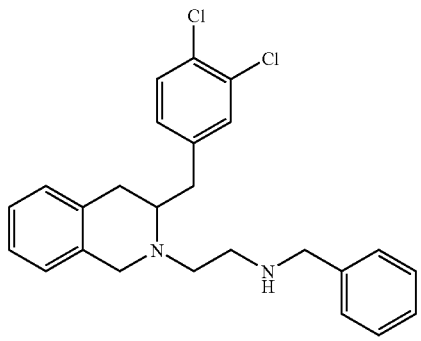

The reaction and treatment were carried out in the same manner as in Examples 1-f and g) to obtain a title compound as a pale yellow oily substance.

$^1$H-NMR (CDCl$_3$) δ: 2.44 (1H, dd, J=9.6, 13.4 Hz), 2.49 (1H, dd, J=3.9, 16.4 Hz), 2.72-2.80 (3H, m), 2.81-2.88 (3H, m), 3.16-3.24 (1H, m), 3.76 (2H, s), 3.81 (2H, s), 7.00-7.05 (3H, m), 7.14-7.17 (3H, m), 7.25-7.31 (6H, m).

Example 10

Production of N-benzyl-2-[3-(4-fluorobenzyl)-3,4-dihydroisoquinolin-2(1H)-yl]ethanamine a) Production of 3-(4-fluorobenzoyl)isoquinoline

[Chem. 48]

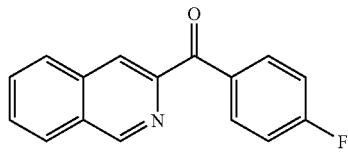

The reaction and treatment were carried out in the same manner as in Example 1-a, b) using 4-fluorophenyl magnesium bromide instead of phenyl magnesium bromide to obtain a title compound as a yellow oily substance.

$^1$H-NMR (CDCl$_3$) δ: 7.19 (2H, dd, J=8.7, 8.7 Hz), 7.76-7.84 (2H, m), 8.03 (1H, d, J=8.0 Hz), 8.10 (1H, d, J=8.0 Hz), 8.16-8.22 (2H, m), 8.51 (1H, s), 9.31 (1H, s).

b) Production of 3-(4-fluorobenzyl)-1,2,3,4-tetrahydroisoquinoline

[Chem. 49]

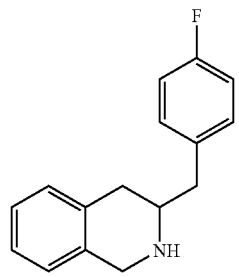

The reaction and treatment were carried out in the same manner as in Examples 1-c and d) to obtain a title compound as a yellow solid.

$^1$H-NMR (CDCl$_3$) δ: 2.60 (1H, dd, J=10.5, 16.1 Hz), 2.70-2.86 (3H, m), 3.05-3.15 (1H, m), 4.01 (2H, s), 6.96-7.06 (4H, m), 6.98-7.11 (2H, m), 7.18-7.22 (2H, m).

c) Production of tert-butyl 2-[3-(4-fluorobenzyl)-3,4-dihydroisoquinolin-2(1H)-yl]ethylcarbamate

[Chem. 50]

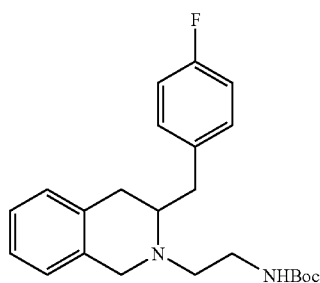

The reaction and treatment were carried out in the same manner as in Example 1-e) to obtain a title compound as a light yellow oily substance.

$^1$H-NMR (CDCl$_3$) δ: 1.44 (9H, s), 2.46-2.60 (2H, m), 2.69-2.76 (1H, m), 2.80-2.95 (3H, m), 3.20-3.38 (3H, m), 3.88 (2H, s), 5.10 (1H, brs), 6.98 (2H, dd, J=8.6, 8.6 Hz), 7.04-7.12 (4H, m), 7.14-7.19 (2H, m).

d) Production of N-benzyl-2-[3-(4-fluorobenzyl)-3,4-dihydroisoquinolin-2(1H)-yl]ethanamine

[Chem. 51]

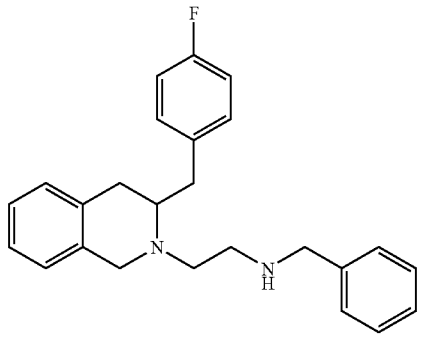

The reaction and treatment were carried out in the same manner as in Examples 1-f and g) to obtain a title compound as a pale yellow oily substance.

$^1$H-NMR (CD$_3$OD) δ: 2.46 (1H, dd, J=9.8, 13.4 Hz), 2.53 (1H, dd, J=4.0, 16.5 Hz), 2.75-2.95 (6H, m), 3.14-3.22 (1H, m), 3.80 (2H, d, J=4.6 Hz), 3.85 (2H, s), 6.96 (2H, dd, J=8.8, 8.8 Hz), 7.01-7.06 (2H, m), 7.07-7.16 (4H, m), 7.27-7.37 (5H, m).

Example 11

Production of N-benzyl-2-[3-(3-fluorobenzyl)-3,4-dihydroisoquinolin-2(1H)-yl]ethanamine a) Production of 3-(3-fluorobenzoyl)isoquinoline

[Chem. 52]

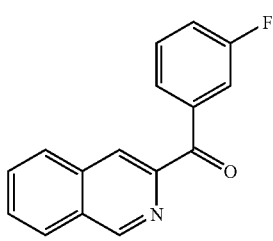

The reaction and treatment were carried out in the same manner as in Example 1-a, b) using 3-fluorophenyl magnesium bromide instead of phenyl magnesium bromide to obtain a title compound as a light yellow oily substance.

$^1$H-NMR (CDCl$_3$) δ: 7.31 (1H, m), 7.49 (1H, m), 7.75-7.92 (4H, m), 8.00-8.10 (2H, m), 8.51 (1H, s), 9.34 (1H, s).

b) Production of 3-(3-fluorobenzyl)isoquinoline

[Chem. 53]

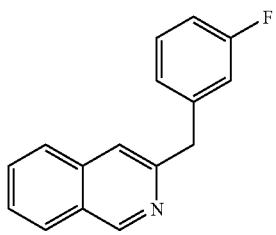

The reaction and treatment were carried out in the same manner as in Example 1-c) to obtain a title compound as a light yellow oily substance.

$^1$H-NMR (CDCl$_3$) δ: 4.30 (2H, s), 6.93 (1H, m), 7.01 (1H, m), 7.10 (1H, m), 7.28 (1H, m), 7.45 (1H, s), 7.56 (1H, m), 7.66 (1H, m), 7.74 (1H, d, J=8.5 Hz), 7.94 (1H, d, J=8.5 Hz), 9.22 (1H, s).

c) Production of 3-(3-fluorobenzyl)-1,2,3,4-tetrahydroisoquinoline

[Chem. 54]

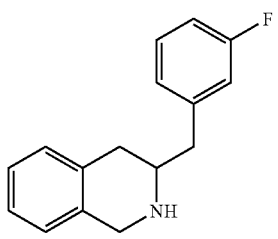

The reaction and treatment were carried out in the same manner as in Example 1-d) to obtain a title compound as a light yellow oily substance.

$^1$H-NMR (CDCl$_3$) δ: 2.58-2.90 (4H, m), 3.16 (1H, m), 4.03 (2H, s), 6.90-7.32 (8H, m).

d) Production of N-benzyl-2-[3-(3-fluorobenzyl)-3,4-dihydroisoquinolin-2(1H)-yl]ethanamine

[Chem. 55]

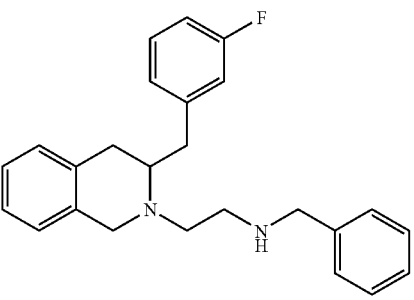

The reaction and treatment were carried out in the same manner as in Examples 1-e, f and g) to obtain a title compound as a pale yellow oily substance.

¹H-NMR (CDCl₃) δ: 2.44-2.56 (2H, m), 2.72-2.94 (6H, m), 3.21 (1H, m), 3.79 (4H, s), 6.80-7.33 (13H, m).

Example 12

Production of N-benzyl-2-[3-(2-fluorobenzyl)-3,4-dihydroisoquinolin-2(1H)-yl]ethanamine a) Production of 3-(2-fluorobenzoyl)isoquinoline

[Chem. 56]

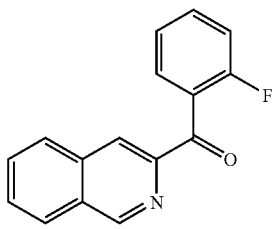

The reaction and treatment were carried out in the same manner as in Example 1-a, b) using 2-fluorophenyl magnesium bromide instead of phenyl magnesium bromide to obtain a title compound as a light yellow oily substance.

¹H-NMR (CDCl₃) δ: 7.21-7.55 (3H, m), 7.70 (1H, m), 7.80-7.90 (2H, m), 8.11-8.20 (2H, m), 8.47 (1H, s), 9.28 (1H, s).

b) Production of 3-(2-fluorobenzyl)isoquinoline

[Chem. 57]

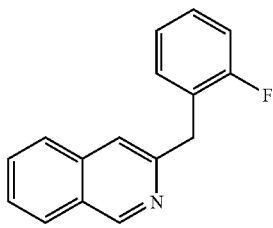

The reaction and treatment were carried out in the same manner as in Example 1-c) to obtain a title compound as a light yellow oily substance.

¹H-NMR (CDCl₃) δ: 4.46 (2H, s), 7.09 (1H, m), 7.25-7.33 (2H, m), 7.38 (1H, m), 7.50-7.75 (4H, m), 7.94 (1H, m), 9.23 (1H, s).

c) Production of 3-(2-fluorobenzyl)-1,2,3,4-tetrahydroisoquinoline

[Chem. 58]

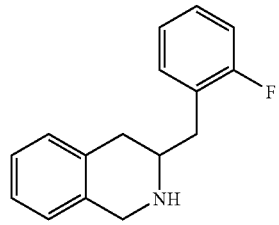

The reaction and treatment were carried out in the same manner as in Example 1-d) to obtain a title compound as a light yellow oily substance.

¹H-NMR (CDCl₃) δ: 2.60-2.95 (4H, m), 3.15 (1H, m), 4.02 (2H, s), 6.98-7.14 (4H, m), 7.22-7.36 (4H, m).

d) Production of N-benzyl-2-[3-(2-fluorobenzyl)-3,4-dihydroisoquinolin-2(1H)-yl]ethanamine

[Chem. 59]

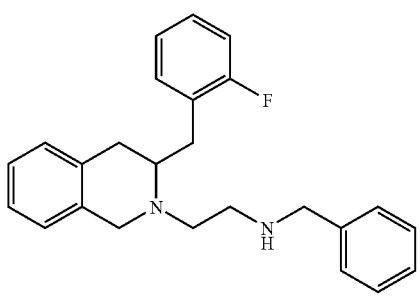

The reaction and treatment were carried out in the same manner as in Examples 1-e, f and g) to obtain a title compound as a colorless yellow oily substance.

¹H-NMR (CDCl₃) δ: 2.44-2.60 (2H, m), 2.70-2.95 (6H, m), 3.22 (1H, m), 3.79 (4H, s), 7.04-7.31 (13H, m).

Example 13

Production of N-benzyl-2-[3-(2,4-difluorobenzyl)-3,4-dihydroisoquinolin-2(1H)-yl]ethanamine a) Production of 3-(2,4-difluorobenzoyl)isoquinoline

[Chem. 60]

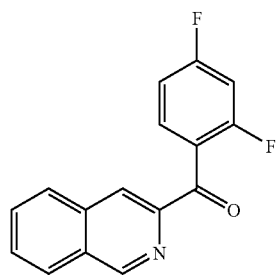

The reaction and treatment were carried out in the same manner as in Example 8-a) using 1-bromo-2,4-difluorobenzene instead of 2-bromochlorobenzene to obtain a title compound as a yellow oily substance.

¹H-NMR (CDCl₃) δ: 6.90 (1H, m), 7.03 (1H, m), 7.75-7.84 (5H, m), 9.63 (1H, s), 9.28 (1H, s).

b) Production of 3-(2,4-difluorobenzyl)isoquinoline

[Chem. 61]

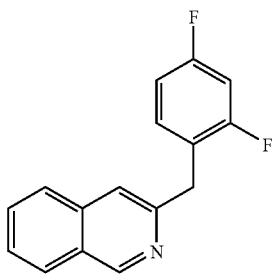

The reaction and treatment were carried out in the same manner as in Example 1-c) to obtain a title compound as a light yellow oily substance.

¹H-NMR (CDCl₃) δ: 4.28 (2H, s), 7.11 (1H, m), 7.14-7.28 (2H, m), 7.38 (1H, s), 7.47 (1H, m), 7.57 (1H, m), 7.66 (1H, m), 7.87 (1H, m), 9.15 (1H, s).

c) Production of 3-(2,4-difluorobenzyl)-1,2,3,4-tetrahydroisoquinoline

[Chem. 62]

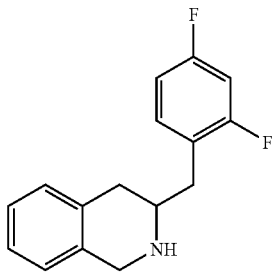

The reaction and treatment were carried out in the same manner as in Example 1-d) to obtain a title compound as a light yellow oily substance.

¹H-NMR (CDCl₃) δ: 2.56-2.94 (4H, m), 3.18 (1H, m), 4.05 (2H, s), 6.83 (1H, m), 6.98-7.14 (4H, m), 7.20-7.30 (2H, m).

d) Production of N-benzyl-2-[3-(2,4-difluorobenzyl)-3,4-dihydroisoquinolin-2(1H)-yl]ethanamine

[Chem. 63]

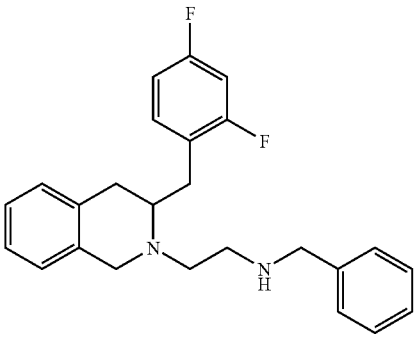

The reaction and treatment were carried out in the same manner as in Examples 1-e, f and g) to obtain a title compound as a yellow oily substance.

¹H-NMR (CDCl₃) δ: 2.45-2.60 (2H, m), 2.70-3.00 (6H, m), 3.25 (1H, m), 3.75-3.82 (4H, m), 6.75 (1H, m), 6.96-7.34 (11H, m).

Example 14

Production of N-benzyl-2-[3-(4-methylbenzyl)-3,4-dihydroisoquinolin-2(1H)-yl]ethanamine a) Production of 2-benzyl-3-(4-methylbenzyl)-1,2,3,4-tetrahydroisoquinoline

[Chem. 64]

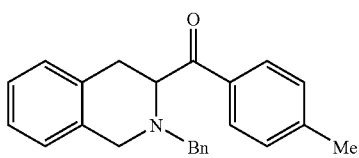

The reaction and treatment were carried out in the same manner as in Example 32-a, b, c, d) using methyl 1,2,3,4-tetrahydroisoquinoline-3-carboxylate instead of methyl 6-fluoro-1,2,3,4-tetrahydroisoquinoline-3-carboxylate to obtain a title compound as a pale yellow oily substance.

¹H-NMR (CDCl₃) δ: 2.41 (3H, s), 3.04 (1H, dd, J=5.6, 17.0 Hz), 3.31 (1H, dd, J=7.6, 17.0 Hz), 3.60 (1H, d, J=15.0 Hz), 3.79-3.83 (2H, m), 3.97 (1H, d, J=15.0 Hz), 4.48 (1H, dd, J=5.6, 7.6 Hz), 6.96 (1H, d, J=7.3 Hz), 7.11-7.27 (10H, m), 8.04 (2H, d, J=8.1 Hz).

b) Production of 3-(4-methylbenzyl)-1,2,3,4-tetrahydroisoquinoline

[Chem. 65]

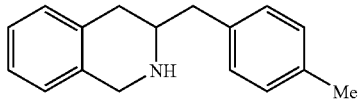

The reaction and treatment were carried out in the same manner as in Example 32-e) to obtain a title compound as a pale yellow oily substance.

¹H-NMR (CDCl₃) δ: 2.34 (3H, s), 2.64-2.84 (4H, m), 3.10-3.17 (1H, m), 4.02 (2H, s), 6.99-7.15 (8H, m).

c) Production of N-benzyl-2-[3-(4-methylbenzyl)-3,4-dihydroisoquinolin-2(1H)-yl]ethanamine

[Chem. 66]

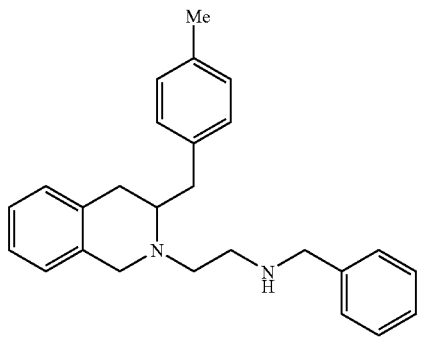

The reaction and treatment were carried out in the same manner as in Examples 32-f and g) to obtain a title compound as a pale yellow oily substance.

¹H-NMR (CDCl₃) δ: 2.29 (3H, s), 2.56-2.64 (2H, m), 2.87-2.99 (5H, m), 3.10-3.18 (1H, m), 3.37-3.44 (1H, m), 3.58 (1H, d, J=15.8 Hz), 3.78 (1H, d, J=15.8 Hz), 4.02 (2H, s), 6.93 (1H, d, J=6.8 Hz), 7.05-7.36 (12H, m).

Example 15

Production of N-benzyl-2-[3-(3-methylbenzyl)-3,4-dihydroisoquinolin-2(1H)-yl]ethanamine a) Production of 3-(3-methylbenzoyl)isoquinoline

[Chem. 67]

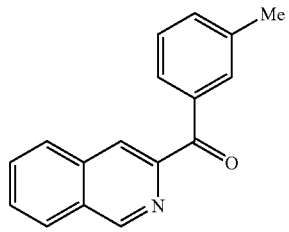

The reaction and treatment were carried out in the same manner as in Example 1-a, b) using 3-methylphenyl magnesium bromide instead of phenyl magnesium bromide to obtain a title compound as a light yellow oily substance.

¹H-NMR (CDCl₃) δ: 2.44 (3H, s), 7.36-7.43 (2H, m), 7.74-7.86 (4H, m), 8.00-8.09 (2H, m), 8.45 (1H, s), 9.34 (1H, s).

b) Production of 3-(3-methylbenzyl)isoquinoline

[Chem. 68]

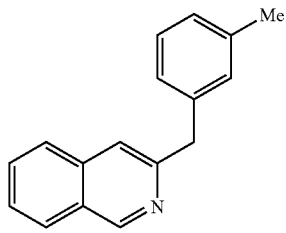

The reaction and treatment were carried out in the same manner as in Example 1-c) to obtain a title compound as a light yellow oily substance.

¹H-NMR (CDCl₃) δ: 2.32 (3H, s), 4.28 (2H, s), 7.03-7.23 (4H, m), 7.43 (1H, m), 7.53 (1H, m), 7.64 (1H, m), 7.72 (1H, m), 7.92 (1H, m), 9.21 (1H, s).

c) Production of 3-(3-methylbenzyl)-1,2,3,4-tetrahydroisoquinoline

[Chem. 69]

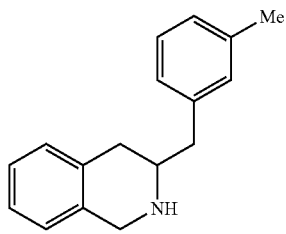

The reaction and treatment were carried out in the same manner as in Example 1-d) to obtain a title compound as a light yellow oily substance.

¹H-NMR (CDCl₃) δ: 2.35 (3H, s), 2.60-2.90 (4H, m), 3.15 (1H, m), 4.02 (2H, s), 6.99-7.14 (7H, m), 7.22 (1H, m).

d) Production of N-benzyl-2-[3-(3-methylbenzyl)-3,4-dihydroisoquinolin-2(1H)-yl]ethanamine

[Chem. 70]

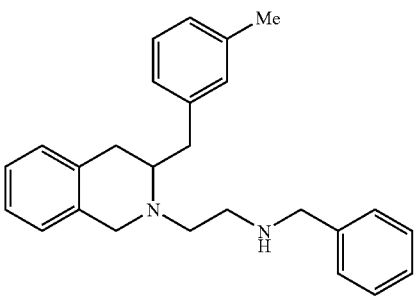

The reaction and treatment were carried out in the same manner as in Examples 1-e, f and g) to obtain a title compound as a yellow oily substance.

¹H-NMR (CDCl₃) δ: 2.31 (3H, s), 2.43 (1H, m), 2.56 (1H, m), 2.75-2.95 (6H, m), 3.22 (1H, m), 3.80 (4H, s), 6.88-7.33 (13H, m).

Example 16

Production of N-benzyl-2-[3-(2-methylbenzyl)-3,4-dihydroisoquinolin-2(1H)-yl]ethanamine a) Production of 3-(2-methylbenzoyl)isoquinoline

[Chem. 71]

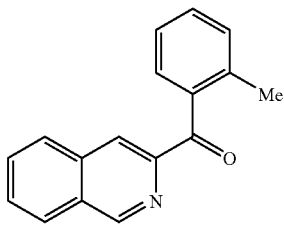

The reaction and treatment were carried out in the same manner as in Example 1-a, b) using 2-methylphenyl magnesium bromide instead of phenyl magnesium bromide to obtain a title compound as a light yellow oily substance.

¹H-NMR (CDCl₃) δ: 2.39 (3H, s), 7.26-7.33 (2H, m), 7.41-7.48 (2H, m), 7.74-7.82 (2H, m), 7.99-8.07 (2H, m), 8.46 (1H, s), 9.32 (1H, s).

b) Production of 3-(2-methylbenzyl)isoquinoline

[Chem. 72]

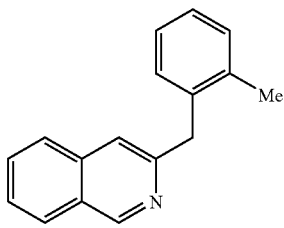

The reaction and treatment were carried out in the same manner as in Example 1-c) to obtain a title compound as a light yellow oily substance.

¹H-NMR (CDCl₃) δ: 2.29 (3H, s), 4.34 (2H, s), 7.18-7.30 (5H, m), 7.53 (1H, m), 7.60-7.67 (2H, m), 7.93 (1H, m), 9.22 (1H, s).

c) Production of 3-(2-methylbenzyl)-1,2,3,4-tetrahydroisoquinoline

[Chem. 73]

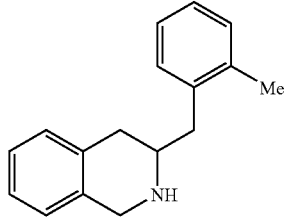

The reaction and treatment were carried out in the same manner as in Example 1-d) to obtain a title compound as a light yellow oily substance.

¹H-NMR (CDCl₃) δ: 2.36 (3H, s), 2.65-2.92 (4H, m), 3.16 (1H, m), 4.03 (2H, s), 7.00-7.24 (8H, m).

d) Production of N-benzyl-2-[3-(2-methylbenzyl)-3,4-dihydroisoquinolin-2(1H)-yl]ethanamine

[Chem. 74]

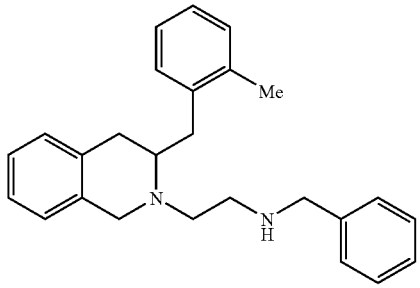

The reaction and treatment were carried out in the same manner as in Examples 1-e, f and g) to obtain a title compound as a yellow oily substance.

¹H-NMR (CDCl₃) δ: 2.22 (3H, s), 2.48-2.60 (2H, m), 2.70-2.98 (6H, m), 3.22 (1H, m), 3.80 (2H, s), 3.82 (2H, s), 7.00-7.32 (13H, m).

Example 17

Production of N-benzyl-2-[3-(4-methoxybenzyl)-3,4-dihydroisoquinolin-2(1H)-yl]ethanamine a) Production of 3-(4-methoxybenzoyl)isoquinoline

[Chem. 75]

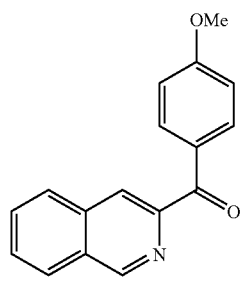

The reaction and treatment were carried out in the same manner as in Example 1-a, b) using 4-methoxyphenyl magnesium bromide instead of phenyl magnesium bromide to obtain a title compound as a light yellow oily substance.

$^1$H-NMR (CDCl$_3$) δ: 3.90 (3H, s), 6.99 (2H, d, J=6.8 Hz), 7.33-7.82 (2H, m), 8.00 (1H, m), 8.07 (1H, m), 8.15 (2H, d, J=6.8 Hz), 8.44 (1H, s), 9.33 (1H, s).

b) Production of 3-(4-methoxybenzyl)isoquinoline

[Chem. 76]

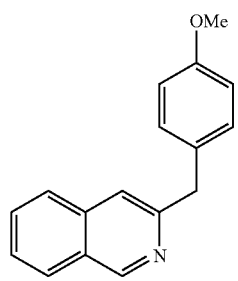

The reaction and treatment were carried out in the same manner as in Example 1-c) to obtain a title compound as a light yellow oily substance.

$^1$H-NMR (CDCl$_3$) δ: 3.80 (3H, s), 4.26 (2H, s), 6.86 (2H, d, J=6.6 Hz), 7.24 (2H, d, J=6.6 Hz), 7.40 (1H, s), 7.53 (1H, m), 7.63 (1H, m), 7.71 (1H, m), 7.92 (1H, m), 9.21 (1H, s).

c) Production of 3-(4-methoxybenzyl)-1,2,3,4-tetrahydroisoquinoline

[Chem. 77]

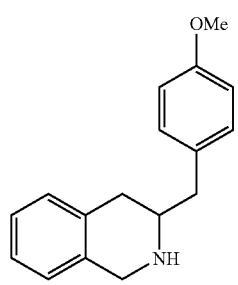

The reaction and treatment were carried out in the same manner as in Example 1-d) to obtain a title compound as a light yellow oily substance.

$^1$H-NMR (CDCl$_3$) δ: 2.58-2.86 (4H, m), 3.10 (1H, m), 3.81 (3H, s), 4.02 (2H, s), 6.87 (2H, d, J=8.8 Hz), 6.98-7.12 (4H, m), 7.17 (2H, d, J=8.8 Hz).

d) Production of N-benzyl-2-[3-(4-methoxybenzyl)-3,4-dihydroisoquinolin-2(1H)-yl]ethanamine

[Chem. 78]

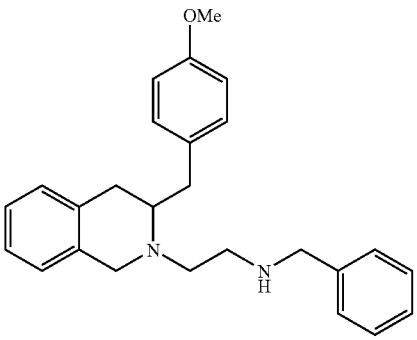

The reaction and treatment were carried out in the same manner as in Examples 1-e, f and g) to obtain a title compound as a yellow oily substance.

$^1$H-NMR (CDCl$_3$) δ: 2.42 (1H, m), 2.55 (1H, m), 2.70-2.92 (6H, m), 3.17 (1H, m), 3.78 (3H, s), 3.79 (2H, s), 6.80 (2H, d, J=8.8 Hz), 6.98-7.08 (4H, m), 7.12-7.18 (2H, m), 7.22-7.34 (5H, m).

Example 18

Production of N-benzyl-2-[3-(4-acetylbenzyl)-3,4-dihydroisoquinolin-2(1H)-yl]ethanamine a) Production of 3-[4-(2-methyl-1,3-dioxolan-2-yl)benzoyl]isoquinoline

[Chem. 79]

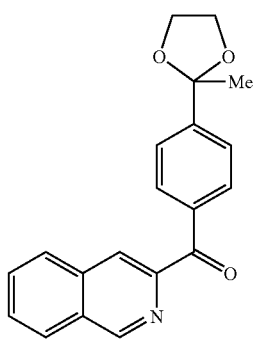

The reaction and treatment were carried out in the same manner as in Example 8-a) using 2-(4-bromophenyl)-2-methyl-1,3-dioxolane instead of 2-bromochlorobenzene to obtain a title compound as a light yellow oily substance.

$^1$H-NMR (CDCl$_3$) δ: 1.69 (3H, s), 3.76-3.85 (2H, m), 4.00-4.12 (2H, m), 7.63 (2H, d, J=8.1 Hz), 7.76-7.83 (2H, m), 8.02-8.10 (4H, m), 8.50 (1H, s), 9.34 (1H, s).

b) Production of 3-[4-(2-methyl-1,3-dioxolan-2-yl)benzyl]isoquinoline

[Chem. 80]

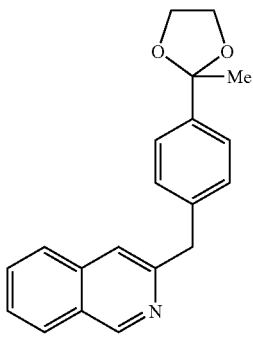

The reaction and treatment were carried out in the same manner as in Example 1-c) to obtain a title compound as a yellow oily substance.

$^1$H-NMR (CDCl$_3$) δ: 1.64 (3H, s), 3.74-3.82 (2H, m), 3.98-4.06 (2H, m), 4.30 (2H, s), 7.29 (2H, d, J=8.1 Hz), 7.42 (2H, d, J=8.1 Hz), 7.47 (1H, s), 7.54 (1H, m), 7.65 (1H, m), 7.74 (1H, m), 7.93 (1H, m), 9.22 (1H, s).

c) Production of 3-[4-(2-methyl-1,3-dioxolan-2-yl)benzyl]-1,2,3,4-tetrahydroisoquinoline

[Chem. 81]

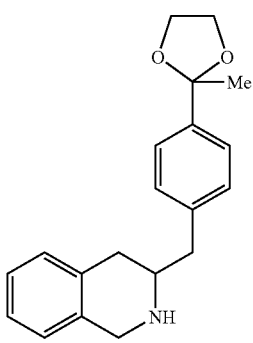

The reaction and treatment were carried out in the same manner as in Example 1-d) to obtain a title compound as a light yellow oily substance.

$^1$H-NMR (CDCl$_3$) δ: 1.67 (3H, s), 2.60-2.90 (4H, m), 3.14 (1H, m), 3.80-3.85 (2H, m), 4.00-4.08 (4H, m), 6.98-7.14 (4H, m), 7.23 (2H, d, J=8.1 Hz), 7.44 (2H, d, J=8.1 Hz).

d) Production of N-benzyl-2-[3-(4-acetylbenzyl)-3,4-dihydroisoquinolin-2(1H)-yl]ethanamine

[Chem. 82]

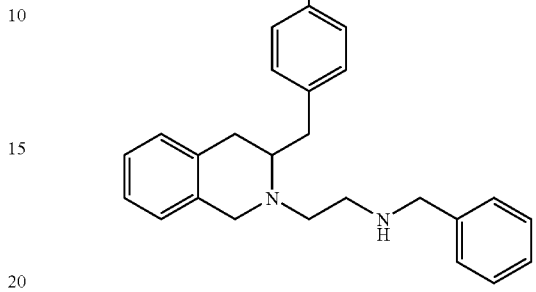

The reaction and treatment were carried out in the same manner as in Example 1-e, f, g), and 4 mL of 4N hydrochloric acid/ethyl acetate was then added thereto, followed by stirring at room temperature for 50 minutes. The organic layer was washed with an aqueous sodium bicarbonate solution and then with brine and then dried over anhydrous sodium sulfate, and the solvent was removed by evaporation to obtain a title compound as a yellow oily substance.

$^1$H-NMR (CDCl$_3$) δ: 2.57 (3H, s), 2.50-2.56 (2H, m), 2.74-2.98 (6H, m), 3.23 (1H, m), 3.79 (2H, s), 3.76-3.84 (2H, m), 7.00-7.38 (11H, m), 7.85 (2H, d, J=8.3 Hz).

Example 19

Production of N-benzyl-2-[3-methyl-3,4-dihydroisoquinolin-2(1H)-yl]ethanamine a) Production of tert-butyl 2-[3-methyl-3,4-dihydroisoquinolin-2(1H)-yl]ethyl carbamate

[Chem. 83]

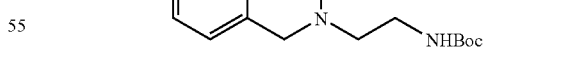

The reaction and treatment were carried out in the same manner as in Example 1-e) using 3-methyl-1,2,3,4-tetrahydroisoquinoline instead of 3-benzyl-1,2,3,4-tetrahydroisoquinoline to obtain a title compound as a light yellow oily substance.

$^1$H-NMR (CDCl$_3$) δ: 1.07 (3H, d, J=6.4 Hz), 1.44 (9H, s), 2.54-2.64 (2H, m), 2.69-2.76 (1H, m), 2.96-3.12 (2H, m), 3.22-3.30 (2H, m), 3.66-3.78 (2H, m), 5.08 (1H, brs), 7.00-7.16 (4H, m).

b) Production of 2-[3-methyl-3,4-dihydroisoquino-lin-2(1H)-yl]ethanamine

[Chem. 84]

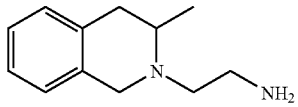

The reaction and treatment were carried out in the same manner as in Example 1-f) to obtain a title compound as a light yellow oily substance.

$^1$H-NMR (CDCl$_3$) δ: 1.11 (3H, d, J=6.4 Hz), 2.56-2.84 (4H, m), 2.94-3.10 (2H, m), 3.28-3.33 (1H, m), 3.67-3.84 (2H, m), 7.01-7.14 (4H, m).

c) Production of N-benzyl-2-[3-methyl-3,4-dihydroisoquinolin-2(1H)-yl]ethanamine

[Chem. 85]

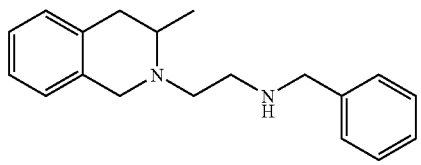

The reaction and treatment were carried out in the same manner as in Example 1-g) to obtain a title compound as a light yellow oily substance.

$^1$H-NMR (CDCl$_3$) δ: 1.06 (3H, d, J=6.6 Hz), 2.56 (1H, dd, J=5.6, 16.1 Hz), 2.62-2.72 (1H, m), 2.74-2.82 (3H, m), 2.98 (1H, dd, J=4.8, 16.1 Hz), 3.02-3.10 (1H, m), 3.65 (1H, d, J=15.6 Hz), 3.72 (1H, d, J=15.6 Hz), 3.83 (2H, s), 6.96-7.01 (1H, m), 7.04-7.15 (3H, m), 7.24-7.33 (5H, m).

Example 20

Production of N-benzyl-2-[3-isobutyl-3,4-dihydroisoquinolin-2(1H)-yl]ethanamine a) Production of isopropyl 3-quinolinoketone

[Chem. 86]

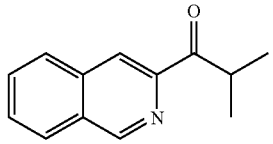

The reaction and treatment were carried out in the same manner as in Example 1-a, b) using isopropyl magnesium bromide instead of phenyl magnesium bromide to obtain a title compound as a yellow solid.

$^1$H-NMR (CDCl$_3$) δ: 1.27 (6H, d, J=6.8 Hz), 4.22 (1H, sept, J=6.8 Hz), 7.71-7.79 (2H, m), 8.00 (1H, d, J=7.8 Hz), 8.05 (1H, d, J=7.8 Hz), 8.49 (1H, s), 9.29 (1H, s).

b) Production of 3-isobutylisoquinoline

[Chem. 87]

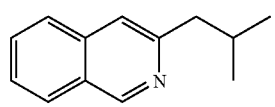

The reaction and treatment were carried out in the same manner as in Example 1-c) to obtain a title compound as a yellow solid.

$^1$H-NMR (CDCl$_3$) δ: 0.95 (3H, d, J=1.2 Hz), 0.97 (3H, d, J=1.2 Hz), 2.15-2.27 (1H, m), 2.79 (2H, d, J=7.3 Hz), 7.43 (1H, s), 7.52 (1H, dd, J=7.4, 7.4 Hz), 7.64 (1H, dd, J=7.4, 7.4 Hz), 7.74 (1H, d, J=8.2 Hz), 7.92 (1H, d, J=8.2 Hz), 9.20 (1H, s).

c) Production of 3-isobutyl tetrahydroisoquinoline

[Chem. 88]

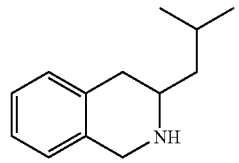

The reaction and treatment were carried out in the same manner as in Example 1-d) to obtain a title compound as a pale yellow oily substance.

$^1$H-NMR (CDCl$_3$) δ: 0.92-0.98 (6H, m), 1.31-1.38 (1H, m), 1.40-1.47 (1H, m), 1.78-1.90 (1H, m), 2.48 (1H, dd, J=10.8, 16.3 Hz), 2.79 (1H, dd, J=3.8, 16.1 Hz), 2.91-2.98 (1H, m), 4.03 (1H, d, J=15.8 Hz), 4.09 (1H, d, J=15.8 Hz), 7.00-7.02 (1H, m), 7.06-7.14 (3H, m).

d) Production of N-benzyl-2-[3-isobutyl-3,4-dihydroisoquinolin-2(1H)-yl]ethanamine

[Chem. 89]

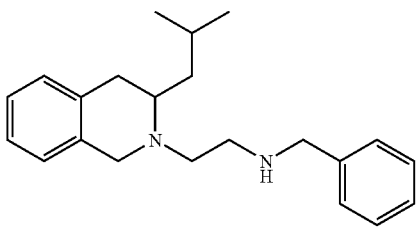

The reaction and treatment were carried out in the same manner as in Examples 32-f and g) to obtain a title compound as a pale yellow oily substance.

$^1$H-NMR (CDCl$_3$) δ: 0.89 (6H, d, J=6.6 Hz), 1.16-1.22 (1H, m), 1.36-1.43 (1H, m), 1.64-1.71 (1H, m), 2.52-2.66

(2H, m), 2.76 (3H, brs), 2.91-3.03 (2H, m), 3.73 (2H, s), 3.84 (2H, s), 6.96-7.00 (1H, m), 7.06-7.14 (3H, m), 7.25-7.34 (5H, m).

Example 21

Production of N-benzyl-2-[3-(2-methylbutyl)-3,4-dihydroisoquinolin-2(1H)-yl]ethanamine a) Production of N-(4-methylpentylidene)-2-methylpropanesulfinamide

[Chem. 90]

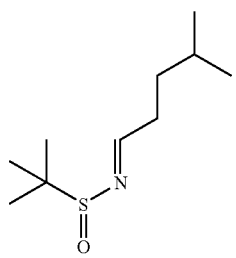

The reaction and treatment were carried out in the same manner as in Example 22-a) using 4-methylpentan-1-one instead of 5-methylhexan-1-one to obtain a title compound as a light yellow oily substance.

$^1$H-NMR (CDCl$_3$) δ: 0.93 (6H, d, J=6.6 Hz), 1.19 (9H, s), 1.47-1.67 (3H, m), 2.50-2.55 (2H, m), 8.07 (1H, t, J=4.6 Hz).

b) Production of 5-methyl-1-phenyl-2-hexylamine

[Chem. 91]

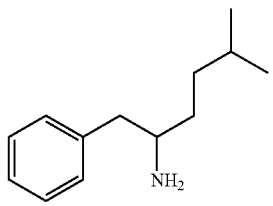

The reaction and treatment were carried out in the same manner as in Example 22-b) to obtain a title compound as a light yellow oily substance.

$^1$H-NMR (CDCl$_3$) δ: 0.89 (3H, d, J=6.6 Hz), 0.90 (3H, d, J=6.6 Hz), 1.22-1.69 (5H, m), 2.44 (1H, dd, J=8.8, 13.4 Hz), 2.82 (1H, dd, J=4.4, 13.4 Hz), 2.92-2.98 (1H, m), 7.18-7.32 (5H, m).

c) Production of 3-(3-methylbutyl)-3,4-dihydroisoquinoline

[Chem. 92]

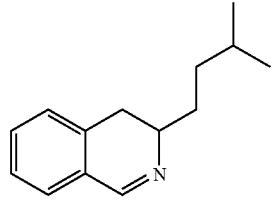

The reaction and treatment were carried out in the same manner as in Examples 37-c and d) to obtain a title compound as a light yellow oily substance.

$^1$H-NMR (CDCl$_3$) δ: 0.92 (3H, d, J=6.6 Hz), 0.93 (3H, d, J=6.6 Hz), 1.29-1.39 (1H, m), 1.42-1.52 (1H, m), 1.54-1.67 (2H, m), 1.75-1.85 (1H, m), 2.56 (1H, dd, J=12.8, 15.9 Hz), 2.77 (1H, dd, J=5.8, 15.9 Hz), 3.44-3.54 (1H, m), 7.15 (1H, d, J=7.3 Hz), 7.27-7.37 (3H, m), 8.33 (1H, d, J=2.7 Hz).

d) Production of 3-(3-methylbutyl)-1,2,3,4-tetrahydroisoquinoline

[Chem. 93]

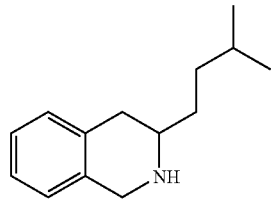

The reaction and treatment were carried out in the same manner as in Example 37-e) to obtain a title compound as a light yellow oily substance.

$^1$H-NMR (CDCl$_3$) δ: 0.92 (6H, d, J=6.6 Hz), 1.25-1.40 (2H, m), 1.45-1.61 (3H, m), 2.51 (1H, dd, J=11.0, 16.6 Hz), 2.78-2.87 (2H, m), 4.04 (1H, d, J=16.0 Hz), 4.09 (1H, d, J=16.0 Hz), 7.00-7.03 (1H, m), 7.06-7.13 (3H, m).

e) Production of tert-butyl benzyl[2-[3-(3-methylbutyl)-3,4-dihydroisoquinolin-2(1H)-yl]ethyl]carbamate

[Chem. 94]

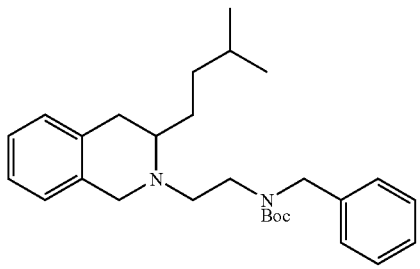

The reaction and treatment were carried out in the same manner as in Example 32-f) to obtain a title compound as a light yellow oily substance.

$^1$H-NMR (CDCl$_3$) δ: 0.86 (3H, d, J=6.4 Hz), 0.88 (3H, d, J=6.4 Hz), 1.19-1.28 (4H, m), 1.43-1.56 (10H, m), 2.46-2.88

(5H, m), 3.22-3.51 (2H, m), 3.74-3.78 (2H, m), 4.47-4.48 (2H, m), 6.98-7.00 (1H, m), 7.03-7.06 (1H, m), 7.09-7.14 (2H, m), 7.22-7.32 (5H, m).

f) Production of N-benzyl-2-[3-(3-methylbutyl)-3,4-dihydroisoquinolin-2(1H)-yl]ethanamine

[Chem. 95]

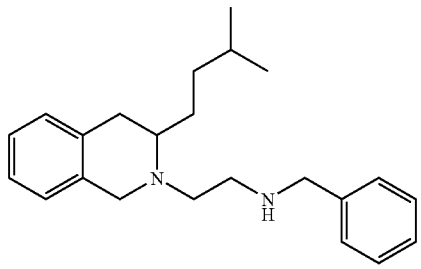

The reaction and treatment were carried out in the same manner as in Example 32-g) to obtain a title compound as a light yellow oily substance.

$^1$H-NMR (CDCl$_3$) δ: 0.85 (3H, d, J=6.6 Hz), 0.86 (3H, d, J=6.6 Hz), 1.20-1.34 (3H, m), 1.45-1.61 (2H, m), 2.53-2.58 (1H, m), 2.63-2.78 (4H, m), 2.84-2.93 (2H, m), 3.70 (1H, d, J=16.1 Hz), 3.77 (1H, d, J=16.1 Hz), 3.83 (2H, s), 6.97-7.00 (1H, m), 7.05-7.07 (1H, m), 7.09-7.15 (2H, m), 7.22-7.32 (5H, m).

Example 22

Production of N-benzyl-2-[3-(4-methylpentyl)-3,4-dihydroisoquinolin-2(1H)-yl]ethanamine a) Production of N-(5-methylhexylidene)-2-methylpropanesulfinamide

[Chem. 96]

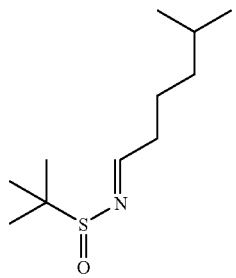

280 mg of 2-methyl-2-propanesulfinamide was dissolved in 10 mL of dichloromethane, and 800 mg of copper sulfate and 260.6 mg of 5-methylhexan-1-one were sequentially added thereto, followed by stirring at room temperature for 2 days. After completion of the reaction, the reaction liquid was filtered through Celite and washed with dichloromethane. The filtrate was concentrated under reduced pressure, and the solvent was removed by evaporation, followed by purification using column chromatography to obtain 457.8 mg (yield 92%) of a title compound as a yellow oily substance.

$^1$H-NMR (CDCl$_3$) δ: 0.89 (6H, d, J=6.6 Hz), 1.20 (9H, s), 1.21-1.27 (1H, m), 1.51-1.67 (4H, m), 2.47-2.53 (2H, m), 8.05-8.08 (1H, m).

b) Production of 6-methyl-1-phenyl-2-heptylamine

[Chem. 97]

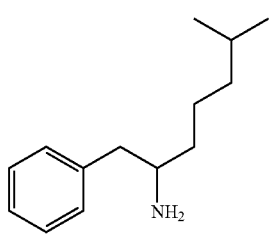

Under an argon atmosphere, 458 mg of N-(5-methylhexylidene)-2-methylpropanesulfinamide was dissolved in 10 mL of anhydrous dichloromethane. Under cooling at −40° C., to the reaction liquid was slowly added 2.9 mL of phenyl magnesium bromide (1 mol/L THF solution), followed by stirring for 1 hour, warming to 0° C., and then further stirring for 3 hours. After completion of the reaction, water was added to the reaction liquid, followed by extraction with chloroform. The organic layer was washed with a saturated aqueous sodium bicarbonate solution and saturated brine, dried over anhydrous sodium sulfate, and then concentrated under reduced pressure. The residue obtained was purified by silica gel chromatography to obtain 498.7 mg of a yellow oily substance.

208 mg of the obtained oily substance was dissolved in 2 mL of methanol, and 0.5 mL of 4N hydrochloric acid.ethyl acetate was added thereto under ice-cooling, followed by stirring, and then stirring at room temperature for 3.5 hours. After completion of the reaction, to the reaction liquid were added a saturated aqueous sodium bicarbonate solution and ethyl acetate under ice-cooling, and the organic layer was separated. Ethyl acetate was added again to the aqueous layer, followed by extraction. The organic layer was combined, and washed with saturated brine. The organic layer was dried over anhydrous sodium sulfate and then concentrated under reduced pressure, and the solvent was removed by evaporation, followed by purification using silica gel chromatography to obtain 96.9 mg (yield 53%) of a desired product as a yellow oily substance.

$^1$H-NMR (CDCl$_3$) δ: 0.87 (6H, d, J=6.6 Hz), 1.17-1.26 (2H, m), 1.31-1.39 (2H, m), 1.41-1.59 (3H, m), 2.50 (1H, dd, J=8.8, 13.4 Hz), 2.81 (1H, dd, J=5.1, 13.4 Hz), 2.98-3.05 (1H, m), 7.18-7.38 (5H, m).

c) Production of N-formyl-6-methyl-1-phenyl-2-heptylamine

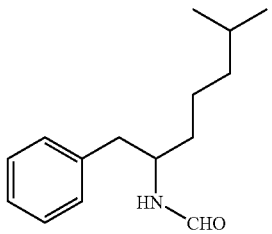

The reaction and treatment were carried out in the same manner as in Example 37-c) to obtain a title compound as a light yellow oily substance.

$^1$H-NMR (CDCl$_3$) δ: 0.85 (6H, d, J=6.6 Hz), 1.08-1.61 (7H, m), 2.66 (1H, dd, J=8.0, 13.9 Hz), 2.76-2.88 (2H, m), 7.12-7.32 (5H, m), 8.13 (1H, s).

d) Production of 3-(4-methyl pentyl)-3,4-dihydroisoquinoline

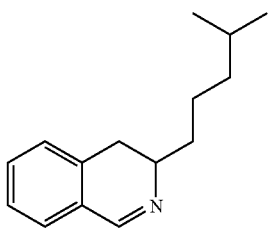

The reaction and treatment were carried out in the same manner as in Example 37-d) to obtain a title compound as a light yellow oily substance.

$^1$H-NMR (CDCl$_3$) δ: 0.89 (6H, d, J=6.6 Hz), 1.20-1.27 (2H, m), 1.42-1.63 (4H, m), 1.72-1.82 (1H, m), 2.56 (1H, dd, J=12.4, 16.1 Hz), 2.77 (1H, dd, J=5.8, 16.1 Hz), 3.49-3.56 (1H, m), 7.15 (1H, d, J=7.3 Hz), 7.27-7.36 (3H, m), 8.33 (1H, d, J=2.7 Hz).

e) Production of 3-(4-methylpentyl)-1,2,3,4-tetrahydroisoquinoline

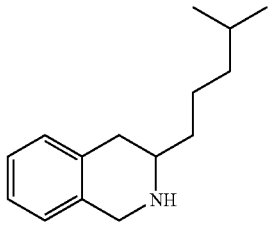

The reaction and treatment were carried out in the same manner as in Example 37-e) to obtain a title compound as a light yellow oily substance.

$^1$H-NMR (CDCl$_3$) δ: 0.89 (6H, d, J=6.8 Hz), 1.19-1.28 (2H, m), 1.39-1.60 (5H, m), 2.52 (1H, dd, J=10.5, 16.1 Hz), 2.81 (1H, dd, J=3.9, 16.1 Hz), 2.84-2.90 (1H, m), 4.05 (1H, d, J=15.8 Hz), 4.10 (1H, d, J=15.8 Hz), 7.00-7.03 (1H, m), 7.06-7.13 (3H, m).

f) Production of tert-butyl benzyl[2-[3-(4-methyl pentyl)-3,4-dihydroisoquinolin-2(1H)-yl]ethyl]carbamate

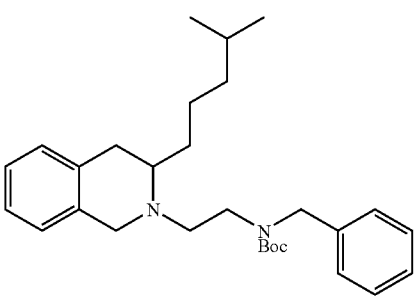

The reaction and treatment were carried out in the same manner as in Example 37-f) to obtain a title compound as a light yellow oily substance.

$^1$H-NMR (CDCl$_3$) δ: 0.86 (6H, d, J=6.8 Hz), 1.12-1.18 (2H, m), 1.24-1.37 (3H, m), 1.43-1.52 (11H, m), 2.47-2.92 (5H, m), 3.22-3.49 (2H, m), 3.74-3.78 (2H, m), 4.47-4.49 (2H, m), 6.97-7.01 (1H, m), 7.03-7.06 (2H, m), 7.10-7.13 (2H, m), 7.20-7.32 (5H, m).

g) Production of N-benzyl-2-[3-(4-methyl pentyl)-3,4-dihydroisoquinolin-2(1H)-yl]ethanamine

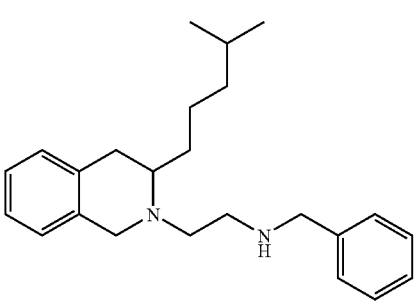

The reaction and treatment were carried out in the same manner as in Example 32-g) to obtain a title compound as a light yellow oily substance.

$^1$H-NMR (CDCl$_3$) δ: 0.85 (6H, d, J=6.6 Hz), 1.12-1.18 (2H, m), 1.26-1.36 (3H, m), 1.45-1.56 (2H, m), 2.57 (1H, dd, J=6.6, 17.6 Hz), 2.61-2.75 (4H, m), 2.87-2.92 (2H, m), 3.71

(1H, d, J=16.1 Hz), 3.76 (1H, d, J=16.1 Hz), 3.81 (2H, s), 6.97-7.00 (1H, m), 7.05-7.13 (3H, m), 7.21-7.34 (5H, m).

Example 23

Production of N-benzyl-2-[3-cyclohexylmethyl-3,4-dihydroisoquinolin-2(1H)-yl]ethanamine a) Production of 3-cyclohexylmethylisoquinoline

[Chem. 103]

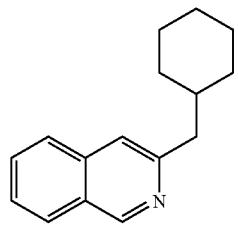

The reaction and treatment were carried out in the same manner as in Example 1-a, b, c) using cyclohexyl magnesium chloride instead of phenyl magnesium bromide to obtain a title compound as a yellow oily substance.

$^1$H-NMR (CDCl$_3$) δ: 0.98-1.32 (5H, m), 1.60-1.78 (5H, m), 1.82-1.95 (1H, m), 2.80 (2H, d, J=7.1 Hz), 7.42 (1H, s), 7.51 (1H, dd, J=7.9, 7.9 Hz), 7.63 (1H, dd, J=7.9, 7.9 Hz), 7.74 (1H, d, J=7.9 Hz), 7.92 (1H, d, J=7.9 Hz), 9.21 (1H, s).

b) Production of 3-cyclohexylmethyl-1,2,3,4-tetrahydroisoquinoline

[Chem. 104]

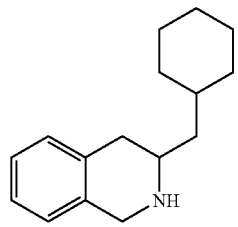

The reaction and treatment were carried out in the same manner as in Example 1-d) to obtain a title compound as a yellow oily substance.

$^1$H-NMR (CDCl$_3$) δ: 0.98-1.02 (2H, m), 1.10-1.58 (6H, m), 1.62-1.80 (5H, m), 2.01 (1H, brs), 2.49 (1H, dd, J=10.5, 16.4 Hz), 2.79 (1H, dd, J=3.6, 16.4 Hz), 2.94-3.04 (1H, m), 4.04 (1H, d, J=16.1 Hz), 4.09 (1H, d, J=16.1 Hz), 6.98-7.03 (1H, m), 7.04-7.08 (1H, m), 7.08-7.14 (2H, m).

c) Production of tert-butyl 2-[3-cyclohexylmethyl-3,4-dihydroisoquinolin-2(1H)-yl]ethylcarbamate

[Chem. 105]

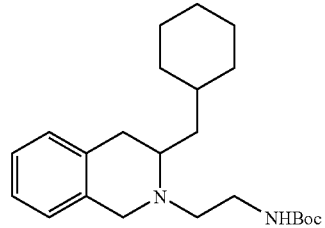

The reaction and treatment were carried out in the same manner as in Example 1-e) to obtain a title compound as a pale yellow oily substance.

$^1$H-NMR (CDCl$_3$) δ: 0.84-0.97 (2H, m), 1.12-1.32 (4H, m), 1.44 (9H, s), 1.42-1.53 (2H, m), 1.60-1.78 (5H, m), 2.55 (1H, dd, J=5.6, 16.6 Hz), 2.57-2.64 (1H, m), 2.66-2.76 (1H, m), 2.92 (1H, dd, J=5.2, 16.6 Hz), 3.08-3.36 (3H, m), 3.80 (2H, s), 5.24 (1H, brs), 7.00-7.10 (2H, m), 7.11-7.17 (2H, m).

d) Production of 2-[3-cyclohexylmethyl-3,4-dihydroisoquinolin-2(1H)-yl]ethanamine

[Chem. 106]

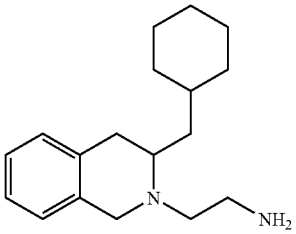

The reaction and treatment were carried out in the same manner as in Example 1-f) to obtain a title compound as a pale yellow oily substance.

$^1$H-NMR (CDCl$_3$) δ: 0.83-0.96 (2H, m), 1.09-1.46 (6H, m), 1.62-1.79 (5H, m), 2.54 (1H, dd, J=5.3, 16.7 Hz), 2.58-2.63 (1H, m), 2.64-2.72 (1H, m), 2.86 (2H, t, J=5.7 Hz), 2.94 (1H, dd, J=5.3, 16.8 Hz), 3.05-3.12 (1H, m), 3.54 (2H, brs), 3.77 (2H, s), 6.98-7.04 (1H, m), 7.05-7.15 (3H, m).

e) Production of N-benzyl-2-[3-cyclohexylmethyl-3,4-dihydroisoquinolin-2(1H)-yl]ethanamine

[Chem. 107]

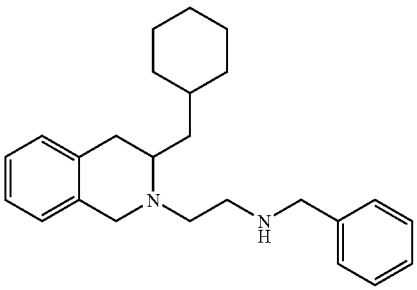

The reaction and treatment were carried out in the same manner as in Example 1-g) to obtain a title compound as a pale yellow oily substance.

$^1$H-NMR (CDCl$_3$) δ: 0.79-0.94 (2H, m), 1.06-1.26 (4H, m), 1.28-1.46 (2H, m), 1.58-1.74 (5H, m), 2.42-2.56 (1H, br), 2.52 (1H, dd, J=5.0, 16.5 Hz), 2.60-2.68 (1H, m), 2.71-2.79 (3H, m), 2.91 (1H, dd, J=5.1, 16.5 Hz), 3.02-3.10 (1H, m), 3.72 (2H, s), 3.84 (2H, s), 6.96-7.00 (1H, m), 7.04-7.15 (3H, m), 7.22-7.34 (5H, m).

Example 24

Production of N-benzyl-2-[3-cyclopentylmethyl-3,4-dihydroisoquinolin-2(1H)-yl]ethanamine a) Production of N-(2-cyclopentylethylidene)-2-methylpropanesulfinamide

[Chem. 108]

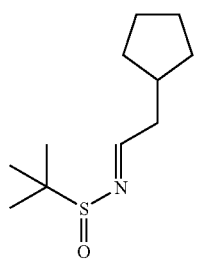

The reaction and treatment were carried out in the same manner as in Example 22-a) using cyclopentane acetaldehyde instead of 5-methylhexan-1-one to obtain a title compound as a light yellow oily substance.

$^1$H-NMR (CDCl$_3$) δ: 1.20 (9H, s), 1.51-1.69 (6H, m), 1.79-1.80 (2H, m), 2.15-2.23 (1H, m), 2.53 (2H, dd, J=5.1, 6.8 Hz), 8.06 (1H, t, J=5.1 Hz).

b) Production of 3-cyclopentylmethyl-1,2,3,4-tetrahydroisoquinoline

[Chem. 109]

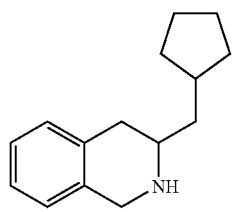

The reaction and treatment were carried out in the same manner as in Examples 22-b, 37-c, d and e) to obtain a title compound as a light yellow oily substance.

$^1$H-NMR (CDCl$_3$) δ: 1.08-1.19 (2H, m), 1.48-1.86 (8H, m), 1.95-2.05 (1H, m), 2.52 (1H, dd, J=10.5, 16.1 Hz), 2.84 (1H, dd, J=3.4, 16.1 Hz), 2.89-2.97 (1H, m), 4.05 (1H, d, J=16.1 Hz), 4.11 (1H, d, J=16.1 Hz), 7.00-7.03 (1H, m), 7.06-7.09 (1H, m), 7.11-7.14 (2H, m).

c) Production of N-benzyl-2-[3-cyclopentylmethyl-3,4-dihydroisoquinolin-2(1H)-yl]ethanamine

[Chem. 110]

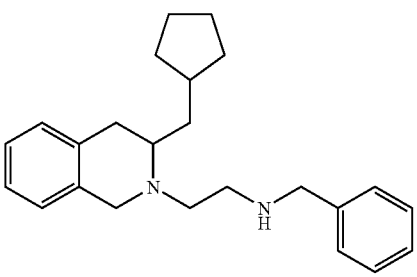

The reaction and treatment were carried out in the same manner as in Examples 32-f and g) to obtain a title compound as a light yellow oily substance.

$^1$H-NMR (CDCl$_3$) δ: 1.01-1.09 (2H, m), 1.18-1.37 (2H, m), 1.46-1.63 (4H, m), 1.69-1.79 (2H, m), 1.80-1.90 (1H, m), 2.58 (1H, dd, J=4.6, 16.4 Hz), 2.63-2.78 (4H, m), 2.90-3.01 (2H, m), 3.73 (2H, s), 3.82 (2H, s), 6.97-7.00 (1H, m), 7.05-7.08 (1H, m), 7.11-7.14 (2H, m), 7.22-7.32 (5H, m).

Example 25

Production of N-benzyl-2-[3-phenyl-3,4-dihydroisoquinolin-2(1H)-yl]ethanamine

[Chem. 111]

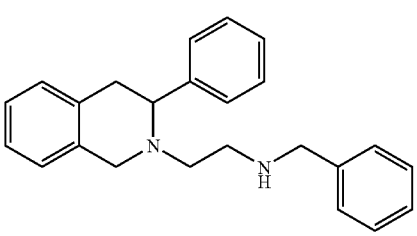

The reaction and treatment were carried out in the same manner as in Example 1-e, f, g) using 3-phenyl-1,2,3,4-tetrahydroisoquinoline synthesized with reference to [J. Med. Chem., 1989, 32(6), 1242-1248] to obtain a title compound as a pale yellow oily substance.

$^1$H-NMR (CDCl$_3$) δ: 2.65-2.85 (4H, m), 3.09 (2H, d, J=7.6 Hz), 3.58 (1H, d, J=15.6 Hz), 3.69-3.74 (3H, m), 3.90 (1H, d,

J=15.6 Hz), 7.03 (1H, dd, J=4.4, 4.4H), 7.10 (1H, dd, J=4.4, 4.4 Hz), 7.16-7.18 (2H, m), 7.26-7.31 (10H, m).

Example 26

Production of N-benzyl-2-[3-(2-phenethyl)-3,4-dihydroisoquinolin-2(1H)-yl]ethanamine a) Production of benzyl 3-isoquinolinoketone

[Chem. 112]

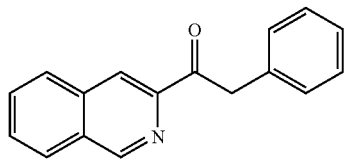

The reaction and treatment were carried out in the same manner as in Example 1-a, b) using benzyl magnesium bromide instead of phenyl magnesium bromide to obtain a title compound as a yellow solid.

$^1$H-NMR (CDCl$_3$) δ: 4.66 (2H, s), 7.23-7.26 (1H, m), 7.30 (1H, d, J=7.4 Hz), 7.32 (1H, d, J=7.4 Hz), 7.39 (2H, d, J=6.8 Hz), 7.72-7.77 (2H, m), 7.98-8.00 (1H, m), 8.05-8.07 (1H, m), 8.50 (1H, s), 9.32 (1H, s).

b) Production of 3-(2-phenethyl)isoquinoline

[Chem. 113]

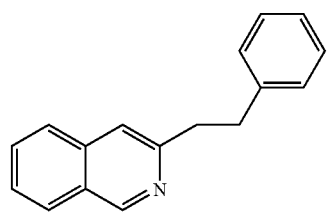

The reaction and treatment were carried out in the same manner as in Example 1-c) to obtain a title compound as a yellow solid.

$^1$H-NMR (CDCl$_3$) δ: 3.05-3.09 (2H, m), 3.15-3.19 (2H, m), 7.15-7.22 (5H, m), 7.35 (1H, s), 7.45-7.49 (1H, m), 7.55-7.59 (1H, m), 7.65 (1H, d, J=8.2 Hz), 7.87 (1H, d, J=8.2 Hz), 9.16 (1H, s).

c) Production of 3-(2-phenethyl)-1,2,3,4-tetrahydroisoquinoline

[Chem. 114]

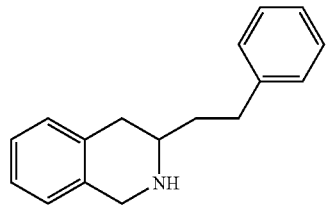

The reaction and treatment were carried out in the same manner as in Example 1-d) to obtain a title compound as a light yellow oily substance.

$^1$H-NMR (CDCl$_3$) δ: 1.84-1.91 (2H, m), 2.59 (1H, dd, J=10.4, 16.2 Hz), 2.78-2.95 (4H, m), 4.07 (2H, s), 7.01-7.03 (1H, m), 7.07-7.14 (3H, m), 7.18-7.31 (5H, m).

d) Production of tert-butyl 2-[3-(2-phenethyl)-3,4-dihydroisoquinolin-2(1H)-yl]ethylcarbamate

[Chem. 115]

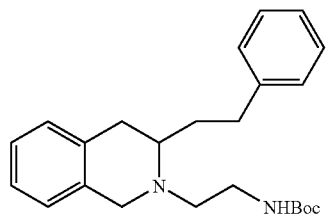

The reaction and treatment were carried out in the same manner as in Example 1-e) to obtain a title compound as a pale yellow oily substance.

$^1$H-NMR (CDCl$_3$) δ: 1.43 (9H, s), 1.60-1.69 (1H, m), 1.84-1.92 (1H, m), 2.56-2.77 (5H, m), 2.90-3.00 (2H, m), 3.18-3.25 (2H, m), 3.76 (1H, d, J=16.3 Hz), 3.81 (1H, d, J=16.3 Hz), 7.00-7.03 (1H, m), 7.07-7.15 (4H, m), 7.18 (2H, d, J=7.3 Hz), 7.25-7.29 (2H, m).

e) Production of N-benzyl-2-[3-(2-phenethyl)-3,4-dihydroisoquinolin-2(1H)-yl]ethanamine

[Chem. 116]

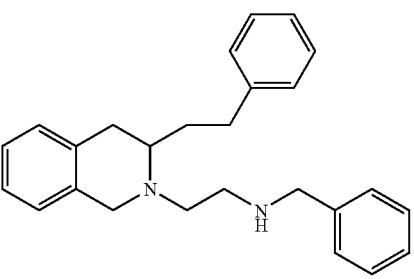

The reaction and treatment were carried out in the same manner as in Examples 1-f and g) to obtain a title compound as a pale yellow oily substance.

$^1$H-NMR (CDCl$_3$) δ: 1.58-1.67 (1H, m), 1.85-1.93 (1H, m), 2.59-2.78 (7H, m), 2.90-3.00 (2H, m), 3.71 (1H, d, J=16.6

Hz), 3.78 (1H, d, J=16.6 Hz), 3.81 (2H, s), 6.96-7.01 (1H, m), 7.06-7.08 (1H, m), 7.12-7.18 (5H, m), 7.23-7.27 (3H, m), 7.31 (4H, m).

Example 27

Production of N-benzyl-2-[3-(3-phenylpropyl)-3,4-dihydroisoquinolin-2(1H)-yl]ethanamine a) Production of N-(4-phenylbutylidene)-2-methylpropanesulfinamide

[Chem. 117]

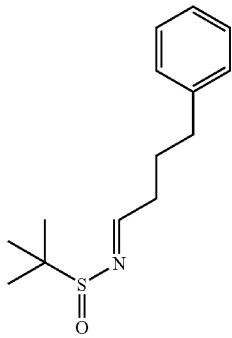

The reaction and treatment were carried out in the same manner as in Example 22-a) using 4-phenylbutyl aldehyde instead of 5-methylhexan-1-one to obtain a title compound as a light yellow oily substance.

$^1$H-NMR (CDCl$_3$) δ: 1.20 (9H, s), 1.97 (2H, tt, J=7.6, 7.6 Hz), 2.55 (2H, dt, J=4.4, 7.6 Hz), 2.70 (2H, t, J=7.6 Hz), 7.17-7.31 (5H, m), 8.09 (1H, t, J=4.4 Hz).

b) Production of 3-(3-phenylpropyl)-3,4-dihydroisoquinoline

[Chem. 118]

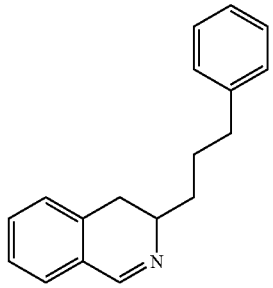

The reaction and treatment were carried out in the same manner as in Examples 22-b, 37-c and d) to obtain a title compound as a light yellow oily substance.

$^1$H-NMR (CDCl$_3$) δ: 1.65-1.97 (4H, m), 2.55 (1H, dd, J=13.4, 16.1 Hz), 2.69 (2H, t, J=7.6 Hz), 2.75 (1H, dd, J=5.9, 16.1 Hz), 3.49-3.59 (1H, m), 7.12-7.36 (9H, m), 8.32 (1H, d, J=2.7 Hz).

c) Production of 3-(3-phenylpropyl)-1,2,3,4-tetrahydroisoquinoline

[Chem. 119]

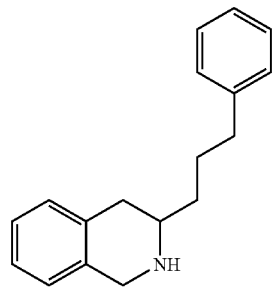

The reaction and treatment were carried out in the same manner as in Example 37-e) to obtain a title compound as a light yellow oily substance.

$^1$H-NMR (CDCl$_3$) δ: 1.54-1.65 (2H, m), 1.73-1.84 (2H, m), 2.51 (1H, dd, J=10.2, 16.4 Hz), 2.67 (2H, t, J=7.7 Hz), 2.81 (1H, dd, J=3.7, 16.4 Hz), 2.86-2.93 (1H, m), 4.03 (1H, d, J=16.1 Hz), 4.08 (1H, d, J=16.1 Hz), 7.00-7.02 (1H, m), 7.05-7.07 (1H, m), 7.10-7.13 (2H, m), 7.16-7.21 (3H, m), 7.25-7.30 (2H, m).

d) Production of tert-butyl benzyl[2-[3-(3-phenylpropyl)-3,4-dihydroisoquinolin-2(1H)-yl]ethyl]carbamate

[Chem. 120]

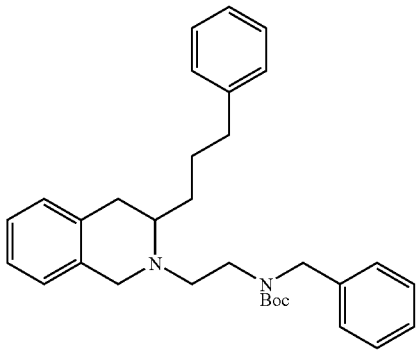

The reaction and treatment were carried out in the same manner as in Example 32-f) to obtain a title compound as a colorless oily substance.

$^1$H-NMR (CDCl$_3$) δ: 1.30-1.58 (12H, m), 1.63-1.71 (2H, m), 2.44-3.00 (6H, m), 3.23-3.45 (2H, m), 3.74-3.78 (2H, m), 4.46 (2H, s), 6.98-7.32 (14H, m).

e) Production of N-benzyl-2-[3-(3-phenylpropyl)-3,4-dihydroisoquinolin-2(1H)-yl]ethanamine

[Chem. 121]

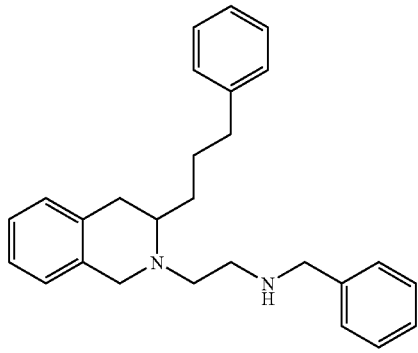

The reaction and treatment were carried out in the same manner as in Example 32-g) to obtain a title compound as a colorless oily substance.

$^1$H-NMR (CDCl$_3$) δ: 1.32-1.41 (1H, m), 1.57-1.73 (3H, m), 2.54-2.75 (7H, m), 2.87-2.98 (2H, m), 3.69 (1H, d, J=16.1 Hz), 3.76 (1H, d, J=16.1 Hz), 3.82 (2H, s), 6.96-6.99 (1H, m), 7.04-7.06 (1H, m), 7.09-7.19 (5H, m), 7.22-7.31 (7H, m).

Example 28

Production of N-benzyl-2-[3-benzyl-5-chloro-3,4-dihydroisoquinolin-2(1H)-yl]ethanamine a) Production of 3-chloro-2-methylbenzylalcohol

[Chem. 122]

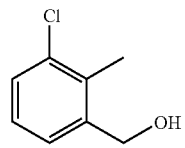

To a solution of 1.70 g of 3-chloro-2-methylbenzoic acid in 20 mL of THF was added dropwise 20 mL of a borane/THF complex under ice-cooling, followed by stirring at room temperature for 2 hours. After completion of the reaction, 1 N hydrochloric acid was added to the reaction liquid, followed by extraction with chloroform. The organic layer was washed with saturated brine, dried over anhydrous sodium sulfate and then concentrated under reduced pressure to obtain 1.52 g (yield 97%) of a title compound as a white crystal.

$^1$H-NMR (CDCl$_3$) δ: 2.39 (3H, s), 4.72 (2H, s), 7.13 (1H, dd, J=7.6, 7.9 Hz), 7.27 (1H, d, J=7.6 Hz), 7.32 (1H, d, J=7.9 Hz).

b) Production of 3-chloro-2-methylbenzyl chloride

[Chem. 123]

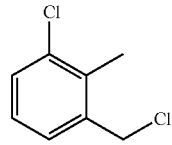

910 mg of 3-chloro-2-methylbenzylalcohol was dissolved in 10 mL of methylene chloride, 1.21 mL of triethylamine and 495 μL of methanesulfonyl chloride were added thereto at room temperature, followed by stirring for 3 hours. After completion of the reaction, a saturated aqueous sodium hydrogen carbonate solution was added to the reaction liquid, followed by extraction with chloroform. The organic layer was washed with saturated brine, dried over anhydrous sodium sulfate and then concentrated under reduced pressure to obtain 700 mg (yield 69%) of a title compound as a white solid.

$^1$H-NMR (CDCl$_3$) δ: 2.47 (3H, s), 4.61 (2H, s), 7.12 (1H, dd, J=7.7, 7.9 Hz), 7.22 (1H, d, J=7.7 Hz), 7.35 (1H, d, J=7.9 Hz).

c) Production of N-(3-chloro-2-methylbenzyl)phthalimide

[Chem. 124]

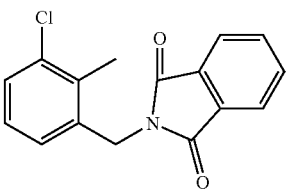

700 mg of 3-chloro-2-methylbenzyl chloride was dissolved in 10 mL of acetonitrile, and 829 mg of potassium carbonate and 889 mg of phthalimide potassium were added thereto at room temperature, followed by warming to 80° C., and then continuously reacting overnight. After completion of the reaction, the reaction liquid was left to be cooled, and water was added thereto, followed by extraction with chloroform. The organic layer was washed with saturated brine, dried over anhydrous sodium sulfate and then concentrated under reduced pressure to obtain 1.15 g (yield 100%) of a title compound as a white crystal.

$^1$H-NMR (CDCl$_3$) δ: 2.52 (3H, s), 4.89 (2H, s), 7.06 (1H, dd, J=7.7, 7.8 Hz), 7.18 (1H, d, J=7.7 Hz), 7.29 (1H, d, J=7.8 Hz), 7.74 (2H, dd, J=3.1, 5.5 Hz), 7.87 (2H, dd, J=3.1, 5.5 Hz).

d) Production of 3-chloro-2-methylbenzylamine

[Chem. 125]

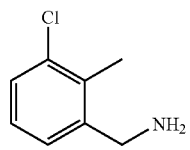

1.15 g of N-(3-chloro-2-methylbenzyl)phthalimide was dissolved in 20 mL of methanol, and 5 mL of hydrazine monohydrate was added thereto at room temperature. Thereafter, it was warmed to 80° C., followed by continuously reacting overnight. After completion of the reaction, the reaction liquid was left to be cooled, and water was added thereto, followed by extraction with chloroform. The organic layer was washed with saturated brine, dried over anhydrous sodium sulfate and then concentrated under reduced pressure to obtain 628 mg (yield 100%) of a title compound as a colorless clear oily substance.

$^1$H-NMR (CDCl$_3$) δ: 2.38 (3H, s), 3.88 (2H, s), 7.11 (1H, dd, J=7.7, 8.1 Hz), 7.22 (1H, d, J=7.7 Hz), 7.27 (1H, d, J=8.1 Hz).

e) Production of tert-butyl(3-chloro-2-methylbenzyl)carbamate

[Chem. 126]

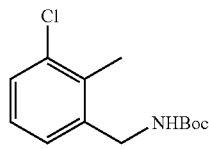

628 mg of 3-chloro-2-methylbenzylamine and 969 mg of di-tert-butyl dicarbonate were dissolved in 10 mL of chloroform, and 1.13 mL of triethylamine was added thereto at room temperature, followed by continuously reacting while keeping the temperature at room temperature for 5 hours. After completion of the reaction, water was added thereto, followed by extraction with chloroform. The organic layer was washed with saturated brine, dried over anhydrous sodium sulfate and then concentrated under reduced pressure. The residue obtained was purified using silica gel chromatography (hexane:ethyl acetate=8:1) to obtain 904 mg (yield 88%) of a title compound as a white crystal.

$^1$H-NMR (CDCl$_3$) δ: 1.46 (9H, s), 2.37 (3H, s), 4.34 (2H, d, J=5.6 Hz), 4.70 (1H, brs), 7.10 (1H, dd, J=7.1, 7.8 Hz), 7.15 (1H, d, J=7.1 Hz), 7.30 (1H, d, J=7.8 Hz).

f) Production of 1-[2-(tert-butoxycarbonylaminomethyl)-6-chlorophenyl]-3-phenyl-2-propanone

[Chem. 127]

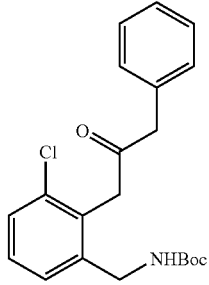

Under an argon gas stream, 573 mg of tert-butyl(3-chloro-2-methylbenzyl)carbamate was dissolved in 10 mL of THF, and 739 μL of TMEDA and 4.88 mL of s-BuLi (1.01 M THF solution) were sequentially added dropwise at −78° C. It was elevated to −30° C., followed by stirring at the same temperature for 5 minutes. It was cooled to −78° C. again, and a solution of 440 mg of N-methoxy-N-methylbenzamide in 3 mL of THF was added dropwise thereto. After stirring at −78° C. for 30 minutes, it was warmed to −30° C., followed by stirring for 2 hours, and it was further warmed to room temperature, followed by stirring for 1 hour. After completion of the reaction, water was added thereto, followed by extraction with chloroform. The organic layer was washed with saturated brine, dried over anhydrous sodium sulfate and then concentrated under reduced pressure. The residue obtained was purified using silica gel chromatography (hexane:ethyl acetate=5:1) to obtain 527 mg (yield 63%) of a title compound as a white solid.

$^1$H-NMR (CDCl$_3$) δ: 1.44 (9H, s), 3.86 (2H, s), 4.01 (2H, s), 4.16 (2H, d, J=5.4 Hz), 4.74 (1H, brs), 7.15-7.22 (2H, m), 7.23-7.37 (6H, m).

g) Production of 3-benzyl-5-chloro-1,2,3,4-tetrahydroisoquinoline

[Chem. 128]

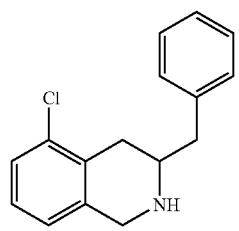

427 mg of 1-[2-(tert-butoxycarbonylaminomethyl)-6-chlorophenyl]-3-phenyl-2-propanone was dissolved in 5 mL of methylene chloride, and 3 mL of trifluoroacetic acid was added thereto under ice-cooling, followed by stirring at room temperature for 1 hour. After confirming the loss of the starting material, it was concentrated under reduced pressure, and the residue obtained was dissolved in 5 mL of ethanol. 173 mg of sodium borohydride was added thereto under ice-cooling, followed by stirring at room temperature for 1 hour. After completion of the reaction, a saturated aqueous sodium hydrogen carbonate solution was added thereto, followed by extraction with chloroform. The organic layer was washed with saturated brine, dried over anhydrous sodium sulfate and then concentrated under reduced pressure. The residue obtained was recrystallized using chloroform hexane to obtain 173 mg of a title compound as a white crystal. Further, a mother liquor upon recrystallization operation was purified using PLC (chloroform:methanol=20:1) to obtain 88.6 mg of a title compound as a pale yellow oily substance. In total, 262 mg (yield 89%) of a title compound was obtained.

$^1$H-NMR (CDCl$_3$) δ: 2.95-3.07 (2H, m), 3.10 (1H, dd, J=10.7, 12.8 Hz), 3.57-3.67 (1H, m), 3.69 (1H, dd, J=3.9, 12.8 Hz), 4.36 (1H, d, J=16.1 Hz), 4.51 (1H, d, J=16.1 Hz), 7.04 (1H, d, J=7.7 Hz), 7.17 (1H, dd, J=7.7, 7.7 Hz), 7.26-7.32 (4H, m), 7.33-7.39 (2H, m).

h) Production of N-benzyl-2-(3-benzyl-5-chloro-3,4-dihydroisoquinolin-2(1H)-yl)ethanamine

[Chem. 129]

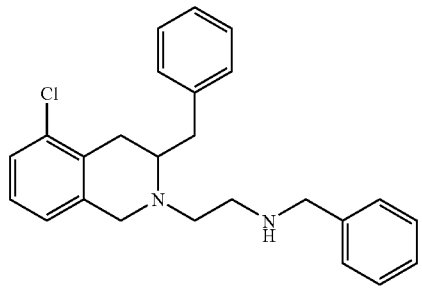

The reaction and treatment were carried out in the same manner as in Examples 32-f and g) to obtain a title compound as a pale yellow oily substance.

$^1$H-NMR (DMSO-d$_6$) δ: 2.39 (1H, dd, J=9.6, 13.1 Hz), 2.56 (1H, dd, J=4.8, 12.3 Hz), 2.60-2.72 (3H, m), 2.73-2.86 (2H, m), 2.88 (1H, dd, J=4.9, 13.1 Hz), 3.22-3.34 (1H, m), 3.75 (2H, s), 3.79 (2H, s), 7.06-7.14 (2H, m), 7.16-7.32 (11H, m).

Example 29

Production of N-benzyl-2-[3-benzyl-6-chloro-3,4-dihydroisoquinolin-2(1H)-yl]ethanamine a) Production of 3-benzyl-6-chloro-1,2,3,4-tetrahydroisoquinoline

[Chem. 130]

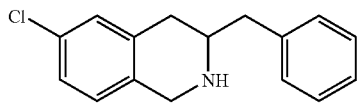

The reaction and treatment were carried out in the same manner as in Example 28-a, b, c, d, e, f, g) using 4-chloro-2-methylbenzoic acid instead of 3-chloro-2-methylbenzoic acid to obtain a title compound as a pale yellow oily substance.

$^1$H-NMR (CDCl$_3$) δ: 2.62 (1H, dd, J=10.2, 16.6 Hz), 2.73-2.77 (1H, m), 2.79 (1H, dd, J=7.8, 13.4 Hz), 2.89 (1H, dd, J=5.8, 13.4 Hz), 3.09-3.17 (1H, m), 3.95 (1H, d, J=15.8 Hz), 4.00 (1H, d, J=15.8 Hz), 6.94 (1H, d, J=8.0 Hz), 7.06-7.09 (2H, m), 7.24-7.28 (3H, m), 7.32-7.36 (2H, m).

b) Production of tert-butyl benzyl[2-[3-benzyl-6-chloro-3,4-dihydroisoquinolin-2(1H)-yl]ethyl]carbamate

[Chem. 131]

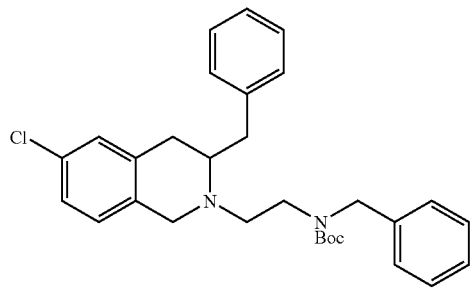

The reaction and treatment were carried out in the same manner as in Example 32-f) to obtain a title compound as a pale yellow oily substance.

$^1$H-NMR (CDCl$_3$) δ: 1.44-1.48 (9H, br), 2.35-2.86 (6H, m), 3.09-3.46 (3H, m), 3.69-3.84 (2H, m), 4.44-4.49 (2H, m), 6.92-7.33 (13H, m).

c) Production of N-benzyl-2-[3-benzyl-6-chloro-3,4-dihydroisoquinolin-2(1H)-yl]ethanamine

[Chem. 132]

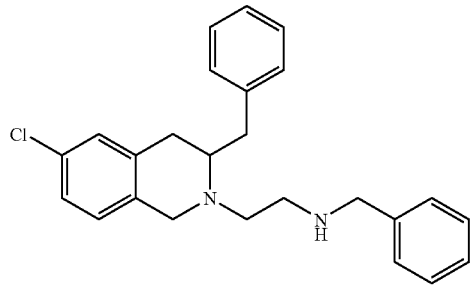

The reaction and treatment were carried out in the same manner as in Example 32-g) to obtain a title compound as a pale yellow oily substance.

$^1$H-NMR (CDCl$_3$) δ: 2.42 (1H, dd, J=10.2, 13.2 Hz), 2.52 (1H, dd, J=3.6, 16.6 Hz), 2.74-2.92 (6H, m), 3.17-3.23 (1H, m), 3.74 (2H, s), 3.79 (2H, s), 6.96 (1H, d, J=8.3 Hz), 7.05

(1H, m), 7.09 (1H, d, J=8.3 Hz), 7.09 (1H, s), 7.12 (1H, dd, J=2.2, 8.3 Hz), 7.17-7.33 (8H, m).

Example 30

Production of N-benzyl-2-[3-benzyl-8-chloro-3,4-dihydroisoquinolin-2(1H)-yl]ethanamine a) Production of 3-benzyl-8-chloro-1,2,3,4-tetrahydroisoquinoline

[Chem. 133]

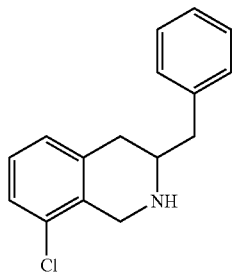

The reaction and treatment were carried out in the same manner as in Example 28-a, b, c, d, e, f, g) using 2-chloro-6-methylbenzoic acid instead of 3-chloro-2-methylbenzoic acid to obtain a title compound as a pale yellow oily substance.

¹H-NMR (CDCl₃) δ: 2.64 (1H, dd, J=10.4, 16.3 Hz), 2.74-2.79 (1H, m), 2.80 (1H, dd, J=7.8, 13.4 Hz), 2.88 (1H, dd, J=5.9, 13.4 Hz), 3.08-3.15 (1H, m), 3.87 (1H, d, J=16.7 Hz), 4.19 (1H, d, J=16.7 Hz), 6.97 (1H, d, J=7.8 Hz), 7.06 (1H, dd, J=7.8, 7.8 Hz), 7.16 (1H, d, J=7.8 Hz), 7.24-7.27 (3H, m), 7.31-7.36 (2H, m).

b) Production of tert-butyl benzyl[2-[3-benzyl-8-chloro-3,4-dihydroisoquinolin-2(1H)-yl]ethyl]carbamate

[Chem. 134]

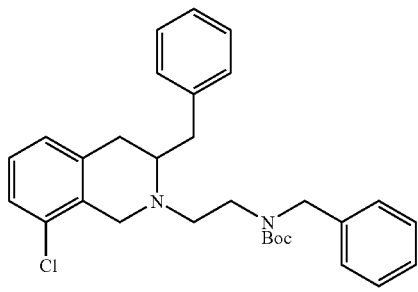

The reaction and treatment were carried out in the same manner as in Example 32-f) to obtain a title compound as a pale yellow oily substance.

¹H-NMR (CDCl₃) δ: 1.44-1.49 (9H, br), 2.34-2.87 (6H, m), 3.08-3.47 (3H, m), 3.69-3.84 (2H, m), 4.44-4.49 (2H, m), 6.95 (1H, d, J=7.8 Hz), 7.05-7.12 (3H, m), 7.18-7.33 (9H, m).

c) Production of N-benzyl-2-[3-benzyl-8-chloro-3,4-dihydroisoquinolin-2(1H)-yl]ethanamine

[Chem. 135]

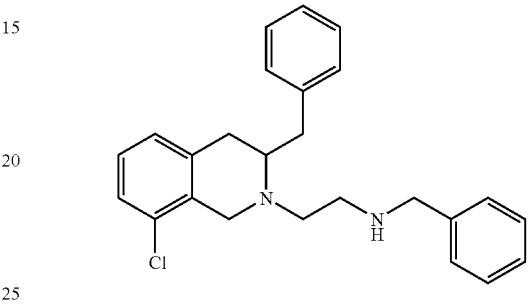

The reaction and treatment were carried out in the same manner as in Example 32-g) to obtain a title compound as a pale yellow oily substance.

¹H-NMR (CDCl₃) δ: 2.41 (1H, dd, J=10.2, 13.2 Hz), 2.56 (1H, dd, J=3.3, 16.4 Hz), 2.76-2.95 (6H, m), 3.19-3.25 (1H, m), 3.68 (1H, d, J=17.1 Hz), 3.81 (2H, s), 3.89 (1H, d, J=17.1 Hz), 6.97 (1H, d, J=7.6 Hz), 7.05-7.12 (3H, m), 7.16-7.33 (9H, m).

Example 31

Production of N-benzyl-2-[3-benzyl-5-fluoro-3,4-dihydroisoquinolin-2(1H)-yl]ethanamine a) Production of 3-fluoro-2-methylbenzyl alcohol

[Chem. 136]

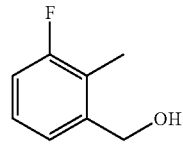

The reaction and treatment were carried out in the same manner as in Example 28-a) using 3-fluoro-2-methylbenzoic acid instead of 3-chloro-2-methylbenzoic acid to obtain a title compound as a colorless clear oily substance.

¹H-NMR (CDCl₃) δ: 2.26 (3H, d, J=2.0 Hz), 4.71 (2H, s), 6.94-7.01 (1H, m), 7.06-7.20 (2H, m).

b) Production of N-(3-fluoro-2-methylbenzyl)phthalimide

[Chem. 137]

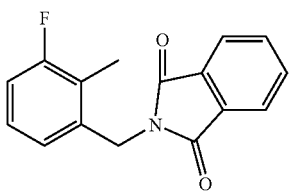

The reaction and treatment were carried out in the same manner as in Examples 28-b and c) to obtain a title compound as a white solid.

$^1$H-NMR (CDCl$_3$) δ: 2.39 (3H, d, J=2.2 Hz), 4.87 (2H, s), 6.91-6.98 (1H, m), 7.04 7.12 (2H, m), 7.74 (2H, dd, J=3.1, 5.4 Hz), 7.87 (2H, dd, J=3.1, 5.4 Hz).

c) Production of 3-fluoro-2-methylbenzylamine

[Chem. 138]

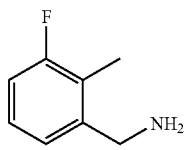

The reaction and treatment were carried out in the same manner as in Example 28-d) to obtain a title compound as a colorless clear oily substance.

$^1$H-NMR (CDCl$_3$) δ: 2.25 (3H, d, J=2.4 Hz), 3.87 (2H, s), 6.93 (1H, dd, J=8.5, 8.5 Hz), 7.08-7.18 (2H, m).

d) Production of tert-butyl(3-fluoro-2-methylbenzyl)carbamate

[Chem. 139]

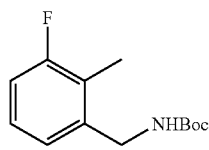

The reaction and treatment were carried out in the same manner as in Example 28-e) to obtain a title compound as a white solid.

$^1$H-NMR (CDCl$_3$) δ: 1.46 (9H, s), 2.23 (3H, d, J=2.0 Hz), 4.32 (2H, d, J=5.6 Hz), 4.70 (1H, brs), 6.96 (1H, dd, J=8.3, 8.3 Hz), 7.03 (1H, d, J=8.3 Hz), 7.09-7.16 (1H, m).

e) Production of 1-[2-(tert-butoxycarbonylaminomethyl)-6-fluorophenyl]-3-phenyl-2-propanone

[Chem. 140]

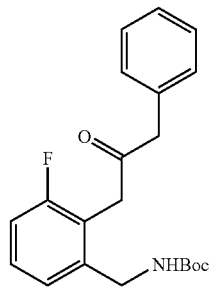

The reaction and treatment were carried out in the same manner as in Example 28-f) to obtain a title compound as a white solid.

$^1$H-NMR (CDCl$_3$) δ: 1.44 (9H, s), 3.83 (2H, s), 3.87 (2H, s), 4.15 (2H, d, J=5.4 Hz), 4.79 (1H, brs), 6.98 (1H, dd, J=8.6, 8.6 Hz), 7.09 (1H, d, J=8.6, 8.6 Hz), 7.18-7.37 (6H, m).

f) Production of 3-benzyl-5-fluoro-1,2,3,4-tetrahydroisoquinoline

[Chem. 141]

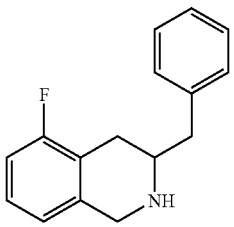

The reaction and treatment were carried out in the same manner as in Example 28-g) to obtain a title compound as a pale yellow oily substance.

$^1$H-NMR (CDCl$_3$) δ: 2.18 (1H, brs), 2.48 (1H, dd, J=10.8, 16.9 Hz), 2.81 (1H, dd, J=8.1, 13.5 Hz), 2.88 (1H, dd, J=3.8, 16.9 Hz), 2.95 (1H, dd, J=5.5, 13.5 Hz), 3.08-3.16 (1H, m), 3.98 (1H, d, J=15.8 Hz), 4.03 (1H, d, J=15.8 Hz), 6.80 (1H, d, J=7.8 Hz), 6.85 (1H, dd, J=8.9, 8.9 Hz), 7.04-7.11 (1H, m), 7.23-7.29 (3H, m), 7.31-7.36 (2H, m).

g) Production of N-benzyl-2-[3-benzyl-5-fluoro-3,4-dihydroisoquinolin-2(1H)-yl]ethanamine

[Chem. 142]

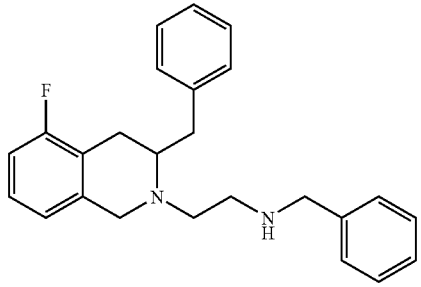

The reaction and treatment were carried out in the same manner as in Examples 32-f and g) to obtain a title compound as a pale yellow oily substance.

$^1$H-NMR (CDCl$_3$) δ: 2.47 (1H, dd, J=9.7, 13.3 Hz), 2.64-2.68 (2H, m), 2.72-2.80 (3H, m), 2.84-2.96 (2H, m), 3.03-3.30 (1H, m), 3.79 (2H, s), 3.80 (2H, s), 6.83 (1H, d, J=7.6 Hz), 6.87 (1H, dd, J=8.7, 8.7 Hz), 7.08-7.15 (3H, m), 7.17-7.32 (8H, m).

Example 32

Production of N-benzyl-2-[3-benzyl-6-fluoro-3,4-dihydroisoquinolin-2(1H)-yl]ethanamine a) Production of methyl 2-benzyl-6-fluoro-1,2,3,4-tetrahydroisoquinoline-3-carboxylate

[Chem. 143]

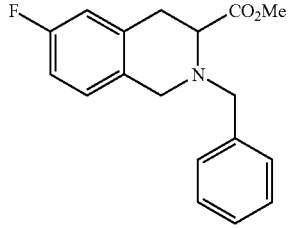

702 mg of methyl 6-fluoro-1,2,3,4-tetrahydroisoquinoline-3-carboxylate, 425 mg of benzyl chloride, and 425 mg of potassium carbonate were dissolved in 5 mL of acetonitrile, followed by stirring under reflux for 3 hours. Water was added to the reaction liquid, followed by extraction with ethyl acetate. The organic layer was then washed with saturated brine, dried over anhydrous sodium sulfate and then concentrated under reduced pressure. The residue obtained was purified using silica gel chromatography (acetone:n-hexane=1:20) to obtain 460 mg (yield 46%) of a title compound as a pale yellow oily substance.

$^1$H-NMR (CDCl$_3$) δ: 3.09 (1H, dd, J=3.7, 16.1 Hz), 3.09 (1H, dd, J=3.7, 16.1 Hz), 3.68 (3H, s), 3.75-3.82 (2H, m), 3.92-4.00 (3H, m), 6.79-6.87 (2H, m), 6.91-6.96 (1H, m), 7.25-7.40 (5H, m).

b) Production of 2-benzyl-6-fluoro-1,2,3,4-tetrahydroisoquinoline-3-carboxylic acid

[Chem. 144]

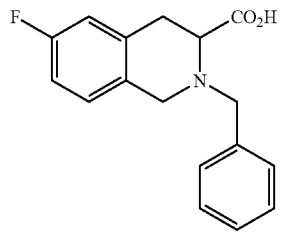

460 mg of methyl 2-benzyl-6-fluoro-1,2,3,4-tetrahydroisoquinoline-3-carboxylate and 640 mg of lithium hydroxide.monohydrate were dissolved in 5 mL of THF:H$_2$O=1:1, followed by stirring under reflux for 1 hour. Water was added to the reaction liquid, followed by neutralization by addition of ammonium chloride and an aqueous sodium bicarbonate solution and extraction with chloroform, and the organic layer was then washed with saturated brine, dried over anhydrous sodium sulfate and then concentrated under reduced pressure to obtain 436 mg (yield 99%) of a title compound as a pale yellow oily substance.

c) Production of N-methoxy-N-methyl-(2-benzyl-6-fluoro-1,2,3,4-tetrahydroisoquinoline)-3-carboxamide

[Chem. 145]

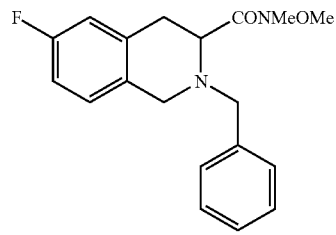

436 mg of 2-benzyl-6-fluoro-1,2,3,4-tetrahydroisoquinoline-3-carboxylic acid, 164 mg of N,O-dimethylhydroxylamine monohydrochloride, 743 mg of a BOP-Reagent, and 340 mg of triethylamine were dissolved in 10 mL of dichloromethane, followed by stirring at room temperature for 3 hours. Water was added to the reaction liquid, followed by extraction with chloroform. The organic layer was then washed with an aqueous sodium bicarbonate solution and then with saturated brine, dried over anhydrous sodium sulfate and then concentrated under reduced pressure. The residue obtained was purified using silica gel chromatography (chloroform:saturated ammonia-methanol=10:1) to obtain 474 mg (yield 94%) of a title compound as a pale yellow solidified product.

¹H-NMR (CDCl₃) δ: 3.06-3.14 (1H, m), 3.15 (3H, s), 3.38-3.49 (1H, m), 3.61 (3H, s), 4.14-4.60 (5H, m), 6.84-6.94 (2H, m), 7.06-7.12 (1H, m), 7.34-7.41 (3H, m), 7.42-7.48 (2H, m).

d) Production of 3-benzoyl-2-benzyl-6-fluoro-1,2,3,4-tetrahydroisoquinoline

[Chem. 146]

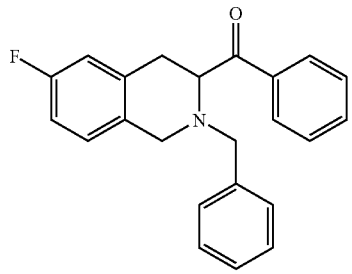

Under an argon gas stream, 200 mg of N-methoxy-N-methyl-(2-benzyl-6-fluoro-1,2,3,4-tetrahydroisoquinoline)-3-carboxyamide was dissolved in 4 mL of anhydrous THF, followed by stirring under cooling with ice. To the reaction liquid was slowly added 0.9 mL of phenyl magnesium chloride (2 mol/L THF solution), followed by continuously stirring for 1.5 hours. Water was added to the reaction liquid, followed by extraction with chloroform. The organic layer was then washed with diluted hydrochloric acid and saturated brine, dried over anhydrous sodium sulfate and then concentrated under reduced pressure. The residue obtained was purified using silica gel chromatography (acetone:hexane=1:8) to obtain 66 mg (yield 31%) of a title compound as a yellow oily substance.

¹H-NMR (CDCl₃) δ: 3.05 (1H, dd, J=6.1, 17.2 Hz), 3.29 (1H, dd, J=6.8, 17.2 Hz), 3.47-3.51 (1H, m), 3.63 (1H, d, J=13.2 Hz), 3.76-3.84 (3H, m), 3.88-3.96 (1H, m), 4.53 (1H, dd, J=6.5, 6.5 Hz), 6.81-6.89 (2H, m), 6.91-6.96 (1H, m), 7.17-7.30 (5H, m), 7.44-7.52 (2H, m), 7.56-7.62 (1H, m), 8.06-8.13 (2H, m).

e) Production of 3-benzyl-6-fluoro-1,2,3,4-tetrahydroisoquinoline

[Chem. 147]

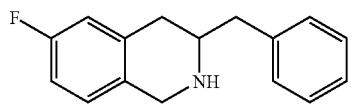

66 mg of 3-benzoyl-2-benzyl-6-fluoro-1,2,3,4-tetrahydroisoquinoline and 30 mg of 10% Pd—C were dissolved in 2 mL of ethanol and 2 mL of 4N hydrochloric acid, followed by stirring at room temperature for 48 hours under a hydrogen atmosphere. The reaction liquid was filtered through Celite, and the filtrate was concentrated under reduced pressure, and the residue obtained was purified using silica gel chromatography (chloroform:methanol=5:1) to obtain 8 mg (yield 18%) of a title compound as a yellow oily substance.

¹H-NMR (CDCl₃) δ: 2.64 (1H, dd, J=10.2, 16.6 Hz), 2.73-2.80 (1H, m), 2.81 (1H, dd, J=7.8, 13.4 Hz), 2.89 (1H, dd, J=5.8, 13.4 Hz), 3.10-3.20 (1H, m), 3.97 (1H, d, J=15.4 Hz), 4.01 (1H, d, J=15.4 Hz), 6.76 (1H, dd, J=2.6, 9.5 Hz), 6.81 (1H, ddd, J=2.6, 8.5, 8.5 Hz), 6.96 (1H, dd, J=5.8, 8.5 Hz), 7.24-7.28 (3H, m), 7.32-7.37 (2H, m).

f) Production of tert-butyl benzyl[2-[3-benzyl-6-fluoro-3,4-dihydroisoquinolin-2(1H)-yl]ethyl]carbamate

[Chem. 148]

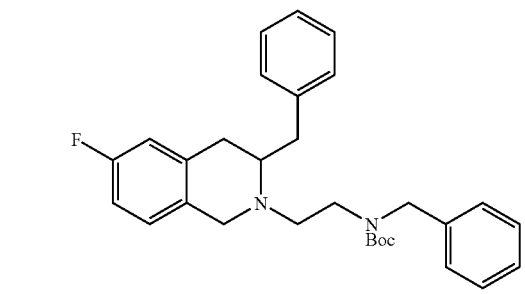

8 mg of 3-benzyl-6-fluoro-1,2,3,4-tetrahydroisoquinoline, 9.3 mg of tert-butyl benzyl(2-oxoethyl)carbamate, 11 mg of sodium triacetoxyborohydride, and 10 μL of acetic acid were dissolved in 0.5 mL of toluene, followed by continuously stirring at room temperature for 30 minutes. Water was added to the reaction liquid, followed by extraction with ethyl acetate, and the organic layer was then washed with an aqueous sodium bicarbonate solution and saturated brine, dried over anhydrous sodium sulfate and then concentrated under reduced pressure. The residue obtained was purified using silica gel chromatography (diethyl ether:hexane=1:2) to obtain 14 mg (yield 85%) of a title compound as a yellow oily substance.

¹H-NMR (CDCl₃) δ: 1.40-1.50 (9H, br), 2.34-3.50 (9H, m), 3.69-3.86 (2H, m), 4.40-4.50 (2H, m), 6.74 (1H, dd, J=2.6, 9.5 Hz), 6.84 (1H, ddd, J=2.6, 8.4, 8.4 Hz), 6.92-7.00 (1H, m), 7.04-7.14 (2H, m), 7.18-7.34 (8H, m).

g) Production of N-benzyl-2-[3-benzyl-6-fluoro-3,4-dihydroisoquinolin-2(1H)-yl]ethanamine

[Chem. 149]

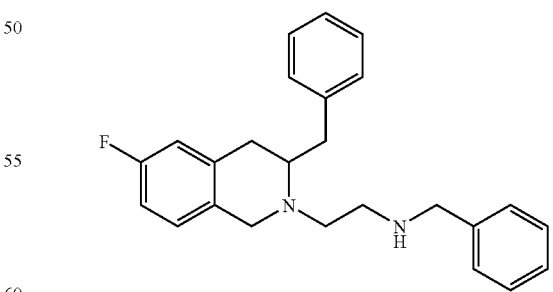

13 mg of tert-butyl benzyl[2-[3-benzyl-6-fluoro-3,4-dihydroisoquinolin-2(1H)-yl]ethyl]carbamate was dissolved in 0.5 mL of a 4N hydrochloric acid-ethyl acetate solution, followed by continuously stirring at room temperature for 30 minutes. The reaction liquid was concentrated under reduced pressure, dissolved in ethyl acetate, washed with an aqueous sodium bicarbonate solution and saturated brine, dried over anhydrous sodium sulfate and then concentrated under reduced pressure. The residue obtained was purified using silica gel chromatography (chloroform:methanol=10:1) to obtain 10 mg (yield 99%) of a title compound as a light yellow oily substance.

$^1$H-NMR (CDCl$_3$) δ: 2.44 (1H, dd, J=10.2, 13.1 Hz), 2.53 (1H, dd, J=3.7, 16.6 Hz), 2.74-2.90 (6H, m), 3.16-3.24 (1H, m), 3.74 (2H, s), 3.80 (2H, s), 6.76 (1H, dd, J=2.7, 9.5 Hz), 6.85 (1H, ddd, J=2.7, 8.3, 8.3 Hz), 6.98 (1H, dd, J=5.8, 8.3 Hz), 7.06-7.12 (2H, m), 7.16-7.34 (8H, m).

Example 33

Production of N-benzyl-2-[3-benzyl-7-fluoro-3,4-dihydroisoquinolin-2(1H)-yl]ethanamine a) Production of N-methoxy-N-methyl-(7-fluoro-2-methoxycarbonyl-1,2,3,4-tetrahydroisoquinoline)-3-carboxyamide

[Chem. 150]

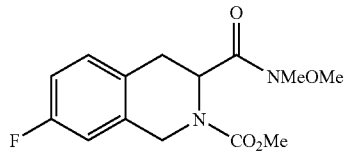

To a solution of 274 mg of 4-fluorophenylalanine and 300 mg of triethylamine in 1 mL of methylene chloride was added dropwise a solution of 284 mg of ice-cooled methylchloroformate in 0.5 mL of methylene chloride, followed by reacting at room temperature for 16 hours. After completion of the reaction, the reaction liquid was diluted by addition of water, acidified with 2N hydrochloric acid, and then extracted with ethyl acetate. The organic layer was washed with a saturated aqueous sodium bicarbonate solution and saturated brine in this order, dried over anhydrous sodium sulfate, and concentrated under reduced pressure to obtain a yellow oily substance. To a solution of 360 mg of the obtained yellow oily substance in 0.6 mL of acetic acid were added 0.2 mL of sulfuric acid and 47 mg of paraformaldehyde, followed by reacting at room temperature for 18 hours. After completion of the reaction, under ice-cooling, the reaction liquid was diluted by addition of water, alkalized with 5 N sodium hydroxide, followed by extraction with ethyl acetate. The organic layer was washed with water and saturated brine, dried over anhydrous sodium sulfate, and concentrated under reduced pressure to obtain a yellow oily substance. 380 mg of the obtained yellow oily substance, 176 mg of N,O-dimethylhydroxylamine monohydrochloride, 797 mg of a BOP reagent, and 450 mg of triethylamine were dissolved in 5 mL of dichloromethane, followed by stirring at room temperature for 3 hours. Water was added to the reaction liquid, followed by extraction with chloroform. The organic layer was then washed with saturated brine, dried over anhydrous sodium sulfate and then concentrated under reduced pressure. The residue obtained was purified by silica gel chromatography (chloroform alone) to obtain 66 mg (yield 23%) of a title compound as a pale yellow oily substance.

$^1$H-NMR (CDCl$_3$) δ: 2.96 (0.7H, m), 3.13-3.20 (3.3H, m), 3.67-3.80 (4H, m), 3.85 (2H, s), 4.56-4.88 (3H, m), 5.05 (0.3H, dd, J=5.9, 5.9 Hz), 5.20 (0.7H, dd, J=5.9, 5.9 Hz), 6.85-7.11 (3H, m).

b) Production of 3-benzoyl-7-fluoro-2-methoxycarbonyl-1,2,3,4-tetrahydroisoquinoline

[Chem. 151]

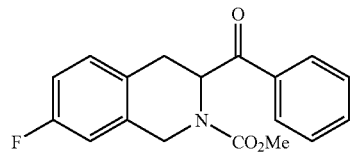

Under an argon gas stream, 60 mg of N-methoxy-N-methyl-(7-fluoro-2-methoxycarbonyl-1,2,3,4-tetrahydroisoquinoline)-3-carboxyamide was dissolved in 1 mL of anhydrous THF, followed by stirring under cooling with ice. To the reaction liquid was slowly added 0.8 mL of phenyl magnesium bromide (1 mol/L THF solution), followed by continuously stirring for 30 minutes. Water was added to the reaction liquid, followed by extraction with chloroform. The organic layer was then washed with diluted hydrochloric acid and saturated brine, dried over anhydrous sodium sulfate and then concentrated under reduced pressure. The residue obtained was purified by silica gel chromatography (chloroform alone) to obtain 15 mg (yield 19%) of a title compound as a yellow oily substance.

$^1$H-NMR (CDCl$_3$) δ: 3.05-3.26 (2H, m), 3.69 (1H, s), 3.79 (2H, s), 4.55 (0.7H, d, J=16.6 Hz), 4.60 (0.3H, d, J=16.4 Hz), 4.81 (0.7H, d, J=16.6 Hz), 4.87 (0.3H, d, J=16.4 Hz), 5.70 (0.3H, dd, J=4.8, 6.5 Hz), 5.92 (0.7H, dd, J=3.7, 6.3 Hz), 6.82-7.02 (3H, m), 7.45-7.62 (3H, m), 7.87-7.93 (2H, m).

c) Production of N-benzyl-2-[3-benzyl-7-fluoro-3,4-dihydroisoquinolin-2(1H)-yl]ethanamine

[Chem. 152]

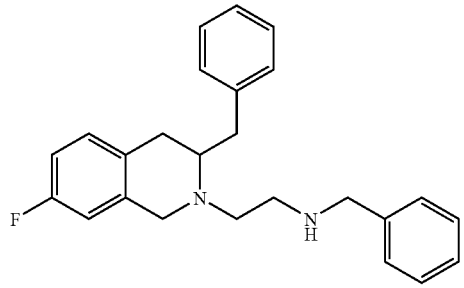

A solution of 12 mg of 3-benzoyl-7-fluoro-2-methoxycarbonyl-1,2,3,4-tetrahydroisoquinoline in 2 mL of a 6 N aqueous hydrochloric acid solution was reacted under reflux for 16 hours. Under ice-cooling, the reaction liquid was diluted by addition of water, alkalized with 5 N sodium hydroxide, and extracted with chloroform. The organic layer was washed with saturated brine, dried over anhydrous sodium sulfate, and concentrated under reduced pressure to obtain a yellow oily substance. 10 mg of the obtained yellow oily substance and 3 mg of 10% Pd-C were dissolved in 2 mL of ethanol and 0.2 mL of a 4N hydrochloric acid/ethyl acetate solution, followed by stirring at room temperature for 48 hours under a hydrogen atmosphere. The reaction liquid was filtered through Celite, and the filtrate was concentrated under reduced pressure to obtain 8 mg of a yellow oily substance. To a solution of 8 mg of the yellow oily substance and 9 mg of N-Boc-2-benzylaminoethanol in 1 mL of toluene were sequentially added 9 mg of sodium triacetoxyborohydride and 5 mg of acetic acid, followed by stirring at room temperature for 2 hours. It was alkalized by addition of an aqueous sodium bicarbonate solution, followed by extraction with ethyl acetate. The organic layer was washed with brine and then dried over anhydrous sodium sulfate, and the solvent was removed by evaporation to obtain 10 mg of a yellow oily substance. To this yellow oily substance was added 2 mL of 4N hydrochloric acid/ethyl acetate, followed by stirring at room temperature for 30 minutes. The organic layer was washed with an aqueous sodium bicarbonate solution and then with brine, and then dried over anhydrous sodium sulfate, and the solvent was removed by evaporation. The residue obtained was purified using silica gel chromatography (chloroform: methanol=10:1) to obtain 2 mg (yield 41%) of a title compound as a yellow oily substance.

$^1$H-NMR (CDCl$_3$) δ: 2.47 (1H, dd, J=9.6, 13.4 Hz), 2.52 (1H, dd, J=3.4, 15.8 Hz), 2.75-2.81 (4H, m), 2.86-2.92 (2H, m), 3.21-3.26 (1H, m), 3.74 (2H, s), 3.80 (2H, s), 6.73 (1H, dd, J=2.4, 9.3 Hz), 6.85 (1H, ddd, J=2.4, 8.3, 8.3 Hz), 7.00 (1H, dd, J=5.6, 8.3 Hz), 7.10 (2H, d, J=7.1 Hz), 7.17-7.32 (8H, m).

Example 34

Production of N-benzyl-2-[3-benzyl-8-fluoro-3,4-dihydroisoquinolin-2(1H)-yl]ethanamine a) Production of t-butyl N-(2-fluoro-6-iodobenzyl)carbamate

[Chem. 153]

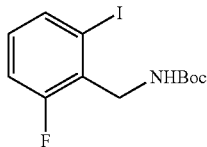

Under an argon atmosphere, 123 mg of 2-fluoro-6-iodobenzonitrile was dissolved in 2 mL of tetrahydrofuran, and 1.5 mL of a borane/tetrahydrofuran complex was added thereto, followed by stirring under reflux overnight. The reaction liquid was cooled to room temperature, and 2N hydrochloric acid was added thereto, followed by further stirring for 1 hour. After completion of the reaction, to the reaction liquid was added an aqueous sodium bicarbonate solution, followed by extraction with ethyl acetate, and the organic layer was then washed with an aqueous sodium bicarbonate solution and saturated brine, dried over anhydrous sodium sulfate and then concentrated under reduced pressure to obtain 87 mg (70%) of 2-fluoro-6-iodobenzylamine as a light yellow oily substance. This product, 68 mg of di-tert-butyl dicarbonate, and 31 mg of triethylamine were dissolved in 1 mL of chloroform, followed by stirring at room temperature for 1 hour. After completion of the reaction, water was added to the reaction liquid, followed by extraction with chloroform. The organic layer was then washed with an aqueous sodium bicarbonate solution and saturated brine, dried over anhydrous sodium sulfate and then concentrated under reduced pressure. The residue obtained was purified using PLC (n-hexane:ethyl acetate=2:1) to obtain 80 mg (yield 81%) of a title compound as a light yellow solid.

$^1$H-NMR (CDCl$_3$) δ: 1.45 (9H, s), 4.50 (2H, s), 6.95-7.00 (1H, m), 7.04-7.08 (1H, m), 7.63 (1H, d, J=7.8 Hz).

b) Production of t-butyl N-(2-fluoro-6-cinnamylbenzyl)carbamate

[Chem. 154]

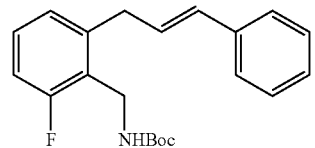

Under an argon atmosphere, 300 mg of t-butyl N-(2-fluoro-6-iodobenzyl)carbamate, 0.29 mL of cinnamyl acetate, 1.28 mL of bistributyltin, and 70 mg of PdCl$_2$(dppf)$_2$ were dissolved in 2.5 mL of DMF, followed by stirring at 120° C. for 2 hours. After completion of the reaction, to the reaction liquid was added diethyl ether, followed by filtration through Celite, and to the filtrate was added water, followed by extraction with diethyl ether. Then, the organic layer was washed with an aqueous sodium bicarbonate solution and saturated brine, dried over anhydrous sodium sulfate and then concentrated under reduced pressure. The residue obtained was purified using PLC (n-hexane:ethyl acetate=3:1) to obtain 121 mg (yield 52%) of a title compound as a yellow solid.

$^1$H-NMR (CDCl$_3$) δ: 1.51 (9H, s), 3.69 (2H, d, J=3.9 Hz), 4.42 (2H, d, J=5.1 Hz), 4.70 (1H, br), 6.33-6.36 (2H, m), 6.95 (1H, dd, J=8.8, 8.8 Hz), 7.04 (1H, d, H=7.6 Hz), 7.17-7.23 (2H, m), 7.25-7.34 (4H, m).

c) Production of N-(2-fluoro-6-cinnamylbenzyl)-2-methoxycarbonylethanesulfonamide

[Chem. 155]

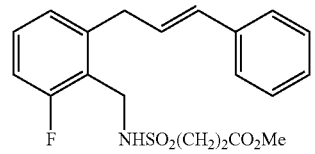

34 mg of t-butyl N-(2-fluoro-6-cinnamylbenzyl)carbamate was dissolved in a 4N hydrochloric acid/ethyl acetate solution, followed by stirring at room temperature for 1 hour. After completion of the reaction, to the reaction liquid was added an aqueous sodium bicarbonate solution, followed by extraction with ethyl acetate, and the organic layer was then washed with an aqueous sodium bicarbonate solution and saturated brine, dried over anhydrous sodium sulfate and then concentrated under reduced pressure to obtain 24 mg of a crude composition of 2-fluoro-6-cinnamylbenzylamine as a light yellow oily substance. The obtained crude composition, 19 mg of 2-methoxycarbonylethylsulfonylchloride, and 21 mg of sodium carbonate were dissolved in 1 mL of methylene chloride and 1 mL of water, followed by stirring under ice-cooling for 1 hour. After completion of the reaction, water was added to the reaction liquid, followed by extraction with chloroform. The organic layer was then washed with an aqueous sodium bicarbonate solution and saturated brine, dried over anhydrous sodium sulfate and then concentrated under reduced pressure. The residue obtained was purified using PLC (n-hexane:ethyl acetate=2:1) to obtain 29 mg (yield 79%) of a title compound as a yellow solid.

$^1$H-NMR (CDCl$_3$) δ: 2.73 (1H, d, J=7.3 Hz), 2.75 (1H, d, J=7.6 Hz), 3.27 (1H, d, J=7.6 Hz), 3.29 (1H, d, J=7.3 Hz), 3.68 (3H, s), 3.69 (2H, d, J=6.8 Hz), 4.40 (2H, d, J=4.4 Hz), 4.72 (1H, br), 6.28-6.36 (2H, m), 6.98 (1H, ddd, J=0.9, 9.1, 9.1 Hz), 7.08 (1H, d, J=7.6 Hz), 7.18-7.22 (2H, m), 7.25-7.34 (4H, m).

d) Production of methyl 3-[(3-benzyl-8-fluoroiso-quinolin-2(1H)-yl)sulfonyl]propanoate

[Chem. 156]

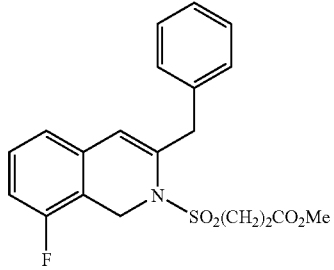

Under an argon atmosphere, 20 mg of N-(2-fluoro-6-cinnamylbenzyl)-2-methoxycarbonylethanesulfonamide, 3 mg of PdCl$_2$(CH$_3$CN)$_2$, 6 mg of benzoquinone, 21 mg of lithium chloride, and 12 mg of sodium carbonate were dissolved in 1 mL of THF, followed by stirring under reflux for 36 hours. After completion of the reaction, to the reaction liquid was added diethyl ether, followed by filtration through Celite, and to the filtrate was added water, followed by extraction with diethyl ether. Then, the organic layer was washed with an aqueous sodium bicarbonate solution and saturated brine, dried over anhydrous sodium sulfate and then concentrated under reduced pressure. The residue obtained was purified using PTLC (n-hexane:ethyl acetate=1:1) to obtain 10 mg (yield 46%) of a title compound as a yellow solid.

$^1$H-NMR (CDCl$_3$) δ: 2.58 (1H, d, J=7.3 Hz), 2.60 (1H, d, J=8.1 Hz), 2.99 (1H, d, J=8.1 Hz), 3.01 (1H, d, J=7.3 Hz), 3.64 (3H, s), 3.96 (2H, s), 4.70 (2H, s), 6.32 (1H, s), 6.90 (1H, d, J=7.3 Hz), 6.98 (1H, dd, J=8.5, 8.5 Hz), 7.20-7.34 (6H, m).

e) Production of methyl 3-[(3-benzyl-8-fluoro-3,4-dihydroisoquinolin-2(1H)-yl)sulfonyl]propanoate

[Chem. 157]

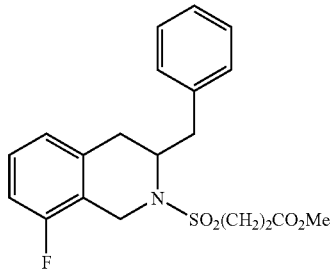

Under a hydrogen atmosphere, 9 mg of methyl 3-[(3-benzyl-8-fluoroisoquinolin-2(1H)-yl)sulfonyl]propanoate and 9 mg of 10% Pd/C were dissolved in 1 mL of ethanol, followed by stirring at room temperature for 2 hours. After completion of the reaction, to the reaction liquid was added diethyl ether, followed by filtration through Celite, and the filtrate was concentrated under reduced pressure to obtain 10 mg (yield 100%) of a title compound as a yellow oily substance.

$^1$H-NMR (CDCl$_3$) δ: 2.44-2.61 (2H, m), 2.71-2.78 (2H, m), 2.89 (1H, dd, J=7.8, 13.2 Hz), 2.91-3.02 (2H, m), 3.10 (1H, dd, J=5.8, 16.3 Hz), 3.64 (3H, s), 4.32 (1H, d, J=17.4 Hz), 4.48-4.53 (1H, m), 4.85 (1H, d, J=17.4 Hz), 6.93 (1H, d, J=8.0 Hz), 6.95 (1H, d, J=8.0 Hz), 7.18-7.25 (4H, m), 7.30-7.34 (2H, m).

f) Production of 3-benzyl-8-fluoro-1,2,3,4-tetrahydroisoquinoline

[Chem. 158]

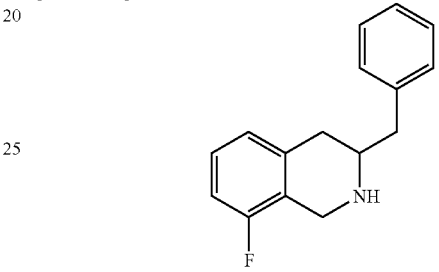

10 mg of methyl 3-[[3-benzyl-8-fluoro-3,4-dihydroisoquinolin-2(1H)-yl]sulfonyl]propanoate was dissolved in 1.5 mL of 3 N hydrochloric acid and 0.5 mL of tert-butanol, followed by stirring at 70° C. for 40 hours.

After completion of the reaction, to the reaction liquid of the filtrate was added water, followed by extraction with ethyl acetate, and the organic layer was then washed with an aqueous sodium bicarbonate solution and saturated brine, dried over anhydrous sodium sulfate and then concentrated under reduced pressure. The residue obtained was purified using PLC (chloroform:methanol=10:1) to obtain 4 mg (yield 77%) of a title compound as a yellow oily substance.

$^1$H-NMR (CDCl$_3$) δ: 2.64 (1H, dd, J=10.5, 16.4 Hz), 2.76-2.91 (3H, m), 3.11-3.18 (1H, m), 3.89 (1H, d, J=16.2 Hz), 4.18 (1H, d, J=16.2 Hz), 6.92-6.97 (2H, m), 6.80-6.85 (2H, m), 7.08 (1H, dd, J=7.8, 13.8 Hz), 7.24-7.28 (3H, m), 7.32-7.36 (2H, m).

g) Production of N-benzyl-2-[3-benzyl-8-fluoro-3,4-dihydroisoquinolin-2(1H)-yl]ethanamine

[Chem. 159]

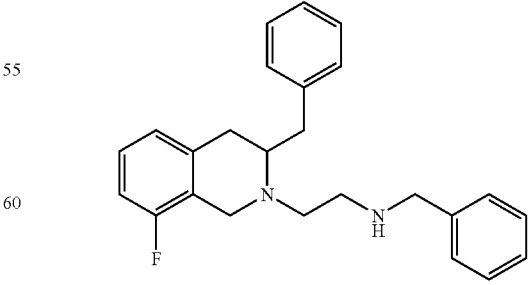

The reaction and treatment were carried out in the same manner as in Examples 32-f and g) to obtain a title compound as a light yellow oily substance.

¹H-NMR (CDCl₃) δ: 2.46 (1H, dd, J=10.0, 13.2 Hz), 2.56 (1H, dd, J=3.4, 16.7 Hz), 2.77-2.95 (6H, m), 3.20-3.25 (1H, m), 3.72 (1H, d, J=16.8 Hz), 3.81 (2H, s), 3.88 (1H, d, J=16.8 Hz), 6.83-6.89 (2H, m), 7.08-7.20 (4H, m), 7.24-7.31 (7H, m).

Example 35

Production of N-benzyl-2-[3-benzyl-6-methoxy-3,4-dihydroisoquinolin-2(1H)-yl]ethanamine a) Production of 4-methoxy-2-methylbenzylalcohol

[Chem. 160]

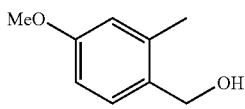

The reaction and treatment were carried out in the same manner as in Example 28-a) using 4-methoxy-2-methylbenzoic acid instead of 3-chloro-2-methylbenzoic acid to obtain a title compound as a colorless clear oily substance.

¹H-NMR (CDCl₃) δ: 1.38 (1H, t, J=5.3 Hz), 2.37 (3H, s), 3.80 (3H, s), 4.64 (2H, d, J=5.3 Hz), 6.72 (1H, dd, J=2.6, 8.1 Hz), 6.75 (1H, d, J=2.6 Hz), 7.24 (1H, d, J=8.1 Hz).

b) Production of 4-methoxy-2-methylbenzyl chloride

[Chem. 161]

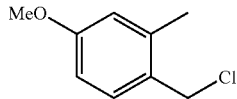

The reaction and treatment were carried out in the same manner as in Example 28-b) to obtain a title compound as a white solid.

¹H-NMR (CDCl₃) δ: 2.41 (3H, s), 3.79 (3H, s), 4.60 (2H, s), 6.71 (1H, d, J=2.6, 8.3 Hz), 6.75 (1H, d, J=2.6 Hz), 7.22 (1H, d, J=8.3 Hz).

c) Production of N-(4-methoxy-2-methylbenzyl)phthalimide

[Chem. 162]

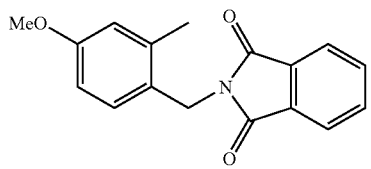

The reaction and treatment were carried out in the same manner as in Example 28-c) to obtain a title compound as a white solid.

¹H-NMR (CDCl₃) δ: 2.47 (3H, s), 3.76 (3H, s), 4.81 (2H, s), 6.68 (1H, dd, J=2.6, 8.3 Hz), 6.71 (1H, d, J=2.6 Hz), 7.28 (1H, d, J=8.3 Hz), 7.71 (2H, dd, J=3.1, 5.4 Hz), 7.84 (2H, d, J=3.1, 5.4 Hz).

d) Production of 4-methoxy-2-methylbenzylamine

[Chem. 163]

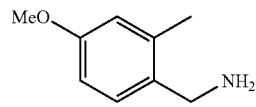

The reaction and treatment were carried out in the same manner as in Example 28-d) to obtain a title compound as a colorless clear oily substance.

¹H-NMR (CDCl₃) δ: 2.33 (3H, s), 3.79 (3H, s), 3.80 (2H, s), 6.70-6.75 (2H, m), 7.20 (1H, d, J=9.0 Hz).

e) Production of tert-butyl (4-methoxy-2-methylbenzyl)carbamate

[Chem. 164]

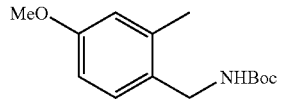

The reaction and treatment were carried out in the same manner as in Example 28-e) to obtain a title compound as a white crystalline powder.

¹H-NMR (CDCl₃) δ: 1.46 (9H, s), 2.31 (3H, s), 3.78 (3H, s), 4.25 (2H, d, J=5.1 Hz), 4.59 (1H, brs), 6.70 (1H, dd, J=2.7, 8.3 Hz), 6.73 (1H, d, J=2.7 Hz), 7.14 (1H, d, J=8.3 Hz).

f) Production of 1-[2-(tert-butoxycarbonylaminomethyl)-5-methoxyphenyl]-3-phenyl-2-propanone

[Chem. 165]

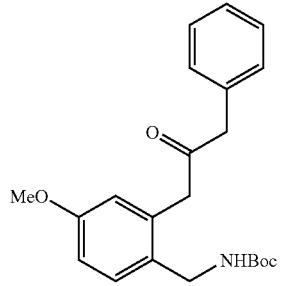

The reaction and treatment were carried out in the same manner as in Example 28-f) to obtain a title compound as a pale yellow oily substance.

¹H-NMR (CDCl₃) δ: 1.43-1.44 (9H, m), 3.75 (2H, s), 3.75 (2H, s), 3.79 (3H, s), 4.11 (1H, d, J=5.4 Hz), 4.18 (1H, d,

J=5.4 Hz), 4.74 (1H, brs), 6.55 (1H, d, J=2.4 Hz), 6.69 (1H, s), 6.71-6.78 (2H, m), 7.15-7.38 (4H, m).

g) Production of 3-benzyl-6-methoxy-1,2,3,4-tetrahydroisoquinoline

[Chem. 166]

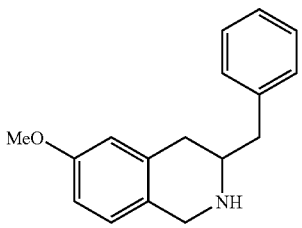

The reaction and treatment were carried out in the same manner as in Example 28-g) to obtain a title compound as a pale yellow oily substance.

$^1$H-NMR (CDCl$_3$) δ: 2.64 (1H, dd, J=10.3, 16.4 Hz), 2.74 (1H, dd, J=3.9, 16.4 Hz), 2.80-2.92 (2H, m), 3.12-3.20 (1H, m), 3.76 (3H, s), 3.95 (1H, d, J=16.2 Hz), 3.99 (1H, d, J=16.2 Hz), 6.59 (1H, d, J=2.6 Hz), 6.69 (1H, dd, J=2.6, 8.4 Hz), 6.92 (1H, d, J=8.4 Hz), 7.22-7.28 (3H, m), 7.31-7.38 (2H, m).

h) Production of N-benzyl-2-[3-benzyl-6-methoxy-3,4-dihydroisoquinolin-2(1H)-yl]ethanamine

[Chem. 167]

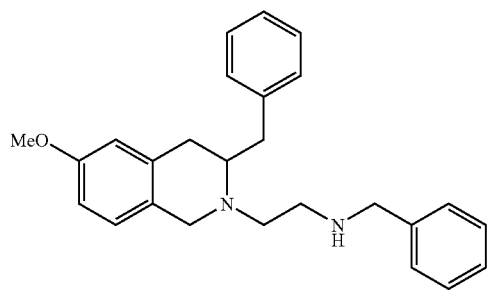

The reaction and treatment were carried out in the same manner as in Examples 32-f and g) to obtain a title compound as a pale yellow oily substance.

$^1$H-NMR (CDCl$_3$) δ: 2.48 (1H, dd, J=10.0, 13.2 Hz), 2.53 (1H, dd, J=3.4, 16.6 Hz), 2.77-2.80 (3H, m), 2.83-2.93 (3H, m), 3.19-3.24 (1H, m), 3.72 (2H, s), 3.78 (3H, s), 3.80 (2H, s), 6.59 (1H, d, J=2.6 Hz), 6.73 (1H, dd, J=2.6, 8.3 Hz), 6.94 (1H, d, J=8.3 Hz), 6.94 (1H, d, J=8.3 Hz), 7.11 (2H, d, J=7.1 Hz), 7.16-7.33 (8H, m).

Example 36

Production of N-benzyl-2-[3-isobutyl-5-methyl-3,4-dihydroisoquinolin-2(1H)-yl]ethanamine a) Production of 2-(2-toluyl)-N-methoxy-N-methylacetamide

[Chem. 168]

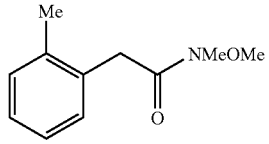

A solution of 2.60 g of 2-methylphenyl acetic acid and 2.53 g of N,O-dimethylhydroxylamine monohydrochloride in 50 mL of chloroform was stirred under ice-cooling for 10 minutes, and 4.98 g of WSC monohydrochloride was added thereto, followed by stirring for 10 minutes. 5.25 g of triethylamine was further added thereto, followed by stirring for 10 minutes, and then reacting at room temperature for 3 hours.

After completion of the reaction, the reaction liquid was diluted by addition of 1 N hydrochloric acid under ice-cooling, followed by extraction with chloroform. The chloroform layer was washed with a saturated aqueous sodium bicarbonate solution and then with saturated brine, dried over anhydrous sodium sulfate, and concentrated under reduced pressure. The residue obtained was purified by silica gel column chromatography (hexane:ethyl acetate=2:1) to obtain 3.20 g (yield 96%) of a title compound as a colorless oily substance.

$^1$H-NMR (CDCl$_3$) δ: 2.31 (3H, s), 3.21 (3H, s), 3.61 (3H, s), 3.77 (2H, s), 7.12-7.21 (4H, m).

b) Production of 4-methyl-1-(2-toluyl)-pentan-4-one

[Chem. 169]

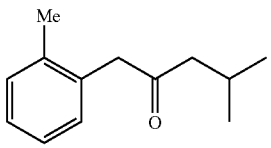

Under an argon atmosphere, to a solution of 3.20 g of 2-(2-toluyl)-N-methoxy-N-methylacetamide in 10 mL of THF was slowly added dropwise 24.8 mL of isobutyl magnesium bromide (2.0 M ether solution) under ice-cooling, followed by reacting for 1 hour.

After completion of the reaction, the reaction liquid was diluted by slow addition of 1 N hydrochloric acid under ice-cooling, followed by extraction with ethyl acetate. The organic layer was washed with a saturated aqueous sodium bicarbonate solution and then with saturated brine, dried over anhydrous sodium sulfate, and concentrated under reduced pressure. The residue obtained was purified by silica gel column chromatography (hexane:ethyl acetate=5:1) and PLC (hexane:ethyl acetate=1:1) to obtain 49 mg (yield 2%) of a title compound as a light yellow oily substance.

$^1$H-NMR (CDCl$_3$) δ: 0.89 (6H, d, J=6.6 Hz), 2.09-2.20 (1H, m), 2.24 (3H, s), 2.30 (2H, d, J=6.8 Hz), 3.68 (2H, s), 7.10-7.18 (4H, m).

c) Production of 4-methyl-1-(2-toluyl)-2-pentylamine

[Chem. 170]

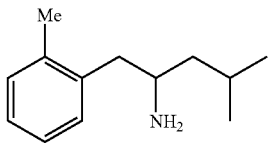

A solution of 49 mg of 4-methyl-1-(2-toluyl)-pentan-4-one, 175 mg of ammonium acetate, and 0.31 mL of sodium cyanoborohydride (1 M tetrahydrofuran solution) in 1 mL of methanol was reacted at 70° C. for 8 hours. 0.5 mL of 5 N sodium hydroxide was added thereto, followed by further reacting at 70° C. for 2 hours.

After completion of the reaction, it was extracted with chloroform, and the organic layer was washed with saturated brine, dried over anhydrous sodium sulfate, and concentrated under reduced pressure. The residue obtained was purified by PLC (chloroform:ammonia saturated methanol=20:1) to obtain 42 mg (yield 85%) of a title compound as a pale yellow oily substance.

$^1$H-NMR (CDCl$_3$) δ: 0.89 (3H, d, J=6.6 Hz), 0.94 (3H, d, J=6.6 Hz), 1.29-1.39 (2H, m), 1.67-1.87 (1H, m), 2.33 (3H, s), 2.43 (1H, dd, J=9.2, 13.5 Hz), 2.81 (1H, dd, J=4.3, 13.5 Hz), 3.01-3.13 (1H, m), 7.09-7.20 (4H, m).

d) Production of methyl 4-methyl-1-(2-toluyl)-pentan-2-ylcarbamate

[Chem. 171]

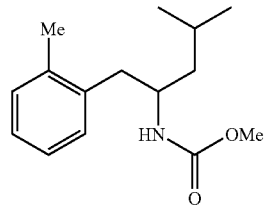

To a solution of 42 mg of 4-methyl-1-(2-toluyl)-2-pentylamine and 70 mg of pyridine in 1 mL of methylene chloride was added dropwise a solution of 82 mg of ice-cooled methylchloroformate in 0.5 mL of methylene chloride, followed by reacting at room temperature for 36 hours.

After completion of the reaction, the reaction liquid was diluted by addition of water, and acidified with 2N hydrochloric acid, and extracted with ethyl acetate. The organic layer was washed with a saturated aqueous sodium bicarbonate solution and then with saturated brine, dried over anhydrous sodium sulfate, and concentrated under reduced pressure. The residue obtained was purified by silica gel column chromatography (hexane:ethyl acetate=10:1 to 8:1) to obtain 53 mg (yield 97%) of a title compound as a colorless oily substance.

$^1$H-NMR (CDCl$_3$) δ: 0.84 (3H, d, J=6.6 Hz), 0.89 (3H, d, J=6.6 Hz), 1.23-1.34 (2H, m), 1.67 (1H, br), 2.35 (3H, s), 2.71 (1H, dd, J=6.8, 13.5 Hz), 2.83 (1H, dd, J=6.1, 13.5 Hz), 3.61 (3H, brs), 3.94 (1H, br), 4.40 (1H, br), 7.08-7.16 (4H, m).

e) Production of methyl 3-isobutyl-5-methyl-3,4-dihydroisoquinoline-2(1H)-carboxylate

[Chem. 172]

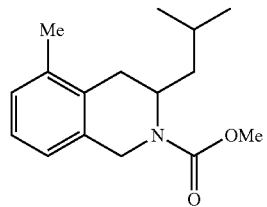

To a solution of 53 mg of methyl 4-methyl-1-(2-toluyl)-pentan-2-ylcarbamate in 0.6 mL of acetic acid were added 0.2 mL of sulfuric acid and 12.6 mg of paraformaldehyde, followed by reacting at room temperature for 18 hours.

After completion of the reaction, under ice-cooling the reaction liquid was diluted by addition of water, and alkalized with 5 N sodium hydroxide, followed by extraction with ethyl acetate. The organic layer was washed with water and saturated brine, dried over anhydrous sodium sulfate, and concentrated under reduced pressure. The residue obtained was purified by PLC (hexane:ethyl acetate=4:1) to obtain 20 mg (yield 36%) of a title compound as a colorless oily substance.

$^1$H-NMR (CDCl$_3$) δ: 0.90 (3H, d, J=6.3 Hz), 0.93 (3H, d, J=6.3 Hz), 1.10 (1H, br), 1.43-1.56 (2H, m), 2.23 (3H, s), 2.58 (1H, m), 2.85 (1H, dd, J=6.1, 16.3 Hz), 3.74 (3H, s), 4.22 (1H, m), 4.55-5.10 (2H, br), 6.95 (1H, m), 7.02-7.11 (2H, m).

f) Production of 3-isobutyl-5-methyl-1,2,3,4-tetrahydroisoquinoline

[Chem. 173]

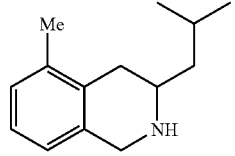

A solution of 20 mg of methyl 3-isobutyl-5-methyl-3,4-dihydroisoquinoline-2(1H)-carboxylate in hydrochloric acid (0.8 mL)-acetic acid (0.3 mL) was reacted at 90° C. for 48 hours. Under ice-cooling, the reaction liquid was diluted by addition of water, alkalized with 5 N sodium hydroxide, and extracted with chloroform. The organic layer was washed with saturated brine, dried over anhydrous sodium sulfate, and concentrated under reduced pressure. The residue obtained was purified by PLC (chloroform:ammonia saturated methanol=20:1) to obtain 13 mg (yield 84%) of a title compound as a light yellow oily substance.

$^1$H-NMR (CDCl$_3$) δ: 0.96 (6H, d, J=6.6 Hz), 1.34-1.51 (2H, m), 1.89-1.99 (1H, m), 2.21 (3H, s), 2.39 (1H, d, J=10.7

Hz), 2.69 (1H, dd, J=4.1, 16.2 Hz), 2.90-2.99 (1H, m), 4.02 (1H, d, J=16.1 Hz), 4.09 (1H, d, J=16.1 Hz), 6.89 (1H, d, J=7.1 Hz), 7.00-7.07 (2H, m).

g) Production of tert-butyl benzyl[2-[3-isobutyl-5-methyl-3,4-dihydroisoquinolin-2(1H)-yl]ethyl]carbamate

[Chem. 174]

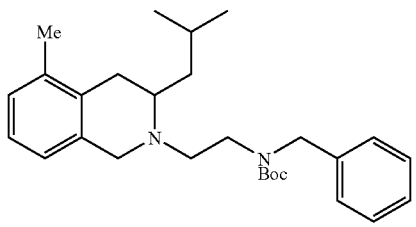

The reaction and treatment were carried out in the same manner as in Example 32-f) to obtain a title compound as a colorless oily substance.

¹H-NMR (CDCl₃) δ: 0.90 (3H, d, J=6.6 Hz), 0.91 (3H, d, J=6.6 Hz), 1.13-1.21 (1H, m), 1.41-1.48 (10H, br), 1.61 (1H, br), 2.20 (3H, s), 2.30-2.72 (4H, m), 2.90-3.45 (3H, m), 3.71-3.80 (2H, m), 4.46 (1H, m), 4.48 (1H, m), 6.85 (1H, br), 7.00 (1H, d, J=6.6 Hz), 7.05-7.07 (1H, m) 7.20-7.33 (5H, m).

h) Production of N-benzyl-2-[3-isobutyl-5-methyl-3,4-dihydroisoquinolin-2(1H)-yl]ethanamine

[Chem. 175]

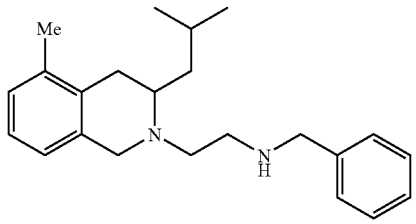

The reaction and treatment were carried out in the same manner as in Example 32-g) to obtain a title compound as a light yellow oily substance.

¹H-NMR (CDCl₃) δ: 0.90 (6H, d, J=6.6 Hz), 1.17-1.25 (1H, m), 1.40-1.48 (1H, m), 1.67-1.77 (1H, m), 2.21 (3H, s), 2.38 (1H, dd, 3=5.6, 16.8 Hz), 2.58-2.74 (5H, m), 3.04-3.11 (1H, m), 3.72 (1H, d, J=16.3 Hz), 3.78 (1H, d, J=16.3 Hz), 3.82 (2H, s), 6.84 (1H, d, J=7.3 Hz), 7.00 (1H, d, J=7.3 Hz), 7.04 (1H, dd, J=7.3, 7.3 Hz), 7.24-7.35 (5H, m).

Example 37

Production of N-benzyl-2-[3-isobutyl-7-methyl-3,4-dihydroisoquinolin-2(1H)-yl]ethanamine a) Production of 4-methyl-1-(4-toluyl)-pentan-2-one

[Chem. 176]

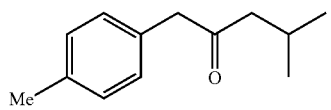

The reaction and treatment were carried out in the same manner as in Example 36-b) using N-methoxy-N-methyl-3-methylbutanamide and 4-methylbenzyl magnesium chloride to obtain a title compound as a light yellow oily substance.

¹H-NMR (CDCl₃) δ: 0.87 (6H, d, J=6.6 Hz), 2.13 (1H, m), 2.30 (2H, d, J=6.8 Hz), 2.33 (3H, s), 3.62 (2H, s), 7.08 (2H, d, J=8.1 Hz), 7.13 (2H, d, J=8.1 Hz).

b) Production of 4-methyl-1-(4-toluyl)-pentan-2-amine

[Chem. 177]

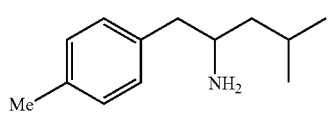

The reaction and treatment were carried out in the same manner as in Example 36-c) to obtain a title compound as a light yellow oily substance.

¹H-NMR (CDCl₃) δ: 0.90 (3H, d, J=6.6 Hz), 0.94 (3H, d, J=6.6 Hz), 1.29 (2H, t, J=7.1 Hz), 1.76 (1H, m), 2.33 (3H, s), 2.38 (1H, d, J=8.8 Hz), 2.41 (1H, d, J=8.8 Hz), 3.04 (1H, m), 7.08 (2H, d, J=8.1 Hz), 7.11 (2H, d, J=8.1 Hz).

c) Production of N-formyl-4-methyl-1-(4-toluyl)-pentan-2-amine

[Chem. 178]

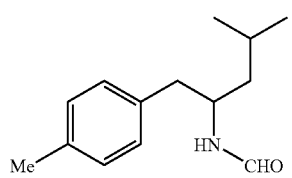

87 mg of 2-methyl-5-(4-toluyl)-pentan-2-amine was added to 994 mg of formic acid, followed by stirring at 50° C. To the reaction liquid was added 404 mg of acetic anhydride, followed by stirring at room temperature for 5.5 hours, and then further stirring at 50° C. for 1.5 hours. The reaction liquid was poured into a mixed liquid of ice and a saturated aqueous sodium bicarbonate solution, followed by extraction with ethyl acetate. The organic layer was washed with an aqueous sodium bicarbonate solution and saturated brine, and dried over anhydrous sodium sulfate, and the solvent was removed by evaporation to obtain 75 mg (yield 75%) of a title compound as a light yellow oily substance.

$^1$H-NMR (CDCl$_3$) δ: 0.86-0.95 (6H, m), 1.24-1.32 (2H, m), 1.66 (1H, m), 2.32 (3H, s), 2.70-2.83 (2H, m), 4.35 (1H, m), 7.00-7.12 (4H, m).

d) Production of 3-isobutyl-7-methyl-3,4-dihydroisoquinoline

[Chem. 179]

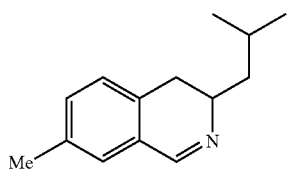

1 g of PPA and 0.2 g of P$_2$O$_5$ were mixed, followed by stirring at 170 to 180° C. for 1 hour. 286 mg of this mixture was mixed with 34 mg of N-formyl 2-methyl-5-(4-toluyl)-pentan-2-amine, followed by stirring at 160 to 170° C. for 1 hour. To the reaction liquid was added ice water, followed by alkalization by addition of potassium carbonate and extraction with ethyl acetate. The organic layer was washed with brine and then dried over anhydrous sodium sulfate, and the solvent was removed by evaporation to obtain 24.5 mg (yield 79%) of a title compound as a light yellow oily substance.

$^1$H-NMR (CDCl$_3$) δ: 0.95 (6H, d, J=6.6 Hz), 1.39 (1H, m), 1.70 (1H, m), 1.97 (1H, m), 2.36 (3H, s), 2.47 (1H, dd, J=12.4, 18.6 Hz), 2.74 (1H, dd, J=5.9, 18.6 Hz); 3.62 (1H, m), 7.04 (1H, d, J=7.6 Hz), 7.10 (1H, s), 7.17 (1H, d, J=7.6 Hz), 8.30 (1H, d, J=2.4 Hz).

e) Production of 3-isobutyl-7-methyl-1,2,3,4-tetrahydroisoquinoline

[Chem. 180]

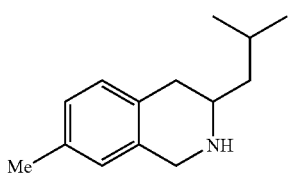

To a solution of 24.5 mg of 3-isobutyl-3-methyl-3,4-dihydroisoquinoline in methanol (1 mL) was added 4.5 mg of sodium borohydride, followed by stirring at room temperature for 5 minutes. After completion of the reaction, to the reaction liquid was added 2N hydrochloric acid, followed by drying under reduced pressure, and a saturated aqueous sodium bicarbonate solution was added thereto, followed by extraction with ethyl acetate. The organic layer was washed with brine and then dried over anhydrous sodium sulfate, and the solvent was removed by evaporation to obtain 24 mg (yield 96%) of a title compound as a light yellow oily substance.

$^1$H-NMR (CDCl$_3$) δ: 0.94 (3H, d, J=6.6 Hz), 0.95 (3H, d, J=6.6 Hz), 1.30-1.46 (2H, m), 1.83 (1H, m), 2.29 (3H, s), 2.43 (1H, m), 2.75 (1H, m), 2.92 (1H, m), 4.00 (1H, d, J=16.3 Hz), 4.06 (1H, d, J=16.3 Hz), 6.84 (1H, s), 6.94 (1H, d, J=8.1 Hz), 6.97 (1H, d, J=8.1 Hz).

f) Production of N-benzyl-2-[3-isobutyl-7-methyl-3,4-dihydroisoquinolin-2(1H)-yl]ethanamine

[Chem. 181]

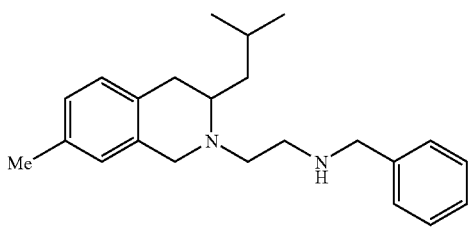

The reaction and treatment were carried out in the same manner as in Examples 32-f and g) to obtain a title compound as a colorless oily substance.

$^1$H-NMR (CDCl$_3$) δ: 0.88 (6H, d, J=6.6 Hz), 1.17 (1H, m), 1.38 (1H, m), 1.65 (1H, m), 2.29 (3H, s), 2.45 (1H, m), 2.62 (1H, m), 2.65-2.75 (3H, m), 2.85 (1H, m), 3.00 (1H, m), 3.70 (2H, s), 3.81 (2H, s), 6.81 (1H, s), 6.95 (2H, s), 7.30-7.40 (5H, m).

Example 38

Production of N-benzyl-2-[3-isobutyl-6-methyl-3,4-dihydroisoquinolin-2(1H)-yl]ethanamine a) Production of 4-methyl-1-(3-toluyl)-pentan-2-one

[Chem. 182]

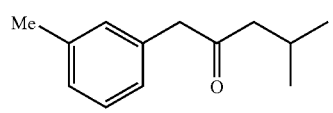

The reaction and treatment were carried out in the same manner as in Example 36-b) using N-methoxy-N-methyl-3-methylbutanamide and 3-methylbenzyl magnesium chloride to obtain a title compound as a light yellow oily substance.

$^1$H-NMR (CDCl$_3$) δ: 0.87 (6H, d, J=6.6 Hz), 2.13 (1H, m), 2.32 (2H, d, J=7.0 Hz), 2.34 (3H, s), 3.62 (2H, s), 6.99 (1H, d, J=7.3 Hz), 7.00 (1H, s), 7.07 (1H, d, J=7.5 Hz), 2.21 (1H, dd, J=7.5, 7.5 Hz).

b) Production of 4-methyl-1-(3-toluyl)-pentan-2-amine

[Chem. 183]

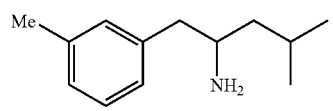

The reaction and treatment were carried out in the same manner as in Example 36-c) to obtain a title compound as a light yellow oily substance.

¹H-NMR (CDCl₃) δ: 0.90 (3H, d, J=6.6 Hz), 0.94 (3H, d, J=6.6 Hz), 1.28 (2H, t, J=7.3 Hz), 1.77 (1H, m), 2.34 (3H, s), 2.36 (1H, dd, J=9.0, 14.4 Hz), 2.76 (1H, dd, J=4.1, 14.4 Hz), 3.05 (1H, m), 6.98-7.04 (3H, m), 7.19 (1H, dd, J=7.6, 7.6 Hz).

c) Production of N-formyl-4-methyl-1-(3-toluyl)-pentan-2-amine

[Chem. 184]

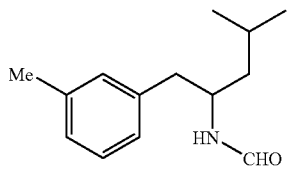

The reaction and treatment were carried out in the same manner as in Example 37-c) to obtain a title compound as a light yellow oily substance.

¹H-NMR (CDCl₃) δ: 0.88-0.95 (6H, m), 1.31 (2H.t, J=7.1 Hz), 1.64 (1H, m), 2.33 (3H, s), 2.70-2.84 (2H, m), 4.38 (1H, m), 6.92-7.05 (3H, m), 7.18 (1H, dd, J=7.6, 7.6 Hz), 8.13 (1H, s).

d) Production of 3-isobutyl-6-methyl-3,4-dihydroisoquinoline

[Chem. 185]

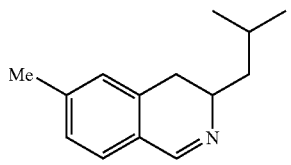

The reaction and treatment were carried out in the same manner as in Example 37-d) to obtain a title compound as a light yellow oily substance.

¹H-NMR (CDCl₃) δ: 0.96 (6H, d, J=6.6 Hz), 1.39 (1H, m), 1.70 (1H, m), 1.97 (1H, m), 2.36 (3H, s), 2.48 (1H, dd, J=5.9, 16.2 Hz), 2.73 (1H, dd, J=5.9, 16.2 Hz), 3.60 (1H, m), 6.96 (1H, s), 7.09 (1H, d, J=7.8 Hz), 7.17 (1H, d, J=7.8 Hz), 8.29 (1H, d, J=2.7 Hz).

e) Production of 3-isobutyl-6-methyl-1,2,3,4-tetrahydroisoquinoline

[Chem. 186]

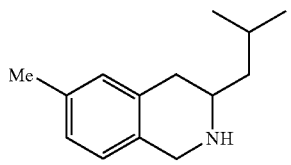

The reaction and treatment were carried out in the same manner as in Example 37-e) to obtain a title compound as a light yellow oily substance.

¹H-NMR (CDCl₃) δ: 0.94 (3H, d, J=6.6 Hz), 0.95 (3H, d, J=6.6 Hz), 1.30-1.48 (2H, m), 1.83 (1H, m), 2.29 (3H, s), 2.44 (1H, m), 2.74 (1H, m), 2.91 (1H, m), 4.00 (1H, d, J=15.6 Hz), 4.04 (1H, d, J=15.6 Hz), 6.89 (1H, s), 6.92-6.96 (2H, m).

f) Production of N-benzyl-2-[3-isobutyl-6-methyl-3,4-dihydroisoquinolin-2(1H)-yl]ethanamine

[Chem. 187]

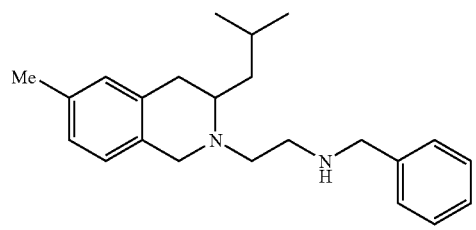

The reaction and treatment were carried out in the same manner as in Examples 32-f and g) to obtain a title compound as a colorless oily substance.

¹H-NMR (CDCl₃) δ: 0.88 (3H, d, J=6.6 Hz), 0.89 (3H, d, J=6.6 Hz), 1.17 (1H, m), 1.38 (1H, m), 1.68 (1H, m), 2.29 (3H, s), 2.48 (1H, dd, J=5.1, 16.1 Hz), 2.67 (1H, m), 2.68-2.75 (3H, m), 2.87 (1H, dd, J=5.4, 16.1 Hz), 3.00 (1H, m), 3.69 (2H, s), 3.82 (2H, s), 6.86-6.96 (3H, m), 7.22-7.32 (5H, m).

Example 39

Production of N-benzyl-2-[3-isobutyl-8-methyl-3,4-dihydroisoquinolin-2(1H)-yl]ethanamine a) Production of 3-isobutyl-8-methyl-3,4-dihydroisoquinoline

[Chem. 188]

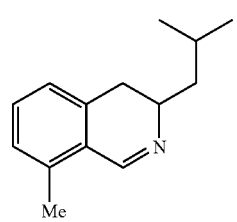

In the reaction of in Example 38-d), the title compound was obtained as an isomer of 3-isobutyl-6-methyl-3,4-dihydroisoquinoline. The title compound was a yellow oily substance.

¹H-NMR (CDCl₃) δ: 0.95 (3H, d, J=6.6 Hz), 0.97 (3H, d, J=6.6 Hz), 1.41 (1H, m), 1.71 (1H, m), 1.98 (1H, m), 2.47 (1H, dd, J=11.7, 16.1 Hz), 2.48 (3H, s), 2.71 (1H, dd, J=5.4, 16.1 Hz), 3.52 (1H, m), 6.97 (1H, d, J=7.8 Hz), 7.07 (1H, d, J=7.8 Hz), 7.22 (1H, dd, J=7.8, 7.8 Hz), 8.63 (1H, d, J=2.7 Hz).

b) Production of 3-isobutyl-8-methyl-1,2,3,4-tetrahydroisoquinoline

[Chem. 189]

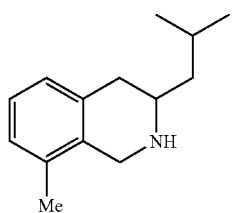

Me

The reaction and treatment were carried out in the same manner as in Example 37-e) to obtain a title compound as a light yellow oily substance.

$^1$H-NMR (CDCl$_3$) δ: 0.94 (3H, d, J=6.6 Hz), 0.95 (3H, d, J=6.6 Hz), 1.30-1.46 (2H, m), 1.83 (1H, m), 2.18 (3H, s), 2.49 (1H, dd, J=10.5, 16.1 Hz), 2.79 (1H, dd, J=3.9, 16.1 Hz), 2.91 (1H, m), 3.92 (1H, d, J=16.1 Hz), 4.04 (1H, d, J=16.1 Hz), 6.89-6.98 (2H, m), 7.05 (1H, dd, J=7.6, 7.6 Hz).

c) Production of N-benzyl-2-[3-isobutyl-8-methyl-3,4-dihydroisoquinolin-2(1H)-yl]ethanamine

[Chem. 190]

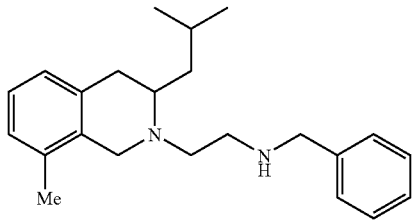

Me

The reaction and treatment were carried out in the same manner as in Examples 32-f and g) to obtain a title compound as a colorless oily substance.

$^1$H-NMR (CDCl$_3$) δ: 0.87 (3H, d, J=6.6 Hz), 0.88 (3H, d, J=6.6 Hz), 1.16 (1H, m), 1.34 (1H, m), 1.70 (1H, m), 2.14 (3H, s), 2.55 (1H, m), 2.66-2.78 (4H, m), 2.95-3.20 (2H, m), 3.54 (1H, d, J=16.6 Hz), 3.63 (1H, d, J=16.6 Hz), 3.81 (1H, s), 3.82 (1H, s), 6.88-6.98 (2H, m), 7.05 (1H, dd, J=7.3, 7.3 Hz), 7.24-7.32 (5H, m).

Example 40

Production of N-benzyl-2-[3-isobutyl-5-nitro-3,4-dihydroisoquinolin-2(1H)-yl]ethanamine a) Production of tert-butyl benzyl[2-[3-isobutyl-5-nitro-3,4-dihydroisoquinolin-2(1H)-yl]ethyl]carbamate

[Chem. 191]

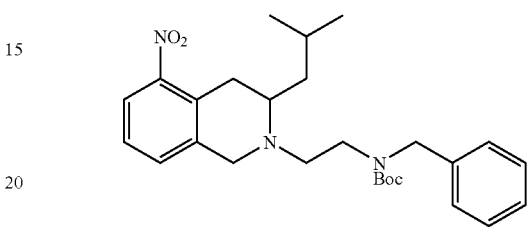

Under an argon atmosphere, to a solution of 405 mg of 3-isobutyl-1,2,3,4-tetrahydroisoquinoline obtained in Example 20-c) in acetonitrile (3 mL) was added 426 mg of nitronium tetrafluoroborate after stirring for 10 minutes under ice-cooling, followed by reacting for 30 minutes. The reaction liquid was neutralized with 10% aqueous ammonia and extracted with chloroform, and the chloroform layer was washed with saturated brine, dried over sodium sulfate, and concentrated under reduced pressure.

The residue obtained was purified by silica gel column chromatography (chloroform:methanol=30:1), and further fractionated by silica gel column chromatography (hexane: ethyl acetate=5:1 to 1:1). Each fraction was purified by P-TLC (hexane:ethyl acetate=1:1) to obtain 200 mg of a mixture as an oily substance.

The reaction and treatment were carried out in the same manner as in Example 32-f) using the obtained oily substance to obtain a title compound as a pale yellow oily substance.

$^1$H-NMR (CDCl$_3$) δ: 0.88 (6H, d, J=6.6 Hz), 1.04-1.14 (1H, m), 1.33 (1H, brs), 1.42-1.49 (9H, br), 1.62-1.73 (1H, m), 2.50-2.79 (3H, m), 2.80-3.10 (2H, m), 3.20-3.46 (2H, m), 3.79-3.89 (2H, m), 4.48 (2H, brs), 7.21-7.34 (7H, m), 7.96 (1H, d, J=10.5 Hz).

b) Production of N-benzyl-2-[3-isobutyl-5-nitro-3,4-dihydroisoquinolin-2(1H)-yl]ethanamine

[Chem. 192]

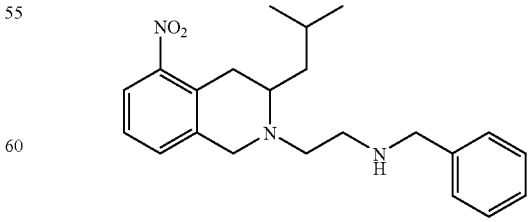

The reaction and treatment were carried out in the same manner as in Example 32-g) to obtain a title compound as a pale yellow oily substance.

¹H-NMR (CDCl₃) δ: 0.88 (6H, d, J=6.6 Hz), 1.09-1.17 (1H, m), 1.34-1.43 (1H, m), 1.61-1.73 (1H, m), 2.59-2.68 (1H, m), 2.71-2.82 (4H, m), 3.02-3.07 (1H, m), 3.10 (1H, dd, J=5.1, 17.6 Hz), 3.76-3.87 (4H, m), 7.22-7.35 (7H, m), 7.78 (1H, dd, J=2.2, 7.3 Hz).

MS (FAB) m/z 368 (M+H)⁺

IR (ATR cm⁻¹): 2953, 1524, 1452, 1346, 733, 698.

Example 41

Production of N-benzyl-2-[3-isobutyl-6-nitro-3,4-dihydroisoquinolin-2(1H)-yl]ethanamine a) Production of tert-butyl benzyl[2-[3-isobutyl-6-nitro-3,4-dihydroisoquinolin-2(1H)-yl]ethyl]carbamate

[Chem. 193]

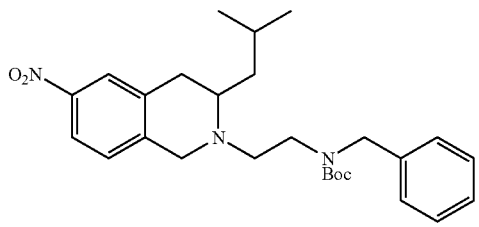

In the reaction of Example 40-a), as an isomer of tert-butyl benzyl[2-[3-isobutyl-5-nitro-3,4-dihydroisoquinolin-2(1H)-yl]ethyl]carbamate, tert-butyl benzyl[2-[3-isobutyl-6-nitro-3,4-dihydroisoquinolin-2(1H)-yl]ethyl]carbamate was obtained as a pale yellow oily substance. The reaction and treatment were carried out in the same manner as in Example 32-f) using the obtained oily substance to obtain a title compound as a pale yellow oily substance.

¹H-NMR (CDCl₃) δ: 0.89 (6H, d, J=6.6 Hz), 1.03-1.19 (1H, m), 1.31 (1H, br), 1.40-1.50 (9H, br), 1.65-1.74 (1H, m), 2.39-2.80 (2H, m), 2.56 (1H, dd, J=5.4, 16.6 Hz), 2.80-3.17 (2H, m), 3.17-3.44 (2H, m), 3.83 (2H, br), 4.47 (2H, brs), 7.13 (1H, brs), 7.20-7.33 (5H, m), 7.94-7.99 (2H, br).

b) Production of N-benzyl-2-[3-isobutyl-6-nitro-3,4-dihydroisoquinolin-2(1H)-yl]ethanamine

[Chem. 194]

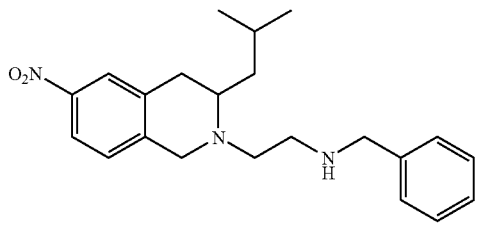

The reaction and treatment were carried out in the same manner as in Example 32-g) to obtain a title compound as a pale yellow oily substance.

¹H-NMR (CDCl₃) δ: 0.89 (6H, d, J=6.6 Hz), 1.08-1.16 (1H, m), 1.34-1.41 (1H, m), 1.61-1.73 (1H, m), 2.59-2.68 (2H, m), 2.72-2.78 (3H, m), 3.01 (1H, dd, J=5.1, 16.3 Hz), 3.01-3.09 (1H, m), 3.78 (2H, s), 3.82 (2H, s), 7.13 (1H, d, J=9.0 Hz), 7.23-7.35 (5H, m), 7.95-7.99 (2H, m).

MS (FAB) m/z 368 (M+H)⁺

Example 42

Production of N-benzyl-2-[3-isobutyl-7-nitro-3,4-dihydroisoquinolin-2(1H)-yl]ethanamine a) Production of 3-isobutyl-7-nitro-1,2,3,4-tetrahydroisoquinoline

[Chem. 195]

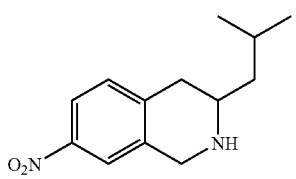

In the reaction of Example 40-a), the title compound which was an isomer of tert-butyl benzyl[2-[3-isobutyl-5-nitro-3,4-dihydroisoquinolin-2(1H)-yl]ethyl]carbamate was obtained as a pale yellow oily substance.

¹H-NMR (CDCl₃) δ: 0.96 (6H, d, J=6.8 Hz), 1.33-1.49 (2H, m), 1.77-1.91 (1H, m), 2.55 (1H, dd, J=10.2, 16.6 Hz), 2.89 (1H, dd, J=3.9, 17.1 Hz), 2.93-3.01 (1H, m), 4.14 (2H, s), 7.22 (1H, d, J=8.3 Hz), 7.92 (1H, d, J=2.2 Hz), 7.98 (1H, dd, J=2.2, 8.3 Hz).

b) Production of tert-butyl benzyl[2-[3-isobutyl-7-nitro-3,4-dihydroisoquinolin-2(1H)-yl]ethyl]carbamate

[Chem. 196]

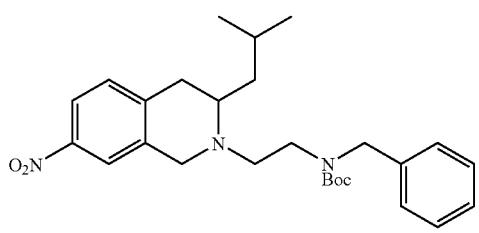

The reaction and treatment were carried out in the same manner as in Example 32-f) to obtain a title compound as a yellow oily substance.

¹H-NMR (CDCl₃) δ: 0.89 (6H, d, J=6.6 Hz), 1.05-1.14 (1H, m), 1.34 (1H, br), 1.40-1.50 (9H, br), 1.68 (1H, br), 2.35-2.75 (3H, m), 2.80-3.25 (2H, m), 3.30-3.43 (2H, br), 3.82 (2H, br), 4.48 (2H, br), 7.17-7.31 (6H, m), 7.87 (1H, br), 7.97 (1H, br).

c) Production of N-benzyl-2-[3-isobutyl-7-nitro-3,4-dihydroisoquinolin-2(1H)-yl]ethanamine

[Chem. 197]

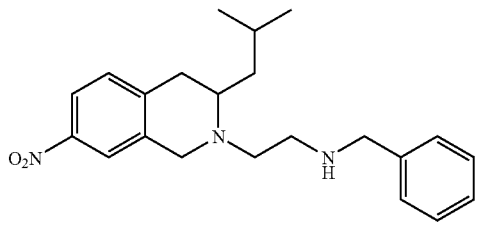

The reaction and treatment were carried out in the same manner as in Example 32-g) to obtain a title compound as a yellow oily substance.

$^1$H-NMR (CDCl$_3$) δ: 0.89 (6H, d, J=6.6 Hz), 1.04-1.16 (1H, m), 1.35-1.43 (1H, m), 1.61-1.72 (1H, m), 2.58-2.67 (2H, m), 2.71-2.78 (3H, m), 2.99 (1H, dd, J=5.4, 168 Hz), 3.03-3.10 (1H, m), 3.78 (2H, s), 3.83 (2H, s), 7.21 (1H, d, J=8.3 Hz), 7.24-7.35 (5H, m), 7.88 (1H, d, J=2.4 Hz), 7.98 (1H, dd, J=2.4, 8.3 Hz).

MS (FAB) m/z 368 (M+H)$^+$

IR (ATR cm$^{-1}$): 2953, 1522, 1343, 739, 699.

Example 43

Production of N-benzyl-2-[3-isobutyl-8-nitro-3,4-dihydroisoquinolin-2(1H)-yl]ethanamine a) Production of 3-isobutyl-8-nitro-1,2,3,4-tetrahydroisoquinoline

[Chem. 198]

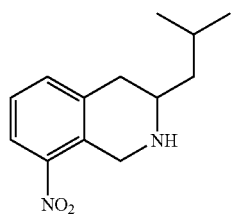

In the reaction of Example 40-a), the title compound which was an isomer of tert-butyl benzyl[2-[3-isobutyl-5-nitro-3,4-dihydroisoquinolin-2(1H)-yl]ethyl]carbamate was obtained as a pale yellow oily substance.

$^1$H-NMR (CDCl$_3$) δ: 0.96 (6H, d, J=6.6 Hz), 1.33-1.49 (2H, m), 1.78-1.90 (1H, m), 2.57 (1H, dd, J=10.2, 16.3 Hz), 2.90 (1H, dd, J=3.9, 16.3 Hz), 2.93-3.00 (1H, m), 4.32 (1H, d, J=17.8 Hz), 4.38 (1H, d, J=17.8 Hz), 7.29 (1H, dd, J=7.8, 7.8 Hz), 7.36 (1H, d, J=7.8 Hz), 7.87 (1H, d, J=7.8 Hz).

b) Production of tert-butyl benzyl[2-[3-isobutyl-8-nitro-3,4-dihydroisoquinolin-2(1H)-yl]ethyl]carbamate

[Chem. 199]

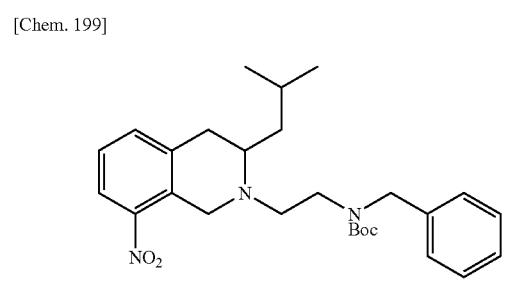

The reaction and treatment were carried out in the same manner as in Example 32-f) to obtain a title compound as a yellow oily substance.

$^1$H-NMR (CDCl$_3$) δ: 0.90 (6H, d, J=6.6 Hz), 1.08-1.17 (1H, m), 1.40-1.50 (10H, m), 1.65-1.74 (1H, br), 2.25-2.75 (2H, m), 2.66 (1H, dd, J=6.1, 16.8 Hz), 2.85-3.41 (4H, br), 3.98-4.01 (2H, br), 4.41-4.52 (2H, br), 7.18-7.34 (7H, m), 7.86 (1H, d, J=7.8 Hz).

c) Production of N-benzyl-2-[3-isobutyl-8-nitro-3,4-dihydroisoquinolin-2(1H)-yl]ethanamine

[Chem. 200]

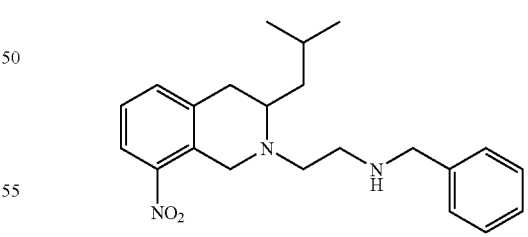

The reaction and treatment were carried out in the same manner as in Example 32-g) to obtain a title compound as a yellow oily substance.

$^1$H-NMR (CDCl$_3$) δ: 0.90 (6H, d, J=6.6 Hz), 1.13-1.21 (1H, m), 1.40-1.47 (1H, m), 1.65-1.74 (1H, m), 2.56-2.65 (2H, m), 2.69-2.78 (3H, m), 2.97-3.07 (2H, m), 3.81 (2H, s), 4.04 (2H, s), 7.20-7.37 (7H, m), 7.86 (1H, dd, J=0.98, 8.0 Hz).

IR (ATR cm$^{-1}$): 2953, 1525, 1345, 733, 698.

Example 44

Production of N-benzyl-2-[7-acetyl-3-isobutyl-3,4-dihydroisoquinolin-2(1H)-yl]ethanamine a) Production of 3-isobutyl-2-trifluoroacetyl-1,2,3,4-tetrahydroisoquinoline

[Chem. 201]

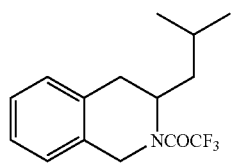

To 206 mg of 3-isobutyl-1,2,3,4-tetrahydroisoquinoline obtained in Example 20 was added 458 mg of anhydrous trifluoroacetic acid, followed by stirring at room temperature for 2 hours. Further, 200 mg of anhydrous trifluoroacetic acid was added thereto, followed by stirring at 40° C. for 1 hour. After completion of the reaction, the reaction liquid was concentrated under reduced pressure, added with ethyl acetate, and washed with an aqueous sodium bicarbonate solution and then with brine. The organic layer was dried over anhydrous sodium sulfate, and the solvent was removed by evaporation to obtain 283 mg (yield 91%) of a title compound as a pale yellow oily substance.

$^1$H-NMR (CDCl$_3$) δ: 0.92-0.97 (6H, m), 1.18-1.62 (3H, m), 2.72 (1H, m), 3.15 (1H, m), 4.25 (0.5H, d, J=17.6 Hz), 4.43 (0.5H, m), 4.49 (0.5H, d, J=17.6 Hz), 4.83 (0.5H, d, J=17.6 Hz), 5.04 (0.5H, m), 5.26 (0.5H, d, J=17.6 Hz), 7.11-7.26 (4H, m).

b) Production of 7-acetyl-3-isobutyl-2-trifluoro-acetyl-1,2,3,4-tetrahydroisoquinoline

[Chem. 202]

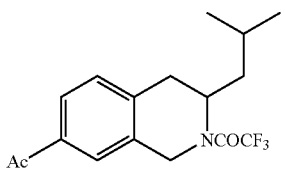

A mixed liquid of 193 mg of 3-isobutyl-2-trifluoroacetyl-1,2,3,4-tetrahydroisoquinoline, 533 mg of aluminum chloride, and 5 mL of carbon disulfide was added 157 mg of acetyl chloride at 44° C., followed by stirring at 45° C. for 1 hour. The reaction liquid was concentrated under reduced pressure, and 2N hydrochloric acid and ice were added thereto, followed by extraction with ethyl acetate. The organic layer was washed with an aqueous sodium bicarbonate solution and then with brine, and dried over anhydrous sodium sulfate. The solvent was removed by evaporation to obtain 202 mg (yield 91%) of a title compound as a yellow oily substance.

$^1$H-NMR (CDCl$_3$) δ: 0.87-0.95 (6H, m), 1.21-1.56 (3H, m), 2.60 (3H, s), 2.80 (1H, m), 3.18 (1H, m), 4.30 (0.5H, d, J=17.1 Hz), 4.46 (0.5H, m), 4.54 (0.5H, d, J=17.1 Hz), 4.90 (0.5H, d, J=17.1 Hz), 5.08 (0.5H, m), 5.33 (0.5H, d, J=17.1 Hz), 7.22-7.27 (1H, m), 7.73-7.83 (2H, m).

c) Production of 7-acetyl-3-isobutyl-1,2,3,4-tetrahydroisoquinoline

[Chem. 203]

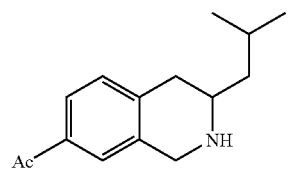

To 40 mg of 7-acetyl-3-isobutyl-2-trifluoroacetyl-1,2,3,4-tetrahydroisoquinoline were added 1 mL of 3 N hydrochloric acid and 0.5 mL of n-butanol, followed by reflux overnight. After completion of the reaction, to the reaction liquid was added an aqueous sodium bicarbonate solution, followed by extraction with ethyl acetate. The organic layer was washed with brine and dried over anhydrous sodium sulfate. The solvent was removed by evaporation to obtain 24 mg (yield 85%) of a title compound as a yellow oily substance.

$^1$H-NMR (CDCl$_3$) δ: 0.96 (6H, d, J=6.6 Hz), 1.34-1.50 (2H, m), 1.83 (1H, m), 2.55 (1H, m), 2.57 (3H, s), 2.85 (1H, m), 3.00 (1H, m), 4.13 (2H, s), 7.16 (1H, d, J=7.8 Hz), 7.64 (1H, s), 7.71 (1H, d, J=7.8 Hz).

d) Production of N-benzyl-2-[7-acetyl-3-isobutyl-3,4-dihydroisoquinolin-2(1H)-yl]ethanamine

[Chem. 204]

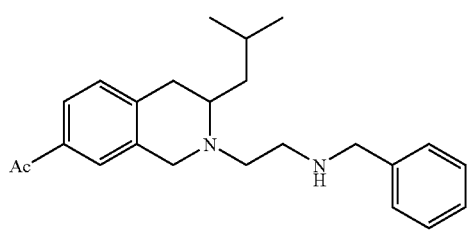

The reaction and treatment were carried out in the same manner as in Examples 32-f and g) to obtain a title compound as a colorless oily substance.

$^1$H-NMR (CDCl$_3$) δ: 0.82 (6H, d, J=6.6 Hz), 1.07 (1H, m), 1.33 (1H, m), 1.61 (1H, m), 2.50 (3H, s), 2.52-2.60 (2H, m), 2.67-2.69 (3H, m), 2.90 (1H, m), 2.97 (1H, m), 3.70 (2H, s), 3.75 (2H, s), 7.08 (1H, d, J=7.8 Hz), 7.15-7.30 (5H, m), 7.53 (1H, s), 7.64 (1H, d, J=7.8 Hz).

Example 45

Production of N-benzyl-2-[5-amino-3-isobutyl-3,4-dihydroisoquinolin-2(1H)-yl]ethanamine a) Production of tert-butyl benzyl[2-[5-amino-3-isobutyl-3,4-dihydroisoquinolin-2(1H)-yl]ethyl]carbamate

[Chem. 205]

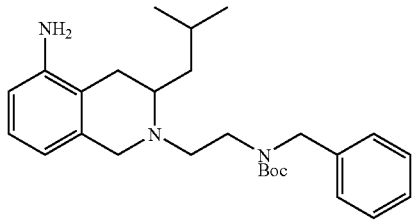

A solution of 28 mg of tert-butyl benzyl[2-[3-isobutyl-5-nitro-3,4-dihydroisoquinolin-2(1H)-yl]ethyl]carbamate obtained in Example 40-a) and 28 mg of nickel (II) chloride in methanol (1 mL) was stirred under ice-cooling for 10 minutes, and then 9 mg of sodium borohydride was added thereto, followed by reacting for 30 minutes.

After completion of the reaction, it was weakly acidified with 1 N hydrochloric acid, stirred for 5 minutes, alkalized with 2N sodium hydroxide, and extracted with chloroform. The chloroform layer was washed with saturated brine, dried over sodium sulfate, and concentrated under reduced pressure. The obtained oily substance was purified by P-TLC (chloroform:methanol=20:1) to obtain 18 mg (yield 69%) of a title compound as a pale yellow oily substance.

$^1$H-NMR (CDCl$_3$) δ: 0.90 (3H, d, J=6.6 Hz), 0.91 (3H, d, J=6.6 Hz), 1.14-1.23 (1H, m), 1.40-1.50 (9H, br), 1.72 (1H, br), 2.15 (1H, br), 2.38-2.71 (3H, m), 3.02-3.78 (6H, m), 4.35-4.50 (2H, br), 6.46 (1H, brs), 6.54 (1H, d, J=7.8 Hz), 6.96 (1H, dd, J=7.8, 7.8 Hz), 7.19-7.33 (5H, m).

b) Production of N-benzyl-2-[5-amino-3-isobutyl-3,4-dihydroisoquinoline-2(1H)-]ethanamine

[Chem. 206]

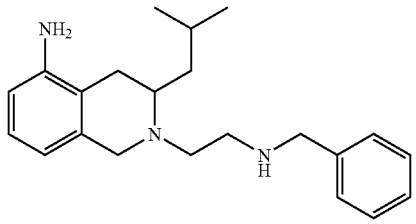

The reaction and treatment were carried out in the same manner as in Example 32-g) to obtain a title compound as a light yellow oily substance.

$^1$H-NMR (CDCl$_3$) δ: 0.90 (3H, d, J=6.6 Hz), 0.91 (3H, d, J=6.6 Hz), 1.19-1.27 (1H, m), 1.43-1.51 (1H, m), 1.65-1.80 (1H, m), 2.19 (1H, dd, J=5.9, 16.1 Hz), 2.51 (1H, dd, J=5.6, 16.1 Hz), 2.56-2.65 (1H, m), 2.65-2.76 (3H, m), 3.07-3.15 (1H, m), 3.56 (2H, s), 3.70 (1H, d, J=16.3 Hz), 3.76 (1H, d, J=16.3 Hz), 3.81 (2H, s), 6.47 (1H, d, J=7.6 Hz), 6.54 (1H, d, J=7.6 Hz), 6.96 (1H, dd, J=7.6, 7.6 Hz), 7.21-7.32 (5H, m).

MS (FAB) m/z 338 (M+H)$^+$

IR (ATR cm$^{-1}$): 2951, 1619, 1591, 1467, 770, 737, 698.

Example 46

Production of N-benzyl-2-[6-amino-3-isobutyl-3,4-dihydroisoquinolin-2(1H)-yl]ethanamine a) Production of tert-butyl benzyl[2-[6-amino-3-isobutyl-3,4-dihydroisoquinolin-2(1H)-yl]ethyl]carbamate

[Chem. 207]

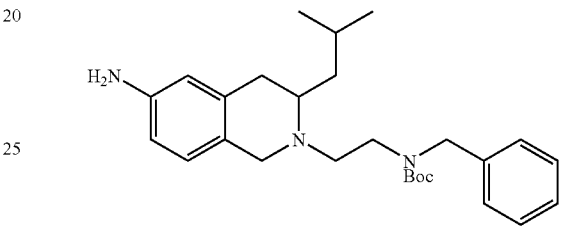

The reaction and treatment were carried out in the same manner as in Example 45-a) using tert-butyl benzyl[2-[3-isobutyl-6-nitro-3,4-dihydroisoquinolin-2(1H)-yl]ethyl]carbamate obtained in Example 41-a) to obtain a title compound as a pale yellow oily substance.

$^1$H-NMR (CDCl$_3$) δ: 0.88 (6H, d, J=6.6 Hz), 1.08-1.17 (1H, m), 1.32 (1H, br), 1.40-1.50 (9H, br), 1.67 (1H, br), 2.35-3.05 (4H, m), 3.15-3.75 (5H, m), 4.45-4.59 (2H, m), 6.40 (1H, d, J=2.2 Hz), 6.49 (1H, dd, J=2.2, 8.1 Hz), 6.77 (1H, brd, J=8.1 Hz), 7.20-7.33 (5H, m).

MS (FAB) m/z 438 (M+H)$^+$ b) Production of N-benzyl-2-[6-amino-3-isobutyl-3,4-dihydroisoquinolin-2(1H)-yl]ethanamine

[Chem. 208]

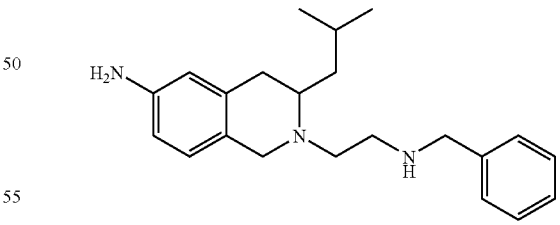

The reaction and treatment were carried out in the same manner as in Example 32-g) to obtain a title compound as a pale yellow oily substance.

$^1$H-NMR (CDCl$_3$) δ: 0.87 (3H, d, J=6.6 Hz), 0.88 (3H, d, J=6.6 Hz), 1.13-1.21 (1H, m), 1.33-1.42 (1H, m), 1.61-1.73 (1H, m), 2.42 (1H, dd, J=5.4, 16.3 Hz), 2.57-2.75 (4H, m), 2.81 (1H, dd, J=5.1, 16.3 Hz), 2.94-3.01 (1H, m), 3.51 (2H, brs), 3.63 (2H, s), 3.81 (2H, s), 6.41 (1H, d, J=2.4 Hz), 6.49 (1H, dd, J=2.4, 8.1 Hz), 6.78 (1H, d, J=8.1 Hz), 7.21-7.32 (5H, m).

MS (FAB) m/z 338 (M+H)+

IR (ATR cm−1): 2952, 2924, 1622, 1507, 1452, 809, 736, 698.

Example 47

Production of N-benzyl-2-[7-amino-3-isobutyl-3,4-dihydroisoquinolin-2(1H)-yl]ethanamine a) Production of tert-butyl benzyl[2-[7-amino-3-isobutyl-3,4-dihydroisoquinolin-2(1H)-yl]ethyl]carbamate

[Chem. 209]

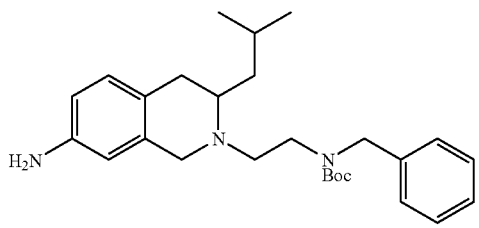

The reaction and treatment were carried out in the same manner as in Example 45-a) using tert-butyl benzyl[2-[3-isobutyl-7-nitro-3,4-dihydroisoquinolin-2(1H)-yl]ethyl]carbamate obtained in Example 42-b) to obtain a title compound as a pale yellow oily substance.

$^1$H-NMR (CDCl$_3$) δ: 0.88 (6H, d, J=6.6 Hz), 1.09-1.18 (1H, m), 1.40-1.50 (9H, br), 1.60-1.75 (1H, br), 2.37 (1H, dd, J=6.6, 16.3 Hz), 2.40-2.70 (3H, m), 2.85-3.00 (1H, br), 3.22-3.70 (5H, m), 4.40-4.55 (2H, br), 6.33 (1H, brs), 6.50 (1H, dd, J=2.4, 8.0 Hz), 6.84 (1H, d, J=8.0 Hz), 7.21-7.33 (5H, m).

b) Production of N-benzyl-2-(7-amino-3-isobutyl-3,4-dihydroisoquinolin-2(1H)-yl)ethanamine

[Chem. 210]

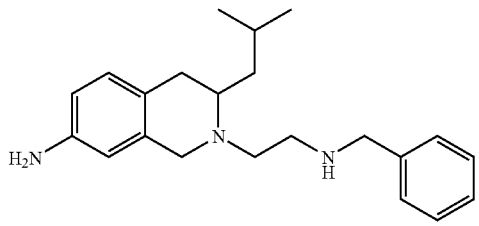

The reaction and treatment were carried out in the same manner as in Example 32-g) to obtain a title compound as a pale yellow oily substance.

$^1$H-NMR (CDCl$_3$) δ: 0.87 (3H, d, J=6.6 Hz), 0.88 (3H, d, J=6.6 Hz), 1.13-1.22 (1H, m), 1.34-1.42 (1H, m), 1.63-1.74 (1H, m), 2.40 (1H, dd, J=5.4, 16.1 Hz), 2.57-2.65 (1H, m), 2.67-2.81 (3H, m), 2.78 (1H, dd, J=5.4, 16.1 Hz), 2.94-3.02 (1H, m), 3.50 (2H, brs), 3.65 (2H, s), 3.81 (2H, s), 6.43 (1H, d, J=2.4 Hz), 6.50 (1H, dd, J=2.4, 8.0 Hz), 6.85 (1H, d, J=8.0 Hz), 7.20-7.33 (5H, m).

MS (FAB) m/z 338 (M+H)+

Example 48

Production of N-benzyl-2-[8-amino-3-isobutyl-3,4-dihydroisoquinolin-2(1H)-yl]ethanamine a) Production of tert-butyl benzyl[2-[8-amino-3-isobutyl-3,4-dihydroisoquinolin-2(1H)-yl]ethyl]carbamate

[Chem. 211]

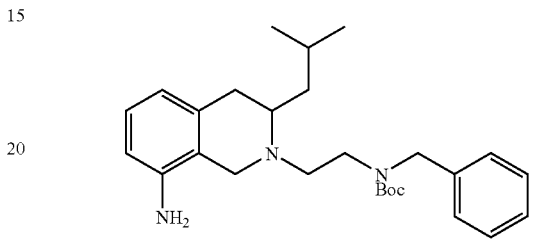

The reaction and treatment were carried out in the same manner as in Example 45-a) using tert-butyl benzyl[2-[3-isobutyl-8-nitro-3,4-dihydroisoquinolin-2(1H)-yl]ethyl]carbamate obtained in Example 43-b) to obtain a title compound as a yellow oily substance.

$^1$H-NMR (CDCl$_3$) δ: 0.87 (6H, d, J=6.6 Hz), 1.09-1.14 (1H, m), 1.25-1.35 (1H, br), 1.40-1.65 (9H, m), 1.60-1.70 (1H, br), 2.49 (1H, dd, J=5.6, 16.3 Hz), 2.50-3.00 (3H, m), 3.27-3.56 (5H, m), 4.50 (2H, brs), 6.51 (1H, dd, J=7.8 Hz), 6.53 (1H, d, J=7.6 Hz), 6.97 (1H, dd, J=7.6, 7.8 Hz), 7.23-7.33 (5H, m).

b) Production of N-benzyl-2-[8-amino-3-isobutyl-3,4-dihydroisoquinolin-2(1H)-yl]ethanamine

[Chem. 212]

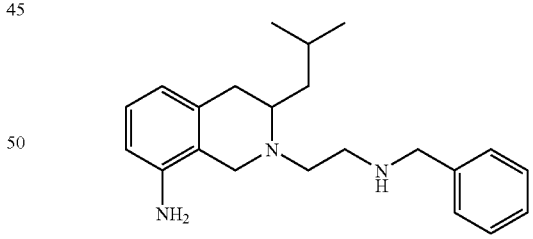

The reaction and treatment were carried out in the same manner as in Example 32-g) to obtain a title compound as a light yellow oily substance.

$^1$H-NMR (CDCl$_3$) δ: 0.87 (6H, d, J=6.6 Hz), 1.12-1.20 (1H, m), 1.30-1.39 (1H, m), 1.59-1.70 (1H, m), 2.52 (1H, dd, J=4.1, 16.1 Hz), 2.65-2.82 (4H, m), 2.93 (1H, dd, J=5.1, 16.1 Hz), 2.95-3.02 (1H, m), 3.41 (2H, brs), 3.42 (1H, d, J=15.4 Hz), 3.51 (1H, d, J=15.6 Hz), 3.80 (1H, d, J=13.4 Hz), 3.83 (1H, d, J=13.4 Hz), 6.51 (1H, d, J=7.8 Hz), 6.54 (1H, d, J=7.6 Hz), 6.97 (1H, dd, J=7.6, 7.8 Hz), 7.21-7.33 (5H, m).

MS (FAB) m/z 338 (M+H)+

IR (ATR cm$^{-1}$): 2952, 2926, 1621, 1591, 1467, 1297, 768, 735, 696.

Example 49

Production of N-benzyl-2-[5-acetamide-3-isobutyl-3,4-dihydroisoquinolin-2(1H)-yl]ethanamine a) Production of tert-butyl benzyl[2-[5-acetamide-3-isobutyl-3,4-dihydroisoquinolin-2(1H)-yl]ethyl]carbamate

[Chem. 213]

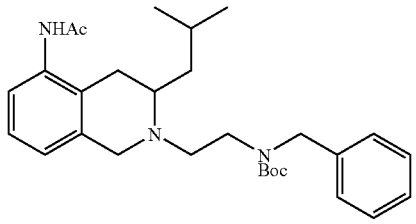

A solution of 14 mg of N-benzyl-2-[5-amino-3-isobutyl-3,4-dihydroisoquinolin-2(1H)-yl]ethanamine obtained in Example 45-a) and 3.8 mg of pyridine in methylene chloride (2 mL) was stirred under ice-cooling for 10 minutes. A solution of 4.9 mg of acetyl chloride in methylene chloride (1 mL) was added dropwise thereto, followed by stirring at room temperature for 16 hours.

Water was added to the reaction liquid, followed by extraction with chloroform. The chloroform layer was washed with saturated brine. It was dried over sodium sulfate, concentrated under reduced pressure, and purified by PLC (chloroform:methanol=20:1) to obtain 16 mg (yield 100%) of a title compound as a light yellow oily substance.

$^1$H-NMR (CDCl$_3$) δ: 0.90 (6H, d, J=6.3 Hz), 1.09-1.19 (1H, m), 1.40-1.50 (9H, br), 1.50-1.68 (2H, br), 2.21 (3H, s), 2.21-2.75 (4H, m), 2.96-3.49 (3H, m), 3.70-3.80 (2H, m), 4.46 (2H, brs), 6.85 (2H, brs), 7.15 (1H, dd, J=7.8, 7.8 Hz), 7.19-7.33 (5H, m), 7.69 (1H, d, J=7.8 Hz).

b) Production of N-benzyl-2-[5-acetamide-3-isobutyl-3,4-dihydroisoquinolin-2(1H)-yl]ethanamine

[Chem. 214]

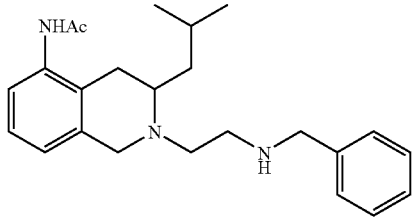

The reaction and treatment were carried out in the same manner as in Example 32-g) to obtain a title compound as a light yellow oily substance.

$^1$H-NMR (CDCl$_3$) δ: 0.90 (6H, d, J=6.6 Hz), 1.13-1.23 (1H, m), 1.40-1.46 (1H, m), 1.65-1.76 (1H, br), 2.20 (3H, s), 2.31 (1H, dd, J=5.1, 16.1 Hz), 2.50-2.74 (5H, m), 3.05-3.15 (1H, br), 3.73 (1H, d, J=16.6 Hz), 3.78 (1H, d, J=16.6 Hz), 3.81 (2H, s), 6.84 (1H, d, J=7.8 Hz), 6.86-6.92 (1H, br), 7.15 (1H, dd, J=7.8, 7.8 Hz), 7.22-7.35 (5H, m), 7.67 (1H, d, J=7.8 Hz).

MS (FAB) m/z 380 (M+H)$^+$

IR (ATR cm$^{-1}$): 2953, 1662, 1536, 1468, 1367, 1269, 749, 698.

Example 50

Production of N-benzyl-2-[6-acetamide-3-isobutyl-3,4-dihydroisoquinolin-2(1H)-yl]ethanamine a) Production of tert-butyl benzyl[2-[6-acetamide-3-isobutyl-3,4-dihydroisoquinolin-2(1H)-yl]ethyl]carbamate

[Chem. 215]

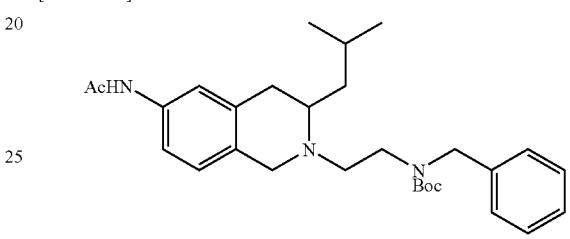

The reaction and treatment were carried out in the same manner as in Example 49-a) using N-benzyl-2-[6-amino-3-isobutyl-3,4-dihydroisoquinolin-2(1H)-yl)ethanamine obtained in Example 46-a) to obtain a title compound as a light yellow oily substance.

$^1$H-NMR (CDCl$_3$) δ: 0.88 (6H, d, J=6.6 Hz), 1.08-1.16 (1H, m), 1.25-1.37 (1H, br), 1.40-1.50 (9H, br), 1.62-1.71 (1H, br), 2.15 (3H, s), 2.35-2.50 (1H, m), 2.46 (1H, dd, J=6.1, 16.6 Hz), 2.50-3.05 (3H, m), 3.24-3.50 (2H, br), 3.62-3.77 (2H, br), 4.37-4.60 (2H, br), 6.92 (1H, d, J=8.0 Hz), 7.17 (2H, brs), 7.19-7.33 (5H, m).

b) Production of N-benzyl-2-[6-acetamide-3-isobutyl-3,4-dihydroisoquinolin-2(1H)-yl]ethanamine

[Chem. 216]

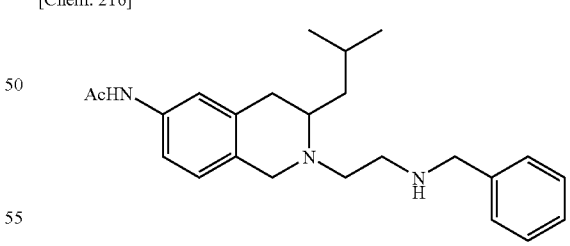

The reaction and treatment were carried out in the same manner as in Example 32-g) to obtain a title compound as a light yellow oily substance.

$^1$H-NMR (CDCl$_3$) δ: 0.87 (6H, d, J=6.6 Hz), 1.11-1.19 (1H, m), 1.33-1.43 (1H, m), 1.61-1.72 (1H, m), 2.15 (3H, s), 2.50 (1H, dd, J=4.9, 16.0 Hz), 2.57-2.67 (1H, m), 2.67-2.76 (3H, m), 2.89 (1H, dd, J=5.1, 16.1 Hz), 2.96-3.03 (1H, m), 3.68 (2H, s), 3.81 (2H, s), 6.93 (1H, d, J=8.0 Hz), 7.15-7.18 (2H, br), 7.21-7.34 (5H, m)

MS (FAB) m/z 380 (M+H)$^+$.

Example 51

Production of N-benzyl-2-[7-acetamide-3-isobutyl-3,4-dihydroisoquinolin-2(1H)-yl]ethanamine a) Production of tert-butyl benzyl[2-[7-acetamide-3-isobutyl-3,4-dihydroisoquinolin-2(1H)-yl]ethyl]carbamate

[Chem. 217]

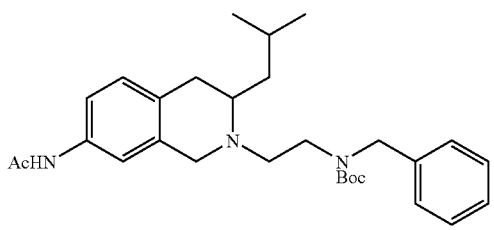

The reaction and treatment were carried out in the same manner as in Example 49-a) using N-benzyl-2-[7-amino-3-isobutyl-3,4-dihydroisoquinolin-2(1H)-yl]ethanamine obtained in Example 47-a) to obtain a title compound as a light yellow oily substance.

$^1$H-NMR (CDCl$_3$) δ: 0.88 (6H, d, J=6.3 Hz), 1.08-1.16 (1H, br), 1.33 (1H, br), 1.40-1.50 (9H, br), 1.67 (1H, br), 2.15 (3H, s), 2.43 (1H, dd, J=5.6, 16.1 Hz), 2.45-3.54 (6H, m), 3.60-3.80 (2H, br), 4.45-4.55 (2H, br), 6.99 (1H, d, J=8.3 Hz), 7.05-7.20 (2H, br), 7.22-7.32 (5H, m).

b) Production of N-benzyl-2-[7-acetamide-3-isobutyl-3,4-dihydroisoquinolin-2(1H)-yl]ethanamine

[Chem. 218]

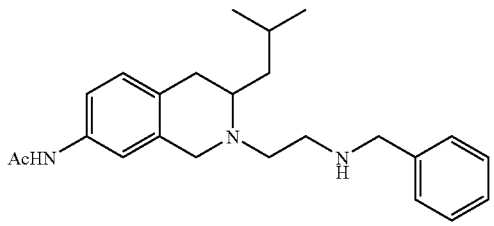

The reaction and treatment were carried out in the same manner as in Example 32-g) to obtain a title compound as a light yellow oily substance.

$^1$H-NMR (CDCl$_3$) δ: 0.88 (6H, d, J=6.3 Hz), 1.11-1.19 (1H, m), 1.33-1.42 (1H, m), 1.63-1.73 (1H, m), 2.15 (3H, s), 2.47 (1H, dd, J=4.9, 16.6 Hz), 2.57-2.65 (1H, m), 2.65-2.74 (3H, m), 2.85 (1H, dd, J=4.9, 16.6 Hz), 2.97-3.04 (1H, m), 3.71 (2H, s), 3.81 (2H, s), 7.00 (1H, d, J=8.3 Hz), 7.01 (1H, br), 7.12 (1H, d, J=8.3 Hz), 7.23-7.32 (5H, m).

MS (FAB) m/z 380 (M+H)$^+$

IR (ATR cm$^{-1}$): 2958, 1665, 1602, 1546, 1504, 1367, 821, 739, 698.

Example 52

Production of N-benzyl-2-[8-acetamide-3-isobutyl-3,4-dihydroisoquinolin-2(1H)-yl]ethanamine a) Production of tert-butyl benzyl[2-[8-acetamide-3-isobutyl-3,4-dihydroisoquinolin-2(1H)-yl]ethyl]carbamate

[Chem. 219]

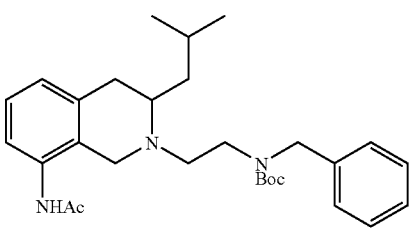

The reaction and treatment were carried out in the same manner as in Example 49-a) using N-benzyl-2-[8-amino-3-isobutyl-3,4-dihydroisoquinolin-2(1H)-yl]ethanamine obtained in Example 48-a) to obtain a title compound as a pale yellow oily substance.

$^1$H-NMR (CDCl$_3$) δ: 0.88 (6H, d, J=6.6 Hz), 1.09-1.24 (1H, br), 1.25-1.35 (1H, br), 1.40-1.50 (9H, br), 1.64-1.83 (1H, m), 2.20 (3H, brs), 2.49 (2H, br), 2.60-2.65 (1H, m), 2.79-2.89 (1H, br), 2.90-2.98 (1H, br), 3.25-3.45 (2H, br), 3.50-3.74 (2H, br), 4.40-4.51 (2H, br), 6.90-6.98 (1H, br), 7.15 (1H, dd, J=7.6, 7.8 Hz), 7.22-7.48 (6H, m).

b) Production of N-benzyl-2-[8-acetamide-3-isobutyl-3,4-dihydroisoquinolin-2(1H)-yl]ethanamine

[Chem. 220]

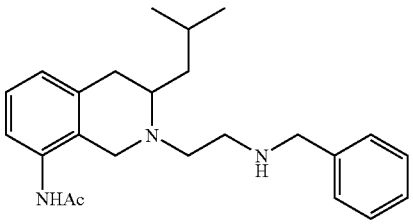

The reaction and treatment were carried out in the same manner as in Example 32-g) to obtain a title compound as a light yellow oily substance.

$^1$H-NMR (CDCl$_3$) δ: 0.87 (6H, d, J=6.6 Hz), 1.10-1.18 (1H, m), 1.30-1.38 (1H, m), 1.61-1.70 (1H, m), 2.16 (3H, s), 2.54 (1H, dd, J=4.1, 16.1 Hz), 2.60-2.78 (4H, m), 2.90-3.03 (2H, m), 3.57 (2H, s), 3.81 (2H, s), 6.71 (1H, br), 6.93 (1H, d, J=7.8 Hz), 7.15 (1H, dd, J=7.8, 7.8 Hz), 7.22-7.34 (5H, m), 7.42 (1H, d, J=7.8 Hz).

MS (FAB) m/z 380 (M+H)$^+$

IR (ATR cm⁻¹): 1662, 1535, 1468, 1453, 1368, 1295, 778, 739, 698.

Example 53

Production of N-benzyl-2-[6-fluoro-3-(4-fluorobenzyl)-3,4-dihydroisoquinolin-2(1H)-yl]ethanamine a) Production of 6-fluoro-3-(4-fluorobenzyl)-1,2,3,4-tetrahydroisoquinoline

[Chem. 221]

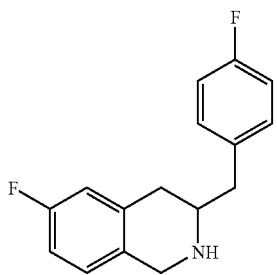

The reaction and treatment were carried out in the same manner as in Example 32-a, b, c, d, e) using 4-fluorophenyl magnesium bromide instead of phenyl magnesium bromide to obtain a title compound as a light yellow oily substance.

¹H-NMR (CDCl₃) δ: 2.80 (1H, dd, J=4.2, 16.8 Hz), 2.92 (1H, dd, J=10.0, 16.8 Hz), 2.95 (1H, dd, J=9.2, 13.2 Hz), 3.33 (1H, dd, J=5.1, 13.2 Hz), 3.34-3.44 (1H, m), 4.19 (1H, m), 4.31 (1H, m), 6.76 (1H, dd, J=2.4, 9.3 Hz), 6.88 (1H, ddd, J=2.4, 8.5, 8.5 Hz), 6.98-7.07 (3H, m), 7.18-7.24 (2H, m).

b) Production of tert-butyl benzyl[2-[6-fluoro-3-(4-fluorobenzyl)-3,4-dihydroisoquinolin-2(1H)-yl]ethyl]carbamate

[Chem. 222]

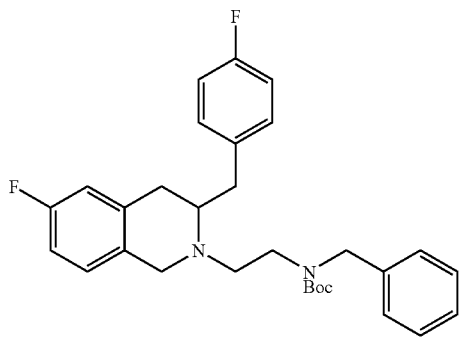

The reaction and treatment were carried out in the same manner as in Example 324) to obtain a title compound as a light yellow oily substance.

¹H-NMR (CDCl₃) δ: 1.40-1.50 (9H, br), 2.34-2.90 (6H, m), 3.00-3.50 (3H, m), 3.60-3.90 (2H, m), 4.40-4.58 (2H, m), 6.73 (1H, dd, J=2.7, 9.5 Hz), 6.85 (1H, ddd, J=2.7, 8.4, 8.4 Hz), 6.90-7.10 (4H, m), 7.10-7.30 (6H, m).

c) Production of N-benzyl-2-[6-fluoro-3-(4-fluorobenzyl)-3,4-dihydroisoquinolin-2(1H)-yl]ethanamine

[Chem. 223]

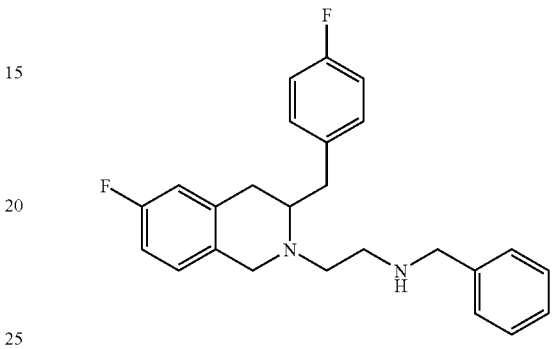

The reaction and treatment were carried out in the same manner as in Example 32-g) to obtain a title compound as a light yellow oily substance.

¹H-NMR (CDCl₃) δ: 2.40-2.52 (2H, m), 2.65-2.90 (6H, m), 3.12-3.22 (1H, m), 3.71 (2H, s), 3.82 (2H, s), 6.76 (1H, dd, J=2.2, 9.2 Hz), 6.80-7.10 (6H, m), 7.16-7.34 (5H, m).

Example 54

Production of N-benzyl-2-[6-fluoro-3-(2-fluorobenzyl)-3,4-dihydroisoquinolin-2(1H)-yl]ethanamine a) Production of 6-fluoro-3-(2-fluorobenzyl)-1,2,3,4-tetrahydroisoquinoline

[Chem. 224]

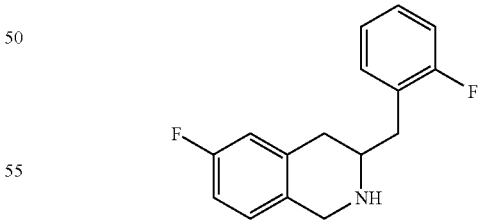

The reaction and treatment were carried out in the same manner as in Example 32-a, b, c, d, e) using 2-fluorophenyl magnesium bromide instead of phenyl magnesium bromide to obtain a title compound as a light yellow oily substance.

¹H-NMR (CDCl₃) δ: 2.68 (1H, dd, J=10.0, 16.6 Hz), 2.76 (1H, dd, J=4.2, 16.6 Hz), 2.94 (2H, d, J=6.6 Hz), 3.24 (1H, dddd, J=4.2, 6.6, 6.6, 10.0 Hz), 4.02 (1H, d, J=15.5 Hz), 4.07 (1H, d, J=15.5 Hz), 6.76 (1H, dd, J=2.4, 9.5 Hz), 6.82 (1H, ddd, J=2.4, 8.6, 8.6 Hz), 6.97 (1H, dd, J=5.9, 8.6 Hz), 7.04-7.10 (1H, m), 7.11 (1H, ddd, J=1.2, 7.6, 7.6 Hz), 7.22-7.29 (3H, m).

b) Production of N-benzyl-2-[6-fluoro-3-(2-fluorobenzyl)-3,4-dihydroisoquinolin-2(1H)-yl]ethanamine

[Chem. 225]

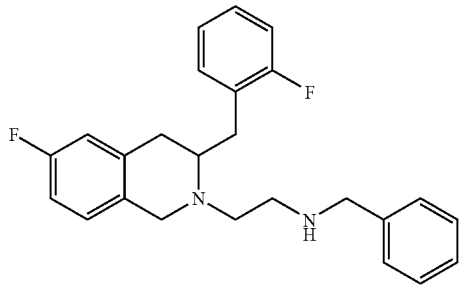

The reaction and treatment were carried out in the same manner as in Examples 32-f and g) to obtain a title compound as a light yellow oily substance.

¹H-NMR (CDCl₃) δ: 2.48 (1H, dd, J=9.8, 13.2 Hz), 2.52 (1H, dd, J=3.4, 17.1 Hz), 2.77-2.99 (6H, m), 3.22-3.30 (1H, m), 3.72 (2H, s), 3.85 (2H, s), 6.76 (1H, dd, J=2.4, 9.5 Hz), 6.84 (1H, ddd, J=2.4, 8.4, 8.4 Hz), 6.95 (1H, dd, J=5.6, 8.4 Hz), 6.98-7.10 (3H, m), 7.16-7.20 (1H, m), 7.24-7.34 (5H, m).

Example 55

Production of N-benzyl-2-[3-(4-chlorobenzyl)-6-fluoro-3,4-dihydroisoquinolin-2(1H)-yl]ethanamine a) Production of 3-(4-chlorobenzyl)-6-fluoro-1,2,3,4-tetrahydroisoquinoline

[Chem. 226]

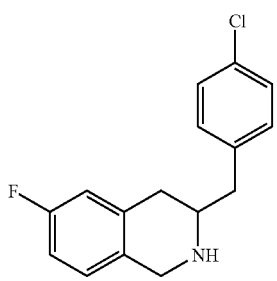

The reaction and treatment were carried out in the same manner as in Example 32-a, b, c, d, e) using 4-chlorophenyl magnesium bromide instead of phenyl magnesium bromide to obtain a title compound as a light yellow oily substance.

¹H-NMR (CDCl₃) δ: 2.59 (1H, dd, J=10.2, 16.3 Hz), 2.70-2.78 (2H, m), 2.83 (1H, dd, J=5.8, 13.6 Hz), 3.05-3.13 (1H, m), 3.94 (1H, d, J=15.5 Hz), 3.99 (1H, d, J=15.5 Hz), 6.75 (1H, dd, J=2.4, 9.8 Hz), 6.80 (1H, ddd, J=2.4, 8.5, 8.5 Hz), 6.95 (1H, dd, J=5.6, 8.5 Hz), 7.18 (2H, dd, J=1.8, 6.5 Hz), 7.30 (2H, dd, J=1.8, 6.5 Hz).

b) Production of tert-butyl 2-[3-(4-chlorobenzyl)-6-fluoro-3,4-dihydroisoquinolin-2(1H)-yl]ethyl carbamate

[Chem. 227]

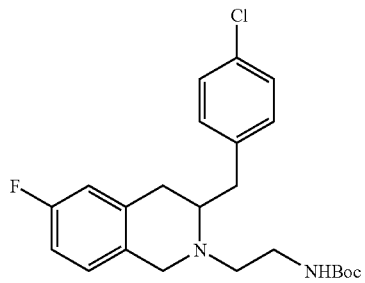

The reaction and treatment were carried out in the same manner as in Example 1-e) to obtain a title compound as a light yellow oily substance.

¹H-NMR (CDCl₃) δ: 1.43 (9H, s), 2.45 (1H, dd, J=9.5, 13.4 Hz), 2.48-2.54 (1H, m), 2.62-2.88 (4H, m), 3.14-3.34 (3H, m), 3.72-3.82 (2H, m), 4.92 (1H, brs), 6.75 (1H, dd, J=2.4, 9.3 Hz), 6.85 (1H, ddd, J=2.4, 8.5, 8.5 Hz), 7.00 (1H, dd, J=5.8, 8.5 Hz), 7.04 (2H, d, J=8.3 Hz), 7.25 (2H, d, J=8.3 Hz).

c) Production of 2-[3-(4-chlorobenzyl)-6-fluoro-3,4-dihydroisoquinolin-2(1H)-yl]ethanamine

[Chem. 228]

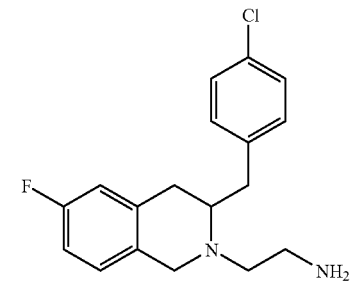

The reaction and treatment were carried out in the same manner as in Example 1-f) to obtain a title compound as a light yellow oily substance.

¹H-NMR (CDCl₃) δ: 2.45 (1H, dd, J=10.0, 13.2 Hz), 2.51 (1H, dd, J=3.8, 16.7 Hz), 2.64-2.87 (5H, m), 2.90 (1H, dd, J=4.5, 13.5 Hz), 3.17-3.23 (1H, m), 3.77 (1H, d, J=15.7 Hz),), 3.83 (1H, d, J=15.7 Hz), 6.73-6.78 (1H, m), 6.83-6.88 (1H, m), 6.99-7.03 (1H, m), 7.05 (2H, dd, J=1.3, 8.0 Hz), 7.25 (2H, dd, J=1.3, 8.0 Hz).

d) Production of N-benzyl-2-[3-(4-chlorobenzyl)-6-fluoro-3,4-dihydroisoquinolin-2(1H)-yl]ethanamine

[Chem. 229]

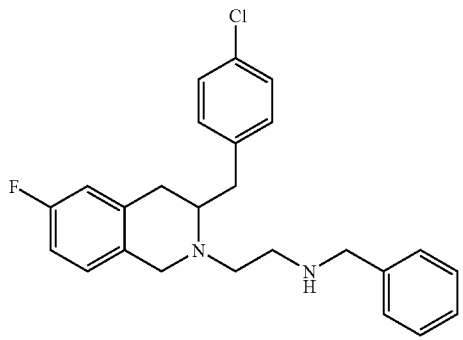

The reaction and treatment were carried out in the same manner as in Example 1-g) to obtain a title compound as a light yellow oily substance.

$^1$H-NMR (CDCl$_3$) δ: 2.42 (1H, dd, J=10.0, 13.0 Hz), 2.49 (1H, dd, J=3.7, 16.6 Hz), 2.72-2.92 (6H, m), 3.13-3.22 (1H, m), 3.73 (2H, s), 3.80 (2H, s), 6.75 (1H, dd, J=2.5, 9.4 Hz), 6.86 (1H, ddd, J=2.5, 8.5, 8.5 Hz), 6.98 (1H, dd, J=5.8, 8.5 Hz), 7.02 (2H, d, J=8.4 Hz), 7.22 (2H, d, J=8.4 Hz), 7.23-7.36 (5H, m).

Example 56

Production of N-benzyl-2-[7-fluoro-3-(4-fluorobenzyl)-3,4-dihydroisoquinolin-2(1H)-yl]ethanamine a) Production of 1,3-bis(4-fluorophenyl)-2-propanone

[Chem. 230]

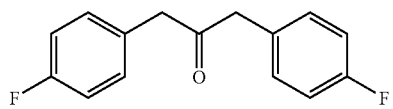

Under a nitrogen atmosphere, 155 g of ethyl 4-fluorophenyl acetate was dissolved in diethyl ether (1 L) at −30° C., and 1.5 kg of isopropyl magnesium bromide was added thereto while the internal temperature was adjusted to be not higher than 0° C. A reagent was added thereto, followed by stirring at room temperature for 3.5 hours. A reaction liquid was poured into ice water (about 1 L) containing 200 mL of concentrated hydrochloric acid, followed by saturation with brine, and the organic layer was separated. The aqueous layer was extracted with ethyl acetate, and the organic layer was combined, washed with a saturated aqueous sodium bicarbonate solution, and brine in this order, and dried over anhydrous sodium sulfate, and the solvent was then removed by evaporation to obtain 140 g of a yellow oily substance. To this yellow oily substance were added 1 L of acetic acid and 200 mL of 6 N hydrochloric acid, followed by reflux for 2 hours. The reaction liquid was concentrated under reduced pressure, and the residue was dissolved in ethyl acetate (1.5 L), washed with a saturated aqueous sodium bicarbonate solution and then with brine, and dried over anhydrous sodium sulfate, and the solvent was then removed by evaporation to obtain 105 g (yield 100%) of a desired product as an orange solid.

$^1$H-NMR (CDCl$_3$) δ: 3.70 (4H, s), 6.96-7.04 (4H, m), 7.06-7.14 (4H, m).

b) Production of 2-amino-1,3-bis(4-fluorophenyl)-2-propanone

[Chem. 231]

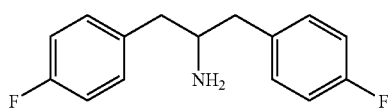

The reaction and treatment were carried out in the same manner as in Example 36-c) to obtain a title compound as a light yellow oily substance.

$^1$H-NMR (CDCl$_3$) δ: 2.52 (2H, dd, J=13.5, 8.8 Hz), 2.80 (2H, dd, J=13.5, 4.5 Hz), 3.21 (1H, m), 6.96-7.02 (4H, m), 7.14-7.18 (4H, m).

c) Production of 7-fluoro-3-(4-fluorobenzyl)-1,2,3,4-tetrahydroisoquinoline

[Chem. 232]

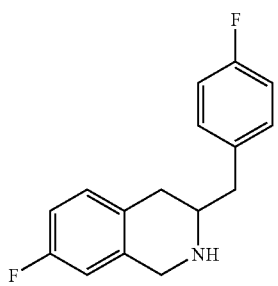

The reaction and treatment were carried out in the same manner as in Examples 37-c, d and e) to obtain a title compound as a light yellow oily substance.

$^1$H-NMR (CDCl$_3$) δ: 2.55 (1H, m), 2.70-2.88 (3H, m), 3.09 (1H, m), 4.00 (2H, s), 6.73 (1H, m), 6.82 (1H, m), 6.97-7.04 (3H, m), 7.14-7.25 (2H, m).

d) Production of tert-butyl benzyl[2-[7-fluoro-3-(4-fluorobenzyl)-3,4-dihydroisoquinolin-2(1H)-yl]ethyl]carbamate

[Chem. 233]

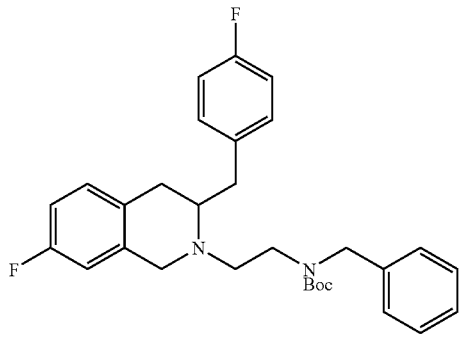

The reaction and treatment were carried out in the same manner as in Example 32-f) to obtain a title compound as a light yellow oily substance.

¹H-NMR (CDCl$_3$) δ: 1.42-1.50 (9H, br), 2.34-2.88 (6H, m), 3.02-3.48 (3H, m), 3.68-3.84 (2H, m), 4.42-4.50 (2H, m), 6.69-6.75 (1H, m), 6.84 (1H, ddd, J=2.4, 8.6, 8.6 Hz), 6.92-7.08 (5H, m), 7.18-7.34 (5H, m).

e) Production of N-benzyl-2-[7-fluoro-3-(4-fluorobenzyl)-3,4-dihydroisoquinolin-2(1H)-yl]ethanamine

[Chem. 234]

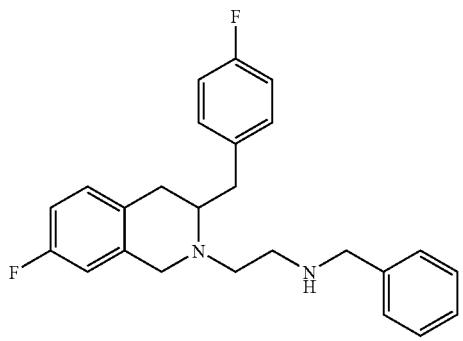

The reaction and treatment were carried out in the same manner as in Example 32-g) to obtain a title compound as a light yellow oily substance.

¹H-NMR (CDCl$_3$) δ: 2.43 (1H, dd, J=9.8, 13.4 Hz), 2.48 (1H, dd, J=3.9, 16.4 Hz), 2.68-2.92 (6H, m), 3.10-3.20 (1H, m), 3.74 (2H, s), 3.79 (2H, s), 6.73 (1H, dd, J=2.5, 9.3 Hz), 6.85 (1H, ddd, J=2.5, 8.6, 8.6 Hz), 6.90-7.05 (5H, m), 7.22-7.34 (5H, m).

Example 57

Production of N-benzyl-2-[6-chloro-3-(4-fluorobenzyl)-3,4-dihydroisoquinolin-2(1H)-yl]ethanamine a) Production of 6-chloro-3-(4-fluorobenzyl)-1,2,3,4-tetrahydroisoquinoline

[Chem. 235]

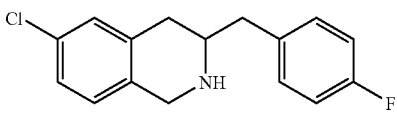

The reaction and treatment were carried out in the same manner as in Example 28-f, g) using tert-butyl (4-chloro-2-methylbenzyl)carbamate instead of tert-butyl (3-chloro-2-methylbenzyl)carbamate to obtain a title compound as a light yellow oily substance.

¹H-NMR (CDCl$_3$) δ: 2.59 (1H, dd, J=10.7, 16.1 Hz), 2.70-2.79 (2H, m), 2.85 (1H, dd, J=5.6, 13.4 Hz), 3.05-3.13 (1H, m), 3.95 (1H, d, J=15.8 Hz), 4.01 (1H, d, J=15.8 Hz), 6.94 (1H, d, J=8.1 Hz), 7.02 (2H, dd, J=8.6, 8.8 Hz), 7.05 (1H, d, J=1.9 Hz), 7.08 (1H, dd, J=1.9, 8.1 Hz), 7.21 (2H, dd, J=5.4, 8.6 Hz).

b) Production of tert-butyl benzyl[2-[6-chloro-3-(4-fluorobenzyl)-3,4-dihydroisoquinolin-2(1H)-yl]ethyl]carbamate

[Chem. 236]

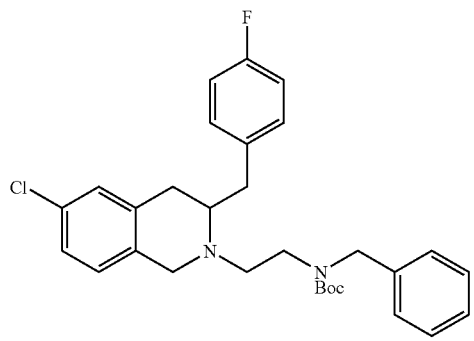

The reaction and treatment were carried out in the same manner as in Example 32-f) to obtain a title compound as a light yellow oily substance.

$^1$H-NMR (CDCl$_3$) δ: 1.44-1.48 (9H, br), 2.34-2.82 (6H, m), 3.05-3.48 (3H, m), 3.72-3.81 (2H, m), 4.43-4.48 (2H, m), 6.93-7.33 (13H, m).

c) Production of N-benzyl-2-[6-chloro-3-(4-fluorobenzyl)-3,4-dihydroisoquinolin-2(1H)-yl]ethanamine

[Chem. 237]

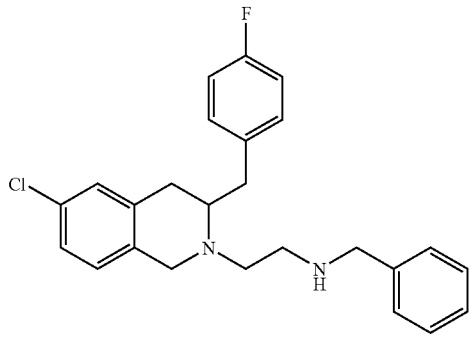

The reaction and treatment were carried out in the same manner as in Example 32-g) to obtain a title compound as a light yellow oily substance.

$^1$H-NMR (CDCl$_3$) δ: 2.41 (1H, dd, J=9.8, 13.2 Hz), 2.49 (1H, dd, J=3.8, 16.4 Hz), 2.73-2.88 (6H, m), 3.13-3.19 (1H, m), 3.74 (2H, s), 3.79 (2H, s), 6.92-6.97 (3H, m), 7.01-7.05 (3H, m), 7.13 (1H, dd, J=2.2, 8.1 Hz), 7.23-7.33 (5H, m).

Example 58

Production of N-benzyl-2-[7-chloro-3-(4-chlorobenzyl)-3,4-dihydroisoquinolin-2(1H)-yl]ethanamine a) Production of 7-chloro-3-(4-chlorobenzyl)-1,2,3,4-tetrahydroisoquinoline

[Chem. 238]

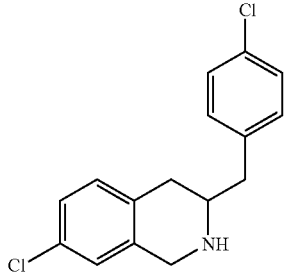

The reaction and treatment were carried out in the same manner as in Examples 56-a), 36-c), 37-c, d, e) using 4-chlorophenyl acetate instead of 4-fluorophenyl acetate to obtain a title compound as a light yellow oily substance.

$^1$H-NMR (CDCl$_3$) δ: 2.54 (1H, dd, J=9.8, 16.1 Hz), 2.68-2.88 (3H, m), 3.05-3.13 (1H, m), 3.98 (2H, s), 6.96-7.32 (7H, m).

b) Production of tert-butyl benzyl[2-[7-chloro-3-(4-chlorobenzyl)-3,4-dihydroisoquinolin-2(1H)-yl]ethyl]carbamate

[Chem. 239]

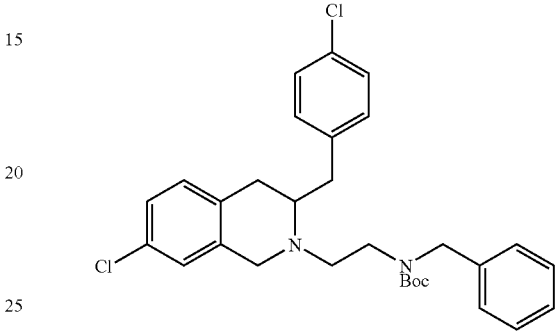

The reaction and treatment were carried out in the same manner as in Example 32-f) to obtain a title compound as a light yellow oily substance.

$^1$H-NMR (CDCl$_3$) δ: 1.42-1.52 (9H, br), 2.34-2.88 (6H, m), 3.02-3.46 (3H, m), 3.66-3.82 (2H, m), 4.38-4.50 (2H, m), 6.92-7.04 (4H, m), 7.11 (1H, dd, J=1.9, 8.0 Hz), 7.16-7.34 (7H, m).

c) Production of N-benzyl-2-[7-chloro-3-(4-chlorobenzyl)-3,4-dihydroisoquinolin-2(1H)-yl]ethanamine

[Chem. 240]

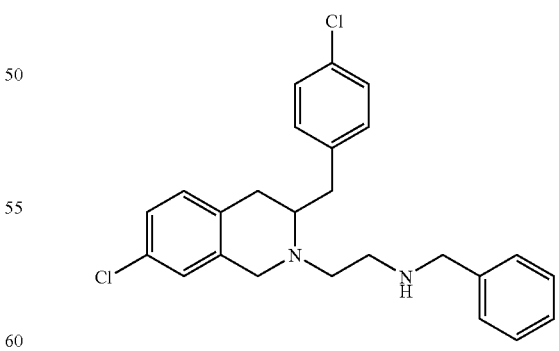

The reaction and treatment were carried out in the same manner as in Example 32-g) to obtain a title compound as a light yellow oily substance.

$^1$H-NMR (CDCl$_3$) δ: 2.42 (1H, dd, J=9.8, 13.4 Hz), 2.46 (1H, dd, J=3.9, 16.6 Hz), 2.70-2.88 (6H, m), 3.13-3.22 (1H, m), 3.74 (2H, s), 3.78 (2H, s), 6.94-7.04 (4H, m), 7.11 (1H, dd, J=1.7, 8.0 Hz), 7.19-7.34 (7H, m).

Example 59

Production of N-(4-chlorobenzyl)-2-[3-benzyl-3,4-dihydroisoquinolin-2(1H)-yl]ethanamine

[Chem. 241]

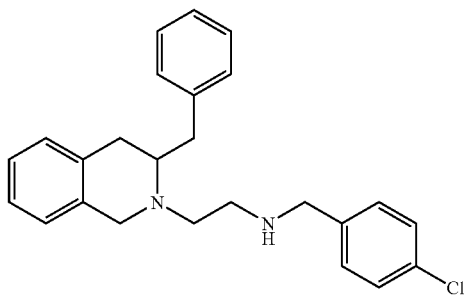

The reaction and treatment were carried out in the same manner as in Example 1-g) using 4-chlorobenzaldehyde instead of benzaldehyde to obtain a title compound as a yellow oily substance.

$^1$H-NMR (CDCl$_3$) δ: 2.49 (1H, dd, J=9.8, 13.2 Hz), 2.57 (1H, dd, J=3.8, 16.5 Hz), 2.72-2.79 (3H, m), 2.83-2.92 (3H, m), 3.20-3.26 (1H, m), 3.75 (2H, s), 3.79 (2H, s), 7.02-7.06 (2H, m), 7.10 (2H, d, J=7.0 Hz), 7.11-7.22 (5H, m), 7.24-7.28 (4H, m).

Example 60

Production of 2-[3-benzyl-3,4-dihydroisoquinolin-2(1H)-yl]-N,N-bis(4-chlorobenzyl)ethanamine

[Chem. 242]

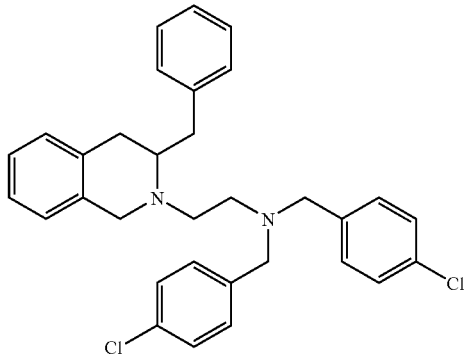

In the reaction of Example 59, the title compound was also simultaneously obtained. The title compound was a yellow oily substance.

$^1$H-NMR (CDCl$_3$) δ: 2.38 (1H, dd, J=10.4, 12.8 Hz), 2.54 (1H, dd, J=4.1, 16.4 Hz), 2.66-2.86 (6H, m), 3.09-3.15 (1H, m), 3.55 (2H, d, J=13.9 Hz), 3.59 (2H, d, J=13.9 Hz), 3.71 (1H, d, J=13.9 Hz), 3.76 (1H, d, J=13.9 Hz), 6.96-7.00 (3H, m), 7.02-7.04 (1H, m), 7.13-7.16 (2H, m), 7.19 (1H, d, J=6.8 Hz), 7.23-7.30 (10H, m).

Example 61

Production of N-(3-chlorobenzyl)-2-[3-benzyl-3,4-dihydroisoquinolin-2(1H)-yl]ethanamine

[Chem. 243]

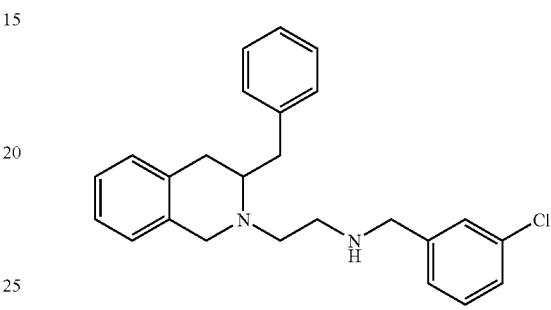

The reaction and treatment were carried out in the same manner as in Example 1-g) using 3-chlorobenzaldehyde instead of benzaldehyde to obtain a title compound as a yellow oily substance.

$^1$H-NMR (CDCl$_3$) δ: 2.49 (1H, dd, J=9.8, 13.2 Hz), 2.57 (1H, dd, J=3.8, 16.3 Hz), 2.71-2.80 (3H, m), 2.83-2.93 (3H, m), 3.21-3.27 (1H, m), 3.73 (1H, d, J=13.8 Hz), 3.77 (1H, d, J=13.8 Hz), 3.81 (2H, s), 7.04 (1H, d, J=5.6 Hz), 7.06 (1H, d, J=5.6 Hz), 7.10-7.18 (6H, m), 7.21-7.29 (5H, m).

Example 62

Production of N-(2-chlorobenzyl)-2-[3-benzyl-3,4-dihydroisoquinolin-2(1H)-yl]ethanamine

[Chem. 244]

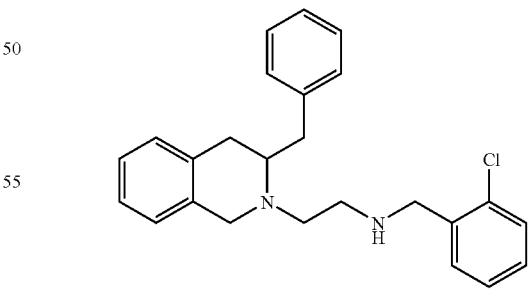

The reaction and treatment were carried out in the same manner as in Example 1-g) using 2-chlorobenzaldehyde instead of benzaldehyde to obtain a title compound as a yellow oily substance.

$^1$H-NMR (CDCl$_3$) δ: 2.47 (1H, dd, J=10.0, 13.1 Hz), 2.55 (1H, dd, J=3.7, 16.4 Hz), 2.78-2.83 (3H, m), 2.86-2.93 (3H, m), 3.19-3.24 (1H, m), 3.79 (2H, s), 3.89 (2H, s), 7.01-7.06 (2H, m), 7.09 (2H, d, J=7.1 Hz), 7.14-7.26 (7H, m), 7.32-7.37 (2H, m).

Example 63

Production of N-(3,4-dichlorobenzyl)-2-[3-benzyl-3,4-dihydroisoquinolin-2(1H)-yl]ethanamine

[Chem. 245]

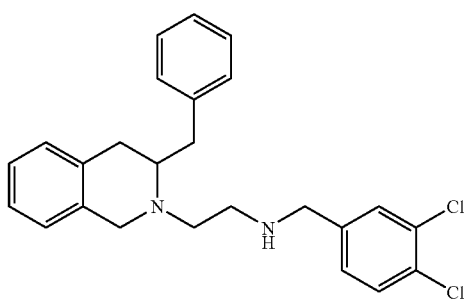

The reaction and treatment were carried out in the same manner as in Example 1-g) using 3,4-dichlorobenzaldehyde instead of benzaldehyde to obtain a title compound as a pale yellow oily substance.

$^1$H-NMR (CDCl$_3$) δ: 2.42 (1H, dd, J=10.5, 12.9 Hz), 2.57 (1H, dd, J=4.2, 16.6 Hz), 2.66-2.92 (6H, m), 3.17-3.23 (1H, m), 3.56 (2H, s), 3.78 (1H, d, J=16.0 Hz), 3.83 (1H, d, J=16.0 Hz), 7.00-7.06 (3H, m), 7.15-7.27 (5H, m), 7.35 (2H, d, J=8.1 Hz), 7.44 (2H, d, J=1.7 Hz).

Example 64

Production of N-(4-fluorobenzyl)-2-[3-benzyl-3,4-dihydroisoquinolin-2(1H)-yl]ethanamine

[Chem. 246]

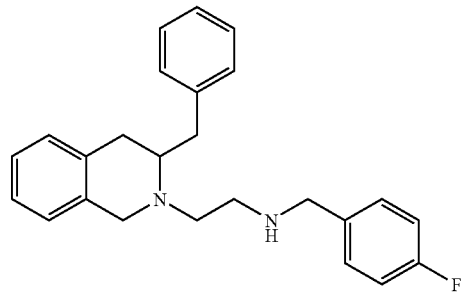

The reaction and treatment were carried out in the same manner as in Example 1-g) using 4-fluorobenzaldehyde instead of benzaldehyde to obtain a title compound as a light yellow oily substance.

$^1$H-NMR (CDCl$_3$) δ: 2.53 (1H, dd, J=9.8, 13.2 Hz), 2.58 (1H, dd, J=3.9, 16.6 Hz), 2.70-2.90 (5H, m), 2.93 (1H, dd, J=4.7, 13.3 Hz), 3.20-3.30 (1H, m), 3.49 (2H, s), 3.86 (2H, s), 7.04-7.32 (13H, m).

Example 65

Production of N-(3-fluorobenzyl)-2-[3-benzyl-3,4-dihydroisoquinolin-2(1H)-yl]ethanamine

[Chem. 247]

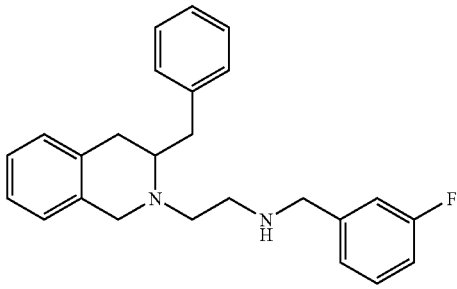

The reaction and treatment were carried out in the same manner as in Example 1-g) using 3-fluorobenzaldehyde instead of benzaldehyde to obtain a title compound as a light yellow oily substance.

$^1$H-NMR (CDCl$_3$) δ: 2.49 (1H, dd, J=9.8, 13.2 Hz), 2.57 (1H, dd, J=3.9, 16.4 Hz), 2.72-2.88 (5H, m), 2.91 (1H, dd, J=4.9, 13.2 Hz), 3.20-3.28 (1H, m), 3.75 (1H, d, J=13.8 Hz), 3.83 (1H, d, J=13.8 Hz), 3.81 (2H, s), 6.90-7.30 (13H, m).

Example 66

Production of N-(2-fluorobenzyl)-2-[3-benzyl-3,4-dihydroisoquinolin-2(1H)-yl]ethanamine

[Chem. 248]

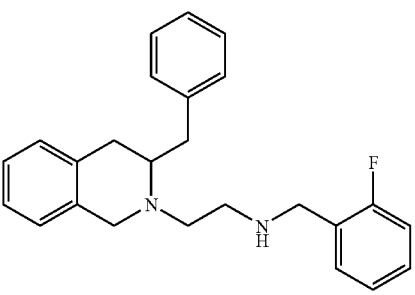

The reaction and treatment were carried out in the same manner as in Example 1-g) using 2-fluorobenzaldehyde instead of benzaldehyde to obtain a title compound as a light yellow oily substance.

$^1$H-NMR (CDCl$_3$) δ: 2.46 (1H, dd, J=10.1, 13.0 Hz), 2.55 (1H, dd, J=3.7, 16.4 Hz), 2.74-2.94 (6H, m), 3.17-3.24 (1H, m), 3.79 (2H, s), 3.85 (2H, s), 6.98-7.32 (13H, m).

Example 67

Production of N-(4-methoxybenzyl)-2-[3-benzyl-3,4-dihydroisoquinolin-2(1H)-yl]ethanamine

[Chem. 249]

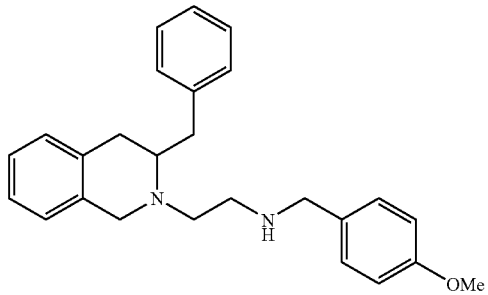

The reaction and treatment were carried out in the same manner as in Example 1-g) using 4-methoxybenzaldehyde instead of benzaldehyde to obtain a title compound as a light yellow oily substance.

$^1$H-NMR (CDCl$_3$) δ: 2.47-2.57 (2H, m), 2.77-2.96 (6H, m), 3.18-3.26 (1H, m), 3.54 (1H, d, J=16.2 Hz), 3.70 (1H, d, J=16.2 Hz), 3.79 (3H, s), 3.92 (2H, s), 6.83 (1H, d, J=8.6 Hz), 6.95-6.98 (1H, m), 7.03-7.06 (1H, m), 7.09-7.30 (10H, m).

Example 68

Production of N-(3-methoxybenzyl)-2-[3-benzyl-3,4-dihydroisoquinolin-2(1H)-yl]ethanamine

[Chem. 250]

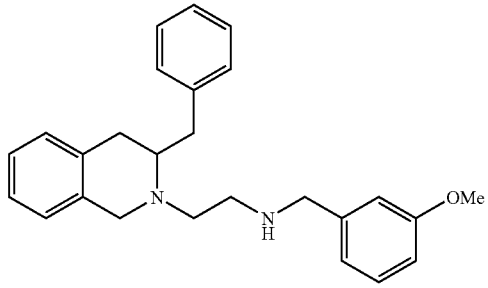

The reaction and treatment were carried out in the same manner as in Example 1-g) using 3-methoxybenzaldehyde instead of benzaldehyde to obtain a title compound as a light yellow oily substance.

$^1$H-NMR (CDCl$_3$) δ: 2.52 (1H, dd, J=9.8, 14.0 Hz), 2.55 (1H, dd, J=3.4, 16.0 Hz), 2.77-2.98 (6H, m), 3.22-3.29 (1H, m), 3.60-3.70 (2H, m), 3.73 (3H, s), 3.89 (2H, s), 6.80-6.88 (2H, m), 6.98-7.38 (11H, m).

Example 69

Production of N-(2-methoxybenzyl)-2-[3-benzyl-3,4-dihydroisoquinolin-2(1H)-yl]ethanamine

[Chem. 251]

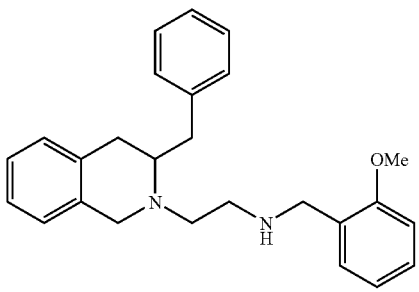

The reaction and treatment were carried out in the same manner as in Example 1-g) using 2-methoxybenzaldehyde instead of benzaldehyde to obtain a title compound as a light yellow oily substance.

$^1$H-NMR (CDCl$_3$) δ: 2.47 (1H, dd, J=9.8, 13.2 Hz), 2.58 (1H, dd, J=3.0, 16.8 Hz), 2.78-2.88 (5H, m), 3.04-3.24 (3H, m), 3.29 (3H, s), 3.50 (1H, d, J=15.6 Hz), 3.92 (1H, d, J=13.4 Hz), 4.29 (1H, d, J=13.4 Hz), 6.63 (1H, d, J=8.3 Hz), 6.81 (1H, d, J=6.4 Hz), 6.95-6.88 (2H, m), 6.98-7.39 (9H, m).

Example 70

Production of N-(2,6-dimethoxybenzyl)-2-[3-benzyl-3,4-dihydroisoquinolin-2(1H)-yl]ethanamine

[Chem. 252]

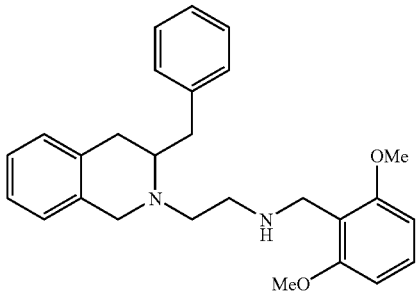

The reaction and treatment were carried out in the same manner as in Example 1-g) using 2,6-dimethoxybenzaldehyde instead of benzaldehyde to obtain a title compound as a pale yellow oily substance.

$^1$H-NMR (CDCl$_3$) δ: 2.44 (1H, dd, J=10.0, 13.2 Hz), 2.57 (11-1, dd, J=3.6, 16.4 Hz), 2.75-2.85 (3H, m), 2.95-3.15 (4H, m), 3.53 (6H, s), 3.80 (2H, s), 4.22 (1H, d, J=13.4 Hz), 4.33

(1H, d, J=13.4 Hz), 6.42 (2H, d, J=8.3 Hz), 6.75 (1H, d, J=6.8 Hz), 7.06 (2H, d, J=6.8 Hz), 7.15-7.30 (7H, m).

Example 71

Production of N-(4-hydroxybenzyl)-2-[3-benzyl-3,4-dihydroisoquinolin-2(1H)-yl]ethanamine

[Chem. 253]

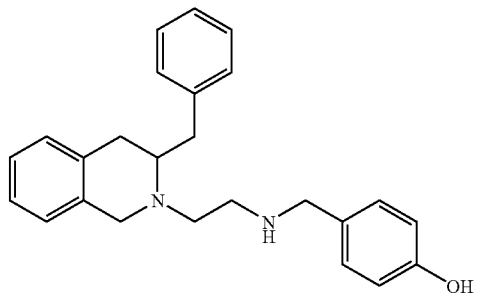

The reaction and treatment were carried out in the same manner as in Example 1-g) using 4-hydroxybenzaldehyde instead of benzaldehyde to obtain a title compound as a white amorphous substance.

$^1$H-NMR (CD$_3$OD) δ: 2.37 (1H, dd, J=10.2, 13.0 Hz), 2.51 (1H, dd, J=3.6, 16.3 Hz), 2.74-2.82 (3H, m), 2.97-3.08 (3H, m), 3.29-3.31 (1H, m), 3.46 (1H, d, J=16.1 Hz), 3.65 (9H, m).

Example 72

Production of N-(4-ethylbenzyl)-2-[3-benzyl-3,4-dihydroisoquinolin-2(1H)-yl]ethanamine

[Chem. 254]

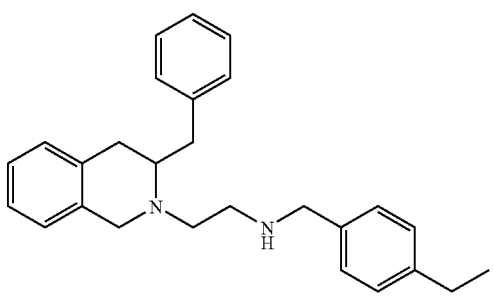

The reaction and treatment were carried out in the same manner as in Example 1-g) using 4-ethylbenzaldehyde instead of benzaldehyde to obtain a title compound as a pale yellow oily substance.

$^1$H-NMR (CDCl$_3$) δ: 1.24 (3H, t, J=7.6 Hz), 2.47 (1H, dd, J=10.0, 12.9 Hz), 2.56 (1H, dd, J=3.6, 16.6 Hz), 2.63 (2H, q, J=7.6 Hz), 2.77-2.80 (3H, m), 2.84-2.94 (3H, m), 3.19-3.25 (1H, m), 3.77 (2H, s), 3.78 (2H, s), 7.01-7.06 (2H, m), 7.09-7.20 (8H, m), 7.24-7.31 (3H, m).

Example 73

Production of N-(3-ethylbenzyl)-2-[3-benzyl-3,4-dihydroisoquinolin-2(1H)-yl]ethanamine

[Chem. 255]

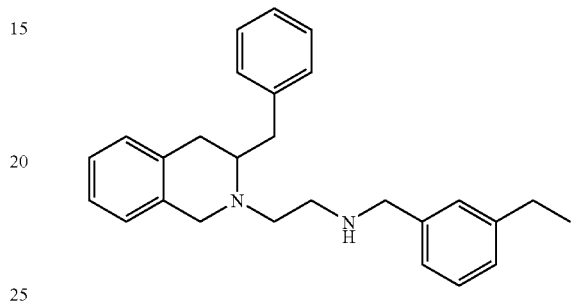

The reaction and treatment were carried out in the same manner as in Example 1-g) using 3-ethylbenzaldehyde instead of benzaldehyde to obtain a title compound as a pale yellow oily substance.

$^1$H-NMR (CDCl$_3$) δ: 1.22 (3H, t, J=7.6 Hz), 2.48 (1H, dd, J=10.0, 12.9 Hz), 2.56 (1H, dd, J=3.6, 16.6 Hz), 2.62 (2H, q, J=7.6 Hz), 2.77-2.82 (3H, m), 2.87-2.94 (3H, m), 3.21-3.28 (1H, m), 3.78 (2H, s), 3.80 (2H, s), 7.02-7.06 (2H, m), 7.08-7.21 (8H, m), 7.24-7.28 (3H, m).

Example 74

Production of N-(2-ethylbenzyl)-2-[3-benzyl-3,4-dihydroisoquinolin-2(1H)-yl]ethanamine

[Chem. 256]

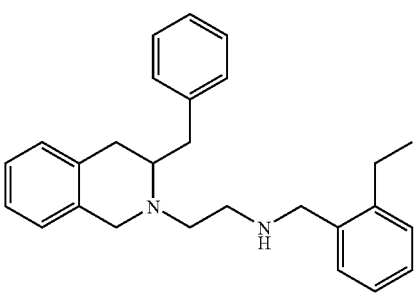

The reaction and treatment were carried out in the same manner as in Example 1-g) using 2-ethylbenzaldehyde instead of benzaldehyde to obtain a title compound as a pale yellow oily substance.

$^1$H-NMR (CDCl$_3$) δ: 1.18 (3H, t, J=7.6 Hz), 2.48 (1H, dd, J=10.0, 13.2 Hz), 2.56 (1H, dd, J=3.6, 16.5 Hz), 2.67 (2H, q, J=7.6 Hz), 2.78-2.86 (4H, m), 2.90-2.96 (2H, m), 3.20-3.27

(1H, m), 3.79 (2H, s), 3.81 (2H, s), 7.01-7.06 (2H, m), 7.10 (2H, d, J=7.1 Hz), 7.14-7.18 (7H, m), 7.24-7.30 (2H, m).

Example 75

Production of N-(4-methylbenzyl)-2-[3-benzyl-3,4-dihydroisoquinolin-2(1H)-yl]ethanamine

[Chem. 257]

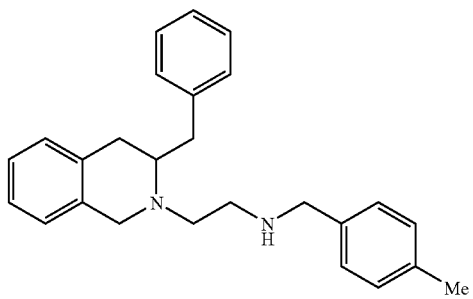

The reaction and treatment were carried out in the same manner as in Example 1-g) using 4-methylbenzaldehyde instead of benzaldehyde to obtain a title compound as a light yellow oily substance.

$^1$H-NMR (CDCl$_3$) δ: 2.33 (3H, s), 2.47 (1H, dd, J=10.0, 13.2 Hz), 2.55 (1H, dd, J=3.7, 16.4 Hz), 2.74-2.93 (6H, m), 3.18-3.24 (1H, m), 3.76 (2H, s), 3.79 (2H, s), 7.02-7.29 (13H, m).

Example 76

Production of N-(3-methylbenzyl)-2-[3-benzyl-3,4-dihydroisoquinolin-2(1H)-yl]ethanamine

[Chem. 258]

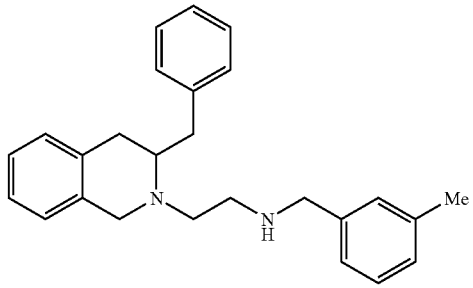

The reaction and treatment were carried out in the same manner as in Example 1-g) using 3-methylbenzaldehyde instead of benzaldehyde to obtain a title compound as a light yellow oily substance.

$^1$H-NMR (CDCl$_3$) δ: 2.32 (3H, s), 2.47 (1H, dd, J=10.0, 12.9 Hz), 2.56 (1H, dd, J=3.6, 16.3 Hz), 2.74-2.95 (6H, m), 3.18-3.26 (1H, m), 3.76 (2H, s), 3.79 (2H, s), 7.00-7.29 (13H, m).

Example 77

Production of N-(2-methylbenzyl)-2-[3-benzyl-3,4-dihydroisoquinolin-2(1H)-yl]ethanamine

[Chem. 259]

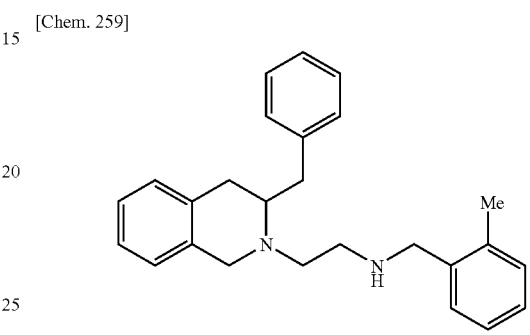

The reaction and treatment were carried out in the same manner as in Example 1-g) using 2-methylbenzaldehyde instead of benzaldehyde to obtain a title compound as a light yellow oily substance.

$^1$H-NMR (CDCl$_3$) δ: 2.29 (3H, s), 2.47 (1H, dd, J=10.0, 13.2 Hz), 2.56 (1H, dd, J=3.8, 16.5 Hz), 2.74-2.94 (6H, m), 3.18-3.26 (1H, m), 3.78 (2H, s), 3.79 (2H, s), 7.00-7.28 (13H, m).

Example 78

Production of N-(4-tert-butylbenzyl)-2-[3-benzyl-3,4-dihydroisoquinolin-2(1H)-yl]ethanamine

[Chem. 260]

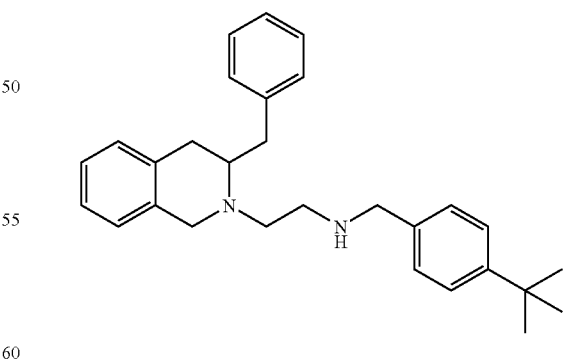

The reaction and treatment were carried out in the same manner as in Example 1-g) using 4-tert-butylbenzaldehyde instead of benzaldehyde to obtain a title compound as a pale yellow oily substance.

$^1$H-NMR (CDCl$_3$) δ: 1.31 (9H, s), 2.48 (1H, dd, J=10.0, 13.2 Hz), 2.56 (1H, dd, J=3.5, 16.4 Hz), 2.77-2.82 (3H, m), 2.85-2.95 (3H, m), 3.20-3.25 (1H, m), 3.78 (4H, s), 7.02-7.08 (2H, m), 7.12-7.28 (9H, m), 7.33 (2H, d, J=8.3 Hz).

Example 79

Production of N-(4-trifluoromethylbenzyl)-2-[3-benzyl-3,4-dihydroisoquinolin-2(1H)-yl]ethanamine

[Chem. 261]

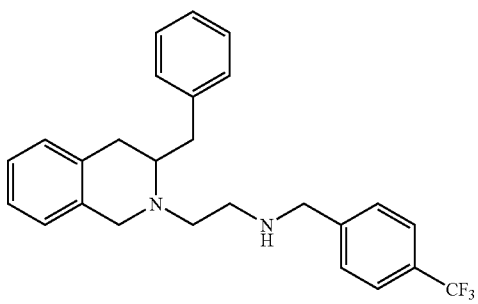

The reaction and treatment were carried out in the same manner as in Example 1-g) using 4-trifluoromethylbenzaldehyde instead of benzaldehyde to obtain a title compound as a light yellow oily substance.

$^1$H-NMR (CDCl$_3$) δ: 2.50 (1H, dd, J=9.9, 13.2 Hz), 2.57 (1H, dd, J=3.8, 16.5 Hz), 2.72-2.94 (6H, m), 3.21-3.28 (1H, m), 3.81 (2H, s), 3.83 (2H, s), 7.02-7.34 (9H, m), 7.39 (2H, d, J=8.0 Hz), 7.56 (2H, d, J=8.0 Hz).

Example 80

Production of N-(4-dimethylaminobenzyl)-2-[3-benzyl-3,4-dihydroisoquinolin-2(1H)-yl]ethanamine

[Chem. 262]

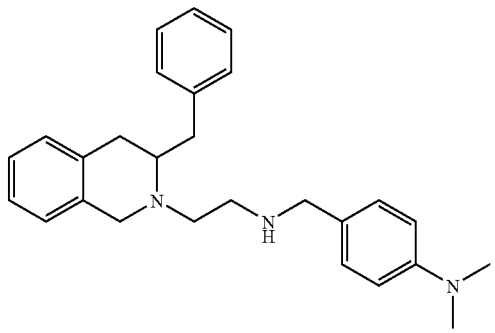

The reaction and treatment were carried out in the same manner as in Example 1-g) using 4-dimethylaminobenzaldehyde instead of benzaldehyde to obtain a title compound as a pale yellow oily substance.

$^1$H-NMR (CDCl$_3$) δ: 2.49 (1H, dd, J=10.0, 13.2 Hz), 2.56 (1H, dd, J=3.6, 16.4 Hz), 2.77-2.92 (6H, m), 2.93 (6H, s), 3.22-3.27 (1H, m), 3.73-3.80 (4H, m), 6.68 (2H, d, J=8.8 Hz), 6.98-7.18 (9H, m), 7.25-7.28 (2H, m).

Example 81

Production of N-(2-dimethylaminobenzyl)-2-[3-benzyl-3,4-dihydroisoquinolin-2(1H)-yl]ethanamine

[Chem. 263]

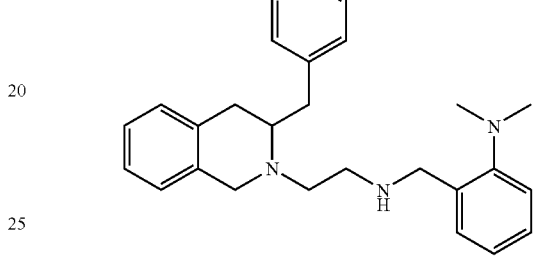

The reaction and treatment were carried out in the same manner as in Example 1-g) using 2-dimethylaminobenzaldehyde instead of benzaldehyde to obtain a title compound as a pale yellow oily substance.

$^1$H-NMR (CDCl$_3$) δ: 2.45 (1H, dd, J=10.4, 12.7 Hz), 2.56 (1H, dd, J=3.6, 16.3 Hz), 2.62 (6H, s), 2.78-2.95 (6H, m), 3.19-3.26 (1H, m), 3.76 (2H, s), 3.86 (1H, d, J=13.4 Hz), 3.91 (1H, d, J=13.4 Hz), 7.00-7.30 (13H, m).

Example 82

Production of N-(3-dimethylaminobenzyl)-2-[3-benzyl-3,4-dihydroisoquinolin-2(1H)-yl]ethanamine

[Chem. 264]

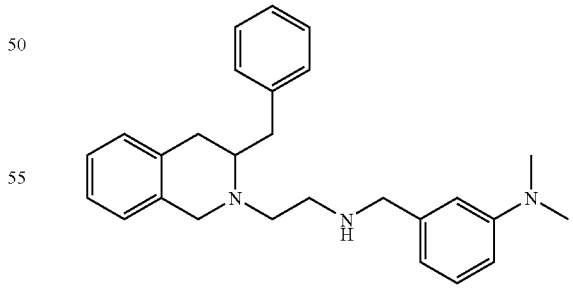

The reaction and treatment were carried out in the same manner as in Example 1-g) using 3-dimethylaminobenzaldehyde instead of benzaldehyde to obtain a title compound as a pale yellow oily substance.

$^1$H-NMR (CDCl$_3$) δ: 2.47 (1H, dd, J=10.2, 13.0 Hz), 2.55 (1H, dd, J=3.9, 16.6 Hz), 2.78-2.94 (6H, m), 2.91 (6H, s), 3.20-3.25 (1H, m), 3.77 (4H, s), 6.23 (2H, dd, J=2.0, 8.0 Hz), 6.67 (1H, s), 7.00-7.05 (2H, m), 7.09-7.20 (6H, m), 7.24-7.28 (2H, m).

Example 83

Production of N-(4-nitrobenzyl)-2-[3-benzyl-3,4-dihydroisoquinolin-2(1H)-yl]ethanamine

[Chem. 265]

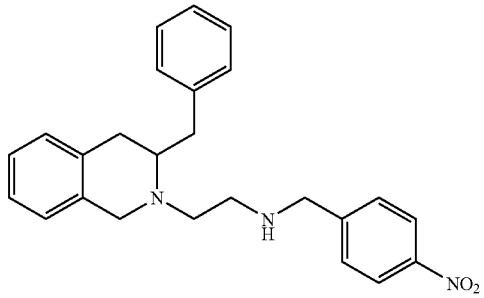

The reaction and treatment were carried out in the same manner as in Example 1-g) using 4-nitrobenzaldehyde instead of benzaldehyde to obtain a title compound as a pale yellow oily substance.

$^1$H-NMR (CDCl$_3$) δ: 2.51 (1H, dd, J=9.6, 13.3 Hz), 2.58 (1H, dd, J=3.8, 16.5 Hz), 2.71-2.81 (3H, m), 2.84-2.94 (3H, m), 3.22-3.28 (1H, m), 3.80 (1H, d, J=16.4 Hz), 3.84 (1H, d, J=16.4 Hz), 3.85 (1H, d, J=14.6 Hz), 3.89 (1H, d, J=14.6 Hz), 7.03-7.08 (2H, m), 7.11-7.20 (5H, m), 7.24-7.28 (2H, m), 7.44 (2H, d, J=8.8 Hz), 8.16 (2H, d, J=8.8 Hz).

Example 84

Production of N-(3-nitrobenzyl)-2-[3-benzyl-3,4-dihydroisoquinolin-2(1H)-yl]ethanamine

[Chem. 266]

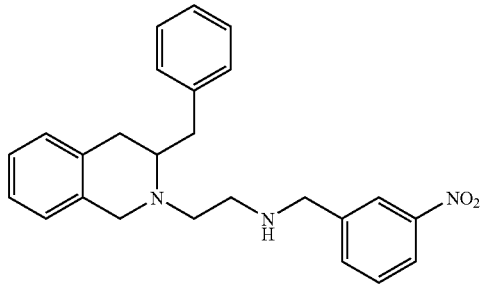

The reaction and treatment were carried out in the same manner as in Example 1-g) using 3-nitrobenzaldehyde instead of benzaldehyde to obtain a title compound as a pale yellow oily substance.

$^1$H-NMR (CDCl$_3$) δ: 2.51 (1H, dd, J=9.5, 13.2 Hz), 2.58 (1H, dd, J=3.9, 16.4 Hz), 2.72-2.94 (6H, m), 3.23-3.28 (1H, m), 3.81 (1H, d, J=16.1 Hz), 3.84 (1H, d, J=14.2 Hz), 3.86 (1H, d, J=16.1 Hz), 3.89 (1H, d, J=14.2 Hz), 7.04-7.28 (9H, m), 7.47 (1H, dd, J=7.8, 7.8 Hz), 7.63 (1H, d, J=7.8 Hz), 8.10 (1H, d, J=7.8 Hz), 8.18 (1H, s).

Example 85

Production of N-(2-nitrobenzyl)-2-[3-benzyl-3,4-dihydroisoquinolin-2(1H)-yl]ethanamine

[Chem. 267]

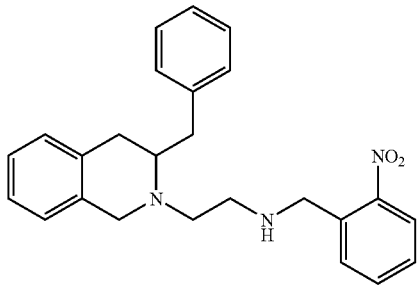

The reaction and treatment were carried out in the same manner as in Example 1-g) using 2-nitrobenzaldehyde instead of benzaldehyde to obtain a title compound as a pale yellow oily substance.

$^1$H-NMR (CDCl$_3$) δ: 2.49 (1H, dd, J=9.8, 13.2 Hz), 2.57 (1H, dd, J=4.2, 16.4 Hz), 2.76-2.94 (6H, m), 3.22-3.28 (1H, m), 3.83 (2H, s), 4.04 (2H, s), 7.03-7.26 (9H, m), 7.37-7.42 (1H, m), 7.56 (1H, dd, J=7.6, 7.6 Hz), 7.61 (1H, d, J=7.6 Hz), 7.94 (1H, d, J=7.6 Hz).

Example 86

Production of N-(4-cyanobenzyl)-2-[3-benzyl-3,4-dihydroisoquinolin-2(1H)-yl]ethanamine

[Chem. 268]

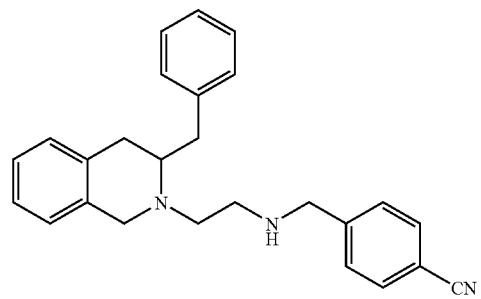

2-[3-benzyl-3,4-dihydroisoquinolin-2(1H)-yl]ethanamine (27 mg, 0.1 mmol) obtained in Example 1-f), 4-cyanobenzyl-bromide (20 mg, 0.1 mmol), and potassium carbonate (17 mg, 0.12 mmol) were dissolved in 1 mL of acetonitrile, followed by stirring at 60° C. for 3 hours. After completion of the reaction, water was added to the reaction liquid, followed by extraction with ethyl acetate, and the organic layer was then washed with saturated brine, dried over anhydrous sodium sulfate, and concentrated under reduced pressure. The residue obtained was purified using silica gel chromatography (chloroform:methanol=10:1) to obtain 14 mg (yield 36.7%) of a title compound as a colorless oily substance.

$^1$H-NMR (CDCl$_3$) δ: 2.51 (1H, dd, J=9.8, 13.2 Hz), 2.57 (1H, dd, J=3.4, 16.2 Hz), 2.70-2.79 (3H, m), 2.83-2.92 (3H, m), 3.23-3.26 (1H, m), 3.82 (4H, s), 7.04-7.20 (7H, m), 7.25-7.30 (2H, m), 7.39 (2H, d, J=7.8 Hz), 7.59 (2H, d, J=7.8 Hz).

Example 87

Production of N-(3-cyanobenzyl)-2-[3-benzyl-3,4-dihydroisoquinolin-2(1H)-yl]ethanamine

[Chem. 269]

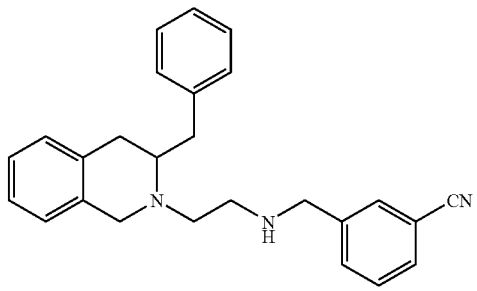

The reaction and treatment were carried out in the same manner as in Example 86 using 3-cyanobenzylbromide instead of 4-cyanobenzylbromide to obtain a title compound as a yellow oily substance.

$^1$H-NMR (CDCl$_3$) δ: 2.53 (1H, dd, J=9.8, 13.2 Hz), 2.58 (1H, dd, J=3.4, 16.2 Hz), 2.71-2.79 (3H, m), 2.84-2.92 (3H, m), 3.23-3.27 (1H, m), 3.74 (1H, d, J=16.4 Hz), 3.80 (1H, d, J=16.4 Hz), 3.82 (2H, s), 7.00-7.02 (1H, m), 7.07-7.20 (6H, m), 7.26 (2H, dd, J=7.3, 7.3 Hz), 7.40 (1H, dd, J=7.8, 7.8 Hz), 7.52-7.56 (2H, m), 7.64 (1H, s).

Example 88

Production of N-(4-acetylbenzyl)-2-[3-benzyl-3,4-dihydroisoquinolin-2(1H)-yl]ethanamine

[Chem. 270]

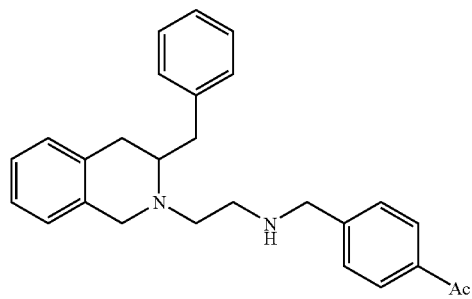

The reaction and treatment were carried out in the same manner as in Example 1-g) using 4-(2-methyl-1,3-dioxolan-2-yl)benzaldehyde instead of benzaldehyde. The obtained yellow oily substance (17 mg) was dissolved in 1 mL of acetone, and 2 mL of 2N hydrochloric acid was added thereto, followed by stirring at room temperature for 1 hour. After the reaction, a saturated aqueous sodium bicarbonate solution was added thereto, followed by extraction with ethyl acetate. The organic layer was washed with brine and then dried over anhydrous sodium sulfate, and the solvent was removed by evaporation to obtain 11 mg (yield 79%) of a title compound as a pale yellow oily substance.

$^1$H-NMR (CDCl$_3$) δ: 2.49 (1H, dd, J=9.5, 13.5 Hz), 2.53 (1H, dd, J=3.4, 16.2 Hz), 2.59 (3H, s), 2.73-2.84 (3H, m), 2.87-2.93 (3H, m), 3.20-3.26 (1H, m), 3.80 (2H, s), 3.84 (2H, s), 7.02-7.07 (2H, m), 7.10 (2H, d, J=7.1 Hz), 7.15-7.20 (3H, m), 7.24-7.27 (2H, m), 7.37 (2H, d, J=8.2 Hz), 7.90 (2H, d, J=8.2 Hz).

Example 89

Production of N-(3-acetylbenzyl)-2-[3-benzyl-3,4-dihydroisoquinolin-2(1H)-yl]ethanamine

[Chem. 271]

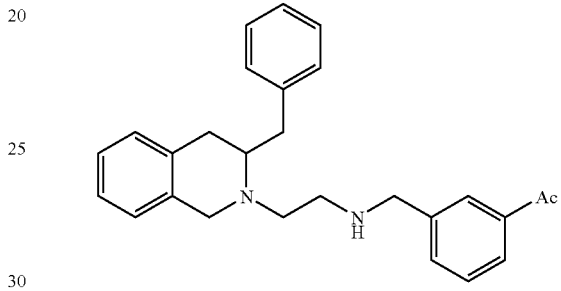

The reaction and treatment were carried out in the same manner as in Example 88 using 3-(2-methyl-1,3-dioxolan-2-yl)benzaldehyde instead of 4-(2-methyl-1,3-dioxolan-2-yl)benzaldehyde to obtain a title compound as a pale yellow oily substance.

$^1$H-NMR (CDCl$_3$) δ: 2.49 (1H, dd, J=9.5, 13.5 Hz), 2.53-2.61 (4H, m), 2.74-2.84 (3H, m), 2.86-2.96 (3H, m), 3.20-3.29 (1H, m), 3.81 (2H, s), 3.84 (2H, s), 7.02-7.08 (2H, m), 7.10 (2H, d, J=7.8 Hz), 7.14-7.19 (3H, m), 7.23-7.27 (2H, m), 7.41 (1H, dd, J=7.8, 7.8 Hz), 7.51 (1H, d, J=7.5 Hz), 7.84 (1H, d, J=7.5 Hz), 7.88 (1H, s).

Example 90

Production of N-[3-(methanesulfonylamino)benzyl]-2-[6-fluoro-3-isobutyl-3,4-dihydroisoquinolin-2(1H)-yl]ethanamine a) Production of 1-(3-fluorophenyl)-4-methyl-2-pentanol

[Chem. 272]

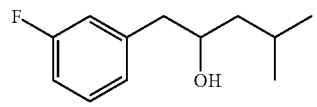

97 mg of 3-fluorobenzeneacetaldehyde and 0.386 mL of isobutyl magnesium bromide (2 M/diethyl ether solution) were dissolved in of 0.2 mL of THF, followed by stirring at room temperature for 1 hour. After completion of the reaction, water was added to the reaction liquid, followed by extraction with chloroform, and the organic layer was then washed with saturated brine, dried over anhydrous sodium sulfate and then concentrated under reduced pressure. The residue obtained was purified using PLC (ethyl acetate:hexane=1:2) to obtain 102 mg (yield 74%) of a title compound as a pale yellow oily substance.

$^1$H-NMR (CDCl$_3$) δ: 0.91 (3H, d, J=6.7 Hz), 0.94 (3H, d, J=6.7 Hz), 1.30 (1H, dd, J=4.2, 9.0 Hz), 1.41-1.49 (1H, m), 1.71-1.86 (1H, m), 2.63 (1H, dd, J=8.3, 13.4 Hz), 2.76-2.87 (1H, m), 3.81-3.92 (1H, m), 6.90-6.95 (2H, m), 6.97-7.02 (1H, m), 7.23-7.30 (1H, m).

b) Production of 1-(3-fluorophenyl)-4-methyl-pentan-2-one

[Chem. 273]

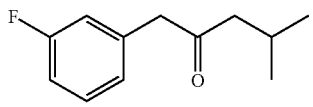

102 mg of 1-(3-fluorophenyl)-4-methyl-2-pentanol, 122 mg of PCC, and 100 mg of MS-4A were dissolved in 1 mL of dichloromethane, followed by stirring at room temperature overnight. After completion of the reaction, the reaction liquid was filtered, water was added to the filtrate, followed by extraction with chloroform, and the organic layer was then washed with saturated brine, dried over anhydrous sodium sulfate and then concentrated under reduced pressure. The residue obtained was purified using PLC (chloroform alone) to obtain 36 mg (yield 36%) of a title compound as a pale yellow oily substance.

$^1$H-NMR (CDCl$_3$) δ: 0.89 (6H, d, J=6.6 Hz), 2.08-2.19 (1H, m), 2.33 (2H, d, J=7.1 Hz), 3.66 (2H, s), 6.88-7.00 (3H, m), 7.26-7.31 (1H, m).

c) Production of 1-(3-fluorophenyl)-4-methyl-pentan-2-amine

[Chem. 274]

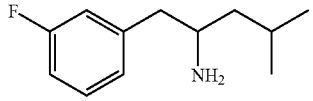

The reaction and treatment were carried out in the same manner as in Example 36-c) to obtain a title compound as a light yellow oily substance.

$^1$H-NMR (CDCl$_3$) δ: 0.89 (3H, d, J=6.6 Hz), 0.94 (311, d, J=6.6 Hz), 1.24-1.32 (4H, m), 1.70-1.82 (1H, m), 2.43 (1H, dd, J=8.8, 13.4 Hz), 2.77 (11-1, dd, J=4.4, 13.4 Hz), 3.01-3.10 (1H, m), 6.86-6.94 (2H, m), 6.95-7.02 (1H, m), 7.22-7.30 (1H, m).

d) Production of 6-fluoro-3-isobutyl-1,2,3,4-tetrahydroisoquinoline

[Chem. 275]

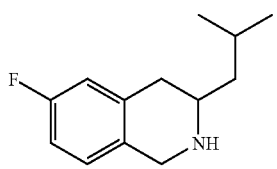

The reaction and treatment were carried out in the same manner as in Examples 36-d, e and f) to obtain a title compound as a light yellow oily substance.

$^1$H-NMR (CDCl$_3$) δ: 0.89 (3H, d, J=6.4 Hz), 0.94 (314, d, J=6.4 Hz), 1.34-1.51 (2H, m), 1.88-1.89 (1H, m), 2.40-2.49 (1H, m), 2.74-2.80 (1H, m), 3.12-3.22 (1H, m), 4.03 (2H, s), 6.80-7.00 (3H, m).

e) Production of N-[3-(methanesulfonylamino)benzyl]-2-[6-fluoro-3-isobutyl-3,4-dihydroisoquinolin-2(1H)-yl]ethanamine

[Chem. 276]

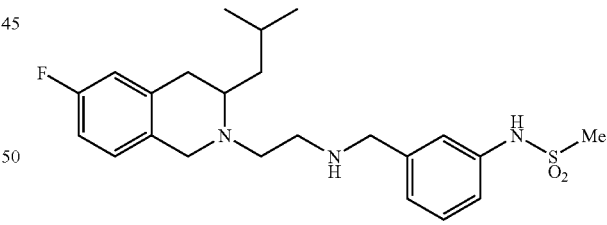

The reaction and treatment were carried out in the same manner as in Examples 117-d, e, f and g) to obtain a title compound as a light yellow oily substance.

$^1$H-NMR (CDCl$_3$) δ: 0.89 (6H, d, J=6.6 Hz), 1.12-1.20 (1H, m), 1.34-1.42 (1H, m), 1.60-1.72 (1H, m), 2.52 (1H, dd, J=4.4, 16.1 Hz), 2.58-2.68 (1H, m), 2.72-2.78 (3H, m), 2.86-3.04 (2H, m), 2.98 (3H, s), 3.71 (2H, s), 3.82 (2H, s), 6.78 (1H, dd, J=2.4, 9.0 Hz), 6.83 (1H, ddd, J=2.4, 8.6, 8.6 Hz), 6.95 (1H, dd, J=5.6, 8.3 Hz), 7.12-7.18 (2H, m), 7.26-7.32 (2H, m).

Example 91

Production of N-(4-phenylbenzyl)-2-[3-benzyl-3,4-dihydroisoquinolin-2(1H)-yl]ethanamine

[Chem. 277]

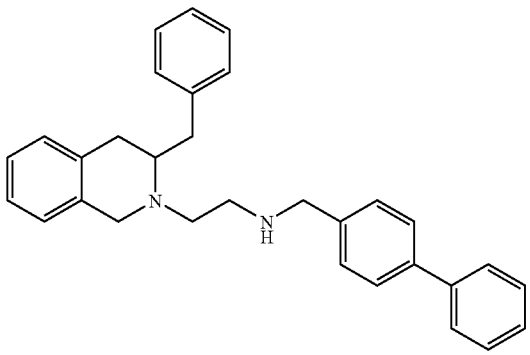

The reaction and treatment were carried out in the same manner as in Example 1-g) using 4-phenylbenzaldehyde instead of benzaldehyde to obtain a title compound as a yellow oily substance.

$^1$H-NMR (CDCl$_3$) δ: 2.48 (1H, dd, J=10.0, 13.1 Hz), 2.57 (1H, dd, J=3.9, 16.4 Hz), 2.75-2.84 (3H, m), 2.87-2.94 (3H, m), 3.21-3.27 (1H, m), 3.79 (1H, d, J=13.6 Hz), 3.84 (2H, s), 3.86 (1H, d, J=13.6 Hz), 7.10-7.25 (9H, m), 7.34-7.36 (2H, m), 7.41-7.45 (3H), m), 7.54 (2H, d, J=7.6 Hz), 7.58 (2H, d, J=7.6 Hz).

Example 92

Production of N-(2,6-dimethylbenzyl)-2-[3-methyl-3,4-dihydroisoquinolin-2(1H)-yl]ethanamine

[Chem. 278]

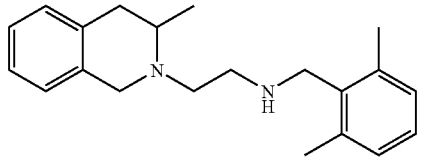

The reaction and treatment were carried out in the same manner as in Example 19-c) using 2,6-dimethylbenzaldehyde instead of benzaldehyde to obtain a title compound as a pale yellow oily substance.

$^1$H-NMR (CDCl$_3$) δ: 1.04 (3H, d, J=6.3 Hz), 2.35 (6H, m), 2.54 (1H, dd, J=4.8, 16.2 Hz), 2.67 (1H, dd, J=6.4, 12.4 Hz), 2.76-2.86 (3H, m), 2.98 (1H, dd, J=4.8, 16.2 Hz), 3.01-3.09 (1H, m), 3.58 (1H, d, J=15.6 Hz), 3.67 (1H, d, J=15.6 Hz), 3.82 (2H, m), 6.94-6.99 (3H, m), 7.03-7.07 (2H, m), 7.10-7.13 (2H, m).

Example 93

Production of N-(4-ethylbenzyl)-2-[3-(4-fluorobenzyl)-3,4-dihydroisoquinoline-2(1H)-yl]ethanamine

[Chem. 279]

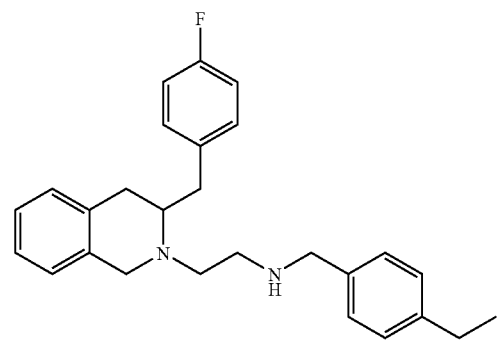

The reaction and treatment were carried out in the same manner as in Example 10-d) using 4-ethylbenzaldehyde instead of benzaldehyde to obtain a title compound as a light yellow oily substance.

$^1$H-NMR (CDCl$_3$) δ: 1.23 (3H, t, J=7.7 Hz), 2.45 (1H, dd, J=10.0, 13.2 Hz), 2.51 (1H, dd, J=3.8, 16.6 Hz), 2.63 (2H, q, J=7.7 Hz), 2.74-2.90 (6H, m), 3.12-3.22 (1H, m), 3.75 (2H, s), 3.78 (2H, s), 6.88-6.96 (2H, m), 7.00-7.06 (4H, m), 7.10-7.21 (6H, m).

Example 94

Production of N-(3-methylbenzyl)-2-[3-(4-fluorobenzyl)-3,4-dihydroisoquinoline-2(1H)-yl]ethanamine

[Chem. 280]

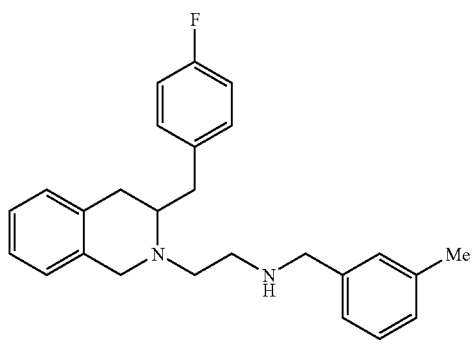

The reaction and treatment were carried out in the same manner as in Example 10-d) using 3-methylbenzaldehyde instead of benzaldehyde to obtain a title compound as a light yellow oily substance.

¹H-NMR (CDCl₃) δ: 2.32 (3H, s), 2.45 (1H, dd, J=9.8, 13.4 Hz), 2.52 (1H, dd, J=3.9, 16.1 Hz), 2.72-2.90 (6H, m), 3.14-3.22 (1H, m), 3.76 (2H, s), 3.79 (2H, s), 6.88-7.22 (12H, m).

Example 95

Production of N-(2-ethylbenzyl)-2-[3-(4-fluorobenzyl)-3,4-dihydroisoquinolin-2(1H)-yl]ethanamine

[Chem. 281]

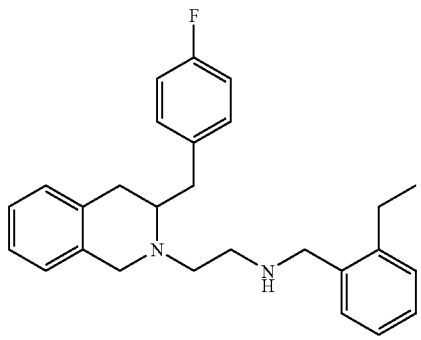

The reaction and treatment were carried out in the same manner as in Example 10-d) using 2-methylbenzaldehyde instead of benzaldehyde to obtain a title compound as a light yellow oily substance.

¹H-NMR (CDCl₃) δ: 1.18 (3H, t, J=7.6 Hz), 2.45 (1H, dd, J=9.8, 13.2 Hz), 2.52 (1H, dd), J=3.8, 16.6 Hz), 2.66 (2H, q, J=7.6 Hz), 2.75-2.91 (6H, m), 3.15-3.23 (1H, m), 3.79 (2H, s), 3.80 (2H, s), 6.90-6.95 (2H, m), 7.00-7.07 (4H, m), 7.10-7.21 (6H, m).

Example 96

Production of N-(4-tert-butylbenzyl)-2-[3-(4-fluorobenzyl)-3,4-dihydroisoquinolin-2(1H)-yl]ethanamine

[Chem. 282]

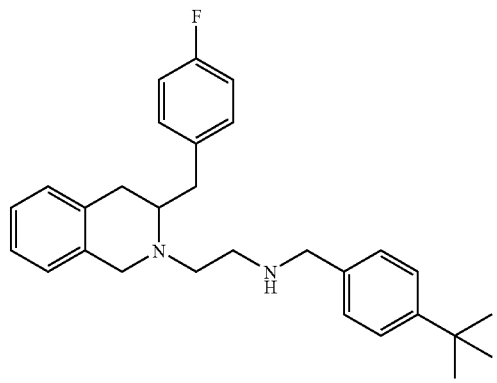

The reaction and treatment were carried out in the same manner as in Example 10-d) using 4-tert-butylbenzaldehyde instead of benzaldehyde to obtain a title compound as a light yellow oily substance.

¹H-NMR (CDCl₃) δ: 1.31 (9H, s), 2.45 (1H, dd, J=9.8, 13.4 Hz), 2.52 (1H, dd, J=3.9, 16.4 Hz), 2.74-2.91 (6H, m), 3.14-3.22 (1H, m), 3.76 (2H, s), 3.78 (2H, s), 6.90-6.96 (2H, m), 7.00-7.07 (4H, m), 7.14-7.18 (2H, m), 7.21 (2H, d, J=8.3 Hz), 7.33 (2H, d, J=8.3 Hz).

Example 97

Production of N-(2,4,6-trimethylbenzyl)-2-[3-(4-fluorobenzyl)-3,4-dihydroisoquinolin-2(1H)-yl]ethanamine

[Chem. 283]

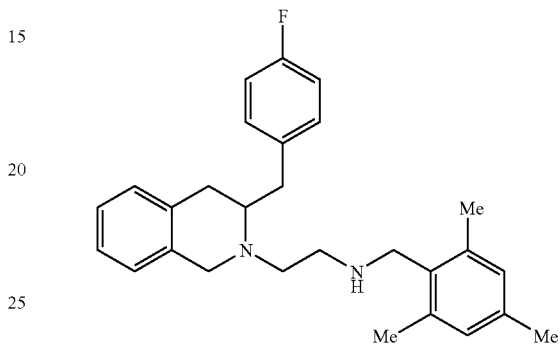

The reaction and treatment were carried out in the same manner as in Example 10-d) using 2,4,6-trimethylbenzaldehyde instead of benzaldehyde to obtain a title compound as a pale yellow oily substance.

¹H-NMR (CDCl₃) δ: 2.24 (3H, s), 2.29 (6H, s) 2.43 (1H, dd, J=9.8, 13.3 Hz), 2.50 (1H, dd, J=3.7, 16.4 Hz), 2.74-2.90 (6H, m), 3.13-3.19 (1H, m), 3.73 (2H, s), 3.77 (2H, s), 6.81 (2H, s), 6.88-6.92 (2H, m), 6.98-7.04 (4H, m), 7.14 (21-1, dd, J=3.4, 5.6 Hz).

Example 98

Production of N-(3-ethylaminobenzyl)-2-[3-(4-fluorobenzyl)-3,4-dihydroisoquinolin-2(1H)-yl]ethanamine a) Production of tert-butyl 3-ethylaminobenzyl[2-[3-(4-fluorobenzyl)-3,4-dihydroisoquinolin-2(1H)-yl]ethyl]carbamate

[Chem. 284]

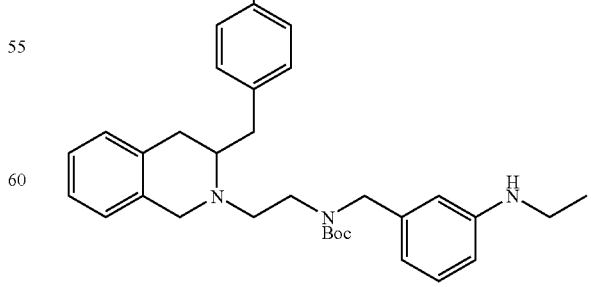

35.4 mg of tert-butyl 3-aminobenzyl[2-[3-(4-fluorobenzyl)-3,4-dihydroisoquinolin-2(1H)-yl]ethyl]carbamate obtained in Example 117-e) was dissolved in 1 mL of toluene, and 3.2 mg of acetaldehyde, 18.4 mg of sodium triacetoxyborohydride, and 1 μL of acetic acid were added thereto under ice-cooling, followed by stirring at room temperature for 1.5 hours. After completion of the reaction, to the reaction liquid were added a saturated aqueous sodium bicarbonate solution and ethyl acetate under ice-cooling, and the organic layer was separated. The aqueous layer was extracted by further addition of ethyl acetate, and the organic layer was combined and washed with saturated brine. The organic layer was dried over anhydrous sodium sulfate and then concentrated under reduced pressure, and the solvent was removed by evaporation to obtain a crude composition.

The crude composition was purified by PLC to obtain 21.6 mg (yield 58%) of a title compound as a light yellow oily substance.

$^1$H-NMR (CDCl$_3$) δ: 1.23 (3H, t, J=7.1 Hz), 1.46 (9H, s), 2.40 (1H, dd, J=10.0, 12.9 Hz), 2.48-2.52 (1H, m), 2.60-2.86 (4H, m), 3.12 (2H, q, J=7.1 Hz), 3.15-3.44 (3H, m), 3.83 (2H, s), 4.38 (2H, s), 6.44-6.55 (3H, m), 6.95 (2H, dd, J=8.7, 8.7 Hz), 7.01-7.14 (7H, m).

b) Production of N-(3-ethylaminobenzyl)-2-[3-(4-fluorobenzyl)-3,4-dihydroisoquinoline-2(1H)-yl]ethanamine

[Chem. 285]

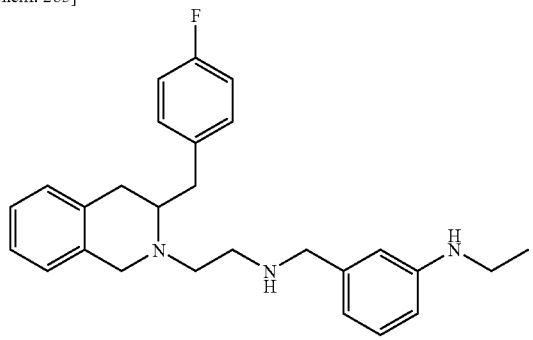

The reaction and treatment were carried out in the same manner as in Example 32-g) to obtain a title compound as a light yellow oily substance.

$^1$H-NMR (CDCl$_3$) δ: 1.22 (3H, t, J=7.2 Hz), 2.44 (1H, dd, J=9.9, 13.4 Hz), 2.52 (1H, dd, J=4.0, 16.4 Hz), 2.74-2.90 (6H, m), 3.12 (2H, q, J=7.2 Hz), 3.15-3.20 (1H, m), 3.72 (2H, s), 3.77 (1H, d, J=16.4 Hz), 3.81 (1H, d, J=16.4 Hz), 6.47-6.50 (1H, m), 6.54 (1H, s), 6.60 (1H, d, J=7.6 Hz), 6.94 (2H, dd, J=8.8, 8.8 Hz), 6.91-7.02 (4H, m), 7.11 (1H, dd, J=7.6, 7.6 Hz), 7.13-7.16 (2H, m).

Example 99

Production of N-(4-aminobenzyl)-2-[3-(4-fluorobenzyl)-3,4-dihydroisoquinoline-2(1H)-yl]ethanamine a) Production of 2-(4-nitrobenzylamino)ethanol

[Chem. 286]

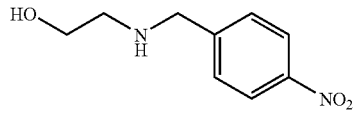

The reaction and treatment were carried out in the same manner as in Example 117-a) using 4-nitrobenzaldehyde instead of 3-nitrobenzaldehyde to obtain a title compound as a light yellow oily substance.

$^1$H-NMR (CDCl$_3$) δ: 2.83 (2H, t, J=5.1 Hz), 3.71 (2H, t, J=5.1 Hz), 3.94 (2H, s), 7.52 (2H, d, J=8.8 Hz), 8.20 (al, d, J=8.8 Hz).

b) Production of tert-butyl 2-hydroxyethyl(4-nitrobenzyl)carbamate

[Chem. 287]

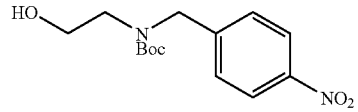

The reaction and treatment were carried out in the same manner as in Example 117-b) to obtain a title compound as a light yellow oily substance.

$^1$H-NMR (CDCl$_3$) δ: 1.41-1.57 (9H, br), 3.47 (2H, brs), 3.76 (2H, brs), 4.59 (2H, brs), 7.40 (2H, d, J=8.5 Hz), 8.21 (2H, d, J=8.5 Hz).

c) Production of tert-butyl 4-nitrobenzyl(2-oxoethyl)carbamate

[Chem. 288]

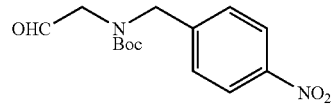

The reaction and treatment were carried out in the same manner as in Example 117-c) to obtain a title compound as a light yellow oily substance.

$^1$H-NMR (CDCl$_3$) δ: 1.45-1.47 (9H, br), 3.91 (1H, s), 4.07 (1H, s), 4.58-4.63 (2H, m), 7.39-7.45 (2H, m), 8.19-8.21 (2H, m), 9.51-9.58 (1H, m).

d) Production of tert-butyl (4-nitrobenzyl)-[2-[3-(4-fluorobenzyl)-3,4-dihydroisoquinolin-2(1H)-yl]ethyl]carbamate

[Chem. 289]

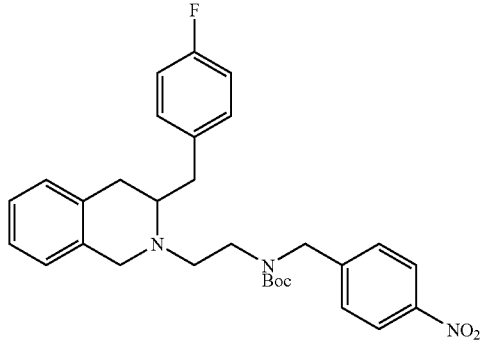

The reaction and treatment were carried out in the same manner as in Example 32-f) to obtain a title compound as a light yellow oily substance.

$^1$H-NMR (CDCl$_3$) δ: 1.38-1.49 (9H, br), 2.46 (1H, dd, J=9.8, 13.6 Hz), 2.49-2.55 (1H, m), 2.60-2.86 (4H, m), 3.12-3.49 (3H, m), 3.81 (2H, s), 4.49-4.55 (2H, m), 6.96 (2H, dd,

J=8.8, 8.8 Hz), 7.00-7.06 (4H, m), 7.13-7.16 (2H, m), 7.29-7.38 (2H, m), 8.15 (2H, d, J=8.8 Hz).

e) Production of tert-butyl (4-aminobenzyl)-[2-[3-(4-fluorobenzyl)-3,4-dihydroisoquinolin-2(1H)-yl]ethyl]carbamate

[Chem. 290]

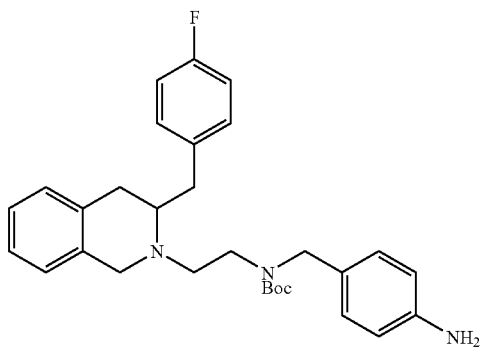

The reaction and treatment were carried out in the same manner as in Example 117-e) to obtain a title compound as a light yellow oily substance.

$^1$H-NMR (CDCl$_3$) δ: 1.47 (9H, s), 2.41 (1H, dd, J=9.8, 13.4 Hz), 2.46-2.52 (1H, m), 2.55-2.83 (4H, m), 3.07-3.62 (3H, m), 3.78-3.86 (2H, m), 4.32 (2H, s), 6.63 (2H, d, J=8.5 Hz), 6.96 (2H, dd, J=8.5, 8.5 Hz), 7.02-7.15 (8H, m).

f) Production of N-(4-aminobenzyl)-2-[3-(4-fluorobenzyl)-3,4-dihydroisoquinolin-2(1H)-yl]ethanamine

[Chem. 291]

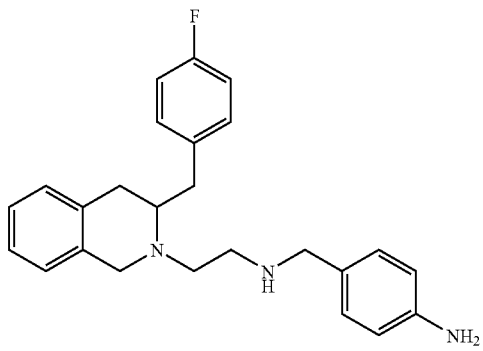

The reaction and treatment were carried out in the same manner as in Example 32-g) to obtain a title compound as a light yellow oily substance.

$^1$H-NMR (CDCl$_3$) δ: 2.50 (1H, dd, J=9.0, 13.0 Hz), 2.51 (1H, dd, J=5.4, 16.1 Hz), 2.78-2.95 (6H, m), 3.20-3.24 (1H, m), 3.64 (1H, d, J=16.1 Hz), 3.72 (1H, d, J=16.1 Hz), 3.76 (1H, d, J=13.4 Hz), 3.80 (1H, d, J=13.4 Hz), 6.62 (2H, d, J=7.8 Hz), 6.92-7.09 (8H, m), 7.13-7.16 (2H, m).

Example 100

Production of N-(4-ethylaminobenzyl)-2-[3-(4-fluorobenzyl)-3,4-dihydroisoquinolin-2(1H)-yl]ethanamine a) Production of tert-butyl 4-ethylaminobenzyl[2-[3-(4-fluorobenzyl)-3,4-dihydroisoquinolin-2(1H)-yl]ethyl]carbamate

[Chem. 292]

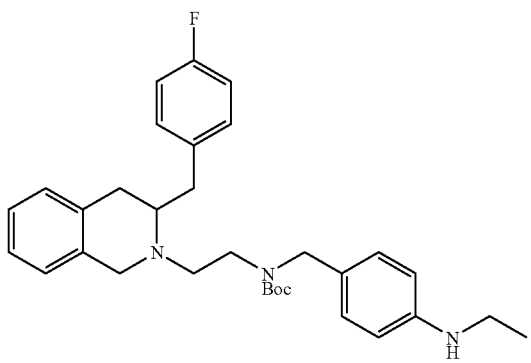

The reaction and treatment were carried out in the same manner as in Example 98-a) using N-(4-aminobenzyl)-2-[3-(4-fluorobenzyl)-3,4-dihydroisoquinolin-2(1H)-yl]ethanamine obtained in Example 99-e) to obtain a title compound as a light yellow oily substance.

$^1$H-NMR (CDCl$_3$) δ: 1.25 (3H, t, J=7.1 Hz), 1.47 (9H, s), 2.39 (1H, dd, J=105., 13.2 Hz), 2.44-2.51 (1H, m), 2.54-2.83 (4H, m), 3.14 (2H, q, J=7.1 Hz), 3.08-3.43 (3H, m), 3.74-3.87 (2H, m), 4.30-4.37 (2H, m), 6.54 (2H, d, J=8.5 Hz), 6.95 (2H, dd, J=8.8, 8.8 Hz), 7.00-7.14 (8H, m).

b) Production of N-(4-ethylaminobenzyl)-2-[3-(4-fluorobenzyl)-3,4-dihydroisoquinolin-2(1H)-yl]ethanamine

[Chem. 293]

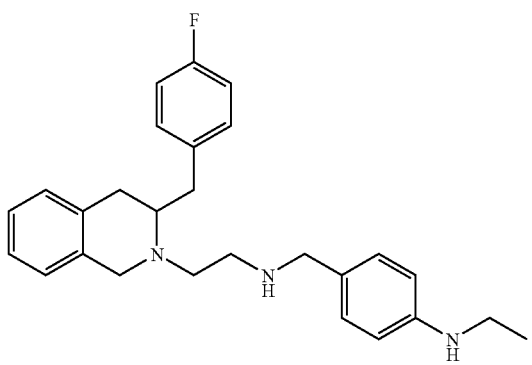

The reaction and treatment were carried out in the same manner as in Example 32-g) to obtain a title compound as a light yellow oily substance.

¹H-NMR (CDCl₃) δ: 1.25 (3H, t, J=7.2 Hz), 2.44 (1H, dd, J=9.8, 13.2 Hz), 2.51 (1H, dd, J=3.9, 16.4 Hz), 2.74-2.88 (6H, m), 3.14 (2H, q, J=7.2 Hz), 3.11-3.18 (1H, m), 3.69 (2H, s), 3.77 (2H, s), 6.55 (2H, d, J=8.3 Hz), 6.93 (2H, dd, J=8.6, 8.6 Hz), 7.01-7.05 (4H, m), 7.08 (2H, d, J=8.3 Hz), 7.13-7.16 (2H, m).

Example 101

Production of N-(4-diethylaminobenzyl)-2-[3-(4-fluorobenzyl)-3,4-dihydroisoquinolin-2(1H)-yl]ethanamine

[Chem. 294]

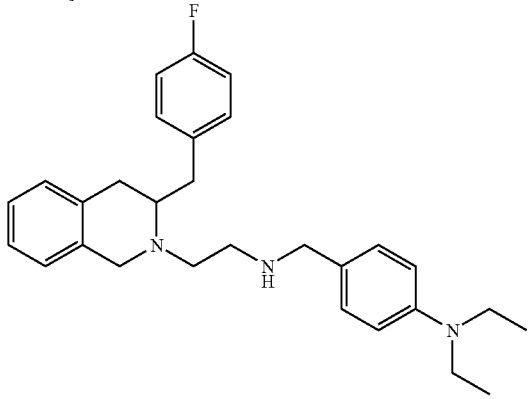

The reaction and treatment were carried out in the same manner as in Example 10-d) using 4-diethylaminobenzaldehyde instead of benzaldehyde to obtain a title compound as a pale yellow oily substance.

¹H-NMR (CDCl₃) δ: 1.14 (6H, t, J=7.1 Hz), 2.43 (1H, dd, J=10.0, 13.4 Hz), 2.51 (1H, dd, J=3.9, 16.4 Hz), 2.74-2.90 (6H, m), 3.13-3.19 (1H, m), 3.33 (4H, q, J=7.1 Hz), 3.67 (1H, d, J=13.4 Hz), 3.70 (1H, d, J=13.4 Hz), 3.76 (1H, d, J=16.1 Hz), 3.80 (1H, d, J=16.1 Hz), 6.63 (2H, d, J=8.8 Hz), 6.93 (2H, dd, J=8.6, 8.6 Hz), 7.01-7.05 (4H, m), 7.11 (2H, d, J=8.8 Hz), 7.13-7.15 (2H, m).

Example 102

Production of N-[4-(4-morpholinyl)benzyl]-2-[3-(4-fluorobenzyl)-3,4-dihydroisoquinolin-2(1H)-yl]ethanamine

[Chem. 295]

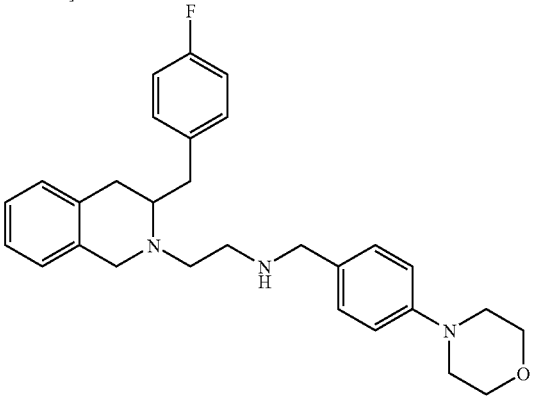

The reaction and treatment were carried out in the same manner as in Example 10-d) using 4-(4-morpholinyl) benzaldehyde instead of benzaldehyde to obtain a title compound as a pale yellow oily substance.

¹H-NMR (CDCl₃) δ: 2.45 (1H, dd, J=9.6, 13.3 Hz), 2.52 (1H, dd, J=3.8, 16.5 Hz), 2.76-2.87 (6H, m), 3.12-3.19 (5H, m), 3.73 (2H, s), 3.78 (2H, s), 3.86 (4H, t, J=4.9 Hz), 6.86 (2H, d, J=8.8 Hz), 6.91-6.96 (2H, m), 7.02-7.05 (4H, m), 7.14-7.20 (4H, m).

Example 103

Production of N-(2-nitrobenzyl)-2-[3-(4-fluorobenzyl)-3,4-dihydroisoquinolin-2(1H)-yl]ethanamine

[Chem. 296]

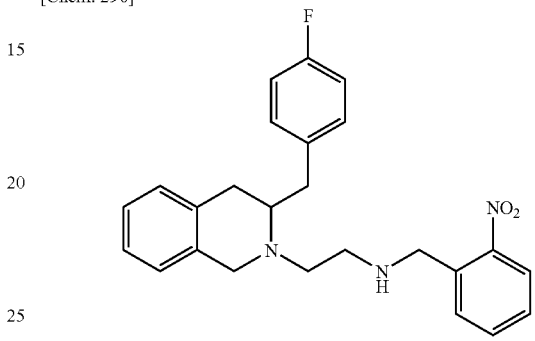

The reaction and treatment were carried out in the same manner as in Example 10-d) using 2-nitrobenzaldehyde instead of benzaldehyde to obtain a title compound as a pale yellow oily substance.

¹H-NMR (CDCl₃) δ: 2.48 (1H, dd, J=9.5, 13.5 Hz), 2.54 (1H, dd, J=3.6, 16.6 Hz), 2.75-2.79 (3H, m), 2.82-2.90 (3H, m), 3.19-3.24 (1H, m), 3.82 (2H, s), 4.04 (2H, s), 6.92 (2H, dd, J=8.8, 8.8 Hz), 7.04-7.08 (4H, m), 7.14-7.16 (2H, m), 7.40 (1H, ddd, J=1.8, 8.0, 8.0 Hz), 7.56-7.60 (2H, m), 7.94 (1H, d, J=7.6 Hz).

Example 104

Production of N-(3-nitrobenzyl)-2-[3-(4-fluorobenzyl)-3,4-dihydroisoquinolin-2(1H)-yl]ethanamine

[Chem. 297]

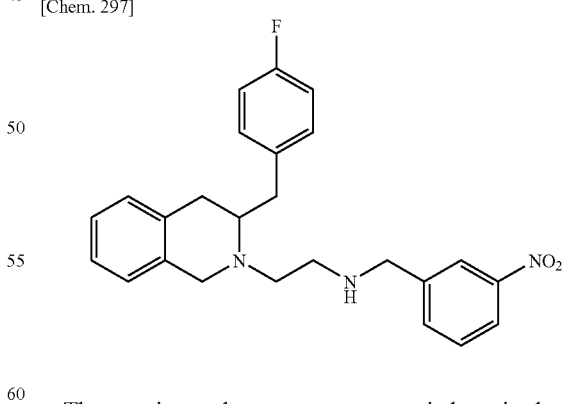

The reaction and treatment were carried out in the same manner as in Example 10-d) using 3-nitrobenzaldehyde instead of benzaldehyde to obtain a title compound as a pale yellow oily substance.

¹H-NMR (CDCl₃) δ: 2.49 (1H, dd, J=9.5, 13.4 Hz), 2.52 (1H, dd, J=3.6, 16.6 Hz), 2.73-2.78 (3H, m), 2.84-2.90 (3H, m), 3.19-3.24 (1H, m), 3.82 (2H, s), 3.87 (2H, s), 6.93 (2H, dd, J=8.8, 8.8 Hz), 7.05-7.07 (4H, m), 7.15-7.17 (2H, m), 7.47 (1H, dd, J=7.8, 7.8 Hz), 7.62 (1H, d, J=7.6 Hz), 8.10 (1H, d, J=7.6 Hz), 8.18 (1H, s).

Example 105

Production of N-(3-cyanobenzyl)-2-[3-(4-fluorobenzyl)-3,4-dihydroisoquinoline-2(1H)-yl]ethanamine

[Chem. 298]

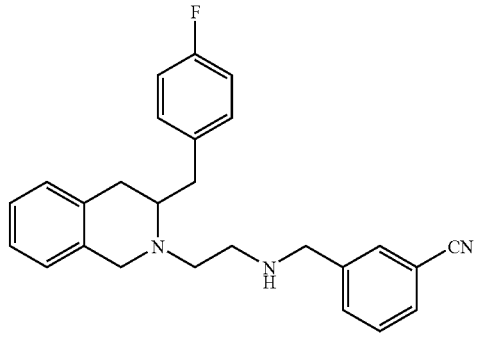

The reaction and treatment were carried out in the same manner as in Example 10-d) using 3-cyanobenzaldehyde instead of benzaldehyde to obtain a title compound as a light yellow oily substance.

$^1$H-NMR (CDCl$_3$) δ: 2.49 (1H, dd, J=9.5, 13.4 Hz), 2.52 (1H, dd, J=4.2, 16.4 Hz), 2.68-2.80 (3H, m), 2.83-2.90 (3H, m), 3.18-3.24 (1H, m), 3.79-3.80 (2H, brs), 3.82 (2H, s), 6.92-6.96 (2H, m), 7.04-7.09 (4H, m), 7.14-7.18 (2H, m), 7.40 (1H, dd, J=7.7, 7.7 Hz), 7.50-7.55 (2H, m), 7.61 (1H, s).

Example 106

Production of N-(3-acetylbenzyl)-2-[3-(4-fluorobenzyl)-3,4-dihydroisoquinolin-2(1H)-yl]ethanamine

[Chem. 299]

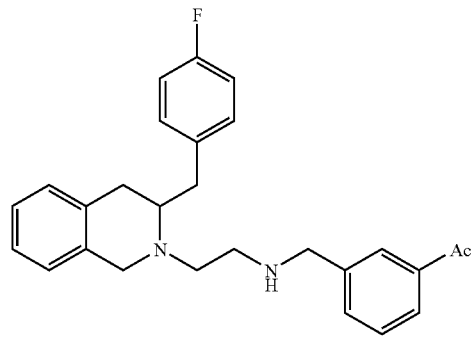

The reaction and treatment were carried out in the same manner as in Example 89 using 3-(4-fluorobenzyl)-1,2,3,4-tetrahydroisoquinoline obtained in Example 10-b) to obtain a title compound as a pale yellow oily substance.

$^1$H-NMR (CDCl$_3$) δ: 2.48 (1H, dd, J=9.3, 13.2 Hz), 2.54 (1H, dd, J=3.4, 16.6 Hz), 2.58 (3H, s), 2.74-2.94 (6H, m), 3.17-3.25 (1H, m), 3.80 (2H, s), 3.86 (2H, s), 6.89-6.95 (2H, m), 6.98-7.08 (4H, m), 7.13-7.18 (2H, m), 7.42 (1H, dd, J=7.6, 7.6 Hz), 7.51 (1H, d, J=7.6 Hz), 7.85 (1H, d, J=7.6 Hz), 7.89 (1H, s).

Example 107

Production of N-(3-methoxycarbonylbenzyl)-2-[3-(4-fluorobenzyl)-3,4-dihydroisoquinolin-2(1H)-yl]ethanamine

[Chem. 300]

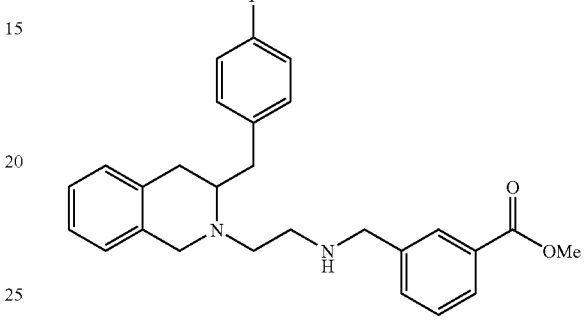

The reaction and treatment were carried out in the same manner as in Example 10-d) using methyl 3-formylbenzoate instead of benzaldehyde to obtain a title compound as a pale yellow oily substance.

$^1$H-NMR (CDCl$_3$) δ: 2.46 (1H, dd, J=9.5, 13.4 Hz), 2.53 (1H, dd, J=3.9, 16.6 Hz), 2.72-2.79 (3H, m), 2.81-2.89 (3H, m), 3.16-3.22 (1H, m), 3.79 (2H, s), 3.83 (2H, s), 3.90 (3H, s), 6.92 (1H, d, J=8.8 Hz), 6.94 (1H, d, J=8.8 Hz), 7.02-7.06 (4H, m), 7.13-7.17 (2H, m), 7.38 (1H, dd, J=7.6, 7.6 Hz), 7.49 (1H, d, J=7.6 Hz), 7.93 (1H, d, J=7.6 Hz), 7.97 (1H, s).

Example 108

Production of N-(4-methoxycarbonylbenzyl)-2-[3-(4-fluorobenzyl)-3,4-dihydroisoquinolin-2(1H)-yl]ethanamine

[Chem. 301]

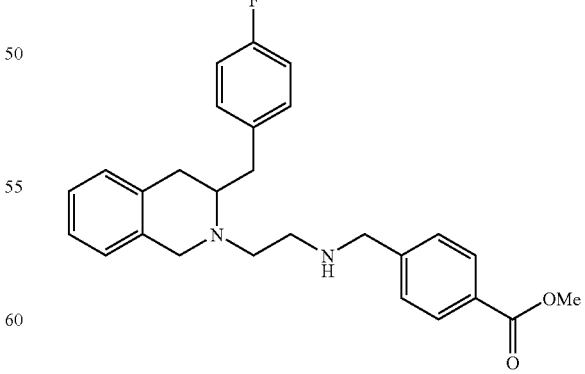

The reaction and treatment were carried out in the same manner as in Example 10-d) using methyl 4-formylbenzoate instead of benzaldehyde to obtain a title compound as a pale yellow oily substance.

$^1$H-NMR (CDCl$_3$) δ: 2.46 (1H, dd, J=9.6, 13.3 Hz), 2.53 (1H, dd, J=4.0, 16.5 Hz), 2.71-2.79 (3H, m), 2.81-2.90 (3H, m), 3.15-3.21 (1H, m), 3.80 (2H, s), 3.83 (2H, d, J=2.6 Hz), 3.91 (3H, s), 6.92 (1H, d, J=8.8 Hz), 6.94 (1H, d, J=8.8 Hz), 7.03 (2H, d, J=5.6), 7.05 (2H, d, J=5.6), 7.14-7.17 (2H, m), 7.35 (2H, d, J=8.3 Hz), 7.98 (2H, d, J=8.3 Hz).

Example 109

Production of 3-[[2-[3-(4-fluorobenzyl)-3,4-dihydroisoquinolin-2(1H)-yl]ethylamino]methyl]benzoic acid

[Chem. 302]

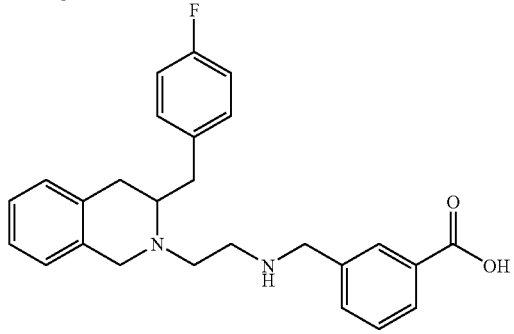

The reaction and treatment were carried out in the same manner as in Example 110 using N-(3-methoxycarbonylbenzyl)-2-[3-(4-fluorobenzyl)-3,4-dihydroisoquinolin-2(1H)-yl]ethanamine obtained in Example 107 to obtain a title compound as a pale yellow oily substance.

$^1$H-NMR (CDCl$_3$) δ: 2.44-2.51 (2H, m), 2.81-2.98 (5H, m), 3.09-3.12 (1H, m), 3.25-3.29 (1H, m), 3.81 (2H, s), 3.95 (2H, s), 6.85 (1H, d, J=8.5 Hz), 6.87 (1H, d, J=8.5 Hz), 6.98-7.04 (4H, m), 7.08-7.11 (2H, m), 7.26-7.35 (2H, m), 8.03 (1H, d, J=7.6 Hz), 8.44-8.48 (1H, m).

Example 110

Production of 4-[[2-[3-(4-fluorobenzyl)-3,4-dihydroisoquinolin-2(1H)-yl]ethylamino]methyl]benzoic acid

[Chem. 303]

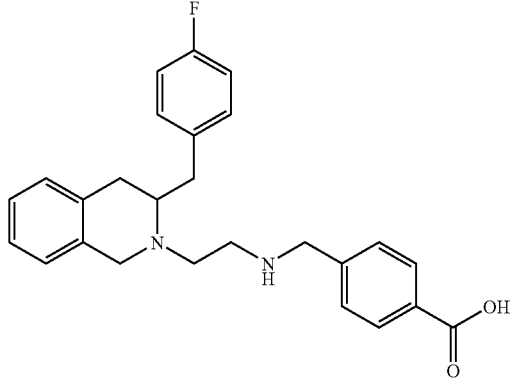

9 mg of N-(4-methoxycarbonylbenzyl)-2-[3-(4-fluorobenzyl)-3,4-dihydroisoquinolin-2(1H)-yl]ethanamine obtained in Example 108 was dissolved in 1 mL of 2.5 N aqueous sodium hydroxide solution and 1 mL of ethanol, followed by stirring at 0° C. for 3 hours. After completion of the reaction, 2N hydrochloric acid was added to the reaction liquid, followed by extraction with chloroform, and the organic layer was then washed with saturated brine, dried over anhydrous sodium sulfate and then concentrated under reduced pressure to obtain 6 mg (yield 76%) of a title compound as a pale yellow oily substance.

$^1$H-NMR (CDCl$_3$) δ: 2.46-2.54 (2H, m), 2.84-2.98 (5H, m), 3.04-3.08 (1H, m), 3.28-3.34 (1H, m), 3.86 (2H, s), 3.98 (2H, s), 6.88 (1H, d, J=8.5 Hz), 6.90 (1H, d, J=8.5 Hz), 7.00-7.06 (4H, m), 7.11-7.14 (2H, m), 7.32 (2H, d, J=7.6 Hz), 7.90 (2H, d, J=7.6 Hz).

Example 111

Production of 3-[[2-[3-(4-fluorobenzyl)-3,4-dihydroisoquinolin-2(1H)-yl]ethylamino]methyl]benzamide

[Chem. 304]

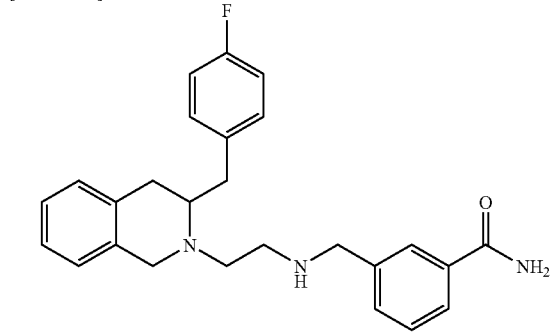

The reaction and treatment were carried out in the same manner as in Example 10-d) using 3-formylbenzamide instead of benzaldehyde to obtain a title compound as a pale yellow oily substance.

$^1$H-NMR (CDCl$_3$) δ: 2.47 (1H, dd, J=9.6, 13.3 Hz), 2.53 (1H, dd, J=3.6, 16.6 Hz), 2.77-2.83 (3H, m), 2.86-2.90 (3H, m), 3.19-3.23 (1H, m), 3.81 (2H, s), 3.84 (2H, s), 5.76 (1H, br), 6.21 (1H, br), 6.92 (1H, d, J=8.5 Hz), 6.94 (1H, d, J=8.5 Hz), 7.03-7.07 (4H, m), 7.14-7.17 (2H, m), 7.39 (1H, dd, J=7.6, 7.6 Hz), 7.41-7.46 (1H, m), 7.71 (1H, d, J=7.6 Hz), 7.81 (1H, s).

Example 112

Production of 4-[[2-[3-(4-fluorobenzyl)-3,4-dihydroisoquinolin-2(1H)-yl]ethylamino]methyl]-benzamide

[Chem. 305]

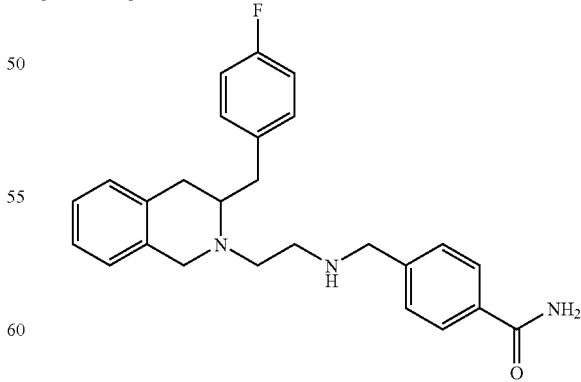

The reaction and treatment were carried out in the same manner as in Example 10-d) using 4-formylbenzamide instead of benzaldehyde to obtain a title compound as a pale yellow oily substance.

¹H-NMR (CDCl₃) δ: 2.48 (1H, dd, J=9.6, 13.5 Hz), 2.54 (1H, dd, J=4.4, 16.8 Hz), 2.73-2.80 (3H, m), 2.83-2.91 (3H, m), 3.18-3.24 (1H, m), 3.80 (2H, s), 3.84 (2H, s), 3.84 (2H, s), 5.73 (1H, br), 6.09 (1H, br), 6.92 (1H, d, J=8.8 Hz), 6.94 (1H, d, J=8.8 Hz), 7.01-7.07 (4H, m), 7.14 (1H, d, J=3.4 Hz), 7.16 (1H, d, J=3.4 Hz), 7.36 (2H, d, J=8.0 Hz), 7.70 (2H, d, J=8.0 Hz).

Example 113

Production of 3-[[2-[3-(4-fluorobenzyl)-3,4-dihydroisoquinolin-2(1H)-yl]ethylamino]methyl]-N-ethylbenzamide a) Production of tert-butyl[(3-methoxycarbonyl)benzyl](2-oxoethyl)carbamate

[Chem. 306]

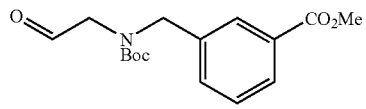

The reaction and treatment were carried out in the same manner as in Example 117-a, b, c) using 3-formylbenzoate instead of 3-nitrobenzaldehyde to obtain a title compound as a pale yellow oily substance.

¹H-NMR (CDCl₃) δ: 1.48-1.50 (9H, br), 3.90-3.93 (5H, m), 4.80 (2H, s), 7.39 (1H, dd, J=7.8, 7.8 Hz), 7.47-7.51 (1H, m), 7.93-7.98 (2H, m), 9.29 (1H, br).

b) Production of 3-[[2-[3-(4-fluorobenzyl)-3,4-dihydroisoquinolin-2(1H)-yl]ethylamino]methyl]-N-ethylbenzamide

[Chem. 307]

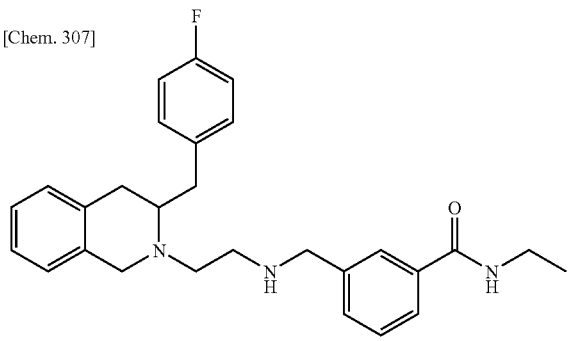

The reaction and treatment were carried out in the same manner as in Example 114-b) to obtain a title compound as a pale yellow oily substance.

¹H-NMR (CDCl₃) δ: 1.24 (3H, t, J=7.2 Hz), 2.47 (1H, dd, J=9.6, 13.3 Hz), 2.53 (1H, dd, J=4.1, 16.5 Hz), 2.76-2.80 (3H, m), 2.82-2.89 (3H, m), 3.16-3.21 (1H, m), 3.44-3.51 (2H, m), 3.80 (2H, s), 3.82 (2H, s), 6.21 (1H, br), 6.92 (1H, d, J=8.8 Hz), 6.94 (1H, d, J=8.8 Hz), 7.03-7.05 (4H, m), 7.14 (1H, d, J=3.4 Hz), 7.16 (1H, d, J=3.4 Hz), 7.35-7.42 (2H, m), 7.66 (1H, d, J=7.2 Hz), 7.72 (1H, s).

Example 114

Production of 4-[[2-[3-(4-fluorobenzyl)-3,4-dihydroisoquinolin-2(1H)-yl]ethylamino]methyl]-N-ethylbenzamide a) Production of tert-butyl[(4-methoxycarbonyl)benzyl](2-oxoethyl)carbamate

[Chem. 308]

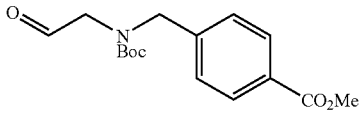

The reaction and treatment were carried out in the same manner as in Example 117-a, b, c) using 4-formylbenzoate instead of 3-nitrobenzaldehyde to obtain a title compound as a pale yellow oily substance.

¹H-NMR (CDCl₃) δ: 1.43-1.49 (9H, m), 3.87-3.95 (5H, m), 4.51-4.59 (2H, m), 7.27-7.34 (2H, m), 7.99-8.02 (2H, m), 9.46-9.54 (1H, m).

b) Production of 4-[[2-[3-(4-fluorobenzyl)-3,4-dihydroisoquinolin-2(1H)-yl]ethylamino]methyl]-N-ethylbenzamide

[Chem. 309]

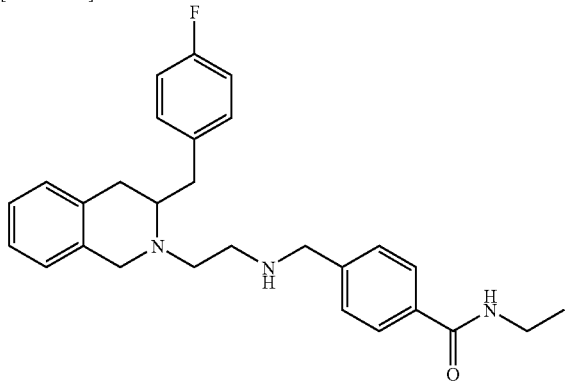

The reaction and treatment were carried out in the same manner as in Example 32-f) and Example 110 using tert-butyl [(3-methoxycarbonyl)benzyl](2-oxoethyl)carbamate to obtain a yellow oily substance. 28 mg of the obtained oily substance and 15 mg of ethylamine hydrochloride were added to dichloromethane (1 mL), followed by stirring, and 31 mg of WSC/HCl and then 16 mg of triethylamine were added thereto, followed by stirring at room temperature for 3 hours. After completion of the reaction, water was added to the reaction liquid, followed by extraction with chloroform, and the organic layer was then washed with saturated brine, dried over anhydrous sodium sulfate and then concentrated under reduced pressure to obtain 30 mg of a crude composition. 30 mg of the residue obtained was dissolved in 1 mL of 4N hydrochloric acid/ethyl acetate solution, followed by stirring at room temperature for 1 hour. After completion of the reaction, a saturated aqueous sodium bicarbonate solution was added to the reaction liquid, followed by extraction with ethyl acetate, and the organic layer was then washed with saturated brine, dried over anhydrous sodium sulfate, concentrated under reduced pressure, and purified using PLC (chloroform:methanol=5:1) to obtain 20 mg (yield 80%) of a title compound as a pale yellow oily substance.

¹H-NMR (CDCl₃) δ: 1.25 (3H, t, J=7.2 Hz), 2.47 (1H, dd, J=9.5, 13.4 Hz), 2.53 (1H, dd, J=3.9, 16.2 Hz), 2.72-2.77 (3H, m), 2.82-2.89 (3H, m), 3.16-3.22 (1H, m), 3.46-3.53 (2H, m), 3.79 (2H, s), 3.82 (2H, s), 6.10 (1H, br), 6.93 (1H, d, J=8.8 Hz), 6.96 (1H, d, J=8.8 Hz), 7.02-7.07 (4H, m), 7.14 (1H, d, J=3.4 Hz), 7.16 (1H, d, J=3.4 Hz), 7.32 (2H, d, J=8.0 Hz), 7.70 (2H, d, J=7.6 Hz).

Example 115

Production of 3-[[2-[3-(4-fluorobenzyl)-3,4-dihydroisoquinolin-2(1H)-yl]ethylamino]methyl]-N,N-diethylbenzamide

[Chem. 310]

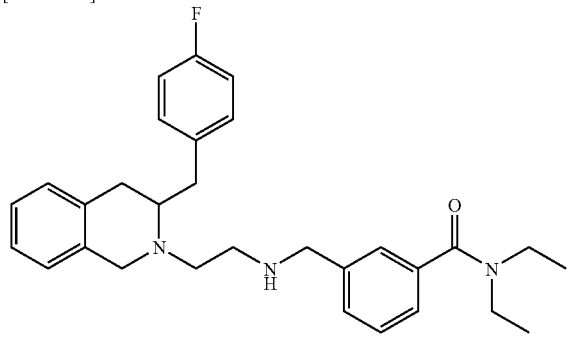

The reaction and treatment were carried out in the same manner as in Example 113-b) using diethylamine instead of ethylamine hydrochloride to obtain a title compound as a pale yellow oily substance.

¹H-NMR (CDCl₃) δ: 1.11 (3H, br), 1.26 (3H, br), 2.48 (1H, dd, J=9.6, 13.6 Hz), 2.53 (1H, dd, J=4.1, 16.6 Hz), 2.75-2.91 (6H, m), 3.19-3.24 (3H, m), 3.47-3.59 (2H, br), 3.80 (2H, s), 3.82 (2H, s), 6.95 (1H, dd, J=8.8, 8.8 Hz), 7.04-7.09 (4H, m), 7.15 (1H, d, J=3.6 Hz), 7.16 (1H, d, J=3.6 Hz), 7.23-7.26 (1H, m), 7.32-7.33 (4H, m).

Example 116

Production of 4-[[2-[3-(4-fluorobenzyl)-3,4-dihydroisoquinolin-2(1H)-yl]ethylamino]methyl]-N,N-diethylbenzamide

[Chem. 311]

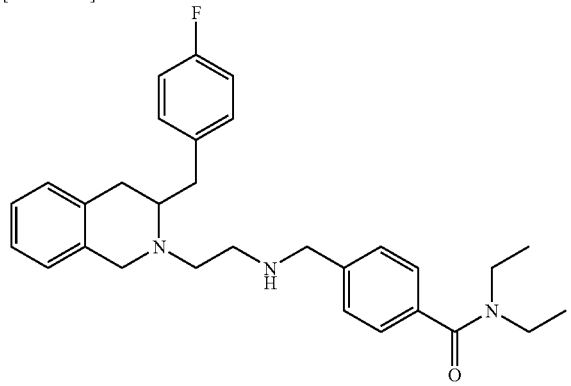

The reaction and treatment were carried out in the same manner as in Example 114-b) using diethylamine instead of ethylamine hydrochloride to obtain a title compound as a pale yellow oily substance.

¹H-NMR (CDCl₃) δ: 1.04-1.16 (3H, br), 1.18-1.32 (3H, br), 2.58 (1H, dd, J=9.5, 13.4 Hz), 2.64 (1H, dd, J=3.9, 16.6 Hz), 2.74-2.90 (6H, m), 3.11-3.24 (3H, m), 3.46-3.55 (2H, br), 3.88-3.94 (2H, m), 4.03 (2H, s), 7.00-7.13 (6H, m), 7.20-7.32 (6H, m).

Example 117

Production of N-(3-methanesulfonylaminobenzyl)-2-[3-(4-fluorobenzyl)-3,4-dihydroisoquinolin-2(1H)-yl]ethanamine a) Production of 2-(3-nitrobenzylamino)ethanol

[Chem. 312]

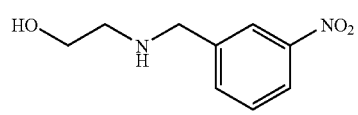

500 mg of 3-nitrobenzaldehyde and 202 mg of ethanolamine were dissolved in 10 mL of ethanol, followed by stirring at 80° C. To this was added 125 mg of sodium borohydride, followed by stirring for 3 hours. After completion of the reaction, water was added to the reaction liquid, followed by extraction with chloroform. The organic layer was then washed with an aqueous sodium bicarbonate solution and saturated brine, dried over anhydrous sodium sulfate and then concentrated under reduced pressure to obtain 594 mg (yield 92%) of a title compound as a yellow solidified product.

¹H-NMR (CDCl₃) δ: 2.83 (2H, t, J=5.2 Hz), 3.72 (2H, t, J=5.2 Hz), 3.95 (2H, s), 7.49-7.64 (2H, m), 8.08-8.18 (2H, m).

b) Production of tert-butyl 2-hydroxyethyl(3-nitrobenzyl)carbamate

[Chem. 313]

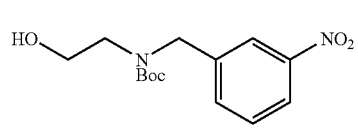

Under an argon atmosphere, 594 mg of 2-(3-nitrobenzylamino)ethanol, 793 mg of di-tert-butyl dicarbonate, and 367 mg of triethylamine were dissolved in 12 mL of chloroform, followed by stirring at room temperature for 6 hours. After completion of the reaction, water was added to the reaction liquid, followed by extraction with chloroform. The organic layer was then washed with an aqueous sodium bicarbonate solution and saturated brine, dried over anhydrous sodium sulfate and then concentrated under reduced pressure. The residue obtained was purified using silica gel chromatography (diethyl ether:n-hexane=3:1) to obtain 549 mg (yield 61%) of a title compound as a light yellow solidified product.

¹H-NMR (CDCl₃) δ: 1.46 (91-1, brs), 3.44 (2H, brs), 3.76 (2H, brs), 4.58 (2H, brs), 7.47-7.53 (1H, m), 7.59 (1H, d, J=7.6 Hz), 8.09-8.16 (2H, m).

c) Production of tert-butyl 3-nitrobenzyl(2-oxoethyl)carbamate

[Chem. 314]

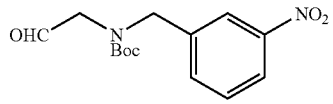

Under an argon atmosphere, 307 mg of oxalyl chloride was dissolved in 3 mL of dichloromethane, followed by stirring under cooling with dry ice-acetone. To this was slowly added dropwise a mixed solution of 376 mg of dimethyl sulfoxide and 2 mL of dichloromethane, and 941 mg of triethylamine was then added dropwise thereto. After 30 minutes, the reaction liquid was elevated to room temperature, followed by further stirring for 2 hours. After completion of the reaction, water was added to the reaction liquid, followed by extraction with chloroform. The organic layer was then washed with an aqueous sodium bicarbonate solution and saturated brine, dried over anhydrous sodium sulfate and then concentrated under reduced pressure. The residue obtained was purified using silica gel chromatography (diethyl ether:n-hexane=3:1) to obtain 475 mg (yield 87%) of a title compound as a light yellow oily substance.

$^1$H-NMR (CDCl$_3$) δ: 1.48 (9H, s), 3.89-4.07 (2H, m), 4.53-4.64 (2H, m), 7.49-7.64 (2H, m), 8.08-8.18 (2H, m), 9.50-9.58 (1H, m).

d) Production of tert-butyl 3-nitrobenzyl[2-[3-(4-fluorobenzyl)-3,4-dihydroisoquinolin-2(1H)-yl]ethyl]carbamate

[Chem. 315]

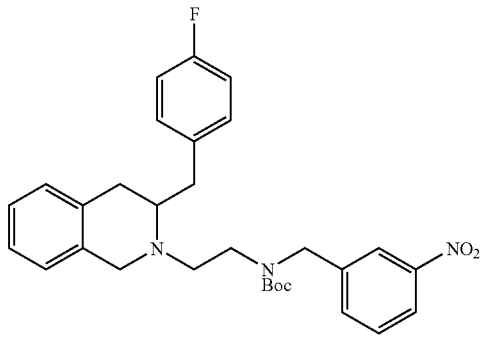

The reaction and treatment were carried out in the same manner as in Example 32-f) using tert-butyl 3-nitrobenzyl(2-oxoethyl)carbamate instead of [(tert-butoxycarbonyl)benzylamino]acetaldehyde to obtain a title compound as a light yellow oily substance.

$^1$H-NMR (CDCl$_3$) δ: 1.38-1.54 (9H, br), 2.45 (1H, dd, J=10.0, 13.2 Hz), 2.52 (1H, dd, J=3.4, 16.6 Hz), 2.62-2.94 (4H, m), 3.06-3.52 (3H, m), 3.82 (2H, s), 4.46-4.58 (2H, m), 6.92-7.00 (2H, m), 7.00-7.10 (4H, m), 7.12-7.18 (2H, m), 7.40-7.60 (2H, m), 8.06-8.12 (2H, m).

e) Production of tert-butyl 3-aminobenzyl[2-[3-(4-fluorobenzyl)-3,4-dihydroisoquinolin-2(1H)-yl]ethyl]carbamate

[Chem. 316]

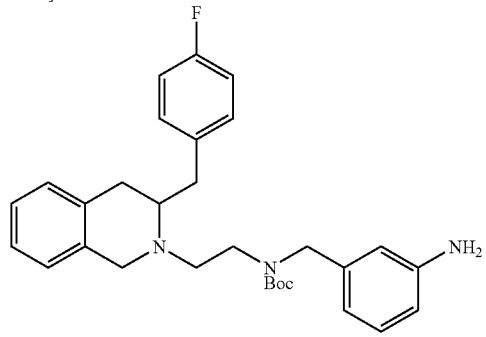

Under an argon atmosphere, 190 mg of tert-butyl 3-nitrobenzyl[2-[6-fluoro-3-(4-fluorobenzyl)-3,4-dihydroisoquinolin-2(1H)-yl]ethyl]carbamate was dissolved in 8 mL of methanol, followed by stirring under ice-cooling. 343 mg of nickel chloride.hexahydrate was added thereto, and then 73 mg of sodium borohydride was slowly added thereto. After completion of addition of a reagent, the reaction liquid was warmed to room temperature, followed by stirring for 10 minutes. After completion of the reaction, water was added to the reaction liquid, followed by extraction with chloroform. The organic layer was then washed with an aqueous sodium bicarbonate solution and saturated brine, dried over anhydrous sodium sulfate and then concentrated under reduced pressure to obtain 155 mg (yield 87%) of a title compound as a yellow oily substance.

$^1$H-NMR (CDCl$_3$) δ: 1.46 (9H, s), 2.42 (1H, dd, J=10.0, 13.2 Hz), 2.48-2.53 (1H, m), 2.60-2.85 (4H, m), 3.10-3.87 (5H, m), 4.36-4.38 (2H, m), 6.51-6.64 (3H, m), 6.96 (2H, dd, J=8.7, 8.7 Hz), 7.01-7.15 (7H, m).

f) Production of tert-butyl 3-methane sulfonamide benzyl[2-[3-(4-fluorobenzyl)-3,4-dihydroisoquinolin-2(1H)-yl]ethyl]carbamate

[Chem. 317]

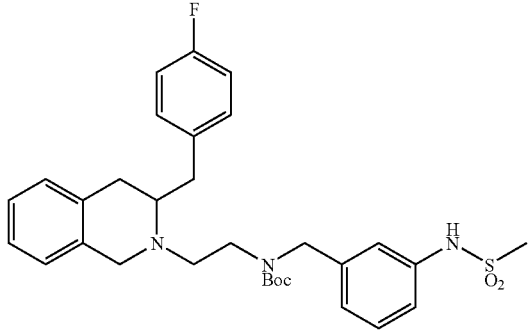

Under an argon atmosphere, 78 mg of tert-butyl 3-aminobenzyl[2-[3-(4-fluorobenzyl)-3,4-dihydroisoquinolin-2(1H)-yl]ethyl]carbamate, 20 mg of methanesulfonyl chloride, and 27 mg of pyridine were dissolved in 1.6 mL of chloroform, followed by stirring under ice-cooling for 30 minutes. After completion of the reaction, water was added to the reaction liquid, followed by extraction with chloroform. The organic layer was then washed with an aqueous sodium bicarbonate solution and saturated brine, dried over anhydrous sodium sulfate and then concentrated under reduced pressure to obtain 59 mg (yield 66%) of a title compound as a light yellow oily substance.

g) Production of N-(3-methanesulfonylaminobenzyl)-2-[3-(4-fluorobenzyl)-3,4-dihydroisoquinolin-2(1H)-yl]ethanamine

[Chem. 318]

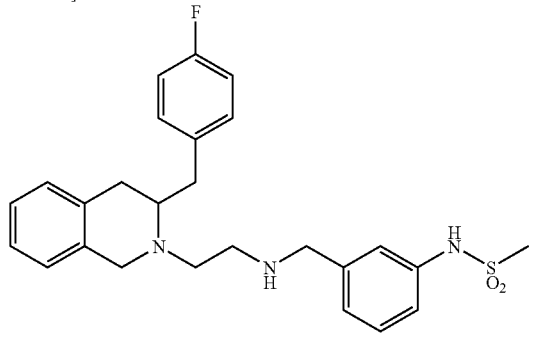

The reaction and treatment were carried out in the same manner as in Example 32-g) to obtain a title compound as a light yellow oily substance.

$^1$H-NMR (CDCl$_3$) δ: 2.48 (1H, dd, J=9.5, 13.2 Hz), 2.54 (1H, dd, J=3.9, 16.6 Hz), 2.75-2.94 (6H, m), 2.95 (3H, s), 3.19-3.30 (1H, m), 3.79 (2H, s), 3.81 (2H, s), 6.90-6.97 (2H, m), 7.02-7.11 (4H, m), 7.12-7.18 (4H, m), 7.27-7.32 (2H, m).

Example 118

Production of N-(4-methanesulfonylaminobenzyl)-2-[3-(4-fluorobenzyl)-3,4-dihydroisoquinolin-2(1H)-yl]ethanamine a) Production of N-(4-methanesulfonylaminobenzyl)-2-[3-(4-fluorobenzyl)-3,4-dihydroisoquinolin-2(1H)-yl]ethanamine

[Chem. 319]

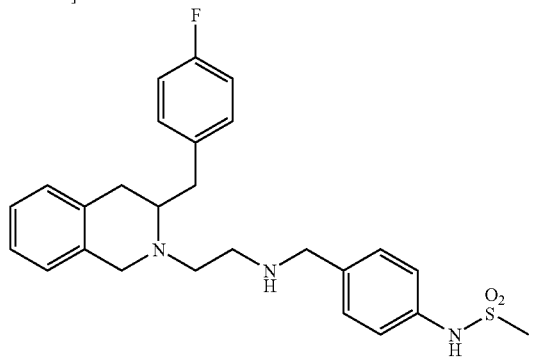

The reaction and treatment were carried out in the same manner as in Examples 117-f) and 32-g) using tert-butyl (4-aminobenzyl)-[2-[3-(4-fluorobenzyl)-3,4-dihydroisoquinolin-2(1H)-yl]ethyl]carbamate obtained in Example 99-e) to obtain a title compound as a light yellow oily substance.

$^1$H-NMR (CDCl$_3$) δ: 2.48 (1H, dd, J=9.3, 13.4 Hz), 2.54 (1H, dd, J=3.9, 16.6 Hz), 2.74-2.91 (6H, m), 2.97 (3H, s), 3.18-3.24 (1H, m), 3.76 (2H, s), 3.80 (2H, s), 6.93 (2H, dd, J=8.7, 8.7 Hz), 7.02-7.17 (8H, m), 7.26 (2H, d, J=8.3 Hz).

Example 119

Production of N-[4-(acetylamino)benzyl]-2-[3-(4-fluorobenzyl)-3,4-dihydroisoquinolin-2(1H)-yl]ethanamine

[Chem. 320]

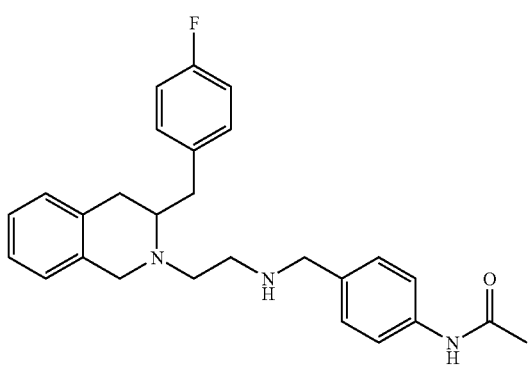

42.9 mg of tert-butyl (4-aminobenzyl)-[2-[3-(4-fluorobenzyl)-3,4-dihydroisoquinolin-2(1H)-yl]ethyl]carbamate obtained in Example 99-e) was taken into a 10-mL eggplant flask and dissolved in 1 mL of dichloromethane, and 12.0 mg of anhydrous acetic acid and 7.0 mg of pyridine were sequentially added thereto under ice-cooling followed by stirring for 1 hour as it was. After completion of the reaction, to the reaction liquid were added a saturated aqueous sodium bicarbonate solution and ethyl acetate under ice-cooling. The organic layer was separated, the aqueous layer was further extracted by addition of ethyl acetate, and the organic layer was combined and washed with saturated brine. The organic layer was dried over anhydrous sodium sulfate and concentrated under reduced pressure, and the solvent was removed by evaporation to obtain 46.6 mg (yield 100%) of a crude composition.

46.6 mg of the obtained crude composition was taken into a 10-mL eggplant flask and dissolved in 1 mL of ethyl acetate, and 1 mL of 4N hydrochloric acid-ethyl acetate was added thereto under ice-cooling, followed by stirring. It was further stirred at room temperature for 2 hours. After completion of the reaction, to the reaction liquid were added a saturated aqueous sodium bicarbonate solution and ethyl acetate under ice-cooling. The organic layer was separated, the aqueous layer was further extracted by addition of ethyl acetate, and the organic layer was combined and washed with saturated brine. The organic layer was dried over anhydrous sodium sulfate and concentrated under reduced pressure, and the solvent was removed by evaporation to obtain 37.8 mg of a crude composition.

The crude composition was purified by PLC to obtain 29.9 mg (yield 79%) of a title compound as a light yellow oily substance.

$^1$H-NMR (CDCl$_3$) δ: 2.17 (3H, s), 2.46 (1H, dd, J=9.8, 13.4 Hz), 2.52 (1H, dd, J=3.8, 16.7 Hz), 2.73-2.88 (6H, m), 3.14-3.21 (1H, m), 3.75 (2H, s), 3.79 (2H, s), 6.93 (2H, dd, J=8.6, 8.6 Hz), 7.02-7.24 (4H, m), 7.13-7.16 (2H, m), 7.23 (2H, d, J=8.1 Hz), 7.43 (2H, d, J=8.1 Hz).

Example 120

Production of N-(4-ethylbenzyl)-2-[6-fluoro-3-(4-fluorobenzyl)-3,4-dihydroisoquinolin-2(1H)-yl]ethanamine a) Production of tert-butyl 2-[6-fluoro-3-(4-fluorobenzyl)-3,4-dihydroisoquinoline-2(1H)-yl]ethyl carbamate

[Chem. 321]

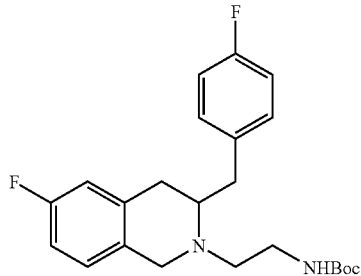

The reaction and treatment were carried out in the same manner as in Example 1-e) using 6-fluoro-3-(4-fluorobenzyl)-1,2,3,4-tetrahydroisoquinoline obtained in Example 53-a) instead of 3-benzyl-1,2,3,4-tetrahydroisoquinoline to obtain a title compound as a light yellow oily substance.

$^1$H-NMR (CDCl$_3$) δ: 1.44 (9H, s), 2.46 (1H, dd, J=9.3, 13.4 Hz), 2.52 (1H, dd, J=2.6, 16.4 Hz), 2.64-2.73 (1H, m), 2.76-2.90 (3H, m), 3.14-3.36 (3H, m), 3.79 (2H, s), 4.90 (1H, brs), 6.77 (1H, dd, J=2.2, 9.5 Hz), 6.87 (1H, ddd, J=2.2, 8.6, 8.6 Hz), 6.94-7.04 (3H, m), 7.04-7.12 (2H, m).

b) Production of 2-[6-fluoro-3-(4-fluorobenzyl)-3,4-dihydroisoquinolin-2(1H)-yl]ethanamine

[Chem. 322]

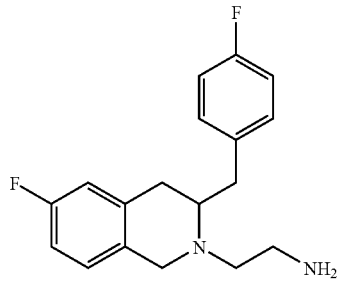

The reaction and treatment were carried out in the same manner as in Example 1-f) to obtain a title compound as a light yellow oily substance.

$^1$H-NMR (CDCl$_3$) δ: 2.40-2.62 (4H, m), 2.66-2.96 (6H, m), 3.16-3.28 (1H, m), 3.80 (2H, s), 6.76 (1H, dd, J=2.0, 9.5 Hz), 6.86 (1H, ddd, J=2.0, 8.3, 8.3 Hz), 6.94-7.04 (3H, m), 7.08 (2H, dd, J=5.9, 8.0 Hz).

c) Production of N-(4-ethylbenzyl)-2-[6-fluoro-3-(4-fluorobenzyl)-3,4-dihydroisoquinolin-2(1H)-yl]ethanamine

[Chem. 323]

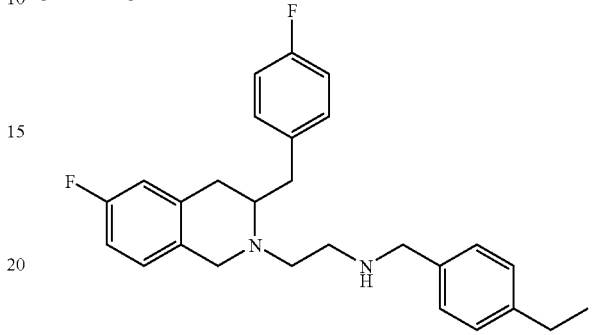

The reaction and treatment were carried out in the same manner as in Example 1-g) using 4-ethylbenzaldehyde instead of benzaldehyde to obtain a title compound as a light yellow oily substance.

$^1$H-NMR (CDCl$_3$) δ: 1.22 (3H, t, J=7.6 Hz), 2.50 (1H, dd, J=4.2, 11.7 Hz), 2.53 (1H, dd, J=8.8, 13.2 Hz), 2.63 (2H, q, J=7.6 Hz), 2.81 (1H, dd, J=6.6, 13.9 Hz), 2.84-3.08 (5H, m), 3.25-3.32 (1H, m), 3.48 (1H, d, J=16.0 Hz), 3.63 (1H, d, J=16.0 Hz), 3.96 (1H, d, J=13.6 Hz), 4.02 (1H, d, J=13.6 Hz), 6.75 (1H, dd, J=2.5, 9.3 Hz), 6.82-6.89 (2H, m), 6.91-6.97 (2H, m), 7.09-7.31 (2H, m), 7.17 (2H, d, J=8.1 Hz), 7.23 (2H, d, J=8.1 Hz).

Example 121

Production of N-(4-tert-butylbenzyl)-2-[6-fluoro-3-(4-fluorobenzyl)-3,4-dihydroisoquinolin-2(1H)-yl]ethanamine

[Chem. 324]

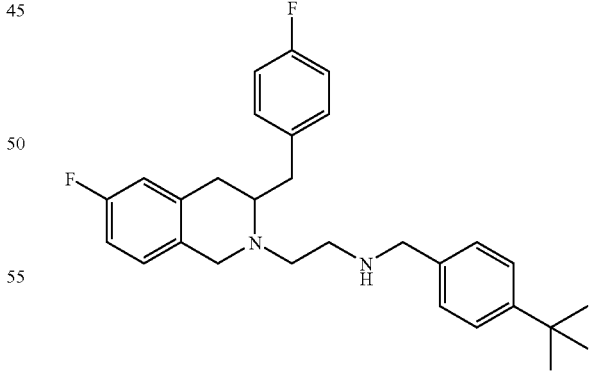

The reaction and treatment were carried out in the same manner as in Example 120-c) using 4-tert-butylbenzaldehyde instead of 4-ethylbenzaldehyde to obtain a title compound as a light yellow oily substance.

$^1$H-NMR (CDCl$_3$) δ: 1.31 (9H, s), 2.42 (1H, dd, J=10.0, 13.4 Hz), 2.49 (1H, dd, J=3.6, 16.6 Hz), 2.72-2.91 (6H, m), 3.12-3.20 (1H, m), 3.73 (2H, s), 3.77 (2H, s), 6.75 (1H, dd,

J=2.5, 9.5 Hz), 6.85 (1H, ddd, J=2.5, 8.3, 8.3 Hz), 6.90-6.96 (3H, m), 7.00-7.07 (2H, m), 7.21 (2H, d, J=8.1 Hz), 7.33 (2H, d, J=8.1 Hz).

Example 122

Production of N-(3-acetylbenzyl)-2-[6-fluoro-3-(4-fluorobenzyl)-3,4-dihydroisoquinolin-2(1H)-yl]ethanamine

[Chem. 325]

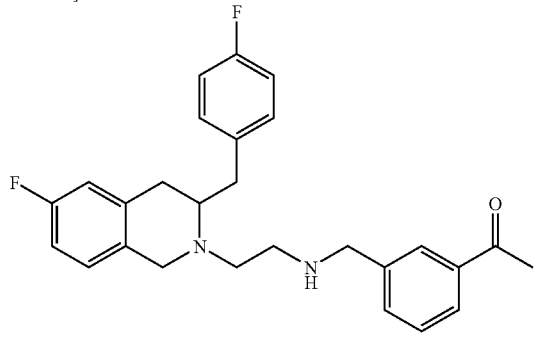

The reaction and treatment were carried out in the same manner as in Example 89 using 2-[6-fluoro-3-(4-fluorobenzyl)-3,4-dihydroisoquinolin-2(1H)-yl]ethanamine obtained in Example 120-b) to obtain a title compound as a light yellow oily substance.

$^1$H-NMR (CDCl$_3$) δ: 2.44 (1H, dd, J=9.5, 13.4 Hz), 2.50 (1H, dd, J=3.9, 16.6 Hz), 2.59 (3H, s), 2.71-2.90 (6H, m), 3.14-3.22 (1H, m), 3.75 (2H, s), 3.84 (2H, s), 6.76 (1H, dd, J=2.6, 9.5 Hz), 6.85 (1H, ddd, J=2.6, 8.3, 8.3 Hz), 6.90-7.06 (5H, m), 7.41 (1H, dd, J=7.7, 7.7 Hz), 7.50 (1H, d, J=7.7 Hz), 7.84 (1H, d, J=7.7 Hz), 7.89 (1H, s).

Example 123

Production of N-(3-nitrobenzyl)-2-[6-fluoro-3-(4-fluorobenzyl)-3,4-dihydroisoquinolin-2(1H)-yl]ethanamine a) Production of tert-butyl 3-nitrobenzyl[2-[6-fluoro-3-(4-fluorobenzyl)-3,4-dihydroisoquinolin-2(1H)-yl]ethyl]carbamate

[Chem. 326]

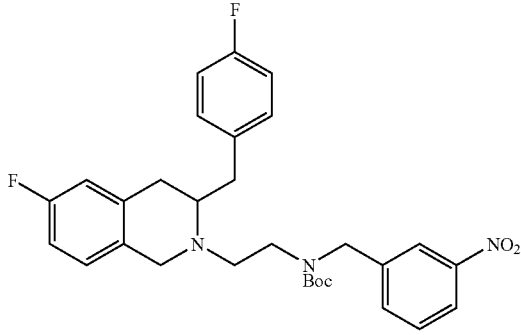

The reaction and treatment were carried out in the same manner as in Example 117-d) using 6-fluoro-3-(4-fluorobenzyl)-1,2,3,4-tetrahydroisoquinoline obtained in Example 53-a) instead of 3-(4-fluorobenzyl)-1,2,3,4-tetrahydroisoquinoline to obtain a title compound as a light yellow oily substance.

$^1$H-NMR (CDCl$_3$) δ: 1.39-1.51 (9H, br), 2.42 (1H, dd, J=9.8, 13.4 Hz), 2.49 (1H, dd, J=4.2, 16.6 Hz), 2.62-2.90 (3H, m), 2.75 (1H, dd, J=5.0, 16.7 Hz), 3.08-3.52 (3H, m), 3.77 (2H, s), 4.46-4.58 (2H, m), 6.74 (1H, dd, J=2.4, 9.5 Hz), 6.85 (1H, ddd, J=2.4, 8.5, 8.5 Hz), 6.94-7.08 (5H, m), 7.42-7.58 (2H, m), 8.07-8.12 (2H, m).

b) Production of N-(3-nitrobenzyl)-2-[6-fluoro-3-(4-fluorobenzyl)-3,4-dihydroisoquinolin-2(1H)-yl]ethanamine

[Chem. 327]

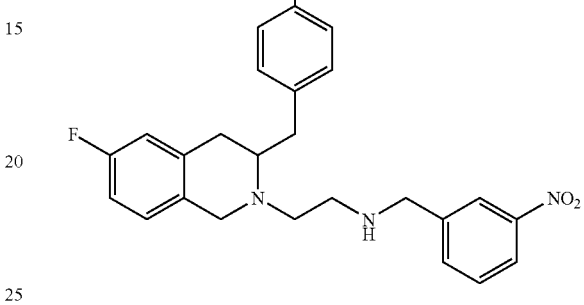

The reaction and treatment were carried out in the same manner as in Example 32-g) to obtain a title compound as a light yellow oily substance.

$^1$H-NMR (CDCl$_3$) δ: 2.48 (1H, dd, J=9.3, 13.4 Hz), 2.53 (1H, dd, J=3.9, 17.1 Hz), 2.72-2.79 (3H, m), 2.81-2.91 (3H, m), 3.18-3.24 (1H, m), 3.79 (2H, s), 3.88 (2H, s), 6.77 (1H, dd, J=2.6, 9.6 Hz), 6.87 (1H, ddd, J=2.6, 8.5, 8.5 Hz), 6.91-6.97 (2H, m), 7.00 (1H, dd, J=5.6, 8.8 Hz), 7.04-7.09 (2H, m), 7.48 (1H, dd, J=7.8, 7.8 Hz), 7.62-7.65 (1H, m), 8.11 (1H, dd, J=1.5, 7.8 Hz), 8.18 (1H, s).

Example 124

Production of N-(3-aminobenzyl)-2-[6-fluoro-3-(4-fluorobenzyl)-3,4-dihydroisoquinolin-2(1H)-yl]ethanamine a) Production of tert-butyl 3-aminobenzyl[2-[6-fluoro-3-(4-fluorobenzyl)-3,4-dihydroisoquinolin-2(1H)-yl]ethyl]carbamate

[Chem. 328]

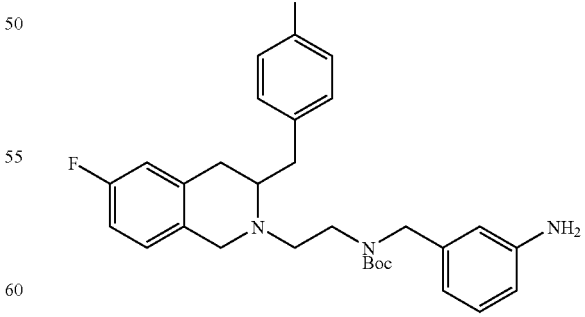

The reaction and treatment were carried out in the same manner as in Example 117-e) using tert-butyl 3-nitrobenzyl [2-[6-fluoro-3-(4-fluorobenzyl)-3,4-dihydroisoquinolin-2 (1H)-yl]ethyl]carbamate obtained in Example 123-a) to obtain a title compound as a light yellow oily substance.

¹H-NMR (CDCl₃) δ: 1.46 (9H, brs), 2.39 (1H, dd, J=9.9, 13.3 Hz), 2.44-2.52 (1H, m), 2.54-3.84 (11H, m), 4.34-4.40 (2H, m), 6.50-6.65 (3H, m), 6.73 (1H, dd, J=2.6, 9.4 Hz), 6.84 (1H, ddd, J=2.6, 8.5, 8.5 Hz), 6.94-7.11 (6H, m).

b) Production of N-(3-aminobenzyl)-2-[6-fluoro-3-(4-fluorobenzyl)-3,4-dihydroisoquinolin-2(1H)-yl]ethanamine

[Chem. 329]

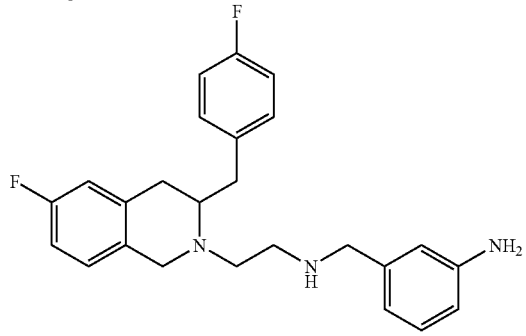

The reaction and treatment were carried out in the same manner as in Example 32-g) to obtain a title compound as a light yellow oily substance.

¹H-NMR (CDCl₃) δ: 2.44 (1H, dd, J=9.8, 13.4 Hz), 2.50 (1H, dd, J=3.9, 16.8 Hz), 2.72-2.92 (6H, m), 3.14-3.25 (1H, m), 3.52-3.68 (2H, m), 3.72-3.74 (4H, m), 6.56-6.60 (1H, m), 6.62-6.68 (2H, m), 6.75 (1H, dd, J=2.5, 9.3 Hz), 6.85 (1H, ddd, J=2.5, 8.3, 8.3 Hz), 6.92-7.01 (3H, m), 7.02-7.12 (3H, m).

Example 125

Production of N-[3-(acetylamino)benzyl]-2-[6-fluoro-3-(4-fluorobenzyl)-3,4-dihydroisoquinolin-2(1H)-yl]ethanamine a) Production of tert-butyl 3-(acetylamino)benzyl[2-[6-fluoro-3-(4-fluorobenzyl)-3,4-dihydroisoquinolin-2(1H)-yl]ethyl]carbamate

[Chem. 330]

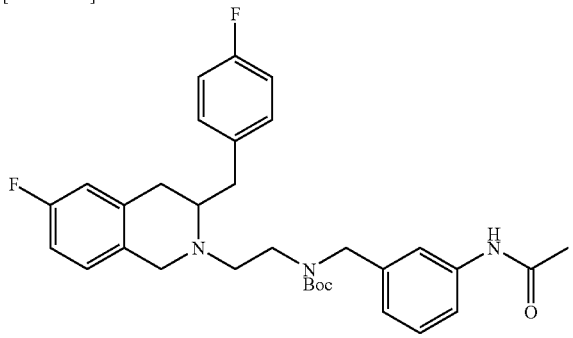

The reaction and treatment were carried out in the same manner as in Example 119 using tert-butyl 3-aminobenzyl[2-[6-fluoro-3-(4-fluorobenzyl)-3,4-dihydroisoquinolin-2(1H)-yl]ethyl]carbamate obtained in Example 124-a) to obtain a title compound as a light yellow oily substance.

¹H-NMR (CDCl₃) δ: 1.44-1.47 (9H, br), 2.14 (3H, s), 2.39 (1H, dd, J=9.9, 13.3 Hz), 2.47 (1H, dd, J=4.0, 16.5 Hz), 2.55-2.88 (4H, m), 3.05-3.49 (3H, m), 3.71-3.81 (2H, m), 4.38-4.46 (2H, m), 6.73 (1H, dd, J=2.6, 9.4 Hz), 6.84 (1H, ddd, J=2.6, 8.7, 8.7 Hz), 6.93-7.48 (10H, m).

b) Production of N-[3-(acetylamino)benzyl]-2-[6-fluoro-3-(4-fluorobenzyl)-3,4-dihydroisoquinolin-2(1H)-yl]ethanamine

[Chem. 331]

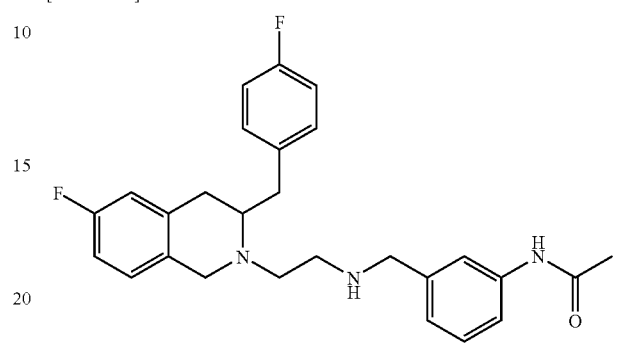

The reaction and treatment were carried out in the same manner as in Example 32-g) to obtain a title compound as a light yellow oily substance.

¹H-NMR (CDCl₃) δ: 2.15 (3H, s), 2.43 (1H, dd, J=9.6, 13.3 Hz), 2.50 (1H, dd, J=3.7, 16.6 Hz), 2.70-2.90 (6H, m), 3.13-3.22 (1H, m), 3.73 (2H, s), 3.77 (2H, s), 6.75 (1H, dd, J=2.6, 9.4 Hz), 6.86 (1H, ddd, J=2.6, 8.6, 8.6 Hz), 6.91-7.07 (7H, m), 7.13 (1H, s), 7.38-7.44 (2H, m).

Example 126

Production of N-[3-(methanesulfonylamino)benzyl]-2-[6-fluoro-3-(4-fluorobenzyl)-3,4-dihydroisoquinolin-2(1H)-yl]ethanamine

[Chem. 332]

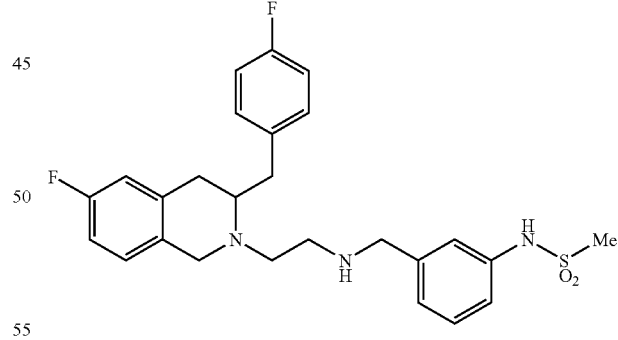

The reaction and treatment were carried out in the same manner as in Examples 117-f) and 32-g) using tert-butyl 3-aminobenzyl[2-[6-fluoro-3-(4-fluorobenzyl)-3,4-dihydroisoquinolin-2(1H)-yl]ethyl]carbamate obtained in Example 124-a) to obtain a title compound as a light yellow oily substance.

¹H-NMR (CDCl₃) δ: 2.44 (1H, dd, J=9.8, 13.4 Hz), 2.50 (1H, dd, J=3.9, 16.6 Hz), 2.72-2.90 (6H, m), 2.95 (3H, s), 3.14-3.22 (1H, m), 3.76 (2H, s), 3.77 (2H, s), 6.75 (1H, dd, J=2.4, 9.5 Hz), 6.86 (1H, ddd, J=2.4, 8.5, 8.5 Hz), 6.94 (2H, ddd, J=2.0, 6.6, 8.6 Hz), 6.99 (1H, dd, J=5.7, 8.5 Hz), 7.02-7.15 (4H, m), 7.26-7.31 (2H, m).

Example 127

Production of N-(4-methyl-3-nitrobenzyl)-2-[6-fluoro-3-(4-fluorobenzyl)-3,4-dihydroisoquinolin-2(1H)-yl]ethanamine a) Production of [(tert-butoxycarbonyl)4-methyl-3-nitrobenzylamino]acetaldehyde

[Chem. 333]

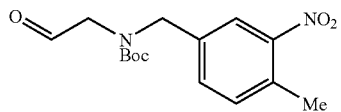

The reaction and treatment were carried out in the same manner as in Example 117-a, b, c) using 4-methyl-3-nitrobenzaldehyde instead of 3-nitrobenzaldehyde to obtain a title compound as a light yellow oily substance.

$^1$H-NMR (CDCl$_3$) δ: 1.47 (9H, s), 2.59 (3H, s), 3.84-4.04 (2H, m), 4.46-4.58 (2H, m), 7.28-7.46 (2H, m), 7.81-7.88 (1H, m), 9.48-9.56 (1H, m).

b) Production of tert-butyl 4-methyl-3-nitrobenzyl[2-[6-fluoro-3-(4-fluorobenzyl)-3,4-dihydroisoquinolin-2(1H)-yl]ethyl]carbamate

[Chem. 334]

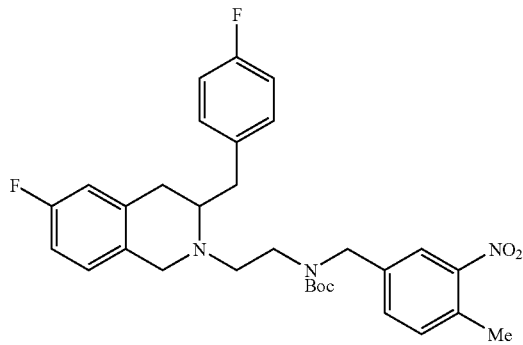

The reaction and treatment were carried out in the same manner as in Example 117-d) using 6-fluoro-3-(4-fluorobenzyl)-1,2,3,4-tetrahydroisoquinoline instead of 3-(4-fluorobenzyl)-1,2,3,4-tetrahydroisoquinoline to obtain a title compound as a light yellow oily substance.

$^1$H-NMR (CDCl$_3$) δ: 1.38-1.50 (9H, br), 2.41 (1H, dd, J=9.8, 13.4 Hz), 2.48 (1H, dd, J=4.2, 16.6 Hz), 2.56 (3H, s), 2.68-2.90 (3H, m), 3.00-3.50 (4H, m), 3.74-3.78 (2H, m), 4.38-4.52 (2H, m), 6.74 (1H, dd, J=2.4, 9.5 Hz), 6.85 (1H, ddd, J=2.4, 8.3, 8.3 Hz), 6.93-7.00 (3H, m), 7.01-7.08 (2H, m), 7.22-7.26 (1H, m), 7.28-7.40 (1H, m), 7.83 (1H, s).

c) Production of N-(4-methyl-3-nitrobenzyl)-2-[6-fluoro-3-(4-fluorobenzyl)-3,4-dihydroisoquinolin-2(1H)-yl]ethanamine

[Chem. 335]

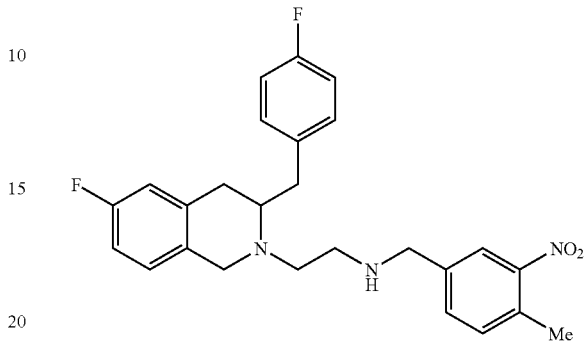

The reaction and treatment were carried out in the same manner as in Example 32-g) to obtain a title compound as a light yellow oily substance.

$^1$H-NMR (CDCl$_3$) δ: 2.48 (1H, dd, J=9.3, 13.4 Hz), 2.53 (1H, dd, J=3.9, 17.1 Hz), 2.58 (3H, s), 2.73-2.92 (6H, m), 3.19-3.26 (1H, m), 3.78 (2H, s), 3.83 (2H, s), 6.77 (1H, dd, J=2.6, 9.5 Hz), 6.86 (1H, ddd, J=2.6, 8.5, 8.5 Hz), 6.91-6.96 (2H, m), 6.99 (1H, dd, J=5.9, 8.5 Hz), 7.07 (2H, dd, J=5.5, 8.4 Hz), 7.28 (1H, d, J=7.8 Hz), 7.46 (1H, d, J=7.8 Hz), 7.90 (1H, s).

Example 128

Production of N-(3-amino-4-methylbenzyl)-2-[6-fluoro-3-(4-fluorobenzyl)-3,4-dihydroisoquinolin-2(1H)-yl]ethanamine

[Chem. 336]

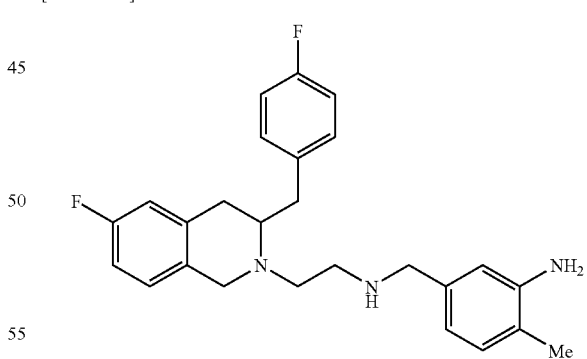

The reaction and treatment were carried out in the same manner as in Example 117-e) using tert-butyl 4-methyl-3-nitrobenzyl[2-[6-fluoro-3-(4-fluorobenzyl)-3,4-dihydroisoquinolin-2(1H)-yl]ethyl]carbamate obtained in Example 127-b), and then the reaction and treatment were carried out in the same manner as in Example 32-g) to obtain a title compound as a light yellow oily substance.

$^1$H-NMR (CDCl$_3$) δ: 2.14 (3H, s), 2.41 (1H, dd, J=10.0, 13.2 Hz), 2.48 (1H, dd, J=3.5, 16.5 Hz), 2.72-2.89 (6H, m), 3.11-3.19 (1H, m), 3.45-3.60 (2H, m), 3.69 (2H, s), 3.74 (2H, s), 6.58-6.62 (2H, m), 6.75 (1H, dd, J=2.6, 9.5 Hz), 6.85 (1H, ddd, J=2.6, 8.5, 8.5 Hz), 6.92-7.06 (6H, m).

Example 129

Production of N-(3-acetylamino-4-methylbenzyl)-2-[6-fluoro-3-(4-fluorobenzyl)-3,4-dihydroisoquinolin-2(1H)-yl]ethanamine

[Chem. 337]

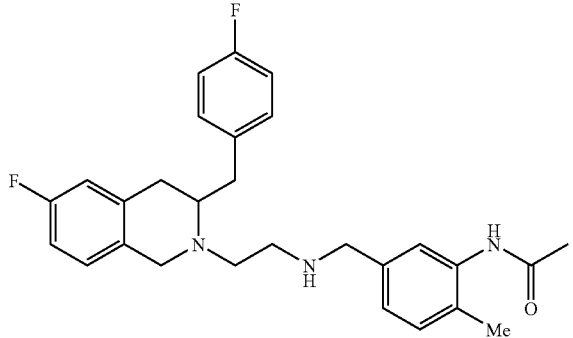

The reaction and treatment were carried out in the same manner as in Examples 117-e), 119, 32-g) using tert-butyl 4-methyl-3-nitrobenzyl[2-[6-fluoro-3-(4-fluorobenzyl)-3,4-dihydroisoquinolin-2(1H)-yl]ethyl]carbamate obtained in Example 127-b) to obtain a title compound as a light yellow oily substance.

$^1$H-NMR (CDCl$_3$) δ: 2.18 (3H, s), 2.23 (3H, s), 2.41 (1H, dd, J=9.9, 13.3 Hz), 2.49 (1H, dd, J=3.5, 16.5 Hz), 2.70-2.90 (6H, m), 3.12-3.20 (1H, m), 3.73 (2H, s), 3.75 (2H, s), 6.74 (1H, dd, J=2.4, 9.5 Hz), 6.85 (1H, ddd, J=2.4, 8.5, 8.5 Hz), 6.93 (2H, ddd, J=2.2, 6.6, 8.8 Hz), 6.98 (1H, dd, J=5.8, 8.5 Hz), 7.00-7.06 (4H, m), 7.12 (1H, d, J=7.8 Hz), 7.69 (1H, s).

Example 130

Production of N-(3-methanesulfonylamino-4-methylbenzyl)-2-[6-fluoro-3-(4-fluorobenzyl)-3,4-dihydroisoquinolin-2(1H)-yl]ethanamine

[Chem. 338]

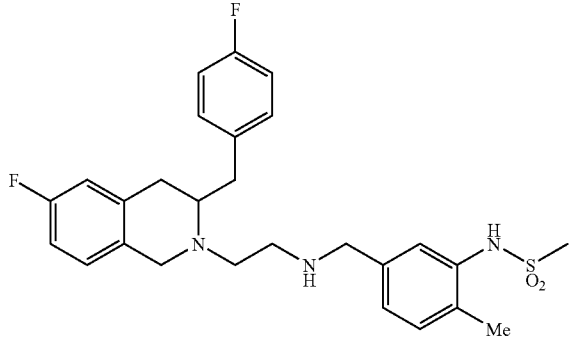

The reaction and treatment were carried out in the same manner as in Examples 117-e, f), 32-g) using tert-butyl 4-methyl-3-nitrobenzyl[2-[6-fluoro-3-(4-fluorobenzyl)-3,4-dihydroisoquinolin-2(1H)-yl]ethyl]carbamate obtained in Example 127-b) to obtain a title compound as a light yellow oily substance.

$^1$H-NMR (CDCl$_3$) δ: 2.29 (3H, s), 2.43 (1H, dd, J=9.8, 13.4 Hz), 2.50 (1H, dd, J=3.9, 16.6 Hz), 2.72-2.90 (6H, m), 2.97 (3H, s), 3.12-3.22 (1H, m), 3.75-3.77 (4H, m), 6.75 (1H, dd, J=2.5, 9.5 Hz), 6.85 (1H, ddd, J=2.5, 8.6, 8.6 Hz), 6.94 (2H, ddd, J=2.0, 6.7, 8.7 Hz), 6.99 (1H, dd, J=5.6, 8.6 Hz), 7.01-7.08 (3H, m), 7.16 (1H, d, J=7.6 Hz), 7.37 (1H, d, J=1.0 Hz).

Example 131

Production of N-[3-(2-propyl sulfonylamino)benzyl]-2-[6-fluoro-3-(4-fluorobenzyl)-3,4-dihydroisoquinolin-2(1H)-yl]ethanamine a) Production of tert-butyl 3-(2-propyl sulfonylamino)benzyl-[2-[6-fluoro-3-(4-fluorobenzyl)-3,4-dihydroisoquinolin-2(1H)-yl]ethyl]carbamate

[Chem. 339]

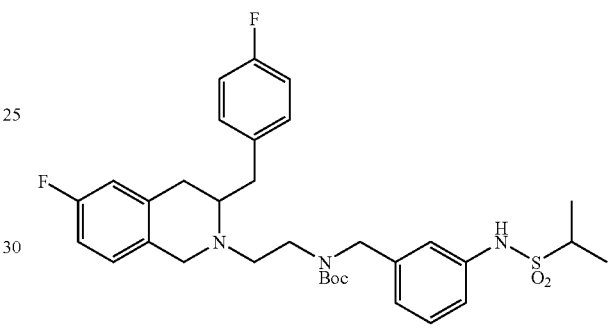

The reaction and treatment were carried out in the same manner as in Example 126 using 2-propanesulfonyl chloride instead of methanesulfonyl chloride to obtain a title compound as a light yellow oily substance.

$^1$H-NMR (CDCl$_3$) δ: 1.36 (6H, d, J=6.8 Hz), 1.44-1.47 (9H, br), 2.41 (1H, dd, J=10.0, 13.4 Hz), 2.48 (1H, dd, J=3.9, 16.4 Hz), 2.61-2.83 (4H, m), 3.02-3.42 (4H, m), 3.72-3.82 (2H, m), 4.39-4.44 (2H, m), 6.74 (1H, dd, J=2.4, 9.5 Hz), 6.85 (1H, ddd, J=2.4, 8.6, 8.6 Hz), 6.94-7.27 (9H, m).

b) Production of N-[3-(2-propyl sulfonylamino)benzyl]-2-[6-fluoro-3-(4-fluorobenzyl)-3,4-dihydroisoquinolin-2(1H)-yl]ethanamine

[Chem. 340]

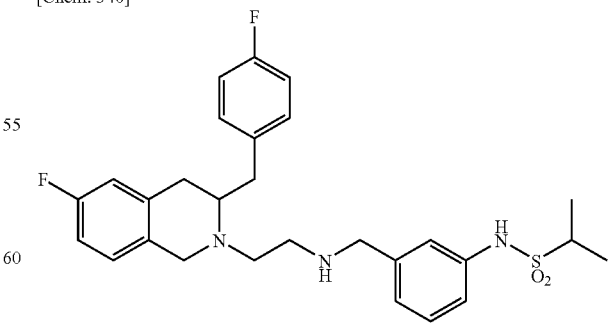

The reaction and treatment were carried out in the same manner as in Example 32-g) to obtain a title compound as a pale yellow oily substance.

¹H-NMR (CDCl₃) δ: 1.37 (6H, d, J=6.8 Hz), 2.42-2.53 (2H, m), 2.74-2.90 (6H, m), 3.16-3.22 (1H, m), 3.25-3.32 (1H, m), 3.76 (2H, s), 3.77 (2H, s), 6.74-7.28 (11H, m).

Example 132

Production of N-[3-(N-methyl-2-propyl sulfonylamino)benzyl]-2-[6-fluoro-3-(4-fluorobenzyl)-3,4-dihydroisoquinolin-2(1H)-yl]ethanamine a) Production of tert-butyl[3-(N-methyl-2-propyl sulfonylamino)benzyl]-[2-[6-fluoro-3-(4-fluorobenzyl-3,4-dihydroisoquinolin-2(1H)-yl)ethyl]carbamate

[Chem. 341]

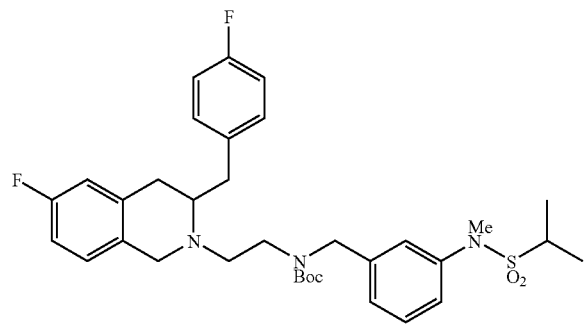

8.7 mg of tert-butyl 3-(2-propyl sulfonylamino)benzyl-[2-[6-fluoro-3-(4-fluorobenzyl)-3,4-dihydroisoquinolin-2(1H)-yl]ethyl]carbamate obtained in Example 131-a) was dissolved in 1 mL of THF, and 0.7 mg of sodium hydride was added thereto under ice-cooling, followed by stirring for 15 minutes. 2.6 mg of iodomethane was added thereto, followed by stirring at room temperature for 3 hours. After completion of the reaction, the reaction liquid was under ice-cooling, and a saturated aqueous sodium bicarbonate solution and ethyl acetate were added thereto. The organic layer was separated, the aqueous layer was further extracted by addition of ethyl acetate, and the organic layer was combined and washed with saturated brine. The organic layer was dried over anhydrous sodium sulfate and then concentrated under reduced pressure, and the solvent was removed by evaporation to obtain 10.0 mg of a crude composition. The crude composition was purified by PLC to obtain 6.3 mg (yield 71%) of a desired product.

¹H-NMR (CDCl₃) δ: 1.34 (6H, d, J=6.6 Hz), 1.42-1.49 (9H, br), 2.41 (1H, dd, J=10.0, 13.4 Hz), 2.45-2.51 (1H, m), 2.59-2.95 (4H, m), 3.11-3.36 (4H, m), 3.34 (3H, s), 3.72-3.84 (2H, m), 4.39-4.49 (2H, m), 6.74 (1H, dd, J=2.4, 9.5 Hz), 6.85 (1H, ddd, J=2.4, 8.5, 8.5 Hz), 6.96 (2H, dd, J=8.5, 8.5 Hz), 7.00-7.31 (7H, m).

b) Production of N-[3-(N-methyl-2-propyl sulfonylamino)benzyl]-2-[6-fluoro-3-(4-fluorobenzyl)-3,4-dihydroisoquinolin-2(1H)-yl]ethanamine

[Chem. 342]

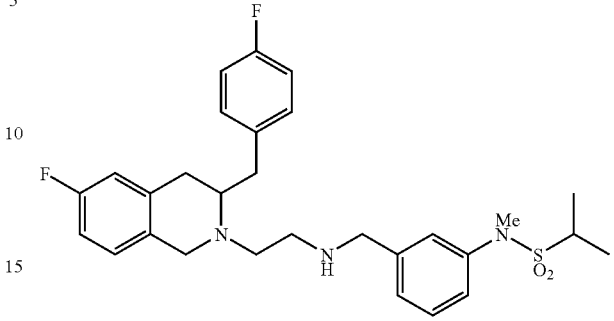

The reaction and treatment were carried out in the same manner as in Example 32-g) to obtain a title compound as a pale yellow oily substance.

¹H-NMR (CDCl₃) δ: 1.35 (6H, d, J=6.8 Hz), 2.44 (1H, dd, J=9.8, 13.2 Hz), 2.51 (1H, dd, J=3.6, 16.6 Hz), 2.74-2.90 (6H, m), 3.15-3.22 (1H, m), 3.24-3.31 (1H, m), 3.35 (3H, s), 3.77 (2H, s), 3.79 (2H, s), 6.76 (1H, d, J=9.5 Hz), 6.86 (1H, dd, J=8.8, 8.8 Hz), 6.94 (2H, dd, J=8.5, 8.5 Hz), 6.98 (1H, dd, J=5.8, 8.8 Hz), 7.05 (2H, dd, J=5.4, 8.5 Hz), 7.18 (1H, d, J=6.8 Hz), 7.21-7.33 (2H, m), 7.36 (1H, s).

Example 133

Production of N-(3,5-dimethanesulfonylaminobenzyl)-2-[6-fluoro-3-(4-fluorobenzyl)-3,4-dihydroisoquinolin-2(1H)-yl]ethanamine a) Production of N-[3,5-bis(tert-butyloxycarbonyl)aminobenzyl]-2-[6-fluoro-3-(4-fluorobenzyl)-3,4-dihydroisoquinolin-2(1H)-yl]ethanamine

[Chem. 343]

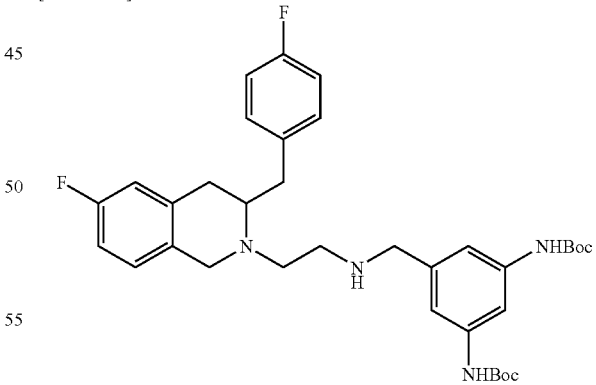

The reaction and treatment were carried out in the same manner as in Example 120-c) using 3,5-bis(tert-butyloxycarbonyl)aminobenzaldehyde instead of 4-ethylbenzaldehyde to obtain a title compound as a light yellow oily substance.

¹H-NMR (CDCl₃) δ: 1.50 (18H, s), 2.41 (1H, dd, J=10.0, 13.2 Hz), 2.45-2.51 (1H, m), 2.71-2.89 (6H, m), 2.13-3.19 (1H, m), 3.70 (1H, d, J=7.1 Hz), 3.72 (2H, s), 3.74 (1H, d, J=7.1 Hz), 6.74 (1H, dd, J=2.4, 9.5 Hz), 6.85 (1H, ddd, J=2.4, 8.6, 8.6 Hz), 6.95 (2H, dd, J=8.6, 8.6 Hz), 6.97-7.01 (3H, m), 7.04 (2H, dd, J=5.6, 8.6 Hz), 7.36 (1H, s).

b) Production of N-(benzyloxycarbonyl)-N-[3,5-bis(tert-butyloxycarbonyl)aminobenzyl]-2-[6-fluoro-3-(4-fluorobenzyl)-3,4-dihydroisoquinolin-2(1H)-yl]ethanamine

[Chem. 344]

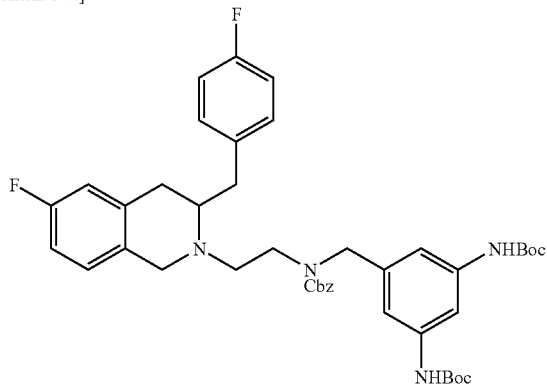

31.5 mg of N-[3,5-bis(tert-butyloxycarbonyl)aminobenzyl]-2-[6-fluoro-3-(4-fluorobenzyl)-3,4-dihydroisoquinolin-2(1H)-yl]ethanamine was taken into a 20-mL eggplant flask and dissolved in 1.5 mL of dichloromethane, and 0.01 mL of triethylamine and 0.01 mL of Cbz-chloride were sequentially added thereto under ice-cooling, followed by stirring for 1 hour at room temperature. After completion of the reaction, to the reaction liquid were added a saturated aqueous sodium bicarbonate solution and chloroform under ice-cooling. The organic layer was separated, the aqueous layer was further extracted by addition of chloroform, and the organic layer was combined and washed with saturated brine. The organic layer was dried over anhydrous sodium sulfate and concentrated under reduced pressure, and the solvent was removed by evaporation to obtain 120.0 mg of a crude composition. The crude composition was purified by PLC to obtain 35.8 mg (yield 93%) of a title compound as a pale yellow oily substance.

$^1$H-NMR (CDCl$_3$) δ: 1.50 (18H, s), 2.28-2.88 (6H, m), 2.98-3.20 (1H, m), 3.33-3.50 (2H, m), 3.73 (1H, d, J=16.1 Hz), 3.78 (1H, d, J=16.1 Hz), 4.41-4.46 (2H, m), 5.15 (1H, d, J=14.9 Hz), 5.19 (1H, d, J=14.9 Hz), 6.28 (I H, s), 6.44 (1H, s), 6.70-7.06 (7H, m), 7.30-7.46 (6H, m).

c) Production of N-(3,5-diaminobenzyl)-N-(benzyloxycarbonyl)-2-[6-fluoro-3-(4-fluorobenzyl)-3,4-dihydroisoquinolin-2(1H)-yl]ethanamine

[Chem. 345]

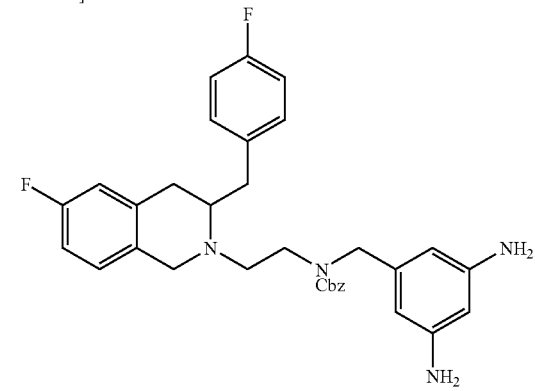

35.8 mg of N-(benzyloxycarbonyl)-N-[3,5-bis(tert-butyloxycarbonyl)aminobenzyl]-2-[6-fluoro-3-(4-fluorobenzyl)-3,4-dihydroisoquinolin-2(1H)-yl]ethanamine was dissolved in 2.5 mL of dichloromethane, and TFA 1.5 mL was added thereto under ice-cooling, followed by followed by stirring for 2 hours as it was. After completion of the reaction, to the reaction liquid were added a saturated aqueous sodium bicarbonate solution and chloroform. The organic layer was separated, the aqueous layer was further extracted by addition of chloroform, and the organic layer was combined and washed with saturated brine. The organic layer was dried over anhydrous sodium sulfate and concentrated under reduced pressure, and the solvent was removed by evaporation to obtain 25.6 mg of a crude composition.

The crude composition was purified by PLC to obtain 20.9 mg (yield 79%) of a desired compound.

$^1$H-NMR (CDCl$_3$) δ: 2.28-3.84 (11H, m), 4.32-4.35 (2H, m), 5.17 (2H, s), 5.87 (1H, s), 5.90-5.93 (1H, m), 6.00 (1H, s), 6.70-7.08 (6H, m), 7.30-7.37 (6H, m).

d) Production of N-(benzyloxycarbonyl)-N-[3,5-bis(methanesulfonyl)aminobenzyl]-2-[6-fluoro-3-(4-fluorobenzyl)-3,4-dihydroisoquinolin-2(1H)-yl]ethanamine

[Chem. 346]

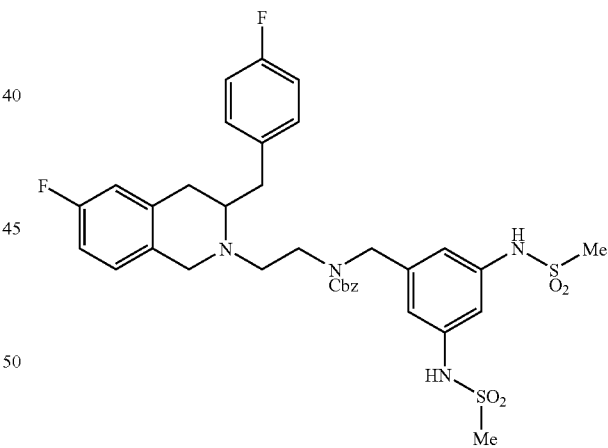

The reaction and treatment were carried out in the same manner as in Example 117-f) to obtain a title compound as a light yellow oily substance.

$^1$H-NMR (CDCl$_3$) δ: 2.32-2.51 (2H, m), 2.62-2.86 (3H, m), 2.92-3.01 (6H, m), 3.06-3.49 (4H, m), 3.67-3.84 (2H, m), 4.40-4.44 (2H, m), 5.16 (2H, s), 6.71-7.07 (9H, m), 7.28-7.36 (6H, m).

e) Production of N-(3,5-dimethanesulfonylaminobenzyl)-2-[6-fluoro-3-(4-fluorobenzyl)-3,4-dihydroisoquinolin-2(1H)-yl]ethanamine

[Chem. 347]

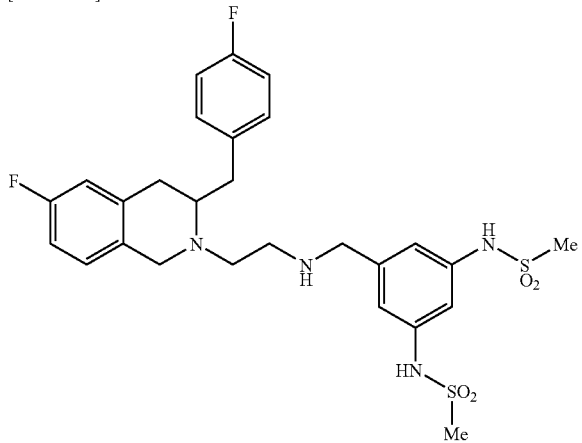

N-(benzyloxycarbonyl)-N-[3,5-bis(methanesulfonyl)aminobenzyl]-2-[6-fluoro-3-(4-fluorobenzyl)-3,4-dihydroisoquinolin-2(1H)-yl]ethanamine (25.0 mg, 0.04 mmol) was dissolved in 1.5 mL of methanol, and 100 mg of Pd—C was added thereto at room temperature, followed by stirring for 1.5 hours under a hydrogen gas atmosphere. After completion of the reaction, the reaction liquid was filtered through Celite. The filtrate was concentrated under reduced pressure, and the solvent was removed by evaporation and purified by PLC to obtain 6.8 mg (yield 33%) of a desired product as a pale yellow oily substance.

$^1$H-NMR (CDCl$_3$) δ: 2.45 (1H, dd, J=9.8, 13.2 Hz), 2.51 (1H, dd, J=3.6, 16.6 Hz), 2.75-2.90 (6H, m), 2.98 (6H, s), 3.12-3.23 (1H, m), 3.73 (2H, s), 3.79 (2H, s), 6.76 (1H, dd, J=2.7, 9.3 Hz), 6.87 (1H, ddd, J=2.7, 8.6, 8.6 Hz), 6.90 (1H, s), 6.91 (1H, s), 6.95 (2H, dd, J=8.6, 8.6 Hz), 6.96 (1H, s), 7.02 (1H, dd, J=5.6, 8.6 Hz), 7.06 (2H, dd, J=5.6, 8.6 Hz).

Example 134

Production of N-(3-trifluoromethanesulfonylaminobenzyl)-2-[6-fluoro-3-(4-fluorobenzyl)-3,4-dihydroisoquinolin-2(1H)-yl]ethanamine a) Production of tert-butyl 3-trifluoromethanesulfonylaminobenzyl[2-[6-fluoro-3-(4-fluorobenzyl-3,4-dihydroisoquinolin-2(1H)-yl)ethyl]carbamate

[Chem. 348]

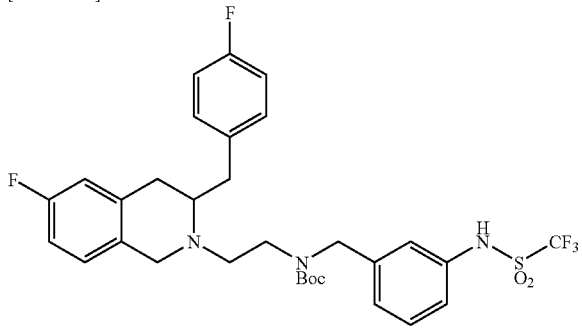

The reaction and treatment were carried out in the same manner as in Example 126 using trifluoromethanesulfonyl chloride instead of methanesulfonyl chloride to obtain a title compound as a light yellow oily substance.

$^1$H-NMR (CDCl$_3$) δ: 1.46 (9H, s), 2.39 (1H, dd, J=10.0, 13.4 Hz), 2.45-2.50 (1H, m), 2.58-2.84 (4H, m), 3.07-3.83 (5H, m), 4.35-4.39 (2H, m), 6.51-6.64 (3H, m), 6.73 (1H, dd, J=2.4, 9.5 Hz), 6.84 (1H, ddd, J=2.4, 8.6, 8.6 Hz), 6.94-7.11 (6H, m).

b) Production of N-(3-trifluoromethanesulfonylaminobenzyl)-2-[6-fluoro-3-(4-fluorobenzyl)-3,4-dihydroisoquinolin-2(1H)-yl]ethanamine

[Chem. 349]

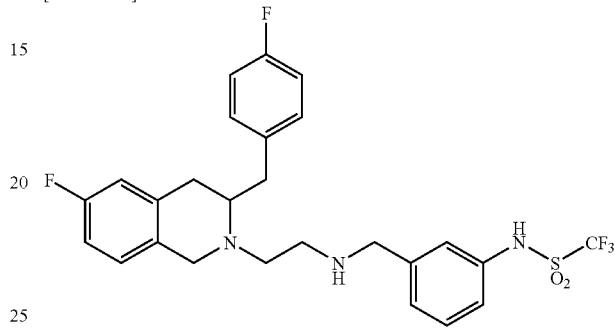

The reaction and treatment were carried out in the same manner as in Example 32-g) to obtain a title compound as a pale yellow oily substance.

$^1$H-NMR (CDCl$_3$) δ: 2.42 (1H, dd, J=9.8, 13.2 Hz), 2.50 (1H, dd, J=3.7, 16.6 Hz), 2.73-2.89 (6H, m), 3.17 (1H, dt, J=4.6, 9.8 Hz), 3.70 (2H, s), 3.72 (1H, d, J=16.1 Hz), 3.77 (1H, d, J=16.1 Hz), 6.57 (1H, dd, J=1.7, 7.8 Hz), 6.62 (1H, s), 6.66 (1H, d, J=7.8 Hz), 6.76 (1H, dd, J=2.7, 9.5 Hz), 6.86 (1H, ddd, J=2.7, 8.5, 8.5 Hz), 6.95 (2H, ddd, J=2.2, 8.5, 8.5 Hz), 6.99 (1H, dd, J=5.8, 8.5 Hz), 7.04 (2H, ddd, J=2.2, 5.6, 8.5 Hz), 7.09 (1H, dd, J=7.8, 7.8 Hz).

Example 135

Production of N-(3-ethanesulfonylaminobenzyl)-2-[6-fluoro-3-(4-fluorobenzyl)-3,4-dihydroisoquinolin-2(1H)-yl]ethanamine a) Production of tert-butyl 3-ethanesulfonylaminobenzyl[2-[6-fluoro-3-(4-fluorobenzyl-3,4-dihydroisoquinolin-2(1H)-yl)ethyl]carbamate

[Chem. 350]

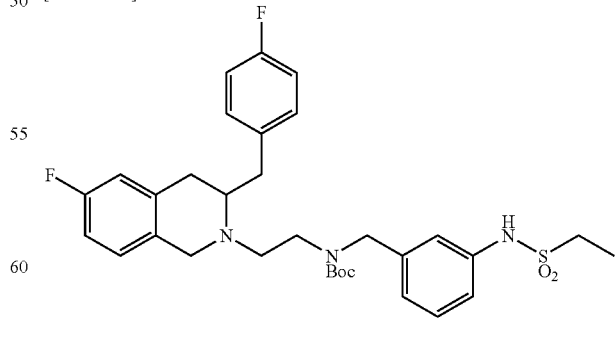

The reaction and treatment were carried out in the same manner as in Example 126 using ethanesulfonyl chloride instead of methanesulfonyl chloride to obtain a title compound as a light yellow oily substance.

¹H-NMR (CDCl₃) δ: 1.34 (3H, t, J=7.3 Hz), 1.43-1.51 (9H, br), 2.41 (1H, dd, J=10.0, 13.4 Hz), 2.48 (1H, dd, J=3.4, 16.8 Hz), 2.57-2.89 (4H, m), 3.10 (2H, q, J=7.3 Hz), 3.15-3.49 (3H, m), 3.77 (1H, d, J=15.6 Hz), 3.81 (1H, d, J=15.6 Hz), 4.40-4.45 (2H, m), 6.74 (1H, dd, J=2.4, 9.5 Hz), 6.86 (1H, ddd, J=2.4, 8.6, 8.6 Hz), 7.00 (2H, dd, J=8.6, 8.6 Hz), 7.01-7.09 (3H, m), 7.09 (1H, s), 7.10-7.14 (2H, m), 7.27 (1H, dd, J=7.3, 7.3 Hz).

b) Production of N-(3-ethanesulfonylaminobenzyl)-2-[6-fluoro-3-(4-fluorobenzyl)-3,4-dihydroisoquinolin-2(1H)-yl]ethanamine

[Chem. 351]

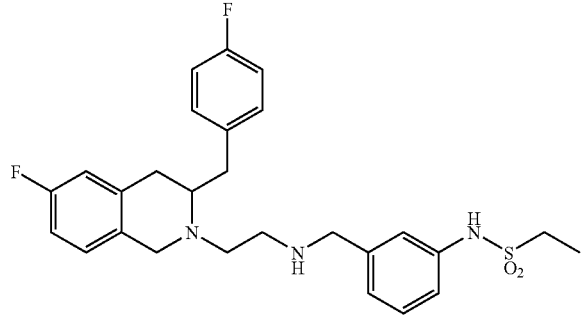

The reaction and treatment were carried out in the same manner as in Example 32-g) to obtain a title compound as a pale yellow oily substance.

¹H-NMR (CDCl₃) δ: 1.30 (3H, t, J=7.3 Hz), 2.43-2.54 (2H, m), 2.82-3.04 (6H, m), 3.09 (2H, q, J=7.3 Hz), 3.20-3.29 (1H, m), 3.74 (2H, s), 3.91 (2H, s), 6.73 (1H, d, J=9.0 Hz), 6.84 (1H, dd, J=8.0, 8.0 Hz), 6.90-6.97 (3H, m), 7.05-7.09 (3H, m), 7.23-7.27 (2H, m), 7.39 (1H, s).

Example 136

Production of N-(3-propanesulfonylaminobenzyl)-2-[6-fluoro-3-(4-fluorobenzyl)-3,4-dihydroisoquinolin-2(1H)-yl]ethanamine a) Production of tert-butyl(3-propanesulfonylaminobenzyl)-[2-[6-fluoro-3-(4-fluorobenzyl-3,4-dihydroisoquinolin-2(1H)-yl)ethyl]carbamate

[Chem. 352]

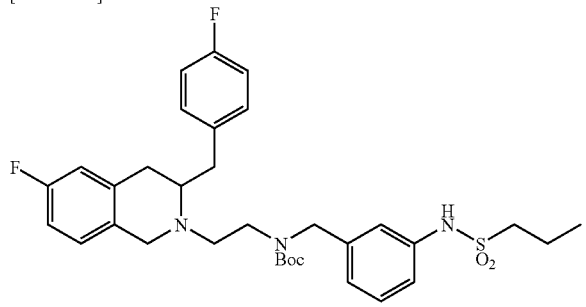

The reaction and treatment were carried out in the same manner as in Example 126 using propanesulfonyl chloride instead of methanesulfonyl chloride to obtain a title compound as a light yellow oily substance.

¹H-NMR (CDCl₃) δ: 1.00 (3H, t, J=7.6 Hz), 1.43-1.51 (9H, br), 1.83 (2H, tq, J=7.6, 7.6 Hz), 2.41 (1H, dd, J=10.0, 13.4 Hz), 2.46-2.53 (1H, m), 2.58-2.88 (4H, m), 3.02-3.06 (2H, m), 3.19-3.48 (3H, m), 3.70-3.83 (2H, m), 4.40-4.45 (2H, m), 6.74 (1H, dd, J=2.4, 9.5 Hz), 6.86 (1H, ddd, J=2.4, 8.3, 8.3 Hz), 6.97 (2H, dd, J=8.5, 8.5 Hz), 7.00-7.10 (6H, m), 7.27 (1H, dd, J=7.8, 7.8 Hz).

b) Production of N-(3-propanesulfonylaminobenzyl)-2-[6-fluoro-3-(4-fluorobenzyl)-3,4-dihydroisoquinolin-2(1H)-yl]ethanamine

[Chem. 353]

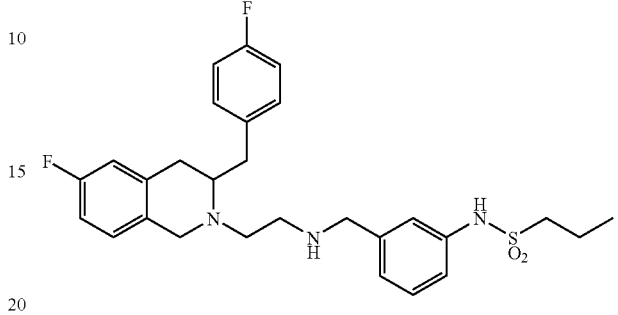

The reaction and treatment were carried out in the same manner as in Example 32-g) to obtain a title compound as a pale yellow oily substance.

1H-NMR (CDCl₃) δ: 1.00 (3H, t, J=7.8 Hz), 1.83 (2H, tq, J=5.4, 7.8 Hz), 2.44 (1H, dd, J=9.8, 13.4 Hz), 2.51 (1H, dd, J=3.9, 16.6 Hz), 2.73-2.89 (6H, m), 3.01-3.05 (2H, m), 3.15-3.21 (1H, m), 3.74 (1H, d, J=16.6 Hz), 3.77 (2H, s), 3.78 (1H, d, J=16.6 Hz), 6.76 (1H, dd, J=2.7, 9.5 Hz), 6.86 (1H, ddd, J=2.7, 8.6, 8.6 Hz), 6.95 (2H, ddd, J=2.2, 8.8, 8.8 Hz), 7.00 (1H, dd, J=5.6, 8.6 Hz), 7.05 (2H, ddd, J=2.2, 5.6, 8.8 Hz), 7.06-7.10 (2H, m), 7.11 (1H, s), 7.27 (1H, dd, J=7.6, 7.6 Hz).

Example 137

Production of N-(3-methanesulfonylamino-5-ethylbenzyl)-2-[6-fluoro-3-(4-fluorobenzyl)-3,4-dihydroisoquinolin-2(1H)-yl]ethanamine a) Production of N-[2-[6-fluoro-3-(4-fluorobenzyl)-3,4-dihydroisoquinolin-2(1H)-yl]ethyl]-3-vinyl-5-nitrobenzamide

[Chem. 354]

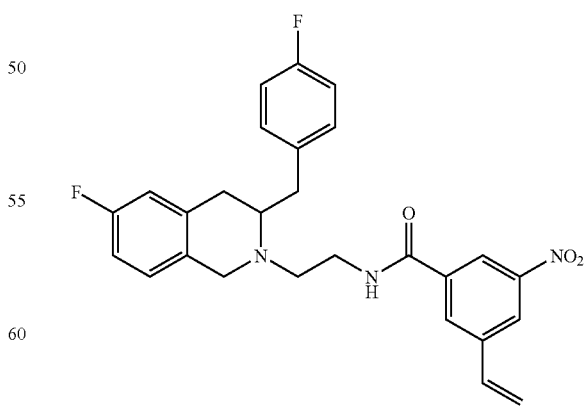

100 mg of 2-[6-fluoro-3-(4-fluorobenzyl)-3,4-dihydroisoquinolin-2(1H)-yl]ethanamine obtained in Example 120-b)

and 65 mg of 3-vinyl-5-nitrobenzoic acid were dissolved in 1 mL of chloroform, and 96 mg of WSC was added thereto, followed by stirring for 30 minutes. After completion of the reaction, water was added to the reaction liquid, followed by extraction with ethyl acetate, and the organic layer was then washed with an aqueous sodium bicarbonate solution and saturated brine, dried over anhydrous sodium sulfate and then concentrated under reduced pressure. The residue obtained was purified using silica gel chromatography (chloroform:methanol=10:1) to obtain 112 mg (yield 74%) of a title compound as a yellow solidified product.

$^1$H-NMR (CDCl$_3$) δ: 2.55 (1H, dd, J=8.5, 13.7 Hz), 2.58 (1H, dd, J=4.6, 16.8 Hz), 2.80-2.97 (4H, m), 3.27-3.34 (1H, m), 3.45-3.54 (1H, m), 3.66-3.73 (1H, m), 3.89 (2H, s), 5.50 (1H, d, J=11.0 Hz), 5.94 (1H, d, J=17.6 Hz), 6.77 (1H, dd, J=11.0, 17.6 Hz), 6.78-6.92 (5H, m), 7.02-7.10 (3H, m), 8.05-8.07 (1H, m), 8.26-8.28 (1H, m), 8.33-8.35 (1H, m).

b) Production of N-[2-[6-fluoro-3-(4-fluorobenzyl)-3,4-dihydroisoquinolin-2(1H)-yl]ethyl]-3-amino-5-ethylbenzamide

[Chem. 355]

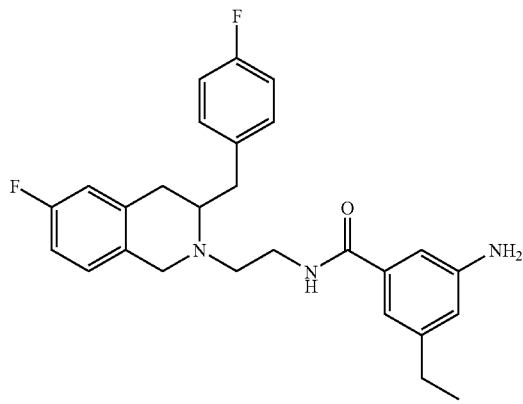

112 mg of N-[2-[6-fluoro-3-(4-fluorobenzyl)-3,4-dihydroisoquinolin-2(1H)-yl]ethyl]-3-vinyl-5-nitrobenzamide was dissolved in 2 mL of methanol, and 12 mg of 10% Pd—C was added thereto, followed by continuously stirring for 4 hours under a hydrogen atmosphere.

After completion of the reaction, the reaction liquid was filtered through Celite to obtain 103 mg (yield 98%) of a title compound as a yellow oily substance.

$^1$H-NMR (CDCl$_3$) δ: 1.19 (3H, t, J=7.6 Hz), 2.47-2.63 (3H, m), 2.57 (2H, q, J=7.6 Hz), 2.80-3.04 (5H, m), 3.28-3.37 (1H, m), 3.46-3.56 (1H, m), 3.64-3.76 (1H, m), 3.93 (2H, brs), 6.64 (1H, brs), 6.77-6.96 (7H, m), 7.02-7.10 (3H, m).

c) Production of N-[2-[6-fluoro-3-(4-fluorobenzyl)-3,4-dihydroisoquinolin-2(1H)-yl]ethyl]-3-ethyl-5-methanesulfonylaminobenzamide

[Chem. 356]

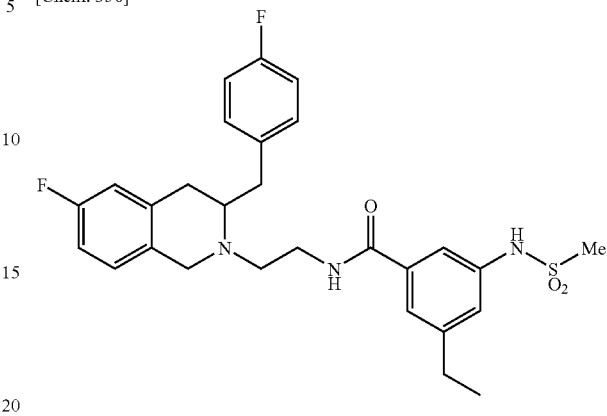

The reaction and treatment were carried out in the same manner as in Example 117-f) to obtain a title compound as a light yellow oily substance.

$^1$H-NMR (CDCl$_3$) δ: 1.20 (3H, t, J=7.6 Hz), 2.47-2.63 (3H, m), 2.60 (2H, q, J=7.6 Hz), 2.80-3.04 (5H, m), 2.99 (3H, s), 3.26-3.93 (3H, m), 6.65 (1H, brs), 6.75-7.12 (10H, m).

d) Production of N-(3-methanesulfonylamino-5-ethylbenzyl)-2-[6-fluoro-3-(4-fluorobenzyl)-3,4-dihydroisoquinolin-2(1H)-yl]ethanamine

[Chem. 357]

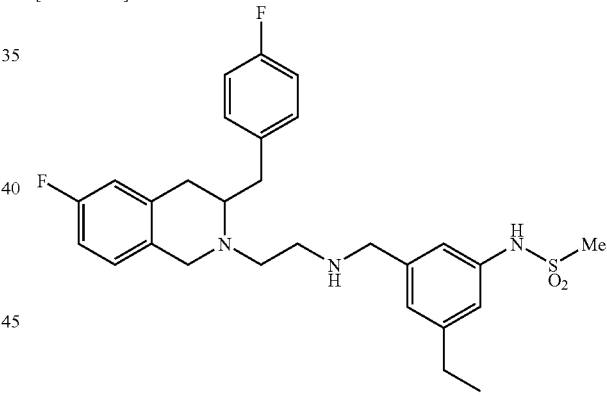

Under an argon atmosphere, 62 mg of N-[2-[6-fluoro-3-(4-fluorobenzyl)-3,4-dihydroisoquinolin-2(1H)-yl]ethyl]-3-ethyl-5-methanesulfonylaminobenzamide was dissolved in 1 mL of THF, and a borane/THF complex (1 ml) was added thereto, followed by stirring at 60° C. overnight. The reaction liquid was cooled to room temperature, and 1 N hydrochloric acid was added thereto, followed by further stirring for 6 hours. After completion of the reaction, an aqueous sodium bicarbonate solution was added to the reaction liquid, followed by extraction with chloroform. The organic layer was then washed with an aqueous sodium bicarbonate solution and saturated brine, dried over anhydrous sodium sulfate and then concentrated under reduced pressure. The residue obtained was purified using silica gel chromatography (chloroform:methanol=10:1) to obtain 42 mg (yield 70%) of a title compound as a light yellow oily substance.

$^1$H-NMR (CDCl$_3$) δ: 1.20 (3H, t, J=7.6 Hz), 2.44 (1H, dd, J=9.8, 13.2 Hz), 2.50 (1H, dd, J=3.7, 16.8 Hz), 2.50-2.54 (1H, m), 2.60 (2H, q, J=7.6 Hz), 2.74-2.90 (5H, m), 2.96 (3H, s), 3.12-3.22 (1H, m), 3.74 (2H, s), 3.76 (2H, s), 6.75 (1H, dd, J=2.6, 9.3 Hz), 6.86 (1H, ddd, J=2.6, 8.0, 8.0 Hz), 6.92-7.08 (8H, m).

Example 138

Production of 4-[[2-[6-fluoro-3-(4-fluorobenzyl)-3,4-dihydroisoquinolin-2(1H)-yl]ethylamino]methyl]-N-isopropylaniline a) Production of tert-butyl(4-aminobenzyl)-[2-[6-fluoro-3-(4-fluorobenzyl)-3,4-dihydroisoquinolin-2(1H)-yl]ethyl]carbamate

[Chem. 358]

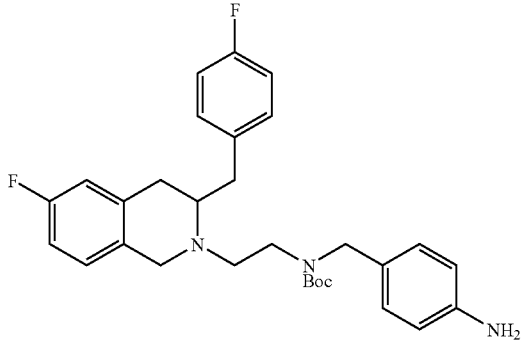

The reaction and treatment were carried out in the same manner as in Example 99-d, e) using 6-fluoro-3-(4-fluorobenzyl)-1,2,3,4-tetrahydroisoquinoline obtained in Example 53-a) instead of 3-benzyl-1,2,3,4-tetrahydroisoquinoline to obtain a title compound as a light yellow oily substance.
$^1$H-NMR (CDCl$_3$) δ: 1.46 (9H, s), 2.34-3.48 (8H, m), 3.62-3.82 (3H, m), 4.29-4.39 (2H, m), 6.62 (2H, d, J=8.3 Hz), 6.70-7.06 (9H, m).

b) Production of tert-butyl(4-isopropylamino)benzyl-[2-[6-fluoro-3-(4-fluorobenzyl)-3,4-dihydroisoquinolin-2(1H)-yl]ethyl]carbamate

[Chem. 359]

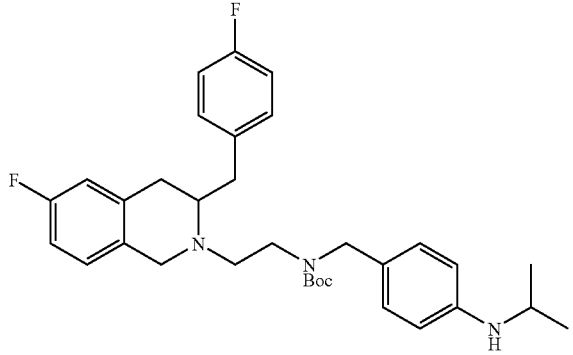

The reaction and treatment were carried out in the same manner as in Example 98-a) using acetone instead of acetaldehyde to obtain a title compound as a pale yellow oily substance.
$^1$H-NMR (CDCl$_3$) δ: 1.20 (6H, d, J=6.1 Hz), 1.47 (9H, s), 2.37 (1H, dd, J=10.2, 13.2 Hz), 2.43-2.48 (1H, m), 2.52-2.89 (4H, m), 3.01-3.44 (3H, m), 3.55-3.65 (1H, m), 3.67-3.82 (2H, m), 4.28-4.38 (2H, m), 6.52 (2H, d, J=8.6 Hz), 6.70-6.74 (1H, m), 6.85 (1H, dd, J=8.5, 8.5 Hz), 6.93-7.08 (7H, m).

c) Production of 4-[[2-[6-fluoro-3-(4-fluorobenzyl)-3,4-dihydroisoquinolin-2(1H)-yl]ethylamino]methyl]-N-isopropylaniline

[Chem. 360]

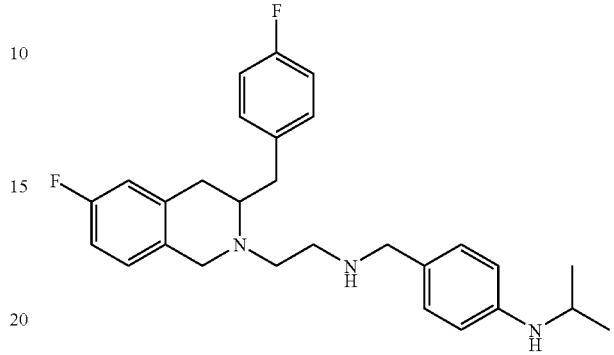

The reaction and treatment were carried out in the same manner as in Example 32-g) to obtain a title compound as a pale yellow oily substance.
$^1$H-NMR (CDCl$_3$) δ: 1.20 (6H, d, J=6.1 Hz), 2.40 (1H, dd, J=10.0, 13.4 Hz), 2.48 (1H, dd, J=3.7, 16.6 Hz), 2.73-2.88 (6H, m), 3.13 (1H, m), 3.56-3.68 (1H, m), 3.67 (2H, s), 3.73 (2H, s), 6.53 (2H, d, J=8.3 Hz), 6.74 (1H, dd, J=2.4, 9.5 Hz), 6.85 (1H, ddd, J=2.4, 8.5, 8.5 Hz), 6.94 (2H, dd, J=8.6, 8.6 Hz), 6.98 (1H, dd, J=5.6, 8.5 Hz), 7.03 (2H, dd, J=5.6, 8.6 Hz), 7.07 (2H, d, J=8.3 Hz).

Example 139

Production of 4-[[2-[6-fluoro-3-(4-fluorobenzyl)-3,4-dihydroisoquinolin-2(1H)-yl]ethylamino]methyl]-N-ethylaniline a) Production of tert-butyl(4-ethylamino)benzyl-[2-[6-fluoro-3-(4-fluorobenzyl)-3,4-dihydroisoquinolin-2(1H)-yl]ethyl]carbamate

[Chem. 361]

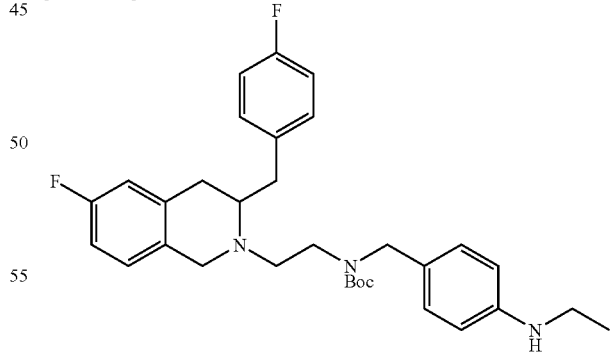

The reaction and treatment were carried out in the same manner as in Example 138-b) using tert-butyl(4-aminobenzyl)-[2-[6-fluoro-3-(4-fluorobenzyl)-3,4-dihydroisoquinolin-2(1H)-yl]ethyl]carbamate obtained in Example 138-a), and using acetaldehyde instead of acetone to obtain a title compound as a pale yellow oily substance.
$^1$H-NMR (CDCl$_3$) δ: 1.25 (3H, d, J=7.1 Hz), 1.47 (9H, s), 2.36 (1H, dd, J=10.5, 12.7 Hz), 2.43-2.48 (1H, m), 2.52-2.89

(4H, m), 3.13 (2H, q, J=7.1 Hz), 3.22-3.45 (3H, m), 3.68-3.84 (2H, m), 4.28-4.39 (2H, m), 6.54 (2H, d, J=8.3 Hz), 6.72 (1H, dd, J=2.2, 9.5 Hz), 6.84 (1H, ddd, J=2.2, 8.5, 8.5 Hz), 6.93-7.09 (7H, m).

b) Production of 4-[[2-[6-fluoro-3-(4-fluorobenzyl)-3,4-dihydroisoquinolin-2(1H)-yl]ethylamino]methyl]-N-ethylaniline

[Chem. 362]

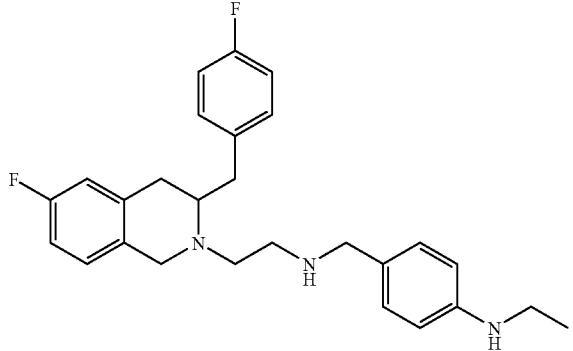

The reaction and treatment were carried out in the same manner as in Example 32-g) to obtain a title compound as a pale yellow oily substance.

$^1$H-NMR (CDCl$_3$) δ: 1.25 (3H, t, J=7.2 Hz), 2.41 (1H, dd, J=9.9, 13.3 Hz), 2.48 (1H, dd, J=3.6, 16.7 Hz), 2.76-2.87 (6H, m), 3.11-3.17 (3H, m), 3.70 (2H, s), 3.71 (2H, s), 6.55 (2H, d, J=8.3 Hz), 6.75 (1H, dd, J=2.2, 9.5 Hz), 6.85 (1H, ddd, J=2.2, 8.5, 8.5 Hz), 6.92-6.99 (3H, m), 7.03 (2H, dd, J=5.4, 8.6 Hz), 7.08 (2H, d, J=8.3 Hz).

Example 140

Production of N-[4-(4-morpholino)benzyl]-2-[6-fluoro-3-(4-fluorobenzyl)-3,4-dihydroisoquinolin-2(1H)-yl]ethanamine

[Chem. 363]

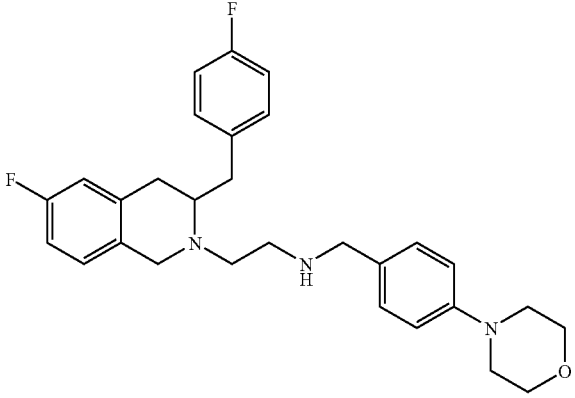

The reaction and treatment were carried out in the same manner as in Example 120-c) using 4-morpholinobenzaldehyde instead of 4-ethylbenzaldehyde to obtain a title compound as a light yellow oily substance.

$^1$H-NMR (CDCl$_3$) δ: 2.42 (1H, dd, J=9.8, 13.4 Hz), 2.49 (1H, dd, J=3.7, 16.6 Hz), 2.74-2.89 (6H, m), 3.12-3.19 (5H, m), 3.72 (2H, s), 3.74 (2H, s), 3.86 (2H, d, J=4.9 Hz), 3.87 (2H, d, J=4.6 Hz), 6.75 (1H, dd, J=2.2, 9.2 Hz), 6.82-6.88 (3H, m), 6.94 (2H, dd, J=8.6, 8.6 Hz), 6.97 (1H, dd, J=5.6, 8.0 Hz), 7.03 (2H, dd, J=5.6, 8.6 Hz), 7.19 (2H, d, J=8.5 Hz).

Example 141

Production of 4-[[2-[6-fluoro-3-(4-fluorobenzyl)-3,4-dihydroisoquinolin-2(1H)-yl]ethylamino]methyl]-N-(4-tetrahydropyranyl)aniline

[Chem. 364]

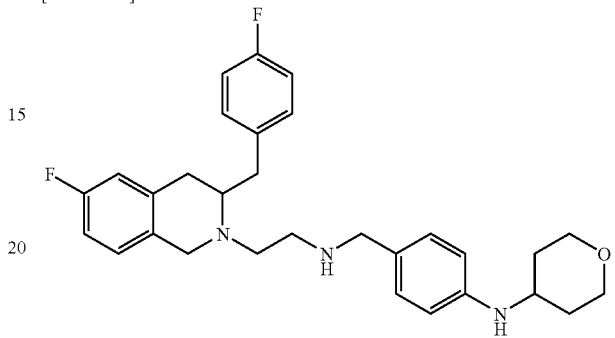

The reaction and treatment were carried out in the same manner as in Example 138-b, c) using tetrahydro-4H-pyran-4-one instead of acetone to obtain a title compound as a pale yellow oily substance.

$^1$H-NMR (CDCl$_3$) δ: 1.41-1.51 (2H, m), 2.02 (2H, d, J=12.9 Hz), 2.43 (1H, dd, J=9.8, 13.5 Hz), 2.48 (1H, dd, J=3.9, 17.0 Hz), 2.76-2.92 (6H, m), 3.16-3.20 (1H, m), 3.47-3.54 (3H, m), 3.71 (2H, s), 3.73 (2H, s), 3.98-4.02 (2H, m), 6.55 (2H, d, J=8.3 Hz), 6.75 (1H, dd, J=2.4, 9.5 Hz), 6.84-6.87 (1H, m), 6.92-6.98 (3H, m), 7.04 (2H, dd, J=5.5, 8.5 Hz), 7.10 (2H, d, J=8.5 Hz).

Example 142

Production of 4-[[2-[6-fluoro-3-(4-fluorobenzyl)-3,4-dihydroisoquinolin-2(1H)-yl]ethylamino]methyl]-N-ethoxycarbonylmethylaniline

[Chem. 365]

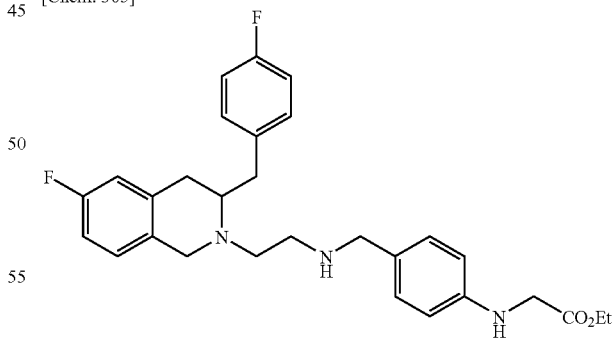

The reaction and treatment were carried out in the same manner as in Example 148 using ethyl bromoacetate instead of bromocyclopropane to obtain a title compound as a pale yellow oily substance.

$^1$H-NMR (CDCl$_3$) δ: 1.30 (3H, t, J=7.1 Hz), 2.42 (1H, dd, J=9.8, 13.4 Hz), 2.49 (1H, dd, J=4.2, 16.8 Hz), 2.75-2.77 (3H, m), 2.83-2.87 (3H, m), 3.13-3.19 (1H, m), 3.70 (4H, s), 3.89 (2H, d, J=5.4 Hz), 4.25 (2H, q, J=7.1 Hz), 6.56 (2H, d, J=8.5

Hz), 6.75 (1H, dd, J=2.4, 9.5 Hz), 6.85 (1H, ddd, J=2.4, 8.6, 8.6 Hz), 6.92-6.97 (3H, m), 6.99-7.06 (2H, m), 7.10 (2H, d, J=8.5 Hz).

Example 143

Production of 4-[[2-[6-fluoro-3-(4-fluorobenzyl)-3, 4-dihydroisoquinolin-2(1H)-yl]ethylamino]methyl]-N-(3-ethoxycarbonylpropyl)aniline

[Chem. 366]

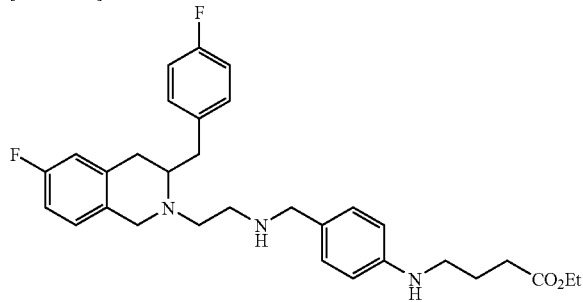

The reaction and treatment were carried out in the same manner as in Example 148 using ethyl 4-bromobutylate instead of bromocyclopropane to obtain a title compound as a pale yellow oily substance.

$^1$H-NMR (CDCl$_3$) δ: 1.25 (3H, t, J=7.2 Hz), 1.94 (2H, q, J=7.1 Hz), 2.39-2.44 (3H, m), 2.48 (1H, dd, J=3.8, 16.5 Hz), 2.73-2.78 (3H, m), 2.81-2.88 (3H, m), 3.13-3.19 (3H, m), 3.69 (2H, s), 3.72 (2H, s), 4.14 (2H, q, J=7.2 Hz), 6.55 (2H, d, J=8.5 Hz), 6.75 (1H, dd, J=2.4, 9.5 Hz), 6.85 (1H, ddd, J=2.4, 8.6, 8.6 Hz), 6.92-6.99 (3H, m), 7.02-7.08 (4H, m).

Example 144

Production of 4-[[2-[6-fluoro-3-(4-fluorobenzyl)-3, 4-dihydroisoquinolin-2(1H)-yl]ethylamino]methyl]-N-carboxymethylaniline

[Chem. 367]

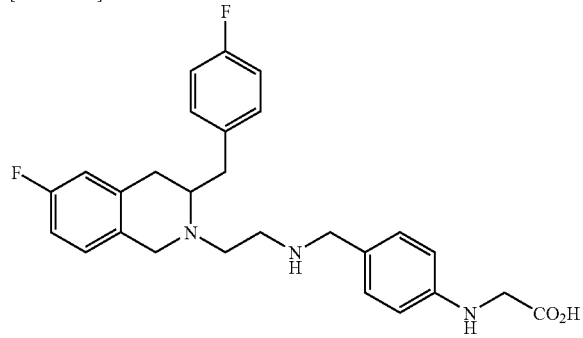

4-[[2-[6-fluoro-3-(4-fluorobenzyl)-3,4-dihydroisoquinolin-2(1H)-yl]ethylamino]methyl]-N-ethoxycarbonylaniline (10 mg, 0.02 mmol) obtained in Example 142 and lithium hydroxide.monohydrate (41 mg, 1.0 mmol) were dissolved in 1 mL of THF and 0.5 mL of water, followed by stirring at room temperature overnight. After completion of the reaction, 2N hydrochloric acid was added to the reaction liquid, followed by extraction with chloroform. The organic layer was then washed with saturated brine, dried over anhydrous sodium sulfate and then concentrated under reduced pressure to obtain 3 mg (yield 44.2%) of a title compound as a pale yellow oily substance.

$^1$H-NMR (CDCl$_3$) δ: 2.38 (1H, dd, J=9.8, 13.0 Hz), 2.47 (1H, dd, J=3.8, 16.8 Hz), 2.68-2.87 (6H, m), 3.04-3.08 (1H, m), 3.83-3.86 (4H, s), 4.33-4.38 (2H, m), 6.60 (2H, d, J=8.8 Hz), 6.72 (1H, dd, J=2.4, 8.6 Hz), 6.85 (1H, ddd, J=2.4, 8.5, 8.5 Hz), 6.94-6.98 (3H, m), 7.04-7.13 (4H, m).

Example 145

Production of 4-[[2-[6-fluoro-3-(4-fluorobenzyl)-3, 4-dihydroisoquinolin-2(1H)-yl]ethylamino]methyl]-N-(3-carboxypropyl)aniline

[Chem. 368]

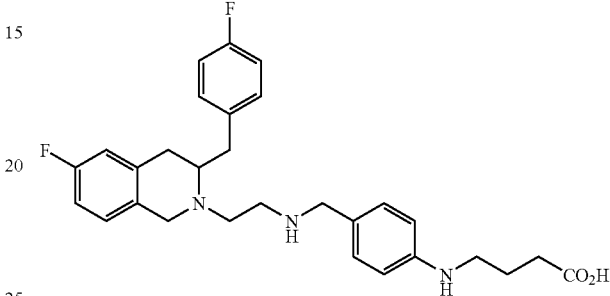

The reaction and treatment were carried out in the same manner as in Example 144 using 4-[[2-[6-fluoro-3-(4-fluorobenzyl)-3,4-dihydroisoquinolin-2(1H)-yl]ethylamino]methyl]-N-(3-ethoxycarbonylpropyl)aniline instead of 4-[[2-[6-fluoro-3-(4-fluorobenzyl)-3,4-dihydroisoquinolin-2(1H)-yl] ethylamino]methyl]-N-ethoxycarbonylaniline to obtain a title compound as a pale yellow oily substance.

$^1$H-NMR (CDCl$_3$) δ: 1.78 (2H, q, J=3.4 Hz), 2.34-2.40 (2H, m), 2.71-2.79 (4H, m), 2.88 (2H, br), 2.96 (2H, br), 3.08-3.16 (1H, m), 3.58 (2H, s), 3.62 (2H, brs), 3.71 (2H, brs), 6.36 (2H, d, J=8.2 Hz), 6.62-6.65 (1H, m), 6.74-6.79 (1H, m), 6.83-6.87 (3H, m), 6.86 (2H, d, J=8.6 Hz), 6.96-7.00 (4H, m).

Example 146

Production of 4-[[2-[6-fluoro-3-(4-fluorobenzyl)-3, 4-dihydroisoquinolin-2(1H)-yl]ethylamino]methyl]-N-(2-hydroxyethyl)aniline

[Chem. 369]

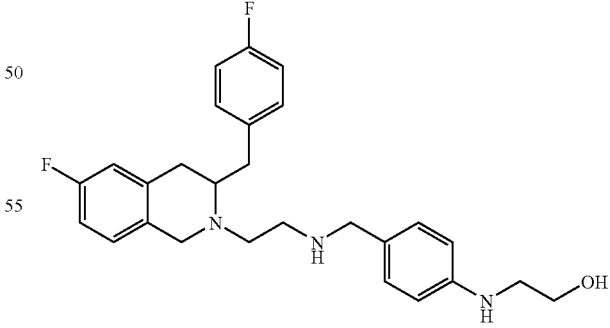

The reaction and treatment were carried out in the same manner as in Example 148 using ethyl 2-bromoethanol instead of bromocyclopropane to obtain a title compound as a pale yellow oily substance.

$^1$H-NMR (CDCl$_3$) δ: 2.43-2.53 (2H, m), 2.76-2.96 (6H, m), 3.19-3.21 (1H, m), 3.29 (2H, t, J=5.1 Hz), 3.64 (2H, s), 3.77 (2H, s), 3.84 (2H, t, J=5.1 Hz), 6.59 (2H, d, J=8.5 Hz), 6.76 (1H, d, J=9.2 Hz), 6.83-6.88 (1H, m), 6.93-7.00 (3H, m), 7.05-7.09 (4H, m).

Example 147

Production of 4-[[2-[6-fluoro-3-(4-fluorobenzyl)-3,4-dihydroisoquinolin-2(1H)-yl]ethylamino]methyl]-N-bis(2-hydroxyethyl)aniline

[Chem. 370]

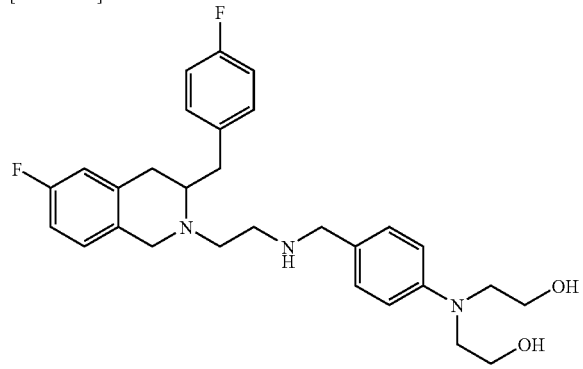

The title compound is simultaneously obtained in the Example 146 as a pale yellow oily substance.

¹H-NMR (CDCl₃) δ: 2.43-2.55 (2H, m), 2.78-2.95 (6H, m), 3.20-3.28 (1H, m), 3.57 (4H, t, J=5.2 Hz), 3.64 (2H, s), 3.78 (2H, s), 3.85 (4H, t, J=5.2 Hz), 6.65 (2H, d, J=8.6 Hz), 6.77 (1H, d, J=9.2 Hz), 6.83-6.89 (1H, m), 6.91-6.99 (3H, m), 7.05-7.14 (4H, m).

Example 148

Production of 4-[[2-[6-fluoro-3-(4-fluorobenzyl)-3,4-dihydroisoquinolin-2(1H)-yl]ethylamino]methyl]-N-cyclopropylaniline

[Chem. 371]

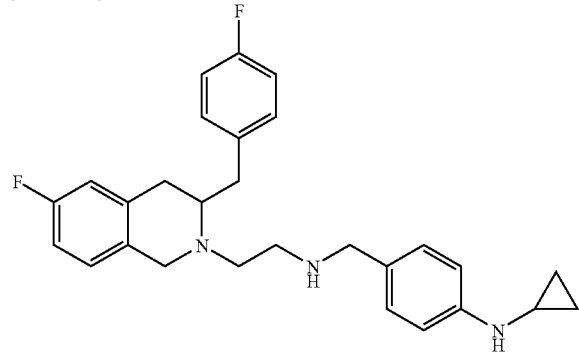

44 mg of tert-butyl(4-aminobenzyl)-[2-[6-fluoro-3-(4-fluorobenzyl)-3,4-dihydroisoquinolin-2(1H)-yl]ethyl]carbamate obtained in Example 138-a), 53 mg of bromocyclopropane, and 70 mg of potassium carbonate were dissolved in 1 mL of acetonitrile, followed by stirring at 60° C. for 3 days. After completion of the reaction, water was added to the reaction liquid, followed by extraction with ethyl acetate. The organic layer was then washed with saturated brine, dried over anhydrous sodium sulfate and then concentrated under reduced pressure, and purified using PLC (chloroform:methanol=10:1) to obtain 3 mg of a yellow oily substance. 3 mg of the residue obtained was dissolved in 1 mL of a 4N-hydrochloric acid/ethyl acetate solution, followed by stirring at room temperature for 1 hour. After completion of the reaction, water was added to the reaction liquid, followed by extraction with ethyl acetate. The organic layer was then washed with saturated brine, dried over anhydrous sodium sulfate, concentrated under reduced pressure, and then purified using PLC (chloroform:methanol=5:1) to obtain 2 mg (yield 82%) of a title compound as a pale yellow oily substance.

¹H-NMR (CDCl₃) δ: 1.21-1.25 (4H, m), 2.49 (1H, dd, J=9.6, 13.5 Hz), 2.52 (1H, dd, J=3.9, 16.8 Hz), 2.79-2.95 (6H, m), 3.17-3.24 (1H, m), 3.62-3.79 (5H, m), 6.36 (2H, d, J=8.6 Hz), 6.77 (1H, dd, J=2.4, 9.2 Hz), 6.83-6.89 (1H, m), 6.94 (1H, d, J=8.5 Hz), 6.97 (2H, d, J=8.6 Hz), 7.04-7.09 (4H, m).

Example 149

Production of 4-[[2-[6-fluoro-3-(4-fluorobenzyl)-3,4-dihydroisoquinolin-2(1H)-yl]ethylamino]methyl]-N-[2-(4-morpholino)ethyl]aniline a) Production of tert-butyl 4-[2-(4-morpholino)ethyl]aminobenzyl[2-[6-fluoro-3-(4-fluorobenzyl)-3,4-dihydroisoquinolin-2(1H)-yl]ethyl]carbamate

[Chem. 372]

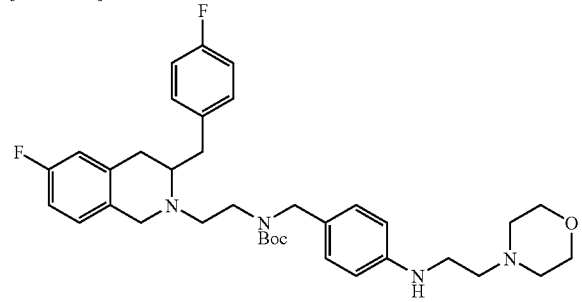

The reaction and treatment were carried out in the same manner as in Examples 138-b and c) using 4-morpholinacetoaldehyde instead of acetone to obtain a title compound as a pale yellow oily substance.

¹H-NMR (CDCl₃) δ: 1.47 (9H, s), 2.37 (1H, dd, J=10.0, 13.2 Hz), 2.43-2.52 (6H, m), 2.63 (2H, t, J=5.6 Hz), 2.66-2.74 (2H, br), 2.77-2.90 (2H, br), 3.15 (2H, t, J=5.6 Hz), 3.24-3.34 (2H, br), 3.66-3.83 (2H, m), 3.72 (4H, t, J=4.4 Hz), 4.34 (2H, d, J=13.9 Hz), 6.58 (2H, d, J=8.3 Hz), 6.73 (1H, dd, J=2.4, 10.5 Hz), 6.84 (1H, ddd, J=2.4, 8.5, 8.5 Hz), 6.96 (2H, dd, J=8.5, 8.5 Hz), 7.00-7.09 (5H, m).

b) Production of 4-[[2-[6-fluoro-3-(4-fluorobenzyl)-3,4-dihydroisoquinolin-2(1H)-yl]ethylamino]methyl]-N-[2-(4-morpholino)ethyl]aniline

[Chem. 373]

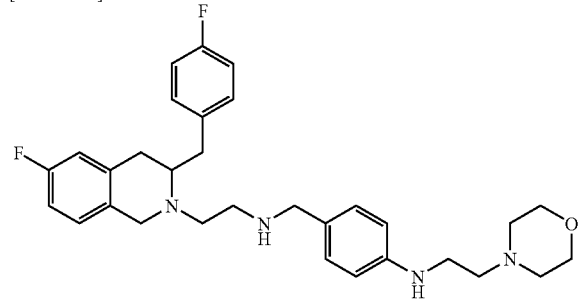

The reaction and treatment were carried out in the same manner as in Example 32-g) to obtain a title compound as a light yellow oily substance.

2.80-2.89 (2H, m), 3.12-3.18 (4H, br), 3.68 (2H, s), 3.70-3.78 (6H, m), 6.59 (2H, d, J=8.5 Hz), 6.75 (1H, dd, J=2.4, 9.5 Hz), 6.85 (1H, ddd, J=2.4, 8.5, 8.5 Hz), 6.94 (2H, dd, J=8.5, 8.5 Hz), 6.91-7.06 (1H, m), 7.02 (2H, dd, J=5.6, 8.5 Hz), 7.95 (2H, d, J=8.5 Hz).

Example 150

Production of 4-[[2-[6-fluoro-3-(4-fluorobenzyl)-3,4-dihydroisoquinolin-2(1H)-yl]ethylamino]methyl]-N-(2-methoxyethyl)aniline a) Production of tert-butyl 4-methoxyacetamidebenzyl[2-[6-fluoro-3-(4-fluorobenzyl)-3,4-dihydroisoquinolin-2(1H)-yl]ethyl]carbamate

[Chem. 374]

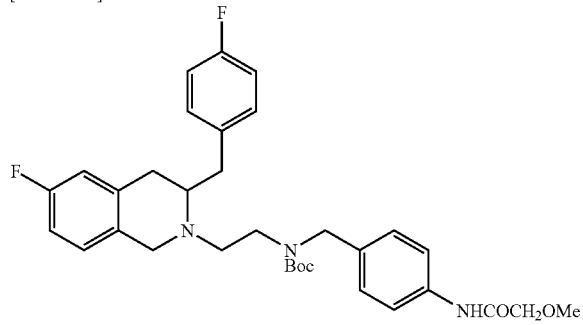

To a solution of 40 mg of tert-butyl(4-aminobenzyl)-[2-[6-fluoro-3-(4-fluorobenzyl)-3,4-dihydroisoquinolin-2(1H)-yl]ethyl]carbamate obtained in Example 138-a) and 1 μL of pyridine in dichloromethane (1 mL) was added 11 mg of methoxyacetyl chloride under ice-cooling, followed by stirring at room temperature for 30 minutes. After completion of the reaction, chloroform was added to the reaction liquid, followed by washing with an aqueous sodium bicarbonate solution and then with brine, and then drying anhydrous sodium sulfate. The solvent was removed by evaporation to obtain 34 mg (yield 74%) of a title compound as a pale yellow oily substance.

$^1$H-NMR (CDCl$_3$) δ: 1.45 (9H, brs), 2.30-3.30 (9H, m), 3.51 (3H, s), 3.60-3.80 (2H, m), 4.02 (2H, s), 4.40-4.44 (2H, m), 6.73 (1H, m), 6.85 (1H, m), 6.95-7.30 (5H, m), 6.97 (2H, d, J=8.5 Hz), 7.52 (2H, d, J=8.5 Hz).

b) Production of N-(4-methoxyacetamidebenzyl)-2-[6-fluoro-3-(4-fluorobenzyl)-3,4-dihydroisoquinolin-2(1H)-yl]ethanamine

[Chem. 375]

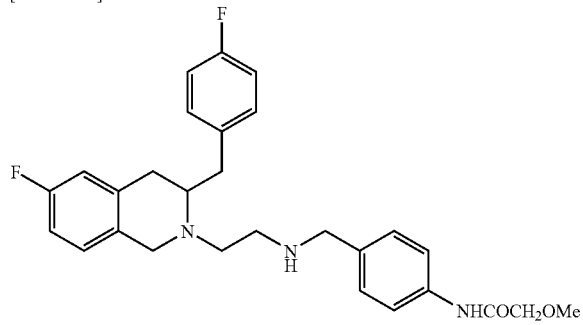

The reaction and treatment were carried out in the same manner as in Example 32-g) to obtain a title compound as a light yellow oily substance.

$^1$H-NMR (CDCl$_3$) δ: 2.40-2.51 (2H, m), 2.70-2.90 (6H, m), 3.15 (1H, m), 3.51 (3H, s), 3.74 (2H, s), 3.76 (2H, s), 4.02 (2H, s), 6.76 (1H, m), 6.80-7.10 (6H, m), 7.24-7.26 (2H, m), 7.52 (2H, d, J=8.3 Hz).

c) Production of 4-[[2-[6-fluoro-3-(4-fluorobenzyl)-3,4-dihydroisoquinolin-2(1H)-yl]ethylamino]methyl]-N-(2-methoxyethyl)aniline

[Chem. 376]

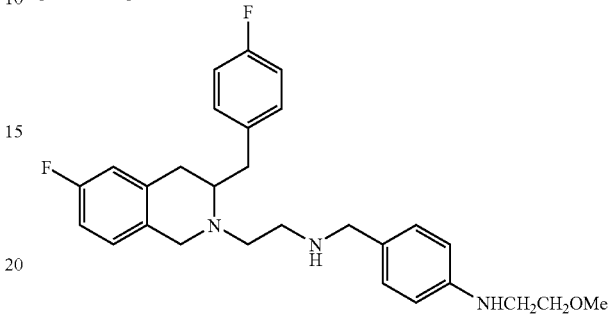

28 mg of N-(4-methoxyacetamidebenzyl)-2-[6-fluoro-3-(4-fluorobenzyl)-3,4-dihydroisoquinolin-2(1H)-yl]ethanamine was dissolved in 0.5 mL of THF, and 1 mL of a borane/tetrahydrofuran (1 M) solution was added thereto, followed by stirring at room temperature for 1 hour. After completion of the reaction, the reaction liquid was concentrated under reduced pressure, and 1 mL of 2N hydrochloric acid was added thereto, followed by stirring at 100° C. for 10 minutes. To the residue was added a saturated aqueous sodium bicarbonate solution, followed by extraction with chloroform, washing with brine and then drying over anhydrous sodium sulfate. The solvent was removed by evaporation to obtain 18 mg (yield 67%) of a title compound as a yellow oily substance.

$^1$H-NMR (CDCl$_3$) δ: 2.3-2.51 (2H, m), 2.70-2.90 (6H, m), 3.15 (1H, m), 3.28 (2H, t, J=5.1 Hz), 3.39 (3H, s), 3.61 (2H, t, J=5.1 Hz), 3.69 (2H, s), 3.72 (2H, s), 6.58 (2H, d, J=8.5 Hz), 6.75 (1H, m), 6.85 (1H, m), 6.93-7.05 (5H, m), 7.08 (2H, d, J=8.5 Hz).

Example 151

Production of 3-[[2-[6-fluoro-3-(4-fluorobenzyl)-3,4-dihydroisoquinolin-2(1H)-yl]ethylamino]methyl]-N,N-diethylbenzamide

[Chem. 377]

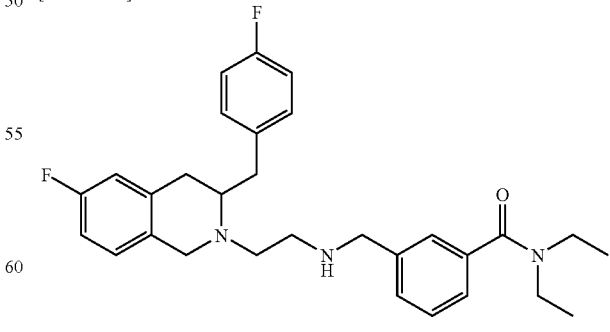

The reaction and treatment were carried out in the same manner as in Example 120-c) using N,N-diethyl 3-formylbenzamide instead of 4-ethylbenzaldehyde to obtain a title compound as a light yellow oily substance.

¹H-NMR (CDCl₃) δ: 1.04-1.14 (3H, br), 1.19-1.29 (3H, br), 2.48 (1H, dd, J=9.6, 13.4 Hz), 2.54 (1H, dd, J=3.6, 16.8 Hz), 2.74-2.94 (6H, m), 3.15-3.29 (3H, br), 3.50 (2H, br) 3.80 (2H, s), 3.82 (2H, s), 6.94 (1H, d, J=8.8 Hz), 6.96 (1H, d, J=8.8 Hz), 7.04-7.07 (3H, m), 7.14-7.16 (2H, m), 7.30-7.33 (4H, m).

Example 152

Production of N-(3-isopropylcarbonylbenzyl)-2-[6-fluoro-3-(4-fluorobenzyl)-3,4-dihydroisoquinolin-2(1H)-yl]ethanamine a) Production of 2-(3-bromophenyl)-2-isopropyl-1,3-dioxolane

[Chem. 378]

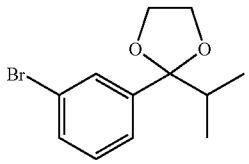

150 mg of 1-bromo-3-isobutyrylbenzene, 204 mg of ethylene glycol, 350 mg of trimethylorthoformate, and 10 mg of p-toluene sulfonic acid were dissolved in 4 mL of toluene, followed by stirring at 60° C. for 2 days. After completion of the reaction, water was added to the reaction liquid, followed by extraction with ethyl acetate. The organic layer was then washed with saturated brine, dried over anhydrous sodium sulfate and then concentrated under reduced pressure to obtain 146 mg (yield 80%) of a title compound as a pale yellow oily substance.

¹H-NMR (CDCl₃) δ: 1.17 (6H, d, J=6.8 Hz), 3.44 (1H, sept, J=6.8 Hz), 3.81-3.84 (2H, m), 4.25-4.28 (2H, m), 7.31 (1H, ddd, J=0.8, 7.9, 7.9 Hz), 7.62-7.65 (1H, m), 7.81-7.84 (1H, m), 8.02-8.08 (1H, m).

b) Production of 2-(3-formylphenyl)-2-isopropyl-1,3-dioxolane

[Chem. 379]

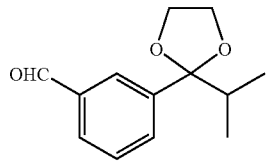

110 mg of 2-(3-bromophenyl)-2-isopropyl-1,3-dioxolane was dissolved in 1 mL of THF, and cooled to –78° C., and 0.36 mL of n-butyl lithium (1.5 M hexane solution) was added thereto, followed by stirring for 15 minutes. Thereafter, DMF (0.53 mL) was added thereto, followed by stirring at room temperature for 1 hour. A saturated aqueous ammonium chloride solution was added to the reaction liquid, followed by extraction with diethyl ether. The organic layer was then washed with saturated brine, dried over anhydrous sodium sulfate and then concentrated under reduced pressure to obtain 57 mg (yield 61%) of a title compound as a pale yellow oily substance.

c) Production of N-(3-isopropylcarbonylbenzyl)-2-[6-fluoro-3-(4-fluorobenzyl)-3,4-dihydroisoquinolin-2(1H)-yl]ethanamine

[Chem. 380]

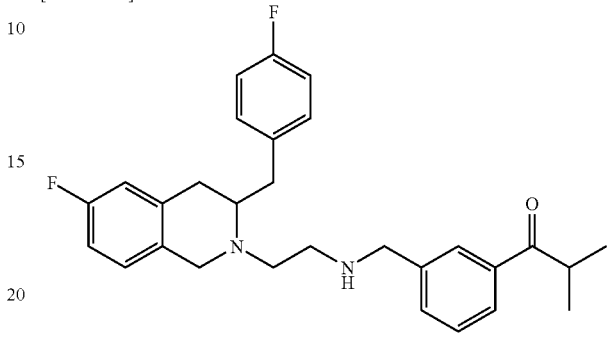

The reaction and treatment were carried out in the same manner as in Example 120-c) using the obtained 2-(3-formylphenyl)-2-isopropyl-1,3-dioxolane instead of 4-ethylbenzaldehyde. Further, a 4N hydrochloric acid-ethyl acetate solution was added thereto, followed by stirring for 2 hours, followed by concentration under reduced pressure. A saturated aqueous sodium bicarbonate solution was added to the residue, followed by extraction with chloroform, washing with brine and then drying over anhydrous sodium sulfate. The solvent was removed by evaporation to obtain a title compound as a yellow oily substance.

¹H-NMR (CDCl₃) δ: 0.69 (3H, d, J=6.8 Hz), 0.93 (3H, d, J=6.8 Hz), 2.00 (1H, sept, J=6.8 Hz), 2.44 (1H, dd, J=9.5, 13.4 Hz), 2.50 (1H, dd, J=3.5, 16.7 Hz), 2.77-2.90 (6H, m), 3.17-3.22 (1H, m), 3.72 (2H, s), 3.84 (2H, s), 6.72-6.78 (1H, m), 6.83-6.89 (1H, m), 6.93-6.97 (3H, m), 7.04-7.07 (2H, m), 7.14 (1H, d, J=7.2 Hz), 7.23-7.27 (2H, m), 7.32 (1H, s).

Example 153

Production of N-(3-cyanobenzyl)-2-[6-fluoro-3-(4-fluorobenzyl)-3,4-dihydroisoquinolin-2(1H)-yl]ethanamine

[Chem. 381]

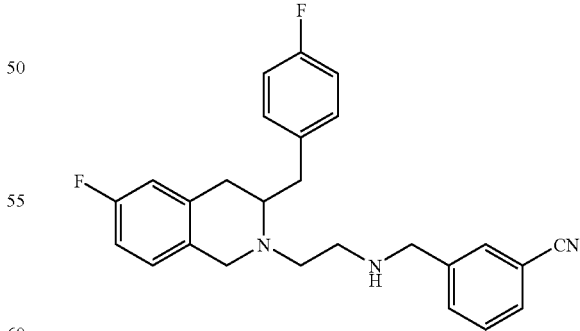

The reaction and treatment were carried out in the same manner as in Example 120-c) using 3-cyanobenzaldehyde instead of 4-ethylbenzaldehyde to obtain a title compound as a light yellow oily substance.

¹H-NMR (CDCl₃) δ: 2.46 (1H, dd, J=9.5, 13.6 Hz), 2.52 (1H, dd, J=3.9, 16.8 Hz), 2.69-2.89 (6H, m), 3.19 (1H, dt,

J=5.1, 9.5 Hz), 3.77 (2H, s), 3.78 (1H, d, J=13.9 Hz), 3.82 (1H, d, J=13.9 Hz), 6.76 (1H, dd, J=2.7, 9.5 Hz), 6.87 (1H, ddd, J=2.7, 8.4, 8.4 Hz), 6.95 (2H, ddd, J=2.2, 8.8, 8.8 Hz), 7.00 (1H, dd, J=5.6, 8.4 Hz), 7.06 (2H, dd, J=5.6, 8.8 Hz), 7.40 (1H, dd, J=7.7 Hz), 7.51-7.55 (2H, m), 7.61 (1H, s).

Example 154

Production of N-[4-(1-hydroxy-1-methylethyl)benzyl]-2-[6-fluoro-3-(4-fluorobenzyl)-3,4-dihydroisoquinolin-2(1H)-yl]ethanamine

[Chem. 382]

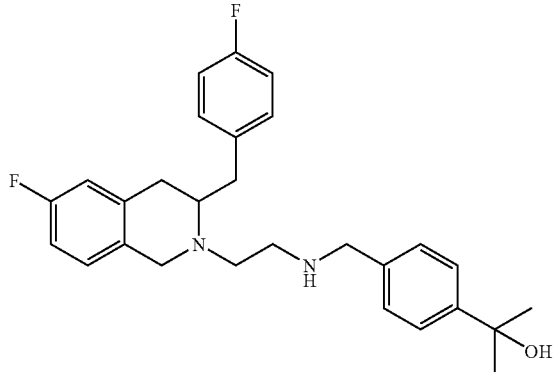

The reaction and treatment were carried out in the same manner as in Example 120-c) using 4-(1-hydroxy-1-methylethyl)benzaldehyde instead of 4-ethylbenzaldehyde to obtain a title compound as a light yellow oily substance.

¹H-NMR (CDCl₃) δ: 1.57 (6H, s), 2.43 (1H, dd, J=9.5, 13.6 Hz), 2.49 (1H, dd, J=3.6, 16.8 Hz), 2.73-2.79 (3H, m), 2.83-2.90 (3H, m), 3.16-3.20 (1H, m), 3.73 (2H, s), 3.79 (2H, s), 6.75 (1H, dd, J=2.4, 9.5 Hz), 6.84 (1H, ddd, J=2.4, 8.3, 8.3 Hz), 6.91-6.99 (3H, m), 7.04 (1H, d, J=5.4 Hz), 7.06 (1H, d, J=5.4 Hz), 7.25 (2H, d, J=8.6 Hz), 7.43 (2H, d, J=8.6 Hz).

Example 155

Production of 3-[[2-[6-fluoro-3-(4-fluorobenzyl)-3,4-dihydroisoquinolin-2(1H)-yl]ethylamino]methyl]benzamide

[Chem. 383]

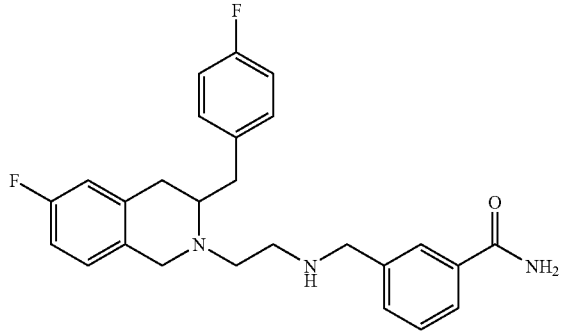

The reaction and treatment were carried out in the same manner as in Example 120-c) using N,N-diethyl 3-formylbenzamide instead of 4-ethylbenzaldehyde to obtain a title compound as a light yellow oily substance.

¹H-NMR (CDCl₃) δ: 2.47 (1H, dd, J=9.5, 13.4 Hz), 2.53 (1H, dd, J=3.9, 16.2 Hz), 2.77-2.83 (3H, m), 2.86-2.90 (3H, m), 3.19-3.23 (1H, m), 3.81 (2H, s), 3.84 (2H, s), 5.76 (1H, brs), 6.21 (1H, brs), 6.75 (1H, d, J=7.6 Hz), 6.85 (1H, dd, J=8.5, 8.5 Hz), 6.86 (1H, dd, J=8.5, 8.5 Hz), 7.03-7.07 (4H, m), 7.39 (1H, dd, J=7.6, 7.6 Hz), 7.45 (1H, d, J=7.6 Hz), 7.70 (1H, d, J=7.6 Hz), 7.81 (1H, s).

Example 156

Production of N-(4-tert-butylbenzyl)-2-[3-(4-chlorobenzyl)-6-fluoro-3,4-dihydroisoquinolin-2(1H)-yl]ethanamine

[Chem. 384]

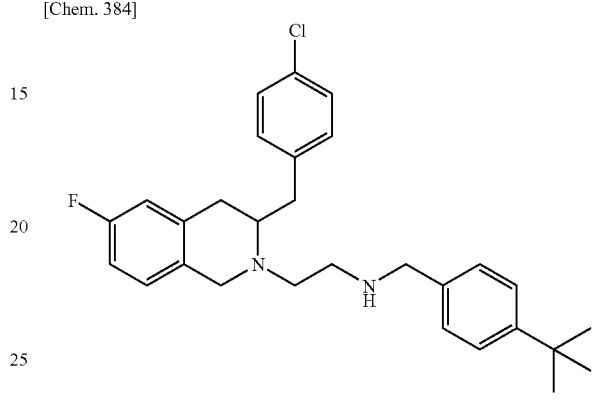

The reaction and treatment were carried out in the same manner as in Example 78 using 3-(4-chlorobenzyl)-6-fluoro-1,2,3,4-tetrahydroisoquinoline obtained in Example 55-a) instead of 3-benzyl-1,2,3,4-tetrahydroisoquinoline to obtain a title compound as a light yellow oily substance.

¹H-NMR (CDCl₃) δ: 1.31 (9H, s), 2.42 (1H, dd, J=9.8, 13.2 Hz), 2.48 (1H, dd, J=3.9, 16.6 Hz), 2.72-2.90 (6H, m), 3.12-3.20 (1H, m), 3.72 (2H, s), 3.77 (2H, s), 6.75 (1H, dd, J=2.4, 9.3 Hz), 6.85 (1H, ddd, J=2.4, 8.3, 8.3 Hz), 6.97 (1H, dd, J=5.9, 8.3 Hz), 7.02 (2H, d, J=8.3 Hz), 7.19-7.24 (4H, m), 7.33 (2H, d, J=8.3 Hz).

Example 157

Production of N-(3-methanesulfonylaminobenzyl)-2-[3-(4-chlorobenzyl)-6-fluoro-3,4-dihydroisoquinolin-2(1H)-yl]ethanamine a) Production of tert-butyl 3-methanesulfonylaminobenzyl[2-[3-(4-chlorobenzyl)-6-fluoro-3,4-dihydroisoquinolin-2(1H)-yl]ethyl]carbamate

[Chem. 385]

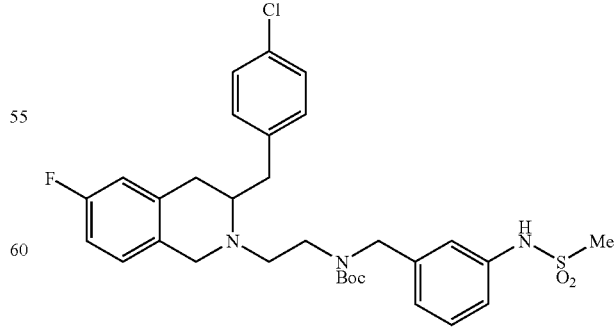

The reaction and treatment were carried out in the same manner as in Example 117-d, e, f) using 3-(4-chlorobenzyl)-6-fluoro-1,2,3,4-tetrahydroisoquinoline obtained in Example 55-a) instead of 3-(4-fluorobenzyl)-1,2,3,4-tetrahydroisoquinoline to obtain a title compound as a light yellow oily substance.

$^1$H-NMR (CDCl$_3$) δ: 1.43-1.51 (9H, br), 2.41 (1H, dd, J=9.8, 13.2 Hz), 2.48 (1H, dd, J=3.9, 16.6 Hz), 2.62-2.85 (4H, m), 2.98 (3H, s), 3.10-3.43 (3H, m), 3.71-3.82 (2H, m), 4.39-4.45 (2H, m), 6.74 (1H, dd, J=2.2, 9.3 Hz), 6.86 (1H, ddd, J=2.2, 8.8, 8.8 Hz), 6.97-7.11 (6H, m), 7.25 (2H, d, J=8.5 Hz), 7.29 (1H, dd, J=7.8, 7.8 Hz).

b) Production of N-(3-methanesulfonylaminobenzyl)-2-[3-(4-chlorobenzyl)-6-fluoro-3,4-dihydroisoquinolin-2(1H)-yl]ethanamine

[Chem. 386]

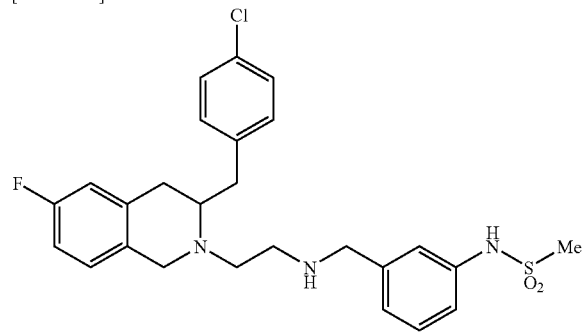

The reaction and treatment were carried out in the same manner as in Example 32-g) to obtain a title compound as a pale yellow oily substance.

$^1$H-NMR (CDCl$_3$) δ: 2.44 (1H, dd, J=10.0, 13.4 Hz), 2.50 (1H, dd, J=3.9, 16.8 Hz), 2.73-2.89 (6H, m), 2.96 (3H, s), 3.15-3.22 (1H, m), 3.74 (1H, d, J=17.1 Hz), 3.77 (2H, s), 3.78 (1H, d, J=17.1 Hz), 6.75 (1H, dd, J=2.4, 9.3 Hz), 6.86 (1H, ddd, J=2.4, 8.5, 8.5 Hz), 6.99 (1H, dd, J=5.6, 8.5 Hz), 7.03 (2H, d, J=8.3 Hz), 7.09-7.12 (2H, m), 7.13 (1H, s), 7.23 (2H, d, J=8.3 Hz), 7.30 (1H, dd, J=7.6, 8.8 Hz).

Example 158

Production of N-(3-methane sulfonamide benzyl)-2-[6-fluoro-3-(2-fluorobenzyl)-3,4-dihydroisoquinolin-2(1H)-yl]ethanamine a) Production of tert-butyl 3-nitrobenzyl[2-[6-fluoro-3-(2-fluorobenzyl)-3,4-dihydroisoquinolin-2(1H)-yl]ethyl]carbamate

[Chem. 387]

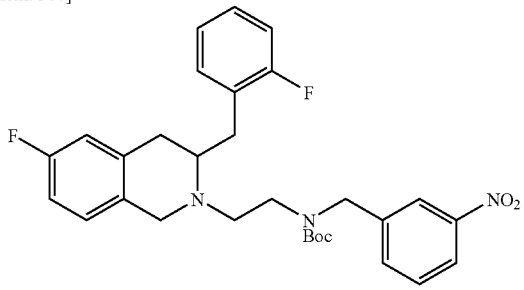

The reaction and treatment were carried out in the same manner as in Example 117-d) using 6-fluoro-3-(2-fluorobenzyl)-1,2,3,4-tetrahydroisoquinoline obtained in Example 54-a) instead of 3-(4-fluorobenzyl)-1,2,3,4-tetrahydroisoquinoline to obtain a title compound as a light yellow oily substance.

$^1$H-NMR (CDCl$_3$) δ: 1.40-1.51 (9H, br), 2.44 (1H, dd, J=9.8, 13.0 Hz), 2.52 (1H, dd, J=4.0, 16.4 Hz), 2.62-2.96 (4H, m), 3.18-3.60 (3H, m), 3.78 (2H, s), 4.46-4.62 (2H, m), 6.72-6.79 (1H, m), 6.82-6.89 (1H, m), 6.95-7.11 (4H, m), 7.16-7.23 (1H, m), 7.46 (1H, dd, J=8.2, 8.2 Hz), 7.50-7.60 (1H, m), 8.07-8.11 (2H, m).

b) Production of tert-butyl 3-aminobenzyl[2-[6-fluoro-3-(2-fluorobenzyl)-3,4-dihydroisoquinolin-2(1H)-yl]ethyl]carbamate

[Chem. 388]

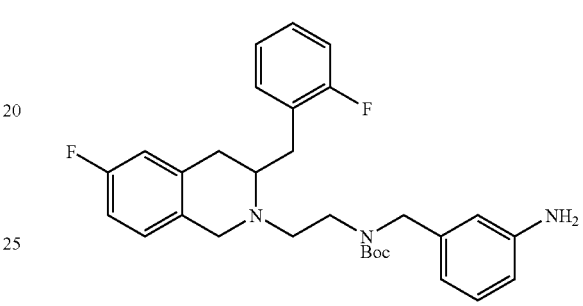

The reaction and treatment were carried out in the same manner as in Example 117-e) to obtain a title compound as a light yellow oily substance.

$^1$H-NMR (CDCl$_3$) δ: 1.41-1.52 (9H, br), 2.38-2.98 (5H, m), 2.52 (1H, dd, J=4.4, 16.0 Hz), 3.20-3.38 (2H, m), 3.44-3.86 (5H, m), 4.32-4.44 (2H, m), 6.50-6.66 (3H, m), 6.72-6.80 (1H, m), 6.82-6.88 (1H, m), 6.96-7.30 (6H, m).

c) Production of tert-butyl 3-methanesulfonylaminobenzyl[2-[6-fluoro-3-(2-fluorobenzyl)-3,4-dihydroisoquinolin-2(1H)-yl]ethyl]carbamate

[Chem. 389]

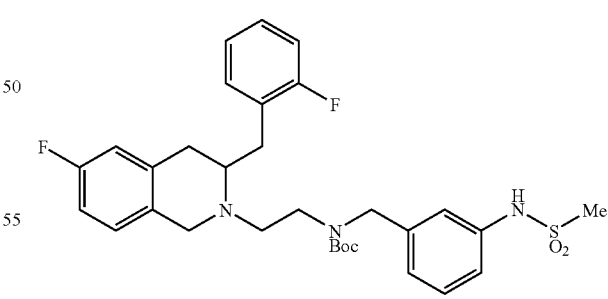

The reaction and treatment were carried out in the same manner as in Example 117-f) to obtain a title compound as a light yellow oily substance.

$^1$H-NMR (CDCl$_3$) δ: 1.48 (9H, brs), 2.38-3.36 (6H, m), 3.60-3.92 (3H, m), 4.20-4.34 (2H, m), 4.46 (2H, brs), 6.80-6.84 (1H, m), 6.96-7.30 (10H, m).

d) Production of N-(3-methanesulfonylaminobenzyl)-2-[6-fluoro-3-(2-fluorobenzyl)-3,4-dihydroisoquinolin-2(1H)-yl]ethanamine

[Chem. 390]

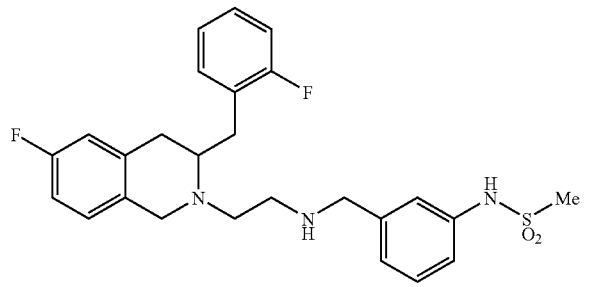

The reaction and treatment were carried out in the same manner as in Example 117-g) to obtain a title compound as a light yellow oily substance.

$^1$H-NMR (CDCl$_3$) δ: 2.48 (1H, dd, J=9.8, 12.9 Hz), 2.54 (1H, dd, J=2.9, 16.6 Hz), 2.74-2.99 (6H, m), 2.95 (3H, s), 3.18-3.32 (1H, m), 3.78 (2H, s), 3.79 (2H, s), 6.77 (1H, dd, J=2.4, 9.2 Hz), 6.89 (1H, ddd, J=2.4, 8.5, 8.5 Hz), 6.97-7.22 (7H, m), 7.25-7.30 (2H, m).

Example 159

Production of N-(3-methanesulfonylaminobenzyl)-2-[6-chloro-3-(4-fluorobenzyl)-3,4-dihydroisoquinolin-2(1H)-yl]ethanamine a) Production of tert-butyl 3-nitrobenzyl[2-[6-chloro-3-(4-fluorobenzyl)-3,4-dihydroisoquinolin-2(1H)-yl]ethyl]carbamate

[Chem. 391]

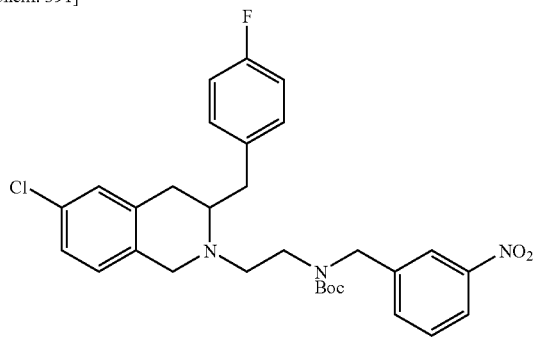

The reaction and treatment were carried out in the same manner as in Example 117-d) using 6-chloro-3-(4-fluorobenzyl)-1,2,3,4-tetrahydroisoquinoline obtained in Example 57-a) instead of 3-(4-fluorobenzyl)-1,2,3,4-tetrahydroisoquinoline to obtain a title compound as a light yellow oily substance.

$^1$H-NMR (CDCl$_3$) δ: 1.38-1.52 (9H, br), 2.41 (1H, dd, J=9.9, 13.3 Hz), 2.48 (1H, dd, J=4.0, 16.6 Hz), 2.58-2.94 (3H, m), 2.74 (1H, dd, J=5.1, 16.6 Hz), 3.05-3.26 (1H, m), 3.30-3.50 (2H, m), 3.77 (2H, s), 4.44-4.58 (2H, m), 6.92-7.00 (3H, m), 7.00-7.09 (3H, m), 7.10-7.16 (1H, m), 7.47 (1H, dd, J=8.0, 8.0 Hz), 7.50-7.60 (1H, m), 8.06-8.12 (2H, m).

b) Production of N-(3-methanesulfonylaminobenzyl)-2-[6-chloro-3-(4-fluorobenzyl)-3,4-dihydroisoquinolin-2(1H)-yl]ethanamine

[Chem. 392]

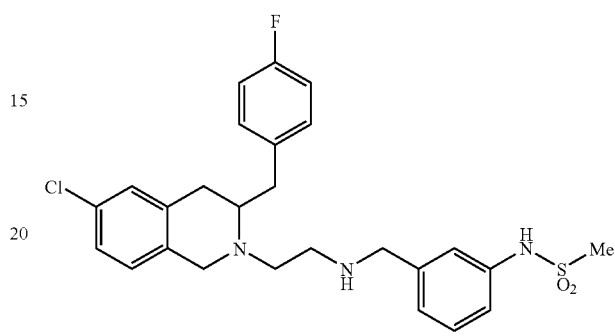

The reaction and treatment were carried out in the same manner as in Examples 117-e, f and g) to obtain a title compound as a light yellow oily substance.

$^1$H-NMR (CDCl$_3$) δ: 2.43 (1H, dd, J=9.5, 13.4 Hz), 2.50 (1H, dd, J=3.8, 16.7 Hz), 2.72-2.92 (6H, m), 2.96 (3H, s), 3.15-3.24 (1H, m), 3.76 (2H, s), 3.78 (2H, s), 6.91-6.99 (3H, m), 7.02-7.16 (6H, m), 7.25-7.33 (2H, m).

Example 160

Production of N-(3-methane sulfonamide benzyl)-2-[7-fluoro-3-(4-fluorobenzyl)-3,4-dihydroisoquinolin-2(1H)-yl]ethanamine a) Production of tert-butyl 3-nitrobenzyl[2-[7-fluoro-3-(4-fluorobenzyl)-3,4-dihydroisoquinolin-2(1H)-yl]ethyl]carbamate

[Chem. 393]

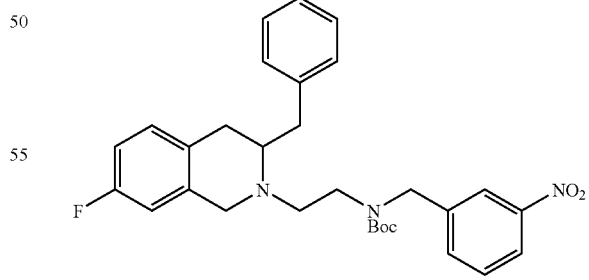

The reaction and treatment were carried out in the same manner as in Example 117-d) using 7-fluoro-3-(4-fluorobenzyl)-1,2,3,4-tetrahydroisoquinoline obtained in Example 56-c) instead of 3-(4-fluorobenzyl)-1,2,3,4-tetrahydroisoquinoline to obtain a title compound as a light yellow oily substance.

¹H-NMR (CDCl₃) δ: 1.42-1.56 (9H, m), 2.40-2.50 (2H, m), 2.60-2.90 (4H, m), 3.20-3.80 (3H, m), 3.79 (2H, s), 4.48-4.55 (2H, m), 6.72-7.08 (7H, m), 7.45-7.58 (2H, m), 8.10 (2H, d, J=7.3 Hz).

b) Production of tert-butyl 3-aminobenzyl[2-[7-fluoro-3-(4-fluorobenzyl)-3,4-dihydroisoquinolin-2(1H)-yl]ethyl]carbamate

[Chem. 394]

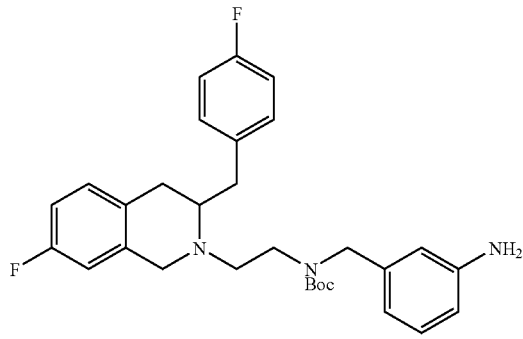

The reaction and treatment were carried out in the same manner as in Example 117-e) to obtain a title compound as a light yellow oily substance.

¹H-NMR (CDCl₃) δ: 1.26 (9H, brs), 2.30-2.50 (2H, m), 2.50-2.80 (3H, m), 3.00-3.50 (3H, m), 3.62 (1H, m), 3.65-3.85 (2H, m), 4.32-4.42 (2H, m), 6.50-7.10 (11H, m).

c) Production of tert-butyl 3-methanesulfonylaminobenzyl[2-[7-fluoro-3-(4-fluorobenzyl)-3,4-dihydroisoquinolin-2(1H)-yl]ethyl]carbamate

[Chem. 395]

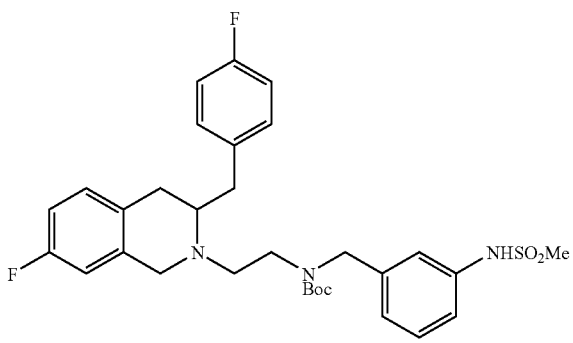

The reaction and treatment were carried out in the same manner as in Example 117-f) to obtain a title compound as a light yellow oily substance.

¹H-NMR (CDCl₃) δ: 1.44-1.48 (9H, m), 2.39-2.50 (2H, m), 2.54-2.80 (3H, m), 3.02 (3H, s), 3.16-3.50 (3H, m), 3.80 (1H, m), 3.92 (2H, s), 3.80-4.00 (2H, m), 6.72-7.10 (7H, m), 7.26-7.31 (4H, m).

d) Production of N-(3-methanesulfonylaminobenzyl)-2-[7-fluoro-3-(4-fluorobenzyl)-3,4-dihydroisoquinolin-2(1H)-yl]ethanamine

[Chem. 396]

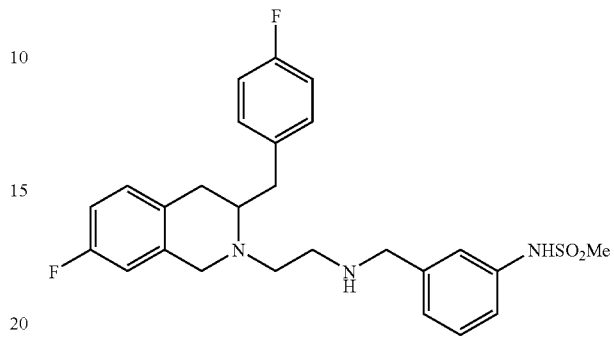

The reaction and treatment were carried out in the same manner as in Example 117-g) to obtain a title compound as a light yellow oily substance.

¹H-NMR (CDCl₃) δ: 2.43-2.52 (2H, m), 2.72-2.90 (6H, m), 2.97 (3H, s), 3.19 (1H, m), 3.77 (2H, s), 3.78 (2H, s), 6.75 (1H, m), 6.84-7.16 (9H, m), 7.32 (1H, m).

Example 161

Production of 4-[[2-[7-fluoro-3-(4-fluorobenzyl)-3,4-dihydroisoquinolin-2(1H)-yl]ethylamino]methyl]-N-isopropylaniline a) Production of tert-butyl 4-nitrobenzyl[2-[7-fluoro-3-(4-fluorobenzyl)-3,4-dihydroisoquinolin-2(1H)-yl]ethyl]carbamate

[Chem. 397]

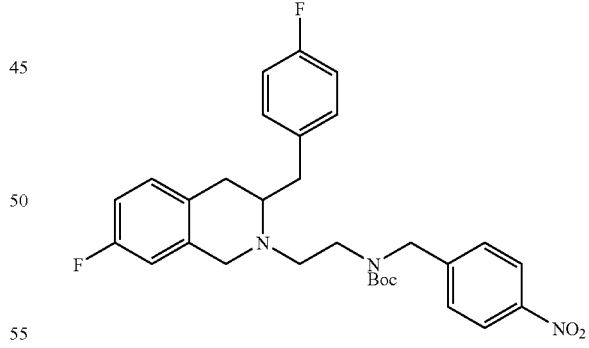

The reaction and treatment were carried out in the same manner as in Example 117-d) using 7-fluoro-3-(4-fluorobenzyl)-1,2,3,4-tetrahydroisoquinoline obtained in Example 56-c) and [N-(tert-butoxycarbonyl)-N-4-nitrobenzylamino]acetaldehyde to obtain a title compound as a light yellow oily substance.

¹H-NMR (CDCl₃) δ: 1.39-1.49 (9H, m), 2.40-2.50 (2H, m), 2.50-3.50 (7H, m), 3.80 (2H, brs), 4.45-4.55 (2H, m), 6.70-7.10 (5H, m), 6.98 (2H, d, J=8.5 Hz), 7.30-7.40 (2H, m), 8.16 (2H, d, J=8.5 Hz).

b) Production of tert-butyl 4-aminobenzyl[2-[7-fluoro-3-(4-fluorobenzyl)-3,4-dihydroisoquinolin-2(1H)-yl]ethyl]carbamate

[Chem. 398]

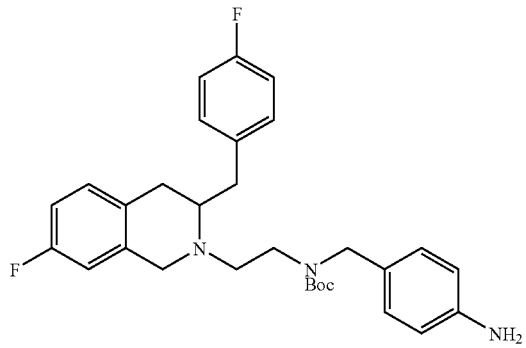

The reaction and treatment were carried out in the same manner as in Example 117-e) to obtain a title compound as a light yellow oily substance.

$^1$H-NMR (CDCl$_3$) δ: 1.47 (9H, s), 2.30-2.50 (2H, m), 2.50-3.70 (9H, m), 4.26-4.38 (2H, m), 6.63 (2H, d, J=8.3 Hz), 6.65-7.10 (9H, m).

c) Production of tert-butyl 4-isopropylaminobenzyl[2-[7-fluoro-3-(4-fluorobenzyl)-3,4-dihydroisoquinolin-2(1H)-yl]ethyl]carbamate

[Chem. 399]

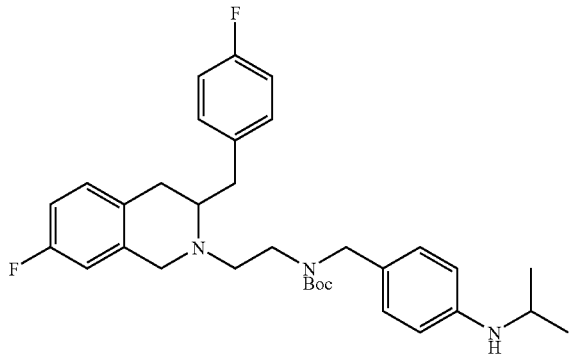

The reaction and treatment were carried out in the same manner as in Example 138-b) to obtain a title compound as a pale yellow oily substance.

$^1$H-NMR (CDCl$_3$) δ: 1.20 (6H, d, J=6.1 Hz), 1.47 (9H, s), 2.30-2.50 (2H, m), 2.50-3.60 (10H, m), 4.28-4.36 (2H, m), 6.52 (2H, d, J=8.3 Hz), 6.70-7.08 (9H, m).

d) Production of 4-[[2-[7-fluoro-3-(4-fluorobenzyl)-3,4-dihydroisoquinolin-2(1H)-yl]ethylamino]methyl]-N-isopropylaniline

[Chem. 400]

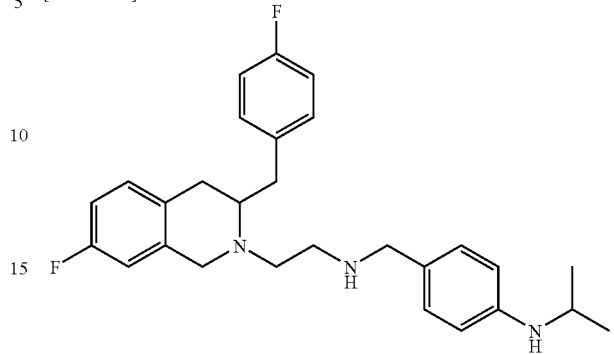

The reaction and treatment were carried out in the same manner as in Example 32-g) to obtain a title compound as a light yellow oily substance.

$^1$H-NMR (CDCl$_3$) δ: 1.21 (6H, d, J=6.3 Hz), 2.40-2.50 (2H, m), 2.70-2.88 (6H, m), 3.16 (1H, m), 3.62 (1H, m), 3.69 (2H, s), 3.72 (2H, s), 6.53 (2H, d, J=8.3 Hz), 6.73 (1H, m), 6.85 (1H, m), 6.95 (2H, d, J=8.3 Hz), 6.92-7.10 (5H, m).

Example 162

Production of N-[3-(methanesulfonylamino)benzyl]-N-[2-[6-fluoro-3-(4-fluorobenzyl)-3,4-dihydroisoquinolin-2(1H)-yl]ethyl]glycine a) Production of N-(3-nitrobenzyl)-N-[2-[6-fluoro-3-(4-fluorobenzyl)-3,4-dihydroisoquinolin-2(1H)-yl]ethyl]glycine ethyl ester

[Chem. 401]

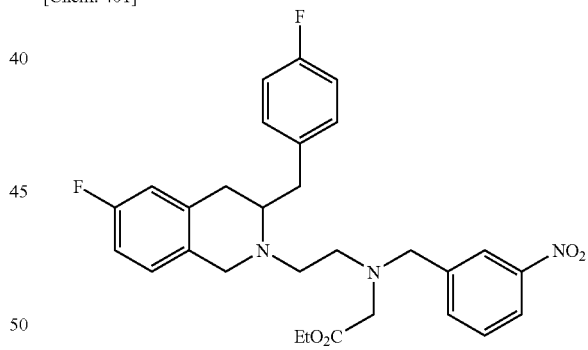

106 mg of N-(3-nitrobenzyl)-2-[6-fluoro-3-(4-fluorobenzyl)-3,4-dihydroisoquinolin-2(1H)-yl]ethanamine obtained in Example 123-b), 40 mg of ethyl bromoacetate, and 33 mg of potassium carbonate were dissolved in 1 mL of acetonitrile, followed by stirring at room temperature for 3 hours. After completion of the reaction, water was added to the reaction liquid, followed by extraction with chloroform. The organic layer was washed with saturated brine, dried over anhydrous sodium sulfate and then concentrated under reduced pressure. The residue obtained was purified using PLC (chloroform:methanol=20:1) to obtain 97 mg (yield 76%) of a title compound as a pale yellow oily substance.

$^1$H-NMR (CDCl$_3$) δ: 1.24 (3H, t, J=7.2 Hz), 2.39 (1H, dd, J=10.0, 13.2 Hz), 2.49 (1H, dd, J=3.8, 16.5 Hz), 2.70-2.92 (6H, m), 3.10-3.19 (1H, m), 3.44 (2H, s), 3.72 (1H, d, J=16.0

Hz), 3.81 (1H, d, J=16.0 Hz), 3.95 (2H, s), 4.12 (2H, q, J=7.2 Hz), 6.74 (1H, dd, J=2.5, 9.5 Hz), 6.85 (1H, ddd, J=2.5, 8.6, 8.6 Hz), 6.91-7.02 (5H, m), 7.46 (1H, dd, J=7.9, 7.9 Hz), 7.68-7.71 (1H, m), 8.08-8.12 (1H, m), 8.26 (1H, brs).

b) Production of N-(3-aminobenzyl)-N-[2-[6-fluoro-3-(4-fluorobenzyl)-3,4-dihydroisoquinolin-2(1H)-yl]ethyl]glycine ethyl ester

[Chem. 402]

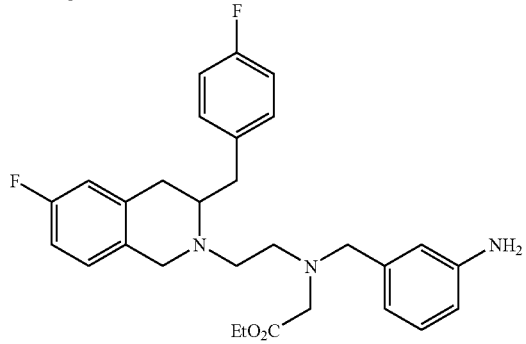

The reaction and treatment were carried out in the same manner as in Example 117-e) to obtain a title compound as a light yellow oily substance.

$^1$H-NMR (CDCl$_3$) δ: 1.25 (3H, t, J=7.1 Hz), 2.50-2.60 (1H, m), 2.71 (1H, dd, J=6.8, 17.8 Hz), 2.92-3.04 (2H, m), 3.12-3.22 (1H, m), 3.28-3.38 (2H, m), 3.44-3.56 (4H, m), 3.56 (2H, s), 3.75 (2H, s), 4.13 (2H, q, J=7.1 Hz), 4.35 (1H, d, J=16.3 Hz), 4.56 (1H, d, J=16.3 Hz), 6.66 (1H, d, J=7.8 Hz), 6.79 (1H, dd, J=2.4, 8.8 Hz), 6.90-7.09 (7H, m), 7.18-7.25 (2H, m).

c) Production of N-[3-(methanesulfonylamino)benzyl]-N-[2-[6-fluoro-3-(4-fluorobenzyl)-3,4-dihydroisoquinolin-2(1H)-yl]ethyl]glycine

[Chem. 403]

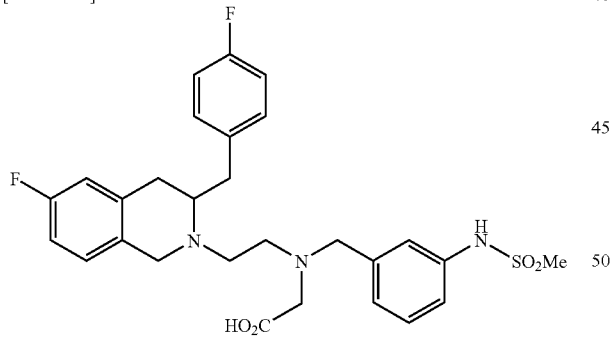

The reaction was carried out in the same manner as in Example 117-f), and dissolution was conducted in 1 mL of a 2N aqueous sodium hydroxide solution and 1 mL of THF, followed by stirring at room temperature for 1 hour. After completion of the reaction, 2N hydrochloric acid was added to the reaction liquid, followed by extraction with chloroform. The organic layer was then washed with saturated brine, dried over anhydrous sodium sulfate and then concentrated under reduced pressure to obtain a title compound as a pale yellow oily substance.

$^1$H-NMR (CDCl$_3$) δ: 2.34-2.42 (1H, m), 2.46-2.56 (1H, m), 2.74-3.00 (6H, m), 2.97 (3H, s), 3.24-3.32 (1H, m), 3.36-3.42 (2H, m), 3.80-3.88 (2H, m), 4.06-4.18 (2H, m), 6.68-6.76 (1H, m), 6.82-6.90 (1H, m), 6.94-7.06 (5H, m), 7.10-7.22 (2H, m), 7.24-7.36 (3H, m).

Example 163

Production of N-[3-(methanesulfonylamino)benzyl]-N-(3-carboxypropyl)-2-[6-fluoro-3-(4-fluorobenzyl)-3,4-dihydroisoquinolin-2(1H)-yl]ethanamine a) Production of N-(3-nitrobenzyl)-N-(3-ethoxy carboxypropyl)-2-[6-fluoro-3-(4-fluorobenzyl)-3,4-dihydroisoquinolin-2(1H)-yl]ethanamine

[Chem. 404]

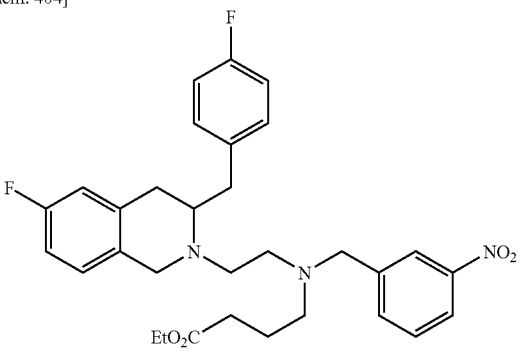

The reaction and treatment were carried out in the same manner as in Example 162-a) using ethyl bromobutylate instead of ethyl bromoacetate to obtain a title compound as a light yellow oily substance.

$^1$H-NMR (CDCl$_3$) δ: 1.22 (3H, t, J=7.2 Hz), 1.81 (2H, tt, J=7.1, 7.1 Hz), 2.33 (2H, t, J=7.1 Hz), 2.39 (1H, dd, J=10.0, 13.2 Hz), 2.48-2.53 (1H, m), 2.53 (2H, t, J=7.1 Hz), 2.62-2.90 (6H, m), 3.08-3.18 (1H, m), 3.71 (2H, s), 3.72 (1H, d, J=15.6 Hz), 3.78 (1H, d, J=15.6 Hz), 4.09 (2H, q, J=7.2 Hz), 6.74 (1H, dd, J=2.4, 9.5 Hz), 6.85 (1H, ddd, J=2.4, 8.5, 8.5 Hz), 6.98-7.05 (5H, m), 7.44 (1H, dd, J=7.9, 7.9 Hz), 7.66 (1H, d, J=7.9 Hz), 8.08 (1H, dd, J=2.1, 7.9 Hz), 8.20-8.23 (1H, br).

b) Production of N-(3-aminobenzyl)-N-(3-ethoxy carboxypropyl)-2-[6-fluoro-3-(4-fluorobenzyl)-3,4-dihydroisoquinolin-2(1H)-yl]ethanamine

[Chem. 405]

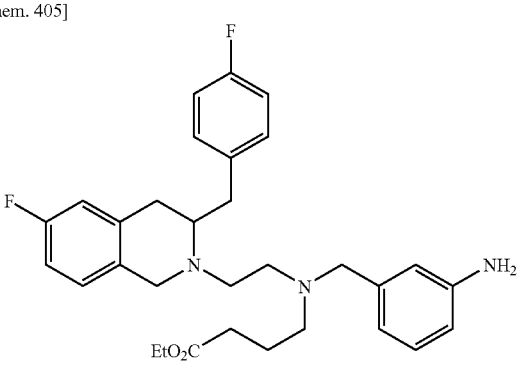

The reaction and treatment were carried out in the same manner as in Example 117-e) to obtain a title compound as a light yellow oily substance.

$^1$H-NMR (CDCl$_3$) δ: 1.21 (3H, t, J=7.1 Hz), 1.90-2.00 (2H, m), 2.24-2.30 (2H, m), 2.34 (2H, t, J=8.2 Hz), 2.44 (1H, dd, J=9.8, 13.4 Hz), 2.51 (1H, dd, J=3.9, 16.6 Hz), 2.68-2.92 (5H, m), 3.20-3.29 (1H, m), 3.34-3.52 (5H, m), 3.82 (1H, d, J=15.9

Hz), 3.88 (1H, d, J=15.9 Hz), 4.03 (2H, q, J=7.1 Hz), 6.48-6.54 (2H, m), 6.58 (1H, d, J=7.3 Hz), 6.75 (1H, dd, J=2.4, 9.3 Hz), 6.86 (1H, ddd, J=2.5, 8.5, 8.5 Hz), 6.94-7.12 (6H, m).

c) Production of N-[3-(methanesulfonylamino)benzyl]-N-(3-carboxypropyl)-2-[6-fluoro-3-(4-fluorobenzyl)-3,4-dihydroisoquinolin-2(1H)-yl]ethanamine

[Chem. 406]

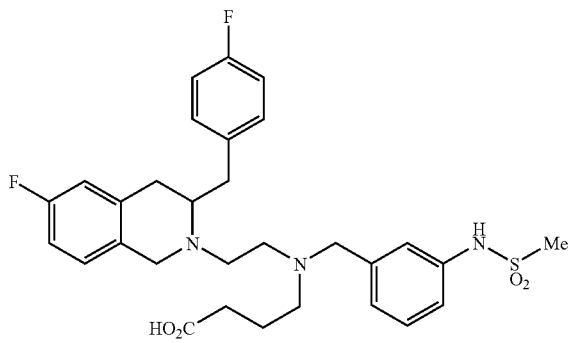

The reaction and treatment were carried out in the same manner as in Example 162-c) to obtain a title compound as a light yellow oily substance.

$^1$H-NMR (CDCl$_3$) δ: 1.97 (2H, tt, J=7.3, 7.3 Hz), 2.30-2.60 (7H, m), 2.80-3.00 (4H, m), 2.99 (3H, s), 3.34-3.56 (4H, m), 3.92 (2H, brs), 6.76 (1H, dd, J=2.2, 9.5 Hz), 6.88 (1H, ddd, J=2.2, 8.6, 8.6 Hz), 6.96-7.35 (10H, m).

Example 164

Production of N-(thiophen-2-yl)methyl-2-[3-benzyl-3,4-dihydroisoquinolin-2(1H)-yl]ethanamine

[Chem. 407]

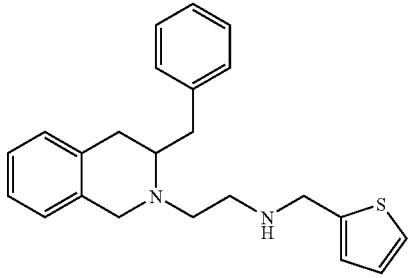

The reaction and treatment were carried out in the same manner as in Example 1-g) using 2-thiophenecarboxyaldehyde instead of benzaldehyde to obtain 11 mg (yield 60%) of a title compound as a pale yellow oily substance.

$^1$H-NMR (CDCl$_3$) δ: 2.47 (1H, dd, J=10.0, 13.2 Hz), 2.55 (1H, dd, J=3.7, 16.4 Hz), 2.74-2.88 (5H, m), 2.91 (1H, dd, J=5.4, 13.2 Hz), 3.18-3.30 (1H, m), 3.81 (2H, s), 3.99 (2H, s), 6.89-6.92 (1H, m), 6.94 (1H, dd, J=3.4, 5.1 Hz), 7.01-7.08 (2H, m), 7.09-7.32 (8H, m).

Example 165

Production of N-(thiophen-3-yl)methyl-2-[3-benzyl-3,4-dihydroisoquinolin-2(1H)-yl]ethanamine

[Chem. 408]

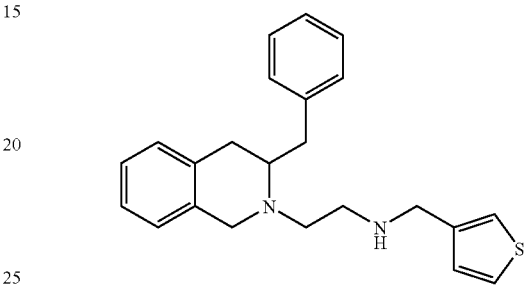

The reaction and treatment were carried out in the same manner as in Example 1-g) using 3-thiophenecarboxyaldehyde instead of benzaldehyde to obtain a title compound as a pale yellow oily substance.

$^1$H-NMR (CDCl$_3$) δ: 2.48 (1H, dd, J=10.0, 13.2 Hz), 2.56 (1H, dd, J=3.8, 16.6 Hz), 2.74-2.95 (6H, m), 3.19-3.27 (1H, m), 3.80 (2H, s), 3.81 (2H, s), 6.99-7.22 (9H, m), 7.23-7.30 (3H, m).

Example 166

Production of N-(furan-2-yl)methyl-2-[3-benzyl-3,4-dihydroisoquinolin-2(1H)-yl]ethanamine

[Chem. 409]

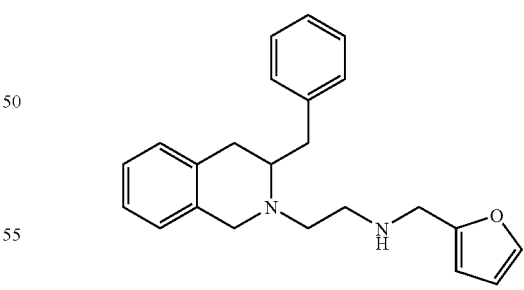

The reaction and treatment were carried out in the same manner as in Example 1-g) using 2-furaldehyde instead of benzaldehyde to obtain a title compound as a pale yellow oily substance.

$^1$H-NMR (CDCl$_3$) δ: 2.47 (1H, dd, J=10.0, 13.2 Hz), 2.56 (1H, dd, J=3.8, 16.5 Hz), 2.75-2.82 (3H, m), 2.85-2.94 (3H, m), 3.19-3.23 (1H, m), 3.78 (2H, s), 3.80 (2H, s), 6.16 (1H, d, J=3.2 Hz), 6.30 (1H, dd, J=2.0, 3.2 Hz), 7.03-7.34 (10H, m).

Example 167

Production of N-(furan-3-yl)methyl-2-[3-benzyl-3,4-dihydroisoquinolin-2(1H)-yl]ethanamine

[Chem. 410]

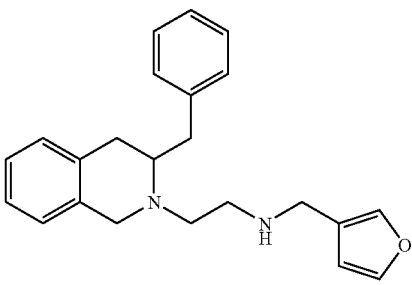

The reaction and treatment were carried out in the same manner as in Example 1-g) using 3-furaldehyde instead of benzaldehyde to obtain a title compound as a pale yellow oily substance.

$^1$H-NMR (CDCl$_3$) δ: 2.49 (1H, dd, J=10.0, 13.2 Hz), 2.57 (1H, dd, J=3.9, 16.6 Hz), 2.77-2.83 (3H, m), 2.86-2.94 (3H, m), 3.22-3.26 (1H, m), 3.64 (2H, s), 3.82 (2H, s), 6.35 (1H, brs), 7.05-7.37 (11H, m).

Example 168

Production of N-(pyridin-2-yl)methyl-2-[3-benzyl-3,4-dihydroisoquinolin-2(1H)-yl]ethanamine

[Chem. 411]

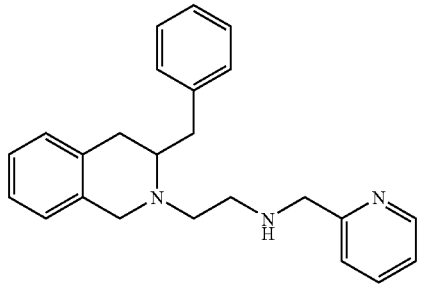

The reaction and treatment were carried out in the same manner as in Example 1-g) using pyridine-2-carboxyaldehyde instead of benzaldehyde to obtain a title compound as a pale yellow oily substance.

$^1$H-NMR (CDCl$_3$) δ: 2.49 (1H, dd, J=10.3, 10.3 Hz), 2.58 (1H, d, J=16.4 Hz), 2.70 (1H, brs), 2.79-3.00 (6H, m), 3.22-3.33 (1H, m), 3.84 (2H, s), 3.96 (2H, s), 7.02-7.32 (11H, m), 7.63 (1H, dd, J=7.7, 7.7 Hz), 8.50-8.56 (1H, m).

Example 169

Production of N-(pyridin-3-yl)methyl-2-[3-benzyl-3,4-dihydroisoquinolin-2(1H)-yl]ethanamine

[Chem. 412]

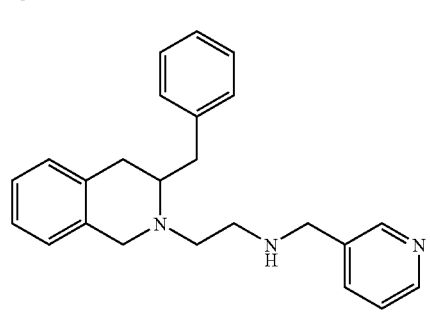

The reaction and treatment were carried out in the same manner as in Example 1-g) using pyridine-3-carboxyaldehyde instead of benzaldehyde to obtain a title compound as a pale yellow oily substance.

$^1$H-NMR (CDCl$_3$) δ: 2.18 (1H, brs), 2.47-2.62 (2H, m), 2.71-2.96 (6H, m), 3.20-3.30 (1H, m), 3.79 (2H, s), 3.82 (2H, s), 7.02-7.30 (10H, m), 7.63 (1H, d, J=7.1 Hz), 8.47-8.55 (2H, m).

Example 170

Production of N-(pyridin-4-yl)methyl-2-[3-benzyl-3,4-dihydroisoquinolin-2(1H)-yl]ethanamine

[Chem. 413]

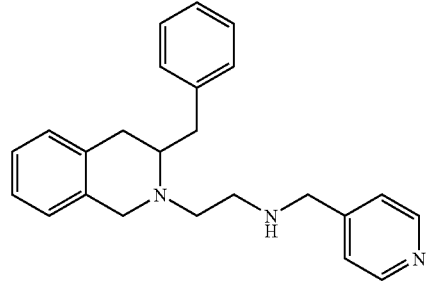

The reaction and treatment were carried out in the same manner as in Example 1-g) using pyridine-4-carboxyaldehyde instead of benzaldehyde to obtain a title compound as a pale yellow oily substance.

$^1$H-NMR (CDCl$_3$) δ: 2.11 (1H, brs), 2.52 (1H, dd, J=9.8, 13.2 Hz), 2.59 (1H, dd, J=3.8, 16.5 Hz), 2.68-2.96 (6H, m), 3.23-3.31 (1H, m), 3.79 (2H, s), 3.82 (2H, s), 7.02-7.30 (11H, m), 8.50-8.54 (2H, m).

Example 171

Production of N-(pyridin-4-yl)methyl-2-[3-(4-fluorobenzyl)-3,4-dihydroisoquinolin-2(1H)-yl]ethanamine a) Production of 2-[3-(4-fluorobenzyl)-3,4-dihydroisoquinolin-2(1H)-yl]ethanamine

[Chem. 414]

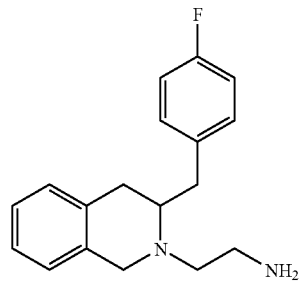

The reaction and treatment were carried out in the same manner as in Example 1-f) using tert-butyl 2-[3-(4-fluorobenzyl)-3,4-dihydroisoquinolin-2(1H)-yl]ethyl carbamate obtained in Example 10-c) to obtain a title compound as a light yellow oily substance.

$^1$H-NMR (CDCl$_3$) δ: 2.53 (1H, dd, J=10.0, 13.2 Hz), 2.59 (1H, dd, J=4.2, 15.8 Hz), 2.64-2.94 (6H, m), 3.17-3.26 (1H, m), 3.83 (2H, s), 4.42 (2H, brs), 6.96 (2H, dd, J=8.6, 8.6 Hz), 7.02-7.16 (6H, m).

b) Production of N-(pyridin-4-yl)methyl-2-[3-(4-fluorobenzyl)-3,4-dihydroisoquinolin-2(1H)-yl]ethanamine

[Chem. 415]

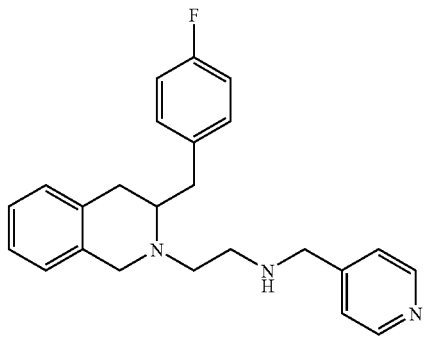

The reaction and treatment were carried out in the same manner as in Example 1-g) using pyridine-4-carboxyaldehyde instead of benzaldehyde to obtain a title compound as a pale yellow oily substance.

$^1$H-NMR (CDCl$_3$) δ: 2.50 (1H, dd, J=9.5, 13.4 Hz), 2.56 (1H, dd, J=3.9, 16.4 Hz), 2.70-2.80 (3H, m), 2.83-2.92 (3H, m), 3.18-3.26 (1H, m), 3.79 (2H, s), 3.82 (2H, s), 6.95 (2H, ddd, J=2.2, 6.6, 8.8 Hz), 7.02-7.09 (4H, m), 7.15-7.18 (2H, m), 7.19-7.22 (2H, m), 8.53 (2H, dd, J=1.6, 4.5 Hz).

Example 172

Production of N-(pyrimidin-5-yl)methyl-2-[3-(4-fluorobenzyl)-3,4-dihydroisoquinolin-2(1H)-yl]ethanamine

[Chem. 416]

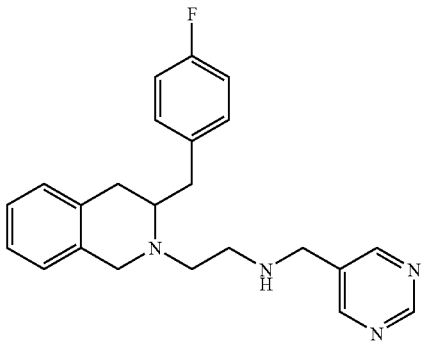

The reaction and treatment were carried out in the same manner as in Example 1-g) using pyrimidine-5-carboxyaldehyde instead of benzaldehyde to obtain a title compound as a pale yellow oily substance.

$^1$H-NMR (CDCl$_3$) δ: 2.50 (1H, dd, J=9.4, 13.3 Hz), 2.55 (1H, dd, J=3.8, 16.2 Hz), 2.69-2.80 (3H, m), 2.83-2.90 (3H, m), 3.18-3.24 (1H, m), 3.76 (1H, d, J=14.2 Hz), 3.81 (1H, d, J=14.2 Hz), 3.83 (2H, s), 6.92-6.97 (2H, m), 7.05-7.09 (4H, m), 7.15-7.17 (2H, m), 8.68 (2H, s), 9.12 (1H, s).

Example 173

Production of N-(1-methyl-1H-pyrrol-2-yl)methyl-2-[3-(4-fluorobenzyl)-3,4-dihydroisoquinolin-2(1H)-yl]ethanamine

[Chem. 417]

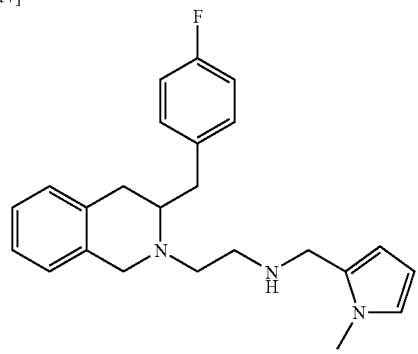

The reaction and treatment were carried out in the same manner as in Example 1-g) using 1-methyl-1H-pyrrole-2-carboaldehyde instead of benzaldehyde to obtain a title compound as a pale yellow oily substance.

$^1$H-NMR (CDCl$_3$) δ: 2.45 (1H, dd, J=9.5, 13.4 Hz), 2.53 (1H, dd, J=3.9, 16.4 Hz), 2.74-2.90 (6H, m), 3.15-3.21 (1H, m), 3.56 (3H, s), 3.74 (2H, s), 3.77 (2H, s), 6.01 (1H, d, J=1.6

Hz), 6.03-6.05 (1H, m), 6.55 (1H, dd, J=2.4, 2.4 Hz), 6.92-6.97 (2H, m), 7.02-7.07 (4H, m), 7.13-7.16 (2H, m).

Example 174

Production of N-(1-methyl-1H-imidazol-5-yl)methyl-2-[3-(4-fluorobenzyl)-3,4-dihydroisoquinolin-2(1H)-yl]ethanamine

[Chem. 418]

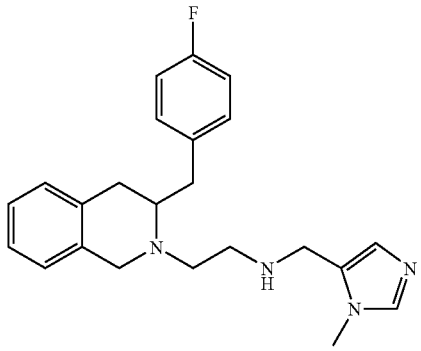

The reaction and treatment were carried out in the same manner as in Example 1-g) using 1-methyl-1H-imidazole-5-carboaldehyde instead of benzaldehyde to obtain a title compound as a pale yellow oily substance.

$^1$H-NMR (CDCl$_3$) δ: 2.45 (1H, dd, J=9.8, 13.3 Hz), 2.52 (1H, dd, J=3.9, 16.3 Hz), 2.73-2.90 (6H, m), 3.16-3.23 (1H, m), 3.63 (3H, s), 3.80 (2H, s), 3.86 (2H, s), 6.81 (1H, d, J=1.2 Hz), 6.92-6.97 (3H, m), 7.03-7.08 (4H, m), 7.14-7.16 (2H, m).

Example 175

Production of N-(1-methyl-1H-imidazol-2-yl)methyl-2-[3-(4-fluorobenzyl)-3,4-dihydroisoquinolin-2(1H)-yl]ethanamine

[Chem. 419]

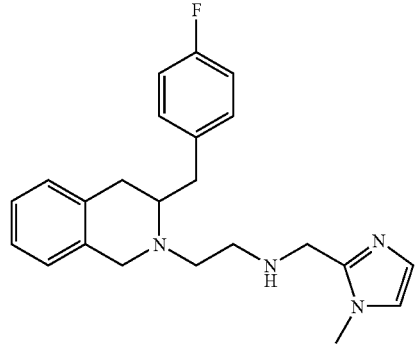

The reaction and treatment were carried out in the same manner as in Example 1-g) using 1-methyl-1H-imidazole-2-carboaldehyde instead of benzaldehyde to obtain a title compound as a pale yellow oily substance.

$^1$H-NMR (CDCl$_3$) δ: 2.45 (1H, dd, J=9.8, 13.3 Hz), 2.53 (1H, dd, J=3.7, 16.2 Hz), 2.76-2.88 (6H, m), 3.14-3.22 (1H, m), 3.63 (3H, s), 3.79 (2H, s), 3.86 (2H, s), 6.81 (2H, s), 6.89-6.98 (3H, m), 7.00-7.05 (3H, m), 7.13-7.16 (2H, m).

Example 176

Production of N-(pyridin-4-yl)methyl-3-[3-(4-fluorobenzyl)-3,4-dihydroisoquinolin-2(1H)-yl]propanamine a) Production of tert-butyl 3-[3-(4-fluorobenzyl)-3,4-dihydroisoquinolin-2(1H)-yl]propyl carbamate

[Chem. 420]

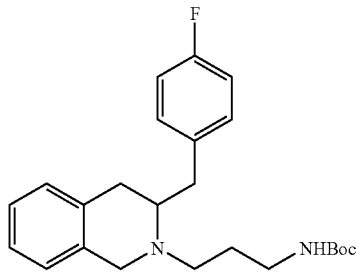

The reaction and treatment were carried out in the same manner as in Example 1-e) using 3-(tert-butoxycarbonylamino)propionaldehyde instead of 2-(tert-butoxycarbonylamino)acetaldehyde to obtain a title compound as a pale yellow oily substance.

$^1$H-NMR (CDCl$_3$) δ: 1.41 (9H, s), 1.75 (2H, tt, J=6.5, 6.5 Hz), 2.44 (1, dd, J=10.2, 13.2 Hz), 2.55 (1H, dd, J=4.0, 16.4 Hz), 2.64-2.78 (2H, m), 2.84 (1H, dd, J=5.1, 16.4 Hz), 2.90 (1H, dd, J=4.1, 13.2 Hz), 3.15-3.27 (3H, m), 3.80 (1H, d, J=16.1 Hz), 3.87 (1H, d, J=16.1 Hz), 5.26 (1H, brs), 6.97 (2H, ddd, J=2.2, 6.5, 8.7 Hz), 7.01-7.09 (4H, m), 7.12-7.17 (2H, m).

b) Production of 3-[3-(4-fluorobenzyl)-3,4-dihydroisoquinolin-2(1H)-yl]propanamine

[Chem. 421]

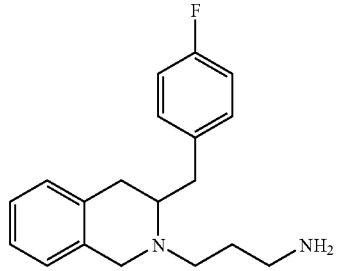

The reaction and treatment were carried out in the same manner as in Example 1-f) to obtain a title compound as a light yellow oily substance.

$^1$H-NMR (CDCl$_3$) δ: 1.66-1.74 (2H, m), 2.45 (1H, dd, J=10.2, 13.0 Hz), 2.59 (1H, dd, J=4.0, 16.5 Hz), 2.68-2.97

(6H, m), 3.21-3.29 (1H, m), 3.84 (1H, d, J=15.9 Hz), 3.89 (1H, d, J=15.9 Hz), 7.00-7.09 (6H, m), 7.12-7.20 (2H, m).

c) Production of N-(pyridin-4-yl)methyl-3-[3-(4-fluorobenzyl)-3,4-dihydroisoquinolin-2(1H)-yl]propanamine

[Chem. 422]

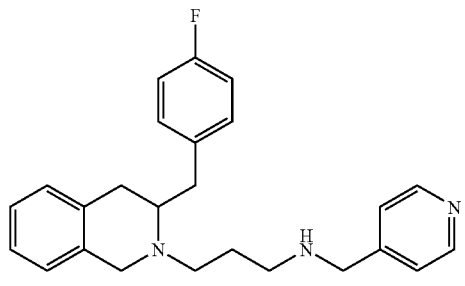

The reaction and treatment were carried out in the same manner as in Example 1-g) using pyridine-4-carboxyaldehyde instead of benzaldehyde to obtain a title compound as a pale yellow oily substance.

$^1$H-NMR (CDCl$_3$) δ: 1.82 (2H, tt, J=6.7, 6.7 Hz), 2.44 (1H, dd, J=10.0, 13.2 Hz), 2.55 (1H, dd, J=4.2, 16.4 Hz), 2.72 (2H, t, J=6.6 Hz), 2.72-2.84 (3H, m), 2.91 (1H, dd, J=4.2, 13.2 Hz), 3.20-3.27 (1H, m), 3.77 (2H, s), 3.83 (1H, d, J=16.0 Hz), 3.90 (1H, d, J=16.0 Hz), 6.96 (2H, ddd, J=2.2, 6.3, 8.5 Hz), 7.02-7.10 (4H, m), 7.14-7.18 (2H, m), 7.18-7.22 (2H, m), 8.49 (2H, dd, J=1.5, 4.4 Hz).

Example 177

Production of N,N-bis[(pyridin-4-yl)methyl]-3-[3-(4-fluorobenzyl)-3,4-dihydroisoquinolin-2(1H)-yl]propanamine

[Chem. 423]

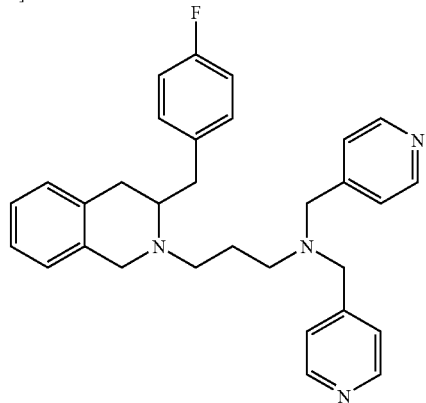

In the reaction of Example 176-c), the title compound was also simultaneously obtained. The title compound was yellow oily substance.

$^1$H-NMR (CDCl$_3$) δ: 1.70-1.86 (2H, m), 2.40 (1H, dd, J=10.3, 13.2 Hz), 2.50 (2H, t, J=7.2 Hz), 2.47-2.55 (1H, m), 2.59-2.70 (3H, m), 2.83-2.90 (1H, m), 3.08-3.17 (1H, m), 3.55 (2H, d, J=14.6 Hz), 3.59 (2H, d, J=14.6 Hz), 3.77 (1H, d, J=16.7 Hz), 3.82 (1H, d, J=16.7 Hz), 6.98 (2H, ddd, J=2.2, 6.6, 8.8 Hz), 7.01-7.07 (4H, m), 7.14-7.18 (2H, m), 7.26-7.29 (4H, m), 8.52 (4H, dd, J=1.5, 4.4 Hz).

Example 178

Production of N-(pyridin-4-yl)methyl-2-[3-(4-chlorobenzyl)-6-fluoro-3,4-dihydroisoquinolin-2(1H)-yl]ethanamine

[Chem. 424]

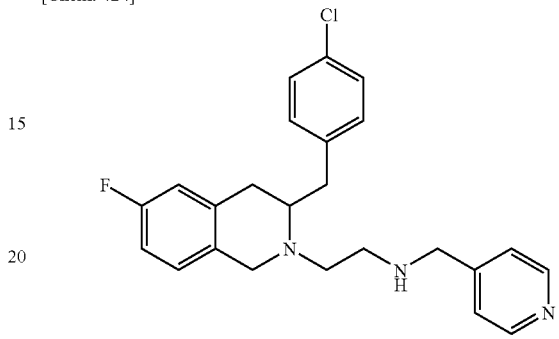

The reaction and treatment were carried out in the same manner as in Example 1-g) using 2-[3-(4-chlorobenzyl)-6-fluoro-3,4-dihydroisoquinolin-2(1H)-yl]ethanamine obtained in Example 55-c) as a starting material, and using pyridine-4-carboxyaldehyde instead of benzaldehyde to obtain a title compound as a pale yellow oily substance.

$^1$H-NMR (CDCl$_3$) δ: 2.47 (1H, dd, J=9.3, 13.4 Hz), 2.51 (1H, dd, J=3.7, 16.2 Hz), 2.68-2.78 (3H, m), 2.81-2.91 (3H, m), 3.17-3.26 (1H, m), 3.76 (2H, s), 3.79 (2H, s), 6.77 (1H, dd, J=2.6, 9.3 Hz), 6.87 (1H, ddd, J=2.6, 8.5, 8.5 Hz), 7.00 (1H, dd, J=5.9, 8.5 Hz), 7.04 (2H, d, J=8.3 Hz), 7.21 (2H, d, J=5.9 Hz), 7.23 (2H, d, J=8.3 Hz), 8.53 (2H, dd, J=1.4, 5.9 Hz).

Example 179

Production of N-(pyridin-4-yl)methyl-2-[7-fluoro-3-(4-fluorobenzyl)-3,4-dihydroisoquinolin-2(1H)-yl]ethanamine a) Production of tert-butyl 2-[3-(4-fluorobenzyl)-7-fluoro-3,4-dihydroisoquinolin-2(1H)-yl]ethyl carbamate

[Chem. 425]

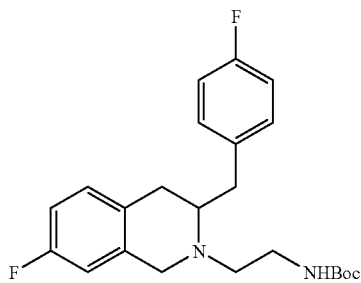

The reaction and treatment were carried out in the same manner as in Example 1-e) using 7-fluoro-3-(4-fluorobenzyl)-1,2,3,4-tetrahydroisoquinoline obtained in Example 56-c) to obtain a title compound as a light yellow oily substance.

¹H-NMR (CDCl₃) δ: 1.44 (9H, s), 2.46-2.54 (2H, m), 2.64-2.87 (4H, m), 3.16-3.32 (3H, m), 3.81 (2H, s), 4.90 (1H, brs), 6.76-7.10 (7H, m).

b) Production of 2-[3-(4-fluorobenzyl)-7-fluoro-3,4-dihydroisoquinolin-2(1H)-yl]ethanamine

[Chem. 426]

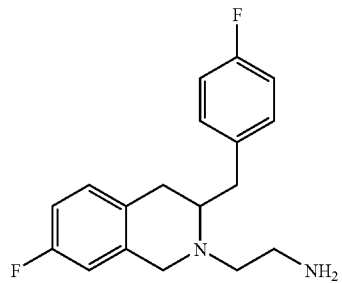

The reaction and treatment were carried out in the same manner as in Example 1-f) to obtain a title compound as a light yellow oily substance.

¹H-NMR (CDCl₃) δ: 2.45-2.53 (2H, m), 2.66-2.92 (6H, m), 3.22 (1H, m), 3.82 (2H, s), 6.75-7.10 (7H, m).

c) Production of N-(pyridin-4-yl)methyl-2-[7-fluoro-3-(4-fluorobenzyl)-3,4-dihydroisoquinolin-2(1H)-yl]ethanamine

[Chem. 427]

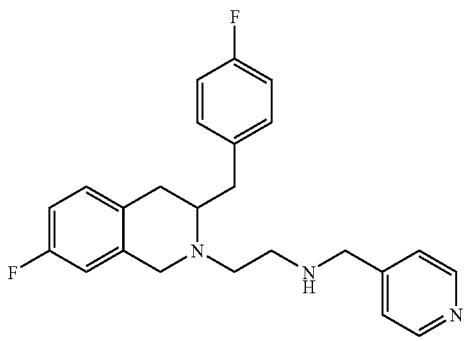

The reaction and treatment were carried out in the same manner as in Example 1-g) using pyridine-4-carboxyaldehyde instead of benzaldehyde to obtain a title compound as a pale yellow oily substance.

¹H-NMR (CDCl₃) δ: 2.45-2.54 (2H, m), 2.70-2.92 (6H, m), 3.21 (1H, m), 3.79 (4H, s), 6.75-7.08 (7H, m), 7.21 (1H, d, J=5.9 Hz), 7.72 (1H, m), 8.52-8.54 (2H, m).

Example 180

Production of N-(pyridin-4-yl)methyl-2-[6-fluoro-3-(4-fluorobenzyl)-3,4-dihydroisoquinolin-2(1H)-yl]ethanamine a) Production of tert-butyl 2-[6-fluoro-3-(4-fluorobenzyl)-3,4-dihydroisoquinolin-2(1H)-yl]ethyl carbamate

[Chem. 428]

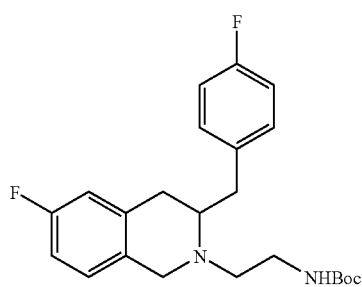

The reaction and treatment were carried out in the same manner as in Example 1-e) using 6-fluoro-3-(4-fluorobenzyl)-1,2,3,4-tetrahydroisoquinoline obtained in Example 53-a) to obtain a title compound as a light yellow oily substance.

¹H-NMR (CDCl₃) δ: 1.44 (9H, s), 2.46 (1H, dd, J=9.3, 13.4 Hz), 2.52 (1H, dd, J=2.6, 16.4 Hz), 2.64-2.73 (1H, m), 2.76-2.90 (3H, m), 3.14-3.36 (3H, m), 3.79 (2H, s), 4.90 (1H, brs), 6.77 (1H, dd, J=2.2, 9.5 Hz), 6.87 (1H, ddd, J=2.2, 8.6, 8.6 Hz), 6.94-7.04 (3H, m), 7.04-7.12 (2H, m).

b) Production of 2-[6-fluoro-3-(4-fluorobenzyl)-3,4-dihydroisoquinolin-2(1H)-yl]ethanamine

[Chem. 429]

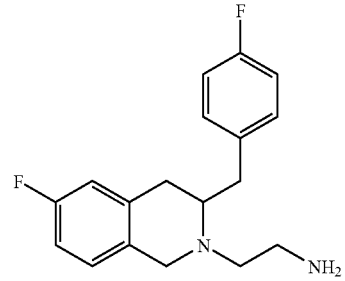

The reaction and treatment were carried out in the same manner as in Example 1-f) to obtain a title compound as a light yellow oily substance.

¹H-NMR (CDCl₃) δ: 2.40-2.62 (4H, m), 2.66-2.96 (6H, m), 3.16-3.28 (1H, m), 3.80 (2H, s), 6.76 (1H, dd, J=2.0, 9.5 Hz), 6.86 (1H, ddd, J=2.0, 8.3, 8.3 Hz), 6.94-7.04 (3H, m), 7.08 (2H, dd, J=5.9, 8.0 Hz).

c) Production of N-(pyridin-4-yl)methyl-2-[6-fluoro-3-(4-fluorobenzyl)-3,4-dihydroisoquinolin-2(1H)-yl]ethanamine

[Chem. 430]

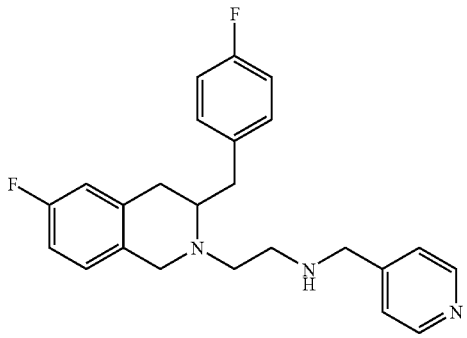

The reaction and treatment were carried out in the same manner as in Example 1-g) using pyridine-4-carboxyaldehyde instead of benzaldehyde to obtain a title compound as a pale yellow oily substance.

$^1$H-NMR (CDCl$_3$) δ: 2.47 (1H, dd, J=9.5, 13.4 Hz), 2.52 (1H, dd, J=3.9, 16.6 Hz), 2.70-2.76 (3H, m), 2.81-2.91 (3H, m), 3.16-3.24 (1H, m), 3.77 (2H, s), 3.79 (2H, s), 6.76 (1H, dd, J=2.4, 9.5 Hz), 6.87 (1H, ddd, J=2.4, 8.3, 8.3 Hz), 6.96 (2H, ddd, J=1.9, 6.4, 8.3 Hz), 7.00 (1H, dd, J=5.6, 8.3 Hz), 7.04-7.08 (2H, m), 7.21 (2H, d, J=5.8 Hz), 8.53-8.56 (2H, m).

Example 181

Production of N,N-bis[(pyridin-4-yl)methyl]-2-[6-fluoro-3-(4-fluorobenzyl)-3,4-dihydroisoquinolin-2(1H)-yl]ethanamine

[Chem. 431]

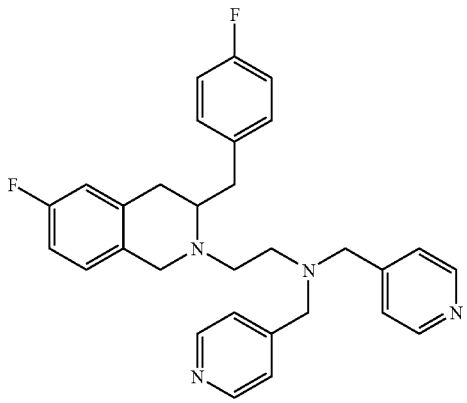

In the reaction of Example 180-c), the title compound was also simultaneously obtained. The title compound was a yellow oily substance.

$^1$H-NMR (CDCl$_3$) δ: 2.38 (1H, dd, J=9.9, 13.4 Hz), 2.49 (1H, dd, J=4.2, 16.4 Hz), 2.63-2.86 (6H, m), 3.06-3.13 (1H, m), 3.64 (4H, brs), 3.69 (2H, brs), 6.75 (1H, dd, J=2.6, 9.5 Hz), 6.86 (1H, ddd, J=2.6, 8.5, 8.5 Hz), 6.92-6.96 (5H, m), 7.29-7.32 (4H, m), 8.53 (4H, dd, J=1.5, 4.4 Hz).

Example 182

Production of N-(thiophen-3-yl)methyl-2-[6-fluoro-3-(4-fluorobenzyl)-3,4-dihydroisoquinolin-2(1H)-yl]ethanamine

[Chem. 432]

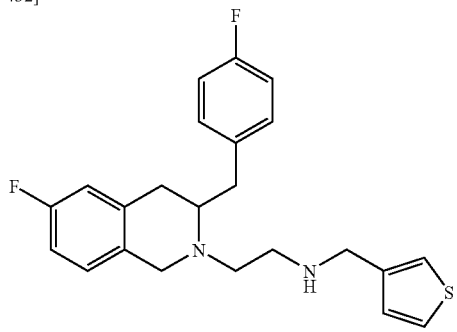

The reaction and treatment were carried out in the same manner as in Example 1-g) using 3-thiophene carboxyaldehyde instead of benzaldehyde to obtain a title compound as a pale yellow oily substance.

$^1$H-NMR (CDCl$_3$) δ: 2.44 (1H, dd, J=9.8, 13.4 Hz), 2.50 (1H, dd, J=3.9, 16.6 Hz), 2.73-2.92 (6H, m), 3.14-3.23 (1H, m), 3.73 (2H, s), 3.84 (2H, s), 6.75 (1H, dd, J=2.4, 9.3 Hz), 6.85 (1H, ddd, J=2.4, 8.5, 8.5 Hz), 6.92-7.02 (5H, m), 7.05 (1H, dd, J=5.6, 8.5 Hz), 7.11-7.14 (1H, br), 7.27 (1H, dd, J=3.0, 4.9 Hz).

Example 183

Production of N,N-bis[(thiophen-3-yl)methyl]-2-[6-fluoro-3-(4-fluorobenzyl)-3,4-dihydroisoquinolin-2(1H)-yl]ethanamine

[Chem. 433]

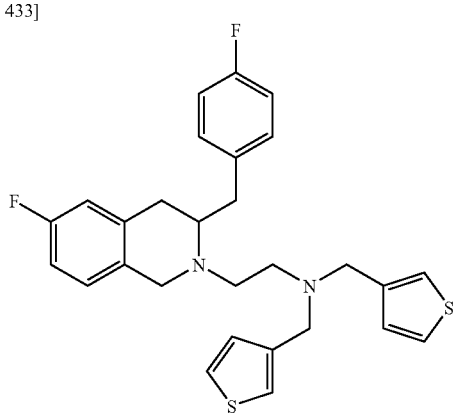

In the reaction of Example 182, the title compound was also simultaneously obtained. The title compound was a yellow oily substance.

$^1$H-NMR (CDCl$_3$) δ: 2.34 (1H, dd, J=10.2, 13.2 Hz), 2.48 (1H, dd, J=4.2, 16.6 Hz), 2.64-2.86 (6H, m), 3.06-3.13 (1H, m), 3.66 (4H, s), 3.70 (1H, d, J=15.1 Hz), 3.76 (1H, d, J=15.1 Hz), 6.73 (1H, dd, J=2.4, 9.5 Hz), 6.84 (1H, ddd, J=2.4, 8.5, 8.5 Hz), 6.92-6.95 (5H, m), 7.07 (2H, dd, J=1.2, 4.9 Hz), 7.13 (2H, dd, J=1.2, 2.9 Hz), 7.26 (2H, dd, J=2.9, 4.9 Hz).

Example 184

Production of N-[1-(pyridin-4-yl)]ethyl-2-[6-fluoro-3-(4-fluorobenzyl)-3,4-dihydroisoquinolin-2(1H)-yl]ethanamine

[Chem. 434]

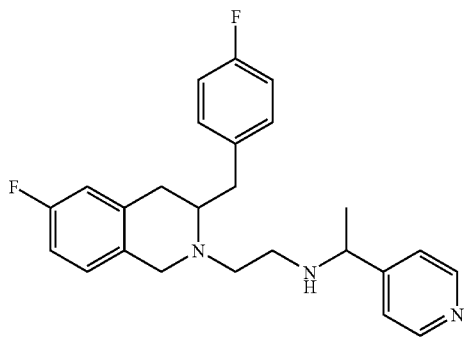

The reaction and treatment were carried out in the same manner as in Example 1-g) using 4-acetylpyridine instead of benzaldehyde to obtain a title compound as a pale yellow oily substance.

$^1$H-NMR (CDCl$_3$) δ: 1.29 (1.5H, d, J=6.6 Hz), 1.30 (1.5H, d, J=6.6 Hz), 2.45 (1H, dd, J=9.5, 13.7 Hz), 2.49-2.84 (7H, m), 3.14-3.24 (1H, m), 3.68-3.74 (1H, m), 3.69 (2H, s), 6.77 (1H, dd, J=2.3, 9.3 Hz), 6.86 (1H, ddd, J=2.3, 8.6, 8.6 Hz), 6.96-7.00 (3H, m), 7.04-7.09 (2H, m), 7.21 (2H, dd, J=1.6, 5.9 Hz), 8.50-8.54 (2H, m).

Example 185

Production of N-(1H-imidazol-2-yl)methyl-2-[6-fluoro-3-(4-fluorobenzyl)-3,4-dihydroisoquinolin-2(1H)-yl]ethanamine

[Chem. 435]

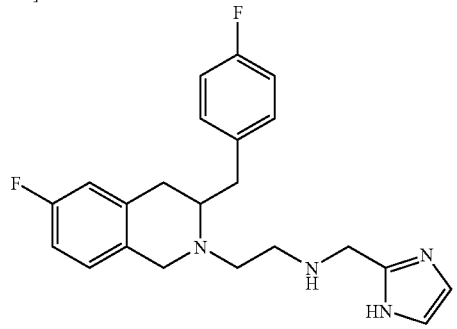

The reaction and treatment were carried out in the same manner as in Example 1-g) using imidazole-2-carboxyaldehyde instead of benzaldehyde to obtain a title compound as a pale yellow oily substance.

$^1$H-NMR (CDCl$_3$) δ: 2.49 (1H, dd, J=9.8, 13.4 Hz), 2.56 (1H, dd, J=3.7, 16.8 Hz), 2.72-2.92 (6H, m), 3.22-3.28 (1H, m), 3.79 (2H, s), 3.96 (2H, s), 6.79 (1H, dd, J=2.4, 9.2 Hz), 6.86 (2H, brs), 6.88 (1H, ddd, J=2.4, 8.3, 8.3 Hz), 6.96 (2H, ddd, J=2.0, 8.8, 8.8 Hz), 7.01 (1H, dd, J=5.6, 8.3 Hz), 7.08 (2H, dd, J=5.6, 8.8 Hz).

Example 186

Production of N-(thiazolin-2-yl)methyl-2-[6-fluoro-3-(4-fluorobenzyl)-3,4-dihydroisoquinolin-2(1H)-yl]ethanamine

[Chem. 436]

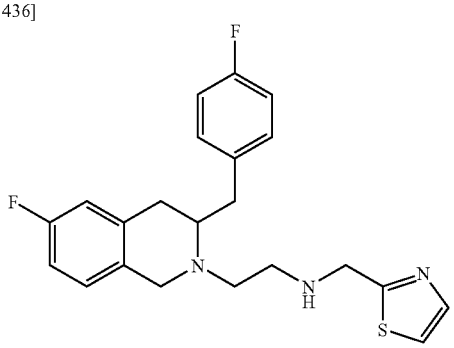

The reaction and treatment were carried out in the same manner as in Example 1-g) using thiazole-2-carboxyaldehyde instead of benzaldehyde to obtain a title compound as a pale yellow oily substance.

$^1$H-NMR (CDCl$_3$) δ: 2.45 (1H, dd, J=9.8, 13.2 Hz), 2.51 (1H, dd, J=3.4, 16.6 Hz), 2.73-2.91 (6H, m), 3.17-3.23 (1H, m), 3.77 (1H, d, J=16.8 Hz), 3.81 (1H, d, J=16.8 Hz), 4.10 (1H, d, J=15.4 Hz), 4.15 (1H, d, J=15.4 Hz), 6.76 (1H, dd, J=2.0, 9.2 Hz), 6.86 (1H, ddd, J=2.0, 8.3, 8.3 Hz), 6.95 (2H, dd, J=8.8, 8.8 Hz), 7.00 (1H, dd, J=5.6, 8.3 Hz), 7.06 (2H, dd, J=5.6, 8.8 Hz), 7.26 (1H, d, J=2.9 Hz), 7.71 (1H, d, J=2.9 Hz).

Example 187

Production of N-(1H-imidazol-5-yl)methyl-2-[6-fluoro-3-(4-fluorobenzyl)-3,4-dihydroisoquinolin-2(1H)-yl]ethanamine

[Chem. 437]

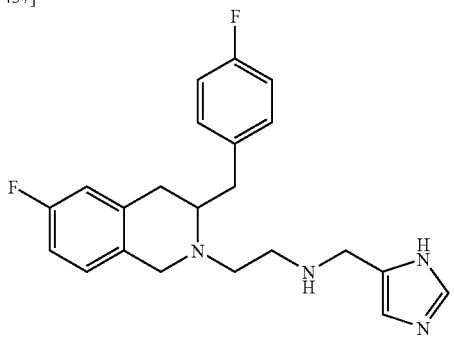

The reaction and treatment were carried out in the same manner as in Example 1-g) using thiazole-4-carboxyaldehyde instead of benzaldehyde to obtain a title compound as a pale yellow oily substance.

$^1$H-NMR (CDCl$_3$) δ: 2.45 (1H, dd, J=9.8, 13.4 Hz), 2.51 (1H, dd, J=3.6, 16.6 Hz), 2.72-2.91 (6H, m), 3.16-3.23 (1H, m), 3.78 (2H, s), 3.80 (2H, s), 6.76 (1H, dd, J=2.4, 9.5 Hz), 6.86 (1H, ddd, J=2.4, 8.3, 8.3 Hz), 6.89 (1H, s), 6.95 (2H, dd, J=8.8, 8.8 Hz), 7.00 (1H, dd, J=5.6, 8.3 Hz), 7.06 (2H, dd, J=5.6, 8.8 Hz), 7.52 (1H, s).

Example 188

Production of N-(pyridin-2-yl)-2-[6-fluoro-3-(4-fluorobenzyl)-3,4-dihydroisoquinolin-2(1H)-yl]ethanamine

[Chem. 438]

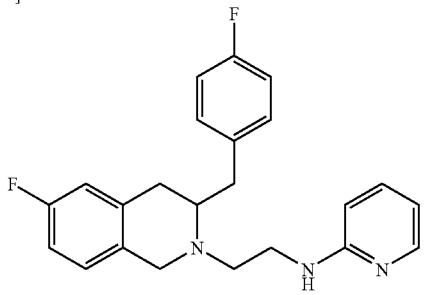

40 mg of 2-[6-fluoro-3-(4-fluorobenzyl)-3,4-dihydroisoquinolin-2(1H)-yl]ethanamine obtained in Example 180-b), 17 mg of 2-chloropyridine, and 36 mg of potassium carbonate were dissolved in 0.4 mL of DMF, followed by stirring at 120° C. overnight. After completion of the reaction, the reaction liquid was left to be cooled, and water was added thereto, followed by extraction with chloroform. The organic layer was washed with saturated brine, dried over anhydrous sodium sulfate and then concentrated under reduced pressure. The residue obtained was purified using silica gel chromatography (chloroform:ammonia saturated methanol=10:1) to obtain 6 mg (yield 13%) of a title compound as a light yellow oily substance.

$^1$H-NMR (CDCl$_3$) δ: 2.49-2.60 (2H, m), 2.70-2.92 (3H, m), 3.12 (1H, dd, J=5.0, 13.0 Hz), 3.18-3.36 (2H, m), 3.44-3.54 (1H, m), 3.81 (2H, s), 5.90-5.99 (1H, br), 6.60-6.82 (3H, m), 6.89 (1H, ddd, J=2.4, 8.4, 8.4 Hz), 6.94-7.16 (6H, m), 8.02-8.10 (1H, br).

Example 189

Production of N-(1-methyl-1H-pyrrol-2-yl)methyl-2-[6-fluoro-3-(4-fluorobenzyl)-3,4-dihydroisoquinolin-2(1H)-yl]ethanamine

[Chem. 439]

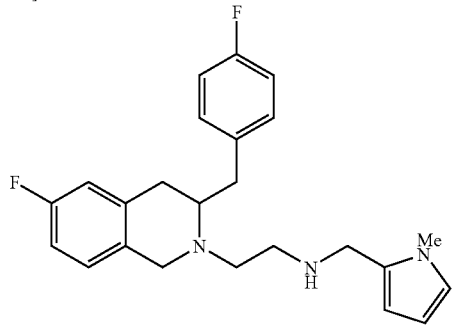

The reaction and treatment were carried out in the same manner as in Example 1-g) using 1-methylpyrrole-4-carboxyaldehyde instead of benzaldehyde to obtain a title compound as a pale yellow oily substance.

$^1$H-NMR (CDCl$_3$) δ: 2.42 (1H, dd, J=9.8, 13.2 Hz), 2.50 (1H, dd, J=3.9, 16.6 Hz), 2.71-2.89 (6H, m), 3.14-3.20 (1H, m), 3.56 (3H, s), 3.71 (2H, s), 3.75 (2H, s), 6.00-6.01 (1H, m), 6.03-6.05 (1H, m), 6.55-6.56 (1H, m), 6.75 (1H, dd, J=2.4, 9.3 Hz), 6.85 (1H, ddd, J=2.4, 8.5, 8.5 Hz), 6.95 (2H, ddd, J=2.0, 8.8, 8.8 Hz), 6.98 (1H, dd, J=5.6, 8.5 Hz), 7.05 (2H, ddd, J=2.2, 5.6, 8.8 Hz).

Example 190

Production of N-(2-fluoropyridin-4-yl)methyl-2-[6-fluoro-3-(4-fluorobenzyl)-3,4-dihydroisoquinolin-2(1H)-yl]ethanamine

[Chem. 440]

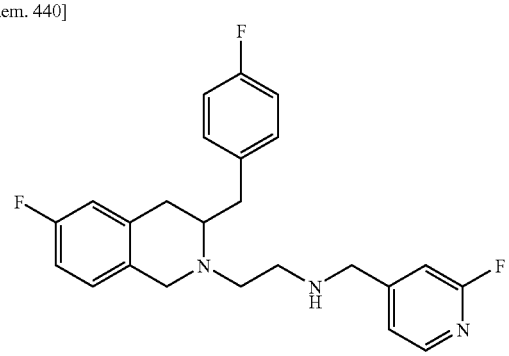

The reaction and treatment were carried out in the same manner as in Example 1-g) using 2-fluoropyridine-4-carboxyaldehyde instead of benzaldehyde to obtain a title compound as a pale yellow oily substance.

$^1$H-NMR (CDCl$_3$) δ: 2.49 (1H, dd, J=9.5, 13.4 Hz), 2.54 (1H, dd, J=3.9, 16.8 Hz), 2.70-2.81 (3H, m), 2.81-2.94 (3H, m), 3.20-3.30 (1H, m), 3.79 (2H, s), 3.83 (2H, s), 6.75-6.80 (1H, m), 6.85-6.92 (2H, m), 6.94-7.04 (3H, m), 7.05-7.12 (3H, m), 8.12-8.16 (1H, m).

Example 191

Production of N-(pyridin-2-yl)methyl-2-[6-fluoro-3-(4-fluorobenzyl)-3,4-dihydroisoquinolin-2(1H)-yl]ethanamine

[Chem. 441]

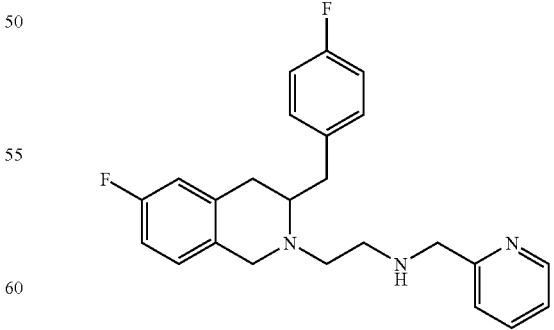

The reaction and treatment were carried out in the same manner as in Example 1-g) using pyridine-2-carboxyaldehyde instead of benzaldehyde to obtain a title compound as a pale yellow oily substance.

$^1$H-NMR (CDCl$_3$) δ: 2.40-2.53 (2H, m), 2.77-2.92 (6H, m), 3.19 (1H, m), 3.75 (1H, d, J=15.9 Hz), 3.81 (1H, d, J=15.9 Hz), 3.92 (2H, s), 6.75-7.30 (9H, m), 7.64 (1H, t, J=7.6 Hz), 8.54 (1H, d, J=4.1 Hz).

Example 192

Production of N-(pyridin-3-yl)methyl-2-[6-fluoro-3-(4-fluorobenzyl)-3,4-dihydroisoquinolin-2(1H)-yl]ethanamine

[Chem. 442]

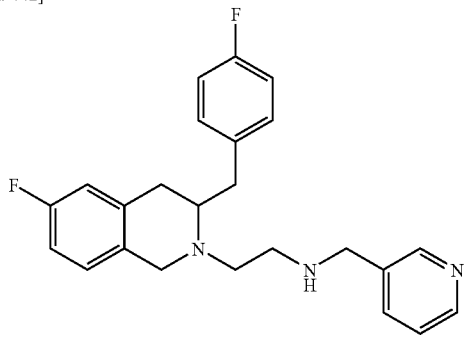

The reaction and treatment were carried out in the same manner as in Example 1-g) using pyridine-3-carboxyaldehyde instead of benzaldehyde to obtain a title compound as a yellow oily substance.

$^1$H-NMR (CDCl$_3$) δ: 2.42-2.54 (2H, m), 2.70-2.90 (6H, m), 3.18 (1H, m), 3.76 (2H, s), 3.79 (2H, s), 6.75-7.26 (8H, m), 7.61 (1H, d, J=7.8 Hz), 8.50 (1H, d, J=4.9 Hz), 8.54 (1H, s).

Example 193

Production of N-(3-fluoropyridin-4-yl)methyl-2-[6-fluoro-3-(4-fluorobenzyl)-3,4-dihydroisoquinolin-2(1H)-yl]ethanamine

[Chem. 443]

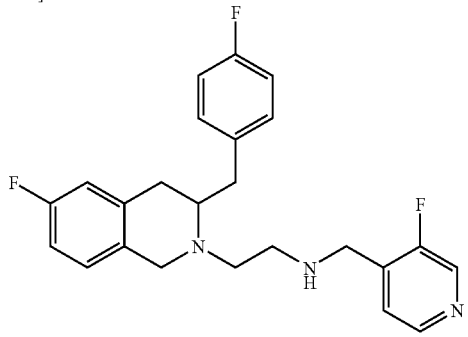

The reaction and treatment were carried out in the same manner as in Example 1-g) using 3-fluoropyridine-4-carboxyaldehyde instead of benzaldehyde to obtain a title compound as a pale yellow oily substance.

$^1$H-NMR (CDCl$_3$) δ: 2.47 (1H, dd, J=9.5, 13.4 Hz), 2.52 (1H, dd, J=3.9, 16.2 Hz), 2.72-2.78 (3H, m), 2.83-2.90 (3H, m), 3.17-3.24 (1H, m), 3.77 (2H, s), 3.86 (2H, s), 6.74-6.78 (1H, m), 6.84-6.90 (1H, m), 6.93-7.01 (3H, m), 7.06 (2H, dd, J=5.5, 8.3 Hz), 7.30 (1H, dd, J=5.5, 5.5 Hz), 8.35 (1H, d, J=4.6 Hz), 8.39 (1H, d, J=1.6 Hz).

Example 194

Production of N-(2-ethylpyridin-4-yl)methyl-2-[6-fluoro-3-(4-fluorobenzyl)-3,4-dihydroisoquinolin-2(1H)-yl]ethanamine a) Production of 2-ethyl-4-[(methyl sulfonyl oxy)methyl]pyridine

[Chem. 444]

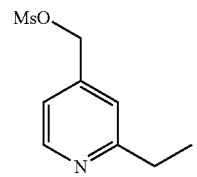

To a solution of 82 mg of 2-ethyl-4-hydroxymethylpyridine and 79 mg of triethylamine in dichloromethane (2 mL) was added 82 mg of methanesulfonyl chloride, followed by stirring at room temperature for 1 hour. It was purified by PLC (chloroform:methanol=10:1), dissolved in ethyl acetate, washed with an aqueous sodium bicarbonate solution and then with brine and then dried over anhydrous sodium sulfate, and the solvent was removed by evaporation to obtain 47 mg (yield 36%) of a title compound as a yellow oily substance.

$^1$H-NMR (CDCl$_3$) δ: 1.32 (3H, t, J=7.6 Hz), 2.86 (2H, q, J=7.6 Hz), 3.05 (3H, s), 5.21 (2H, s), 7.13 (1H, d, J=5.1 Hz), 7.18 (1H, s), 8.57 (1H, d, J=5.1 Hz).

b) Production of N-(2-ethylpyridin-4-yl)methyl-2-[6-fluoro-3-(4-fluorobenzyl)-3,4-dihydroisoquinolin-2(1H)-yl]ethanamine

[Chem. 445]

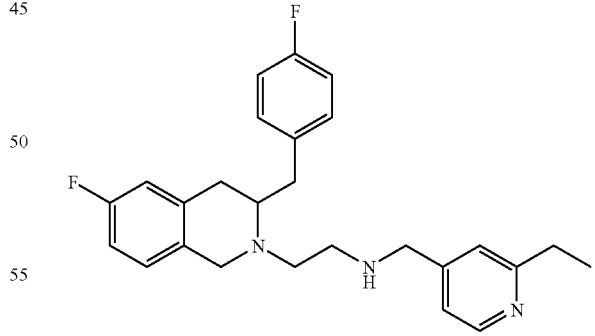

67 mg of 2-[6-fluoro-3-(4-fluorobenzyl)-3,4-dihydroisoquinolin-2(1H)-yl]ethanamine obtained in Example 180-b), 47 mg of 2-ethyl-4-[(methyl sulfonyl oxy)methyl]pyridine, and 30 mg of potassium carbonate were added to acetonitrile (2 ml), followed by stirring at 60° C. for 2 hours. After concentration, it was purified by PLC (chloroform:methanol=10:1) to obtain 26 mg (yield 28%) of a title compound as a yellow oily substance.

$^1$H-NMR (CDCl$_3$) δ: 1.29 (3H, t, J=7.6 Hz), 2.42-2.56 (2H, m), 2.70-2.90 (8H, m), 3.20 (1H, m), 3.77 (4H, brs), 6.74-7.10 (9H, m), 8.44 (1H, d, J=5.0 Hz).

Example 195

Production of N-(1-oxidopyridin-4-yl)methyl-2-[6-fluoro-3-(4-fluorobenzyl)-3,4-dihydroisoquinolin-2(1H)-yl]ethanamine

[Chem. 446]

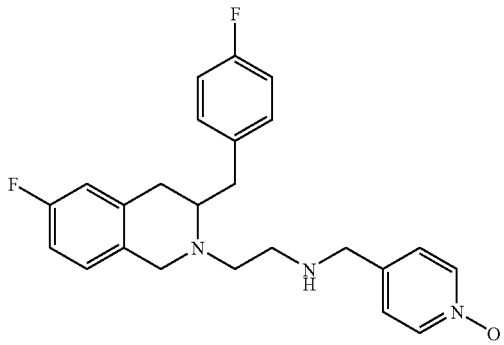

The reaction and treatment were carried out in the same manner as in Example 1-g) using 4-pyridine carboxyaldehyde N-oxide instead of benzaldehyde to obtain a title compound as a pale yellow oily substance.

$^1$H-NMR (CDCl$_3$) δ: 2.48 (1H, dd, J=9.5, 13.7 Hz), 2.53 (1H, dd, J=3.9, 16.4 Hz), 2.67-2.78 (3H, m), 2.82-2.91 (3H, m), 3.18-3.24 (1H, m), 3.73 (1H, d, J=15.4 Hz), 3.77 (1H, d, J=15.4 Hz), 3.78 (2H, s), 6.77 (1H, dd, J=2.7, 9.4 Hz), 6.88 (1H, ddd, J=2.7, 8.4, 8.4 Hz), 6.97 (2H, ddd, J=2.1, 6.7, 8.8 Hz), 7.01 (1H, dd, J=5.6, 8.4 Hz), 7.08-7.10 (2H, m), 7.22 (2H, d, J=7.1 Hz), 8.14 (2H, d, J=7.1 Hz).

Example 196

Production of N-(2-methoxypyridin-4-yl)methyl-2-[6-fluoro-3-(4-fluorobenzyl)-3,4-dihydroisoquinolin-2(1H)-yl]ethanamine

[Chem. 447]

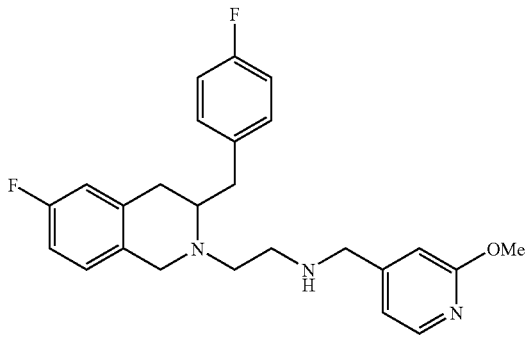

The reaction and treatment were carried out in the same manner as in Example 1-g) using 2-methoxypyridine-4-carboxyaldehyde instead of benzaldehyde to obtain a title compound as a pale yellow oily substance.

$^1$H-NMR (CDCl$_3$) δ: 2.42-2.56 (2H, m), 2.68-2.92 (6H, m), 3.19 (1H, m), 3.74 (2H, s), 3.77 (2H, s), 3.94 (3H, s), 6.68 (1H, s), 6.74-7.08 (8H, m), 8.08 (1H, d, J=5.1 Hz).

Example 197

Production of N-(3-ethylpyridin-4-yl)methyl-2-[6-fluoro-3-(4-fluorobenzyl)-3,4-dihydroisoquinolin-2(1H)-yl]ethanamine a) Production of 3-ethyl-4-[(methyl sulfonyl oxy)methyl]pyridine

[Chem. 448]

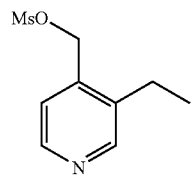

The reaction and treatment were carried out in the same manner as in Example 194-a) using 3-ethyl-4-hydroxymethylpyridine instead of 2-ethyl-4-hydroxymethylpyridine to obtain a title compound as a yellow oily substance.

$^1$H-NMR (CDCl$_3$) δ: 1.24 (3H, t, J=7.6 Hz), 2.64 (2H, q, J=7.6 Hz), 4.78 (2H, s), 7.41 (1H, d, J=4.9 Hz), 8.37 (1H, s), 8.44 (1H, d, J=4.9 Hz).

b) Production of N-(3-ethylpyridin-4-yl)methyl-2-[6-fluoro-3-(4-fluorobenzyl)-3,4-dihydroisoquinolin-2(1H)-yl]ethanamine

[Chem. 449]

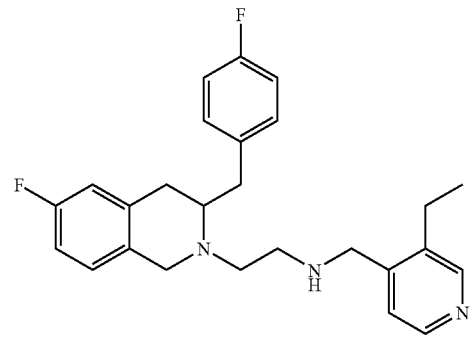

The reaction and treatment were carried out in the same manner as in Example 194-b) to obtain a title compound as a yellow oily substance.

$^1$H-NMR (CDCl$_3$) δ: 1.21 (3H, t, J=7.6 Hz), 2.44-2.58 (2H, m), 2.64 (2H, q, J=7.6 Hz), 2.70-2.92 (6H, m), 3.21 (1H, m), 3.77 (2H, s), 3.79 (2H, s), 6.74-7.12 (8H, m), 7.22 (1H, d, J=5.1 Hz), 8.38 (1H, s).

Example 198

Production of N-(1H-indole-5-yl)methyl-2-[6-fluoro-3-(4-fluorobenzyl)-3,4-dihydroisoquinolin-2(1H)-yl]ethanamine

[Chem. 450]

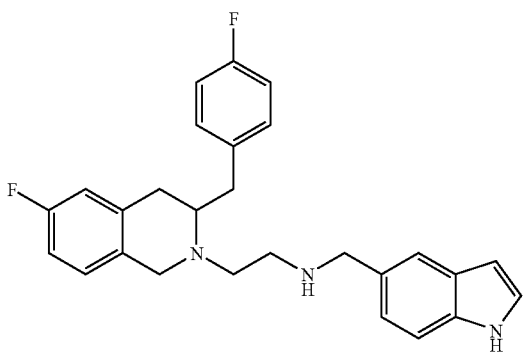

The reaction and treatment were carried out in the same manner as in Example 1-g) using 5-indole carboxyaldehyde instead of benzaldehyde to obtain a title compound as a pale yellow oily substance.

$^1$H-NMR (CDCl$_3$) δ: 2.39 (1H, dd, J=9.8, 13.4 Hz), 2.45 (1H, dd, J=3.7, 16.6 Hz), 2.73-2.90 (6H, m), 3.07-3.12 (1H, m), 3.61 (1H, d, J=16.6 Hz), 3.66 (1H, d, J=16.6 Hz), 3.94 (2H, s), 6.51 (1H, s), 6.74 (1H, dd, J=2.7, 9.5 Hz), 6.83 (1H, ddd, J=2.7, 8.6, 8.6 Hz), 6.89 (1H, dd, J=5.6, 8.6 Hz), 6.90 (2H, ddd, J=2.2, 8.8, 8.8 Hz), 6.97 (2H, ddd, J=2.2, 5.6, 8.8 Hz), 7.09 (1H, dd, J=1.7, 8.3 Hz), 7.23 (1H, dd, J=2.7, 2.7 Hz), 7.32 (1H, d, J=8.3 Hz), 7.52 (1H, s).

Example 199

Production of N-(quinolin-4-yl)methyl-2-[6-fluoro-3-(4-fluorobenzyl)-3,4-dihydroisoquinolin-2(1H)-yl]ethanamine

[Chem. 451]

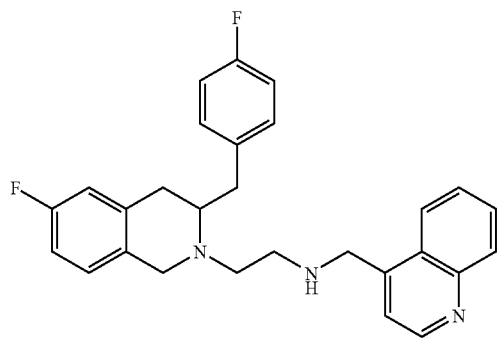

The reaction and treatment were carried out in the same manner as in Example 1-g) using quinoline-4-carboxyaldehyde instead of benzaldehyde to obtain a title compound as a pale yellow oily substance.

$^1$H-NMR (CDCl$_3$) δ: 2.40-2.52 (2H, m), 2.76-2.94 (6H, m), 3.14-3.22 (1H, m), 3.75 (2H, s), 4.26 (2H, s), 6.73-6.78 (1H, m), 6.83-6.89 (1H, m), 6.90-7.00 (3H, m), 7.00-7.07 (2H, m), 7.36-7.40 (1H, m), 7.46-7.52 (1H, m), 7.65-7.72 (1H, m), 8.04 (1H, brd, J=8.4 Hz), 8.11 (1H, brd, J=8.4 Hz), 8.85 (1H, dd, J=2.0, 4.2 Hz).

Example 200

Production of N-(quinolin-3-yl)methyl-2-[6-fluoro-3-(4-fluorobenzyl)-3,4-dihydroisoquinolin-2(1H)-yl]ethanamine

[Chem. 452]

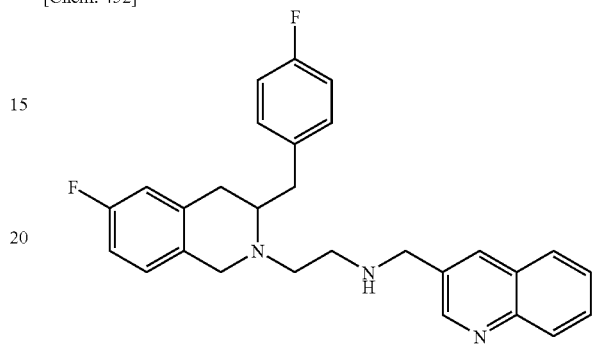

The reaction and treatment were carried out in the same manner as in Example 1-g) using quinoline-3-carboxyaldehyde instead of benzaldehyde to obtain a title compound as a pale yellow oily substance.

$^1$H-NMR (CDCl$_3$) δ: 2.44 (1H, dd, J=9.8, 13.4 Hz), 2.51 (1H, dd, J=3.9, 16.8 Hz), 2.74-2.92 (6H, m), 3.15-3.22 (1H, m), 3.77 (2H, s), 3.99 (2H, s), 6.76 (1H, dd, J=2.4, 9.2 Hz), 6.85 (1H, ddd, J=2.4, 8.4, 8.4 Hz), 6.88-6.97 (2H, m), 6.97 (1H, dd, J=5.7, 8.4 Hz), 7.00-7.06 (2H, m), 7.54 (1H, ddd, J=1.5, 8.3, 8.3 Hz), 7.69 (1H, ddd, J=1.5, 8.3, 8.3 Hz), 7.77 (1H, brd, J=8.3 Hz), 8.06 (1H, d, J=2.0 Hz), 8.10 (1H, brd, J=8.3 Hz), 8.87 (1H, d, J=2.0 Hz).

Example 201

Production of N-(2-fluoropyridin-5-yl)methyl-2-[6-fluoro-3-(4-fluorobenzyl)-3,4-dihydroisoquinolin-2(1H)-yl]ethanamine

[Chem. 453]

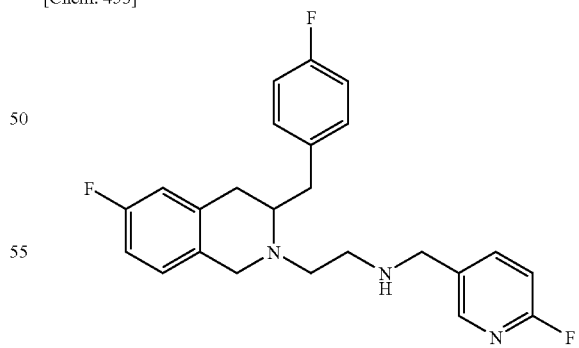

The reaction and treatment were carried out in the same manner as in Example 1-g) using 2-fluoropyridine-5-carboxyaldehyde instead of benzaldehyde to obtain a title compound as a pale yellow oily substance.

$^1$H-NMR (CDCl$_3$) δ: 2.45 (1H, dd, J=9.6, 13.6 Hz), 2.51 (1H, dd, J=3.9, 16.6 Hz), 2.73-2.77 (3H, m), 2.81-2.89 (3H, m), 3.15-3.21 (1H, m), 3.77 (2H, s), 3.81 (2H, s), 6.76 (1H, dd, J=2.4, 9.5 Hz), 6.86 (1H, ddd, J=2.6, 8.3, 8.3 Hz), 6.93-7.07 (5H, m), 7.13-7.17 (1H, m), 7.73-7.76 (1H, m), 8.10 (1H, d, J=4.6 Hz).

Example 202

Production of N-(2-fluoropyridin-3-yl)methyl-2-[6-fluoro-3-(4-fluorobenzyl)-3,4-dihydroisoquinolin-2(1H)-yl]ethanamine

[Chem. 454]

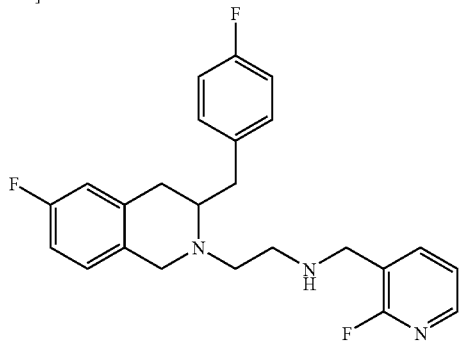

The reaction and treatment were carried out in the same manner as in Example 1-g) using 2-fluoropyridine-3-carboxyaldehyde instead of benzaldehyde to obtain a title compound as a pale yellow oily substance.

$^1$H-NMR (CDCl$_3$) δ: 2.46 (1H, dd, J=9.6, 13.5 Hz), 2.52 (1H, dd, J=3.9, 16.8 Hz), 2.80-2.77 (3H, m), 2.82-2.90 (3H, m), 3.15-3.23 (1H, m), 3.77 (2H, s), 3.82 (2H, s), 6.76 (1H, dd, J=2.5, 9.4 Hz), 6.86 (1H, ddd, J=2.7, 8.3, 8.3 Hz), 6.93-7.01 (3H, m), 7.04-7.08 (2H, m), 7.13-7.17 (1H, m), 7.73-7.78 (1H, m), 8.10 (1H, d, J=4.8 Hz).

Example 203

Production of N-(1H-benzimidazol-5-yl)methyl-2-[6-fluoro-3-(4-fluorobenzyl)-3,4-dihydroisoquinolin-2(1H)-yl]ethanamine a) Production of N-[1-(tert-butoxycarbonyl)-1H-benzimidazol-5-yl]methyl-2-[6-fluoro-3-(4-fluorobenzyl)-3,4-dihydroisoquinolin-2(1H)-yl]ethanamine

[Chem. 455]

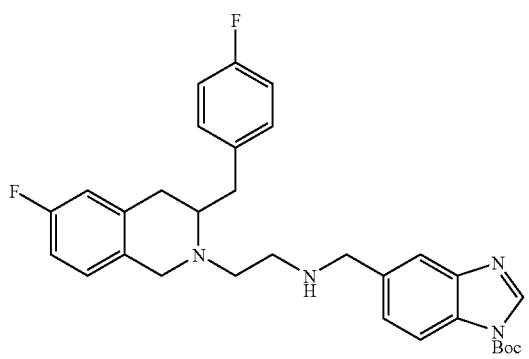

The reaction and treatment were carried out in the same manner as in Example 1-g) using 1-(tert-butoxycarbonyl)-1H-benzimidazole-5-carboxyaldehyde instead of benzaldehyde to obtain a title compound as a pale yellow oily substance.

$^1$H-NMR (CDCl$_3$) δ: 1.70 (9H, s), 2.37-2.50 (2H, m), 2.77-2.88 (6H, m), 3.07-3.18 (1H, m), 3.73 (2H, s), 3.93 (2H, s), 6.75 (1H, d, J=9.0 Hz), 6.83-7.03 (6H, m), 7.33 (1H, d, J=8.3 Hz), 7.70 (1H, s), 7.91 (1H, d, J=8.3 Hz), 8.42 (1H, s).

b) Production of N-(1H-benzimidazol-5-yl)methyl-2-[6-fluoro-3-(4-fluorobenzyl)-3,4-dihydroisoquinolin-2(1H)-yl]ethanamine

[Chem. 456]

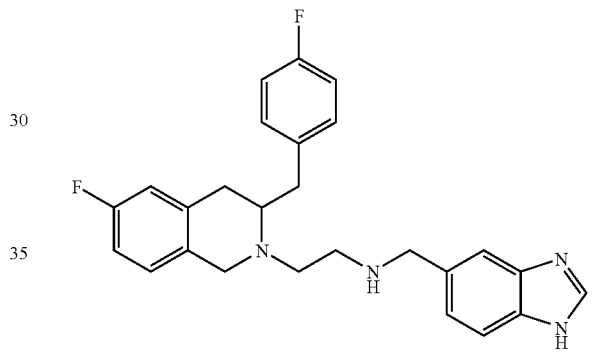

4.1 mg of N-[1-(tert-butoxycarbonyl)-1H-benzimidazol-5-yl]methyl-2-[6-fluoro-3-(4-fluorobenzyl)-3,4-dihydroisoquinolin-2(1H)-yl]ethanamine was dissolved in 0.5 mL of ethyl acetate, and 0.5 mL of 4N hydrochloric acid-ethyl acetate was added thereto under ice-cooling, followed by stirring at room temperature overnight. After completion of the reaction, to the reaction liquid were added a saturated aqueous sodium bicarbonate solution and ethyl acetate under ice-cooling. The organic layer was separated, the aqueous layer was further extracted by addition of ethyl acetate, and the organic layer was combined and washed with saturated brine. The organic layer was dried over anhydrous sodium sulfate and then concentrated under reduced pressure, and the solvent was removed by evaporation to obtain a crude composition.

The crude composition was purified by PLC to obtain 2.9 mg (yield 88%) of a desired product.

$^1$H-NMR (CDCl$_3$) δ: 2.42 (1H, dd, J=9.8, 13.4 Hz), 2.49 (1H, dd, J=3.7, 16.8 Hz), 2.75-2.90 (6H, m), 3.14-3.18 (1H, m), 3.73 (2H, s), 3.92 (2H, s), 6.75 (1H, dd, J=2.4, 9.3 Hz), 6.85 (1H, ddd, J=2.4, 8.3, 8.3 Hz), 6.92 (2H, ddd, J=2.0, 8.8, 8.8 Hz), 6.95 (1H, dd, J=5.6, 8.3 Hz), 7.01 (2H, ddd, J=2.2, 5.6, 8.8 Hz), 7.21 (1H, dd, J=1.5, 8.3 Hz), 7.52-7.64 (2H, m), 8.03 (1H, s).

Example 204

Production of N-(pyridin-4-yl)methyl-2-[6-fluoro-3-(4-fluorobenzyl)-3,4-dihydroisoquinolin-2(1H)-yl]-[(S)-1-methyl]ethanamine a) Production of tert-butyl 2-[6-fluoro-3-(4-fluorobenzyl)-3,4-dihydroisoquinolin-2(1H)-yl]-[(S)-1-methyl]ethyl carbamate

[Chem. 457]

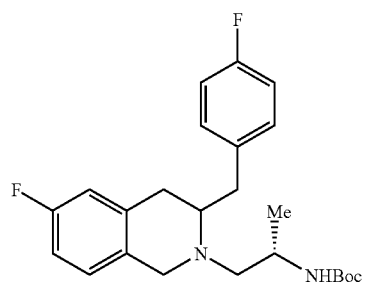

The reaction and treatment were carried out in the same manner as in Example 1-e) using 6-fluoro-3-(4-fluorobenzyl)-1,2,3,4-tetrahydroisoquinoline obtained in Example 53-a), and using (S)-2-(tert-butoxycarbonylamino)propionaldehyde instead of 2-(tert-butoxycarbonylamino)acetaldehyde to obtain a title compound as a pale yellow oily substance.

$^1$H-NMR (CDCl$_3$) δ: 1.17 (3H, d, J=8.6 Hz), 1.43 (9H, s), 2.40-2.65 (4H, m), 2.77-2.90 (2H, m), 3.17 (1H, m), 3.70-3.90 (2H, m), 4.68 (1H, m), 6.75-7.11 (7H, m).

b) Production of 2-[6-fluoro-3-(4-fluorobenzyl)-3,4-dihydroisoquinolin-2(1H)-yl]-[(S)-1-methyl]ethanamine

[Chem. 458]

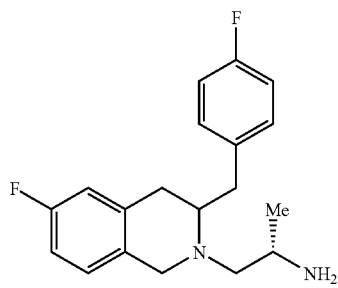

The reaction and treatment were carried out in the same manner as in Example 1-f) to obtain a title compound as a light yellow oily substance.

$^1$H-NMR (CDCl$_3$) δ: 1.20-1.28 (3H, m), 2.42-2.55 (2H, m), 2.85-2.96 (2H, m), 3.15-3.25 (2H, m), 3.70 (1H, m), 3.89 (1H, m), 4.11 (1H, d, J=14.4 Hz), 4.13 (1H, d, J=14.4 Hz), 6.73-7.11 (7H, m).

c) Production of N-(pyridin-4-yl)methyl-2-[6-fluoro-3-(4-fluorobenzyl)-3,4-dihydroisoquinolin-2(1H)-yl]-[(S)-1-methyl]ethanamine

[Chem. 459]

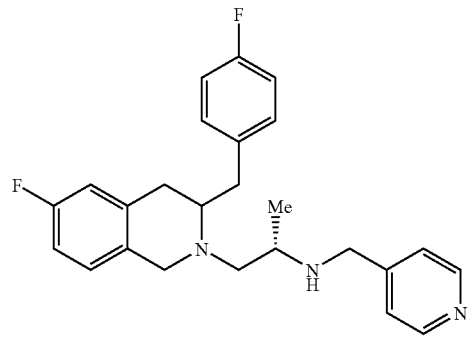

The reaction and treatment were carried out in the same manner as in Example 1-g) using pyridine-4-carboxyaldehyde instead of benzaldehyde to obtain a title compound as a yellow oily substance.

$^1$H-NMR (CDCl$_3$) δ: 0.99 (1.5H, d, J=6.1 Hz), 1.00 (1.5H, d, J=6.1 Hz), 2.36-2.90 (2H, m), 3.13 (0.5H, m), 3.20 (0.5H, m), 3.50-3.89 (4H, m), 6.77-7.17 (9H, m), 8.47-8.52 (2H, m).

Example 205

Production of N-(pyridin-4-yl)methyl-2-[6-fluoro-3-(4-fluorobenzyl)-3,4-dihydroisoquinolin-2(1H)-yl]-[(R)-1-methyl]ethanamine a) Production of tert-butyl 2-[6-fluoro-3-(4-fluorobenzyl)-3,4-dihydroisoquinolin-2(1H)-yl]-[(R)-1-methyl]ethyl carbamate

[Chem. 460]

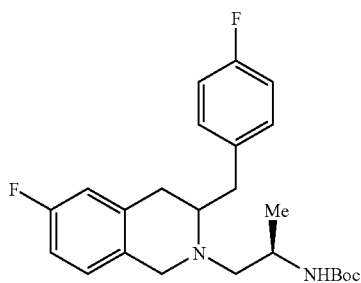

The reaction and treatment were carried out in the same manner as in Example 1-e) using 6-fluoro-3-(4-fluorobenzyl)-1,2,3,4-tetrahydroisoquinoline obtained in Example 53-a), and using (R)-2-(tert-butoxycarbonylamino)propionaldehyde instead of 2-(tert-butoxycarbonylamino)acetaldehyde to obtain a title compound as a light yellow oily substance.

$^1$H-NMR (CDCl$_3$) δ: 1.17 (3H, d, J=6.3 Hz), 1.43 (9H, s), 2.39-2.46 (4H, m), 2.79-2.89 (2H, m), 3.21-3.23 (1H, m), 3.67-3.89 (3H, m), 6.76 (1H, dd, J=2.4, 9.5 Hz), 6.87 (1H, ddd, J=2.4, 8.5, 8.5 Hz), 6.95-7.12 (3H, m), 7.04-7.12 (2H, m).

b) Production of 2-[6-fluoro-3-(4-fluorobenzyl)-3,4-dihydroisoquinolin-2(1H)-yl]-[(R)-1-methyl]ethanamine

[Chem. 461]

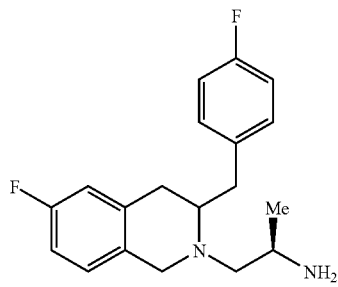

The reaction and treatment were carried out in the same manner as in Example 1-f) to obtain a title compound as a light yellow oily substance.

$^1$H-NMR (CDCl$_3$) δ: 1.04 (1.5H, d, J=6.3 Hz), 1.05 (1.5H, d, J=6.3 Hz), 2.23-2.37 (1H, m), 2.40-2.68 (3H, m), 2.81-2.92 (2H, m), 3.14-3.24 (2H, m), 3.69-3.76 (1H, m), 3.89 (1H, d, J=16.1 Hz), 6.77 (1H, dd, J=2.4, 9.5 Hz), 6.87 (1H, ddd, J=2.4, 8.5, 8.5 Hz), 6.94-7.04 (3H, m), 7.07 (2H, dd, J=5.6, 8.5 Hz).

c) Production of N-(pyridin-4-yl)methyl-2-[6-fluoro-3-(4-fluorobenzyl)-3,4-dihydroisoquinolin-2(1H)-yl]-[(R)-1-methyl]ethanamine

[Chem. 462]

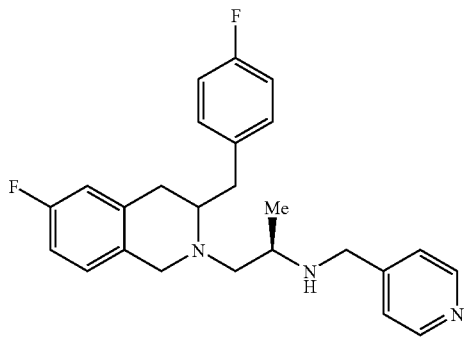

The reaction and treatment were carried out in the same manner as in Example 1-g) using pyridine-4-carboxyaldehyde instead of benzaldehyde to obtain a title compound as a yellow oily substance.

$^1$H-NMR (CDCl$_3$) δ: 1.00 (1.5H, d, J=6.1 Hz), 1.01 (1.5H, d, J=6.1 Hz), 2.34-2.69 (4H, m), 2.72-2.90 (3H, m), 3.10-3.24 (1H, m), 3.50-3.90 (4H, m), 6.78 (1H, dd, J=2.4, 9.5 Hz), 6.83-6.99 (4H, m), 7.03-7.17 (4H, m), 8.46 (1H, dd, J=1.5, 4.4 Hz), 8.51 (1H, dd, J=1.5, 4.4 Hz).

IR (ATR cm$^{-1}$): 1601, 1560, 1221, 1139, 860, 811, 757.

MS (FAB) m/z 408 (M)$^+$

Example 206

Production of N-(thiazol-4-yl)methyl-2-[6-fluoro-3-(4-fluorobenzyl)-3,4-dihydroisoquinolin-2(1H)-yl]ethanamine

[Chem. 463]

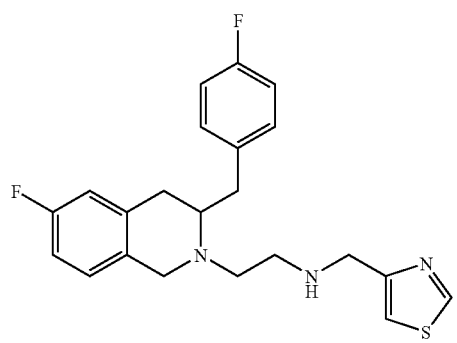

The reaction and treatment were carried out in the same manner as in Example 1-g) using 4-thiazole carboaldehyde instead of benzaldehyde to obtain a title compound as a yellow oily substance.

$^1$H-NMR (CDCl$_3$) δ: 2.40-2.53 (2H, m), 2.75-2.92 (6H, m), 3.17 (1H, m), 3.78 (2H, brs), 3.98 (2H, s), 6.75-7.07 (7H, m), 7.14 (1H, d, J=2.0 Hz), 8.76 (1H, d, J=2.0 Hz).

Example 207

Production of N-[(1-naphthyl)methyl]-2-[3-benzyl-3,4-dihydroisoquinolin-2(1H)-yl]ethanamine

[Chem. 464]

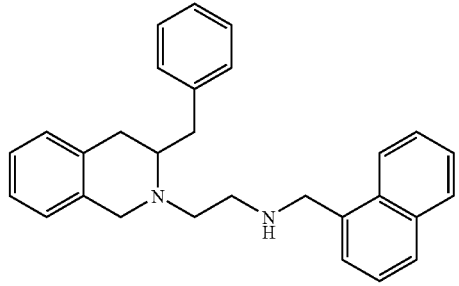

The reaction and treatment were carried out in the same manner as in Example 1-g) using 1-naphthylaldehyde instead of benzaldehyde to obtain a title compound as a yellow oily substance.

$^1$H-NMR (CDCl$_3$) δ: 2.44 (1H, dd, J=10.0, 13.2 Hz), 2.51 (1H, dd, J=3.6, 16.5 Hz), 2.73-2.82 (3H, m), 2.86-2.94 (3H, m), 3.16-3.21 (1H, m), 3.77 (2H, s), 4.24 (1H, d, J=14.4 Hz), 4.27 (1H, d, J=14.4 Hz), 7.00-7.07 (5H, m), 7.13-7.25 (4H, m), 7.41-7.44 (4H, m), 7.76 (1H, d, J=7.8 Hz), 7.82-7.85 (1H, m), 8.05-8.08 (1H, m).

Example 208

Production of 1-[2-[3-benzyl-3,4-dihydroisoquinolin-2(1H)-yl]ethyl]-3-phenylurea

[Chem. 465]

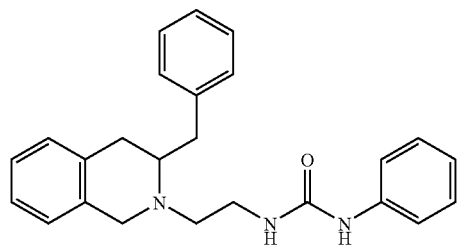

To a solution of 30 mg of 2-[3-benzyl-3,4-dihydroisoquinolin-2(1H)-yl]ethanamine obtained in Example 1-f) in 1 mL of methylene chloride was added 13.8 mg of phenyl isocyanate at room temperature, followed by stirring at room temperature for 1 hour. After completion of the reaction, the reaction liquid was concentrated under reduced pressure. The residue obtained was purified using PLC (chloroform:methanol=10:1) to obtain 32.2 mg (yield 60%) of a title compound as a pale yellow oily substance.

$^1$H-NMR (CDCl$_3$) δ: 2.55-2.65 (2H, m), 2.68-2.76 (1H, m), 2.80-2.90 (2H, m), 2.91 (1H, dd, J=5.6, 11.9 Hz), 3.27-3.40 (3H, m), 3.88 (1H, d, J=18.1 Hz), 3.94 (1H, d, J=18.1 Hz), 5.15-5.30 (1H, br), 6.95-7.00 (1H, m), 7.05-7.10 (2H, m), 7.13-7.35 (11H, m).

Example 209

Production of 1-[2-[3-benzyl-3,4-dihydroisoquinolin-2(1H)-yl]ethyl]-3-(3,4,5-trimethoxyphenyl)urea

[Chem. 466]

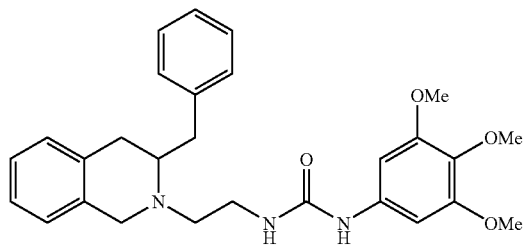

The reaction and treatment were carried out in the same manner as in Example 208 using trimethoxyphenyl isocyanate instead of phenyl isocyanate to obtain a title compound as a pale yellow amorphous substance.

$^1$H-NMR (CDCl$_3$) δ: 2.50-2.61 (1H, m), 2.62 (1H, dd, J=4.5, 17.0 Hz), 2.72-2.90 (3H, m), 2.93 (1H, dd, J=5.4, 13.7 Hz), 3.31-3.40 (3H, m), 3.67 (6H, s), 3.75 (3H, s), 3.91 (1H, d, J=18.4 Hz), 3.95 (1H, d, J=18.4 Hz), 5.30-5.51 (1H, br), 6.54 (2H, s), 7.05-7.10 (2H, s), 7.12-7.25 (5H, m), 7.29-7.34 (2H, m).

Example 210

Production of 1-benzyl-3-[2-[3-(4-fluorobenzyl)-3,4-dihydroisoquinolin-2(1H)-yl]ethyl]urea a) Production of 2-[3-(4-fluorobenzyl)-3,4-dihydroisoquinolin-2(1H)-yl]ethanamine

[Chem. 467]

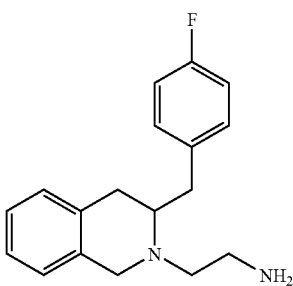

The reaction and treatment were carried out in the same manner as in Example 1-f) using tert-butyl 2-[3-(4-fluorobenzyl)-3,4-dihydroisoquinolin-2(1H)-yl]ethyl carbamate obtained in Example 10-c) to obtain a title compound as a light yellow oily substance.

$^1$H-NMR (CDCl$_3$) δ: 2.53 (1H, dd, J=10.0, 13.2 Hz), 2.59 (1H, dd, J=4.2, 15.8 Hz), 2.64-2.94 (6H, m), 3.17-3.26 (1H, m), 3.83 (2H, s), 4.42 (2H, brs), 6.96 (2H, dd, J=8.6, 8.6 Hz), 7.02-7.16 (6H, m).

b) Production of 1-benzyl-3-[2-[3-(4-fluorobenzyl)-3,4-dihydroisoquinolin-2(1H)-yl]ethyl]urea

[Chem. 468]

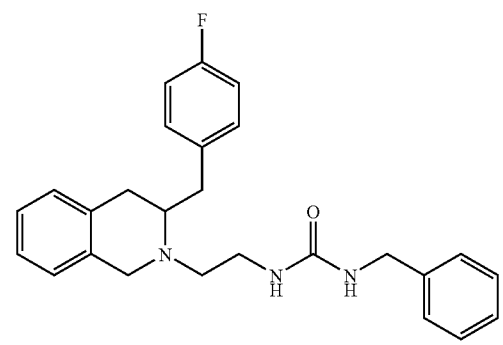

The reaction and treatment were carried out in the same manner as in Example 208 using benzyl isocyanate instead of phenyl isocyanate to obtain a title compound as a pale yellow amorphous substance.

$^1$H-NMR (CDCl$_3$) δ: 2.48 (1H, dd, J=9.5, 13.6 Hz), 2.62 (1H, dd, J=4.4, 15.6 Hz), 2.66-2.88 (4H, m), 3.16-3.23 (1H, m), 3.24-3.40 (2H, m), 3.78 (1H, d, J=16.1 Hz), 3.82 (1H, d, J=16.1 Hz), 4.29 (2H, d, J=5.6 Hz), 4.80-4.90 (1H, br), 5.00-

5.18 (1H, br), 6.95 (2H, dd, J=8.7, 8.7 Hz), 7.02-7.09 (4H, m), 7.14-7.20 (2H, m), 7.20-7.28 (5H, m).

Example 211

Production of 1-[2-[3-(4-fluorobenzyl)-3,4-dihydroisoquinolin-2(1H)-yl]ethyl]-3-(2-phenyl ethyl)urea

[Chem. 469]

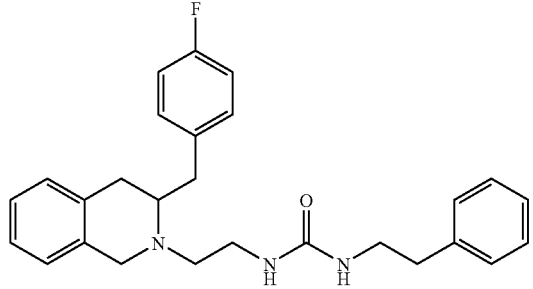

The reaction and treatment were carried out in the same manner as in Example 208 using 2-[3-(4-fluorobenzyl)-3,4-dihydroisoquinolin-2(1H)-yl]ethanamine obtained in Example 210-a) as a starting material, and using phenethyl isocyanate instead of phenyl isocyanate to obtain a title compound as a pale yellow amorphous substance.

$^1$H-NMR (CDCl$_3$) δ: 2.50 (1H, dd, J=9.2, 13.6 Hz), 2.55 (1H, dd, J=4.2, 17.0 Hz), 2.64-2.89 (6H, m), 3.18-3.44 (5H, m), 3.89 (2H, brs), 4.32 (1H, brs), 4.68-4.86 (1H, br), 6.95 (2H, dd, J=8.7, 8.7 Hz), 7.02-7.09 (4H, m), 7.12-7.30 (7H, m).

Example 212

Production of 1-[2-[3-(4-fluorobenzyl)-3,4-dihydroisoquinolin-2(1H)-yl]ethyl]-3-phenylurea

[Chem. 470]

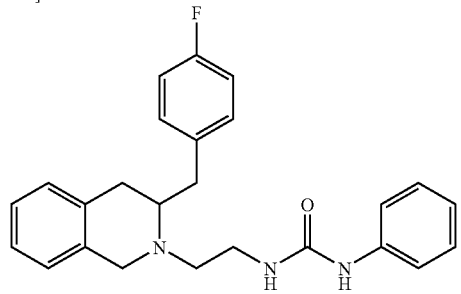

The reaction and treatment were carried out in the same manner as in Example 208 using 2-[3-(4-fluorobenzyl)-3,4-dihydroisoquinolin-2(1H)-yl]ethanamine obtained in Example 210-a) as a starting material to obtain a title compound as a pale yellow amorphous substance.

$^1$H-NMR (CDCl$_3$) δ: 2.55 (1H, dd, J=9.3, 13.4 Hz), 2.58 (1H, dd, J=4.9, 16.4 Hz), 2.72-2.94 (4H, m), 3.24-3.30 (1H, m), 3.34-3.42 (2H, m), 3.90 (2H, brs), 5.11-5.17 (1H, br), 6.99 (2H, ddd, J=2.2, 6.4, 8.6 Hz), 6.99-7.02 (1H, m), 7.06-7.12 (4H, m), 7.18-7.29 (7H, m).

Example 213

Production of 1-(3-cyanophenyl)-3-[2-[3-(4-fluorobenzyl)-3,4-dihydroisoquinolin-2(1H)-yl]ethyl]urea

[Chem. 471]

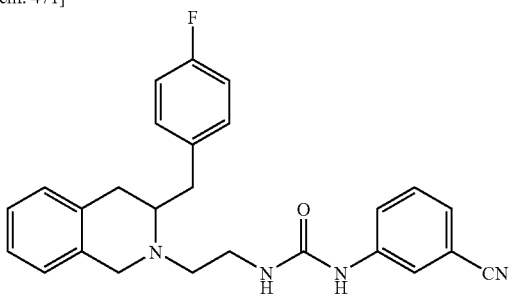

The reaction and treatment were carried out in the same manner as in Example 208 using 2-[3-(4-fluorobenzyl)-3,4-dihydroisoquinolin-2(1H)-yl]ethanamine obtained in Example 210-a) as a starting material, and using 3-cyanophenyl isocyanate instead of phenyl isocyanate to obtain a title compound as a pale yellow amorphous substance.

$^1$H-NMR (CDCl$_3$) δ: 2.61 (1H, dd, J=8.8, 13.6 Hz), 2.65 (1H, dd, J=5.1, 15.6 Hz), 2.75-2.83 (1H, m), 2.85-2.95 (3H, m), 3.30-3.40 (3H, m), 3.95 (2H, brs), 5.08-5.15 (1H, br), 7.00 (2H, ddd, J=8.7, 8.7 Hz), 7.09-7.15 (2H, m), 7.19-7.26 (4H, m), 7.36-7.48 (3H, m), 7.52-7.60 (1H, m), 7.66-7.71 (1H, m).

Example 214

Production of 1-[3-[3-(4-fluorobenzyl)-3,4-dihydroisoquinolin-2(1H)-yl]propyl]-3-phenylurea a) Production of tert-butyl 3-[3-(4-fluorobenzyl)-3,4-dihydroisoquinolin-2(1H)-yl]propyl carbamate

[Chem. 472]

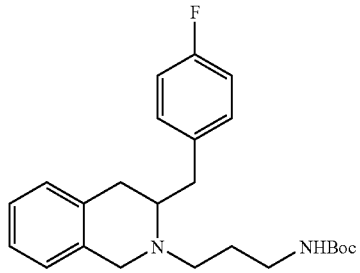

The reaction and treatment were carried out in the same manner as in Example 1-e) using 3-(tert-butoxycarbonylamino)propionaldehyde instead of 2-(tert-butoxycarbonylamino)acetaldehyde to obtain a title compound as a pale yellow oily substance.

$^1$H-NMR (CDCl$_3$) δ: 1.41 (9H, s), 1.75 (2H, tt, J=6.5, 6.5 Hz), 2.44 (1, dd, J=10.2, 13.2 Hz), 2.55 (1H, dd, J=4.0, 16.4 Hz), 2.64-2.78 (2H, m), 2.84 (1H, dd, J=5.1, 16.4 Hz), 2.90 (1H, dd, J=4.1, 13.2 Hz), 3.15-3.27 (3H, m), 3.80 (1H, d,

J=16.1 Hz), 3.87 (1H, d, J=16.1 Hz), 5.26 (1H, brs), 6.97 (2H, ddd, J=2.2, 6.5, 8.7 Hz), 7.01-7.09 (4H, m), 7.12-7.17 (2H, m).

b) Production of 3-[3-(4-fluorobenzyl)-3,4-dihydroisoquinolin-2(1H)-yl]propanamine

[Chem. 473]

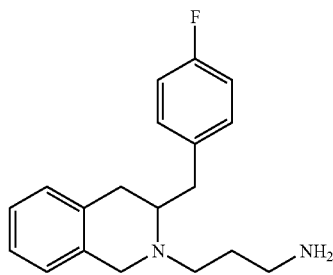

The reaction and treatment were carried out in the same manner as in Example 1-f) to obtain a title compound as a light yellow oily substance.

$^1$H-NMR (CDCl$_3$) δ: 1.66-1.74 (2H, m), 2.45 (1H, dd, J=10.2, 13.0 Hz), 2.59 (1H, dd, J=4.0, 16.5 Hz), 2.68-2.97 (6H, m), 3.21-3.29 (1H, m), 3.84 (1H, d, J=15.9 Hz), 3.89 (1H, d, J=15.9 Hz), 7.00-7.09 (6H, m), 7.12-7.20 (2H, m).

c) Production of 1-[3-[3-(4-fluorobenzyl)-3,4-dihydroisoquinolin-2(1H)-yl]propyl]-3-phenylurea

[Chem. 474]

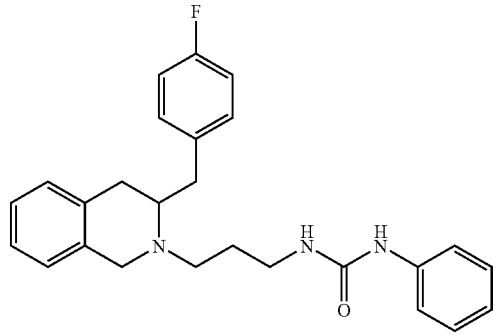

The reaction and treatment were carried out in the same manner as in Example 208 to obtain a title compound as a pale yellow amorphous substance.

$^1$H-NMR (CDCl$_3$) δ: 1.75-1.84 (2H, m), 2.42 (1H, dd, J=10.1, 13.2 Hz), 2.53 (1H, dd, J=4.0, 16.6 Hz), 2.71 (1H, dd, J=4.8, 16.6 Hz), 2.79 (2H, t, J=6.1 Hz), 2.86 (1H, dd, J=4.4, 13.2 Hz), 3.16-3.24 (1H, m), 3.30-3.48 (2H, m), 3.81 (2H, brs), 6.36-6.58 (1H, br), 6.97 (2H, dd, J=8.7, 8.7 Hz), 6.99-7.09 (5H, m), 7.12-7.20 (7H, m).

Example 215

Production of 1-benzyl-3-[3-[3-(4-fluorobenzyl)-3,4-dihydroisoquinolin-2(1H)-yl]propyl]urea

[Chem. 475]

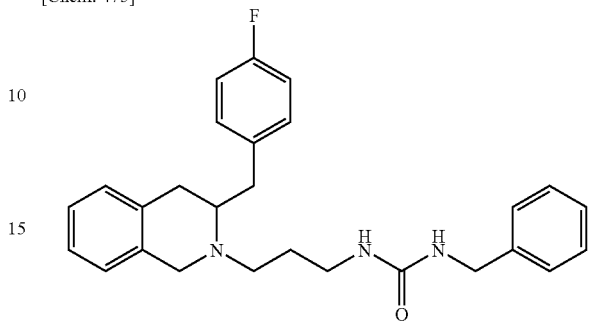

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using benzyl isocyanate instead of phenyl isocyanate to obtain a title compound as a pale yellow amorphous substance.

$^1$H-NMR (CDCl$_3$) δ: 1.70-1.80 (2H, m), 2.41 (1H, dd, J=10.0, 13.2 Hz), 2.51 (1H, dd, J=3.6, 16.6 Hz), 2.72-2.80 (3H, m), 2.88 (1H, dd, J=4.2, 13.2 Hz), 3.17-3.24 (1H, m), 3.25-3.36 (2H, m), 3.77 (2H, brs), 4.12 (1H, dd, J=5.6, 15.1 Hz), 4.28 (1H, dd, J=6.1, 15.1 Hz), 4.98-5.22 (1H, br), 6.95 (2H, dd, J=8.7, 8.7 Hz), 6.99-7.06 (4H, m), 7.12-7.18 (5H, m), 7.19-7.24 (3H, m).

Example 216

Production of 1-[3-[3-(4-fluorobenzyl)-3,4-dihydroisoquinolin-2(1H)-yl]propyl]-3-(2-phenyl ethyl) urea

[Chem. 476]

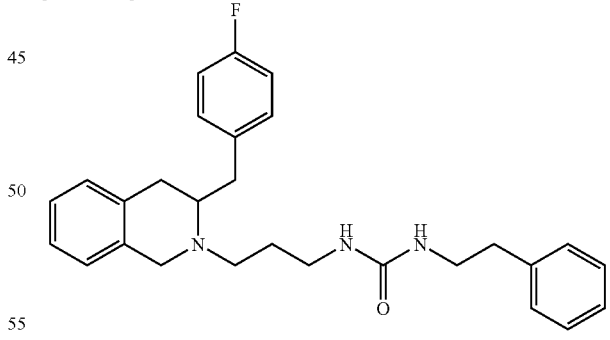

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using phenethyl isocyanate instead of phenyl isocyanate to obtain a title compound as a pale yellow amorphous substance.

$^1$H-NMR (CDCl$_3$) δ: 1.68-1.79 (2H, m), 2.43 (1H, dd, J=10.0, 13.4 Hz), 2.55 (1H, dd, J=3.4, 16.6 Hz), 2.64 (2H, t, J=6.8 Hz), 2.76 (1H, dd, J=5.9, 16.6 Hz), 2.78 (2H, t, J=6.1 Hz), 2.88 (1H, dd, J=4.4, 13.4 Hz), 3.11-3.34 (6H, m), 3.80

(2H, brs), 4.58-4.80 (1H, br), 6.96 (2H, ddd, J=2.2, 6.6, 8.8 Hz), 7.02-7.08 (6H, m), 7.16-7.20 (3H, m), 7.22-7.24 (2H, m).

Example 217

Production of 1-(2-ethyl phenyl)-3-[3-[3-(4-fluorobenzyl)-3,4-dihydroisoquinolin-2(1H)-yl]propyl]urea

[Chem. 477]

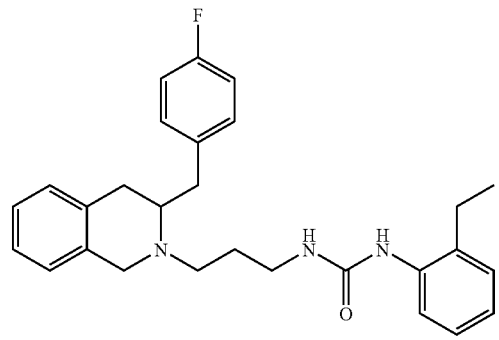

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 2-ethylphenyl isocyanate instead of phenyl isocyanate to obtain a title compound as a pale yellow amorphous substance.

MS (EI) m/z 445 (M)+

Example 218

Production of 1-(3-ethyl phenyl)-3-[3-[3-(4-fluorobenzyl)-3,4-dihydroisoquinolin-2(1H)-yl]propyl]urea

[Chem. 478]

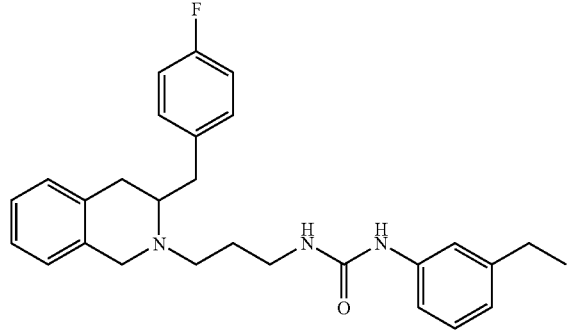

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 3-ethylphenyl isocyanate instead of phenyl isocyanate to obtain a title compound as a pale yellow amorphous substance.

MS (EI) m/z 445 (M)+

Example 219

Production of 1-(4-ethyl phenyl)-3-[3-[3-(4-fluorobenzyl)-3,4-dihydroisoquinolin-2(1H)-yl]propyl]urea

[Chem. 479]

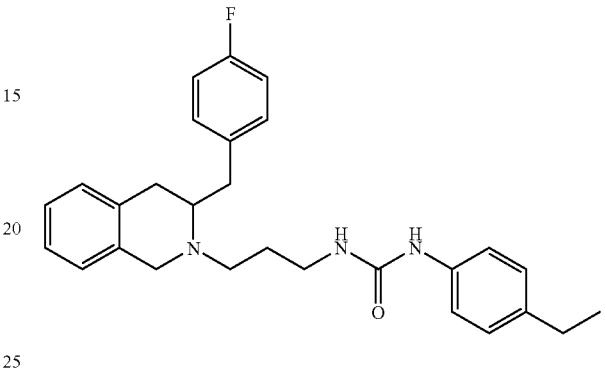

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 4-ethylphenyl isocyanate instead of phenyl isocyanate to obtain a title compound as a pale yellow amorphous substance.

MS (EI) m/z 445 (M)+

Example 220

Production of 1-[3-[3-(4-fluorobenzyl)-3,4-dihydroisoquinolin-2(1H)-yl]propyl]-3-(2-methoxyphenyl)urea

[Chem. 480]

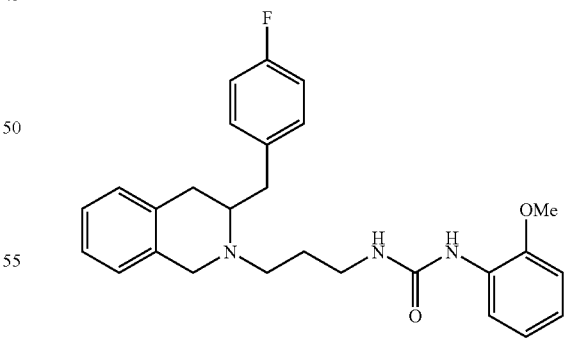

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 2-methoxyphenyl isocyanate instead of phenyl isocyanate to obtain a title compound as a pale yellow amorphous substance.

MS (FAB) m/z 448 (M+H)+

Example 221

Production of 1-[3-[3-(4-fluorobenzyl)-3,4-dihydroisoquinolin-2(1H)-yl]propyl]-3-(3-methoxyphenyl)urea

[Chem. 481]

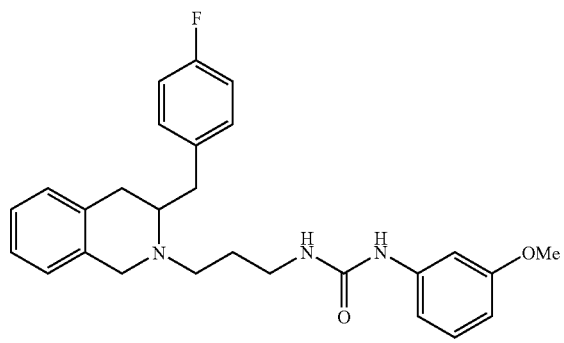

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 3-methoxyphenyl isocyanate instead of phenyl isocyanate to obtain a title compound as a pale yellow amorphous substance.

MS (FAB) m/z 448 (M+H)$^+$

Example 222

Production of 1-[3-[3-(4-fluorobenzyl)-3,4-dihydroisoquinolin-2(1H)-yl]propyl]-3-(4-methoxyphenyl)urea

[Chem. 482]

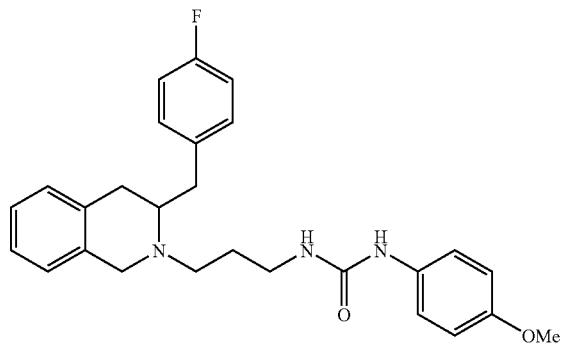

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 4-methoxyphenyl isocyanate instead of phenyl isocyanate to obtain a title compound as a pale yellow amorphous substance.

MS (FAB) m/z 448 (M+H)$^+$

Example 223

Production of 1-(3-dimethylaminophenyl)-3-[3-[3-(4-fluorobenzyl)-3,4-dihydroisoquinolin-2(1H)-yl]propyl]urea

[Chem. 483]

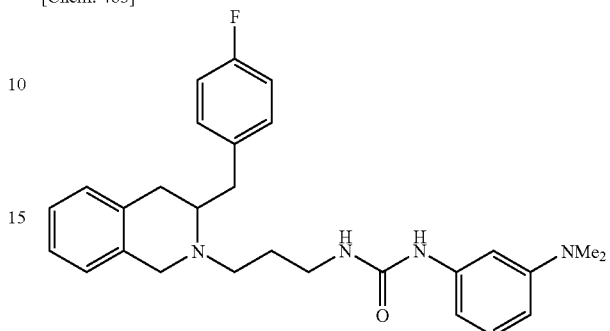

30 mg of 3-[3-(4-fluorobenzyl)-3,4-dihydroisoquinolin-2(1H)-yl]propanamine obtained in Example 214-b), 28 mg of (3-dimethylaminophenyl)phenyl carbamate, and 31 mg of triethylamine were dissolved in 1 mL of toluene, followed by stirring under reflux for 30 minutes. After completion of the reaction, water was added to the reaction liquid, followed by extraction with ethyl acetate. The organic layer was then washed with saturated brine, dried over anhydrous sodium sulfate and then concentrated under reduced pressure. The residue obtained was purified using PLC (chloroform:methanol=10:1) to obtain 22.3 mg (yield 48%) of a title compound as a pale yellow oily substance.

$^1$H-NMR (CDCl$_3$) δ: 1.76 (2H, tt, J=6.1, 6.1 Hz), 2.37 (1H, dd, J=10.3, 12.9 Hz), 2.47 (1H, dd, J=4.0, 16.7 Hz), 2.62-2.88 (4H, m), 2.86 (6H, s), 3.23-3.24 (1H, m), 3.25-3.29 (2H, m), 3.75 (1H, d, J=16.1 Hz), 3.81 (1H, d, J=16.1 Hz), 5.98 (1H, brs), 6.35-6.39 (1H, m), 6.45 (1H, d, J=7.8 Hz), 6.49 (1H, brs), 6.66 (1H, brs), 6.80-7.04 (6H, m), 7.10-7.24 (3H, m).

Example 224

Production of 1-(2-chlorophenyl)-3-[3-[3-(4-fluorobenzyl)-3,4-dihydroisoquinolin-2(1H)-yl]propyl]urea

[Chem. 484]

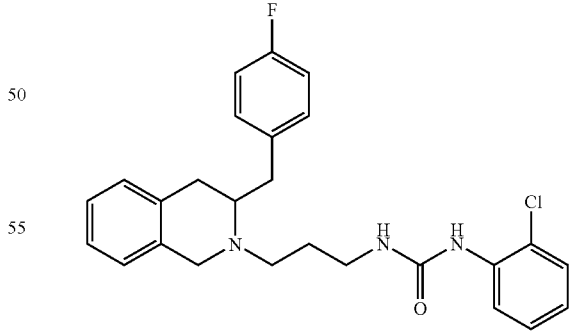

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 2-chlorophenyl isocyanate instead of phenyl isocyanate to obtain a title compound as a pale yellow amorphous substance MS (FAB) m/z 452, 454 (M+H)$^+$.

Example 225

Production of 1-(3-chlorophenyl)-3-[3-[3-(4-fluorobenzyl)-3,4-dihydroisoquinolin-2(1H)-yl]propyl]urea

[Chem. 485]

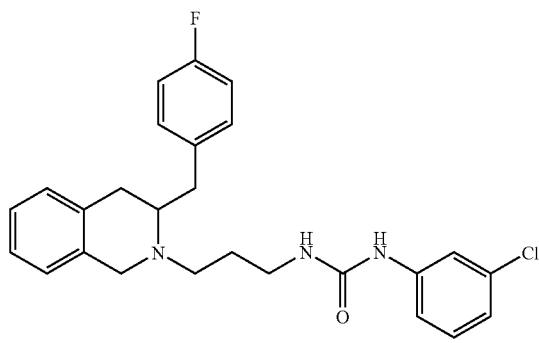

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 3-chlorophenyl isocyanate instead of phenyl isocyanate to obtain a title compound as a pale yellow amorphous substance.

MS (FAB) m/z 452, 454 (M+H)$^+$

Example 226

Production of 1-(4-chlorophenyl)-3-[3-[3-(4-fluorobenzyl)-3,4-dihydroisoquinolin-2(1H)-yl]propyl]urea

[Chem. 486]

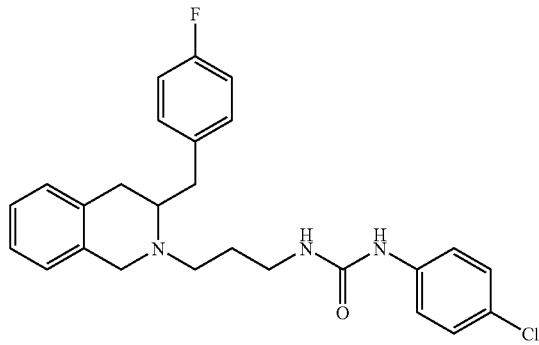

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 4-chlorophenyl isocyanate instead of phenyl isocyanate to obtain a title compound as a pale yellow amorphous substance.

MS (FAB) m/z 452, 454 (M+H)$^+$

Example 227

Production of 1-(2-cyanophenyl)-3-[3-[3-(4-fluorobenzyl)-3,4-dihydroisoquinolin-2(1H)-yl]propyl]urea

[Chem. 487]

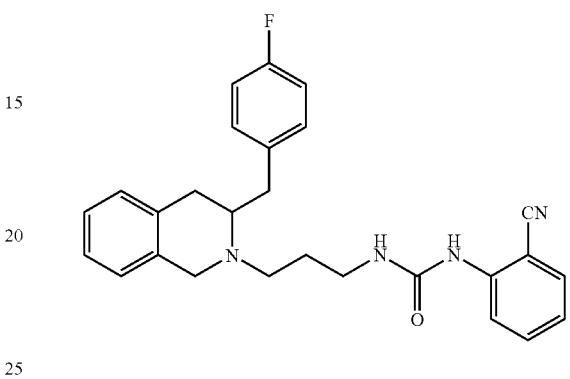

The reaction and treatment were carried out in the same manner as in Example 223 using (2-cyanophenyl)phenyl carbamate instead of (3-dimethylaminophenyl)phenyl carbamate to obtain a title compound as a pale yellow amorphous substance.

$^1$H-NMR (CDCl$_3$) δ: 1.82 (2H, tt, J=6.4, 6.4 Hz), 2.46 (1H, dd, J=10.0, 13.2 Hz), 2.47 (1H, dd, J=4.0, 17.1 Hz), 2.70-2.89 (4H, m), 3.23-3.34 (1H, m), 3.25-3.42 (2H, m), 3.75-3.79 (2H, br), 4.15-4.25 (1H, br), 6.25-6.45 (1H, br), 6.81 (1H, dd, J=2.2, 6.4 Hz), 6.85-7.24 (10H, m), 7.40-7.46 (1H, m).

Example 228

Production of 1-(3-acetylphenyl)-3-[3-[3-(4-fluorobenzyl)-3,4-dihydroisoquinolin-2(1H)-yl]propyl]urea

[Chem. 488]

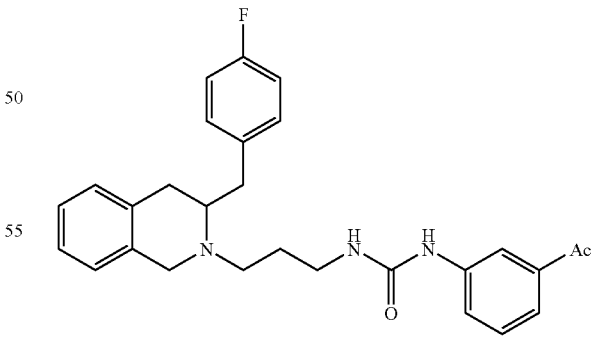

The reaction and treatment were carried out in the same manner as in Example 223 using (3-acetylphenyl)phenyl carbamate instead of (3-dimethylaminophenyl)phenyl carbamate to obtain a title compound as a pale yellow amorphous substance.

MS (FAB) m/z 460 (M+H)$^+$

Example 229

Production of 1-(4-acetylphenyl)-3-[3-[3-(4-fluorobenzyl)-3,4-dihydroisoquinolin-2(1H)-yl]propyl]urea

[Chem. 489]

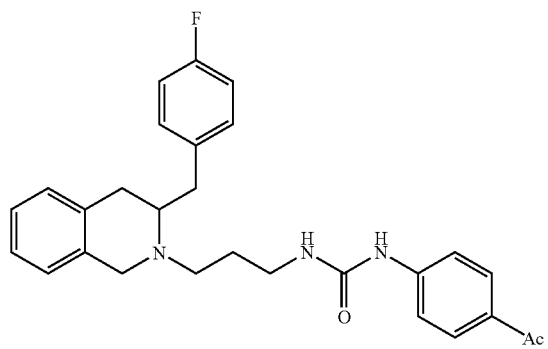

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 4-acetylphenyl isocyanate instead of phenyl isocyanate to obtain a title compound as a pale yellow amorphous substance.

MS (FAB) m/z 460 (M+H)$^+$

Example 230

Production of 1-(3-cyanophenyl)-3-[3-[3-(4-fluorobenzyl)-3,4-dihydroisoquinolin-2(1H)-yl]propyl]urea

[Chem. 490]

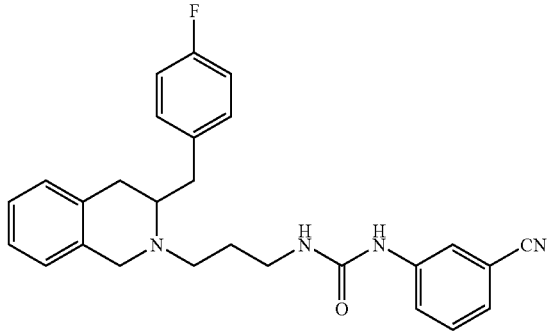

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 3-cyanophenyl isocyanate instead of phenyl isocyanate to obtain a title compound as a pale yellow amorphous substance.

MS (FAB) m/z 443 (M+H)$^+$

Example 231

Production of 1-(4-cyanophenyl)-3-[3-[3-(4-fluorobenzyl)-3,4-dihydroisoquinolin-2(1H)-yl]propyl]urea

[Chem. 491]

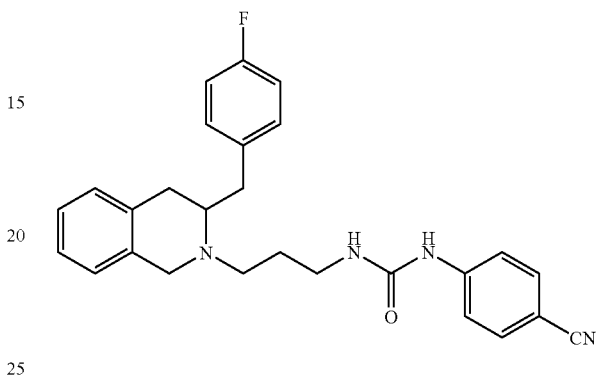

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 4-cyanophenyl isocyanate instead of phenyl isocyanate to obtain a title compound as a pale yellow amorphous substance.

MS (FAB) m/z 443 (M+H)$^+$

Example 232

Production of 1-[3-[3-(4-fluorobenzyl)-3,4-dihydroisoquinolin-2(1H)-yl]propyl]-3-(2-nitrophenyl)urea

[Chem. 492]

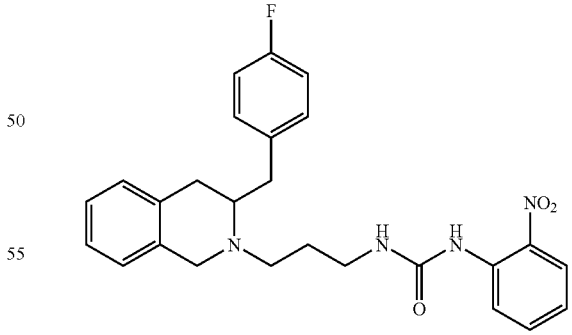

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 2-nitrophenyl isocyanate instead of phenyl isocyanate to obtain a title compound as a pale yellow amorphous substance.

MS (FAB) m/z 463 (M+H)$^+$

Example 233

Production of 1-[3-[3-(4-fluorobenzyl)-3,4-dihydroisoquinolin-2(1H)-yl]propyl]-3-(3-nitrophenyl)urea

[Chem. 493]

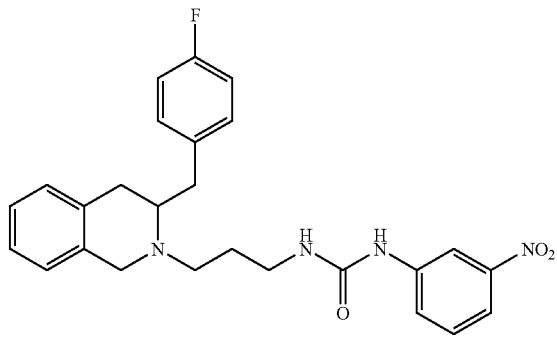

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 3-nitrophenyl isocyanate instead of phenyl isocyanate to obtain a title compound as a pale yellow amorphous substance.

MS (FAB) m/z 463 (M+H)$^+$

Example 234

Production of 1-[3-[3-(4-fluorobenzyl)-3,4-dihydroisoquinolin-2(1H)-yl]propyl]-3-(4-nitrophenyl)urea

[Chem. 494]

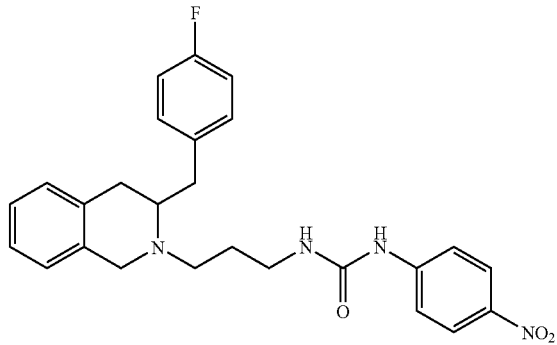

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 4-nitrophenyl isocyanate instead of phenyl isocyanate to obtain a title compound as a pale yellow amorphous substance.

MS (FAB) m/z 463 (M+H)$^+$

Example 235

Production of 1-(4-dimethylaminophenyl)-3-[3-[3-(4-fluorobenzyl)-3,4-dihydroisoquinolin-2(1H)-yl]propyl]urea

[Chem. 495]

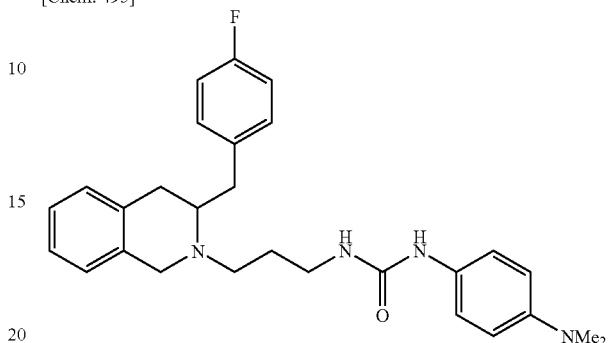

The reaction and treatment were carried out in the same manner as in Example 208 using 3-[3-(4-fluorobenzyl)-3,4-dihydroisoquinolin-2(1H)-yl]propanamine obtained in Example 214-b) as a starting material, and using 4-dimethylaminophenyl isocyanate instead of phenyl isocyanate to obtain a title compound as a pale yellow amorphous substance.

MS (FAB) m/z 461 (M+H)$^+$

Example 236

Production of 1-[3-[3-(4-chlorobenzyl)-6-fluoro-3,4-dihydroisoquinolin-2(1H)-yl]propyl]-3-phenylurea a) Production of tert-butyl 3-[3-(4-chlorobenzyl)-6-fluoro-3,4-dihydroisoquinolin-2(1H)-yl]propyl carbamate

[Chem. 496]

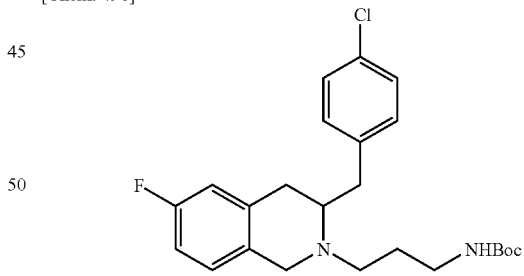

The reaction and treatment were carried out in the same manner as in Example 1-e) using 3-(4-chlorobenzyl)-6-fluoro-1,2,3,4-tetrahydroisoquinoline obtained in Example 55-a) as a starting material, and using 3-(tert-butoxycarbonylamino)propionaldehyde instead of 2-(tert-butoxycarbonylamino)acetaldehyde to obtain a title compound as a pale yellow oily substance.

$^1$H-NMR (CDCl$_3$) δ: 1.41 (9H, s), 1.70-1.79 (2H, m), 2.40 (1H, dd, J=10.3, 13.2 Hz), 2.51 (1H, dd, J=3.5, 16.7 Hz), 2.64-2.78 (2H, m), 2.81 (1H, dd, J=5.0, 16.7 Hz), 2.89 (1H, dd, J=3.9, 13.2 Hz), 3.15-3.26 (3H, m), 3.74 (1H, d, J=15.7 Hz), 3.83 (1H, d, J=15.7 Hz), 5.10-5.23 (1H, br), 6.75 (1H, dd, J=2.4, 9.3 Hz), 6.86 (1H, ddd, J=2.4, 8.3, 8.3 Hz), 7.01 (1H, dd, J=5.9, 8.3 Hz), 7.04 (2H, d, J=8.0 Hz), 7.25 (2H, d, J=8.0 Hz).

b) Production of 3-[3-(4-chlorobenzyl)-6-fluoro-3,4-dihydroisoquinolin-2(1H)-yl]propanamine

[Chem. 497]

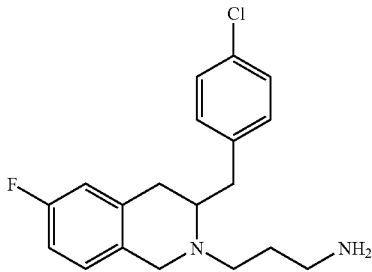

The reaction and treatment were carried out in the same manner as in Example 1-f) to obtain a title compound as a pale yellow oily substance.

$^1$H-NMR (CDCl$_3$) δ: 1.60-1.72 (2H, m), 2.40 (1H, dd, J=10.2, 13.1 Hz), 2.54 (1H, dd, J=3.9, 16.7 Hz), 2.64-2.95 (6H, m), 3.18-3.29 (3H, m), 3.79 (1H, d, J=15.9 Hz), 3.87 (1H, d, J=15.9 Hz), 6.76 (1H, dd, J=2.5, 9.3 Hz), 6.88 (1H, ddd, J=2.5, 8.4, 8.4 Hz), 7.00 (1H, dd, J=5.7, 8.4 Hz), 7.02 (2H, d, J=8.0 Hz), 7.27 (2H, d, J=8.0 Hz).

c) Production of 1-[3-[3-(4-chlorobenzyl)-6-fluoro-3,4-dihydroisoquinolin-2(1H)-yl]propyl]-3-phenylurea

[Chem. 498]

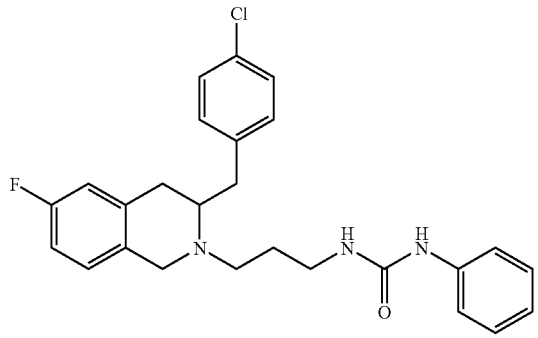

The reaction and treatment were carried out in the same manner as in Example 208 to obtain a title compound as a pale yellow amorphous.

$^1$H-NMR (CDCl$_3$) δ: 1.74-1.82 (2H, m), 2.37 (1H, dd, J=10.0, 13.2 Hz), 2.46 (1H, dd, J=3.8, 17.1 Hz), 2.66 (1H, dd, J=5.6, 17.1 Hz), 2.73-2.78 (2H, m), 2.83 (1H, dd, J=4.1, 13.2 Hz), 3.13-3.20 (1H, m), 3.29-3.45 (2H, m), 3.71 (1H, d, J=15.8 Hz), 3.78 (1H, d, J=15.8 Hz), 6.42-6.45 (1H, br), 6.73 (1H, dd, J=2.7, 9.2 Hz), 6.80-7.02 (1H, m), 6.87 (1H, ddd, J=2.7, 8.6, 8.6 Hz), 6.98 (1H, dd, J=5.6, 8.6 Hz), 6.99 (2H, d, J=8.3 Hz), 7.13-7.19 (4H, m), 7.25 (2H, d, J=8.3 Hz).

Example 237

Production of 1-[6-chloro-3-(4-fluorobenzyl)-3,4-dihydroisoquinolin-2(1H)-yl]propyl]-3-phenylurea a) Production of tert-butyl 3-[6-chloro-3-(4-fluorobenzyl)-3,4-dihydroisoquinolin-2(1H)-yl]propyl carbamate

[Chem. 499]

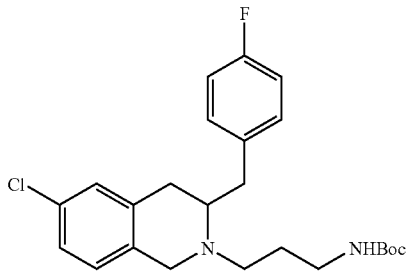

The reaction and treatment were carried out in the same manner as in Example 1-e) using 6-chloro-3-(4-fluorobenzyl)-1,2,3,4-tetrahydroisoquinoline obtained in Example 57-a) as a starting material, and using 3-(tert-butoxycarbonylamino)propionaldehyde instead of 2-(tert-butoxycarbonylamino)acetaldehyde to obtain a title compound as a pale yellow oily substance.

$^1$H-NMR (CDCl$_3$) δ: 1.41 (9H, s), 1.70-1.77 (2H, m), 2.40 (1H, dd, J=10.3, 13.2 Hz), 2.51 (1H, dd, J=3.9, 1.8 Hz), 2.64-2.84 (3H, m), 2.89 (1H, dd, J=3.9, 12.9 Hz), 3.17-3.24 (3H, m), 3.75 (1H, d, J=15.9 Hz), 3.83 (1H, d, J=15.9 Hz), 6.95-7.01 (3H, m), 7.04-7.08 (3H, m), 7.13 (1H, dd, J=2.0, 8.0 Hz).

b) Production of 3-[6-chloro-3-(4-fluorobenzyl)-3,4-dihydroisoquinolin-2(1H)-yl]propanamine

[Chem. 500]

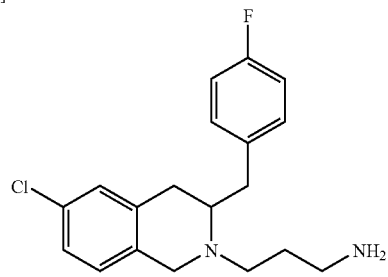

The reaction and treatment were carried out in the same manner as in Example 1-f) to obtain a title compound as a pale yellow oily substance.

$^1$H-NMR (CDCl$_3$) δ: 1.71-1.79 (2H, m), 2.37 (1H, dd, J=10.2, 13.2 Hz), 2.49 (1H, dd, J=3.6, 17.1 Hz), 2.63-2.82

(5H, m), 2.89 (1H, dd, J=3.4, 12.7 Hz), 3.15-3.22 (1H, m), 3.73 (1H, d, J=16.4 Hz), 3.83 (1H, d, J=16.4 Hz), 6.94-7.11 (7H, m).

c) Production of 1-[3-[6-chloro-3-(4-fluorobenzyl)-3,4-dihydroisoquinolin-2(1H)-yl]propyl]-3-phenylurea

[Chem. 501]

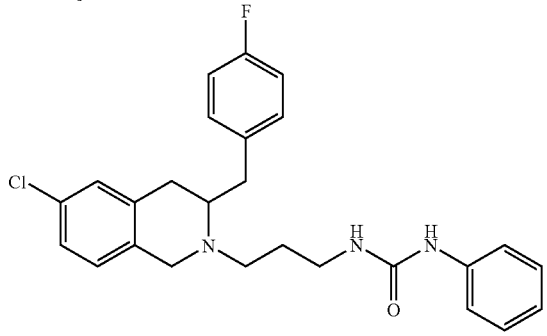

The reaction and treatment were carried out in the same manner as in Example 208 to obtain a title compound as a pale yellow amorphous.

$^1$H-NMR (CDCl$_3$) δ: 1.51-1.86 (2H, m), 2.36 (1H, dd, J=10.2, 13.0 Hz), 2.46 (1H, dd, J=3.1, 16.6 Hz), 2.64 (1H, dd, J=5.2, 16.6 Hz), 2.73-2.81 (2H, m), 2.84 (1H, dd, J=4.1, 13.5 Hz), 3.14-3.21 (1H, m), 3.29-3.46 (2H, m), 3.72 (1H, d, J=16.6 Hz), 3.78 (1H, d, J=16.6 Hz), 6.94-7.04 (7H, m), 7.13-7.19 (5H, m).

Example 238

Production of 1-[3-[6-fluoro-3-(4-fluorobenzyl)-3,4-dihydroisoquinolin-2(1H)-yl]propyl]-3-phenylurea a) Production of tert-butyl 3-[6-fluoro-3-(4-fluorobenzyl)-3,4-dihydroisoquinolin-2(1H)-yl]propyl carbamate

[Chem. 502]

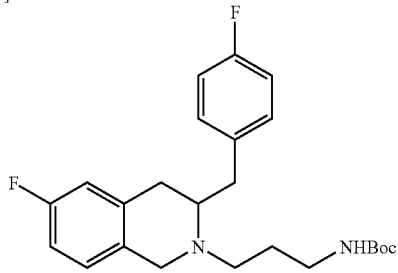

The reaction and treatment were carried out in the same manner as in Example 1-e) using 6-fluoro-3-(4-fluorobenzyl)-1,2,3,4-tetrahydroisoquinoline obtained in Example 53-a) as a starting material, and using 3-(tert-butoxycarbonylamino)propionaldehyde instead of 2-(tert-butoxycarbonylamino)acetaldehyde to obtain a title compound as a pale yellow oily substance.

$^1$H-NMR (CDCl$_3$) δ: 1.41 (9H, s), 1.70-1.80 (2H, m), 2.42 (1H, dd, J=10.3, 13.3 Hz), 2.53 (1H, dd, J=3.9, 16.0 Hz), 2.66-2.80 (2H, m), 2.82 (1H, dd, J=5.2, 16.0 Hz), 2.93 (1H, dd, J=4.2, 13.2 Hz), 3.14-3.29 (3H, m), 3.77 (1H, d, J=15.8 Hz), 3.86 (1H, d, J=15.8 Hz), 5.18 (1H, brs), 6.76 (1H, dd, J=2.4, 9.2 Hz), 6.87 (1H, ddd, J=2.4, 8.6, 8.6 Hz), 6.98 (2H, ddd, J=2.0, 6.6, 8.6 Hz), 7.00-7.10 (3H, m).

b) Production of 3-[6-fluoro-3-(4-fluorobenzyl)-3,4-dihydroisoquinolin-2(1H)-yl]propanamine

[Chem. 503]

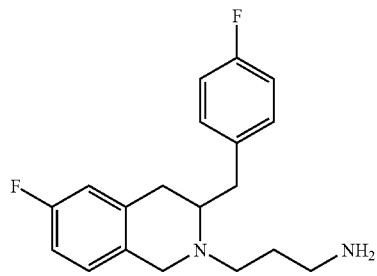

The reaction and treatment were carried out in the same manner as in Example 1-f) to obtain a title compound as a pale yellow oily substance.

$^1$H-NMR (CDCl$_3$) δ: 1.68-1.78 (2H, m), 2.40 (1H, dd, J=10.2, 13.2 Hz), 2.52 (1H, dd, J=4.0, 16.3 Hz), 2.65-2.83 (5H, m), 2.92 (1H, dd, J=4.9, 13.2 Hz), 3.16-3.24 (1H, m), 3.76 (1H, d, J=15.7 Hz), 3.85 (1H, d, J=15.7 Hz), 6.75 (1H, dd, J=2.2, 9.5 Hz), 6.85 (1H, ddd, J=2.2, 8.6, 8.6 Hz), 6.97 (2H, ddd, J=2.0, 6.8, 8.8 Hz), 7.00-7.10 (3H, m).

c) Production of 1-[3-[6-fluoro-3-(4-fluorobenzyl)-3,4-dihydroisoquinolin-2(1H)-yl]propyl]-3-phenylurea

[Chem. 504]

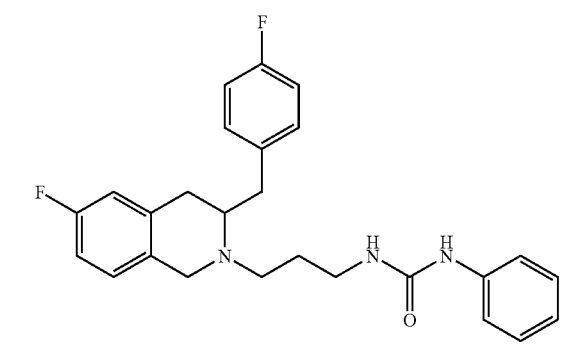

The reaction and treatment were carried out in the same manner as in Example 208 to obtain a title compound as a pale yellow amorphous.

$^1$H-NMR (CDCl$_3$) δ: 1.70-1.80 (2H, m), 2.35 (1H, dd, J=10.3, 13.2 Hz), 2.46 (1H, dd, J=3.9, 16.7 Hz), 2.65 (1H, dd, J=5.0, 16.7 Hz), 2.68-2.76 (2H, m), 2.82 (1H, dd, J=4.1, 13.2 Hz), 3.08-3.18 (1H, m), 3.24-3.40 (2H, m), 3.68 (1H, d, J=15.2 Hz), 3.75 (1H, d, J=15.2 Hz), 5.85 (1H, brs), 6.72 (1H, dd, J=2.2, 9.3 Hz), 6.86 (1H, ddd, J=2.4, 8.5, 8.5 Hz), 6.92-7.02 (6H, m), 7.12-7.18 (4H, m).

Example 239

Production of 1-(3-ethyl phenyl)-3-[3-[6-fluoro-3-(4-fluorobenzyl)-3,4-dihydroisoquinolin-2 (1H)-yl]propyl]urea

[Chem. 505]

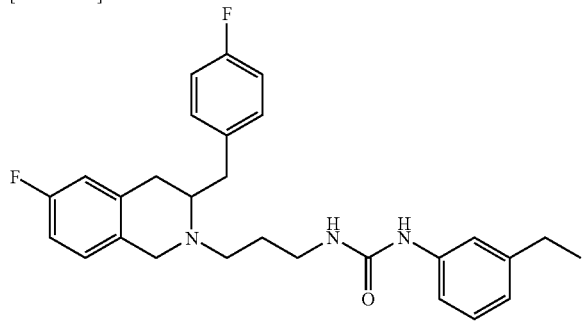

The reaction and treatment were carried out in the same manner as in Example 208 using 3-[6-fluoro-3-(4-fluorobenzyl)-3,4-dihydroisoquinolin-2(1H)-yl]propanamine obtained in Example 238-b) as a starting material, and using 3-ethylphenyl isocyanate instead of phenyl isocyanate to obtain a title compound as a pale yellow amorphous substance.

$^1$H-NMR (CDCl$_3$) δ: 1.14 (3H, t, J=7.6 Hz), 1.70-1.80 (2H, m), 2.33 (1H, dd, J=10.2, 13.2 Hz), 2.45 (1H, dd, J=3.9, 15.6 Hz), 2.49 (2H, q, J=7.6 Hz), 2.65 (1H, dd, J=5.0, 15.6 Hz), 2.67-2.76 (2H, m), 2.81 (1H, dd, J=4.2, 13.2 Hz), 3.09-3.18 (1H, m), 3.24-3.38 (2H, m), 3.68 (1H, d, J=15.5 Hz), 3.75 (1H, d, J=15.5 Hz), 5.86 (1H, brs), 6.71 (1H, dd, J=2.6, 9.3 Hz), 6.85 (1H, ddd, J=2.6, 8.3, 8.3 Hz), 6.91-7.08 (8H, m), 7.26 (1H, s).

Example 240

Production of 1-[3-[6-fluoro-3-(4-fluorobenzyl)-3,4-dihydroisoquinolin-2(1H)-yl]propyl]-3-(3-methoxyphenyl)urea

[Chem. 506]

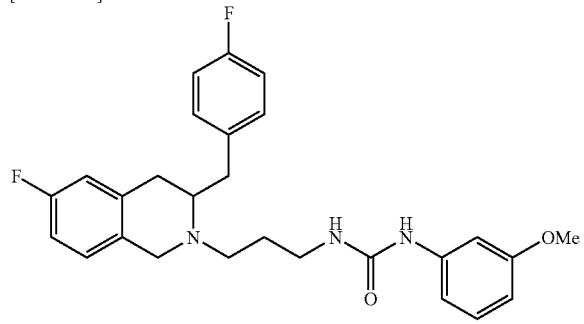

The reaction and treatment were carried out in the same manner as in Example 208 using 3-[6-fluoro-3-(4-fluorobenzyl)-3,4-dihydroisoquinolin-2(1H)-yl]propanamine obtained in Example 238-b) as a starting material, and using 3-methoxyphenyl isocyanate instead of phenyl isocyanate to obtain a title compound as a pale yellow amorphous substance.

$^1$H-NMR (CDCl$_3$) δ: 1.70-1.79 (2H, m), 2.35 (1H, dd, J=10.0, 13.4 Hz), 2.45 (1H, dd, J=4.0, 16.6 Hz), 2.62-2.72 (3H, m), 2.82 (1H, dd, J=3.6, 13.4 Hz), 3.10-3.18 (1H, m), 3.25-3.40 (2H, m), 3.69 (1H, d, J=15.4 Hz), 3.70 (3H, s), 3.75 (1H, d, J=15.4 Hz), 5.94 (1H, brs), 6.51 (1H, dd, J=2.4, 8.3 Hz), 6.67 (1H, d, J=7.8 Hz), 6.71 (1H, d, J=9.5 Hz), 6.85 (1H, ddd, J=2.4, 8.3, 8.3 Hz), 6.91-7.06 (8H, m).

Example 241

Production of 1-(3-ethoxy phenyl)-3-[3-[6-fluoro-3-(4-fluorobenzyl)-3,4-dihydroisoquinolin-2(1H)-yl]propyl]urea

[Chem. 507]

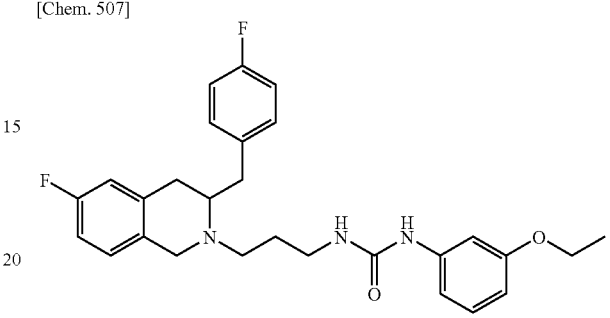

The reaction and treatment were carried out in the same manner as in Example 208 using 3-[6-fluoro-3-(4-fluorobenzyl)-3,4-dihydroisoquinolin-2(1H)-yl]propanamine obtained in Example 238-b) as a starting material, and using 3-ethoxyphenyl isocyanate instead of phenyl isocyanate to obtain a title compound as a pale yellow amorphous substance.

$^1$H-NMR (CDCl$_3$) δ: 1.33 (3H, t, J=6.9 Hz), 1.68-1.79 (2H, m), 2.33 (1H, dd, J=10.4, 13.2 Hz), 2.45 (1H, dd, J=3.8, 16.6 Hz), 2.61-2.77 (3H, m), 2.81 (1H, dd, J=4.0, 13.2 Hz), 3.08-3.19 (1H, m), 3.24-3.40 (2H, m), 3.68 (1H, d, J=16.1 Hz), 3.75 (1H, d, J=16.1 Hz), 3.90 (2H, q, J=6.9 Hz), 5.99 (1H, brs), 6.50 (1H, dd, J=2.4, 8.3 Hz), 6.65-6.74 (2H, m), 6.85 (1H, ddd, J=2.4, 8.6, 8.6 Hz), 6.88-7.07 (8H, m).

Example 242

Production of 1-[3-[6-fluoro-3-(4-fluorobenzyl)-3,4-dihydroisoquinolin-2(1H)-yl]propyl]-3-(3-thiomethoxyphenyl)urea

[Chem. 508]

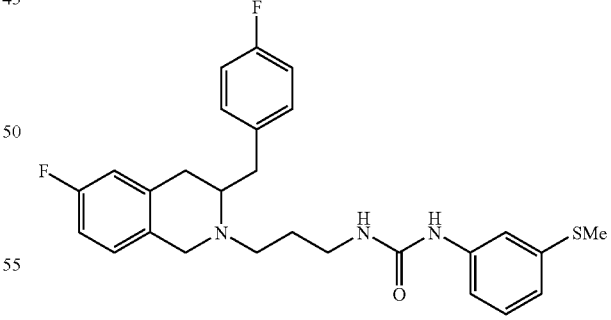

The reaction and treatment were carried out in the same manner as in Example 208 using 3-[6-fluoro-3-(4-fluorobenzyl)-3,4-dihydroisoquinolin-2(1H)-yl]propanamine obtained in Example 238-b) as a starting material, and using 3-thiomethoxyphenyl isocyanate instead of phenyl isocyanate to obtain a title compound as a pale yellow amorphous substance.

$^1$H-NMR (CDCl$_3$) δ: 1.70-1.81 (2H, m), 2.36 (1H, dd, J=10.2, 13.4 Hz), 2.39 (3H, s), 2.47 (1H, dd, J=3.6, 17.1 Hz), 2.64-2.78 (3H, m), 2.83 (1H, dd, J=4.1, 13.4 Hz), 3.12-3.20 (1H, m), 3.24-3.40 (2H, m), 3.69 (1H, d, J=15.9 Hz), 3.76 (1H, d, J=15.9 Hz), 5.91 (1H, brs), 6.73 (1H, dd, J=2.4, 9.2 Hz), 6.82 (1H, dd, J=1.8, 7.1 Hz), 6.85-6.90 (2H, m), 6.74-7.06 (7H, m), 7.18 (1H, dd, J=1.8, 1.8 Hz).

Example 243

Production of 1-(3,5-dimethoxyphenyl)-3-[3-[6-fluoro-3-(4-fluorobenzyl)-3,4-dihydroisoquinolin-2(1H)-yl]propyl]urea

[Chem. 509]

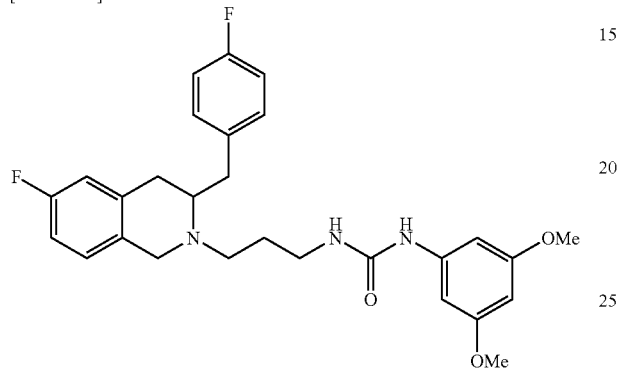

The reaction and treatment were carried out in the same manner as in Example 208 using 3-[6-fluoro-3-(4-fluorobenzyl)-3,4-dihydroisoquinolin-2(1H)-yl]propanamine obtained in Example 238-b) as a starting material, and using 3,5-dimethoxyphenyl isocyanate instead of phenyl isocyanate to obtain a title compound as a pale yellow amorphous substance.

$^1$H-NMR (CDCl$_3$) δ: 1.69-1.78 (2H, m), 2.34 (1H, dd, J=10.3, 13.2 Hz), 2.45 (1H, dd, J=3.9, 16.6 Hz), 2.63-2.76 (3H, m), 2.82 (1H, dd, J=4.2, 13.2 Hz), 3.08-3.18 (1H, m), 3.23-3.38 (2H, m), 3.66 (6H, s), 3.67 (1H, d, J=15.9 Hz), 3.75 (1H, d, J=15.9 Hz), 6.04 (1H, brs), 6.08 (1H, dd, J=2.2, 2.2 Hz), 6.45 (2H, d, J=2.2 Hz), 6.70 (1H, dd, J=2.4, 9.5 Hz), 6.84 (1H, ddd, J=2.4, 8.6, 8.6 Hz), 6.92-7.03 (5H, m), 7.12 (1H, brs).

Example 244

Production of 1-(3-acetylphenyl)-3-[3-[6-fluoro-3-(4-fluorobenzyl)-3,4-dihydroisoquinolin-2(1H)-yl]propyl]urea

[Chem. 510]

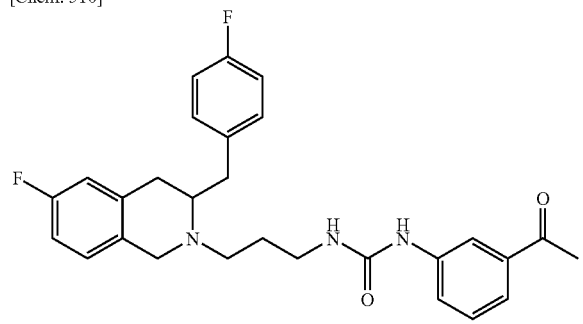

The reaction and treatment were carried out in the same manner as in Example 208 using 3-[6-fluoro-3-(4-fluorobenzyl)-3,4-dihydroisoquinolin-2(1H)-yl]propanamine obtained in Example 238-b) as a starting material, and using 3-acetylphenyl isocyanate instead of phenyl isocyanate to obtain a title compound as a pale yellow amorphous substance.

$^1$H-NMR (CDCl$_3$) δ: 1.74-1.84 (2H, m), 2.39 (1H, dd, J=10.1, 13.3 Hz), 2.50 (1H, dd, J=3.4, 15.6 Hz), 2.52 (3H, s), 2.72 (1H, dd, J=4.9, 15.6 Hz), 2.73-2.83 (2H, m), 2.86 (1H, dd, J=4.5, 13.3 Hz), 3.18-3.26 (1H, m), 3.29-3.43 (2H, m), 3.72 (1H, d, J=15.9 Hz), 3.78 (1H, d, J=15.9 Hz), 5.88 (1H, brs), 6.73 (1H, dd, J=2.4, 9.3 Hz), 6.85 (1H, ddd, J=2.4, 8.6, 8.6 Hz), 6.92-7.00 (3H, m), 7.01-7.06 (2H, m), 7.24 (1H, d, J=8.0 Hz), 7.51 (1H, dd, J=1.7, 7.8 Hz), 7.48-7.55 (1H, m), 7.75 (1H, dd, J=1.7, 1.7 Hz).

Example 245

Production of 1-(3-cyanophenyl)-3-[3-[6-fluoro-3-(4-fluorobenzyl)-3,4-dihydroisoquinolin-2(1H)-yl]propyl]urea

[Chem. 511]

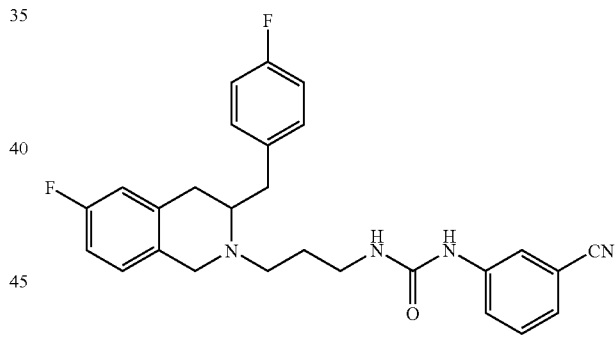

The reaction and treatment were carried out in the same manner as in Example 208 using 3-[6-fluoro-3-(4-fluorobenzyl)-3,4-dihydroisoquinolin-2(1H)-yl]propanamine obtained in Example 238-b) as a starting material, and using 3-cyanophenyl isocyanate instead of phenyl isocyanate to obtain a title compound as a pale yellow amorphous substance.

$^1$H-NMR (CDCl$_3$) δ: 1.72-1.88 (2H, m), 2.43 (1H, dd, J=10.0, 13.4 Hz), 2.57 (1H, dd, J=2.9, 16.8 Hz), 2.76-2.85 (3H, m), 2.89 (1H, dd, J=4.6, 13.4 Hz), 3.24-3.32 (1H, m), 3.32-3.42 (2H, m), 3.78 (2H, s), 5.73 (1H, brs), 6.79 (1H, dd, J=2.7, 9.3 Hz), 6.89 (1H, ddd, J=2.7, 8.6, 8.6 Hz), 6.96-7.02 (3H, m), 7.03-7.09 (2H, m), 7.17-7.21 (2H, m), 7.30-7.37 (1H, m), 7.53 (1H, brs).

Example 246

Production of 1-[3-[6-fluoro-3-(4-fluorobenzyl)-3,4-dihydroisoquinolin-2(1H)-yl]propyl]-3-(4-pyridinyl)urea

[Chem. 512]

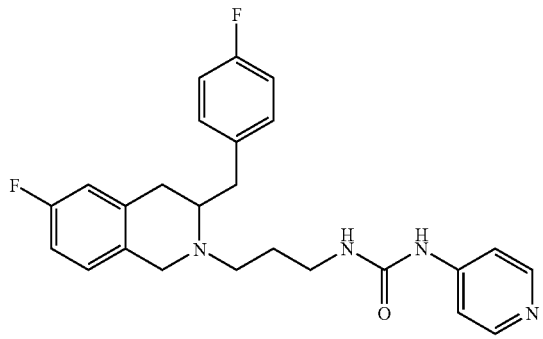

60 mg of 3-[6-fluoro-3-(4-fluorobenzyl)-3,4-dihydroisoquinolin-2(1H)-yl]propanamine obtained in Example 238-b), 20 mg of 4-aminopyridine, and 34 mg of CDI were dissolved in 1.2 mL of THF, followed by stirring at 60° C. for 3 hours. After completion of the reaction, water was added to the reaction liquid, followed by extraction with chloroform. The organic layer was then washed with saturated brine, dried over anhydrous sodium sulfate and then concentrated under reduced pressure. The residue obtained was purified using silica gel chromatography (chloroform:methanol=10:1) to obtain 10 mg (yield 12%) of a title compound as a yellow oily substance.

$^1$H-NMR (CDCl$_3$) δ: 1.68-1.80 (2H, m), 2.41 (1H, dd, J=10.3, 13.2 Hz), 2.52 (1H, dd, J=3.7, 16.6 Hz), 2.66-2.84 (5H, m), 2.92 (1H, dd, J=4.0, 13.2 Hz), 3.17-3.26 (1H, m), 3.76 (1H, d, J=15.9 Hz), 3.85 (1H, d, J=15.9 Hz), 4.11 (1H, brs), 6.52 (2H, dd, J=1.5, 4.6 Hz), 6.75 (1H, dd, J=2.4, 9.2 Hz), 6.86 (1H, ddd, J=2.4, 8.6, 8.6 Hz), 6.98 (2H, ddd, J=2.0, 6.8, 8.8 Hz), 7.02 (1H, dd, J=5.8, 8.6 Hz), 7.04-7.09 (2H, m), 7.11 (1H, brs), 8.22 (2H, dd, J=1.5, 4.6 Hz).

Test Example 1 Test of a CCR3 Antagonistic Action

Guinea pig eosinophils were prepared with reference to a literature (Pinkus, Blood. 52 (1978) 127-134). That is, to a six-week old male Hartley guinea pig (Japan SLC, Inc.) was intraperitoneally injected polymyxin B (SIGMA) diluted with PBS (−) at 2 mg per animal once a week. After repeating the same operation four times for 24 hours, the abdominal cavity of each individual under anesthesia with diethyl ether was injected with 50 mL of PBS (−) containing 6 U/mL of heparin and 1 mM EDTA, and the liquid was collected. It was washed with PBS (−) containing 1 mM EDTA, and the cells were suspended in a Percoll solution having a specific density of 1.070 were centrifuged using a discontinuous Percoll gradient liquid to obtain an eosinophilic crude fraction. After washing with PBS (−), they were suspended in RPMI-1640 culture medium (SIGMA) containing 1% FCS, and cultured in a $CO_2$ incubator overnight. Next day, the cells were harvested, a compound to be tested was added to the eosinophils suspended in the RPMI-1640 culture medium containing 0.1% BSA (bovine serum albumin, SIGMA), and then pre-treatment was performed by leaving it to stand still at 37° C. for 30 minutes. A mixed liquid of guinea pig eotaxin (Chemical Synthesis Services) and the compound to be tested that had been prepared to be at a final concentration of 100 ng/mL was added into a lower chamber of 96-well chemotaxis chambers (Neuroprobe), and then a mixed liquid of 12.0×10$^5$ eosinophils per well and the compound to be tested was sequentially set in an upper chamber of a polycarbonate filter (Neuroprobe) having a pore size of 5 μm after completion of the treatment with polyvinyl pyrrolidone (PVP), and allowed to undergo a reaction in a $CO_2$ incubator for 1 hour. After completion of the reaction, the filter was taken out, the cells were stained in a Diff-Quik stain kit (International Reagents Co., Ltd.), and the migrated eosinophils were microscopically counted. Five fields of view per well were counted, and an average value of the counts was taken as a count of migrated eosinophils. An inhibition rate was calculated when the reaction of eotaxin alone was set at 100%, and a concentration exhibiting a 50% inhibition (IC50 value) was calculated from a concentration-inhibition rate curve. The results are shown in Table 1.

TABLE 1

| No. | IC50 value (nM) |
|---|---|
| Example 96 | 30 |
| Example 106 | 7 |
| Example 126 | 1 |
| Example 138 | 4 |
| Example 139 | 40 |
| Example 150 | 4 |
| Example 154 | 20 |
| Example 156 | 80 |
| Example 157 | 25 |
| Example 161 | 25 |
| Example 171 | 14 |
| Example 180 | 2 |

Test Example 2 Inhibitory Action on Pulmonary Eosinophilic Infiltration in an Ovalbumin-Induced Guinea Pig Eosinophil Infiltration Model A suspension of 10 μg of ovalbumin (OVA, SIGMA) and 100 mg of aluminum hydroxide (Wako Chemical Co. Ltd.) was intraperitoneally administered to male Std/Hartley guinea pigs (n=8) to carry out sensitization (first sensitization), and then after 2 days, sensitization was carried out again under the same condition.

After 16 days from the first sensitization, 0.5% OVA was inhaled for 30 minutes, and before 30 minutes and after 4 hours therefrom, the compound of the present invention (Example 126) that had been suspended in a 0.5% aqueous methyl cellulose solution was administered at a dose of 10 mg/kg. In addition, for the control group, a solvent (a 0.5% aqueous methyl cellulose solution) alone was administered, and for the normal group, untreated animals were used.

After 17 days from the first sensitization, the alveoli was washed with PBS containing 0.1% BSA (10 mL×5 round trips×twice) to recover the alveolar lavage fluid.

For the recovered alveolar lavage fluid, the number of eosinophils was measured by a Multi-Parameter Automated Hematology Analyzer XT-2000i (Sysmex). The results are shown in FIG. 1.

Test Example 3 Inhibitory Action on Pulmonary
Eosinophilic Infiltration in an Eotaxin-Induced
Guinea Pig Eosinophil Infiltration Model A suspension of 10 µg of ovalbumin (OVA, SIGMA) and 100 mg of aluminum hydroxide (Wako Chemical Co. Ltd.) was intraperitoneally administered to male Std/Hartley guinea pigs to carry out sensitization (first sensitization), and then after 2 days, sensitization was carried out again under the same condition.

After 16 days from the first sensitization, the test substance (Example 180) that had been dissolved in physiological saline was intravenously administered at a dose of 3 mg/kg, and after 5 minutes therefrom, 100 ng of eotaxin (PeproTech) was administered to the trachea.

In addition, for the control group, a solvent (physiological saline) alone was administered, and for the normal group, untreated animals were used.

After 2 hours from the administration of eotaxin into the trachea, the alveoli was washed with PBS containing 0.1% BSA (10 mL×5 round trips×twice) to recover the alveolar lavage fluid.

Figure 2:
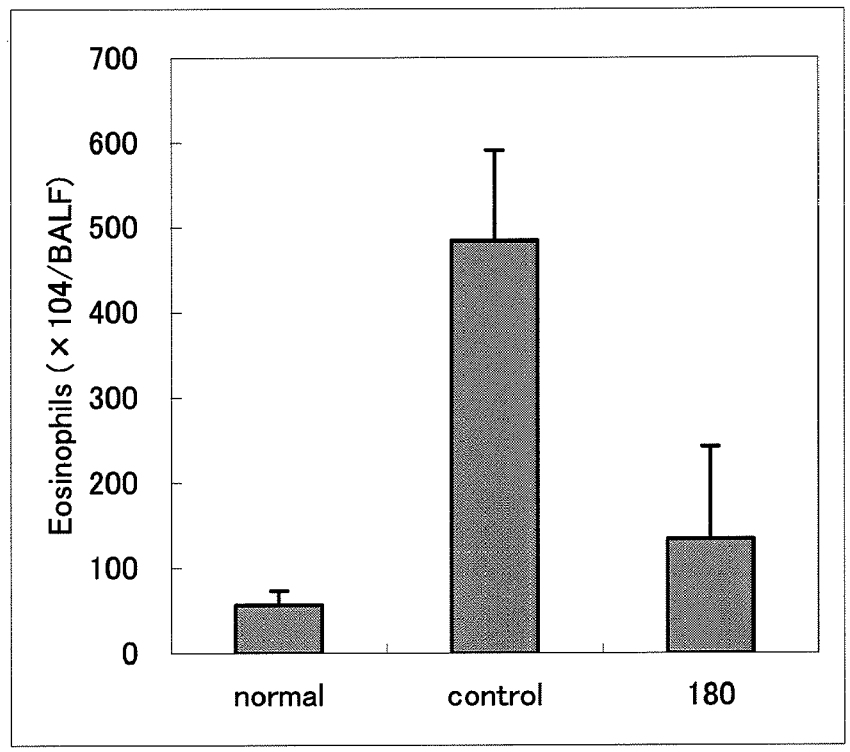
FIG. 2 is a graph showing an inhibitory action on pulmonary eosinophilic infiltration in an eotaxin-induced guinea pig eosinophil infiltration model by the compound according to the present invention.

For the recovered alveolar lavage fluid, the total number of leukocytes was counted, the ratio of the eosinophils was determined by Diff-Quick staining of the prepared coated sample, and thus, the number of the eosinophils was calculated. The results are shown in FIG. 2.

Test Example 4 Inhibitory Action on Airway
Hyperresponsiveness in an Ovalbumin-Induced
Guinea Pig Asthma Model A suspension of 10 µg of ovalbumin (OVA, SIGMA) and 100 mg of aluminum hydroxide (Wako Chemical Co. Ltd.) was intraperitoneally administered to male Std/Hartley guinea pigs (n=10) to carry out sensitization.

0.5% OVA was inhaled for 5 minutes after 7, 14, and 21 days from the sensitization, 0.5% OVA was inhaled for 30 minutes after 28 days from the sensitization, and the compound of the present invention (Example 161) that had been suspended in a 0.5% aqueous methyl cellulose solution was administered at a dose of 10 mg/kg, before 30 minutes and after 4 hours from OVA inhalation, respectively. Further, after 8 to 13, 15 to 20, and 22 to 27 days from the sensitization, the compound of the present invention was administered at a dose of 30 mg/kg once per day in the same manner. In addition, for the control group, a solvent (a 0.5% aqueous methyl cellulose solution) alone was administered, and for the normal group, untreated animals were used.

Figure 3:
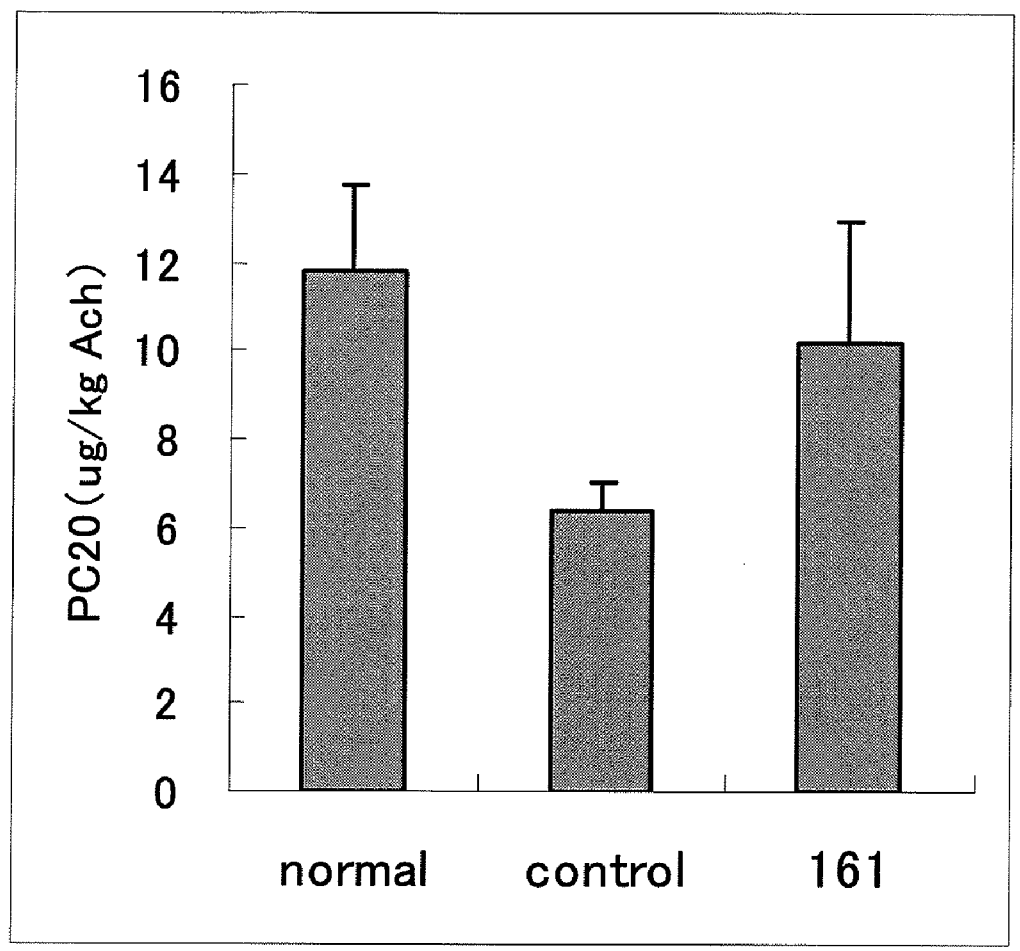
FIG. 3 is a graph showing an inhibitory action on airway hyperresponsiveness in an ovalbumin-induced guinea pig asthma model by the compound according to the present invention.

After 29 days from the sensitization, the airway contraction by the intravenous administration of 1.25 to 80 µg/kg of acetylcholine (Ach) under pentobarbital anesthesia/artificial respiration was measured, and an Ach concentration (PC20) for inducing 20% airway contraction was calculated as an indicator of the airway hyperresponsiveness. The results are shown in FIG. 3.

From the above, it can be seen that the compound of the present invention has a more excellent CCR3 antagonistic action, as compared with that in Test Example 1, and effectively acts on a model with a specific allergic disease, as compared with Test Examples 2, 3, and 4. Therefore, it is shown that the compound exhibits an excellent effect as a prophylactic and/or therapeutic agent for CCR3-participated diseases, in particular, diseases such as asthma, allergic rhinitis, allergic conjunctivitis, atopic dermatitis, and the like.

Also, it is confirmed that the compound of the present invention has substantially no toxicity, and is therefore useful as a pharmaceutical.

The present invention is described in detail as above with reference to specific embodiments, but it will be apparent to a person skilled in the art that various modifications or alterations may be made without departing from the spirit and scope of the present invention.

The present Application is based on U.S. Provisional Patent Application No. 60/909,997 filed on Apr. 4, 2007 and U.S. Provisional Patent Application No. 60/939,415 filed on May 22, 2007, each content of which is hereby incorporated by reference in its entirety.

INDUSTRIAL AVAILABILITY

The tetrahydroisoquinoline compound of the present invention is useful as an active ingredient of a pharmaceutical. In particular, the compound of the present invention has an inhibitory action on the activation of a CCR3-expressing cell by binding to the CCR3 (CCR3 antagonistic action), and is therefore useful as an agent for preventing or treating CCR3-participated diseases (particularly, allergic or autoimmune diseases such as asthma, allergic rhinitis, sinusitis, allergic conjunctivitis, atopic dermatitis, ulcerative colitis, Crohn's disease, rheumatoid arthritis, and the like, HIV infections and encephalitis and dementia caused therefrom, and the like).

The invention claimed is:
1. A tetrahydroisoquinoline compound represented by the following formula (1):

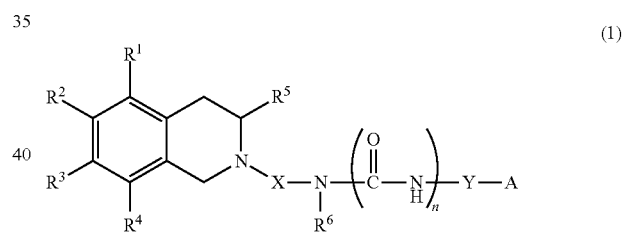

or a pharmaceutically acceptable salt thereof, wherein
$R^1$, $R^2$, $R^3$, and $R^4$, which are the same or different, each represent —H, -halogen, $C_{1-6}$ alkyl which may be substituted, —OH, —O—$C_{1-6}$ alkyl, —SH, —S—$C_{1-6}$ alkyl, —COOH, —CO—$C_{1-6}$ alkyl, —CO—O—$C_{1-6}$ alkyl, —CO—NH—$C_{1-6}$ alkyl, —NO$_2$, —NH$_2$, —NH—$C_{1-6}$ alkyl, —N($C_{1-6}$ alkyl)$_2$, or —NH—CO—$C_{1-6}$ alkyl;
$R^5$ represents $C_{1-6}$ alkyl which may be substituted, $C_{3-10}$ cycloalkyl which may be substituted, $C_{6-14}$ aryl which may be substituted, —$C_{1-6}$ alkylene-$C_{3-10}$ cycloalkyl which may be substituted, or —$C_{1-6}$ alkylene-$C_{6-14}$ aryl which may be substituted;
$R^6$ represents —H, —$C_{1-6}$ alkyl which may be substituted, or —Y'-A';
X represents $C_{1-6}$ alkylene;
Y and Y', which are the same or different, each represent a single bond or $C_{1-6}$ alkylene;
A and A', which are the same or different, each represent $C_{6-14}$ aryl which may be substituted or 3- to 15-membered heterocyclic group which may be substituted; and
n represents 0 or 1.

2. The tetrahydroisoquinoline compound or a pharmaceutically acceptable salt thereof according to claim 1, wherein n is 0; and
A is a group represented by the following formula:

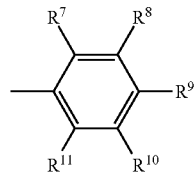

wherein $R^7$, $R^8$, $R^9$, $R^{10}$, and $R^{11}$, which are the same or different, each represent —H, -halogen, —OH, $C_{1-6}$ alkyl which may be substituted, —O—$C_{1-6}$ alkyl, —S—$C_{1-6}$ alkyl, —$SO_2$—$C_{1-6}$ alkyl, —$SO_2$-halogeno-$C_{1-6}$ alkyl, —COOH, —CO—$C_{1-6}$ alkyl, —CO—$C_{1-6}$ alkyl, —CO—$NH_2$, —CO—NH($C_{1-6}$ alkyl), —CO—N($C_{1-6}$ alkyl)$_2$, —$SO_2$NH($C_{1-6}$ alkyl), —$SO_2$N($C_{1-6}$ alkyl)$_2$, —$NO_2$, —CN, $C_{6-14}$ aryl, a 3- to 15-membered heterocyclic group, or —N($R^{12}$)($R^{13}$), wherein $R^{12}$ and $R^{13}$, which are the same or different, each represent —H, $C_{3-10}$ cycloalkyl, $C_{6-14}$ aryl, 3- to 15-membered heterocyclic group, —$C_{1-6}$ alkylene-$C_{3-10}$ cycloalkyl, —$C_{1-6}$ alkylene-$C_{6-14}$ aryl, —$C_{1-6}$ alkylene-3- to 15-membered hetero ring, $C_{1-6}$ alkyl which may be substituted, —CO—$C_{1-6}$ alkyl, —$SO_2$—$C_{1-6}$ alkyl, or —$SO_2$-halogeno-$C_{1-6}$ alkyl.

3. The tetrahydroisoquinoline compound or a pharmaceutically acceptable salt thereof according to claim 2, wherein X is ethylene, Y is methylene, and $R^6$ is —H.

4. The tetrahydroisoquinoline compound or a pharmaceutically acceptable salt thereof according to claim 3, wherein $R^1$ and $R^4$ are —H, and $R^2$ and $R^3$, which are the same or different, each represent —H or -halogen.

5. The tetrahydroisoquinoline compound or a pharmaceutically acceptable salt thereof according to claim 4, wherein $R^5$ is benzyl which may be substituted.

6. The tetrahydroisoquinoline compound or a pharmaceutically acceptable salt thereof according to claim 5, wherein $R^5$ is halogenobenzyl.

7. The tetrahydroisoquinoline compound or a pharmaceutically acceptable salt thereof according to claim 1, wherein n is 0, $R^5$ is —$C_{1-6}$ alkylene-$C_{6-14}$ aryl which may be substituted, and A and A', which are the same or different, each represent a 3- to 15-membered heterocyclic group which may be substituted, or naphthyl.

8. The tetrahydroisoquinoline compound or a pharmaceutically acceptable salt thereof according to claim 7, wherein A and A', which are the same or different, each represent a heterocyclic group which may be substituted, said heterocyclic group being selected from pyridyl, pyridyl N-oxide, pyrimidinyl, imidazolyl, pyrrolyl, thienyl, furyl, thiazolyl, quinolyl, indolyl, and benzoimidazolyl, or naphthyl.

9. The tetrahydroisoquinoline compound or a pharmaceutically acceptable salt thereof according to claim 8, wherein $R^1$, $R^2$, $R^3$, and $R^4$, which are the same or different, each represent —H or -halogen, X is ethylene, Y is methylene, and $R^6$ is —H.

10. A tetrahydroisoquinoline compound or a pharmaceutically acceptable salt thereof selected from:

N-(4-tert-butylbenzyl)-2-[3-(4-fluorobenzyl)-3,4-dihydroisoquinolin-2(1H)-yl]ethanamine,
N-(3-acetylbenzyl)-2-[3-(4-fluorobenzyl)-3,4-dihydroisoquinolin-2(1H)-yl]ethanamine,
3-[[2-[3-(4-fluorobenzyl)-3,4-dihydroisoquinolin-2(1H)-yl]ethylamino]methyl]-N,N-diethylbenzamide,
N-(4-tert-butylbenzyl)-2-[6-fluoro-3-(4-fluorobenzyl)-3,4-dihydroisoquinolin-2(1H)-yl]ethanamine,
N-(3-acetylbenzyl)-2-[6-fluoro-3-(4-fluorobenzyl)-3,4-dihydroisoquinolin-2(1H)-yl]ethanamine,
N-[3-(methanesulfonylamino)benzyl]-2-[6-fluoro-3-(4-fluorobenzyl)-3,4-dihydroisoquinolin-2(1H)-yl]ethanamine,
N-(3,5-dimethanesulfonylaminobenzyl)-2-[6-fluoro-3-(4-fluorobenzyl)-3,4-dihydroisoquinolin-2(1H)-yl]ethanamine,
4-[[2-[6-fluoro-3-(4-fluorobenzyl)-3,4-dihydroisoquinolin-2(1H)-yl]ethylamino]methyl]-N-isopropylaniline,
4-[[2-[6-fluoro-3-(4-fluorobenzyl)-3,4-dihydroisoquinolin-2(1H)-yl]ethylamino]methyl]-N-ethylaniline,
N-[4-(4-morpholino)benzyl]-2-[6-fluoro-3-(4-fluorobenzyl)-3,4-dihydroisoquinolin-2(1H)-yl]ethanamine,
4-[[2-[6-fluoro-3-(4-fluorobenzyl)-3,4-dihydroisoquinolin-2(1H)-yl]ethylamino]methyl]-N-(2-methoxyethyl)aniline,
3-[[2-[6-fluoro-3-(4-fluorobenzyl)-3,4-dihydroisoquinolin-2(1H)-yl]ethylamino]methyl]-N,N-diethylbenzamide,
N-[4-(1-hydroxy-1-methylethyl)benzyl]-2-[6-fluoro-3-(4-fluorobenzyl)-3,4-dihydroisoquinolin-2(1H)-yl]ethanamine,
3-[[2-[6-fluoro-3-(4-fluorobenzyl)-3,4-dihydroisoquinolin-2(1H)-yl]ethylamino]methyl]benzamide,
N-(4-tert-butylbenzyl)-2-[3-(4-chlorobenzyl)-6-fluoro-3,4-dihydroisoquinolin-2(1H)-yl]ethanamine,
N-(3-methanesulfonylaminobenzyl)-2-[3-(4-chlorobenzyl)-6-fluoro-3,4-dihydroisoquinolin-2(1H)-yl]ethanamine,
4-[[2-[7-fluoro-3-(4-fluorobenzyl)-3,4-dihydroisoquinolin-2(1H)-yl]ethylamino]methyl]-N-isopropylaniline,
N-(pyridin-4-yl)methyl-2-[3-(4-fluorobenzyl)-3,4-dihydroisoquinolin-2(1H)-yl]ethanamine, and
N-(pyridin-4-yl)methyl-2-[6-fluoro-3-(4-fluorobenzyl)-3,4-dihydroisoquinolin-2(1H)-yl]ethanamine.

11. A pharmaceutical composition comprising the tetrahydroisoquinoline compound or a pharmaceutically acceptable salt thereof as described in claim 1, and a pharmaceutically acceptable carrier.

12. A chemokine receptor type 3 (CCR3) antagonist comprising the tetrahydroisoquinoline compound or a pharmaceutically acceptable salt thereof as described in claim 1 as an active ingredient.

13. An agent for preventing or treating asthma, allergic rhinitis, sinusitis, allergic conjunctivitis, atopic dermatitis, ulcerative colitis, Crohn's disease, rheumatoid arthritis, an autoimmune disease, HIV infection or a disease caused from HIV infection, comprising the tetrahydroisoquinoline compound or a pharmaceutically acceptable salt thereof as described in claim 1 as an active ingredient.

* * * * *